United States Patent
Bloom

(10) Patent No.: US 9,546,205 B2
(45) Date of Patent: Jan. 17, 2017

(54) PEPTIDE ANALOGUES OF GLUCAGON AND GLP1

(71) Applicant: IMPERIAL INNOVATIONS LIMITED, London (GB)

(72) Inventor: Stephen Robert Bloom, London (GB)

(73) Assignee: IMPERIAL INNOVATIONS LIMITED, London (GB)

( * ) Notice: Subject to any disclaimer, the term of this patent is extended or adjusted under 35 U.S.C. 154(b) by 0 days.

(21) Appl. No.: 14/428,599

(22) PCT Filed: Sep. 17, 2013

(86) PCT No.: PCT/GB2013/052422
§ 371 (c)(1),
(2) Date: Mar. 16, 2015

(87) PCT Pub. No.: WO2014/041375
PCT Pub. Date: Mar. 20, 2014

(65) Prior Publication Data
US 2015/0252091 A1    Sep. 10, 2015

(30) Foreign Application Priority Data

Sep. 17, 2012 (GB) .................................. 1216548.6
Sep. 17, 2012 (GB) .................................. 1216551.0

(51) Int. Cl.
*C07K 14/605*    (2006.01)
*A61K 38/26*    (2006.01)

(52) U.S. Cl.
CPC ............. *C07K 14/605* (2013.01); *A61K 38/26* (2013.01)

(58) Field of Classification Search
None
See application file for complete search history.

(56) References Cited

U.S. PATENT DOCUMENTS

2006/0178304 A1    8/2006  Juul-Mortensen et al.
2012/0122783 A1*   5/2012  Dimarchi ............. C07K 14/605
                                                         514/11.7

FOREIGN PATENT DOCUMENTS

| JP | 2007524592 | 8/2007 |
| WO | WO 2007/056362 | 5/2007 |
| WO | WO 2008/086086 | 7/2008 |
| WO | WO 2010/070253 | 6/2010 |
| WO | WO 2010/148089 | 12/2010 |
| WO | WO 2011/075393 | 6/2011 |
| WO | WO 2011/117417 | 9/2011 |
| WO | WO 2011/160630 | 12/2011 |

OTHER PUBLICATIONS

Pengyun et al., Design, synthesis and crystallization of a novel glucagon analog as a therapeutic agent, Acta Cryst Sec F, Struct Biol and Cryst Comm, 63(7): 599-601 (2007).

* cited by examiner

*Primary Examiner* — Julie Ha
*Assistant Examiner* — Kristina M Hellman
(74) *Attorney, Agent, or Firm* — Yankwich & Associates, P.C.; Leon R. Yankwich; Michael R. Wesolowski

(57) ABSTRACT

Peptide analogs of glucagon and peptide analogs of GLP1 are provided herein. Also provided herein are pharmaceutical compositions comprising the analogs, and methods of using the analogs for the treatment and/or prevention of conditions such as obesity and diabetes.

23 Claims, 86 Drawing Sheets

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 1 | 1 | G | His | Ser | Gln | Gly | Thr | Phe | Thr | Ser | Asp | Tyr | Ser | Lys | Tyr | Leu | Glu | Glu |
| 2 | 2 | G | His | Ser | Gln | Gly | Thr | Phe | Thr | Ser | Asp | Tyr | Ser | Lys | Tyr | Leu | Asp | Ser |
| 3 | 3 | G | His | Ser | Gln | Gly | Thr | Phe | Thr | Ser | Asp | Tyr | Ser | Lys | Tyr | Leu | Asp | Ser |
| 4 | 4 | G | His | Ser | Gln | Gly | Thr | Phe | Thr | Ser | Asp | Tyr | Ser | His | Tyr | Leu | Asp | Ser |
| 5 | 5 | G | His | Ser | Gln | Gly | Thr | Phe | Thr | Ser | Asp | Tyr | Ser | Arg | Tyr | Leu | Asp | Ser |
| 6 | 6 | G | His | Ser | Gln | Gly | Thr | Phe | Thr | Ser | Asp | Tyr | Ser | Lys | Tyr | Leu | Asp | Ser |
| 7 | 7 | G | His | Ser | Gln | Gly | Thr | Phe | Thr | Ser | Asp | Tyr | Ser | His | Tyr | Leu | Asp | Ser |
| 8 | 8 | G | His | Ser | Gln | Gly | Thr | Phe | Thr | Ser | Asp | Tyr | Ser | Arg | Tyr | Leu | Asp | Ser |
| 9 | 9 | G | His | Ser | Gln | Gly | Thr | Phe | Thr | Ser | Asp | Tyr | Ser | Lys | Tyr | Leu | Asp | Ser |
| 10 | 10 | G | His | Ser | Gln | Gly | Thr | Phe | Thr | Ser | Asp | Tyr | Ser | His | Tyr | Leu | Asp | Ser |
| 11 | 11 | G | His | Ser | Gln | Gly | Thr | Phe | Thr | Ser | Asp | Tyr | Ser | Lys | Tyr | Leu | Asp | Ser |
| 12 | 12 | G | His | Ser | Gln | Gly | Thr | Phe | Thr | Ser | Asp | Tyr | Ser | Lys | Tyr | Leu | Asp | Ser |
| 13 | 13 | G | His | Ser | Gln | Gly | Thr | Phe | Thr | Ser | Asp | Tyr | Ser | Lys | Tyr | Leu | Asp | Ser |
| 14 | 14 | G | His | Ser | Gln | Gly | Thr | Phe | Thr | Ser | Asp | Tyr | Ser | Lys | Tyr | Leu | Asp | Ser |
| 15 | 15 | G | His | Ser | Gln | Gly | Thr | Phe | Thr | Ser | Asp | Tyr | Ser | Lys | Tyr | Leu | Asp | Ser |
| 16 | 16 | G | His | Ser | Gln | Gly | Thr | Phe | Thr | Ser | Asp | Tyr | Ser | Lys | Tyr | Leu | Asp | Ser |
| 17 | 17 | G | His | Ser | Gln | Gly | Thr | Phe | Thr | Ser | Asp | Tyr | Ser | Lys | Tyr | Leu | Asp | Ser |
| 18 | 18 | G | His | Ser | Gln | Gly | Thr | Phe | Thr | Ser | Asp | Tyr | Ser | Arg | Tyr | Leu | Asp | Ser |
| 19 | 19 | G | His | Ser | Gln | Gly | Thr | Phe | Thr | Ser | Asp | Tyr | Ser | Lys | Tyr | Leu | Asp | Ser |
| 20 | 20 | G | His | Ser | Gln | Gly | Thr | Phe | Thr | Ser | Asp | Tyr | Ser | Lys | Tyr | Leu | Asp | Ser |
| 21 | 21 | G | His | Ser | Gln | Gly | Thr | Phe | Thr | Ser | Asp | Tyr | Ser | His | Tyr | Leu | Asp | Ser |
| 22 | 22 | G | His | Ser | Gln | Gly | Thr | Phe | Thr | Ser | Asp | Tyr | Ser | Lys | Tyr | Leu | Glu | Ser |
| 23 | 23 | G | His | Ser | Gln | Gly | Thr | Phe | Thr | Ser | Asp | Tyr | Ser | Lys | Tyr | Leu | Asp | Ser |
| 24 | 24 | G | His | Ser | Gln | Gly | Thr | Phe | Thr | Ser | Asp | Tyr | Ser | Lys | Tyr | Leu | Asp | Ser |
| 25 | 25 | G | His | Ser | Gln | Gly | Thr | Phe | Thr | Ser | Asp | Tyr | Ser | His | Tyr | Leu | Asp | Ser |
| 26 | 26 | G | His | Ser | Gln | Gly | Thr | Phe | Thr | Ser | Asp | Tyr | Ser | His | Tyr | Leu | Asp | Ser |
| 27 | 27 | G | His | Ser | Gln | Gly | Thr | Phe | Thr | Ser | Asp | Tyr | Ser | His | Tyr | Leu | Asp | Ser |
| 28 | 28 | G | His | Ser | Gln | Gly | Thr | Phe | Thr | Ser | Asp | Tyr | Ser | Lys | Tyr | Leu | Asp | Ser |
| 29 | 29 | G | His | Ser | Gln | Gly | Thr | Phe | Thr | Ser | Asp | Tyr | Ser | Lys | Tyr | Leu | Asp | Ser |
| 30 | 30 | G | His | Ser | Gln | Gly | Thr | Phe | Thr | Ser | Asp | Tyr | Ser | Lys | Tyr | Leu | Asp | Ser |
| 31 | 31 | G | His | Ser | Gln | Gly | Thr | Phe | Thr | Ser | Asp | Tyr | Ser | Lys | Tyr | Leu | Asp | Ser |
| 32 | 32 | G | His | Ser | Gln | Gly | Thr | Phe | Thr | Ser | Asp | Tyr | Ser | Lys | Tyr | Leu | Asp | Ser |
| 33 | 33 | G | His | Ser | Gln | Gly | Thr | Phe | Thr | Ser | Asp | Tyr | Ser | Arg | Tyr | Leu | Asp | Ser |
| 34 | 34 | G | His | Ser | Gln | Gly | Thr | Phe | Thr | Ser | Asp | Tyr | Ser | Lys | Tyr | Leu | Asp | Ser |
| 35 | 35 | G | His | Ser | Gln | Gly | Thr | Phe | Thr | Ser | Asp | Tyr | Ser | Lys | Tyr | Leu | Asp | Ser |
| 36 | 36 | G | His | Ser | Gln | Gly | Thr | Phe | Thr | Ser | Asp | Tyr | Ser | His | Tyr | Leu | Asp | Ser |
| 37 | 37 | G | His | Ser | Gln | Gly | Thr | Phe | Thr | Ser | Asp | Tyr | Ser | His | Tyr | Leu | Asp | Ser |
| 38 | 38 | G | His | Ser | Gln | Gly | Thr | Phe | Thr | Ser | Asp | Tyr | Ser | Lys | Tyr | Leu | Asp | Ser |
| 39 | 39 | G | His | Ser | Gln | Gly | Thr | Phe | Thr | Ser | Asp | Tyr | Ser | His | Tyr | Leu | Asp | Ser |
| 40 | 40 | G | His | Ser | Gln | Gly | Thr | Phe | Thr | Ser | Asp | Tyr | Ser | Lys | Tyr | Leu | Asp | Ser |
| 41 | 41 | G | His | Ser | Gln | Gly | Thr | Phe | Thr | Ser | Asp | Tyr | Ser | Lys | Tyr | Leu | Asp | Ser |
| 42 | 42 | G | His | Ser | Gln | Gly | Thr | Phe | Thr | Ser | Asp | Tyr | Ser | His | Tyr | Leu | Asp | Ser |
| 43 | 43 | G | His | Ser | Gln | Gly | Thr | Phe | Thr | Ser | Asp | Tyr | Ser | His | Tyr | Leu | Asp | Ser |
| 44 | 44 | G | His | Ser | Gln | Gly | Thr | Phe | Thr | Ser | Asp | Tyr | Ser | His | Tyr | Leu | Asp | Ser |
| 45 | 45 | G | His | Ser | Gln | Gly | Thr | Phe | Thr | Ser | Asp | Tyr | Ser | Lys | Tyr | Leu | Glu | Ser |
| 46 | 46 | G | His | Ser | Gln | Gly | Thr | Phe | Thr | Ser | Asp | Tyr | Ser | Lys | Tyr | Leu | Glu | Ser |
| 47 | 47 | G | His | Ser | Gln | Gly | Thr | Phe | Thr | Ser | Asp | Tyr | Ser | His | Tyr | Leu | Glu | Ser |
| 48 | 48 | G | His | Ser | Gln | Gly | Thr | Phe | Thr | Ser | Asp | Tyr | Ser | His | Tyr | Leu | Asp | Ser |
| 49 | 49 | G | His | Ser | Gln | Gly | Thr | Phe | Thr | Ser | Asp | Tyr | Ser | His | Tyr | Leu | Asp | Ser |
| 50 | 50 | G | His | Ser | Gln | Gly | Thr | Phe | Thr | Ser | Asp | Tyr | Ser | His | Tyr | Leu | Asp | Ser |

Fig. 1

| SEQ ID NO. | Analogue no. | G no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 1 | 1 | G | Lys | Lys | Ala | Gln | Glu | Phe | Ile | Glu | Trp | Leu | Leu | Asn | Gly | Gly | His | NH2 | |
| 2 | 2 | G | Arg | Arg | Ala | Gln | Asp | Phe | Val | Gln | Trp | Leu | Leu | Asn | Gly | His | NH2 | | |
| 3 | 3 | G | Arg | Arg | Ala | His | Asp | Phe | Val | Gln | Trp | Leu | Leu | Asn | Thr | His | NH2 | | |
| 4 | 4 | G | Arg | Arg | Ala | Gln | Asp | Phe | Val | Gln | Trp | Leu | Leu | Asn | Thr | His | NH2 | | |
| 5 | 5 | G | Lys | Lys | Ala | Gln | Glu | Phe | Val | Gln | Trp | Leu | Leu | Asn | Thr | His | NH2 | | |
| 6 | 6 | G | Arg | Arg | Ala | Gln | Asp | Phe | Val | Gln | Trp | Leu | Leu | Asn | Thr | His | NH2 | | |
| 7 | 7 | G | Lys | Lys | Ala | Gln | Asp | Phe | Val | Gln | Trp | Leu | Leu | Asn | Thr | His | NH2 | | |
| 8 | 8 | G | His | Arg | Ala | Gln | Glu | Phe | Val | Gln | Trp | Leu | Leu | Asn | Gly | His | His | NH2 | |
| 9 | 9 | G | Arg | Arg | Ala | His | Asp | Phe | Val | Gln | Trp | Leu | Leu | Asn | Thr | His | His | NH2 | |
| 10 | 10 | G | Arg | Arg | Ala | His | His | Phe | Val | Gln | Trp | Leu | Leu | Asn | Thr | His | NH2 | | |
| 11 | 11 | G | Arg | Arg | Ala | Gln | His | Phe | Val | Gln | Trp | Leu | Leu | Asn | Thr | His | NH2 | | |
| 12 | 12 | G | Arg | Arg | Ala | His | Glu | Phe | Val | Gln | Trp | Leu | Leu | Asn | Thr | His | NH2 | | |
| 13 | 13 | G | Arg | Arg | Ala | His | Asp | Phe | Val | Gln | Trp | Leu | Leu | Asn | Gly | His | His | NH2 | |
| 14 | 14 | G | Arg | Arg | Ala | His | Glu | Phe | Val | Gln | Trp | Leu | Leu | Asn | Thr | His | His | NH2 | |
| 15 | 15 | G | Arg | Arg | Ala | His | Asp | Phe | Val | Gln | Trp | Leu | Leu | Asn | Thr | His | His | NH2 | |
| 16 | 16 | G | Arg | Arg | Ala | His | Glu | Phe | Val | Gln | Trp | Leu | Leu | Asn | Gly | His | His | NH2 | |
| 17 | 17 | G | Arg | Arg | Ala | His | Glu | Phe | Val | Gln | Trp | Leu | Leu | Asn | Gly | Gly | His | NH2 | |
| 18 | 18 | G | Lys | Lys | Ala | His | Glu | Phe | Val | Gln | Trp | Leu | Leu | Asn | Thr | His | His | NH2 | |
| 19 | 19 | G | Arg | Arg | Ala | His | Asp | Phe | Val | Gln | Trp | Leu | Leu | Asn | Thr | His | His | NH2 | NH2 |
| 20 | 20 | G | Arg | Arg | Ala | His | Asp | Phe | Val | Gln | Trp | Leu | Leu | Asn | Thr | His | NH2 | | |
| 21 | 21 | G | Arg | Arg | Ala | His | Ala | Phe | Val | Glu | Trp | Leu | Leu | Asn | Thr | His | NH2 | | |
| 22 | 22 | G | Arg | Arg | Ala | His | Asp | Phe | Val | Gln | Trp | Leu | Leu | Asn | Thr | His | NH2 | | |
| 23 | 23 | G | Arg | Arg | Ala | His | Asp | Phe | Val | Gln | Trp | Leu | Leu | Asn | Thr | His | NH2 | | |
| 24 | 24 | G | Lys | Arg | Ala | His | Glu | Phe | Val | Gln | Trp | Leu | Leu | Asn | Thr | His | NH2 | | |
| 25 | 25 | G | Arg | Arg | Ala | His | Glu | Phe | Val | Glu | Trp | Leu | Leu | Asn | Thr | His | NH2 | | |
| 26 | 26 | G | Arg | Arg | Ala | His | Glu | Phe | Val | Gln | Trp | Leu | Leu | Asn | Thr | His | His | | |
| 27 | 27 | G | Arg | Arg | Ala | His | Asp | Phe | Val | Gln | Trp | Leu | Leu | Asn | Thr | His | His | NH2 | |
| 28 | 28 | G | Arg | Arg | Ala | His | Glu | Phe | Val | Glu | Trp | Leu | Leu | Asn | Thr | His | | | |
| 29 | 29 | G | Arg | Arg | Ala | His | Glu | Phe | Val | Gln | Trp | Leu | Leu | Asn | Thr | His | His | NH2 | |
| 30 | 30 | G | Arg | Arg | Ala | His | Gly | Phe | Val | Gln | Trp | Leu | Leu | Asn | Thr | His | His | | |
| 31 | 31 | G | Arg | Arg | Ala | Gln | Gly | Phe | Val | Glu | Trp | Leu | Leu | Asn | Thr | Gly | His | His | |
| 32 | 32 | G | Arg | Arg | Ala | His | Glu | Phe | Val | Gln | Trp | Leu | Leu | Asn | Thr | Gly | His | His | |
| 33 | 33 | G | Arg | Arg | Ala | His | Glu | Phe | Val | Gln | Trp | Leu | Leu | Asn | Thr | Gly | NH2 | | |
| 34 | 34 | G | Arg | Lys | Ala | His | Gly | Phe | Val | Gln | Trp | Leu | Leu | Asn | Thr | Gly | His | His | |
| 35 | 35 | G | Arg | Arg | Ala | Gln | Gly | Phe | Val | Gln | Trp | Leu | Leu | Asn | Thr | Gly | His | His | |
| 36 | 36 | G | Arg | Arg | Ala | His | Asp | Phe | Ile | Gln | Trp | Leu | Leu | Asn | Thr | His | His | His | |
| 37 | 37 | G | Arg | Arg | Ala | His | Glu | Phe | Val | Gln | Trp | Leu | Leu | Asn | Thr | His | His | His | |
| 38 | 38 | G | Arg | Arg | Ala | His | Glu | Phe | Val | Gln | Trp | Leu | Leu | Asn | Thr | His | His | NH2 | |
| 39 | 39 | G | Arg | Arg | Ala | His | Glu | Phe | Val | Gln | Trp | Leu | Leu | Asn | Thr | His | His | NH2 | |
| 40 | 40 | G | Arg | Arg | Ala | Gln | Asp | Phe | Ile | Gln | Trp | Leu | Leu | Asn | Thr | His | NH2 | | |
| 41 | 41 | G | Arg | Arg | Ala | His | Glu | Phe | Val | Gln | Trp | Leu | Leu | Asn | Thr | His | His | His | |
| 42 | 42 | G | Arg | Arg | Ala | His | Asp | Phe | Ile | Gln | Trp | Leu | Leu | Asn | Thr | His | His | NH2 | |
| 43 | 43 | G | Arg | Arg | Ala | His | Glu | Phe | Val | Gln | Trp | Leu | Leu | Asn | Thr | His | NH2 | | |
| 44 | 44 | G | Lys | Lys | Ala | His | Asp | Phe | Val | Gln | Trp | Leu | Leu | Asn | Thr | His | NH2 | | |
| 45 | 45 | G | Lys | Lys | Ala | Gln | Asp | Phe | Val | Gln | Trp | Leu | Leu | Asn | Thr | His | His | NH2 | |
| 46 | 46 | G | Lys | Lys | Ala | His | Glu | Phe | Val | Gln | Trp | Leu | Leu | Asn | Gly | His | His | | |
| 47 | 47 | G | Lys | Lys | Ala | His | Glu | Phe | Val | Gln | Trp | Leu | Leu | Asn | Thr | His | NH2 | | |
| 48 | 48 | G | Arg | Arg | Ala | His | Glu | Phe | Ile | Gln | Trp | Leu | Leu | Asn | Thr | His | NH2 | | |
| 49 | 49 | G | Arg | Arg | Ala | His | Glu | Phe | Val | Gln | Trp | Leu | Leu | Asn | Gly | Gly | His | | |
| 50 | 50 | G | Arg | Arg | Ala | His | Glu | Phe | Val | Gln | Trp | Leu | Leu | Asn | Gly | Gly | NH2 | | |

Fig. 1 (continued)

| SEQ ID NO. | Analogue no. | G no. | n | hGCGr cAMP vs hGCG | n | hGLP-1r cAMP vs hGLP-1 | 0-1 | 0-4 | 0-8 | Mouse food intake inhibition (500 nmol/kg) 4-8 | 8-24 | 24-32 | 0-24 | 0-1 | 0-4 | 0-8 | 4-8 | 8-24 | Rat food intake inhibition (500 nmol/kg with 1:1 Zn) 24-32 | 32-48 | 48-72 | 0-24 | 0-48 | 0-72 |
|---|---|---|---|---|---|---|---|---|---|---|---|---|---|---|---|---|---|---|---|---|---|---|---|---|
| 1 | 1 | G | 2 | 1.4 | 1 | 10.6 | 99 | 69 | 37 | -38 | -21 | | 1 | 66 | 47 | 29 | -23 | -24 | -5 | -16 | -10 | 1 | -6 | -7 |
| 2 | 2 | G | 2 | 0.9 | | | 78 | 10 | 1 | -14 | -5 | | -3 | | | | | | | | | | | |
| 3 | 3 | G | 4 | 1.0 | 2 | 5.9 | 96 | 62 | 9 | -83 | -14 | | -5 | | | | | | | | | | | |
| 4 | 4 | G | 3 | 3.2 | 1 | 2.6 | 93 | 37 | 24 | -1 | 4 | | 10 | | | | | | | | | | | |
| 5 | 5 | G | 3 | 4.5 | | | | | | | | | | | | | | | | | | | | |
| 6 | 6 | G | 2 | 2.1 | | | | | | | | | | | | | | | | | | | | |
| 7 | 7 | G | 2 | 50.6 | | | | | | | | | | | | | | | | | | | | |
| 8 | 8 | G | 3 | 2.2 | | | 97 | 27 | 4 | -41 | 11 | | 9 | | | | | | | | | | | |
| 9 | 9 | G | 2 | 3.2 | | | | | | | | | | | | | | | | | | | | |
| 10 | 10 | G | 2 | 2.3 | | | | | | | | | | | | | | | | | | | | |
| 11 | 11 | G | 2 | 11.4 | | | | | | | | | | | | | | | | | | | | |
| 12 | 12 | G | 2 | 2.3 | 2 | 3.0 | | | | | | | | | | | | | | | | | | |
| 13 | 13 | G | 2 | 1.8 | | | | | | | | | | | | | | | | | | | | |
| 14 | 14 | G | 7 | 3.3 | 7 | 26.4 | 98.5 | 59.5 | 21.5 | -33.5 | -7 | | 2 | -13 | -5 | 12 | 56 | 7 | 41 | -2 | 7 | 9 | 10 | 9 |
| 15 | 15 | G | 4 | 0.9 | 2 | 4.9 | 93 | 65 | 12 | -91 | 7 | | 9 | | | | | | | | | | | |
| 16 | 16 | G | 2 | 5.8 | 1 | 1.0 | | | | | | | | | | | | | | | | | | |
| 17 | 17 | G | 2 | 1.6 | | | | | | | | | | | | | | | | | | | | |
| 18 | 18 | G | 2 | 2.5 | | | | | | | | | | | | | | | | | | | | |
| 19 | 19 | G | 2 | 2.3 | | | | | | | | | | | | | | | | | | | | |
| 20 | 20 | G | 2 | 4.4 | | | | | | | | | | | | | | | | | | | | |
| 21 | 21 | G | 3 | 3.3 | 3 | 5.8 | | | | | | | | | | | | | | | | | | |
| 22 | 22 | G | 2 | 9.5 | | | 95 | 65 | 12 | -91 | -5 | | 1 | | | | | | | | | | | |
| 23 | 23 | G | 2 | 2.4 | | | | | | | | | | | | | | | | | | | | |
| 24 | 24 | G | 2 | 3.2 | | | | | | | | | | | | | | | | | | | | |
| 25 | 25 | G | 2 | 2.4 | | | | | | | | | | | | | | | | | | | | |
| 26 | 26 | G | 3 | 4.3 | 1 | 2.6 | | | | | | | | | | | | | | | | | | |
| 27 | 27 | G | 2 | 9.9 | | | | | | | | | | | | | | | | | | | | |
| 28 | 28 | G | 2 | 2.2 | | | | | | | | | | | | | | | | | | | | |
| 29 | 29 | G | 3 | 4.3 | | | | | | | | | | | | | | | | | | | | |
| 30 | 30 | G | 7 | 0.8 | 5 | 19.4 | 97.5 | 11.5 | -6 | -31.5 | 7 | | 2 | 1 | -7 | -1 | 13 | 51 | 83 | 19 | -5 | 30 | 33 | 21 |
| 31 | 31 | G | 3 | 1.7 | | | | | | | | | | | | | | | | | | | | |
| 32 | 32 | G | 7 | 2.2 | 5 | 27.6 | 93.5 | 78.5 | 47.5 | 3 | -11 | | 9 | | | | | | | | | | | |
| 33 | 33 | G | 2 | 0.6 | | | | | | | | | | | | | | | | | | | | |
| 34 | 34 | G | 3 | 0.4 | | | | | | | | | | | | | | | | | | | | |
| 35 | 35 | G | 4 | 1.4 | | | | | | | | | | | | | | | | | | | | |
| 36 | 36 | G | 2 | 1.1 | 1 | 371.5 | | | | | | | | | | | | | | | | | | |
| 37 | 37 | G | 4 | 0.8 | 2 | 1.9 | | | | | | | | | | | | | | | | | | |
| 38 | 38 | G | 7 | 0.2 | 5 | 4.7 | 99.5 | 38.5 | 17 | -14 | 1.5 | | 6.5 | -10 | -1 | 14 | 52 | 84 | 88 | 23 | -3 | 55 | 49 | 33 |
| 39 | 39 | G | 3 | 0.4 | 2 | 5.3 | 35 | -5 | -5 | -7 | 7 | | 4 | | | | | | | | | | | |
| 40 | 40 | G | 2 | 4.9 | | | | | | | | | | | | | | | | | | | | |
| 41 | 41 | G | 2 | 6.1 | | | | | | | | | | | | | | | | | | | | |
| 42 | 42 | G | 2 | 32.6 | | | | | | | | | | | | | | | | | | | | |
| 43 | 43 | G | 4 | 2.1 | | | | | | | | | | | | | | | | | | | | |
| 44 | 44 | G | 2 | 1.2 | | | | | | | | | | | | | | | | | | | | |
| 45 | 45 | G | 2 | 1.2 | | | | | | | | | | | | | | | | | | | | |
| 46 | 46 | G | 1 | 4.1 | | | | | | | | | | | | | | | | | | | | |
| 47 | 47 | G | 2 | 2.4 | | | | | | | | | | | | | | | | | | | | |
| 48 | 48 | G | 3 | 6.0 | | | | | | | | | | | | | | | | | | | | |
| 49 | 49 | G | 2 | 0.7 | | | | | | | | | | | | | | | | | | | | |
| 50 | 50 | G | 3 | 2.0 | | | | | | | | | | | | | | | | | | | | |

Fig. 1 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 51 | 51 | G | 1139 | His | Ser | Gln | Gly | Thr | Phe | Thr | Ser | Asp | Tyr | Ser | His | Tyr | Leu | Asp | Ser |
| 52 | 52 | G | 1140 | His | Ser | Gln | Gly | Thr | Phe | Thr | Ser | Asp | Tyr | Ser | His | Tyr | Leu | Glu | Ser |
| 53 | 53 | G | 1141 | His | Ser | Gln | Gly | Thr | Phe | Thr | Ser | Asp | Tyr | Ser | His | Tyr | Leu | Glu | Ser |
| 54 | 54 | G | 1155 | His | Ser | Gln | Gly | Thr | Phe | Thr | Ser | Asp | Tyr | Ser | His | Tyr | Leu | Asp | Ser |
| 55 | 55 | G | 1156 | His | Ser | Gln | Gly | Thr | Phe | Thr | Ser | Asp | Tyr | Ser | His | Tyr | Leu | Glu | Ser |
| 56 | 56 | G | 1157 | His | Ser | Gln | Gly | Thr | Phe | Thr | Ser | Asp | Tyr | Ser | His | Tyr | Leu | Asp | Ser |
| 57 | 57 | G | 1163 | His | Ser | Gln | Gly | Thr | Phe | Thr | Ser | Asp | Tyr | Ser | His | Tyr | Leu | Asp | Ser |
| 58 | 58 | G | 1164 | His | Ser | Gln | Gly | Thr | Phe | Thr | Ser | Asp | Tyr | Ser | His | Tyr | Leu | Asp | Ser |
| 59 | 59 | G | 1165 | His | Ser | Gln | Gly | Thr | Phe | Thr | Ser | Asp | Tyr | Ser | His | Tyr | Leu | Asp | Glu |
| 60 | 60 | G | 1166 | His | Ser | Gln | Gly | Thr | Phe | Thr | Ser | Asp | Tyr | Ser | Lys | Tyr | Leu | Asp | Glu |
| 61 | 61 | G | 1167 | His | Ser | Gln | Gly | Thr | Phe | Thr | Ser | Asp | Tyr | Ser | Lys | Tyr | Leu | Asp | Glu |
| 62 | 62 | G | 1168 | His | Ser | Gln | Gly | Thr | Phe | Thr | Ser | Asp | Tyr | Ser | Lys | Tyr | Leu | Asp | Glu |
| 63 | 63 | G | 1169 | His | Ser | Gln | Gly | Thr | Phe | Thr | Ser | Asp | Tyr | Ser | His | Tyr | Leu | Asp | Ser |
| 64 | 64 | G | 1170 | His | Ser | Gln | Gly | Thr | Phe | Thr | Ser | Asp | Tyr | Ser | His | Tyr | Leu | Asp | Ser |
| 65 | 65 | G | 1171 | His | Ser | Gln | Gly | Thr | Phe | Thr | Ser | Asp | Tyr | Ser | His | Tyr | Leu | Asp | Ser |
| 66 | 66 | G | 1194 | His | Ser | Gln | Gly | Thr | Phe | Thr | Ser | Asp | Tyr | Ser | His | Tyr | Leu | Asp | Ser |
| 67 | 67 | G | 1195 | His | Ser | Gln | Gly | Thr | Phe | Thr | Ser | Asp | Tyr | Ser | His | Tyr | Leu | Asp | Ser |
| 68 | 68 | G | 1196 | His | Ser | Gln | Gly | Thr | Phe | Thr | Ser | Asp | Tyr | Ser | His | Tyr | Leu | Asp | Ser |
| 69 | 69 | G | 1197 | His | Ser | Gln | Gly | Thr | Phe | Thr | Ser | Asp | Tyr | Ser | His | Tyr | Leu | Asp | Ser |
| 70 | 70 | G | 1198 | His | Ser | Gln | Gly | Thr | Phe | Thr | Ser | Asp | Leu | Ser | His | Tyr | Leu | Asp | Ser |
| 71 | 71 | G | 1199 | His | Ser | Gln | Gly | Thr | Phe | Thr | Ser | Asp | Leu | Ser | His | Tyr | Leu | Asp | Ser |
| 72 | 72 | G | 1200 | His | Ser | Gln | Gly | Thr | Phe | Thr | Ser | Asp | Tyr | Ser | His | Gln | Leu | Asp | Ser |
| 73 | 73 | G | 1201 | His | Ser | Gln | Gly | Thr | Phe | Thr | Ser | Asp | Tyr | Ser | His | Tyr | Leu | Asp | Ser |
| 74 | 74 | G | 1202 | His | Ser | Gln | Gly | Thr | Phe | Thr | Ser | Asp | Tyr | Ser | His | Tyr | Leu | Asp | Ser |
| 75 | 75 | G | 1204 | His | Ser | Gln | Gly | Thr | Phe | Thr | Ser | Asp | Tyr | Ser | His | Tyr | Leu | Asp | Ser |
| 76 | 76 | G | 1209 | His | Ser | Gln | Gly | Thr | Phe | Thr | Ser | Asp | Tyr | Ser | His | Tyr | Leu | Asp | Ser |
| 77 | 77 | G | 1210 | His | Ser | Gln | Gly | Thr | Phe | Thr | Ser | Asp | Tyr | Ser | Lys | Tyr | Leu | Asp | Ser |
| 78 | 78 | G | 1211 | His | Ser | Gln | Gly | Thr | Phe | Thr | Ser | Asp | Tyr | Ser | Lys | Tyr | Leu | Asp | Ser |
| 79 | 79 | G | 1212 | His | Ser | Gln | Gly | Thr | Phe | Thr | Ser | Asp | Tyr | Ser | Lys | Tyr | Leu | Asp | Ser |
| 80 | 80 | G | 1213 | His | Ser | Gln | Gly | Thr | Phe | Thr | Ser | Asp | Tyr | Ser | Arg | Tyr | Leu | Asp | Ser |
| 81 | 81 | G | 1214 | His | Ser | Gln | Gly | Thr | Phe | Thr | Ser | Asp | Tyr | Ser | Arg | Tyr | Leu | Asp | Ser |
| 82 | 82 | G | 1215 | His | Ser | Gln | Gly | Thr | Phe | Thr | Ser | Asp | Tyr | Ser | Arg | Tyr | Leu | Asp | Ser |
| 83 | 83 | G | 1216 | His | Ser | Gln | Gly | Thr | Phe | Thr | Ser | Asp | Tyr | Ser | Lys | Tyr | Leu | Asp | Ser |
| 84 | 84 | G | 1224 | His | Ser | Gln | Gly | Thr | Phe | Thr | Ser | Asp | Tyr | Ser | Lys | Tyr | Leu | Asp | Ser |
| 85 | 85 | G | 1225 | His | Ser | Gln | Gly | Thr | Phe | Thr | Ser | Asp | Tyr | Ser | Lys | Tyr | Leu | Asp | Ser |
| 86 | 86 | G | 1226 | His | Ser | Gln | Gly | Thr | Phe | Thr | Ser | Asp | Tyr | Ser | Lys | Tyr | Leu | Asp | Ser |
| 87 | 87 | G | 1227 | His | Ser | Gln | Gly | Thr | Phe | Thr | Ser | Asp | Tyr | Ser | His | Tyr | Leu | Asp | Ser |
| 88 | 88 | G | 1228 | His | Ser | Gln | Gly | Thr | Phe | Thr | Ser | Asp | Tyr | Ser | Lys | His | Leu | Asp | Ser |
| 89 | 89 | G | 1229 | His | Ser | Gln | Gly | Thr | Phe | Thr | Ser | Asp | Tyr | Ser | Lys | His | Leu | Asp | Ser |
| 90 | 90 | G | 1230 | His | Ser | Gln | Gly | Thr | Phe | Thr | Ser | Asp | Tyr | Ser | Lys | His | Leu | Asp | Ser |
| 91 | 91 | G | 1231 | His | Ser | Gln | Gly | Thr | Phe | Thr | Ser | Asp | Tyr | Ser | His | His | Leu | Asp | Ser |
| 92 | 92 | G | 1233 | His | Ser | Gln | Gly | Thr | Phe | Thr | Ser | Asp | Tyr | Ser | His | Tyr | Leu | Asp | Ser |
| 93 | 93 | G | 1240 | His | Ser | Gln | Gly | Thr | Phe | Thr | Ser | Asp | Leu | Ser | His | Tyr | Leu | Asp | Ser |
| 94 | 94 | G | 1242 | His | Ser | Gln | Gly | Thr | Phe | Thr | Ser | Asp | Tyr | Ser | Lys | Tyr | Leu | Glu | Ser |
| 95 | 95 | G | 1243 | His | Ser | Gln | Gly | Thr | Phe | Thr | Ser | Asp | Tyr | Ser | Lys | His | Leu | Glu | Ser |
| 96 | 96 | G | 1244 | His | Ser | Gln | Gly | Thr | Phe | Thr | Ser | Asp | Tyr | Ser | Lys | His | Leu | Glu | Ser |
| 97 | 97 | G | 1245 | His | Ser | Gln | Gly | Thr | Phe | Thr | Ser | Asp | Tyr | Ser | His | His | Leu | Asp | Ser |
| 98 | 98 | G | 1246 | His | Ser | Gln | Gly | Thr | Phe | Thr | Ser | Asp | Tyr | Ser | Arg | Tyr | Leu | Glu | Ser |
| 99 | 99 | G | 1268 | His | Ser | Gln | Gly | Thr | Phe | Thr | Ser | Asp | Tyr | Ser | His | Tyr | Leu | Glu | Ser |
| 100 | 100 | G | 1269 | His | Ser | Gln | Gly | Thr | Phe | Thr | Ser | Asp | Tyr | Ser | Lys | Tyr | Leu | Glu | Ser |

Fig. 1 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 51 | 51 | G | 1139 | Lys | Lys | Ala | His | Glu | Phe | Val | Glu | Trp | Leu | Leu | Asn | Gly | Gly | His | | |
| 52 | 52 | G | 1140 | Arg | Arg | Ala | His | Glu | Phe | Val | Gln | Trp | Leu | Leu | Asn | Gly | Gly | His | | |
| 53 | 53 | G | 1141 | Lys | Lys | Ala | His | Glu | Phe | Val | Glu | Trp | Leu | Leu | Asn | Gly | Gly | His | | |
| 54 | 54 | G | 1155 | Arg | Arg | Ala | His | Glu | Phe | Val | Glu | Trp | Leu | Leu | Asn | Thr | His | NH2 | | |
| 55 | 55 | G | 1156 | Arg | Arg | Ala | His | Glu | Phe | Val | Glu | Trp | Leu | Leu | Asn | Gly | His | NH2 | | |
| 56 | 56 | G | 1157 | Arg | Arg | Ala | His | Glu | Phe | Val | Glu | Trp | Leu | Leu | Asn | Gly | His | His | | |
| 57 | 57 | G | 1163 | Arg | Arg | Ala | His | Glu | Phe | Val | Glu | Trp | Leu | Leu | Asn | Gly | His | | | |
| 58 | 58 | G | 1164 | Lys | Arg | Ala | His | Glu | Phe | Val | Gln | Trp | Leu | Leu | Asn | Gly | His | NH2 | | |
| 59 | 59 | G | 1165 | Lys | Lys | Ala | His | Glu | Phe | Val | Glu | Trp | Leu | Leu | Asn | Gly | His | His | | |
| 60 | 60 | G | 1166 | Arg | Arg | Ala | His | Asp | Phe | Val | Gln | Trp | Leu | Leu | Asn | Gly | His | NH2 | | |
| 61 | 61 | G | 1167 | Arg | Arg | Ala | His | Glu | Phe | Val | Gln | Trp | Leu | Leu | Asn | Thr | His | NH2 | | |
| 62 | 62 | G | 1168 | Arg | Arg | Ala | His | Asp | Phe | Val | Glu | Trp | Leu | Leu | Asn | Gly | His | NH2 | | |
| 63 | 63 | G | 1169 | Lys | Arg | Ala | His | Glu | Phe | Val | Gln | Trp | Leu | Leu | Asn | Gly | His | NH2 | | |
| 64 | 64 | G | 1170 | Arg | Arg | Ala | His | Asp | Phe | Ile | Gln | Trp | Leu | Leu | Asn | Gly | His | His | | |
| 65 | 65 | G | 1171 | Arg | Arg | Ala | His | Glu | Phe | Val | Gln | Trp | Leu | Leu | Asn | Gly | His | His | | |
| 66 | 66 | G | 1194 | Lys | Lys | Ala | His | Glu | Phe | Val | Gln | Trp | Leu | Leu | Asn | Gly | His | His | | |
| 67 | 67 | G | 1195 | Arg | Arg | Ala | His | Asp | Phe | Val | Glu | Trp | Leu | Leu | Asn | Thr | His | NH2 | | |
| 68 | 68 | G | 1196 | Arg | Arg | Ala | His | Glu | Phe | Val | Gln | Trp | Leu | Leu | Asn | Gly | His | | | |
| 69 | 69 | G | 1197 | Arg | Arg | Ala | His | Asp | Phe | Val | Glu | Trp | Leu | Leu | Asn | Thr | His | NH2 | | |
| 70 | 70 | G | 1198 | Arg | Arg | Ala | His | Asp | Phe | Val | Glu | Trp | Leu | Leu | Asn | Thr | His | NH2 | | |
| 71 | 71 | G | 1199 | Lys | Arg | Ala | His | Asp | Phe | Val | Glu | Trp | Leu | Leu | Asn | Gly | His | NH2 | | |
| 72 | 72 | G | 1200 | Lys | Arg | Ala | His | Asp | Phe | Val | Gln | Trp | Leu | Leu | Asn | Thr | His | NH2 | | |
| 73 | 73 | G | 1201 | Lys | Arg | Ala | His | Asp | Phe | Val | Gln | Trp | Leu | Leu | Asn | Gly | His | His | | |
| 74 | 74 | G | 1202 | Lys | Arg | Ala | His | Asp | Phe | Ile | Glu | Trp | Leu | Leu | Asn | Thr | His | NH2 | | |
| 75 | 75 | G | 1204 | Lys | Arg | Ala | His | Asp | Phe | Ile | Gln | Trp | Leu | Leu | Asn | Gly | His | His | | |
| 76 | 76 | G | 1209 | Arg | Arg | Ala | His | Asp | Phe | Val | Glu | Trp | Leu | Leu | Asn | Thr | His | NH2 | | |
| 77 | 77 | G | 1210 | Lys | Arg | Ala | His | Glu | Phe | Val | Glu | Trp | Leu | Leu | Asn | Gly | His | NH2 | | |
| 78 | 78 | G | 1211 | Lys | Arg | Ala | His | Glu | Phe | Val | Glu | Trp | Leu | Leu | Asn | Thr | His | NH2 | | |
| 79 | 79 | G | 1212 | Arg | Arg | Ala | His | Glu | Phe | Val | Glu | Trp | Leu | Leu | Asn | Gly | Gly | His | | |
| 80 | 80 | G | 1213 | Lys | Arg | Ala | His | Glu | Phe | Val | Gln | Trp | Leu | Leu | Asn | Gly | Gly | His | | |
| 81 | 81 | G | 1214 | Arg | Arg | Ala | His | Glu | Phe | Val | Glu | Trp | Leu | Leu | Asn | Thr | Gly | His | | |
| 82 | 82 | G | 1215 | Lys | Lys | Ala | His | Glu | Phe | Val | Glu | Trp | Leu | Leu | Asn | Gly | Gly | His | | |
| 83 | 83 | G | 1216 | Lys | Lys | Ala | His | Glu | Phe | Val | Glu | Trp | Leu | Leu | Asn | Gly | His | His | | |
| 84 | 84 | G | 1224 | Arg | Arg | Ala | His | Glu | Phe | Val | Glu | Trp | Leu | Leu | Asn | Gly | Gly | His | NH2 | |
| 85 | 85 | G | 1225 | Arg | Arg | Ala | His | Glu | Phe | Val | Gln | Trp | Leu | Leu | Asn | Gly | Gly | His | NH2 | |
| 86 | 86 | G | 1226 | Arg | Arg | Ala | His | Glu | Phe | Val | Gln | Trp | Leu | Leu | Asn | Thr | Gly | His | NH2 | |
| 87 | 87 | G | 1227 | Arg | Arg | Ala | His | Glu | Phe | Val | Gln | Trp | Leu | Leu | Asn | Thr | His | His | NH2 | |
| 88 | 88 | G | 1228 | Lys | Arg | Ala | His | Glu | Phe | Val | Gln | Trp | Leu | Leu | Asn | Gly | Gly | His | NH2 | |
| 89 | 89 | G | 1229 | Arg | Arg | Ala | His | Glu | Phe | Val | Gln | Trp | Leu | Leu | Asn | Thr | Gly | His | | |
| 90 | 90 | G | 1230 | Lys | Arg | Ala | His | Glu | Phe | Val | Gln | Trp | Leu | Leu | Asn | Thr | Gly | His | | |
| 91 | 91 | G | 1231 | Lys | Arg | Ala | His | Glu | Phe | Val | Gln | Trp | Leu | Leu | Asn | Thr | His | His | | |
| 92 | 92 | G | 1233 | Lys | Arg | Ala | His | Glu | Phe | Val | Gln | Trp | Leu | Leu | Asn | Thr | Gly | His | NH2 | |
| 93 | 93 | G | 1240 | Lys | Arg | Ala | His | Glu | Phe | Val | Glu | Trp | Leu | Leu | Asn | Thr | His | NH2 | | |
| 94 | 94 | G | 1242 | Arg | Arg | Ala | His | Glu | Phe | Val | Glu | Trp | Leu | Leu | Asn | Thr | Gly | His | | |
| 95 | 95 | G | 1243 | Arg | Arg | Ala | His | Glu | Phe | Ile | Glu | Trp | Leu | Leu | Asn | Thr | Gly | His | | |
| 96 | 96 | G | 1244 | Arg | Arg | Ala | His | Glu | Phe | Ile | Glu | Trp | Leu | Leu | Asn | Gly | Gly | His | | |
| 97 | 97 | G | 1245 | Arg | Arg | Ala | His | Glu | Phe | Ile | Glu | Trp | Leu | Leu | Asn | Thr | Gly | His | | |
| 98 | 98 | G | 1246 | Arg | Arg | Ala | His | Glu | Phe | Val | Glu | Trp | Leu | Leu | Asn | Thr | Gly | His | | |
| 99 | 99 | G | 1268 | Lys | Lys | Ala | His | Glu | Phe | Ile | Glu | Trp | Leu | Leu | Asn | Thr | Gly | His | | |
| 100 | 100 | G | 1269 | Lys | Arg | Ala | His | Glu | Phe | Ile | Glu | Trp | Leu | Leu | Asn | Thr | Gly | His | | |

Fig. 1 (continued)

| SEQ ID NO. | Analogue no. | G no. | | hGCGr cAMP vs hGCG | hGLP-1r cAMP vs hGLP-1 | Mouse food intake inhibition (500nmol/kg) | | | | | | | Rat food intake inhibition (500 nmol/kg with 1:1 Zn) | | | | | | |
|---|---|---|---|---|---|---|---|---|---|---|---|---|---|---|---|---|---|---|---|
| | | | n | | | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 51 | 51 | G | 1139 | 2 | 1.2 | | | | | | | | | | | | | | | | | | |
| 52 | 52 | G | 1140 | 1 | 3.3 | 80 | 34 | 24 | 1 | 16 | | 19 | -19 | 8 | 7 | 2 | -2 | | 4 | -3 | 7 | 2 | 1 | 3 |
| 53 | 53 | G | 1141 | 1 | 2.2 | | | | | | | | | | | | | | | | | | |
| 54 | 54 | G | 1155 | 2 | 1.5 | | | | | | | | | | | | | | | | | | |
| 55 | 55 | G | 1156 | 1 | 2.2 | | | | | | | | | | | | | | | | | | |
| 56 | 56 | G | 1157 | 2 | 1.4 | | | | | | | | | | | | | | | | | | |
| 57 | 57 | G | 1163 | 3 | 2.3 | | | | | | | | | | | | | | | | | | |
| 58 | 58 | G | 1164 | 1 | 2.9 | | | | | | | | | | | | | | | | | | |
| 59 | 59 | G | 1165 | 2 | 0.6 | | | | | | | | | | | | | | | | | | |
| 60 | 60 | G | 1166 | 3 | 2.2 | | | | | | | | | | | | | | | | | | |
| 61 | 61 | G | 1167 | 5 | 0.8 | 85 | 50 | 7 | -66 | -11 | | -4 | -10 | 3 | 8 | 21 | 73 | | 94 | 27 | 30 | 46 | 46 | 41 |
| 62 | 62 | G | 1168 | 4 | 0.7 | 96 | 36 | 6 | -52 | -4 | | 1 | | | | | | | | | | | | |
| 63 | 63 | G | 1169 | 3 | 1.0 | | | | | | | | | | | | | | | | | | |
| 64 | 64 | G | 1170 | 3 | 1.0 | 69 | 20 | -4 | -45 | -8 | | -7 | | | | | | | | | | | | |
| 65 | 65 | G | 1171 | 2 | 0.7 | | | | | | | | | | | | | | | | | | |
| 66 | 66 | G | 1194 | 3 | 0.8 | | | | | | | | | | | | | | | | | | |
| 67 | 67 | G | 1195 | 2 | 1.6 | | | | | | | | | | | | | | | | | | |
| 68 | 68 | G | 1196 | 2 | 4.3 | | | | | | | | | | | | | | | | | | |
| 69 | 69 | G | 1197 | 3 | 2.3 | | | | | | | | | | | | | | | | | | |
| 70 | 70 | G | 1198 | 1 | 10.3 | | | | | | | | | | | | | | | | | | |
| 71 | 71 | G | 1199 | 2 | 1.0 | | | | | | | | | | | | | | | | | | |
| 72 | 72 | G | 1200 | 4 | 10.6 | | | | | | | | | | | | | | | | | | |
| 73 | 73 | G | 1201 | 2 | 3.7 | | | | | | | | | | | | | | | | | | |
| 74 | 74 | G | 1202 | 1 | 4.6 | | | | | | | | | | | | | | | | | | |
| 75 | 75 | G | 1204 | 1 | 6.9 | | | | | | | | | | | | | | | | | | |
| 76 | 76 | G | 1209 | 1 | 6.5 | | | | | | | | | | | | | | | | | | |
| 77 | 77 | G | 1210 | 1 | 4.5 | | | | | | | | | | | | | | | | | | |
| 78 | 78 | G | 1211 | 2 | 0.7 | | | | | | | | | | | | | | | | | | |
| 79 | 79 | G | 1212 | 2 | 0.6 | | | | | | | | | | | | | | | | | | |
| 80 | 80 | G | 1213 | 2 | 0.6 | | | | | | | | | | | | | | | | | | |
| 81 | 81 | G | 1214 | 3 | 0.9 | | | | | | | | | | | | | | | | | | |
| 82 | 82 | G | 1215 | 2 | 2.2 | | | | | | | | | | | | | | | | | | |
| 83 | 83 | G | 1216 | 2 | 0.4 | | | | | | | | | | | | | | | | | | |
| 84 | 84 | G | 1224 | 4 | 1.0 | 87 | 9 | 2 | -12 | -13 | | -8 | | | | | | | | | | | | |
| 85 | 85 | G | 1225 | 5 | 1.1 | | | | | | | | | | | | | | | | | | |
| 86 | 86 | G | 1226 | 3 | 1.0 | | | | | | | | | | | | | | | | | | |
| 87 | 87 | G | 1227 | 2 | 1.2 | | | | | | | | | | | | | | | | | | |
| 88 | 88 | G | 1228 | 4 | 0.4 | | | | | | | | | | | | | | | | | | |
| 89 | 89 | G | 1229 | 2 | 1.4 | | | | | | | | | | | | | | | | | | |
| 90 | 90 | G | 1230 | 3 | 1.4 | | | | | | | | | | | | | | | | | | |
| 91 | 91 | G | 1231 | 1 | 8.7 | | | | | | | | | | | | | | | | | | |
| 92 | 92 | G | 1233 | 7 | 0.9 | 93 | 30 | 1 | -40 | -4 | | -3 | 19 | 48 | 40 | 5 | -3 | | -31 | -17 | -4 | 17 | 1 | -1 |
| 93 | 93 | G | 1240 | 4 | 3.0 | | | | | | | | | | | | | | | | | | |
| 94 | 94 | G | 1242 | 2 | 1.5 | | | | | | | | | | | | | | | | | | |
| 95 | 95 | G | 1243 | 1 | 3.1 | | | | | | | | | | | | | | | | | | |
| 96 | 96 | G | 1244 | 2 | 2.8 | | | | | | | | | | | | | | | | | | |
| 97 | 97 | G | 1245 | 1 | 4.0 | | | | | | | | | | | | | | | | | | |
| 98 | 98 | G | 1246 | 2 | 1.4 | | | | | | | | | | | | | | | | | | |
| 99 | 99 | G | 1268 | 2 | 2.6 | | | | | | | | | | | | | | | | | | |
| 100 | 100 | G | 1269 | 1 | 3.9 | | | | | | | | | | | | | | | | | | |

Fig. 1 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 101 | 101 | G | His | Ser | Gln | Gly | Thr | Phe | Thr | Ser | Asp | Tyr | Ser | Lys | Tyr | Leu | Glu | Ser |
| 102 | 102 | G | His | Ser | Gln | Gly | Thr | Phe | Thr | Ser | Asp | Tyr | Ser | His | Tyr | Leu | Glu | Ser |
| 103 | 103 | G | His | Ser | Gln | Gly | Thr | Phe | Thr | Ser | Asp | Tyr | Ser | Lys | His | Leu | Glu | Ser |
| 104 | 104 | G | His | Ser | Gln | Gly | Thr | Phe | Thr | Ser | Asp | Tyr | Ser | Lys | His | Leu | Glu | Ser |
| 105 | 105 | G | His | Ser | Gln | Gly | Thr | Phe | Thr | Ser | Asp | Tyr | Ser | Lys | His | Leu | Asp | Ser |
| 106 | 106 | G | His | Ser | Gln | Gly | Thr | Phe | Thr | Ser | Asp | Tyr | Ser | Lys | His | Leu | Glu | Glu |
| 107 | 107 | G | His | Ser | Gln | Gly | Thr | Phe | Thr | Ser | Asp | Tyr | Ser | Lys | His | Leu | Asp | Glu |
| 108 | 108 | G | His | Ser | Gln | Gly | Thr | Phe | Thr | Ser | Asp | Tyr | Ser | Lys | His | Leu | Glu | Glu |
| 109 | 109 | G | His | Ser | Gln | Gly | Thr | Phe | Thr | Ser | Asp | Tyr | Ser | Lys | His | Leu | Glu | Glu |
| 110 | 110 | G | His | Ser | Gln | Gly | Thr | Phe | Thr | Ser | Asp | Tyr | Ser | Lys | His | Leu | Asp | Ser |
| 111 | 111 | G | His | Ser | Gln | Gly | Thr | Phe | Thr | Ser | Asp | Tyr | Ser | Lys | His | Leu | Glu | Ser |
| 112 | 112 | G | His | Ser | Gln | Gly | Thr | Phe | Thr | Ser | Asp | Tyr | Ser | Lys | His | Leu | Glu | Ser |
| 113 | 113 | G | His | Ser | Gln | Gly | Thr | Phe | Thr | Ser | Asp | Tyr | Ser | Lys | His | Leu | Glu | Ser |
| 114 | 114 | G | His | Ser | Gln | Gly | Thr | Phe | Thr | Ser | Asp | Tyr | Ser | Lys | His | Leu | Glu | Ser |
| 115 | 115 | G | His | Ser | Gln | Gly | Thr | Phe | Thr | Ser | Asp | Tyr | Ser | Lys | Tyr | Leu | Asp | Ser |
| 116 | 116 | G | His | Ser | Gln | Gly | Thr | Phe | Thr | Ser | Asp | Tyr | Ser | Lys | Tyr | Leu | Asp | Ser |
| 117 | 117 | G | His | Ser | Gln | Gly | Thr | Phe | Thr | Ser | Asp | Tyr | Ser | Lys | Tyr | Leu | Asp | Ser |
| 118 | 118 | G | His | Ser | Gln | Gly | Thr | Phe | Thr | Ser | Asp | Tyr | Ser | Lys | Tyr | Leu | Asp | Ser |
| 119 | 119 | G | His | Ser | Gln | Gly | Thr | Phe | Thr | Ser | Asp | Tyr | Ser | Lys | Tyr | Leu | Asp | Ser |
| 120 | 120 | G | His | Ser | Gln | Gly | Thr | Phe | Thr | Ser | Asp | Tyr | Ser | Lys | Tyr | Leu | Asp | Ser |
| 121 | 121 | G | His | Ser | Gln | Gly | Thr | Phe | Thr | Ser | Asp | Tyr | Ser | Lys | Tyr | Leu | Asp | Ser |
| 122 | 122 | G | His | Ser | Gln | Gly | Thr | Phe | Thr | Ser | Asp | Tyr | Ser | Lys | Tyr | Leu | Asp | Ser |
| 123 | 123 | G | His | Ser | Gln | Gly | Thr | Phe | Thr | Ser | Asp | Tyr | Ser | Lys | Tyr | Leu | Asp | Ser |
| 124 | 124 | G | His | Ser | Gln | Gly | Thr | Phe | Thr | Ser | Asp | Tyr | Ser | His | Tyr | Leu | Asp | Ser |
| 125 | 125 | G | His | Ser | Gln | Gly | Thr | Phe | Thr | Ser | Asp | Tyr | Ser | His | Tyr | Leu | Asp | Ser |
| 126 | 126 | G | His | Ser | Gln | Gly | Thr | Phe | Thr | Ser | Asp | Tyr | Ser | His | Tyr | Leu | Asp | Ser |
| 127 | 127 | G | His | Ser | Gln | Gly | Thr | Phe | Thr | Ser | Asp | Tyr | Ser | His | Tyr | Leu | Asp | Ser |
| 128 | 128 | G | His | Ser | Gln | Gly | Thr | Phe | Thr | Ser | Asp | Tyr | Ser | Arg | Tyr | Leu | Asp | Ser |
| 129 | 129 | G | His | Ser | Gln | Gly | Thr | Phe | Thr | Ser | Asp | Tyr | Ser | Arg | Tyr | Leu | Asp | Ser |
| 130 | 130 | G | His | Ser | Gln | Gly | Thr | Phe | Thr | Ser | Asp | Tyr | Ser | Arg | Tyr | Leu | Asp | Ser |
| 131 | 131 | G | His | Ser | Gln | Gly | Thr | Phe | Thr | Ser | Asp | Tyr | Ser | Arg | Tyr | Leu | Asp | Ser |
| 132 | 132 | G | His | Ser | Gln | Gly | Thr | Phe | Thr | Ser | Asp | Tyr | Ser | Arg | Tyr | Leu | Asp | Ser |
| 133 | 133 | G | His | Ser | Gln | Gly | Thr | Phe | Thr | Ser | Asp | Tyr | Ser | Lys | Tyr | Leu | Asp | Ser |
| 134 | 134 | G | His | Ser | Gln | Gly | Thr | Phe | Thr | Ser | Asp | Tyr | Ser | Lys | Tyr | Leu | Asp | Ser |
| 135 | 135 | G | His | Ser | Gln | Gly | Thr | Phe | Thr | Ser | Asp | Tyr | Ser | Lys | His | Leu | Glu | Ser |
| 136 | 136 | G | His | Ser | Gln | Gly | Thr | Phe | Thr | Ser | Asp | Tyr | Ser | Lys | His | Leu | Glu | Ser |
| 137 | 137 | G | His | Ser | Gln | Gly | Thr | Phe | Thr | Ser | Asp | Tyr | Ser | Lys | His | Leu | Asp | Ser |
| 138 | 138 | G | His | Ser | Gln | Gly | Thr | Phe | Thr | Ser | Asp | Tyr | Ser | Lys | Tyr | Leu | Asp | Ser |
| 139 | 139 | G | His | Ser | Gln | Gly | Thr | Phe | Thr | Ser | Asp | Leu | Ser | Arg | Tyr | Leu | Glu | Ser |
| 140 | 140 | G | His | Ser | Gln | Gly | Thr | Phe | Thr | Ser | Asp | Tyr | Ser | Lys | Tyr | Leu | Asp | Ser |
| 141 | 141 | G | His | Ser | Gln | Gly | Thr | Phe | Thr | Ser | Asp | Leu | Ser | Lys | Tyr | Leu | Glu | Ser |
| 142 | 142 | G | His | Ser | Gln | Gly | Thr | Phe | Thr | Ser | Asp | Tyr | Ser | Lys | His | Leu | Asp | Ser |
| 143 | 143 | G | His | Ser | Gln | Gly | Thr | Phe | Thr | Ser | Asp | Tyr | Ser | Lys | His | Leu | Glu | Ser |
| 144 | 144 | G | His | Ser | Gln | Gly | Thr | Phe | Thr | Ser | Asp | Tyr | Ser | Lys | Tyr | Leu | Asp | Ser |
| 145 | 145 | G | His | Ser | Gln | Gly | Thr | Phe | Thr | Ser | Asp | Tyr | Ser | Lys | Gln | Leu | Glu | Ser |
| 146 | 146 | G | His | Ser | Gln | Gly | Thr | Phe | Thr | Ser | Asp | Tyr | Ser | Lys | Tyr | Leu | Asp | Ser |
| 147 | 147 | G | His | Ser | Gln | Gly | Thr | Phe | Thr | Ser | Asp | Tyr | Ser | Lys | Tyr | Leu | Asp | Ser |
| 148 | 148 | G | His | Ser | Gln | Gly | Thr | Phe | Thr | Ser | Asp | Tyr | Ser | Lys | His | Leu | Asp | Ser |
| 149 | 149 | G | His | Ser | Gln | Gly | Thr | Phe | Thr | Ser | Asp | Tyr | Ser | Lys | Tyr | Leu | Asp | Ser |
| 150 | 150 | G | His | Ser | Gln | Gly | Thr | Phe | Thr | Ser | Asp | Tyr | Ser | His | Tyr | Leu | Asp | Ser |

Fig. 1 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 101 | 101 | G | Arg | Lys | Ala | His | Glu | Phe | Ile | Glu | Trp | Leu | Leu | Asn | Thr | Gly | His | | |
| 102 | 102 | G | Arg | Arg | Ala | His | Glu | Phe | Ile | Glu | Trp | Leu | Leu | Asn | Thr | Gly | His | | |
| 103 | 103 | G | Lys | Arg | Ala | His | Glu | Phe | Ile | Glu | Trp | Leu | Leu | Asn | Gly | Gly | His | NH2 | |
| 104 | 104 | G | Lys | Arg | Ala | His | Glu | Phe | Val | Gln | Trp | Leu | Leu | Asn | Thr | Gly | His | | |
| 105 | 105 | G | Lys | Arg | Ala | His | Glu | Phe | Val | Glu | Trp | Leu | Leu | Asn | Gly | Gly | His | | |
| 106 | 106 | G | Lys | Arg | Ala | His | Glu | Phe | Val | Gln | Trp | Leu | Leu | Asn | Gly | Gly | His | NH2 | |
| 107 | 107 | G | Lys | Arg | Ala | His | Glu | Phe | Val | Glu | Trp | Leu | Leu | Asn | Gly | Gly | His | | |
| 108 | 108 | G | Lys | Arg | Ala | His | Glu | Phe | Val | Gln | Trp | Leu | Leu | Asn | Gly | Gly | His | | |
| 109 | 109 | G | Lys | Lys | Ala | His | Glu | Phe | Val | Glu | Trp | Leu | Leu | Asn | Gly | Gly | His | NH2 | |
| 110 | 110 | G | Lys | Arg | Ala | His | Glu | Phe | Val | Gln | Trp | Leu | Leu | Asn | Gly | Gly | His | NH2 | |
| 111 | 111 | G | Lys | Arg | Ala | His | Glu | Phe | Val | Glu | Trp | Leu | Leu | Asn | Gly | Gly | His | | |
| 112 | 112 | G | Lys | Arg | Ala | His | Glu | Phe | Ile | Gln | Trp | Leu | Leu | Asn | Thr | Gly | NH2 | | |
| 113 | 113 | G | Lys | Arg | Ala | His | Glu | Phe | Ile | Glu | Trp | Leu | Leu | Asn | Thr | Gly | His | NH2 | |
| 114 | 114 | G | Lys | Arg | Ala | His | Glu | Phe | Ile | Glu | Trp | Leu | Leu | Asn | Thr | Gly | His | | |
| 115 | 115 | G | Arg | Arg | Ala | His | Glu | Phe | Val | Glu | Trp | Leu | Leu | Asn | Thr | His | NH2 | | |
| 116 | 116 | G | Arg | Arg | Ala | His | Glu | Phe | Val | Glu | Trp | Leu | Leu | Asn | Gly | His | His | | |
| 117 | 117 | G | Arg | Arg | Ala | His | Glu | Phe | Val | Glu | Trp | Leu | Leu | Asn | Gly | His | His | NH2 | |
| 118 | 118 | G | Arg | Arg | Ala | His | Glu | Phe | Val | Glu | Trp | Leu | Leu | Asn | Gly | His | His | NH2 | |
| 119 | 119 | G | Arg | Arg | Ala | His | Asp | Phe | Val | Glu | Trp | Leu | Leu | Asn | Thr | His | His | NH2 | |
| 120 | 120 | G | Arg | Arg | Ala | His | Asp | Phe | Val | Glu | Trp | Leu | Leu | Asn | Thr | His | His | NH2 | |
| 121 | 121 | G | Arg | Arg | Ala | His | Asp | Phe | Val | Glu | Trp | Leu | Leu | Asn | Thr | His | His | NH2 | |
| 122 | 122 | G | Arg | Arg | Ala | His | Glu | Phe | Val | Glu | Trp | Leu | Leu | Asn | Gly | His | His | NH2 | |
| 123 | 123 | G | Arg | Arg | Ala | His | Glu | Phe | Val | Gln | Trp | Leu | Leu | Asn | Gly | His | | | |
| 124 | 124 | G | Arg | Arg | Ala | His | Glu | Phe | Val | Gln | Trp | Leu | Leu | Asn | Gly | His | NH2 | | |
| 125 | 125 | G | Arg | Arg | Ala | His | Glu | Phe | Val | Gln | Trp | Leu | Leu | Asn | Gly | His | NH2 | | |
| 126 | 126 | G | Arg | Arg | Ala | His | Glu | Phe | Val | Gln | Trp | Leu | Leu | Asn | Thr | His | His | NH2 | |
| 127 | 127 | G | Arg | Arg | Ala | His | Glu | Phe | Val | Gln | Trp | Leu | Leu | Asn | Thr | His | His | NH2 | |
| 128 | 128 | G | Arg | Arg | Ala | His | Glu | Phe | Val | Gln | Trp | Leu | Leu | Asn | Thr | Gly | His | NH2 | |
| 129 | 129 | G | Arg | Arg | Ala | His | Glu | Phe | Val | Gln | Trp | Leu | Leu | Asn | Thr | His | His | NH2 | |
| 130 | 130 | G | Arg | Arg | Ala | His | Glu | Phe | Val | Gln | Trp | Leu | Leu | Asn | Gly | Gly | His | NH2 | |
| 131 | 131 | G | Arg | Arg | Ala | His | Glu | Phe | Val | Gln | Trp | Leu | Leu | Asn | Thr | His | His | NH2 | |
| 132 | 132 | G | Lys | Arg | Ala | His | Glu | Phe | Val | Gln | Trp | Leu | Leu | Asn | Thr | His | His | NH2 | |
| 133 | 133 | G | Arg | Arg | Ala | His | Glu | Phe | Val | Gln | Trp | Leu | Leu | Asn | Thr | His | His | NH2 | |
| 134 | 134 | G | Arg | Arg | Ala | His | Glu | Phe | Val | Gln | Trp | Leu | Leu | Asn | Thr | His | His | NH2 | |
| 135 | 135 | G | Lys | Arg | Ala | His | Glu | Phe | Val | Gln | Trp | Leu | Leu | Asn | Thr | Gly | His | NH2 | |
| 136 | 136 | G | Lys | Arg | Ala | His | Glu | Phe | Val | Gln | Trp | Leu | Leu | Asn | Thr | His | His | NH2 | |
| 137 | 137 | G | Arg | Arg | Ala | His | Glu | Phe | Val | Gln | Trp | Leu | Leu | Asn | Thr | Gly | His | NH2 | |
| 138 | 138 | G | Arg | Arg | Ala | His | Glu | Phe | Val | Gln | Trp | Leu | Leu | Asn | Thr | His | His | NH2 | |
| 139 | 139 | G | Arg | Arg | Ala | His | Glu | Phe | Val | Gln | Trp | Leu | Leu | Asn | Thr | His | His | NH2 | |
| 140 | 140 | G | Arg | Arg | Ala | His | Glu | Phe | Val | Gln | Trp | Leu | Leu | Asn | Thr | His | His | NH2 | |
| 141 | 141 | G | Arg | Arg | Ala | Gln | Glu | Phe | Val | Gln | Trp | Leu | Leu | Asn | Thr | His | His | NH2 | |
| 142 | 142 | G | Arg | Arg | Ala | Gln | Glu | Phe | Val | Gln | Trp | Leu | Leu | Asn | Thr | His | His | NH2 | |
| 143 | 143 | G | Arg | Arg | Ala | Gln | His | Phe | Val | Gln | Trp | Leu | Leu | Asn | Thr | His | His | NH2 | |
| 144 | 144 | G | Arg | Arg | Ala | Ala | His | Phe | Val | Gln | Trp | Leu | Leu | Asn | Thr | His | His | NH2 | |
| 145 | 145 | G | Arg | Arg | Ala | Ala | His | Phe | Val | Gln | Trp | Leu | Leu | Asn | Thr | His | His | NH2 | |
| 146 | 146 | G | Arg | Arg | Ala | Ala | His | Phe | Val | Gln | Trp | Leu | Leu | Asn | Thr | His | His | NH2 | |
| 147 | 147 | G | Arg | Arg | Ala | Ala | His | Phe | Val | Gln | Trp | Leu | Leu | Asn | Thr | His | His | NH2 | |
| 148 | 148 | G | Lys | Arg | Ala | Ala | His | Phe | Val | Gln | Trp | Leu | Leu | Asn | Thr | His | His | NH2 | |
| 149 | 149 | G | Lys | Arg | Ala | Ala | His | Phe | Val | Gln | Trp | Leu | Leu | Asn | Thr | His | His | NH2 | |
| 150 | 150 | G | Lys | Arg | Ala | Ala | His | Phe | Val | Gln | Trp | Leu | Leu | Asn | Thr | His | His | NH2 | |

Fig. 1 (continued)

| | | | hGCGr cAMP | hGLP-1r cAMP | | Mouse food intake inhibition (500 nmol/kg) | | | | | | | Rat food intake inhibition (500 nmol/kg with 1:1 Zn) | | | | | | |
|---|---|---|---|---|---|---|---|---|---|---|---|---|---|---|---|---|---|---|---|---|
| SEQ ID NO. | Analogue no. | G no. | n | vs hGCG | n | vs hGLP-1 | 0-1 | 0-4 | 0-8 | 4-8 | 8-24 | 24-32 | 0-24 | 0-1 | 0-4 | 0-8 | 4-8 | 8-24 | 24-32 | 48-72 | 0-24 | 0-48 | 0-72 |
| 101 | 101 | G | 2 | 0.7 | 2 | 363.9 | 95 | 51 | 10 | -71 | -5 | | 1 | | | | | | | | | | |
| 102 | 102 | G | 3 | 1.7 | | | | | | | | | | | | | | | | | | | |
| 103 | 103 | G | 2 | 1.3 | | | | | | | | | | | | | | | | | | | |
| 104 | 104 | G | 2 | 1.1 | | | | | | | | | | | | | | | | | | | |
| 105 | 105 | G | 2 | 1.5 | | | | | | | | | | | | | | | | | | | |
| 106 | 106 | G | 1 | 3.3 | | | | | | | | | | | | | | | | | | | |
| 107 | 107 | G | 3 | 1.6 | | | | | | | | | | | | | | | | | | | |
| 108 | 108 | G | 1 | 5.3 | | | | | | | | | | | | | | | | | | | |
| 109 | 109 | G | 3 | 2.5 | | | | | | | | | | | | | | | | | | | |
| 110 | 110 | G | 5 | 1.1 | 2 | 5.2 | | | | | | | | | | | | | | | | | |
| 111 | 111 | G | 2 | 3.5 | | | | | | | | | | | | | | | | | | | |
| 112 | 112 | G | 1 | 5.4 | | | | | | | | | | | | | | | | | | | |
| 113 | 113 | G | 1 | 4.0 | | | | | | | | | | | | | | | | | | | |
| 114 | 114 | G | 1 | 7.6 | | | | | | | | | | | | | | | | | | | |
| 115 | 115 | G | 4 | 0.8 | 1 | 17.4 | 98 | 9 | 5 | -1 | 14 | | 11 | | | | | | | | | | |
| 116 | 116 | G | 3 | 1.5 | | | | | | | | | | | | | | | | | | | |
| 117 | 117 | G | 5 | 0.9 | 2 | 10.8 | 96 | 14 | 10 | 3 | -25 | | -13 | | | | | | | | | | |
| 118 | 118 | G | 3 | 0.7 | | | | | | | | | | | | | | | | | | | |
| 119 | 119 | G | 2 | 1.3 | | | | | | | | | | | | | | | | | | | |
| 120 | 120 | G | 4 | 1.0 | 1 | 12.7 | 93 | 82 | 30 | -73 | -5 | | 7 | | | | | | | | | | |
| 121 | 121 | G | 4 | 0.9 | 2 | 106.4 | | | | | | | | | | | | | | | | | |
| 122 | 122 | G | 4 | 1.1 | | | | | | | | | | | | | | | | | | | |
| 123 | 123 | G | 4 | 4.7 | | | | | | | | | | | | | | | | | | | |
| 124 | 124 | G | 2 | 1.8 | | | | | | | | | | | | | | | | | | | |
| 125 | 125 | C | 2 | 1.5 | | | | | | | | | | | | | | | | | | | |
| 126 | 126 | G | 1 | 3.4 | | | | | | | | | | | | | | | | | | | |
| 127 | 127 | G | 2 | 1.4 | 1 | 2.3 | | | | | | | | | | | | | | | | | |
| 128 | 128 | G | 1 | 1.4 | 0 | 0.0 | | | | | | | | | | | | | | | | | |
| 129 | 129 | G | 3 | 1.3 | 1 | 47.4 | 93 | 96 | 71 | 23 | -19 | | 14 | -13 | -5 | -5 | -6 | 60 | 31 | 1 | 33 | 38 | 26 |
| 130 | 130 | G | 5 | 1.0 | 2 | 1.2 | 94 | 33 | 6.5 | -30 | 17.5 | | 14 | | | | | | | | | | |
| 131 | 131 | G | 2 | 1.3 | | | | | | | | | | | | | | | | | | | |
| 132 | 132 | G | 3 | 1.2 | | | | | | | | | | | | | | | | | | | |
| 133 | 133 | G | 1 | 2.8 | | | | | | | | | | | | | | | | | | | |
| 134 | 134 | G | 2 | 1.4 | | | | | | | | | | | | | | | | | | | |
| 135 | 135 | G | 2 | 3.5 | | | | | | | | | | | | | | | | | | | |
| 136 | 136 | G | 1 | 1.0 | | | | | | | | | | | | | | | | | | | |
| 137 | 137 | G | 3 | 2.9 | | | | | | | | | | | | | | | | | | | |
| 138 | 138 | G | 3 | 1.0 | | | | | | | | | | | | | | | | | | | |
| 139 | 139 | G | 3 | 3.5 | | | | | | | | | | | | | | | | | | | |
| 140 | 140 | G | 3 | 1.3 | | | | | | | | | | | | | | | | | | | |
| 141 | 141 | G | 5 | 0.9 | 2 | 20.7 | 95 | 61 | 23.5 | -26.5 | -4.5 | | 5.5 | -24 | -17 | -2 | 36 | 26 | 51 | 22 | -3 | 22 | 14 |
| 142 | 142 | G | 2 | 0.5 | 2 | 34.8 | 97 | 14 | -6 | -47 | -5 | | -6 | | | | | | | | | | |
| 143 | 143 | G | 5 | 0.6 | 1 | 8.5 | 96 | 24 | 2 | -41 | 5 | | 4 | | | | | | | | | | |
| 144 | 144 | G | 2 | 5.0 | | | | | | | | | | | | | | | | | | | |
| 145 | 145 | G | 2 | 1.7 | | | 86 | 1 | 1 | -1 | 1 | | 1 | | | | | | | | | | |
| 146 | 146 | G | 2 | 1.7 | | | | | | | | | | | | | | | | | | | |
| 147 | 147 | G | | | | | | | | | | | | | | | | | | | | | |
| 148 | 148 | G | 2 | 2.5 | | | | | | | | | | | | | | | | | | | |
| 149 | 149 | G | 2 | 7.0 | | | | | | | | | | | | | | | | | | | |
| 150 | 150 | G | 2 | 26.9 | | | | | | | | | | | | | | | | | | | |

Fig. 1 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 151 | 151 | G | 1379 | His | Ser | Gln | Gly | Thr | Phe | Thr | Ser | Asp | Tyr | Ser | His | Tyr | Leu | Asp | Ser |
| 152 | 152 | G | 1380 | His | Ser | Gln | Gly | Thr | Phe | Thr | Ser | Asp | Tyr | Ser | His | Tyr | Leu | Asp | Ser |
| 153 | 153 | G | 1381 | His | Ser | Gln | Gly | Thr | Phe | Thr | Ser | Asp | Tyr | Ser | His | Tyr | Leu | Glu | Ser |
| 154 | 154 | G | 1382 | His | Ser | Gln | Gly | Thr | Phe | Thr | Ser | Asp | Tyr | Ser | His | Tyr | Leu | Glu | Ser |
| 155 | 155 | G | 1385 | His | Ser | Gln | Gly | Thr | Phe | Thr | Ser | Asp | Tyr | Ser | His | Tyr | Leu | Asp | Ser |
| 156 | 156 | G | 1386 | His | Ser | Gln | Gly | Thr | Phe | Thr | Ser | Asp | Tyr | Ser | Arg | Tyr | Leu | Asp | Ser |
| 157 | 157 | G | 1387 | His | Ser | Gln | Gly | Thr | Phe | Thr | Ser | Asp | Tyr | Ser | Arg | Tyr | Leu | Asp | Ser |
| 158 | 158 | G | 1388 | His | Ser | Gln | Gly | Thr | Phe | Thr | Ser | Asp | Tyr | Ser | Lys | Tyr | Leu | Asp | Ser |
| 159 | 159 | G | 1395 | His | Ser | Gln | Gly | Thr | Phe | Thr | Ser | Asp | Tyr | Ser | His | Tyr | Leu | Asp | Ser |
| 160 | 160 | G | 1396 | His | Ser | Gln | Gly | Thr | Phe | Thr | Ser | Asp | Tyr | Ser | His | Tyr | Leu | Asp | Ser |
| 161 | 161 | G | 1397 | His | Ser | Gln | Gly | Thr | Phe | Thr | Ser | Asp | Tyr | Ser | His | Tyr | Leu | Asp | Ser |
| 162 | 162 | G | 1399 | His | Ser | Gln | Gly | Thr | Phe | Thr | Ser | Asp | Tyr | Ser | His | Tyr | Leu | Glu | Ser |
| 163 | 163 | G | 1400 | His | Ser | Gln | Gly | Thr | Phe | Thr | Ser | Asp | Tyr | Ser | His | Tyr | Leu | Glu | Ser |
| 164 | 164 | G | 1401 | His | Ser | Gln | Gly | Thr | Phe | Thr | Ser | Asp | Tyr | Ser | Lys | His | Leu | Asp | Ser |
| 165 | 165 | G | 1402 | His | Ser | Gln | Gly | Thr | Phe | Thr | Ser | Asp | Tyr | Ser | Lys | Tyr | Leu | Glu | Glu |
| 166 | 166 | G | 1403 | His | Ser | Gln | Gly | Thr | Phe | Thr | Ser | Asp | Tyr | Ser | Lys | His | Leu | Glu | Glu |
| 167 | 167 | G | 1405 | His | Ser | Gln | Gly | Thr | Phe | Thr | Ser | Asp | Tyr | Ser | Lys | Tyr | Leu | Glu | Glu |
| 168 | 168 | G | 1428 | His | Ser | Gln | Gly | Thr | Phe | Thr | Ser | Asp | Tyr | Ser | His | Tyr | Leu | Glu | Glu |
| 169 | 169 | G | 1429 | His | Ser | Gln | Gly | Thr | Phe | Thr | Ser | Asp | Ile | Ser | His | Tyr | Leu | Asp | Ser |
| 170 | 170 | G | 1430 | His | Ser | Gln | Gly | Thr | Phe | Thr | Ser | Asp | Tyr | Ser | His | Tyr | Leu | Asp | Ser |
| 171 | 171 | G | 1431 | His | Ser | Gln | Gly | Thr | Phe | Thr | Ser | Asp | Tyr | Ser | His | Tyr | Leu | Asp | Ser |
| 172 | 172 | G | 1447 | His | Ser | Gln | Gly | Thr | Phe | Thr | Ser | Asp | Tyr | Ser | Lys | Tyr | Leu | Asp | Ser |
| 173 | 173 | G | 1448 | His | Ser | Gln | Gly | Thr | Phe | Thr | Ser | Asp | Tyr | Ser | Lys | Tyr | Leu | Asp | Glu |
| 174 | 174 | G | 1449 | His | Ser | Gln | Gly | Thr | Phe | Thr | Ser | Asp | Tyr | Ser | Lys | Tyr | Leu | Asp | Glu |
| 175 | 175 | G | 1450 | His | Ser | Gln | Gly | Thr | Phe | Thr | Ser | Asp | Tyr | Ser | Lys | Tyr | Leu | Asp | Glu |
| 176 | 176 | G | 1451 | His | Ser | Gln | Gly | Thr | Phe | Thr | Ser | Asp | Tyr | Ser | His | Tyr | Leu | Asp | Ser |
| 177 | 177 | G | 1452 | His | Ser | Gln | Gly | Thr | Phe | Thr | Ser | Asp | Tyr | Ser | Lys | Tyr | Leu | Asp | Glu |
| 178 | 178 | G | 1453 | His | Ser | Gln | Gly | Thr | Phe | Thr | Ser | Asp | Tyr | Ser | Lys | Tyr | Leu | Glu | Glu |
| 179 | 179 | G | 1454 | His | Ser | Gln | Gly | Thr | Phe | Thr | Ser | Asp | Tyr | Ser | Lys | Tyr | Leu | Glu | Glu |
| 180 | 180 | G | 1456 | His | Ser | Gln | Gly | Thr | Phe | Thr | Ser | Asp | Tyr | Ser | Lys | Tyr | Leu | Asp | Ser |
| 181 | 181 | G | 1457 | His | Ser | Gln | Gly | Thr | Phe | Thr | Ser | Asp | Tyr | Ser | Lys | Tyr | Leu | Asp | Ser |
| 182 | 182 | G | 1458 | His | Ser | Gln | Gly | Thr | Phe | Thr | Ser | Asp | Tyr | Ser | Lys | Tyr | Leu | Asp | Ser |
| 183 | 183 | G | 1459 | His | Ser | Gln | Gly | Thr | Phe | Thr | Ser | Asp | Tyr | Ser | Lys | Tyr | Leu | Asp | Glu |
| 184 | 184 | G | 1460 | His | Ser | Gln | Gly | Thr | Phe | Thr | Ser | Asp | Tyr | Ser | Lys | Tyr | Leu | Asp | Glu |
| 185 | 185 | G | 1461 | His | Ser | Gln | Gly | Thr | Phe | Thr | Ser | Asp | Tyr | Ser | His | Tyr | Leu | Asp | Ser |
| 186 | 186 | G | 1462 | His | Ser | Gln | Gly | Thr | Phe | Thr | Ser | Asp | Tyr | Ser | His | Tyr | Leu | Asp | Ser |
| 187 | 187 | G | 1463 | His | Ser | Gln | Gly | Thr | Phe | Thr | Ser | Asp | Tyr | Ser | His | Tyr | Leu | Asp | Ser |
| 188 | 188 | G | 1464 | His | Ser | Gln | Gly | Thr | Phe | Thr | Ser | Asp | Tyr | Ser | Arg | Tyr | Leu | Asp | Ser |
| 189 | 189 | G | 1465 | His | Ser | Gln | Gly | Thr | Phe | Thr | Ser | Asp | Tyr | Ser | Arg | Tyr | Leu | Asp | Ser |
| 190 | 190 | G | 1466 | His | Ser | Gln | Gly | Thr | Phe | Thr | Ser | Asp | Tyr | Ser | Arg | Tyr | Leu | Asp | Ser |
| 191 | 191 | G | 1467 | His | Ser | Gln | Gly | Thr | Phe | Thr | Ser | Asp | Tyr | Ser | His | His | Leu | Asp | Ser |
| 192 | 192 | G | 1468 | His | Ser | Gln | Gly | Thr | Phe | Thr | Ser | Asp | Tyr | Ser | His | His | Leu | Asp | Ser |
| 193 | 193 | G | 1469 | His | Ser | Gln | Gly | Thr | Phe | Thr | Ser | Asp | Tyr | Ser | Arg | Tyr | Leu | Asp | Glu |
| 194 | 194 | G | 1470 | His | Ser | Gln | Gly | Thr | Phe | Thr | Ser | Asp | Leu | Ser | Lys | Gln | Leu | Asp | Glu |
| 195 | 195 | G | 1471 | His | Ser | Gln | Gly | Thr | Phe | Thr | Ser | Asp | Tyr | Ser | Arg | Tyr | Leu | Asp | Ser |
| 196 | 196 | G | 1472 | His | Ser | Gln | Gly | Thr | Phe | Thr | Ser | Asp | Tyr | Ser | His | Tyr | Leu | Asp | Ser |
| 197 | 197 | G | 1473 | His | Ser | Gln | Gly | Thr | Phe | Thr | Ser | Asp | Tyr | Ser | Arg | Tyr | Leu | Asp | Ser |
| 198 | 198 | G | 1474 | His | Ser | Gln | Gly | Thr | Phe | Thr | Ser | Asp | Tyr | Ser | Arg | Tyr | Leu | Asp | Glu |
| 199 | 199 | G | 1475 | His | Ser | Gln | Gly | Thr | Phe | Thr | Ser | Asp | Tyr | Ser | Lys | Tyr | Leu | Asp | Ser |
| 200 | 200 | G | 1476 | His | Ser | Gln | Gly | Thr | Phe | Thr | Ser | Asp | Tyr | Ser | Lys | Tyr | Leu | Asp | Ser |

Fig. 1 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 151 | 151 | G | Lys | Arg | Ala | His | Asp | Phe | Val | Glu | Trp | Leu | Leu | Asn | Thr | His | His | NH2 | |
| 152 | 152 | G | Lys | Arg | Ala | His | Asp | Phe | Val | Glu | Trp | Leu | Leu | Asn | Thr | Gly | His | NH2 | |
| 153 | 153 | G | Lys | Arg | Ala | His | Glu | Phe | Val | Glu | Trp | Leu | Leu | Asn | Thr | His | NH2 | | |
| 154 | 154 | G | Lys | Arg | Ala | His | Asp | Phe | Val | Gln | Trp | Leu | Leu | Asn | Thr | His | NH2 | | |
| 155 | 155 | G | Lys | Arg | Ala | His | Glu | Phe | Val | Glu | Trp | Leu | Leu | Asn | Gly | Gly | His | | |
| 156 | 156 | G | Arg | Arg | Ala | His | Glu | Phe | Val | Gln | Trp | Leu | Leu | Asn | Thr | Gly | His | | |
| 157 | 157 | G | Lys | Arg | Ala | His | Glu | Phe | Val | Gln | Trp | Leu | Leu | Asn | Thr | Gly | His | | |
| 158 | 158 | G | Lys | Arg | Ala | His | Glu | Phe | Val | Gln | Trp | Leu | Leu | Ala | Thr | Gly | His | | |
| 159 | 159 | G | Lys | Arg | Ala | His | Asp | Phe | Val | Gln | Trp | Leu | Leu | Asn | Thr | His | His | | |
| 160 | 160 | G | Lys | Arg | Ala | His | Glu | Phe | Val | Gln | Trp | Leu | Leu | Asn | Thr | His | NH2 | | |
| 161 | 161 | G | Lys | Arg | Ala | His | Asp | Phe | Val | Glu | Trp | Leu | Leu | Asn | Thr | Gly | NH2 | | |
| 162 | 162 | G | Arg | Arg | Ala | His | Glu | Phe | Val | Glu | Trp | Leu | Leu | Asn | Thr | Gly | His | | |
| 163 | 163 | G | Arg | Arg | Ala | His | Glu | Phe | Val | Glu | Trp | Leu | Leu | Asn | Thr | Gly | His | NH2 | |
| 164 | 164 | G | His | Arg | Ala | His | Glu | Phe | Val | Gln | Trp | Leu | Leu | Asn | Gly | Gly | His | NH2 | |
| 165 | 165 | G | Arg | Arg | Ala | His | Glu | Phe | Val | Gln | Trp | Leu | Leu | Asn | Gly | Gly | His | NH2 | |
| 166 | 166 | G | Lys | Arg | Ala | His | Glu | Phe | Val | Glu | Trp | Leu | Leu | Asn | Gly | Gly | His | NH2 | |
| 167 | 167 | G | Arg | Arg | Ala | His | Asp | Phe | Val | Glu | Trp | Leu | Leu | Asn | Thr | His | NH2 | | |
| 168 | 168 | G | Arg | Arg | Ala | Gln | Asp | Phe | Val | Gln | Trp | Leu | Leu | Asn | Gly | Gly | His | | |
| 169 | 169 | G | Arg | Arg | Ala | Gln | Asp | Phe | Val | Gln | Trp | Leu | Leu | Asn | Thr | Gly | His | | |
| 170 | 170 | G | Arg | Arg | Ala | Gln | Asp | Phe | Ile | Glu | Trp | Leu | Leu | Asn | Thr | Gly | His | | |
| 171 | 171 | G | Arg | Arg | Ala | Gln | Glu | Phe | Ile | Gln | Trp | Leu | Leu | Asn | Gly | Gly | His | NH2 | |
| 172 | 172 | G | Arg | Arg | Ala | His | Glu | Phe | Val | Glu | Trp | Leu | Leu | Asn | Thr | Gly | His | NH2 | |
| 173 | 173 | G | Arg | Arg | Ala | His | Glu | Phe | Val | Glu | Trp | Leu | Leu | Asn | Gly | Gly | His | NH2 | |
| 174 | 174 | G | Arg | Arg | Ala | His | Glu | Phe | Val | Glu | Trp | Leu | Leu | Asn | Gly | Gly | His | | |
| 175 | 175 | G | Arg | Arg | Ala | His | Glu | Phe | Val | Gln | Trp | Leu | Leu | Asn | Thr | Gly | His | NH2 | |
| 176 | 176 | G | Arg | Arg | Ala | His | Glu | Phe | Val | Glu | Trp | Leu | Leu | Asn | Gly | Gly | His | | |
| 177 | 177 | G | Arg | Lys | Ala | His | Glu | Phe | Val | Gln | Trp | Leu | Leu | Asn | Thr | Gly | His | | |
| 178 | 178 | G | Arg | Lys | Ala | His | Glu | Phe | Val | Glu | Trp | Leu | Leu | Asn | Thr | Gly | His | NH2 | |
| 179 | 179 | G | Arg | Lys | Ala | His | Glu | Phe | Val | Gln | Trp | Leu | Leu | Asn | Thr | Gly | His | | |
| 180 | 180 | G | Arg | Arg | Ala | His | Glu | Phe | Val | Gln | Trp | Leu | Leu | Asn | Thr | Gly | His | NH2 | |
| 181 | 181 | G | Arg | Arg | Ala | His | Glu | Phe | Val | Glu | Trp | Leu | Leu | Asn | Thr | Gly | His | | |
| 182 | 182 | G | Arg | Arg | Ala | His | Glu | Phe | Val | Glu | Trp | Leu | Leu | Asn | Thr | His | His | NH2 | |
| 183 | 183 | G | Arg | Arg | Ala | His | Glu | Phe | Val | Gln | Trp | Leu | Leu | Asn | Thr | Gly | His | | |
| 184 | 184 | G | Arg | Arg | Ala | His | Glu | Phe | Val | Gln | Trp | Leu | Leu | Asn | Thr | Gly | His | | |
| 185 | 185 | G | Arg | Arg | Ala | His | Glu | Phe | Val | Glu | Trp | Leu | Leu | Asn | Gly | His | His | NH2 | |
| 186 | 186 | G | Arg | Arg | Ala | His | Glu | Phe | Val | Glu | Trp | Leu | Leu | Asn | Gly | His | His | | |
| 187 | 187 | G | Arg | Arg | Ala | His | Glu | Phe | Val | Gln | Trp | Leu | Leu | Asn | Thr | His | His | NH2 | |
| 188 | 188 | G | Arg | Arg | Ala | His | Glu | Phe | Val | Gln | Trp | Leu | Leu | Asn | Thr | His | His | | |
| 189 | 189 | G | Arg | Arg | Ala | His | Glu | Phe | Val | Gln | Trp | Leu | Leu | Asn | Gly | His | His | NH2 | |
| 190 | 190 | G | Arg | Arg | Ala | His | Glu | Phe | Val | Gln | Trp | Leu | Leu | Asn | Gly | His | His | | |
| 191 | 191 | G | Arg | Arg | Ala | His | Glu | Phe | Val | Glu | Trp | Leu | Leu | Asn | Thr | His | His | | |
| 192 | 192 | G | Arg | Arg | Ala | His | Glu | Phe | Val | Glu | Trp | Leu | Leu | Asn | Thr | His | His | | |
| 193 | 193 | G | Arg | Arg | Ala | His | Glu | Phe | Val | Glu | Trp | Leu | Leu | Asn | Thr | His | His | | |
| 194 | 194 | G | Arg | Arg | Ala | His | Glu | Phe | Val | Glu | Trp | Leu | Leu | Asn | Thr | His | His | | |
| 195 | 195 | G | Arg | Arg | Ala | His | Glu | Phe | Val | Glu | Trp | Leu | Leu | Asn | Gly | His | His | | |
| 196 | 196 | G | Arg | Arg | Ala | His | Glu | Phe | Val | Glu | Trp | Leu | Leu | Asn | Gly | His | His | | |
| 197 | 197 | G | Arg | Arg | Ala | His | Glu | Phe | Val | Glu | Trp | Leu | Leu | Asn | Thr | His | His | | |
| 198 | 198 | G | Arg | Arg | Ala | His | Glu | Phe | Val | Glu | Trp | Leu | Leu | Asn | Thr | His | His | | |
| 199 | 199 | G | Arg | Arg | Ala | His | Glu | Phe | Val | Glu | Trp | Leu | Leu | Asn | Thr | His | His | | |
| 200 | 200 | G | Arg | Arg | Ala | His | Glu | Phe | Val | Glu | Trp | Leu | Leu | Asn | Gly | His | His | | |

Fig. 1 (continued)

| SEQ ID NO. | Analogue no. | G no. | n | hGCGr cAMP vs hGCG | n | hGLP-1r cAMP vs hGLP-1 | Mouse food intake inhibition (500nmol/kg) | | | | | | Rat food intake inhibition (500 nmol/kg with 1:1 Zn) | | | | | | | |
|---|---|---|---|---|---|---|---|---|---|---|---|---|---|---|---|---|---|---|---|---|
| | | | | | | | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 151 | 151 | G | 2 | 2.1 | | | | | | | | | | | | | | | | | | | | |
| 152 | 152 | G | 2 | 2.8 | | | | | | | | | | | | | | | | | | | | |
| 153 | 153 | G | 2 | 1.1 | | | | | | | | | | | | | | | | | | | | |
| 154 | 154 | G | 2 | 15.2 | | | 68 | 89 | 93 | 102 | 47 | | | | | | | | | | | | | |
| 155 | 155 | G | 5 | 1.0 | 3 | 14.9 | | | | | | | | | | | | | | | | | | |
| 156 | 156 | G | 2 | 8.1 | | | | | | | | | | | | | | | | | | | | |
| 157 | 157 | G | 2 | 0.9 | 4 | 18.4 | 73 | 88 | 87 | 85 | -23 | | | | | | | | | | | | | |
| 158 | 158 | G | 2 | 0.5 | | | 75.5 | 85.5212 | 55.9724 | 25.0505 | 3.4282 | 9.69163 | | | | | | | | | | | | |
| 159 | 159 | G | 3 | 2.2 | | | | | | | | | | | | | | | | | | | | |
| 160 | 160 | G | 3 | 2.0 | | | | | | | | | | | | | | | | | | | | |
| 161 | 161 | G | 3 | 1.9 | | | 65 | 10 | -3 | -30 | -7 | | | | | | | | | | | | | |
| 162 | 162 | G | 2 | 4.7 | | | | | | | | | | | | | | | | | | | | |
| 163 | 163 | G | 2 | 6.8 | | | | | | | | | | | | | | | | | | | | |
| 164 | 164 | G | 1 | 146221.3 | | | | | | | | | | | | | | | | | | | | |
| 165 | 165 | G | 2 | 2.6 | 2 | 516.5 | 65.3333 | 69.3333 | 55 | 28.3333 | -6 | | | | | | | | | | | | | |
| 166 | 166 | G | 2 | 37924.5 | | | | | | | | | | | | | | | | | | | | |
| 167 | 167 | G | 1 | 14.1 | | | | | | | | | | | | | | | | | | | | |
| 168 | 168 | G | 1 | 2.1 | | | | | | | | | | | | | | | | | | | | |
| 169 | 169 | G | 2 | 0.7 | 2 | 14.0 | | | | | | | | | | | | | | | | | | |
| 170 | 170 | C | 1 | 3.5 | | | | | | | | | | | | | | | | | | | | |
| 171 | 171 | G | 1 | 5.4 | | | | | | | | | | | | | | | | | | | | |
| 172 | 172 | G | 2 | 1.2 | 1 | 40.3 | 80.5 | 86 | 88.5 | 93.5 | 18 | | | | | | | | | | | | | |
| 173 | 173 | G | 2 | 0.4 | | | 78 | 78.1853 | 59.5262 | 40 | 3.75162 | 22.6872 | | | | | | | | | | | | |
| 174 | 174 | G | 5 | 0.5 | 2 | 4.3 | 97 | 42 | 14 | -40 | 9 | | | | | | | | | | | | | |
| 175 | 175 | G | 3 | 2.8 | | | | | | | | | | | | | | | | | | | | |
| 176 | 176 | G | 3 | 1.4 | | | | | | | | | | | | | | | | | | | | |
| 177 | 177 | G | 2 | 0.8 | | | | | | | | | | | | | | | | | | | | |
| 178 | 178 | G | 2 | 1.0 | | | | | | | | | | | | | | | | | | | | |
| 179 | 179 | G | 2 | 1.5 | | | | | | | | | | | | | | | | | | | | |
| 180 | 180 | G | 3 | 1.1 | 3 | 4.0 | 61 | 78 | 84.5 | 95.5 | 31 | | | -22 | -3 | -1 | 11 | 65 | 97 | 52 | -9 | 38 | 50 | 33 |
| 181 | 181 | G | 4 | 0.6 | 4 | 13.5 | 79.3333 | 86 | 87.6667 | 92 | 16 | | | -8.5 | 3.5 | 8.5 | 30 | 45 | 64.5 | -7.5 | -11.5 | 30.5 | 21.5 | 11.5 |
| 182 | 182 | G | 2 | 0.6 | 1 | 3.9 | | | | | | | | | | | | | | | | | | | |
| 183 | 183 | G | 2 | 0.8 | | | | | | | | | | | | | | | | | | | | |
| 184 | 184 | G | 5 | 0.7 | 4 | 8.0 | 77.6667 | 86.3333 | 88.3333 | 91.3333 | 7.66667 | | | 1 | -4 | -7 | -21 | 51 | 85 | 29 | 4 | 28 | 35 | 26 |
| 185 | 185 | G | 3 | 1.1 | | | 81.5 | 84.5 | 74 | 61 | -15.5 | | | | | | | | | | | | | |
| 186 | 186 | G | 2 | 1.4 | 2 | 9.5 | | | | | | | | | | | | | | | | | | | |
| 187 | 187 | G | 2 | 1.6 | | | | 11.2 | 99 | 63 | 20 | -65 | | | | | | | | | | | | | |
| 188 | 188 | G | 7 | 0.7 | 4 | 8.0 | 1 | 85 | 90 | 100 | 18 | | | | | | | | | | | | | | 
| 189 | 189 | G | 2 | 0.8 | | | 78 | | | | | | 12 | | | | | | | | | | | |
| 190 | 190 | G | 6 | 0.5 | 6 | 2.8 | 89.1667 | 83.0911 | 49.2176 | 16.9444 | -9.8021 | -52.34 | -0.2597 | 24.2925 | 21.9194 | 17.6836 | -11.382 | 17.8803 | -14.1133 | -0.8264 | 6.61806 | 17.7995 | 8.74384 | 8.09516 |
| 191 | 191 | G | 2 | 1.7 | | | | | | | | | | | | | | | | | | | | | |
| 192 | 192 | G | 3 | 0.6 | | | | | | | | | | | | | | | | | | | | | |
| 193 | 193 | G | 6 | 0.7 | 5 | 11.0 | 84.6667 | 85.6667 | 79.3333 | 71.6667 | 20.3333 | -40 | | -22.5 | -2.5 | -7.5 | -29 | 29.5 | 55 | 11 | -1.5 | 14.5 | 18 | 12 |
| 194 | 194 | G | 2 | 1.2 | | | 90.5 | 78.5 | 50.5 | 12 | -1 | | | | | | | | | | | | | | |
| 195 | 195 | G | 4 | 0.8 | 3 | 8.1 | 61 | 73.3333 | 80 | 92.6667 | 35 | | | -9.5 | 4 | 0 | -23.5 | 14 | 35.5 | -10.5 | -8.5 | 8.5 | 5.5 | 1 |
| 196 | 196 | G | 3 | 1.3 | | | 73 | 81 | 88 | 100 | -8 | | | | | | | | | | | | | | |
| 197 | 197 | G | 4 | 1.1 | | | | | | | | | | | | | | | | | | | | | |
| 198 | 198 | G | 4 | 1.1 | 3 | 23.7 | 78 | 87.5 | 86 | 81 | -9.5 | | | -12 | 6 | 1.5 | -28.5 | 26 | 46.5 | 6 | -3 | 16.5 | 16.5 | 10.5 |
| 199 | 199 | G | 4 | 2.2 | | | | | | | | | | | | | | | | | | | | | |
| 200 | 200 | G | 4 | 0.8 | 3 | 10.0 | 61 | 67 | 67 | 66.5 | 2 | | | 7.5 | 11 | 9.5 | -1 | 28.5 | 45.5 | 0 | -6 | 21 | 17 | 10 |

Fig. 1 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 201 | 201 | G | His | Ser | Gln | Gly | Thr | Phe | Thr | Ser | Asp | Tyr | Ser | Lys | Tyr | Leu | Asp | Ser |
| 202 | 202 | G | His | Ser | Gln | Gly | Thr | Phe | Thr | Ser | Asp | Tyr | Ser | Lys | Tyr | Leu | Asp | Ser |
| 203 | 203 | G | His | Ser | Gln | Gly | Thr | Phe | Thr | Ser | Asp | Tyr | Ser | Arg | Tyr | Leu | Asp | Ser |
| 204 | 204 | G | His | Ser | Gln | Gly | Thr | Phe | Thr | Ser | Asp | Leu | Ser | Arg | Gln | Leu | Asp | Ser |
| 205 | 205 | G | His | Ser | Gln | Gly | Thr | Phe | Thr | Ser | Asp | Leu | Ser | Arg | Gln | Leu | Asp | Ser |
| 206 | 206 | G | His | Ser | Gln | Gly | Thr | Phe | Thr | Ser | Asp | Tyr | Ser | Lys | Tyr | Leu | Asp | Ser |
| 207 | 207 | G | His | Ser | Gln | Gly | Thr | Phe | Thr | Ser | Asp | Tyr | Ser | Lys | Tyr | Leu | Asp | Ser |
| 208 | 208 | G | His | Ser | Gln | Gly | Thr | Phe | Thr | Ser | Asp | Tyr | Ser | Lys | Tyr | Leu | Asp | Ser |
| 209 | 209 | G | His | Ser | Gln | Gly | Thr | Phe | Thr | Ser | Asp | Tyr | Ser | Lys | Tyr | Leu | Glu | Ser |
| 210 | 210 | G | His | Ser | Gln | Gly | Thr | Phe | Thr | Ser | Asp | Leu | Ser | Lys | Tyr | Leu | Asp | Ser |
| 211 | 211 | G | His | Ser | Gln | Gly | Thr | Phe | Thr | Ser | Asp | Leu | Ser | Lys | Gln | Leu | Asp | Ser |
| 212 | 212 | G | His | Ser | Gln | Gly | Thr | Phe | Thr | Ser | Asp | Tyr | Ser | Lys | Tyr | Leu | Asp | Ser |
| 213 | 213 | G | His | Ser | Gln | Gly | Thr | Phe | Thr | Ser | Asp | Leu | Ser | Arg | Gln | Leu | Asp | Ser |
| 214 | 214 | G | His | Ser | Gln | Gly | Thr | Phe | Thr | Ser | Asp | Tyr | Ser | Arg | Gln | Leu | Asp | Ser |
| 215 | 215 | G | His | Ser | Gln | Gly | Thr | Phe | Thr | Ser | Asp | Tyr | Ser | Arg | Gln | Leu | Asp | Ser |
| 216 | 216 | G | His | Ser | Gln | Gly | Thr | Phe | Thr | Ser | Asp | Tyr | Ser | Arg | Tyr | Leu | Asp | Ser |
| 217 | 217 | G | His | Ser | Gln | Gly | Thr | Phe | Thr | Ser | Asp | Tyr | Ser | Arg | Tyr | Leu | Asp | Ser |
| 218 | 218 | G | His | Ser | Gln | Gly | Thr | Phe | Thr | Ser | Asp | Tyr | Ser | Lys | Tyr | Leu | Asp | Ser |
| 219 | 219 | G | His | Ser | Gln | Gly | Thr | Phe | Thr | Ser | Asp | Tyr | Ser | Lys | Tyr | Leu | Asp | Ser |
| 220 | 220 | G | His | Ser | Gln | Gly | Thr | Phe | Thr | Ser | Ala | Tyr | Ser | Arg | Tyr | Leu | Asp | Ser |
| 221 | 221 | G | His | Ser | Gln | Gly | Thr | Phe | Thr | Ser | Asp | Tyr | Ser | His | Tyr | Leu | Asp | Ser |
| 222 | 222 | G | His | Ser | Gln | Gly | Thr | Phe | Thr | Ser | Asp | Tyr | Ser | His | Tyr | Leu | Asp | Ser |
| 223 | 223 | G | His | Ser | Gln | Gly | Thr | Phe | Thr | Ser | Asp | Tyr | Ser | Arg | Tyr | Leu | Asp | Glu |
| 224 | 224 | G | His | Ser | Gln | Gly | Thr | Phe | Thr | Ser | Asp | Tyr | Ser | Arg | Tyr | Leu | Asp | Glu |
| 225 | 225 | G | His | Ser | Gln | Gly | Thr | Phe | Thr | Ser | Asp | Tyr | Ser | Arg | Tyr | Leu | Asp | Glu |
| 226 | 226 | G | His | Ser | Gln | Gly | Thr | Phe | Thr | Ser | Asp | Tyr | Ser | Arg | Tyr | Leu | Asp | Glu |
| 227 | 227 | G | His | Ser | Gln | Gly | Thr | Phe | Thr | Ser | Asp | Tyr | Ser | Lys | Tyr | Leu | Asp | Glu |
| 228 | 228 | G | His | Ser | Gln | Gly | Thr | Phe | Thr | Ser | Asp | Tyr | Ser | Lys | Tyr | Leu | Asp | Ser |
| 229 | 229 | G | His | Ser | Gln | Gly | Thr | Phe | Thr | Ser | Asp | Tyr | Ser | Arg | Tyr | Leu | Asp | Ser |
| 230 | 230 | G | His | Ser | Gln | Gly | Thr | Phe | Thr | Ser | Asp | Tyr | Ser | Arg | Tyr | Leu | Asp | Ser |
| 231 | 231 | G | His | Ser | Gln | Gly | Thr | Phe | Thr | Ser | Asp | Tyr | Ser | Arg | Tyr | Leu | Asp | Ser |
| 232 | 232 | G | His | Ser | Gln | Gly | Thr | Phe | Thr | Ser | Asp | Tyr | Ser | Arg | Tyr | Leu | Asp | Ser |
| 233 | 233 | G | His | Ser | Gln | Gly | Thr | Phe | Thr | Ser | Asp | Tyr | Ser | Arg | Tyr | Leu | Asp | Ser |
| 234 | 234 | G | His | Ser | Gln | Gly | Thr | Phe | Thr | Ser | Asp | Tyr | Ser | Arg | His | Leu | Asp | Ser |
| 235 | 235 | G | His | Ser | Gln | Gly | Thr | Phe | Thr | Ser | Asp | Tyr | Ser | Arg | His | Leu | Asp | Ser |
| 236 | 236 | G | His | Ser | Gln | Gly | Thr | Phe | Thr | Ser | Asp | Tyr | Ser | Arg | His | Leu | Asp | Ser |
| 237 | 237 | G | His | Ser | Gln | Gly | Thr | Phe | Thr | Ser | Asp | Tyr | Ser | Arg | His | Leu | Asp | Ser |
| 238 | 238 | G | His | Ser | Gln | Gly | Thr | Phe | Thr | Ser | Asp | Tyr | Ser | Arg | Tyr | Leu | Asp | Ser |
| 239 | 239 | G | His | Ser | Gln | Gly | Thr | Phe | Thr | Ser | Asp | Tyr | Ser | Arg | Tyr | Leu | Asp | Ser |
| 240 | 240 | G | His | Ser | Gln | Gly | Thr | Phe | Thr | Ser | Asp | Tyr | Ser | Arg | Tyr | Leu | Asp | Ser |
| 241 | 241 | G | His | Ser | Gln | Gly | Thr | Phe | Thr | Ser | Asp | Tyr | Ser | Arg | Tyr | Leu | Asp | Ser |
| 242 | 242 | G | His | Ser | Gln | Gly | Thr | Phe | Thr | Ser | Asp | Tyr | Ser | Lys | Tyr | Leu | Asp | Ser |
| 243 | 243 | G | His | Ser | Gln | Gly | Thr | Phe | Thr | Ser | Asp | Tyr | Ser | Lys | Tyr | Leu | Asp | Ser |
| 244 | 244 | G | His | Ser | Gln | Gly | Thr | Phe | Thr | Ser | Asp | Leu | Ser | Lys | Tyr | Leu | Asp | Ser |
| 245 | 245 | G | His | Ser | Gln | Gly | Thr | Phe | Thr | Ser | Asp | Leu | Ser | Lys | Gln | Leu | Asp | Glu |
| 246 | 246 | G | His | Ser | Gln | Gly | Thr | Phe | Thr | Ser | Asp | Tyr | Ser | Lys | Gln | Leu | Asp | Glu |
| 247 | 247 | G | His | Ser | Gln | Gly | Thr | Phe | Thr | Ser | Asp | Tyr | Ser | Lys | Tyr | Leu | Asp | Glu |
| 248 | 248 | G | His | Ser | Gln | Gly | Thr | Phe | Thr | Ser | Asp | Tyr | Ser | Arg | Gln | Leu | Asp | Glu |
| 249 | 249 | G | His | Ser | Gln | Gly | Thr | Phe | Thr | Ser | Asp | Leu | Ser | Arg | Gln | Leu | Asp | Ser |
| 250 | 250 | G | His | Ser | Gln | Gly | Thr | Phe | Thr | Ser | Asp | Leu | Ser | Arg | Gln | Leu | Asp | Ser |

Fig. 1 (continued)

| SEQ ID NO. | Analogue no. | G-no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 201 | 201 | G | Arg | Arg | Ala | His | Glu | Phe | Val | Glu | Trp | Leu | Leu | Asn | Gly | Gly | His | | |
| 202 | 202 | G | Arg | Arg | Ala | His | Asp | Phe | Val | Glu | Trp | Leu | Leu | Asn | Gly | Gly | His | | |
| 203 | 203 | G | Arg | Arg | Ala | His | Glu | Phe | Val | Glu | Trp | Leu | Leu | Asn | Gly | Gly | His | | |
| 204 | 204 | G | Arg | Arg | Ala | His | Glu | Phe | Val | Gln | Trp | Leu | Leu | Asn | Gly | Gly | His | | |
| 205 | 205 | G | Arg | Arg | Ala | His | Glu | Phe | Ile | Gln | Trp | Leu | Leu | Asn | Gly | Gly | His | | |
| 206 | 206 | G | Arg | Arg | Ala | His | Glu | Phe | Ile | Gln | Trp | Leu | Leu | Asn | Gly | Gly | His | | |
| 207 | 207 | G | Arg | Arg | Ala | His | Glu | Phe | Val | Gln | Trp | Leu | Leu | Asn | Gly | Gly | His | His | |
| 208 | 208 | G | Arg | Arg | Ala | His | Glu | Phe | Val | Gln | Trp | Leu | Leu | Asn | Gly | Gly | His | | |
| 209 | 209 | G | Arg | Arg | Ala | His | Glu | Phe | Val | Gln | Trp | Leu | Leu | Asn | Gly | Lys | His | | |
| 210 | 210 | G | Arg | Arg | Ala | His | Glu | Phe | Val | Gln | Trp | Leu | Leu | Asn | Gly | Gly | His | | |
| 211 | 211 | G | Arg | Arg | Ala | His | Glu | Phe | Val | Gln | Trp | Leu | Leu | Asn | Gly | Gly | His | | |
| 212 | 212 | G | Arg | Arg | Ala | His | Glu | Phe | Val | Gln | Trp | Leu | Leu | Asn | Gly | Gly | His | | |
| 213 | 213 | G | Arg | Arg | Ala | His | Glu | Phe | Val | Glu | Trp | Leu | Leu | Asn | Gly | Gly | His | | |
| 214 | 214 | G | Arg | Arg | Ala | His | Glu | Phe | Val | Glu | Trp | Leu | Leu | Asn | Gly | Gly | His | | |
| 215 | 215 | G | Arg | Arg | Ala | His | Glu | Phe | Ile | Gln | Trp | Leu | Leu | Asn | Gly | Gly | His | | |
| 216 | 216 | G | Arg | Arg | Ala | His | Glu | Phe | Ile | Gln | Trp | Leu | Leu | Asn | Gly | Gly | His | | |
| 217 | 217 | G | Arg | Arg | Ala | His | Glu | Phe | Ile | Glu | Trp | Leu | Leu | Asn | Gly | Gly | His | | |
| 218 | 218 | G | Lys | Arg | Ala | His | Glu | Phe | Ile | Glu | Trp | Leu | Leu | Asn | Gly | Gly | His | | |
| 219 | 219 | G | Lys | Arg | Ala | His | Glu | Phe | Ile | Glu | Trp | Leu | Leu | Asn | Gly | Gly | His | | |
| 220 | 220 | G | Arg | Arg | Ala | His | Glu | Phe | Val | Glu | Trp | Leu | Leu | Asn | Gly | Gly | His | | |
| 221 | 221 | G | Arg | Arg | Ala | His | Glu | Phe | Ile | Glu | Trp | Leu | Leu | Asn | Gly | Gly | His | NH2 | |
| 222 | 222 | G | Arg | Arg | Ala | His | Glu | Phe | Ile | Glu | Trp | Leu | Leu | Asn | Gly | Gly | His | | |
| 223 | 223 | G | Arg | Arg | Ala | His | Glu | Phe | Ile | Glu | Trp | Leu | Leu | Asn | Gly | Gly | His | | |
| 224 | 224 | G | Arg | Arg | Ala | His | Glu | Phe | Val | Glu | Trp | Leu | Leu | Asn | Gly | Gly | His | | |
| 225 | 225 | G | Arg | Arg | Ala | His | Glu | Phe | Val | Glu | Trp | Leu | Leu | Asn | Gly | Gly | His | | |
| 226 | 226 | G | Arg | Arg | Ala | His | Glu | Phe | Ile | Gln | Trp | Leu | Leu | Asn | Gly | Gly | His | | |
| 227 | 227 | G | Arg | Arg | Ala | His | Glu | Phe | Val | Glu | Trp | Leu | Leu | Asn | Gly | His | His | | |
| 228 | 228 | G | Arg | Arg | Ala | His | Glu | Phe | Ile | Gln | Trp | Leu | Leu | Asn | Thr | Gly | His | | |
| 229 | 229 | G | Arg | Arg | Ala | His | Glu | Phe | Val | Glu | Trp | Leu | Leu | Asn | Thr | Gly | His | NH2 | |
| 230 | 230 | G | Arg | Arg | Ala | His | Glu | Phe | Val | Glu | Trp | Leu | Leu | Asn | Thr | His | His | NH2 | |
| 231 | 231 | G | Arg | Arg | Ala | His | Glu | Phe | Ile | Gln | Trp | Leu | Leu | Asn | Thr | His | His | NH2 | |
| 232 | 232 | G | Arg | Arg | Ala | His | Glu | Phe | Val | Glu | Trp | Leu | Leu | Asn | Gly | His | His | NH2 | |
| 233 | 233 | G | Lys | Arg | Ala | His | Glu | Phe | Ile | Gln | Trp | Leu | Leu | Asn | Thr | His | His | NH2 | |
| 234 | 234 | G | Lys | Arg | Ala | His | Glu | Phe | Ile | Gln | Trp | Leu | Leu | Asn | Thr | His | His | NH2 | |
| 235 | 235 | G | Lys | Arg | Ala | His | Glu | Phe | Val | Glu | Trp | Leu | Leu | Asn | Thr | His | His | NH2 | |
| 236 | 236 | G | Lys | Arg | Ala | His | Glu | Phe | Val | Glu | Trp | Leu | Leu | Asn | Gly | His | His | NH2 | |
| 237 | 237 | G | Arg | Arg | Ala | His | Glu | Phe | Val | Glu | Trp | Leu | Leu | Asn | Gly | Gly | His | | |
| 238 | 238 | G | Lys | Arg | Ala | His | Glu | Phe | Ile | Glu | Trp | Leu | Leu | Asn | Thr | Gly | His | | |
| 239 | 239 | G | Lys | Arg | Ala | His | Glu | Phe | Val | Glu | Trp | Leu | Leu | Asn | Thr | Gly | His | | |
| 240 | 240 | G | Lys | Arg | Ala | His | Glu | Phe | Val | Glu | Trp | Leu | Leu | Asn | Thr | Gly | His | | |
| 241 | 241 | G | Arg | Arg | Ala | His | Glu | Phe | Val | Glu | Trp | Leu | Leu | Asn | Gly | Gly | His | | |
| 242 | 242 | G | Arg | Arg | Ala | His | Glu | Phe | Val | Glu | Trp | Leu | Leu | Asn | Thr | Gly | His | NH2 | |
| 243 | 243 | G | Lys | Lys | Ala | His | Glu | Phe | Val | Glu | Trp | Leu | Leu | Asn | Thr | Gly | His | | |
| 244 | 244 | G | Arg | Arg | Ala | His | Glu | Phe | Ile | Glu | Trp | Leu | Leu | Asn | Gly | His | His | | |
| 245 | 245 | G | Arg | Arg | Ala | His | Glu | Phe | Val | Glu | Trp | Leu | Leu | Asn | Thr | Gly | His | | |
| 246 | 246 | G | Arg | Arg | Ala | His | Glu | Phe | Val | Glu | Trp | Leu | Leu | Asn | Gly | Gly | His | | |
| 247 | 247 | G | Lys | Arg | Ala | His | Glu | Phe | Ile | Glu | Trp | Leu | Leu | Asn | Thr | Gly | His | | |
| 248 | 248 | G | Arg | Arg | Ala | His | Glu | Phe | Ile | Glu | Trp | Leu | Leu | Asn | Gly | His | His | NH2 | |
| 249 | 249 | G | Arg | Arg | Ala | His | Glu | Phe | Ile | Glu | Trp | Leu | Leu | Asn | Gly | His | His | | |
| 250 | 250 | G | Arg | Arg | Ala | His | Glu | Phe | Ile | Glu | Trp | Leu | Leu | Asn | Thr | His | NH2 | NH2 | |

Fig. 1 (continued)

| SEQ ID NO. | Analogue no. | G no. | hGCGr cAMP | | hGLP-1r cAMP | | Mouse food intake inhibition (500 nmol/kg) | | | | | | | Rat food intake inhibition (500 nmol/kg with 1:1 Zn) | | | | | | |
|---|---|---|---|---|---|---|---|---|---|---|---|---|---|---|---|---|---|---|---|---|
| | | | vs hGCG | n | vs hGLP-1 | n | 0-1 | 0-4 | 0.8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 201 | | G | 0.5 | 3 | 9.3 | 2 | 77 | 87.5 | 79 | 60.5 | -6 | | | | | | | | | | | | |
| 202 | | G | 0.9 | 3 | 12.7 | 2 | 71 | 77 | 70.5 | 56 | -5 | | | | | | | | | | | | |
| 203 | | G | 0.9 | 4 | 8.5 | 2 | 60.5 | 73.5 | 73.5 | 74.5 | 1 | | | | | | | | | | | | |
| 204 | 1478 | G | 0.8 | 2 | 634.1 | 1 | 88 | 72 | 65 | 49 | 10 | | | | | | | | | | | | |
| 205 | 1481 | G | 0.7 | 4 | | | 55 | 27 | 3 | -52 | -8 | | | | | | | | | | | | |
| 206 | 1482 | G | 1.0 | 4 | 6.6 | 1 | | | | | | | | | | | | | | | | | |
| 207 | 1488 | G | 1.4 | 4 | 2.4 | 2 | 83.5 | 72 | 62 | 47.5 | -17 | | | | | | | | | | | | |
| 208 | 1489 | G | 0.4 | 3 | 2.8 | 1 | 87 | 76 | 20 | -109 | -19 | | | | | | | | | | | | |
| 209 | 1491 | G | 2.8 | 2 | | | | | | | | | | | | | | | | | | | |
| 210 | 1492 | G | 0.9 | 3 | | | 89 | 97 | 99 | 103 | 21 | | | | | | | | | | | | |
| 211 | 1493 | G | 0.8 | 3 | | | 100 | 18 | 22 | 34 | 8 | | | | | | | | | | | | |
| 212 | 1494 | G | 0.7 | 2 | | | 75 | 55 | 11 | -69 | -7 | | | | | | | | | | | | |
| 213 | 1495 | G | 0.6 | 2 | | | 74.5 | 80.5 | 74.5 | 64 | 6.5 | | | | | | | | | | | | |
| 214 | 1496 | G | 0.9 | 2 | | | 67 | 64 | 34 | -25 | 10 | | | | | | | | | | | | |
| 215 | 1497 | G | 0.7 | 2 | | | 52 | 48 | 28 | -26 | -4 | | | | | | | | | | | | |
| 216 | 1498 | G | 0.3 | 2 | 2.0 | 1 | 83 | 89 | 84 | 74 | -6 | | | | | | | | | | | | |
| 217 | 1499 | G | 0.8 | 4 | 5.1 | 3 | 66 | 82 | 83.6667 | 87 | -2.3333 | | | -11 | 0.5 | 1 | -8 | 29.5 | 54 | 6 | 2 | 18 | 18 | 13 |
| 218 | 1500 | G | 0.6 | 4 | 1.3 | 3 | 80.6667 | 77.3333 | 74.6667 | 71.6667 | 14.6667 | 37 | | 9 | 0 | 6 | 36.5 | 32 | 67.5 | 21 | 1 | 21.5 | 31 | 19.5 |
| 219 | 1501 | G | 1.1 | 3 | 1.4 | 2 | 87 | 79.5 | 76 | 72.5 | -18.5 | | | | | | | | | | | | |
| 220 | 1502 | G | 1.8 | 2 | | | | | | | | | | | | | | | | | | | |
| 221 | 1503 | G | 1.8 | 2 | | | | | | | | | | | | | | | | | | | |
| 222 | 1504 | G | 0.8 | 2 | | | | | | | | | | | | | | | | | | | |
| 223 | 1505 | G | 0.4 | 2 | | | 72 | 84 | 90 | 100 | 30 | | | | | | | | | | | | |
| 224 | 1506 | G | 0.4 | 3 | | | 92.5 | 95.5 | 97.5 | 101 | 22 | | | | | | | | | | | | |
| 225 | 1507 | G | 0.5 | 3 | | | 63 | 79 | 87 | 102 | -11 | | | | | | | | | | | | |
| 226 | 1508 | G | 0.4 | 3 | 1.2 | 2 | 83.5 | 68.5 | 59 | 47 | -37 | | | | | | | | | | | | |
| 227 | 1509 | G | 0.6 | 3 | 3.0 | 4 | 85.6667 | 80 | 74.6667 | 68 | -8.3333 | | | | | | | | | | | | |
| 228 | 1510 | G | 0.8 | 6 | 10.3 | 5 | 87.5 | 92.25 | 90.5 | 87 | 31.25 | -34.255 | | 14.5 | 13.5 | 18 | 27 | 27.5 | 59.5 | 7 | 1.5 | 23.5 | 22.5 | 16 |
| 229 | 1511 | G | 0.6 | 4 | 8.6 | 3 | 45.4167 | 19.0962 | 42.5986 | 3.88889 | 13.8841 | | 0.4329 | 13.7972 | 12.5 | 27.5812 | 28.8618 | 2.90447 | -13.2 | -3.3058 | 3.40269 | 13.4605 | 3.28325 | 3.0403 |
| 230 | 1512 | G | 1.4 | 3 | 8.0 | 2 | 0 | 0 | 38.9527 | 0 | 7.89043 | | | 0 | 0 | 13 | 0 | 0 | 0 | 0 | 7 | 6 | 3 | 4 |
| 231 | 1513 | G | 1.6 | 3 | | | 0 | 0 | 33.9719 | 0 | 15.5571 | | | 0 | 0 | 17 | 0 | 0 | 0 | 0 | 0 | 8 | 1 | 1 |
| 232 | 1516 | G | 0.5 | 5 | 4.0 | 5 | 0 | 81 | 70 | 52 | -8 | | | | | | | | | | | | |
| 233 | 1517 | G | 1.2 | 3 | 30.1 | 3 | 72 | 79.5 | 79 | 78 | 7 | | | | | | | | | | | | |
| 234 | 1518 | G | 1.0 | 3 | | | | | | | | | | | | | | | | | | | |
| 235 | 1519 | G | 3.0 | 3 | | | | | | | | | | | | | | | | | | | |
| 236 | 1520 | G | 0.5 | 3 | | | 89 | 88 | 47 | -26 | -22 | | | | | | | | | | | | |
| 237 | 1521 | G | 0.8 | 2 | | | 91 | 94 | 26 | -98 | -13 | | | | | | | | | | | | |
| 238 | 1522 | G | 0.6 | 3 | | | 87.5 | 89.5 | 61 | 13 | -14.5 | | | | | | | | | | | | |
| 239 | 1523 | G | 3.1 | 2 | | | | | | | | | | | | | | | | | | | |
| 240 | 1524 | G | 0.9 | 3 | | | 88 | 95 | 97 | 99 | 25 | | | | | | | | | | | | |
| 241 | 1525 | G | 1.8 | 2 | | | | | | | | | | | | | | | | | | | |
| 242 | 1526 | G | 1.4 | 2 | | | | | | | | | | | | | | | | | | | |
| 243 | 1527 | G | 7.4 | 3 | | | | | | | | | | | | | | | | | | | |
| 244 | 1528 | C | 0.7 | 2 | | | | | | | | | | | | | | | | | | | |
| 245 | 1529 | G | 0.8 | 2 | | | 92 | 19 | 24 | 37 | 4 | | | | | | | | | | | | |
| 246 | 1530 | G | 0.7 | 3 | | | 67 | 52 | 17 | -48 | -13 | | | | | | | | | | | | |
| 247 | 1531 | G | 0.9 | 2 | | | 0 | 0 | 0 | 0 | 0 | | | | | | | | | | | | |
| 248 | 1532 | C | 1.2 | 2 | | | 0 | 0 | 0 | 0 | 0 | | | | | | | | | | | | |
| 249 | 1533 | C | 2.2 | 2 | | | 0 | 0 | 0 | 0 | 0 | | | | | | | | | | | | |
| 250 | 1534 | C | 1.5 | 2 | | | 0 | 0 | 0 | 0 | 0 | | | | | | | | | | | | |

Fig. 1 (continued)

| SEQ ID NO. | Analogue no. | G no. |  | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|---|
| 251 | 251 | G | 1535 | His | Ser | Gln | Gly | Thr | Phe | Thr | Ser | Asp | Leu | Ser | His | Gln | Leu | Asp | Ser |
| 252 | 252 | G | 1536 | His | Ser | Gln | Gly | Thr | Phe | Thr | Ser | Asp | Leu | Ser | Arg | Gln | Leu | Asp | Ser |
| 253 | 253 | G | 1537 | His | Ser | Gln | Gly | Thr | Phe | Thr | Ser | Asp | Leu | Ser | Arg | His | Leu | Asp | Ser |
| 254 | 254 | G | 1538 | His | Ser | Gln | Gly | Thr | Phe | Thr | Ser | Asp | Leu | Ser | Arg | Gln | Leu | Asp | Ser |
| 255 | 255 | G | 1539 | His | Ser | Gln | Gly | Thr | Phe | Thr | Ser | Asp | Leu | Ser | Arg | Gln | Leu | Asp | Ser |
| 256 | 256 | G | 1540 | His | Ser | Gln | Gly | Thr | Phe | Thr | Ser | Asp | Leu | Ser | Arg | Gln | Leu | Asp | Glu |
| 257 | 257 | G | 1545 | His | Ser | Gln | Gly | Thr | Phe | Thr | Ser | Asp | Leu | Ser | Arg | Gln | Leu | Asp | Glu |
| 258 | 258 | G | 1546 | His | Ser | Gln | Gly | Thr | Phe | Thr | Ser | Asp | Tyr | Ser | Lys | Gln | Leu | Asp | Ser |
| 259 | 259 | G | 1550 | His | Ser | Gln | Gly | Thr | Phe | Thr | Ser | Asp | Leu | Ser | Lys | Gln | Leu | Asp | Ser |
| 260 | 260 | G | 1551 | His | Ser | Gln | Gly | Thr | Phe | Thr | Ser | Asp | Leu | Ser | Arg | Gln | Leu | Asp | Glu |
| 261 | 261 | G | 1552 | His | Ser | Gln | Gly | Thr | Phe | Thr | Ser | Asp | Tyr | Ser | Arg | Tyr | Leu | Asp | Ser |
| 262 | 262 | G | 1553 | His | Ser | Gln | Gly | Thr | Phe | Thr | Ser | Asp | Tyr | Ser | Arg | His | Leu | Asp | Ser |
| 263 | 263 | G | 1554 | His | Ser | Gln | Gly | Thr | Phe | Thr | Ser | Asp | Tyr | Ser | Lys | Tyr | Leu | Asp | Ser |
| 264 | 264 | G | 1555 | His | Ser | Gln | Gly | Thr | Phe | Thr | Ser | Asp | Tyr | Ser | Arg | Tyr | Leu | Asp | Ser |
| 265 | 265 | G | 1556 | His | Ser | Gln | Gly | Thr | Phe | Thr | Ser | Asp | Leu | Ser | Arg | Gln | Leu | Glu | Gln |
| 266 | 266 | G | 1557 | His | Ser | Gln | Gly | Thr | Phe | Thr | Ser | Asp | Tyr | Ser | Arg | Gln | Leu | Glu | Gln |
| 267 | 267 | G | 1558 | His | Ser | Gln | Gly | Thr | Phe | Thr | Ser | Asp | Leu | Ser | Arg | Gln | Leu | Glu | Gln |
| 268 | 268 | G | 1559 | His | Ser | Gln | Gly | Thr | Phe | Thr | Ser | Asp | Leu | Ser | Arg | Gln | Leu | Asp | Gln |
| 269 | 269 | G | 1560 | His | Ser | Gln | Gly | Thr | Phe | Thr | Ser | Asp | Leu | Ser | Arg | Gln | Leu | Glu | Gln |
| 270 | 270 | G | 1561 | His | Ser | Gln | Gly | Thr | Phe | Thr | Ser | Asp | Leu | Ser | Arg | Gln | Leu | Asp | Gln |
| 271 | 271 | G | 1562 | His | Ser | Gln | Gly | Thr | Phe | Thr | Ser | Asp | Leu | Ser | Lys | Gln | Leu | Asp | Gln |
| 272 | 272 | G | 1563 | His | Ser | Gln | Gly | Thr | Phe | Thr | Ser | Asp | Tyr | Ser | Lys | Gln | Leu | Asp | Gln |
| 273 | 273 | G | 1564 | His | Ser | Gln | Gly | Thr | Phe | Thr | Ser | Asp | Tyr | Ser | Lys | Tyr | Leu | Asp | Gln |
| 274 | 274 | G | 1565 | His | Ser | Gln | Gly | Thr | Phe | Thr | Ser | Asp | Tyr | Ser | Lys | Tyr | Leu | Asp | Gln |
| 275 | 275 | G | 1566 | His | Ser | Gln | Gly | Thr | Phe | Thr | Ser | Asp | Tyr | Ser | Lys | Tyr | Leu | Asp | Gln |
| 276 | 276 | G | 1567 | His | Ser | Gln | Gly | Thr | Phe | Thr | Ser | Asp | Tyr | Ser | Lys | Tyr | Leu | Asp | Gln |
| 277 | 277 | G | 1568 | His | Ser | Gln | Gly | Thr | Phe | Thr | Ser | Asp | Leu | Ser | Arg | Gln | Leu | Asp | Gln |
| 278 | 278 | G | 1569 | His | Ser | Gln | Gly | Thr | Phe | Thr | Ser | Asp | Tyr | Ser | Arg | Tyr | Leu | Glu | Gln |
| 279 | 279 | G | 1570 | His | Ser | Gln | Gly | Thr | Phe | Thr | Ser | Asp | Leu | Ser | Arg | Gln | Leu | Glu | Gln |
| 280 | 280 | G | 1571 | His | Ser | Gln | Gly | Thr | Phe | Thr | Ser | Asp | Tyr | Ser | Arg | Gln | Leu | Glu | Ser |
| 281 | 281 | G | 1572 | His | Ser | Gln | Gly | Thr | Phe | Thr | Ser | Asp | Leu | Ser | Arg | Gln | Leu | Glu | Gln |
| 282 | 282 | G | 1573 | His | Ser | Gln | Gly | Thr | Phe | Thr | Ser | Asp | Tyr | Ser | Lys | Tyr | Leu | Glu | Gln |
| 283 | 283 | G | 1574 | His | Ser | Gln | Gly | Thr | Phe | Thr | Ser | Asp | Tyr | Ser | Lys | Gln | Leu | Glu | Gln |
| 284 | 284 | G | 1575 | His | Ser | Gln | Gly | Thr | Phe | Thr | Ser | Asp | Leu | Ser | Arg | Tyr | Leu | Glu | Gln |
| 285 | 285 | G | 1576 | His | Ser | Gln | Gly | Thr | Phe | Thr | Ser | Asp | Tyr | Ser | Lys | Tyr | Leu | Asp | Gln |
| 286 | 286 | G | 1577 | His | Ser | Gln | Gly | Thr | Phe | Thr | Ser | Asp | Tyr | Ser | Arg | Tyr | Leu | Glu | Gln |
| 287 | 287 | G | 1578 | His | Ser | Gln | Gly | Thr | Phe | Thr | Ser | Asp | Tyr | Ser | Lys | Tyr | Leu | Glu | Gln |
| 288 | 288 | G | 1579 | His | Ser | Gln | Gly | Thr | Phe | Thr | Ser | Asp | Tyr | Ser | Arg | Tyr | Leu | Glu | Gln |
| 289 | 289 | G | 1580 | His | Ser | Gln | Gly | Thr | Phe | Thr | Ser | Asp | Tyr | Ser | Lys | Tyr | Leu | Glu | Gln |
| 290 | 290 | G | 1581 | His | Ser | Gln | Gly | Thr | Phe | Thr | Ser | Asp | Tyr | Ser | Lys | Tyr | Leu | Glu | Gln |
| 291 | 291 | G | 1582 | His | Ser | Gln | Gly | Thr | Phe | Thr | Ser | Asp | Tyr | Ser | Lys | Tyr | Leu | Asp | Gln |
| 292 | 292 | G | 1583 | His | Ser | Gln | Gly | Thr | Phe | Thr | Ser | Asp | Tyr | Ser | Arg | His | Leu | Asp | Ser |
| 293 | 293 | G | 1584 | His | Ser | Gln | Gly | Thr | Phe | Thr | Ser | Asp | Tyr | Ser | Arg | His | Leu | Asp | Ser |
| 294 | 294 | G | 1585 | His | Ser | Gln | Gly | Thr | Phe | Thr | Ser | Asp | Tyr | Ser | Arg | His | Leu | Asp | Ser |
| 295 | 295 | G | 1586 | His | Ser | Gln | Gly | Thr | Phe | Thr | Ser | Asp | Tyr | Ser | His | Tyr | Leu | Asp | Ser |

Fig. 1 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 251 | 251 | G | Arg | Arg | Ala | His | Glu | Phe | Ile | Glu | Trp | Leu | Leu | Asn | Thr | His | NH2 | | |
| 252 | 252 | G | Arg | Arg | Ala | His | Glu | Phe | Ile | Glu | Trp | Leu | Leu | Asn | Thr | His | His | NH2 | |
| 253 | 253 | G | Lys | Arg | Ala | His | Glu | Phe | Val | Gln | Trp | Leu | Leu | Asn | Thr | His | His | NH2 | |
| 254 | 254 | G | Arg | Arg | Ala | His | Glu | Phe | Ile | Glu | Trp | Leu | Leu | Asn | Thr | His | His | | |
| 255 | 255 | G | Arg | Arg | Ala | His | Glu | Phe | Val | Gln | Trp | Leu | Leu | Asn | Thr | His | NH2 | | |
| 256 | 256 | G | Arg | Arg | Ala | His | Glu | Phe | Val | Glu | Trp | Leu | Leu | Asn | Thr | His | His | NH2 | |
| 257 | 257 | G | Arg | Arg | Ala | His | Glu | Phe | Val | Gln | Trp | Leu | Leu | Asn | Thr | His | His | NH2 | |
| 258 | 258 | G | Arg | Arg | Ala | His | Glu | Phe | Val | Gln | Trp | Leu | Leu | Asn | Thr | His | His | NH2 | |
| 259 | 259 | G | Arg | Arg | Ala | His | Glu | Phe | Val | Gln | Trp | Leu | Leu | Asn | Thr | His | His | | |
| 260 | 260 | G | Arg | Arg | Ala | His | Glu | Phe | Val | Gln | Trp | Leu | Leu | Asn | Thr | His | His | | |
| 261 | 261 | G | Lys | Arg | Ala | His | Glu | Phe | Val | Gln | Trp | Leu | Leu | Asn | Thr | His | His | | |
| 262 | 262 | G | Lys | Arg | Ala | His | Glu | Phe | Val | Gln | Trp | Leu | Leu | Asn | Thr | His | His | | |
| 263 | 263 | G | Lys | Arg | Ala | His | Glu | Phe | Val | Gln | Trp | Leu | Leu | Asn | Thr | His | His | | |
| 264 | 264 | G | Lys | Arg | Ala | His | Glu | Phe | Val | Gln | Trp | Leu | Leu | Asn | Thr | His | His | | |
| 265 | 265 | G | Lys | Arg | Ala | His | Glu | Phe | Val | Gln | Trp | Leu | Leu | Asn | Thr | His | His | NH2 | |
| 266 | 266 | G | Arg | Arg | Ala | His | Glu | Phe | Val | Gln | Trp | Leu | Leu | Asn | Thr | His | His | NH2 | |
| 267 | 267 | G | Arg | Arg | Ala | His | Glu | Phe | Val | Glu | Trp | Leu | Leu | Asn | Gly | Gly | His | | |
| 268 | 268 | G | Arg | Arg | Ala | His | Glu | Phe | Val | Gln | Trp | Leu | Leu | Asn | Gly | Gly | His | | |
| 269 | 269 | G | Arg | Arg | Ala | His | Glu | Phe | Val | Glu | Trp | Leu | Leu | Asn | Gly | Gly | His | | |
| 270 | 270 | G | Lys | Arg | Ala | His | Glu | Phe | Val | Gln | Trp | Leu | Leu | Asn | Gly | Gly | His | | |
| 271 | 271 | G | Arg | Arg | Ala | His | Glu | Phe | Val | Glu | Trp | Leu | Leu | Asn | Thr | His | His | | |
| 272 | 272 | G | Arg | Arg | Ala | His | Glu | Phe | Val | Gln | Trp | Leu | Leu | Asn | Thr | His | His | | |
| 273 | 273 | G | Lys | Arg | Ala | His | Glu | Phe | Val | Glu | Trp | Leu | Leu | Asn | Gly | Gly | His | | |
| 274 | 274 | G | Arg | Arg | Ala | His | Glu | Phe | Val | Glu | Trp | Leu | Leu | Asn | Thr | His | His | | |
| 275 | 275 | G | Arg | Arg | Ala | His | Glu | Phe | Val | Glu | Trp | Leu | Leu | Asn | Gly | His | His | | |
| 276 | 276 | G | Lys | Arg | Ala | His | Glu | Phe | Val | Glu | Trp | Leu | Leu | Asn | Thr | His | His | | |
| 277 | 277 | G | Arg | Arg | Ala | His | Glu | Phe | Val | Gln | Trp | Leu | Leu | Asn | Thr | His | His | | |
| 278 | 278 | G | Arg | Arg | Ala | His | Glu | Phe | Val | Glu | Trp | Leu | Leu | Asn | Gly | His | His | NH2 | |
| 279 | 279 | G | Arg | Arg | Ala | His | Glu | Phe | Ile | Glu | Trp | Leu | Leu | Asn | Gly | Gly | His | NH2 | |
| 280 | 280 | G | Arg | Arg | Ala | His | Glu | Phe | Ile | Glu | Trp | Leu | Leu | Asn | Gly | Gly | His | NH2 | |
| 281 | 281 | G | Arg | Arg | Ala | His | Glu | Phe | Val | Glu | Trp | Leu | Leu | Asn | Gly | Gly | His | | |
| 282 | 282 | G | Arg | Arg | Ala | His | Glu | Phe | Val | Glu | Trp | Leu | Leu | Asn | Gly | Gly | His | NH2 | |
| 283 | 283 | G | Arg | Arg | Ala | His | Glu | Phe | Val | Gln | Trp | Leu | Leu | Asn | Gly | His | His | NH2 | |
| 284 | 284 | G | Arg | Arg | Ala | His | Glu | Phe | Val | Gln | Trp | Leu | Leu | Asn | Gly | His | His | NH2 | |
| 285 | 285 | G | Arg | Arg | Ala | His | Glu | Phe | Val | Gln | Trp | Leu | Leu | Asn | Thr | His | His | NH2 | |
| 286 | 286 | G | Arg | Arg | Ala | His | Glu | Phe | Val | Gln | Trp | Leu | Leu | Asn | Gly | His | His | NH2 | |
| 287 | 287 | G | Arg | Arg | Ala | His | Glu | Phe | Val | Glu | Trp | Leu | Leu | Asn | Gly | Gly | His | NH2 | |
| 288 | 288 | G | Arg | Arg | Ala | His | Glu | Phe | Val | Gln | Trp | Leu | Leu | Asn | Thr | His | His | NH2 | |
| 289 | 289 | G | Arg | Arg | Ala | His | Glu | Phe | Val | Gln | Trp | Leu | Leu | Asn | Gly | Gly | His | | |
| 290 | 290 | G | Arg | Arg | Ala | His | Glu | Phe | Val | Glu | Trp | Leu | Leu | Asn | Gly | Gly | His | | |
| 291 | 291 | G | Arg | Arg | Ala | His | Glu | Phe | Val | Gln | Trp | Leu | Leu | Asn | Thr | His | NH2 | | |
| 292 | 292 | G | Lys | Arg | Ala | His | Glu | Phe | Val | Glu | Trp | Leu | Leu | Asn | Gly | Gly | His | NH2 | |
| 293 | 293 | G | Lys | Arg | Ala | His | Glu | Phe | Val | Glu | Trp | Leu | Leu | Asn | Thr | His | His | NH2 | |
| 294 | 294 | G | Lys | Arg | Ala | His | Asp | Phe | Val | Glu | Trp | Leu | Leu | Asn | Gly | Gly | His | NH2 | |
| 295 | 295 | G | Arg | Arg | Ala | His | Glu | Phe | Ile | Gln | Trp | Leu | Leu | Asn | Gly | His | His | | |

Fig. 1 (continued)

| SEQ ID NO. | Analogue no. | G no. | hGCGr cAMP vs hGCG | n | hGLP-1r cAMP vs hGLP-1 | n | Mouse food intake inhibition (500nmol/kg) 0-1 | 0-4 | 0-8 | 4-8 | 8-24 | 24-32 | 0-24 | Rat food intake inhibition (500 nmol/kg with 1:1 Zn) 0-1 | 0-4 | 0-8 | 4-8 | 8-24 | 24-32 | 32-48 | 48-72 | 0-24 | 0-48 | 0-72 |
|---|---|---|---|---|---|---|---|---|---|---|---|---|---|---|---|---|---|---|---|---|---|---|---|---|
| 251 | 1535 | G | 3.0 | 2 | | | | | | | | | | | | | | | | | | | | |
| 252 | 1536 | G | 2.7 | 2 | | | | | | | | | | | | | | | | | | | | |
| 253 | 1537 | G | 1.6 | 2 | | | | | | | | | | | | | | | | | | | | |
| 254 | 1538 | G | 16.9 | 1 | | | | | | | | | | | | | | | | | | | | |
| 255 | 1539 | G | 2.0 | 2 | | | | | | | | | | | | | | | | | | | | |
| 256 | 1540 | G | 1.5 | 2 | | | | | | | | | | | | | | | | | | | | |
| 257 | 1545 | G | 1.9 | 2 | | | | | | | | | | | | | | | | | | | | |
| 258 | 1546 | G | 2.1 | 2 | | | | | | | | | | | | | | | | | | | | |
| 259 | 1550 | G | 0.8 | 2 | | | 33 | 26 | 13 | -10 | -12 | | | | | | | | | | | | | |
| 260 | 1551 | G | 1.9 | 2 | | | | | | | | | | | | | | | | | | | | |
| 261 | 1552 | G | 2.3 | 2 | | | | | | | | | | | | | | | | | | | | |
| 262 | 1553 | G | 1.8 | 2 | | | | | | | | | | | | | | | | | | | | |
| 263 | 1554 | G | 0.7 | 4 | 27.8 | 3 | 84.5 | 81 | 65 | 35.5 | -7.5 | | -14 | | | -3 | -24 | 25 | 36 | -29 | -8 | 14 | 2 | |
| 264 | 1555 | G | 0.4 | 3 | 4.4 | 3 | 83 | 88.3 | 87.0 | 84.3 | 0.7 | | | | | | | | | | | | | |
| 265 | 1556 | G | 0.9 | 4 | 19.7 | 3 | 72.5 | 85.5 | 90.5 | 99.5 | -12 | | | | | | | | | | | | | |
| 266 | 1557 | G | 4.5 | 2 | | | | | | | | | | | | | | | | | | | | |
| 267 | 1558 | G | 6.8 | 1 | | | | | | | | | | | | | | | | | | | | |
| 268 | 1559 | G | 2.5 | 1 | | | | | | | | | | | | | | | | | | | | |
| 269 | 1560 | G | 2.5 | 2 | | | | | | | | | | | | | | | | | | | | |
| 270 | 1561 | G | 2.9 | 2 | | | | | | | | | | | | | | | | | | | | |
| 271 | 1562 | G | 0.4 | 2 | | | 81 | 81 | 37 | -32 | -10 | | | | | | | | | | | | | |
| 272 | 1563 | G | 0.3 | 3 | 87.2 | 1 | 36.5 | 23.0 | 11.7 | 1.0 | 8.3 | -18.9 | | | | | | | | | | | | |
| 273 | 1564 | G | 0.5 | 2 | | | 88.0 | 91.7 | 73.2 | 53.9 | 20.0 | 11.7 | | | | | | | | | | | | |
| 274 | 1565 | G | 1.4 | 3 | | | | | | | | | | | | | | | | | | | | |
| 275 | 1566 | G | 1.9 | 3 | | | | | | | | | | | | | | | | | | | | |
| 276 | 1567 | G | 1.4 | 3 | | | | | | | | | | | | | | | | | | | | |
| 277 | 1568 | G | 4.7 | 2 | | | | | | | | | | | | | | | | | | | | |
| 278 | 1569 | G | 2.0 | 2 | | | | | | | | | | | | | | | | | | | | |
| 279 | 1570 | G | 2.3 | 2 | | | | | | | | | | | | | | | | | | | | |
| 280 | 1571 | G | 1.4 | 2 | | | | | | | | | | | | | | | | | | | | |
| 281 | 1572 | G | 0.7 | 2 | | | 82 | 96 | 97 | 101 | 28 | | | | | | | | | | | | | |
| 282 | 1573 | G | 4.7 | 2 | | | 62 | 17 | -6 | -36 | -22 | | | | | | | | | | | | | |
| 283 | 1574 | G | 3.4 | 2 | | | 83 | 91 | 93.5 | 99 | 73 | -55 | | | | | | | | | | | | |
| 284 | 1575 | G | 1.8 | 2 | | | 91 | 95 | 95 | 95 | -1 | | | | | | | | | | | | | |
| 285 | 1576 | G | 2.7 | 3 | | | | | | | | | | | | | | | | | | | | |
| 286 | 1577 | G | 2.2 | 2 | | | | | | | | | | | | | | | | | | | | |
| 287 | 1578 | G | 1.1 | 2 | | | 61.5 | 31 | 3 | -44.5 | -18.5 | 0 | 0 | | | | | | | | | | | | |
| 288 | 1579 | G | 0.6 | 2 | | | 45 | 40 | 15.5 | -23.5 | -11.5 | 0 | 0 | | | | | | | | | | | | |
| 289 | 1580 | G | 1.2 | 2 | | | | | | | | | | | | | | | | | | | | |
| 290 | 1581 | G | 1.0 | 2 | | | | | | | | | | | | | | | | | | | | |
| 291 | 1582 | G | 0.6 | 3 | | | | | | | | | | | | | | | | | | | | |
| 292 | 1583 | G | 1.4 | 2 | | | | | | | | | | | | | | | | | | | | |
| 293 | 1584 | G | 0.6 | 4 | | | 69 | 80.3333 | 85 | 94 | 56 | 0 | | | | | | | | | | | | |
| 294 | 1585 | G | 0.9 | 2 | 42.9 | 2 | | | | | | | | -3.5 | 5.5 | 0.5 | -22.5 | 30.5 | 49.5 | 3 | 1.5 | 18.5 | 17 | 12.5 |
| 295 | 1586 | G | 0.8 | 5 | 2.3 | 3 | | | | | | | | | | | | | | | | | | |

Fig. 1 (continued)

| SEQ ID NO. | Analogue no. | G no. | | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|---|
| 296 | 296 | G | 1587 | His | Ser | Gln | Gly | Thr | Phe | Thr | Ser | Asp | Tyr | Ser | His | Tyr | Leu | Asp | Glu |
| 297 | 297 | G | 1588 | His | Ser | Gln | Gly | Thr | Phe | Thr | Ser | Asp | Tyr | Ser | His | Tyr | Leu | Asp | Gln |
| 298 | 298 | G | 1589 | His | Ser | Gln | Gly | Thr | Phe | Thr | Ser | Asp | Tyr | Ser | His | Tyr | Leu | Asp | Gln |
| 299 | 299 | G | 1590 | His | Ser | Gln | Gly | Thr | Phe | Thr | Ser | Asp | Tyr | Ser | His | Tyr | Leu | Asp | Gln |
| 300 | 300 | G | 1591 | His | Ser | Gln | Gly | Thr | Phe | Thr | Ser | Asp | Tyr | Ser | His | Tyr | Leu | Asp | Ser |
| 301 | 301 | G | 1592 | His | Ser | Gln | Gly | Thr | Phe | Thr | Ser | Asp | Tyr | Ser | His | Tyr | Leu | Asp | Ser |
| 302 | 302 | G | 1593 | His | Ser | Gln | Gly | Thr | Phe | Thr | Ser | Asp | Tyr | Ser | His | Tyr | Leu | Asp | Ser |
| 303 | 303 | G | 1594 | His | Ser | Gln | Gly | Thr | Phe | Thr | Ser | Asp | Tyr | Ser | His | Tyr | Leu | Asp | Ser |
| 304 | 304 | G | 1595 | His | Ser | Gln | Gly | Thr | Phe | Thr | Ser | Asp | Tyr | Ser | His | Tyr | Leu | Asp | Ser |
| 305 | 305 | G | 1596 | His | Ser | Gln | Gly | Thr | Phe | Thr | Ser | Asp | Tyr | Ser | Arg | Tyr | Leu | Asp | Glu |
| 306 | 306 | G | 1597 | His | Ser | Gln | Gly | Thr | Phe | Thr | Ser | Asp | Tyr | Ser | His | His | Leu | Asp | Glu |
| 307 | 307 | G | 1598 | His | Ser | Gln | Gly | Thr | Phe | Thr | Ser | Asp | Tyr | Ser | Arg | Tyr | Leu | Asp | Glu |
| 308 | 308 | G | 1599 | His | Ser | Gln | Gly | Thr | Phe | Thr | Ser | Asp | Tyr | Ser | Lys | Tyr | Leu | Asp | Glu |
| 309 | 309 | G | 1600 | His | Ser | Gln | Gly | Thr | Phe | Thr | Ser | Asp | Tyr | Ser | Arg | Tyr | Leu | Asp | Glu |
| 310 | 310 | G | 1601 | His | Ser | Gln | Gly | Thr | Phe | Thr | Ser | Asp | Tyr | Ser | Lys | Tyr | Leu | Asp | Glu |
| 311 | 311 | G | 1603 | His | Ser | Gln | Gly | Thr | Phe | Thr | Ser | Asp | Tyr | Ser | Arg | Tyr | Leu | Asp | Glu |
| 312 | 312 | G | 1606 | His | Ser | Gln | Gly | Thr | Phe | Thr | Ser | Asp | Tyr | Ser | Arg | Tyr | Leu | Asp | Glu |
| 313 | 313 | G | 1607 | His | Ser | Gln | Gly | Thr | Phe | Thr | Ser | Asp | Tyr | Ser | Lys | Tyr | Leu | Asp | Glu |
| 314 | 314 | G | 1608 | His | Ser | Gln | Gly | Thr | Phe | Thr | Ser | Asp | Tyr | Ser | Lys | His | Leu | Asp | Glu |
| 315 | 315 | G | 1609 | His | Ser | Gln | Gly | Thr | Phe | Thr | Ser | Asp | Tyr | Ser | Arg | Tyr | Leu | Asp | Glu |
| 316 | 316 | G | 1610 | His | Ser | Gln | Gly | Thr | Phe | Thr | Ser | Asp | Tyr | Ser | Arg | Tyr | Leu | Asp | Glu |
| 317 | 317 | G | 1611 | His | Ser | Gln | Gly | Thr | Phe | Thr | Ser | Asp | Tyr | Ser | Lys | Gln | Leu | Asp | Glu |
| 318 | 318 | G | 1612 | His | Ser | Gln | Gly | Thr | Phe | Thr | Ser | Asp | Tyr | Ser | Arg | Gln | Leu | Asp | Glu |
| 319 | 319 | G | 1613 | His | Ser | Gln | Gly | Thr | Phe | Thr | Ser | Asp | Tyr | Ser | Lys | Tyr | Leu | Asp | Glu |
| 320 | 320 | G | 1614 | His | Ser | Gln | Gly | Thr | Phe | Thr | Ser | Asp | Tyr | Ser | Lys | Gln | Leu | Asp | Glu |
| 321 | 321 | G | 1615 | His | Ser | Gln | Gly | Thr | Phe | Thr | Ser | Asp | Tyr | Ser | Lys | Gln | Leu | Asp | Glu |
| 322 | 322 | G | 1616 | His | Ser | Gln | Gly | Thr | Phe | Thr | Ser | Asp | Tyr | Ser | Lys | Tyr | Leu | Asp | Glu |
| 323 | 323 | G | 1617 | His | Ser | Gln | Gly | Thr | Phe | Thr | Ser | Asp | Tyr | Ser | His | Tyr | Leu | Asp | Glu |
| 324 | 324 | G | 1618 | His | Ser | Gln | Gly | Thr | Phe | Thr | Ser | Asp | Tyr | Ser | His | Tyr | Leu | Asp | Glu |
| 325 | 325 | G | 1619 | His | Ser | Gln | Gly | Thr | Phe | Thr | Ser | Asp | Tyr | Ser | Lys | Tyr | Leu | Asp | Glu |
| 326 | 326 | G | 1620 | His | Ser | Gln | Gly | Thr | Phe | Thr | Ser | Asp | Tyr | Ser | Lys | Tyr | Leu | Asp | Glu |
| 327 | 327 | G | 1621 | His | Ser | Gln | Gly | Thr | Phe | Thr | Ser | Asp | Tyr | Ser | Lys | Tyr | Leu | Asp | Glu |
| 328 | 328 | G | 1622 | His | Ser | Gln | Gly | Thr | Phe | Thr | Ser | Asp | Tyr | Ser | Lys | Tyr | Leu | Asp | Glu |
| 329 | 329 | G | 1623 | His | Ser | Gln | Gly | Thr | Phe | Thr | Ser | Asp | Tyr | Ser | Arg | Tyr | Leu | Asp | Glu |
| 330 | 330 | G | 1624 | His | Ser | Gln | Gly | Thr | Phe | Thr | Ser | Asp | Tyr | Ser | Arg | Tyr | Leu | Asp | Glu |
| 331 | 331 | G | 1625 | His | Ser | Gln | Gly | Thr | Phe | Thr | Ser | Asp | Tyr | Ser | Lys | Gln | Leu | Asp | Glu |
| 332 | 332 | G | 1626 | His | Ser | Gln | Gly | Thr | Phe | Thr | Ser | Asp | Tyr | Ser | Arg | Gln | Leu | Asp | Glu |
| 333 | 333 | G | 1627 | His | Ser | Gln | Gly | Thr | Phe | Thr | Ser | Asp | Tyr | Ser | Lys | Tyr | Leu | Asp | Glu |
| 334 | 334 | G | 1628 | His | Ser | Gln | Gly | Thr | Phe | Thr | Ser | Asp | Tyr | Ser | Lys | Tyr | Leu | Asp | Glu |
| 335 | 335 | G | 1629 | His | Ser | Gln | Gly | Thr | Phe | Thr | Ser | Asp | Tyr | Ser | Arg | Tyr | Leu | Asp | Glu |
| 336 | 336 | G | 1630 | His | Ser | Gln | Gly | Thr | Phe | Thr | Ser | Asp | Tyr | Ser | Arg | Tyr | Leu | Asp | Glu |
| 337 | 337 | G | 1631 | His | Ser | Gln | Gly | Thr | Phe | Thr | Ser | Asp | Tyr | Ser | Lys | Tyr | Leu | Asp | Glu |
| 338 | 338 | G | 1632 | His | Ser | Gln | Gly | Thr | Phe | Thr | Ser | Asp | Tyr | Ser | Arg | Gln | Leu | Asp | Glu |
| 339 | 339 | G | 1633 | His | Ser | Gln | Gly | Thr | Phe | Thr | Ser | Asp | Tyr | Ser | Arg | Tyr | Leu | Asp | Glu |
| 340 | 340 | G | 1634 | His | Ser | Gln | Gly | Thr | Phe | Thr | Ser | Asp | Tyr | Ser | His | Tyr | Leu | Asp | Glu |
| 341 | 341 | G | 1635 | His | Ser | Gln | Gly | Thr | Phe | Thr | Ser | Asp | Tyr | Ser | His | Tyr | Leu | Asp | Glu |
| 342 | 342 | G | 1636 | His | Ser | Gln | Gly | Thr | Phe | Thr | Ser | Asp | Tyr | Ser | Lys | Tyr | Leu | Asp | Glu |
| 343 | 343 | G | 1637 | His | Ser | Gln | Gly | Thr | Phe | Thr | Ser | Asp | Tyr | Ser | Lys | Tyr | Leu | Asp | Glu |
| 344 | 344 | G | 1641 | His | Ser | Gln | Gly | Thr | Phe | Thr | Ser | Asp | Tyr | Ser | His | His | Leu | Asp | Glu |
| 345 | 345 | G | 1642 | His | Ser | Gln | Gly | Thr | Phe | Thr | Ser | Asp | Tyr | Ser | His | Tyr | Leu | Asp | Glu |
| 346 | 346 | G | 1643 | His | Ser | Gln | Gly | Thr | Phe | Thr | Ser | Asp | Tyr | Ser | His | Tyr | Leu | Asp | Glu |
| 347 | 347 | G | 1644 | His | Ser | Gln | Gly | Thr | Phe | Thr | Ser | Asp | Tyr | Ser | Arg | Tyr | Leu | Asp | Glu |
| 348 | 348 | G | 1645 | His | Ser | Gln | Gly | Thr | Phe | Thr | Ser | Asp | Tyr | Ser | Arg | Tyr | Leu | Asp | Glu |
| 349 | 349 | G | 1646 | His | Ser | Gln | Gly | Thr | Phe | Thr | Ser | Asp | Tyr | Ser | Arg | His | Leu | Asp | Ser |
| 350 | 350 | G | 1647 | His | Ser | Gln | Gly | Thr | Phe | Thr | Ser | Asp | Tyr | Ser | Arg | Tyr | Leu | Asp | Ser |
| 351 | 351 | G | 1648 | His | Ser | Gln | Gly | Thr | Phe | Thr | Ser | Asp | Tyr | Ser | Lys | His | Leu | Asp | Glu |
| 352 | 352 | G | 1649 | His | Ser | Gln | Gly | Thr | Phe | Thr | Ser | Asp | Tyr | Ser | Lys | His | Leu | Asp | Glu |

Fig. 1 (continued)

| SEQ ID NO. | Analogue no. | C no. | | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|---|
| 296 | 296 | G | 1587 | Arg | Arg | Ala | His | Gln | Phe | Val | Gln | Trp | Leu | Leu | Asn | Gly | His | His | | |
| 297 | 297 | G | 1588 | Lys | Arg | Ala | His | Gln | Phe | Val | Gln | Trp | Leu | Leu | Asn | Gly | His | His | | |
| 298 | 298 | G | 1589 | Arg | Arg | Ala | His | Gln | Phe | Val | Gln | Trp | Leu | Leu | Asn | Gly | His | His | | |
| 299 | 299 | G | 1590 | Lys | Arg | Ala | His | Gln | Phe | Val | Gln | Trp | Leu | Leu | Asn | Gly | His | His | | |
| 300 | 300 | G | 1591 | Lys | Arg | Ala | His | Gln | Phe | Val | Gln | Trp | Leu | Leu | Lys | Gly | His | His | | |
| 301 | 301 | G | 1592 | Lys | Arg | Ala | His | Gln | Phe | Val | Gln | Trp | Leu | Leu | Asn | Gly | Lys | His | | |
| 302 | 302 | G | 1593 | Lys | Arg | Ala | His | Gln | Phe | Val | Gln | Trp | Leu | Leu | Asn | Gly | His | His | | |
| 303 | 303 | G | 1594 | Arg | Arg | Ala | His | Gln | Phe | Val | Gln | Trp | Leu | Leu | Asn | Gly | His | His | | |
| 304 | 304 | G | 1595 | Lys | Lys | Ala | His | Gln | Phe | Val | Gln | Trp | Leu | Leu | Asn | Gly | His | His | | |
| 305 | 305 | G | 1596 | Lys | Arg | Ala | His | Gln | Phe | Val | Gln | Trp | Leu | Leu | Asn | Gly | His | His | | |
| 306 | 306 | G | 1597 | Lys | Arg | Ala | His | Gln | Phe | Val | Gln | Trp | Leu | Leu | Asn | Gly | His | His | | |
| 307 | 307 | G | 1598 | Arg | Arg | Ala | His | Gln | Phe | Ile | Gln | Trp | Leu | Leu | Asn | Gly | His | His | NH2 | |
| 308 | 308 | G | 1599 | Arg | Arg | Ala | His | Gln | Phe | Val | Gln | Trp | Leu | Leu | Asn | Gly | His | His | NH2 | |
| 309 | 309 | G | 1600 | Arg | Arg | Ala | His | Gln | Phe | Val | Gln | Trp | Leu | Leu | Asn | Gly | His | His | NH2 | |
| 310 | 310 | G | 1601 | Arg | Arg | Ala | His | Gln | Phe | Val | Gln | Trp | Leu | Leu | Asn | Gly | His | His | NH2 | |
| 311 | 311 | C | 1603 | Lys | Arg | Ala | His | Gln | Phe | Val | Gln | Trp | Leu | Leu | Asn | Gly | His | His | | |
| 312 | 312 | G | 1606 | Arg | Arg | Ala | His | Gln | Phe | Ile | Gln | Trp | Leu | Leu | Asn | Thr | His | His | | |
| 313 | 313 | G | 1607 | Arg | Arg | Ala | His | Gln | Phe | Val | Gln | Trp | Leu | Leu | Asn | Thr | His | His | | |
| 314 | 314 | G | 1608 | Arg | Arg | Ala | His | Gln | Phe | Ile | Gln | Trp | Leu | Leu | Asn | Thr | His | His | | |
| 315 | 315 | G | 1609 | Arg | Arg | Ala | His | Gln | Phe | Val | Gln | Trp | Leu | Leu | Asn | Thr | His | His | | |
| 316 | 316 | G | 1610 | Arg | Arg | Ala | His | Gln | Phe | Ile | Gln | Trp | Leu | Leu | Asn | Gly | Gly | His | His | |
| 317 | 317 | C | 1611 | Lys | Arg | Ala | His | Gln | Phe | Val | Gln | Trp | Leu | Leu | Asn | Thr | His | His | | |
| 318 | 318 | G | 1612 | Lys | Arg | Ala | His | Gln | Phe | Ile | Gln | Trp | Leu | Leu | Asn | Thr | His | His | | |
| 319 | 319 | G | 1613 | Arg | Arg | Ala | His | Gln | Phe | Val | Gln | Trp | Leu | Leu | Asn | Thr | His | His | | |
| 320 | 320 | G | 1614 | Arg | Arg | Ala | His | Gln | Phe | Ile | Gln | Trp | Leu | Leu | Asn | Thr | His | His | | |
| 321 | 321 | G | 1615 | Lys | Arg | Ala | His | Gln | Phe | Val | Gln | Trp | Leu | Leu | Asn | Thr | His | His | | |
| 322 | 322 | G | 1616 | Arg | Arg | Ala | His | Gln | Phe | Ile | Gln | Trp | Leu | Leu | Asn | Thr | His | His | | |
| 323 | 323 | G | 1617 | Lys | Arg | Ala | His | Gln | Phe | Val | Gln | Trp | Leu | Leu | Asn | Thr | His | His | | |
| 324 | 324 | G | 1618 | Arg | Arg | Ala | His | Gln | Phe | Ile | Gln | Trp | Leu | Leu | Asn | Thr | His | His | | |
| 325 | 325 | G | 1619 | Lys | Arg | Ala | His | Gln | Phe | Val | Gln | Trp | Leu | Leu | Asn | Thr | His | His | | |
| 326 | 326 | G | 1620 | Lys | Arg | Ala | His | Gln | Phe | Val | Gln | Trp | Leu | Leu | Asn | Thr | His | His | | |
| 327 | 327 | G | 1621 | Arg | Arg | Ala | His | Gln | Phe | Val | Gln | Trp | Leu | Leu | Asn | Thr | His | His | | |
| 328 | 328 | G | 1622 | Lys | Arg | Ala | His | Gln | Phe | Ile | Gln | Trp | Leu | Leu | Asn | Thr | His | His | | |
| 329 | 329 | G | 1623 | Arg | Arg | Ala | His | Gln | Phe | Val | Gln | Trp | Leu | Leu | Asn | Thr | His | His | | |
| 330 | 330 | G | 1624 | Arg | Arg | Ala | His | Gln | Phe | Val | Gln | Trp | Leu | Leu | Asn | Thr | His | His | | |
| 331 | 331 | G | 1625 | Lys | Arg | Ala | His | Gln | Phe | Ile | Gln | Trp | Leu | Leu | Asn | Thr | His | His | NH2 | |
| 332 | 332 | G | 1626 | Arg | Arg | Ala | His | Gln | Phe | Val | Gln | Trp | Leu | Leu | Asn | Thr | His | His | NH2 | |
| 333 | 333 | G | 1627 | Lys | Arg | Ala | His | Gln | Phe | Ile | Gln | Trp | Leu | Leu | Asn | Thr | His | His | NH2 | |
| 334 | 334 | G | 1628 | Lys | Arg | Ala | His | Gln | Phe | Val | Gln | Trp | Leu | Leu | Asn | Thr | His | His | NH2 | |
| 335 | 335 | G | 1629 | Arg | Arg | Ala | His | Gln | Phe | Val | Gln | Trp | Leu | Leu | Asn | Thr | His | His | | |
| 336 | 336 | G | 1630 | Lys | Arg | Ala | His | Gln | Phe | Val | Gln | Trp | Leu | Leu | Asn | Gly | His | His | | |
| 337 | 337 | G | 1631 | Lys | Arg | Ala | His | Gln | Phe | Val | Gln | Trp | Leu | Leu | Asn | Gly | His | His | | |
| 338 | 338 | G | 1632 | Lys | Arg | Ala | His | Gln | Phe | Val | Gln | Trp | Leu | Leu | Asn | Gly | His | His | | |
| 339 | 339 | G | 1633 | Lys | Arg | Ala | His | Gln | Phe | Val | Gln | Trp | Leu | Leu | Asn | Gly | His | His | NH2 | |
| 340 | 340 | G | 1634 | Arg | Arg | Ala | His | Gln | Phe | Val | Gln | Trp | Leu | Leu | Asn | Gly | His | His | | |
| 341 | 341 | G | 1635 | Arg | Arg | Ala | His | Gln | Phe | Val | Gln | Trp | Leu | Leu | Asn | Gly | His | His | | |
| 342 | 342 | G | 1636 | Arg | Arg | Ala | His | Gln | Phe | Val | Gln | Trp | Leu | Leu | Asn | Gly | His | His | NH2 | |
| 343 | 343 | G | 1637 | Arg | Arg | Ala | His | Gln | Phe | Val | Gln | Trp | Leu | Leu | Asn | Thr | His | His | NH2 | |
| 344 | 344 | G | 1641 | Arg | Arg | Ala | His | Gln | Phe | Val | Gln | Trp | Leu | Leu | Asn | Gly | His | His | | |
| 345 | 345 | G | 1642 | Arg | Arg | Ala | His | Gln | Phe | Ile | Gln | Trp | Leu | Leu | Asn | Gly | His | His | His | |
| 346 | 346 | G | 1643 | Lys | Arg | Ala | His | Gln | Phe | Val | Gln | Trp | Leu | Leu | Asn | Thr | His | His | NH2 | |
| 347 | 347 | G | 1644 | Lys | Arg | Ala | His | Gln | Phe | Ile | Gln | Trp | Leu | Leu | Asn | Gly | His | His | | |
| 348 | 348 | G | 1645 | Arg | Arg | Ala | His | Gln | Phe | Val | Gln | Trp | Leu | Leu | Asn | Gly | His | His | | |
| 349 | 349 | G | 1646 | Arg | Arg | Ala | His | Gln | Phe | Ile | Gln | Trp | Leu | Leu | Asn | Thr | His | His | | |
| 350 | 350 | G | 1647 | Arg | Arg | Ala | His | Gln | Phe | Ile | Gln | Trp | Leu | Leu | Asn | Gly | His | His | | |
| 351 | 351 | G | 1648 | Arg | Arg | Ala | His | Gln | Phe | Ile | Gln | Trp | Leu | Leu | Asn | Thr | His | His | | |
| 352 | 352 | G | 1649 | Arg | Arg | Ala | His | Gln | Phe | Ile | Gln | Trp | Leu | Leu | Asn | Thr | His | His | | |

Fig. 1 (continued)

| SEQ ID NO. | Analogue nr. | G nr. |  | hGCGr cAMP vs hGCG | n | hGLP-1r cAMP vs hGLP-1 | n | Mouse food intake inhibition (500 nmol/kg) | | | | | | Rat food intake inhibition (500 nmol/kg with 1:1 Zn) | | | | | | | | |
|---|---|---|---|---|---|---|---|---|---|---|---|---|---|---|---|---|---|---|---|---|---|---|
| | | | | | | | | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 296 | 297 | G | | 11.6 | 2 | | | | | | | | | | | | | | | | | | | | |
| 297 | 298 | G | | 1.1 | 3 | 3.2 | 2 | 79 | 89 | 85.5 | 80.5 | 37.5 | | | | 3.5 | 2 | -14 | 30 | 49.5 | -2.5 | -6.5 | 18.5 | 15.5 | 9 |
| 298 | 299 | G | | 0.9 | 4 | 5.5 | 3 | 82.3 | 92.3 | 93.3 | 94.3 | 25.7 | | | | -1 | -6 | -29 | 45 | 70 | 0 | 0 | 24 | 0 | 13 |
| 299 | 300 | G | | 1.3 | 4 | 4.9 | 4 | 75.5 | 84.5 | 89.5 | 99 | 12 | | | 5 | | | | | | | | | | |
| 300 | 301 | C | | 1.2 | 3 | | | 85 | 67.5 | 57 | 44.5 | -23 | | | | | | | | | | | | | |
| 301 | 302 | C | | 3.2 | 3 | | | | | | | | | | | | | | | | | | | | |
| 302 | 303 | G | | 1.6 | 3 | | | | | | | | | | | | | | | | | | | | |
| 303 | 304 | G | | 1.4 | 2 | | | | | | | | | | | | | | | | | | | | |
| 304 | 305 | G | | 1.4 | 4 | | | | | | | | | | | | | | | | | | | | |
| 305 | 306 | G | | 0.7 | 2 | 18.2 | 2 | 85 | 91 | 70 | 33 | 7 | | | | | | | | | | | | | |
| 306 | 307 | G | | 0.8 | 3 | | | | | | | | | | | | | | | | | | | | |
| 307 | 308 | C | | 1.0 | 3 | | | | | | | | | 18 | 5 | -11 | -6 | 19 | 41 | 90 | 0 | 0 | 22 | 0 | 18 |
| 308 | 309 | G | | 0.9 | 4 | 2.3 | 4 | 83 | 90.7 | 92.3 | 95.7 | 76 | 7 | | | | | | | | | | | | |
| 309 | 310 | G | | 1.2 | 3 | | | | | | | | | | | | | | | | | | | | |
| 310 | 311 | C | | 0.7 | 2 | | | | | | | | -2 | | | | | | | | | | | | |
| 311 | 312 | G | | 0.6 | 3 | 11.2 | 1 | 91.5 | 95 | 97 | 99.5 | 74 | | | 9 | -5 | 2 | 37 | 46 | 80 | 0 | 0 | 29 | 0 | 26 |
| 312 | 313 | G | | 0.9 | 3 | | | 88 | 92 | 94 | 98 | 47 | -74 | | | | | | | | | | | | |
| 313 | 314 | G | | 1.0 | 3 | | | 94 | 96 | 98 | 100 | 95 | | | | | | | | | | | | | |
| 314 | 315 | G | | 1.8 | 2 | | | | | | | | | | | | | | | | | | | | |
| 315 | 316 | G | | 0.5 | 3 | | | 84 | 92 | 95 | 99 | 24 | | | | | | | | | | | | | |
| 316 | 317 | G | | 1.3 | 4 | | | | | | | | | | | | | | | | | | | | |
| 317 | 318 | G | | 2.4 | 2 | | | | | | | | | | | | | | | | | | | | |
| 318 | 319 | G | | 1.1 | 3 | | | 65 | 54 | 40 | 14 | -1 | | | | | | | | | | | | | |
| 319 | 320 | G | | 1.0 | 3 | | | | | | | | | | | | | | | | | | | | |
| 320 | 321 | G | | 1.0 | 2 | | | | | | | | | | | | | | | | | | | | |
| 321 | 322 | G | | 1.6 | 2 | | | | | | | | | | | | | | | | | | | | |
| 322 | 323 | G | | 0.8 | 2 | | | | | | | | | | | | | | | | | | | | |
| 323 | 324 | G | | 0.6 | 2 | | | | | | | | | | | | | | | | | | | | |
| 324 | 325 | G | | 1.1 | 3 | | | | | | | | | | | | | | | | | | | | |
| 325 | 326 | G | | 0.6 | 3 | 4.0 | 1 | 89.5 | 92.5 | 91 | 87 | 67.5 | 43 | 65 | 3 | 6 | 11 | 37 | 55 | 72 | 0 | 0 | 38 | 0 | 25 |
| 326 | 327 | G | | 1.2 | 5 | | | 79.5 | 86 | 84.5 | 79.5 | 64.5 | 66 | | | | | | | | | | | | |
| 327 | 328 | G | | 0.7 | 4 | | | 90 | 94.5 | 96 | 100.5 | 61.5 | 20 | | | | | | | | | | | | |
| 328 | 329 | G | | 0.7 | 4 | | | 95 | 98 | 97 | 96 | 45 | | | | | | | | | | | | | |
| 329 | 330 | G | | 0.8 | 4 | | | | | | | | | | | | | | | | | | | | |
| 330 | 331 | G | | 0.6 | 2 | | | 57 | 77 | 87 | 99 | 65 | 50 | | | | | | | | | | | | |
| 331 | 332 | G | | 2.9 | 4 | | | | | | | | | | | | | | | | | | | | |
| 332 | 333 | G | | 0.8 | 4 | | | 92 | 97 | 96 | 94 | 64 | | | | | | | | | | | | | |
| 333 | 334 | G | | 1.3 | 3 | | | | | | | | | | | | | | | | | | | | |
| 334 | 335 | G | | 2.1 | 6 | 54.4 | 1 | 55.5 | 71.5 | 77.5 | 87.5 | 49.5 | | | | | | | | | | | | | |
| 335 | 336 | G | | 1.3 | 2 | | | | | | | | | | | | | | | | | | | | |
| 336 | 337 | G | | 0.8 | 3 | | | | | | | | | | | | | | | | | | | | |
| 337 | 338 | G | | 1.6 | 3 | | | | | | | | | | | | | | | | | | | | |
| 338 | 339 | G | | 1.1 | 2 | | | | | | | | | | | | | | | | | | | | |
| 339 | 340 | G | | 0.8 | 2 | | | 81 | 80 | 82 | 87 | 42 | | | 2 | -5 | -5 | -3 | 16 | 39 | 0 | 0 | 8 | 0 | -1 |
| 340 | 341 | G | | 1.2 | 4 | 4.7 | 2 | 57 | 67 | 74 | 88 | 83 | | | | | | | | | | | | | |
| 341 | 342 | G | | 0.6 | 4 | 5.2 | 2 | 83 | 83 | 85 | 90 | 73 | | | | | | | | | | | | | |
| 342 | 343 | G | | 0.9 | 3 | 6.8 | 2 | 71 | 75 | 79 | 89 | 81 | | | | | | | | | | | | | |
| 343 | 344 | G | | 0.5 | 3 | 3.2 | 1 | 77 | 76 | 79 | 86 | 72 | | | 29 | 42 | 39 | 27 | 23 | 58 | 0 | -5 | 30 | 17 | 11 |
| 344 | 345 | G | | 1.6 | 2 | 4.3 | 2 | 75.5 | 82 | 87 | 94.5 | 70 | 63 | | -1 | 2 | -8 | -58 | 41 | 72 | -21 | 0 | 22 | 0 | 4 |
| 345 | 346 | G | | 1.2 | 3 | | | | | | | | | | | | | | | | | | | | |
| 346 | 347 | C | | 0.6 | 3 | | | | | | | | | | | | | | | | | | | | |
| 347 | 348 | C | | 0.7 | 3 | | | | | | | | | | | | | | | | | | | | |
| 348 | 349 | G | | 1.0 | 2 | | | | | | | | | | | | | | | | | | | | |
| 349 | 350 | G | | 1.3 | 3 | | | | | | | | | | | | | | | | | | | | |
| 350 | 351 | G | | 1.4 | 4 | | | | | | | | | | | | | | | | | | | | |
| 351 | 352 | G | | 1.0 | 3 | | | | | | | | | | | | | | | | | | | | |

Fig. 1 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 353 | 353 | G | His | Ser | Gln | Gly | Thr | Phe | Thr | Ser | Asp | Tyr | Ser | Lys | His | Leu | Asp | Glu |
| 354 | 354 | G | His | Ser | Gln | Gly | Thr | Phe | Thr | Ser | Asp | Tyr | Ser | Lys | His | Leu | Asp | Glu |
| 355 | 355 | G | His | Ser | Gln | Gly | Thr | Phe | Thr | Ser | Asp | Tyr | Ser | Lys | His | Leu | Asp | Glu |
| 356 | 356 | G | His | Ser | Gln | Gly | Thr | Phe | Thr | Ser | Asp | Tyr | Ser | Lys | His | Leu | Asp | Glu |
| 357 | 357 | G | His | Ser | Gln | Gly | Thr | Phe | Thr | Ser | Asp | Tyr | Ser | Lys | His | Leu | Asp | Glu |
| 358 | 358 | G | His | Ser | Gln | Gly | Thr | Phe | Thr | Ser | Asp | Tyr | Ser | Lys | His | Leu | Asp | Glu |
| 359 | 359 | G | His | Ser | Gln | Gly | Thr | Phe | Thr | Ser | Asp | Tyr | Ser | Lys | His | Leu | Asp | Ser |
| 360 | 360 | G | His | Ser | Gln | Gly | Thr | Phe | Thr | Ser | Asp | Tyr | Ser | Lys | Tyr | Leu | Asp | Ser |
| 361 | 361 | G | His | Ser | Gln | Gly | Thr | Phe | Thr | Ser | Asp | Tyr | Ser | His | Tyr | Leu | Asp | Ser |
| 362 | 362 | G | His | Ser | Gln | Gly | Thr | Phe | Thr | Ser | Asp | Tyr | Ser | His | Tyr | Leu | Asp | Ser |
| 363 | 363 | G | His | Ser | Gln | Gly | Thr | Phe | Thr | Ser | Asp | Tyr | Ser | Arg | Tyr | Leu | Asp | Ser |
| 364 | 364 | G | His | Ser | Gln | Gly | Thr | Phe | Thr | Ser | Asp | Tyr | Ser | Arg | Tyr | Leu | Asp | Glu |
| 365 | 365 | G | His | Ser | Gln | Gly | Thr | Phe | Thr | Ser | Asp | Tyr | Ser | Arg | His | Leu | Asp | Glu |
| 366 | 366 | G | His | Ser | Gln | Gly | Thr | Phe | Thr | Ser | Asp | Tyr | Ser | Lys | Tyr | Leu | Asp | Gln |
| 367 | 367 | G | His | Ser | Gln | Gly | Thr | Phe | Thr | Ser | Asp | Tyr | Ser | Lys | Tyr | Leu | Asp | Gln |
| 368 | 368 | G | His | Ser | Gln | Gly | Thr | Phe | Thr | Ser | Asp | Tyr | Ser | Lys | His | Leu | Asp | Glu |
| 369 | 369 | G | His | Ser | Gln | Gly | Thr | Phe | Thr | Ser | Asp | Tyr | Ser | His | Tyr | Leu | Asp | Ser |
| 370 | 370 | G | His | Ser | Gln | Gly | Thr | Phe | Thr | Ser | Asp | Tyr | Ser | Arg | Tyr | Leu | Asp | Glu |
| 371 | 371 | G | His | Ser | Gln | Gly | Thr | Phe | Thr | Ser | Asp | Tyr | Ser | Lys | Tyr | Leu | Asp | Glu |
| 372 | 372 | G | His | Ser | Gln | Gly | Thr | Phe | Thr | Ser | Asp | Tyr | Ser | Lys | Tyr | Leu | Asp | Glu |
| 373 | 373 | G | His | Ser | Gln | Gly | Thr | Phe | Thr | Ser | Asp | Tyr | Ser | Lys | Tyr | Leu | Asp | Glu |
| 374 | 374 | G | His | Ser | Gln | Gly | Thr | Phe | Thr | Ser | Asp | Tyr | Ser | His | Tyr | Leu | Asp | Glu |
| 375 | 375 | G | His | Ser | Gln | Gly | Thr | Phe | Thr | Ser | Asp | Tyr | Ser | Lys | Tyr | Leu | Asp | Ser |
| 376 | 376 | G | His | Ser | Gln | Gly | Thr | Phe | Thr | Ser | Asp | Tyr | Ser | Lys | Tyr | Leu | Asp | Glu |
| 377 | 377 | G | His | Ser | Gln | Gly | Thr | Phe | Thr | Ser | Asp | Tyr | Ser | Arg | Tyr | Leu | Asp | Gln |
| 378 | 378 | G | His | Ser | Gln | Gly | Thr | Phe | Thr | Ser | Asp | Tyr | Ser | Lys | Tyr | Leu | Asp | Gln |
| 379 | 379 | G | His | Ser | Gln | Gly | Thr | Phe | Thr | Ser | Asp | Tyr | Ser | Lys | Tyr | Leu | Asp | Ser |
| 380 | 380 | G | His | Ser | Gln | Gly | Thr | Phe | Thr | Ser | Asp | Tyr | Ser | Lys | Tyr | Leu | Asp | Glu |
| 381 | 381 | G | His | Ser | Gln | Gly | Thr | Phe | Thr | Ser | Asp | Tyr | Ser | His | Tyr | Leu | Asp | Glu |
| 382 | 382 | G | His | Ser | Gln | Gly | Thr | Phe | Thr | Ser | Asp | Tyr | Ser | Lys | Tyr | Leu | Asp | Glu |
| 383 | 383 | G | His | Ser | Gln | Gly | Thr | Phe | Thr | Ser | Asp | Tyr | Ser | Lys | Tyr | Leu | Asp | Glu |
| 384 | 384 | G | His | Ser | Gln | Gly | Thr | Phe | Thr | Ser | Asp | Tyr | Ser | Lys | Tyr | Leu | Asp | Gln |
| 385 | 385 | G | His | Ser | Gln | Gly | Thr | Phe | Thr | Ser | Asp | Tyr | Ser | Lys | Tyr | Leu | Asp | Ser |
| 386 | 386 | G | His | Ser | Gln | Gly | Thr | Phe | Thr | Ser | Asp | Tyr | Ser | His | Tyr | Leu | Asp | Glu |
| 387 | 387 | G | His | Ser | Gln | Gly | Thr | Phe | Thr | Ser | Asp | Tyr | Ser | Lys | Tyr | Leu | Asp | Glu |
| 388 | 388 | G | His | Ser | Gln | Gly | Thr | Phe | Thr | Ser | Asp | Tyr | Ser | Lys | Tyr | Leu | Asp | Glu |
| 389 | 389 | G | His | Ser | Gln | Gly | Thr | Phe | Thr | Ser | Asp | Tyr | Ser | Lys | Tyr | Leu | Asp | Ser |
| 390 | 390 | G | His | Ser | Gln | Gly | Thr | Phe | Thr | Ser | Asp | Tyr | Ser | Lys | Tyr | Leu | Asp | Glu |
| 391 | 391 | G | His | Ser | Gln | Gly | Thr | Phe | Thr | Ser | Asp | Tyr | Ser | Lys | Tyr | Leu | Asp | Glu |
| 392 | 392 | G | His | Ser | Gln | Gly | Thr | Phe | Thr | Ser | Asp | Tyr | Ser | Lys | Tyr | Leu | Asp | Glu |
| 393 | 393 | G | His | Ser | Gln | Gly | Thr | Phe | Thr | Ser | Asp | Tyr | Ser | Lys | Tyr | Leu | Asp | Glu |
| 394 | 394 | G | His | Ser | Gln | Gly | Thr | Phe | Thr | Ser | Asp | Tyr | Ser | Lys | Tyr | Leu | Asp | Glu |
| 395 | 395 | G | His | Ser | Gln | Gly | Thr | Phe | Thr | Ser | Asp | Tyr | Ser | Lys | Tyr | Leu | Asp | Ser |

Fig. 1 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 353 | 353 | G | Lys | Arg | Ala | His | Glu | Phe | Val | Glu | Trp | Leu | Leu | Asn | Thr | His | His | | |
| 354 | 354 | G | Lys | Arg | Ala | His | Glu | Phe | Ile | Glu | Trp | Leu | Leu | Asn | Thr | His | His | | |
| 355 | 355 | G | Arg | Arg | Ala | His | Glu | Phe | Ile | Glu | Trp | Leu | Leu | Asn | Thr | His | His | NH2 | |
| 356 | 356 | G | Arg | Arg | Ala | His | Glu | Phe | Ile | Glu | Trp | Leu | Leu | Asn | Thr | His | His | NH2 | |
| 357 | 357 | G | Arg | Arg | Ala | His | Glu | Phe | Ile | Glu | Trp | Leu | Leu | Asn | Gly | Gly | His | NH2 | |
| 358 | 358 | G | Arg | Arg | Ala | His | Glu | Phe | Ile | Gln | Trp | Leu | Leu | Asn | Gly | Gly | His | | |
| 359 | 359 | G | Arg | Arg | Ala | His | Glu | Phe | Ile | Gln | Trp | Leu | Leu | Asn | Gly | Gly | His | | |
| 360 | 360 | G | Arg | Arg | Ala | His | Glu | Phe | Ile | Glu | Trp | Leu | Leu | Asn | Gly | Gly | His | | |
| 361 | 361 | G | Arg | Arg | Ala | His | Glu | Phe | Ile | Glu | Trp | Leu | Leu | Asn | Thr | His | His | | |
| 362 | 362 | G | Lys | Arg | Ala | His | Glu | Phe | Ile | Gln | Trp | Leu | Leu | Asn | Thr | His | His | | |
| 363 | 363 | G | Arg | Arg | Ala | His | Glu | Phe | Ile | Glu | Trp | Leu | Leu | Asn | Gly | Gly | His | His | |
| 364 | 364 | G | Lys | Arg | Ala | His | Glu | Phe | Ile | Glu | Trp | Leu | Leu | Asn | Gly | Gly | His | | |
| 365 | 365 | G | Lys | Arg | Ala | His | Glu | Phe | Ile | Glu | Trp | Leu | Leu | Asn | Gly | Gly | His | | |
| 366 | 366 | G | Lys | Arg | Ala | His | Glu | Phe | Ile | Gln | Trp | Leu | Leu | Asn | Gly | His | His | NH2 | |
| 367 | 367 | G | Lys | Arg | Ala | His | Glu | Phe | Ile | Glu | Trp | Leu | Leu | Asn | Gly | His | His | NH2 | |
| 368 | 368 | G | Arg | Arg | Ala | His | Glu | Phe | Ile | Glu | Trp | Leu | Leu | Asn | Gly | Gly | His | NH2 | |
| 369 | 369 | G | Arg | Arg | Ala | His | Glu | Phe | Val | Gln | Trp | Leu | Leu | Asn | Gly | Gly | His | NH2 | |
| 370 | 370 | G | Arg | Arg | Ala | His | Glu | Phe | Val | Gln | Trp | Leu | Leu | Asn | Gly | Gly | His | NH2 | |
| 371 | 371 | G | Arg | Arg | Ala | His | Glu | Phe | Ile | Glu | Trp | Leu | Leu | Asn | Gly | Gly | His | His | NH2 |
| 372 | 372 | G | Arg | Arg | Ala | His | Glu | Phe | Ile | Glu | Trp | Leu | Leu | Asn | Gly | Gly | His | NH2 | |
| 373 | 373 | G | Lys | Arg | Ala | His | Glu | Phe | Ile | Gln | Trp | Leu | Leu | Asn | Gly | Gly | His | NH2 | |
| 374 | 374 | G | Arg | Arg | Ala | His | Glu | Phe | Ile | Glu | Trp | Leu | Leu | Asn | Gly | His | His | NH2 | |
| 375 | 375 | G | Lys | Arg | Ala | His | Glu | Phe | Ile | Glu | Trp | Leu | Leu | Asn | Gly | Gly | His | | |
| 376 | 376 | G | Arg | Arg | Ala | His | Glu | Phe | Ile | Gln | Trp | Leu | Leu | Asn | Gly | His | His | | |
| 377 | 377 | G | Arg | Arg | Ala | His | Glu | Phe | Ile | Gln | Trp | Leu | Leu | Asn | Thr | His | His | | |
| 378 | 378 | G | Arg | Arg | Ala | His | Glu | Phe | Ile | Gln | Trp | Leu | Leu | Asn | Gly | His | His | | |
| 379 | 379 | G | Arg | Arg | Ala | His | Glu | Phe | Ile | Glu | Trp | Leu | Leu | Asn | Thr | His | His | | |
| 380 | 380 | G | Arg | Arg | Ala | His | Glu | Phe | Ile | Gln | Trp | Leu | Leu | Asn | Gly | Gly | His | | |
| 381 | 381 | G | Arg | Arg | Ala | His | Glu | Phe | Ile | Gln | Trp | Leu | Leu | Asn | Gly | His | His | | |
| 382 | 382 | G | Lys | Arg | Ala | His | Glu | Phe | Ile | Gln | Trp | Leu | Leu | Asn | Gly | Gly | His | His | NH2 |
| 383 | 383 | G | Lys | Arg | Ala | His | Glu | Phe | Ile | Glu | Trp | Leu | Leu | Asn | Gly | Gly | His | His | NH2 |
| 384 | 384 | G | Arg | Arg | Ala | His | Glu | Phe | Ile | Gln | Trp | Leu | Leu | Asn | Gly | Gly | His | NH2 | |
| 385 | 385 | G | Lys | Arg | Ala | His | Glu | Phe | Ile | Gln | Trp | Leu | Leu | Asn | Thr | Gly | His | NH2 | |
| 386 | 386 | G | Arg | Arg | Ala | His | Glu | Phe | Ile | Gln | Trp | Leu | Leu | Asn | Thr | Gly | His | | |
| 387 | 387 | G | Arg | Arg | Ala | His | Glu | Phe | Ile | Glu | Trp | Leu | Leu | Asn | Thr | Gly | His | | |
| 388 | 388 | G | Lys | Arg | Ala | His | Glu | Phe | Ile | Gln | Trp | Leu | Leu | Asn | Thr | His | His | His | NH2 |
| 389 | 389 | G | Arg | Arg | Ala | His | Glu | Phe | Ile | Gln | Trp | Leu | Leu | Asn | Gly | His | His | NH2 | |
| 390 | 390 | G | Arg | Arg | Ala | His | Glu | Phe | Ile | Gln | Trp | Leu | Leu | Asn | Thr | His | His | NH2 | |
| 391 | 391 | G | Lys | Arg | Ala | His | Glu | Phe | Ile | Gln | Trp | Leu | Leu | Asn | Gly | His | His | NH2 | |
| 392 | 392 | G | Arg | Arg | Ala | His | Glu | Phe | Ile | Glu | Trp | Leu | Leu | Asn | Thr | His | His | NH2 | |
| 393 | 393 | G | Arg | Arg | Ala | His | Glu | Phe | Ile | Glu | Trp | Leu | Leu | Asn | Gly | His | His | | |
| 394 | 394 | G | Arg | Arg | Ala | His | Glu | Phe | Val | Glu | Trp | Leu | Leu | Asn | Gly | His | His | His | |
| 395 | 395 | G | Arg | Arg | Ala | His | Glu | Phe | Val | Gln | Trp | Leu | Leu | Asn | Gly | Lys | His | His | |

Fig. 1 (continued)

| SEQ ID NO. | Analogue no. | G no. | hGCGr cAMP | | hGLP-1r cAMP | | Mouse food intake inhibition (≤50nmol/kg) | | | | | | Rat food intake inhibition (200 nmol/kg with 1:1 Zn) | | | | | | | | |
|---|---|---|---|---|---|---|---|---|---|---|---|---|---|---|---|---|---|---|---|---|
| | | | n | vs hGCG | n | vs hGLP-1 | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 353 | 353 | 1650 | 2 | 1.2 | | | | | | | | | | | | | | | | | | | | |
| 354 | 354 | 1651 | 3 | 1.1 | | | | | | | | | | | | | | | | | | | | |
| 355 | 355 | 1652 | 3 | 1.3 | | | | | | | | | | | | | | | | | | | | |
| 356 | 356 | 1653 | 2 | 1.7 | | | | | | | | | | | | | | | | | | | | |
| 357 | 357 | 1654 | 2 | 1.3 | | | | | | | | | | | | | | | | | | | | |
| 358 | 358 | 1655 | 2 | 1.2 | | | | | | | | | | 11 | 15 | 20 | 37 | 53 | | | -11 | | 38 | 16 | 8 |
| 359 | 359 | 1656 | 2 | 1.2 | | | | | | | | | | | | | | | | | | | | |
| 360 | 360 | 1657 | 3 | 1.3 | | | | | | | | | | | | | | | | | | | | |
| 361 | 361 | 1658 | 2 | 1.4 | | | | | | | | | | | | | | | | | | | | |
| 362 | 362 | 1659 | 2 | 0.8 | | | 78 | 78 | 82 | 90 | 60 | | | -9 | 24 | 25 | 28 | 46 | 45 | -18 | -17 | 36 | 20 | 9 |
| 363 | 363 | 1660 | 2 | 0.9 | | | 69 | 75 | 80 | 90 | 59 | | | 14 | 34 | 41 | 63 | 50 | 45 | -14 | -2 | 46 | 27 | 18 |
| 364 | 364 | 1661 | 2 | 0.6 | | | 77 | 77 | 80 | 85 | 26 | | | | | | | | | | | | | |
| 365 | 365 | 1662 | 4 | 1.7 | | | 78 | 78 | 67 | 53 | 13 | 37 | | 10 | 3 | -1 | -23 | 11 | 37 | 0 | 0 | 0 | 0 | 4 |
| 366 | 366 | 1664 | 3 | 1.3 | | | | | | | | | | | | | | | | | | | | |
| 367 | 367 | 1665 | 3 | 1.0 | | | 69 | 83 | 89 | 96 | 61 | 18 | | 1 | 1 | -8 | -46 | 50 | 91 | 0 | 0 | 27 | 0 | 22 |
| 368 | 368 | 1666 | 3 | 1.3 | | | | | | | | | | | | | | | | | | | | |
| 369 | 369 | 1667 | 2 | 1.6 | | | | | | | | | | | | | | | | | | | | |
| 370 | 370 | 1668 | 2 | 1.2 | | | | | | 93.5 | 68 | 19 | | 14 | 9 | 11 | 19 | 30 | 66 | -18 | -14 | 21 | 15 | 6 |
| 371 | 371 | 1670 | 3 | 0.7 | 2 | 4.7 | 60.5 | 74.5 | 82 | 90 | 53 | 38 | | 1 | -5 | 1 | 29 | 12 | 70 | 0 | 0 | 8 | 0 | 4 |
| 372 | 372 | 1671 | 3 | 0.7 | | | | | | | | | | | | | | | | | | | | |
| 373 | 373 | 1672 | 3 | 1.4 | | | 64 | 80 | 85 | | | | | | | | | | | | | | | |
| 374 | 374 | 1673 | 1 | 4.2 | | | | | | | | | | | | | | | | | | | | |
| 375 | 375 | 1674 | 3 | 1.1 | | | 70 | 82 | 90 | 100 | 39 | 54 | | 21 | 2 | 0 | -8 | 55 | 56 | 23 | 5 | 31 | 32 | 24 |
| 376 | 376 | 1675 | 4 | 1.9 | | | | | | | | | | | | | | | | | | | | |
| 377 | 377 | 1676 | 3 | 1.4 | | | | | | | | | | | | | | | | | | | | |
| 378 | 378 | 1677 | 3 | 0.7 | | | 81 | 80 | 82 | 88 | 47 | | | 24 | 11 | 5 | -13 | 53 | 68 | -7 | -16 | 31 | 24 | 12 |
| 379 | 379 | 1678 | 2 | 0.9 | | | 75 | 77 | 81 | 89 | 43 | | 7 | | | | | | | | | | | |
| 380 | 380 | 1679 | 2 | 0.9 | | | | | | | | | | | | | | | | | | | | |
| 381 | 381 | 1680 | 3 | 0.8 | 2 | 3.7 | 74 | 81 | 85.5 | 94.5 | 71 | 52 | | -5 | -4 | 1 | 16 | 31 | 43 | 0 | 0 | 18 | 0 | 5 |
| 382 | 382 | 1681 | 3 | 1.3 | | | 89 | 94 | 96 | 100 | 37 | 6 | | 12.5 | 38.5 | 41 | 47 | 72.5 | 61 | -11 | 0.5 | 58.5 | 37.5 | 25.5 |
| 383 | 383 | 1682 | 1 | 1.0 | | | 42.5 | 39.5 | 70.8 | 31.7 | 4.3 | -8.5 | 2.2 | 20.1651 | 26.3033 | 56.6117 | 24.7967 | 34.8255 | -4.1333 | -5.9354 | -10.888 | 44.051 | 19.298 | 10.0793 |
| 384 | 384 | 1684 | 2 | 1.5 | | | | | | | | | | | | | | | | | | | | |
| 385 | 385 | 1685 | 1 | 2.2 | | | | | | | | | | | | | | | | | | | | |
| 386 | 386 | 1686 | 3 | 1.1 | 1 | 1.7 | 89 | 91 | 94 | 98 | 60 | 5 | 15 | 22 | 27 | 31 | 43 | 60 | 51 | -18 | -5 | 47 | 28 | 18 |
| 387 | 387 | 1687 | 0 | 0.0 | | | 83 | 89 | 93 | 99 | 76 | 33 | | | | | | | | | | | | |
| 388 | 388 | 1690 | 1 | 1.1 | | | | | | | | | | | | | | | | | | | | |
| 389 | 389 | 1691 | 1 | 8.2 | | | | | | | | | | | | | | | | | | | | |
| 390 | 390 | 1692 | 2 | 0.0 | | | 81 | 89 | 94 | 99 | 69 | 56 | | 3 | 21 | 22 | 27 | 66 | 67 | 21 | 8 | 47 | 41 | 31 |
| 391 | 391 | 1693 | 1 | 0.7 | | | | | | | | | | | | | | | | | | | | |
| 392 | 392 | 1695 | 0 | 0.0 | | | | | | | | | | | | | | | | | | | | |
| 393 | 393 | 1696 | 2 | 0.6 | | | 76 | 83 | 90 | 99 | 74 | 46 | | 18 | 22 | 21 | 16 | 70 | 74 | 36 | 10 | 49 | 48 | 37 |
| 394 | 394 | 1697 | 3 | 1.2 | 2 | 2.0 | 76 | 87 | 91.5 | 99 | 81.5 | 62.5 | 44 | 24 | 32 | 10 | -58 | 65 | 57 | -6 | 11 | 41 | 28 | 23 |
| 395 | 395 | 1699 | 3 | 1.8 | | | 90 | 94 | 89 | 81 | 26 | 33 | 22 | 31 | 27 | 22 | 5 | -6 | -4 | -4 | 4 | 8 | 3 | 3 |

Fig. 1 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 396 | 396 | G | His | Ser | Gln | Gly | Thr | Phe | Thr | Ser | Asp | Tyr | Ser | Lys | Tyr | Leu | Asp | Ser |
| 397 | 397 | G | His | Ser | Gln | Gly | Thr | Phe | Thr | Ser | Asp | Tyr | Ser | Lys | Tyr | Leu | Asp | Glu |
| 398 | 398 | G | His | Ser | Gln | Gly | Thr | Phe | Thr | Ser | Asp | Tyr | Ser | His | Tyr | Leu | Asp | Gln |
| 399 | 399 | G | His | Ser | Gln | Gly | Thr | Phe | Thr | Ser | Asp | Tyr | Ser | His | Tyr | Leu | Asp | Gln |
| 400 | 400 | G | His | Ser | Gln | Gly | Thr | Phe | Thr | Ser | Asp | Tyr | Ser | His | Tyr | Leu | Asp | Gln |
| 401 | 401 | G | His | Ser | Gln | Gly | Thr | Phe | Thr | Ser | Asp | Tyr | Ser | His | Tyr | Leu | Asp | Gln |
| 402 | 402 | G | His | Ser | Gln | Gly | Thr | Phe | Thr | Ser | Asp | Tyr | Ser | His | Tyr | Leu | Asp | Gln |
| 403 | 403 | G | His | Ser | Gln | Gly | Thr | Phe | Thr | Ser | Asp | Tyr | Ser | His | Tyr | Leu | Asp | Gln |
| 404 | 404 | G | His | Ser | Gln | Gly | Thr | Phe | Thr | Ser | Asp | Tyr | Ser | His | Tyr | Leu | Asp | Gln |
| 405 | 405 | G | His | Ser | Gln | Gly | Thr | Phe | Thr | Ser | Asp | Tyr | Ser | His | Tyr | Leu | Asp | Gln |
| 406 | 406 | G | His | Ser | Gln | Gly | Thr | Phe | Thr | Ser | Asp | Tyr | Ser | Lys | Tyr | Leu | Asp | Gln |
| 407 | 407 | G | His | Ser | Gln | Gly | Thr | Phe | Thr | Ser | Asp | Tyr | Ser | His | Tyr | Leu | Asp | Gln |
| 408 | 408 | G | His | Ser | Gln | Gly | Thr | Phe | Thr | Ser | Asp | Tyr | Ser | His | Tyr | Leu | Asp | Gln |
| 409 | 409 | G | His | Ser | Gln | Gly | Thr | Phe | Thr | Ser | Asp | Tyr | Ser | His | Tyr | Leu | Asp | Ser |
| 410 | 410 | G | His | Ser | Gln | Gly | Thr | Phe | Thr | Ser | Asp | Tyr | Ser | His | Tyr | Leu | Asp | Ser |
| 411 | 411 | G | His | Ser | Gln | Gly | Thr | Phe | Thr | Ser | Asp | Tyr | Ser | His | Tyr | Leu | Asp | Glu |
| 412 | 412 | G | His | Ser | Gln | Gly | Thr | Phe | Thr | Ser | Asp | Tyr | Ser | His | Tyr | Leu | Asp | Gln |
| 413 | 413 | G | His | Ser | Gln | Gly | Thr | Phe | Thr | Ser | Asp | Tyr | Ser | Lys | Tyr | Leu | Asp | Gln |
| 414 | 414 | G | His | Ser | Gln | Gly | Thr | Phe | Thr | Ser | Asp | Tyr | Ser | His | Tyr | Leu | Asp | Gln |
| 415 | 415 | G | His | Ser | Gln | Gly | Thr | Phe | Thr | Ser | Asp | Tyr | Ser | His | Tyr | Leu | Asp | Gln |
| 416 | 416 | G | His | Ser | Gln | Gly | Thr | Phe | Thr | Ser | Asp | Tyr | Ser | Lys | Tyr | Leu | Asp | Gln |
| 417 | 417 | G | His | Ser | Gln | Gly | Thr | Phe | Thr | Ser | Asp | Tyr | Ser | Lys | Tyr | Leu | Asp | Gln |
| 418 | 418 | G | His | Ser | Gln | Gly | Thr | Phe | Thr | Ser | Asp | Tyr | Ser | Lys | Tyr | Leu | Asp | Gln |
| 419 | 419 | G | His | Ser | Gln | Gly | Thr | Phe | Thr | Ser | Asp | Tyr | Ser | Lys | Tyr | Leu | Asp | Gln |
| 420 | 420 | G | His | Ser | Gln | Gly | Thr | Phe | Thr | Ser | Asp | Tyr | Ser | Lys | Tyr | Leu | Asp | Gln |
| 421 | 421 | G | His | Ser | Gln | Gly | Thr | Phe | Thr | Ser | Asp | Tyr | Ser | His | Tyr | Leu | Asp | Ser |
| 422 | 422 | G | His | Ser | Gln | Gly | Thr | Phe | Thr | Ser | Asp | Tyr | Ser | His | Tyr | Leu | Asp | Ser |
| 423 | 423 | G | His | Ser | Gln | Gly | Thr | Phe | Thr | Ser | Asp | Tyr | Ser | His | Tyr | Leu | Asp | Ser |
| 424 | 424 | G | His | Ser | Gln | Gly | Thr | Phe | Thr | Ser | Asp | Tyr | Ser | Lys | Tyr | Leu | Asp | Gln |
| 425 | 425 | G | His | Ser | Gln | Gly | Thr | Phe | Thr | Ser | Asp | Tyr | Ser | Lys | Tyr | Leu | Asp | Glu |
| 426 | 426 | G | His | Ser | Gln | Gly | Thr | Phe | Thr | Ser | Asp | Tyr | Ser | Lys | Tyr | Leu | Asp | Glu |

Fig. 1 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|
| 396 | 396 | 1701 | Arg | Arg | Ala | His | Glu | Phe | Val | Glu | Trp | Leu | Leu | Asn | Gly | Gly | His | His | |
| 397 | 397 | 1702 | Lys | Arg | Ala | His | Glu | Phe | Ile | Glu | Trp | Leu | Leu | Asn | Gly | His | His | His | |
| 398 | 398 | 1703 | Lys | Arg | Ala | His | Glu | Phe | Ile | Glu | Trp | Leu | Leu | Asn | Gly | His | His | | |
| 399 | 399 | 1704 | Arg | Arg | Ala | His | Glu | Phe | Ile | Glu | Trp | Leu | Leu | Asn | Gly | His | His | NH2 | |
| 400 | 400 | 1705 | Arg | Arg | Ala | His | Glu | Phe | Val | Glu | Trp | Leu | Leu | Asn | Gly | His | His | His | |
| 401 | 401 | 1706 | Arg | Arg | Ala | His | Glu | Phe | Ile | Gln | Trp | Leu | Leu | Asn | Gly | His | His | NH2 | |
| 402 | 402 | 1707 | Arg | Arg | Ala | His | Glu | Phe | Ile | Glu | Trp | Leu | Leu | Asn | Gly | His | His | | |
| 403 | 403 | 1708 | Lys | Arg | Ala | His | Glu | Phe | Val | Glu | Trp | Leu | Leu | Asn | Gly | His | His | NH2 | |
| 404 | 404 | 1709 | Lys | Arg | Ala | His | Glu | Phe | Ile | Glu | Trp | Leu | Leu | Asn | Gly | His | His | NH2 | |
| 405 | 405 | 1710 | Arg | Arg | Ala | His | Glu | Phe | Val | Glu | Trp | Leu | Leu | Asn | Gly | His | His | His | NH2 |
| 406 | 406 | 1711 | Arg | Arg | Ala | His | Glu | Phe | Ile | Glu | Trp | Leu | Leu | Asn | Gly | His | His | His | |
| 407 | 407 | 1714 | Arg | Arg | Ala | His | Glu | Phe | Ile | Glu | Trp | Leu | Leu | Asn | Gly | His | His | His | NH2 |
| 408 | 408 | 1715 | Arg | Arg | Ala | His | Glu | Phe | Ile | Glu | Trp | Leu | Leu | Asn | Gly | His | His | His | |
| 409 | 409 | 1717 | Arg | Arg | Ala | His | Glu | Phe | Ile | Glu | Trp | Leu | Leu | Asn | Gly | His | His | His | NH2 |
| 410 | 410 | 1719 | Arg | Arg | Ala | His | Glu | Phe | Ile | Gln | Trp | Leu | Leu | Asn | Gly | His | His | His | |
| 411 | 411 | 1721 | Lys | Arg | Ala | His | Glu | Phe | Ile | Glu | Trp | Leu | Leu | Asn | Gly | His | His | His | NH2 |
| 412 | 412 | 1723 | Lys | Arg | Ala | His | Glu | Phe | Val | Glu | Trp | Leu | Leu | Asn | Gly | His | His | His | NH2 |
| 413 | 413 | 1724 | Arg | Arg | Ala | His | Glu | Phe | Ile | Glu | Trp | Leu | Leu | Asn | Gly | His | His | His | NH2 |
| 414 | 414 | 1725 | Lys | Arg | Ala | His | Glu | Phe | Ile | Glu | Trp | Leu | Leu | Asn | Gly | His | His | His | NH2 |
| 415 | 415 | 1726 | Lys | Arg | Ala | His | Glu | Phe | Ile | Glu | Trp | Leu | Leu | Asn | Gly | His | His | His | |
| 416 | 416 | 1727 | Arg | Arg | Ala | His | Glu | Phe | Ile | Glu | Trp | Leu | Leu | Asn | Thr | Gly | His | NH2 | |
| 417 | 417 | 1728 | Arg | Arg | Ala | His | Glu | Phe | Ile | Glu | Trp | Leu | Leu | Asn | Thr | Gly | His | His | |
| 418 | 418 | 1732 | Lys | Arg | Ala | His | Glu | Phe | Ile | Gln | Trp | Leu | Leu | Asn | Thr | Gly | His | | |
| 419 | 419 | 1733 | Lys | Arg | Ala | His | Glu | Phe | Ile | Glu | Trp | Leu | Leu | Asn | Thr | Gly | His | His | |
| 420 | 420 | 1734 | Lys | Arg | Ala | His | Glu | Phe | Ile | Glu | Trp | Leu | Leu | Asn | Thr | Gly | His | His | NH2 |
| 421 | 421 | 1738 | Lys | Arg | Ala | His | Glu | Phe | Val | Glu | Trp | Leu | Leu | Asn | Thr | Gly | His | | |
| 422 | 422 | 1739 | Lys | Arg | Ala | His | Glu | Phe | Ile | Gln | Trp | Leu | Leu | Asn | Thr | Gly | His | | |
| 423 | 423 | 1740 | Lys | Arg | Ala | His | Glu | Phe | Ile | Glu | Trp | Leu | Leu | Asn | Thr | Gly | His | His | NH2 |
| 424 | 424 | 1787 | Arg | Arg | Ala | His | Glu | Phe | Val | Glu | Trp | Leu | Leu | Asn | Thr | Gly | His | His | |
| 425 | 425 | 1790 | Arg | Arg | Ala | His | Glu | Phe | Ile | Glu | Trp | Leu | Leu | Asn | Thr | His | His | His | NH2 |
| 426 | 426 | 1843 | Lys | Arg | Ala | His | Glu | Phe | Ile | Glu | Trp | Leu | Leu | Asn | Thr | His | His | His | NH2 |

Fig. 1 (continued)

| SEQ ID NO. | Analogue no. | G no. | hGCGr-cAMP vs hGCG | hGLP-1r cAMP vs hGLP-1 | Mouse food intake inhibition (200 nmol/kg) | | | | | | Rat food intake inhibition (200 nmol/kg with 1:1 Zn) | | | | | | | | | |
|---|---|---|---|---|---|---|---|---|---|---|---|---|---|---|---|---|---|---|---|---|
| | | | | | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 396 | 396 | G | 0.7 | | 80.0 | 88.0 | 92.0 | 100.0 | 57.0 | 28.0 | -5.0 | -29 | 16 | 24 | 53 | 24 | 9 | -40 | -32 | 24 | 1 | -8 |
| 397 | 397 | G | 1.8 | | 77.0 | 89.0 | 92.0 | 97.0 | 83.0 | 62.0 | 59.0 | 22 | 28 | 30 | 39 | 37 | 26 | -24 | -21 | 34 | 14 | 4 |
| 398 | 398 | G | 1.1 | | 84.0 | 88.5 | 91.5 | 97.5 | 47.0 | 10.5 | 36.5 | 4 | 19.5 | 17.5 | 11 | 39.5 | 36.5 | -12.5 | -16 | 30.5 | 17 | 7.5 |
| 399 | 399 | G | 3.5 | | | | | | | | | | | | | | | | | | | |
| 400 | 400 | G | 1.0 | | 72.0 | 85.0 | 90.0 | 97.0 | 15.0 | 48.0 | 6.0 | 10 | 23 | 26 | 39 | 30 | -13 | -18 | -6 | 28 | 19 | 11 |
| 401 | 401 | G | 5.5 | | | | | | | | | | | | | | | | | | | |
| 402 | 402 | G | 2.0 | | | | | | | | | | | | | | | | | | | |
| 403 | 403 | G | 4.7 | | | | | | | | | | | | | | | | | | | |
| 404 | 404 | G | 2.7 | | | | | | | | | | | | | | | | | | | |
| 405 | 405 | G | 4.0 | | 77.0 | 87.0 | 83.0 | 89.0 | 17.0 | -9.0 | 14.0 | 14 | -2 | 6 | 33 | 5 | 42 | -17 | -13 | 5 | 2 | -2 |
| 406 | 406 | G | 2.6 | | 72.0 | 80.3 | 85.0 | 93.0 | 8.0 | 15.0 | 4.0 | 7 | 14 | 19 | 36 | 38 | 67 | -6 | -20 | 30 | 22 | 10 |
| 407 | 407 | G | 3.2 | | 68.0 | 79.0 | 76.0 | 70.0 | 17.0 | -11.0 | 4.0 | 29 | 12 | 12 | 4 | 18 | 65 | 1 | 0 | 16 | 16 | 11 |
| 408 | 408 | G | 1.9 | | 75.0 | 81.3 | 75.0 | 65.0 | 36.0 | -8.0 | -1.0 | -4 | 6 | 17 | 52 | 19 | 88 | -2 | -3 | 18 | 19 | 12 |
| 409 | 409 | G | 2.1 | | 62.0 | 79.3 | 86.0 | 98.0 | 20.0 | 50.0 | 1.0 | 5 | 6 | 14 | 38 | 44 | 55 | 11 | -10 | 32 | 27 | 17 |
| 410 | 410 | G | 6.4 | | 69.0 | 82.0 | 89.0 | 100.0 | 15.0 | -11.0 | -2.0 | 4 | 9 | 13 | 27 | 15 | 50 | -21 | 0 | 14 | 6 | 5 |
| 411 | 411 | G | 1.9 | | 83.5 | 77.2 | 81.7 | 86.5 | 31.5 | -11.5 | 0.0 | -1 | 13 | 12 | 8 | 42 | 12 | 5 | -15 | 29 | 19 | 9 |
| 412 | 412 | G | 2.5 | | 75.5 | 83.8 | 81.9 | 80.0 | 37.0 | 18.9 | 0.0 | 5 | 21 | 18 | 6 | 5 | -19 | -13 | -10 | 10 | -1 | -3 |
| 413 | 413 | G | 1.6 | | 76.0 | 89.0 | 90.0 | 91.0 | -2.0 | 7.0 | 11.0 | 8 | 10 | 22 | 64 | 58 | 59 | -24 | -14 | 42 | 24 | 12 |
| 414 | 414 | G | 1.9 | 5.0 | 83.0 | 91.0 | 93.0 | 98.0 | 36.0 | 1.0 | 7.0 | 24 | 23 | 17 | -4 | 33 | 51 | -7 | -6 | 26 | 19 | 11 |
| 415 | 415 | G | 1.3 | | 89.0 | 93.0 | 90.0 | 84.0 | -15.0 | -19.0 | 6.0 | 20 | -5 | 2 | 28 | 23 | 14 | -5 | 2 | 14 | 8 | 6 |
| 416 | 416 | G | 2.1 | | -26.0 | 48.0 | 71.0 | 94.0 | 27.0 | -7.0 | -11.0 | 22 | 25 | 27 | 35 | 35 | 25 | -27 | -20 | 31 | 13 | 3 |
| 417 | 417 | G | 2.1 | | 76.5 | 86.5 | 83.8 | 91.3 | 44.8 | 7.0 | 0.0 | 14 | 31 | 32 | 35 | 63 | -11 | -17 | -4 | 48 | 31 | 20 |
| 418 | 418 | G | 0.8 | | 72.0 | 59.0 | 60.0 | 61.0 | 23.0 | -24.0 | -7.0 | 24 | 50 | 53 | 66 | 37 | 36 | -3 | -13 | 44 | 29 | 16 |
| 419 | 419 | G | 2.0 | | 83.0 | 89.0 | 89.0 | 88.0 | -2.0 | 21.0 | -2.0 | 36 | 42 | 47 | 61 | 59 | 64 | -40 | -11 | 53 | 26 | 15 |
| 420 | 420 | G | 0.0 | | | | | | | | | | | | | | | | | | | |
| 421 | 421 | G | 7.1 | | | | | | | | | | | | | | | | | | | |
| 422 | 422 | G | 4.2 | | 61.0 | 76.0 | 71.0 | 66.0 | 47.0 | -4.0 | 13.0 | 8 | 16 | 11 | -5 | 14 | -3 | -7 | 14 | 13 | 13 | 13 |
| 423 | 423 | G | 2.1 | | | | | | | | | | | | | | | | | | | |
| 424 | 424 | G | 1.8 | | 88.0 | 92.0 | 92.0 | 93.0 | 67.0 | 30.0 | 29.0 | -7 | 13 | 16 | 26 | 50 | 24 | -5 | -12 | 35 | 21 | 11 |
| 425 | 425 | G | 1.6 | | 88.1 | 75.7 | 42.5 | 9.4 | 8.1 | 12.6 | -1.5 | 48.0287 | 28.86 | 24.6277 | 8.33333 | -1.6961 | -8.0221 | -18.303 | -7.8836 | 9.50292 | -1.0281 | -3.1822 |
| 426 | 426 | G | 2.4 | | 94.9 | 90.3 | 71.8 | 53.3 | 41.5 | 13.6 | 9.0 | 57.5269 | 38.5281 | 39.5189 | 43.3333 | 46.8193 | -13.655 | -29.647 | -12.614 | 43.7135 | 14.3929 | 5.90701 |

| SEQ ID NO | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 427 | 427 | G | His | Ser | Gln | Gly | Thr | Phe | Thr | Ser | Asp | Tyr | Ser | Lys | Tyr | Leu | Glu | Ser |
| 428 | 428 | G | His | Ser | Gln | Gly | Thr | Phe | Thr | Ser | Asp | Tyr | Ser | Lys | Tyr | Leu | Glu | Ser |
| 429 | 429 | G | His | Ser | Gln | Gly | Thr | Phe | Thr | Ser | Asp | Tyr | Ser | Lys | Tyr | Leu | Glu | Ser |
| 430 | 430 | G | His | Ser | Gln | Gly | Thr | Phe | Thr | Ser | Asp | Tyr | Ser | Lys | Tyr | Leu | Glu | Ser |
| 431 | 431 | G | His | Ser | Gln | Gly | Thr | Phe | Thr | Ser | Asp | Tyr | Ser | Lys | Tyr | Leu | Glu | Glu |
| 432 | 432 | G | His | Ser | Gln | Gly | Thr | Phe | Thr | Ser | Asp | Tyr | Ser | Lys | Tyr | Leu | Glu | Glu |
| 433 | 433 | G | His | Ser | Gln | Gly | Thr | Phe | Thr | Ser | Asp | Tyr | Ser | Lys | Tyr | Leu | Glu | Glu |
| 434 | 434 | G | His | Ser | Gln | Gly | Thr | Phe | Thr | Ser | Asp | Tyr | Ser | Lys | Tyr | Leu | Glu | Glu |
| 435 | 435 | G | His | Ser | Gln | Gly | Thr | Phe | Thr | Ser | Asp | Tyr | Ser | Lys | Tyr | Leu | Glu | Glu |
| 436 | 436 | G | His | Ser | Gln | Gly | Thr | Phe | Thr | Ser | Asp | Tyr | Ser | Lys | Tyr | Leu | Glu | Glu |
| 437 | 437 | G | His | Ser | Gln | Gly | Thr | Phe | Thr | Ser | Asp | Tyr | Ser | Lys | Tyr | Leu | Glu | Glu |
| 438 | 438 | G | His | Ser | Gln | Gly | Thr | Phe | Thr | Ser | Asp | Tyr | Ser | Lys | Tyr | Leu | Glu | Ser |
| 439 | 439 | G | His | Ser | Gln | Gly | Thr | Phe | Thr | Ser | Asp | Tyr | Ser | Lys | Tyr | Leu | Glu | Ser |
| 440 | 440 | G | His | Ser | Gln | Gly | Thr | Phe | Thr | Ser | Asp | Tyr | Ser | Lys | Tyr | Leu | Glu | Glu |
| 441 | 441 | G | His | Ser | Gln | Gly | Thr | Phe | Thr | Ser | Asp | Tyr | Ser | Lys | Tyr | Leu | Glu | Glu |
| 442 | 442 | G | His | Ser | Gln | Gly | Thr | Phe | Thr | Ser | Asp | Tyr | Ser | Lys | Tyr | Leu | Glu | Glu |
| 443 | 443 | G | His | Ser | Gln | Gly | Thr | Phe | Thr | Ser | Asp | Tyr | Ser | Lys | Tyr | Leu | Glu | Glu |
| 444 | 444 | G | His | Ser | Gln | Gly | Thr | Phe | Thr | Ser | Asp | Tyr | Ser | Lys | Tyr | Leu | Glu | Glu |
| 445 | 445 | G | His | Ser | Gln | Gly | Thr | Phe | Thr | Ser | Asp | Tyr | Ser | Lys | Tyr | Leu | Glu | Glu |
| 446 | 446 | G | His | Ser | Gln | Gly | Thr | Phe | Thr | Ser | Asp | Tyr | Ser | Lys | Tyr | Leu | Glu | Glu |
| 447 | 447 | G | His | Ser | Gln | Gly | Thr | Phe | Thr | Ser | Asp | Tyr | Ser | Lys | Tyr | Leu | Glu | Glu |
| 448 | 448 | G | His | Ser | Gln | Gly | Thr | Phe | Thr | Ser | Asp | Tyr | Ser | Lys | Tyr | Leu | Glu | Ser |
| 449 | 449 | G | His | Ser | Gln | Gly | Thr | Phe | Thr | Ser | Asp | Tyr | Ser | Lys | Tyr | Leu | Glu | Ser |
| 450 | 450 | G | His | Ser | Gln | Gly | Thr | Phe | Thr | Ser | Asp | Tyr | Ser | Lys | Tyr | Leu | Glu | Glu |
| 451 | 451 | G | His | Ser | Gln | Gly | Thr | Phe | Thr | Ser | Asp | Tyr | Ser | Lys | Tyr | Leu | Glu | Glu |
| 452 | 452 | G | His | Ser | Gln | Gly | Thr | Phe | Thr | Ser | Asp | Tyr | Ser | Lys | Tyr | Leu | Glu | Glu |
| 453 | 453 | G | His | Ser | Gln | Gly | Thr | Phe | Thr | Ser | Asp | Tyr | Ser | Lys | Tyr | Leu | Glu | Glu |
| 454 | 454 | G | His | Ser | Gln | Gly | Thr | Phe | Thr | Ser | Asp | Tyr | Ser | Lys | Tyr | Leu | Glu | Ser |
| 455 | 455 | G | His | Ser | Gln | Gly | Thr | Phe | Thr | Ser | Asp | Tyr | Ser | Lys | Tyr | Leu | Glu | Ser |
| 456 | 456 | G | His | Ser | Gln | Gly | Thr | Phe | Thr | Ser | Asp | Tyr | Ser | Lys | Tyr | Leu | Glu | Glu |
| 457 | 457 | G | His | Ser | Gln | Gly | Thr | Phe | Thr | Ser | Asp | Tyr | Ser | Lys | Tyr | Leu | Glu | Glu |
| 458 | 458 | G | His | Ser | Gln | Gly | Thr | Phe | Thr | Ser | Asp | Tyr | Ser | Lys | Tyr | Leu | Glu | Glu |
| 459 | 459 | G | His | Ser | Gln | Gly | Thr | Phe | Thr | Ser | Asp | Tyr | Ser | Lys | Tyr | Leu | Glu | Glu |
| 460 | 460 | G | His | Ser | Gln | Gly | Thr | Phe | Thr | Ser | Asp | Tyr | Ser | Lys | Tyr | Leu | Glu | Ser |
| 461 | 461 | G | His | Ser | Gln | Gly | Thr | Phe | Thr | Ser | Asp | Tyr | Ser | Lys | Tyr | Leu | Glu | Ser |
| 462 | 462 | G | His | Ser | Gln | Gly | Thr | Phe | Thr | Ser | Asp | Tyr | Ser | Lys | Tyr | Leu | Glu | Glu |
| 463 | 463 | G | His | Ser | Gln | Gly | Thr | Phe | Thr | Ser | Asp | Tyr | Ser | Lys | Tyr | Leu | Glu | Glu |
| 464 | 464 | G | His | Ser | Gln | Gly | Thr | Phe | Thr | Ser | Asp | Tyr | Ser | Lys | Tyr | Leu | Glu | Glu |
| 465 | 465 | G | His | Ser | Gln | Gly | Thr | Phe | Thr | Ser | Asp | Tyr | Ser | Lys | Tyr | Leu | Glu | Glu |
| 466 | 466 | G | His | Ser | Gln | Gly | Thr | Phe | Thr | Ser | Asp | Tyr | Ser | Lys | Tyr | Leu | Glu | Ser |
| 467 | 467 | G | His | Ser | Gln | Gly | Thr | Phe | Thr | Ser | Asp | Tyr | Ser | Lys | Tyr | Leu | Glu | Ser |
| 468 | 468 | G | His | Ser | Gln | Gly | Thr | Phe | Thr | Ser | Asp | Tyr | Ser | Lys | Tyr | Leu | Glu | Glu |
| 469 | 469 | G | His | Ser | Gln | Gly | Thr | Phe | Thr | Ser | Asp | Tyr | Ser | Lys | Tyr | Leu | Glu | Glu |
| 470 | 470 | G | His | Ser | Gln | Gly | Thr | Phe | Thr | Ser | Asp | Tyr | Ser | Lys | Tyr | Leu | Glu | Ser |
| 471 | 471 | G | His | Gly | Gln | Gly | Thr | Phe | Thr | Ser | Asp | Leu | Ser | Lys | Gln | Leu | Glu | Ser |
| 472 | 472 | G | His | Gly | Glu | Gly | Thr | Phe | Thr | Ser | Asp | Tyr | Ser | Lys | Gln | Leu | Glu | Glu |
| 473 | 473 | G | His | Ser | Gln | Gly | Thr | Phe | Thr | Ser | Asp | Tyr | Ser | Lys | Tyr | Leu | Glu | Ser |
| 474 | 474 | G | His | Ser | Gln | Gly | Thr | Phe | Thr | Ser | Asp | Tyr | Ser | Lys | Tyr | Leu | Glu | Ser |
| 475 | 475 | G | His | Ser | Gln | Gly | Thr | Phe | Thr | Ser | Asp | Tyr | Ser | Lys | Tyr | Leu | Glu | Ser |
| 476 | 476 | G | His | Ser | Gln | Gly | Thr | Phe | Thr | Ser | Asp | Tyr | Ser | Lys | Tyr | Leu | Glu | Glu |

| SEQ ID NO | Analogue no. | G no. | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|
| 427 | 427 | G | Glu | Ala | Val | Arg | Leu | Phe | Ile | Glu | Trp | Leu | Leu | Asn | Thr | | NH2 | |
| 428 | 428 | G | Glu | Ala | Val | Arg | Leu | Phe | Ile | Glu | Trp | Leu | Leu | Asn | Thr | | | |
| 429 | 429 | G | Glu | Ala | Val | Arg | Leu | Phe | Ile | Glu | Trp | Leu | Leu | Asn | Thr | | NH2 | |
| 430 | 430 | G | Gln | Ala | Val | Arg | Leu | Phe | Ile | Gln | Trp | Leu | Leu | Asn | Thr | | NH2 | |
| 431 | 431 | G | Gln | Ala | Val | Arg | Leu | Phe | Ile | Gln | Trp | Leu | Leu | Asn | Thr | | NH2 | |
| 432 | 432 | G | Glu | Ala | Val | Arg | Leu | Phe | Ile | Glu | Trp | Leu | Leu | Asn | Gly | | | |
| 433 | 433 | G | Glu | Ala | Val | Arg | Leu | Phe | Ile | Glu | Trp | Leu | Leu | Asn | Gly | Gly | NH2 | |
| 434 | 434 | G | Glu | Ala | Val | Arg | Leu | Phe | Ile | Glu | Trp | Leu | Leu | Asn | Gly | | | |
| 435 | 435 | G | Glu | Ala | Val | Arg | Leu | Phe | Ile | Glu | Trp | Leu | Leu | Asn | Thr | | | |
| 436 | 436 | G | Glu | Ala | Val | Arg | Leu | Phe | Ile | Glu | Trp | Leu | Lys | Asn | Thr | | NH2 | |
| 437 | 437 | G | Gln | Ala | Val | Arg | Leu | Phe | Ile | Glu | Trp | Leu | Lys | Asn | Thr | | NH2 | |
| 438 | 438 | G | Glu | Ala | Val | Arg | Leu | Phe | Ile | Glu | Trp | Leu | Lys | Asn | Thr | | NH2 | |
| 439 | 439 | G | Gln | Ala | Val | Arg | Leu | Phe | Ile | Glu | Trp | Leu | Leu | Asn | Thr | | | |
| 440 | 440 | G | Glu | Ala | Val | Arg | Leu | Phe | Ile | Glu | Trp | Leu | Leu | Asn | Gly | Gly | | NH2 |
| 441 | 441 | G | Glu | Ala | Val | Arg | Leu | Phe | Ile | Glu | Trp | Leu | Lys | Asn | Thr | Gly | | |
| 442 | 442 | G | Glu | Ala | Val | Arg | Leu | Phe | Ile | Glu | Trp | Leu | Leu | Asn | Gly | Gly | | |
| 443 | 443 | G | Glu | Ala | Val | Arg | Leu | Phe | Ile | Glu | Trp | Leu | Leu | Asn | Gly | Gly | | |
| 444 | 444 | G | Glu | Ala | Val | Arg | Leu | Phe | Ile | Glu | Trp | Leu | Leu | Asn | Gly | Gly | | |
| 445 | 445 | G | Glu | Ala | Val | Arg | Leu | Phe | Ile | Glu | Trp | Leu | Leu | Asn | Gly | Gly | | |
| 446 | 446 | G | Glu | Ala | Val | Arg | Leu | Phe | Ile | Glu | Trp | Leu | Leu | Asn | Gly | Gly | | |
| 447 | 447 | G | Glu | Ala | Val | Arg | Leu | Phe | Ile | Glu | Trp | Leu | Leu | Asn | Gly | Lys | | |
| 448 | 448 | G | Glu | Ala | Val | Arg | Leu | Phe | Ile | Glu | Trp | Leu | Leu | Asn | Gly | Gly | | NH2 |
| 449 | 449 | G | Glu | Ala | Val | Arg | Leu | Phe | Ile | Glu | Trp | Leu | Leu | Asn | Gly | Gly | | NH2 |
| 450 | 450 | G | Glu | Ala | Val | Arg | Leu | Phe | Ile | Glu | Trp | Leu | Leu | Asn | Gly | Gly | | |
| 451 | 451 | G | Glu | Ala | Val | Arg | Leu | Phe | Ile | Glu | Trp | Leu | Leu | Asn | Gly | Gly | | |
| 452 | 452 | G | Glu | Ala | Val | Arg | Leu | Phe | Ile | Glu | Trp | Leu | Leu | Asn | Thr | Gly | | |
| 453 | 453 | G | Gln | Ala | Val | Arg | Leu | Phe | Ile | Glu | Trp | Leu | Leu | Asn | Gly | Gly | | |
| 454 | 454 | G | Gln | Ala | Val | Arg | Leu | Phe | Ile | Glu | Trp | Leu | Leu | Asn | Gly | Gly | | |
| 455 | 455 | G | Gln | Ala | Val | Arg | Leu | Phe | Ile | Glu | Trp | Leu | Leu | Asn | Gly | Gly | | |
| 456 | 456 | G | Glu | Ala | Val | Arg | Leu | Phe | Ile | Glu | Trp | Leu | Leu | Asn | Gly | Gly | | NH2 |
| 457 | 457 | G | Glu | Ala | Val | Arg | Leu | Phe | Ile | Glu | Trp | Leu | Leu | Asn | Thr | Gly | | |
| 458 | 458 | G | Glu | Ala | Val | Arg | Leu | Phe | Ile | Glu | Trp | Leu | Leu | Asn | Gly | Gly | | |
| 459 | 459 | G | Glu | Ala | Val | Arg | Leu | Phe | Ile | Glu | Trp | Leu | Leu | Asn | Gly | Gly | | NH2 |
| 460 | 460 | G | Glu | Ala | Val | Arg | Leu | Phe | Val | Glu | Trp | Leu | Leu | Asn | Gly | Gly | | |
| 461 | 461 | G | Glu | Ala | Val | Arg | Leu | Phe | Ile | Glu | Trp | Leu | Leu | Asn | Gly | Gly | | NH2 |
| 462 | 462 | G | Glu | Ala | Val | Arg | Leu | Phe | Ile | Glu | Trp | Leu | Leu | Asn | Gly | Gly | NH2 | |
| 463 | 463 | G | Glu | Ala | Val | Arg | Leu | Phe | Ile | Glu | Trp | Leu | Lys | Asn | Gly | Gly | | NH2 |
| 464 | 464 | G | Glu | Ala | Val | Arg | Leu | Phe | Ile | Glu | Trp | Leu | Leu | Asn | Thr | Gly | | |
| 465 | 465 | G | Glu | Ala | Val | Arg | Leu | Phe | Ile | Glu | Trp | Leu | Lys | Asn | Thr | Gly | | NH2 |
| 466 | 466 | G | Glu | Ala | Val | Arg | Leu | Phe | Ile | Glu | Trp | Leu | Lys | Asn | Gly | Gly | | NH2 |
| 467 | 467 | G | Gln | Ala | Val | Arg | Leu | Phe | Ile | Glu | Trp | Leu | Lys | Asn | Gly | Gly | | NH2 |
| 468 | 468 | G | Gln | Ala | Val | Arg | Leu | Phe | Ile | Glu | Trp | Leu | Leu | Asn | Gly | Lys | | NH2 |
| 469 | 469 | G | Glu | Ala | Val | Arg | Leu | Phe | Ile | Glu | Trp | Leu | Leu | Asn | Gly | Gly | | |
| 470 | 470 | G | Gln | Ala | Val | Arg | Leu | Phe | Ile | Glu | Trp | Leu | Leu | Asn | Gly | Gly | NH2 | |
| 471 | 471 | G | Gln | Ala | Val | Arg | Leu | Phe | Ile | Glu | Trp | Leu | Lys | Asn | Thr | Gly | NH2 | |
| 472 | 472 | G | Gln | Ala | Val | Arg | Leu | Phe | Ile | Glu | Trp | Leu | Lys | Asn | Gly | Gly | NH2 | |
| 473 | 473 | G | Gln | Ala | Val | Arg | Leu | Phe | Ile | Glu | Trp | Leu | Lys | Asn | Gly | Gly | | NH2 |
| 474 | 474 | G | Gln | Ala | Val | Arg | Leu | Phe | Ile | Glu | Trp | Leu | Leu | Asn | Gly | Gly | | NH2 |
| 475 | 475 | G | Gln | Ala | Val | Arg | Leu | Phe | Ile | Glu | Trp | Leu | Leu | Asn | Thr | Gly | | NH2 |
| 476 | 476 | G | Gln | Ala | Val | Arg | Leu | Phe | Ile | Glu | Trp | Leu | Leu | Asn | Gly | Gly | | NH2 |

Fig. 2 (continued)

| SEQ ID NO. | Analogue no. | G no. | hCGCr cAMP vs hCGCG n | hCGCr cAMP vs hCGCG | hGLP-1r cAMP vs hGLP-1 n | hGLP-1r cAMP vs hGLP-1 | Mouse food intake inhibition (500nmol/kg) 0-1 | 0-4 | 0-8 | 4-8 | 8-24 | 24-32 | 0-24 | Rat food intake inhibition (500 nmol/kg with 1:1 Zn) 0-1 | 0-4 | 0-8 | 4-8 | 8-24 | 24-32 | 32-48 | 48-72 | 0-24 | 0-48 | 0-72 |
|---|---|---|---|---|---|---|---|---|---|---|---|---|---|---|---|---|---|---|---|---|---|---|---|---|
| 427 | 427 | G | 416 | 2760145I | 2 | 0.2 | 28 | 39 | 43 | 47 | 10 |  | 21 |  |  |  |  |  |  |  |  |  |  |  |
| 428 | 428 | G | 417 |  | 1 | 1.2 | 46 | 45 | 40 | 32 | 1 | -11 | 15 |  |  |  |  |  |  |  |  |  |  |  |
| 429 | 429 | G | 418 | 64 | 2 | 2.9 | 55 | 71 | 68 | 79 | 13 |  | 55 | 10 | -11 | 3 | 39 | 1 | 22 | -20 | -14 | 2 | -2 | -5 |
| 430 | 430 | G | 419 |  | 1 |  | 19 | 11 | 13 | 11 | 1 |  | 9 | -9 | -2 | 8 | 56 | -3 | -22 | -8 | -3 | 1 | -4 | -4 |
| 431 | 431 | G | 454 | 85 |  |  | 8 | 46 | 52 | 64 | 1 | -28 | 19 |  |  |  |  |  |  |  |  |  |  |  |
| 432 | 432 | G | 488 | 7 | 3 | 1.0 | 85 | 86 | 88 | 92 | 29 |  | 49 | -13 | 39 | 48 | 73 | 84 | 86 | 41 | -7 | -7 | 69 | 62 | 40 |
| 433 | 433 | G | 489 | 4 | 1 | 2.0 | 83 | 86 | 88 | 94 | 24 |  | 46 | 17 | 57 | 58 | 61 | 80 | 68 | 40 | -3 | -4 | 70 | 61 | 41 |
| 434 | 434 | G | 490 | 4 | 2 | 0.6 | 80 | 87 | 90 | 94 | 10 |  | 39 | -11 | 45 | 54 | 97 | 100 | 97 | 51 | 10 | -3 | 79 | 74 | 54 |
| 435 | 435 | G | 495 | 10 | 1 | 1.7 | 89 | 94 | 88 | 80 | -21 |  | 24 | -1 | 45 | 54 | 96 | 84 | 32 | 1 | -11 | -11 | 71 | 43 | 26 |
| 436 | 436 | G | 504 | 9 | 2 | 2.7 | 73 | 80 | 81 | 82 | 8 | -6 | 35 | -5 | -12 | -1 | 38 | 74 | 46 | 20 | -9 | -9 | 42 | 35 | 23 |
| 437 | 437 | G | 509 | 1797926 | 3 | 1.3 | 97 | 93 | 80 | 57 | 4 | -12 | 33 | -12 | 9 | 23 | 58 | 48 | 26 | 2 | -7 | -7 | 38 | 25 | 14 |
| 438 | 438 | G | 512 | 929510 | 4 | 0.9 | 98 | 96 | 90 | 77 | 4 | 1 | 36 | -14 | 14 | 50 | 67 | 77 | 54 | 11 | -1 | -1 | 61 | 43 | 28 |
| 439 | 439 | G | 514 | 2 |  |  | 93 | 94 | 84 | 67 | 0 |  | 32 | -22 | -10 | 0 | 28 | -3 | -12 | 12 | -1 | -1 | -2 | 2 | 1 |
| 440 | 440 | G | 535 | 5 | 3 | 0.7 | 70 | 85 | 86 | 87 | 3 |  | 37 | -8 | 1 | 29 | 97 | 100 | 99 | 61 | 9 | -11 | 73 | 70 | 40 |
| 441 | 441 | G | 536 | 43 | 3 | 2.4 | 70 | 90 | 91 | 92 | 23 |  | 44 | 9 | 33 | 52 | 100 | 99 | 91 | 49 | -7 | 9 | 77 | 70 | 51 |
| 442 | 442 | G | 537 | 1143 | 2 | 0.4 | 96 | 99 | 99 | -46 | -4 | -12 | 13 | 82 | 83 | 83 | 85 | 60 | -6 | 1 | -1 | -6 | 69 | 38 | 23 |
| 443 | 443 | G | 538 | 30945 | 3 | 0.3 | 54 | 83 | 77 | 65 | 4 |  | 27 | 20 | 47 | 60 | 92 | 99 | 98 | 52 | -12 | -12 | 84 | 73 | 45 |
| 444 | 444 | G | 539 | 21 | 3 | 3.3 | 95 | 99 | 97 | 92 | 12 |  | 39 | 21 | 14 | 36 | 92 | 77 | 45 | 23 | 37 | -8 | 62 | 46 | 43 |
| 445 | 445 | G | 540 | 196 | 3 | 0.9 | 99 | 100 | 84 | 52 | 6 |  | 31 | 23 | 5 | 24 | 72 | 73 | 42 | 15 | -8 | -3 | 54 | 38 | 23 |
| 446 | 446 | G | 541 | 11 | 4 | 0.4 | 58 | 85 | 86 | 88 | 9 |  | 33 | 21 | 53 | 66 | 98 | 100 | 97 | 67 | -2 | -2 | 87 | 80 | 53 |
| 447 | 447 | G | 543 | 36 | 4 | 1.0 | 95 | 99 | 98 | 95 | 18 |  | 51 | 3 | 27 | 39 | 83 | 97 | 85 | 25 | -3 | -3 | 73 | 58 | 38 |
| 448 | 448 | G | 544 | 26 | 3 | 2.2 | 45 | 73 | 91 | 97 | 34 | -1 | 51 | 8 | 18 | 35 | 93 | 92 | 76 | 35 | -4 | -4 | 66 | 57 | 39 |
| 449 | 449 | G | 545 | 435 | 2 | 0.6 | 75 | 85 | 88 | 94 | 19 | -2 | 43 | 32 | 28 | 33 | 46 | 68 | 59 | 28 | 12 | 12 | 52 | 45 | 35 |
| 450 | 450 | G | 546 | 22 | 3 | 0.8 | 103 | 102 | 77 | 26 | -1 |  | 25 | 8 | 33 | 47 | 84 | 93 | 84 | 32 | 2 | 2 | 60 | 42 | 35 |
| 451 | 451 | G | 547 | 30 | 4 | 0.4 | 79 | 82 | 85 | 90 | 15 |  | 41 | 10 | 2 | 15 | 49 | 55 | 54 | 49 | 4 | 4 | 36 | 43 | 31 |
| 452 | 452 | G | 550 | 7 | 1 | 0.4 | 54 | 84 | 75 | 58 | 3 |  | 25 | 32 | 39 | 45 | 62 | 78 | 23 | 27 | -10 | -10 | 66 | 48 | 29 |
| 453 | 453 | G | 557 | 6 | 2 | 0.3 | 91 | 96 | 98 | 100 | 21 | -30 | 46 | 43 | 69 | 69 | 69 | 77 | 19 | 4 | -1 | -8 | 74 | 42 | 27 |
| 454 | 454 | G | 559 |  | 2 | 0.5 | 87 | 89 | 87 | 81 | -6 | 6 | 29 | 33 | 63 | 69 | 96 | 91 | 57 | 16 | -8 | -17 | 82 | 55 | 34 |
| 455 | 455 | G | 560 | 67 | 4 | 0.6 | 84 | 87 | 80 | 70 | 13 |  | 38 | 22 | 48 | 54 | 74 | 95 | 70 | 23 | 4 | 4 | 78 | 61 | 44 |
| 456 | 456 | G | 561 |  | 3 | 1.6 | 71 | 84 | 88 | 95 | 15 | 15 | 37 | 16 | 10 | 20 | 46 | 11 | -21 | 7 | -3 | -3 | 15 | 8 | 5 |
| 457 | 457 | G | 562 | 7 | 1 | 1.1 | 66 | 80 | 81 | 84 | 8 | 6 | 31 | 13 | 27 | 43 | 82 | 60 | 49 | 13 | -1 | -1 | 52 | 39 | 27 |
| 458 | 458 | G | 563 | 11 | 3 | 0.5 | 86 | 89 | 90 | 93 | 13 | -8 | 42 | 26 | 42 | 54 | 88 | 81 | 68 | 33 | 2 | -2 | 69 | 57 | 39 |
| 459 | 459 | G | 570 | 22 | 3 | 4.6 | 81 | 86 | 87 | 89 | -1 |  | 33 | 34 | 58 | 64 | 97 | 89 | 74 | 38 | 49 | 7 | 79 | 63 | 43 |
| 460 | 460 | G | 571 | 23 | 2 | 0.6 | 91 | 95 | 86 | 77 | -6 |  | 33 | 35 | 69 | 66 | 100 | 100 | 70 | 33 | 27 | 4 | 87 | 65 | 43 |
| 461 | 461 | G | 576 |  |  |  | 86 | 70 | 45 | 10 | -6 |  | 13 | 22 | 48 | 37 | -22 | 1 | -1 | -2 | 4 | -12 | 16 | 8 | 2 |
| 462 | 462 | G | 581 | 3 | 1 | 1.7 | 90 | 93 | 93 | 94 | 2 |  | 30 | 18 | 55 | 15 | 10 | 47 | 57 | 9 | -12 | 2 | 34 | 28 | 20 |
| 463 | 463 | G | 582 |  | 1 | 1.2 | 77 | 89 | 91 | 95 | 10 |  | 35 | 6 | 16 | 13 | -1 | 30 | 49 | -7 | 2 | -1 | 23 | 16 | 11 |
| 464 | 464 | G | 583 | 3 | 2 | 2.0 | 76 | 86 | 86 | 95 | -2 |  | 26 | 9 | 38 | 47 | 93 | 97 | 76 | 11 | 1 | 1 | 76 | 54 | 38 |
| 465 | 465 | G | 600 | 25 | 1 | 4.3 | 65 | 69 | 73 | 69 | 11 |  | 38 | -5 | 43 | 58 | 98 | 100 | 91 | 38 | 7 | 7 | 83 | 69 | 49 |
| 466 | 466 | G | 622 |  | 3 | 0.7 | 84 | 75 | 72 | 47 | -8 |  | 26 | 30 | 45 | 49 | 58 | 47 | 8 | -1 | -2 | -2 | 48 | 27 | 19 |
| 467 | 467 | G | 630 | 5 | 2 | 0.7 | 94 | 95 | 94 | 93 | 50 |  | 68 | 16 | 48 | 86 | 100 | 85 | 40 | 16 | 5 | 4 | 59 | 42 | 30 |
| 468 | 468 | G | 640 |  | 2 | 2.6 | 80 | 88 | 91 | 96 | 6 |  | 36 | 24 | 21 | 22 | 23 | 10 | 28 | 5 | -14 | -14 | 22 | 17 | 9 |
| 469 | 469 | G | 662 |  | 1 | 1.2 | 100 | 93 | 93 | -65 | 2 |  | 14 | 48 | 51 | 60 | 85 | 71 | 31 | 13 | -21 | -21 | 66 | 35 | 20 |
| 470 | 470 | G | 663 |  | 1 | 1.2 | 100 | 99 | 93 | -19 | -1 |  | 17 | 51 | 50 | 58 | 79 | 48 | 11 | -10 | -12 | -12 | 53 | 26 | 16 |
| 471 | 471 | G | 665 |  | 1 | 1.7 | 100 | 82 | 86 | 54 | -17 |  | 26 | 19 | 61 | 58 | 48 | 14 | 25 | 1 | 0 | 0 | 33 | 22 | 15 |
| 472 | 472 | G | 667 |  |  |  | 94 | 67 | 75 | -20 | -8 |  | 38 | 10 | 42 | 43 | 47 | 44 | -2 | -2 | -1 | -1 | 43 | 27 | 18 |
| 473 | 473 | G | 668 |  | 3 | 1.6 | 67 | 91 | 90 | 88 | 26 |  | 50 | 38 | 68 | 75 | 100 | 85 | 47 | 18 | 4 | -4 | 81 | 57 | 37 |
| 474 | 474 | G | 696 |  |  |  | 39 | 64 | 56 | 45 | 2 |  | 22 | 23 | 26 | 31 | 54 | 10 | 13 | 5 | -14 | -14 | 19 | 11 | 7 |
| 475 | 475 | G | 697 |  | 2 |  | -8 | 43 | 52 | 64 | -6 |  | 15 | -1 | -6 | 7 | 52 | 6 | 13 | -13 | -3 | -3 | 7 | 4 | 2 |
| 476 | 476 | G | 710 | 23 | 2 | 1.9 | 63 | 78 | 82 | 87 | 9 |  | 37 | -16 | 3 | 15 | 41 | 27 | 6 | -13 | 17 | 17 | 21 | 10 | 13 |

Fig. 2 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 477 | 477 | G | His | Gly | Gln | Gly | Thr | Phe | Thr | Ser | Asp | Leu | Ser | Lys | Tyr | Leu | Glu | Gln |
| 478 | 478 | G | His | Gly | Gln | Gly | Thr | Phe | Thr | Ser | Asp | Leu | Ser | Lys | Gln | Leu | Glu | Gln |
| 479 | 479 | G | His | Ser | Gln | Gly | Thr | Phe | Thr | Ser | Asp | Tyr | Ser | His | Tyr | Leu | Glu | Gln |
| 480 | 480 | G | His | Gly | Gln | Gly | Thr | Phe | Thr | Ser | Asp | Leu | Ser | His | Gln | Leu | Glu | Gln |
| 481 | 481 | G | His | Ser | Gln | Gly | Thr | Phe | Thr | Ser | Asp | Tyr | Ser | Lys | Tyr | Leu | Glu | Gln |
| 482 | 482 | G | His | Ser | Gln | Gly | Thr | Phe | Thr | Ser | Asp | Tyr | Ser | Lys | Tyr | Leu | Glu | Gln |
| 483 | 483 | G | His | Ser | Gln | Gly | Thr | Phe | Thr | Ser | Asp | Tyr | Ser | Lys | Tyr | Leu | Glu | Gln |
| 484 | 484 | G | His | Ser | Gln | Gly | Thr | Phe | Thr | Ser | Asp | Tyr | Ser | Lys | Tyr | Leu | Glu | Gln |
| 485 | 485 | G | His | Ser | Gln | Gly | Thr | Phe | Thr | Ser | Asp | Tyr | Ser | Lys | Tyr | Leu | Glu | Gln |
| 486 | 486 | G | His | Ser | Gln | Gly | Thr | Phe | Thr | Ser | Asp | Tyr | Ser | Lys | Tyr | Leu | Glu | Gln |
| 487 | 487 | G | His | Ser | Gln | Gly | Thr | Phe | Thr | Ser | Asp | Tyr | Ser | Lys | Tyr | Leu | Glu | Gln |
| 488 | 488 | G | His | Ser | Gln | Gly | Thr | Phe | Thr | Ser | Asp | Leu | Ser | Lys | Tyr | Leu | Glu | Gln |
| 489 | 489 | G | His | Ser | Gln | Gly | Thr | Phe | Thr | Ser | Asp | Leu | Ser | His | Gln | Leu | Glu | Gln |
| 490 | 490 | G | His | Gly | Gln | Gly | Thr | Phe | Thr | Ser | Asp | Leu | Ser | His | Gln | Leu | Glu | Gln |
| 491 | 491 | G | His | Gly | Gln | Gly | Thr | Phe | Thr | Ser | Asp | Tyr | Ser | Lys | Tyr | Leu | Glu | Gln |
| 492 | 492 | G | His | Gly | Gln | Gly | Thr | Phe | Thr | Ser | Asp | Tyr | Ser | Lys | Tyr | Leu | Glu | Gln |
| 493 | 493 | G | His | Gly | Gln | Gly | Thr | Phe | Thr | Ser | Asp | Tyr | Ser | Lys | Tyr | Leu | Glu | Gln |
| 494 | 494 | G | His | Ser | Gln | Gly | Thr | Phe | Thr | Ser | Asp | Leu | Ser | Lys | Gln | Leu | Glu | Gln |
| 495 | 495 | G | His | Ser | Gln | Gly | Thr | Phe | Thr | Ser | Asp | Leu | Ser | Lys | Gln | Leu | Glu | Gln |
| 496 | 496 | G | His | Ser | Gln | Gly | Thr | Phe | Thr | Ser | Asp | Leu | Ser | Lys | Gln | Leu | Glu | Gln |
| 497 | 497 | G | His | Ser | Gln | Gly | Thr | Phe | Thr | Ser | Asp | Leu | Ser | Lys | Gln | Leu | Glu | Gln |
| 498 | 498 | G | His | Ser | Gln | Gly | Thr | Phe | Thr | Ser | Asp | Leu | Ser | Lys | Tyr | Leu | Glu | Gln |
| 499 | 499 | G | His | Ser | Gln | Gly | Thr | Phe | Thr | Ser | Asp | Tyr | Ser | Lys | Tyr | Leu | Glu | Gln |
| 500 | 500 | G | His | Ser | Gln | Gly | Thr | Phe | Thr | Ser | Asp | Leu | Ser | Lys | Tyr | Leu | Glu | Gln |
| 501 | 501 | G | His | Gly | Gln | Gly | Thr | Phe | Thr | Ser | Asp | Tyr | Ser | His | Tyr | Leu | Glu | Gln |
| 502 | 502 | G | His | Ser | Gln | Gly | Thr | Phe | Thr | Ser | Asp | Tyr | Ser | His | Tyr | Leu | Glu | Gln |
| 503 | 503 | G | His | Gly | Gln | Gly | Thr | Phe | Thr | Ser | Asp | Tyr | Ser | Lys | Tyr | Leu | Glu | Gln |
| 504 | 504 | G | His | Ser | Gln | Gly | Thr | Phe | Thr | Ser | Asp | Tyr | Ser | Lys | Tyr | Leu | Glu | Gln |
| 505 | 505 | G | His | Gly | Gln | Gly | Thr | Phe | Thr | Ser | Asp | Leu | Ser | His | Gln | Leu | Glu | Gln |
| 506 | 506 | G | His | Gly | Gln | Gly | Thr | Phe | Thr | Ser | Asp | Leu | Ser | His | Gln | Leu | Glu | Gln |
| 507 | 507 | G | His | Gly | Gln | Gly | Thr | Phe | Thr | Ser | Asp | Tyr | Ser | His | Gln | Leu | Glu | Gln |
| 508 | 508 | G | His | Gly | Gln | Gly | Thr | Phe | Thr | Ser | Asp | Tyr | Ser | His | Gln | Leu | Glu | Gln |
| 509 | 509 | G | His | Gly | Gln | Gly | Thr | Phe | Thr | Ser | Asp | Leu | Ser | His | Tyr | Leu | Glu | Ser |
| 510 | 510 | G | His | Ser | Gln | Gly | Thr | Phe | Thr | Ser | Asp | Tyr | Ser | His | Tyr | Leu | Glu | Ser |
| 511 | 511 | G | His | Ser | Gln | Gly | Thr | Phe | Thr | Ser | Asp | Tyr | Ser | His | Tyr | Leu | Glu | Ser |
| 512 | 512 | G | His | Gly | Gln | Gly | Thr | Phe | Thr | Ser | Asp | Tyr | Ser | His | Tyr | Leu | Glu | Ser |
| 513 | 513 | G | His | Gly | Gln | Gly | Thr | Phe | Thr | Ser | Asp | Tyr | Ser | His | Tyr | Leu | Glu | Ser |
| 514 | 514 | G | His | Gly | Gln | Gly | Thr | Phe | Thr | Ser | Asp | Tyr | Ser | Lys | Tyr | Leu | Glu | Gln |
| 515 | 515 | G | His | Gly | Gln | Gly | Thr | Phe | Thr | Ser | Asp | Tyr | Ser | Lys | Tyr | Leu | Glu | Gln |
| 516 | 516 | G | His | Ser | Gln | Gly | Thr | Phe | Thr | Ser | Asp | Leu | Ser | Lys | Tyr | Leu | Glu | Gln |
| 517 | 517 | G | His | Gly | Gln | Gly | Thr | Phe | Thr | Ser | Asp | Tyr | Ser | Lys | Tyr | Leu | Glu | Gln |
| 518 | 518 | G | His | Gly | Gln | Gly | Thr | Phe | Thr | Ser | Asp | Tyr | Ser | Lys | Tyr | Leu | Glu | Gln |
| 519 | 519 | G | His | Ser | Gln | Gly | Thr | Phe | Thr | Ser | Asp | Leu | Ser | His | Tyr | Leu | Glu | Gln |
| 520 | 520 | G | His | Ser | Gln | Gly | Thr | Phe | Thr | Ser | Asp | Tyr | Ser | His | Tyr | Leu | Glu | Gln |
| 521 | 521 | G | His | Gly | Gln | Gly | Thr | Phe | Thr | Ser | Asp | Tyr | Ser | His | Tyr | Leu | Glu | Gln |
| 522 | 522 | G | His | Ser | Gln | Gly | Thr | Phe | Thr | Ser | Asp | Tyr | Ser | His | Tyr | Leu | Glu | Gln |
| 523 | 523 | G | His | Gly | Gln | Gly | Thr | Phe | Thr | Ser | Asp | Tyr | Ser | His | Tyr | Leu | Glu | Gln |
| 524 | 524 | G | His | Ser | Gln | Gly | Thr | Phe | Thr | Ser | Asp | Tyr | Ser | His | Tyr | Leu | Glu | Gln |
| 525 | 525 | G | His | Ser | Gln | Gly | Thr | Phe | Thr | Ser | Asp | Tyr | Ser | His | Tyr | Leu | Glu | Gln |
| 526 | 526 | G | His | Ser | Gln | Gly | Thr | Phe | Thr | Ser | Asp | Leu | Ser | His | Gln | Leu | Glu | Gln |

Fig. 2 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|
| 477 | 477 | G | Glu | Ala | Val | Arg | Leu | Phe | Ile | Glu | Trp | Leu | Lys | Asn | Gly | Gly | His | NH2 |
| 478 | 478 | G | Glu | Ala | Val | Arg | Leu | Phe | Ile | Glu | Trp | Leu | Lys | Asn | Gly | Gly | His | NH2 |
| 479 | 479 | G | Glu | Ala | Val | His | Leu | Phe | Ile | Glu | Trp | Leu | Lys | Asn | Gly | His | NH2 | |
| 480 | 480 | G | Glu | Ala | Val | His | Leu | Phe | Ile | Glu | Trp | Leu | Lys | Asn | Gly | His | NH2 | |
| 481 | 481 | G | Glu | Ala | Leu | Arg | Leu | Phe | Ile | Glu | Trp | Leu | Lys | Asn | Thr | His | His | |
| 482 | 482 | G | Glu | Ala | Leu | Arg | Leu | Phe | Ile | Glu | Trp | Leu | Leu | Asn | Gly | His | His | |
| 483 | 483 | G | Glu | Ala | Leu | Arg | Leu | Phe | Ile | Glu | Trp | Leu | Leu | Asn | Thr | His | NH2 | |
| 484 | 484 | G | Glu | Ala | Leu | His | Leu | Phe | Ile | Glu | Trp | Leu | Lys | Asn | Gly | Gly | His | NH2 |
| 485 | 485 | G | Gln | Ala | Leu | Arg | Leu | Phe | Ile | Glu | Trp | Leu | Lys | Asn | Thr | His | NH2 | |
| 486 | 486 | G | Glu | Ala | Leu | His | Leu | Phe | Ile | Glu | Trp | Leu | Leu | Asn | Gly | His | NH2 | |
| 487 | 487 | G | Glu | Ala | Val | Arg | Ile | Phe | Ile | Glu | Trp | Leu | Leu | Asn | Gly | His | His | |
| 488 | 488 | G | Glu | Ala | Leu | Arg | Ile | Phe | Ile | Glu | Trp | Leu | Leu | Asn | Thr | His | NH2 | |
| 489 | 489 | G | Glu | Ala | Val | His | Ile | Phe | Ile | Glu | Trp | Leu | Lys | Asn | Gly | His | NH2 | |
| 490 | 490 | G | Glu | Ala | Leu | His | Ile | Phe | Ile | Glu | Trp | Leu | Lys | Asn | Thr | His | NH2 | |
| 491 | 491 | G | Gln | Ala | Val | His | Ile | Phe | Ile | Gln | Trp | Leu | Lys | Asn | Gly | His | His | |
| 492 | 492 | G | Glu | Ala | Val | Arg | Ile | Phe | Ile | Glu | Trp | Leu | Leu | Asn | Gly | His | His | |
| 493 | 493 | G | Glu | Ala | Val | Arg | Ile | Phe | Ile | Glu | Trp | Leu | Leu | Asn | Thr | Gly | His | NH2 |
| 494 | 494 | G | Glu | Ala | Val | Arg | Ile | Phe | Ile | Glu | Trp | Leu | Leu | Asn | Gly | Gly | His | NH2 |
| 495 | 495 | G | Gln | Ala | Val | Arg | Ile | Phe | Ile | Gln | Trp | Leu | Lys | Asn | Gly | Gly | His | NH2 |
| 496 | 496 | G | Gln | Ala | Val | His | Val | Phe | Ile | Glu | Trp | Leu | Leu | Asn | Gly | His | His | |
| 497 | 497 | G | Glu | Ala | Val | Arg | Leu | Phe | Ile | Glu | Trp | Leu | Lys | Asn | Gly | His | NH2 | |
| 498 | 498 | G | Glu | Ala | Val | Arg | Leu | Phe | Ile | Gln | Trp | Leu | Lys | Asn | Thr | His | NH2 | |
| 499 | 499 | G | Gln | Ala | Val | Arg | Leu | Phe | Ile | Gln | Trp | Leu | Lys | Asn | Gly | His | NH2 | |
| 500 | 500 | G | Glu | Ala | Val | Arg | Leu | Phe | Ile | Glu | Trp | Leu | Lys | Asn | Gly | Gly | His | NH2 |
| 501 | 501 | G | Glu | Ala | Val | Arg | Leu | Phe | Ile | Gln | Trp | Leu | Lys | Asn | Gly | Gly | His | NH2 |
| 502 | 502 | G | Gln | Ala | Val | Arg | Leu | Phe | Ile | Gln | Trp | Leu | Lys | Asn | Gly | Gly | His | NH2 |
| 503 | 503 | G | Glu | Ala | Val | Arg | Leu | Phe | Ile | Glu | Trp | Leu | Lys | Asn | Gly | Gly | His | NH2 |
| 504 | 504 | G | Gln | Ala | Leu | Arg | Leu | Phe | Ile | Glu | Trp | Leu | Lys | Asn | Gly | Gly | His | NH2 |
| 505 | 505 | G | Gln | Ala | Val | Arg | Leu | Phe | Ile | Glu | Trp | Leu | Lys | Asn | Gly | Gly | His | NH2 |
| 506 | 506 | G | Glu | Ala | Val | His | Leu | Phe | Ile | Glu | Trp | Leu | Lys | Asn | Thr | His | NH2 | |
| 507 | 507 | G | Glu | Ala | Val | His | Leu | Phe | Ile | Glu | Trp | Leu | Lys | Asn | Thr | His | NH2 | |
| 508 | 508 | G | Glu | Ala | Val | His | Leu | Phe | Ile | Glu | Trp | Leu | Lys | Asn | Gly | His | NH2 | |
| 509 | 509 | G | Glu | Ala | Val | His | Leu | Phe | Ile | Glu | Trp | Leu | Lys | Asn | Gly | His | NH2 | |
| 510 | 510 | G | Gln | Ala | Leu | Arg | Leu | Phe | Ile | Glu | Trp | Leu | Lys | Asn | Thr | His | NH2 | |
| 511 | 511 | G | Glu | Ala | Leu | Arg | Leu | Phe | Ile | Glu | Trp | Leu | Leu | Asn | Thr | His | NH2 | |
| 512 | 512 | G | Glu | Ala | Leu | Arg | Leu | Phe | Ile | Glu | Trp | Leu | Leu | Asn | Thr | His | NH2 | |
| 513 | 513 | G | Glu | Ala | Leu | His | Leu | Phe | Ile | Glu | Trp | Leu | Lys | Asn | Gly | Gly | His | NH2 |
| 514 | 514 | G | Glu | Ala | Leu | His | Leu | Phe | Ile | Glu | Trp | Leu | Lys | Asn | Gly | Gly | His | NH2 |
| 515 | 515 | G | Glu | Ala | Val | His | Leu | Phe | Ile | Glu | Trp | Leu | Lys | Asn | Gly | Gly | His | NH2 |
| 516 | 516 | G | Glu | Ala | Val | Arg | Leu | Phe | Ile | Glu | Trp | Leu | Lys | Asn | Thr | His | NH2 | |
| 517 | 517 | G | Gln | Ala | Val | Arg | Leu | Phe | Ile | Glu | Trp | Leu | Lys | Asn | Thr | His | NH2 | |
| 518 | 518 | G | Glu | Ala | Val | Arg | Leu | Phe | Ile | Glu | Trp | Leu | Lys | Asn | Thr | His | NH2 | |
| 519 | 519 | G | Gln | Ala | Val | Arg | Leu | Phe | Ile | Glu | Trp | Leu | Lys | Asn | Thr | His | NH2 | |
| 520 | 520 | G | Glu | Ala | Val | Arg | Leu | Phe | Ile | Glu | Trp | Leu | Lys | Asn | Thr | His | NH2 | |
| 521 | 521 | G | Glu | Ala | Val | Arg | Leu | Phe | Ile | Glu | Trp | Leu | Lys | Asn | Thr | His | NH2 | |
| 522 | 522 | G | Gln | Ala | Val | Arg | Leu | Phe | Ile | Glu | Trp | Leu | Lys | Asn | Thr | His | NH2 | |
| 523 | 523 | G | Gln | Ala | Val | Arg | Leu | Phe | Ile | Glu | Trp | Leu | Lys | Asn | Thr | His | NH2 | |
| 524 | 524 | G | Gln | Ala | Val | Arg | Leu | Phe | Ile | Glu | Trp | Leu | Lys | Asn | Thr | Gly | His | NH2 |
| 525 | 525 | G | Gln | Ala | Val | His | Leu | Phe | Ile | Glu | Trp | Leu | Lys | Asn | Thr | His | NH2 | |
| 526 | 526 | G | Gln | Ala | Val | His | Ile | Phe | Ile | Glu | Trp | Leu | Lys | Asn | Thr | His | NH2 | |

Fig. 2 (continued)

| SEQ ID NO. | Analogue no. | G mo. | | hCGCr cAMP vs hGCG | | hGLP-1r cAMP vs hGLP-1 | | Mouse food intake inhibition (500nmol/kg) | | | | | | | Rat food intake inhibition (500 nmol/kg with 1:1 Zn) | | | | | | | | |
|---|---|---|---|---|---|---|---|---|---|---|---|---|---|---|---|---|---|---|---|---|---|---|---|
| | | | | | n | | n | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 477 | 477 | G | | | | 1.4 | 2 | 82 | 89 | 81 | 63 | 5 | -1 | 33 | 59 | 80 | 85 | 97 | 100 | 95 | 69 | 39 | 92 | 87 | 70 |
| 478 | 478 | G | | | | 0.4 | 2 | 82 | 86 | 74 | 52 | -4 | | 23 | 88 | 94 | 95 | 98 | 66 | 18 | -22 | 10 | 81 | 45 | 33 |
| 479 | 479 | G | | | | 0.6 | 2 | 82 | 82 | 59 | 16 | -19 | | 13 | 79 | 89 | 93 | 100 | 81 | 11 | -19 | 9 | 87 | 48 | 34 |
| 480 | 480 | G | | | | 1.0 | 3 | 77 | 60 | 25 | -48 | 3 | 1 | 11 | 78 | 88 | 78 | 58 | -5 | 15 | -31 | 13 | 38 | 17 | 15 |
| 481 | 481 | G | | | | 1.1 | 4 | 78 | 69 | 33 | -19 | 10 | | 18 | 75 | 77 | 63 | -45 | 39 | -23 | 1 | -8 | 47 | 25 | 15 |
| 482 | 482 | G | | | | 0.5 | 2 | 73 | 82 | 84 | 88 | -8 | | 31 | -29 | 26 | 27 | 54 | 97 | 99 | 28 | -6 | 72 | 60 | 39 |
| 483 | 483 | G | | | | 1.0 | 3 | 54 | 69 | 76 | 88 | 9 | | 39 | 12 | 9 | 21 | 78 | 27 | 12 | 6 | 0 | 25 | 17 | 12 |
| 484 | 484 | G | | 240691 | 2 | 0.3 | 3 | 76 | 87 | 89 | 94 | 23 | | 50 | -16 | 43 | 46 | 100 | 98 | 90 | 41 | -2 | 80 | 68 | 45 |
| 485 | 485 | G | | 674499 | 1 | 1.0 | 3 | 74 | 82 | 60 | 20 | -22 | | 17 | -51 | 27 | 23 | -50 | 15 | 6 | -5 | 9 | 18 | 9 | 5 |
| 486 | 486 | G | | | | 1.3 | 2 | 50 | 72 | 81 | 96 | -4 | | 33 | 33 | 37 | 45 | 87 | 81 | 70 | 23 | 9 | 65 | 52 | 39 |
| 487 | 487 | G | | | | 1.1 | 2 | 85 | 91 | 94 | 97 | 11 | | 45 | 26 | 44 | 53 | 99 | 92 | 89 | 38 | -12 | 74 | 65 | 41 |
| 488 | 488 | G | | | | 1.7 | 2 | 63 | 72 | 72 | 71 | 9 | | 37 | 20 | 27 | 30 | 46 | 39 | -25 | 10 | 7 | 35 | 19 | 15 |
| 489 | 489 | G | | | | 1.6 | 2 | 87 | 88 | 84 | 77 | 18 | | 47 | 59 | 54 | 51 | 32 | -11 | 10 | -4 | -4 | 17 | 9 | 5 |
| 490 | 490 | G | | | | 1.2 | 2 | 86 | 90 | 77 | 55 | -19 | | 24 | 43 | 49 | 51 | 62 | 3 | 1 | -4 | 5 | 25 | 16 | 13 |
| 491 | 491 | G | | | | 3.1 | 3 | 62 | 76 | 75 | 74 | 2 | | 35 | 16 | 46 | 53 | 93 | 85 | 46 | 7 | -1 | 70 | 48 | 33 |
| 492 | 492 | G | | | | 1.0 | 3 | 88 | 92 | 93 | 94 | 48 | | 69 | 20 | 45 | 54 | 99 | 100 | 100 | 92 | 26 | 80 | 86 | 67 |
| 493 | 493 | G | | | | 1.6 | 3 | 80 | 87 | 87 | 88 | 14 | | 50 | 50 | 58 | 64 | 98 | 98 | 67 | 16 | -9 | 83 | 61 | 49 |
| 494 | 494 | G | | | | 1.1 | 3 | 79 | 86 | 83 | 78 | 15 | | 48 | 4 | 11 | 24 | 97 | 97 | 78 | 31 | 7 | 65 | 74 | 61 |
| 495 | 495 | G | | | | 2.3 | 2 | 61 | 77 | 82 | 89 | 3 | | 41 | 13 | 37 | 42 | 77 | 94 | 96 | 66 | -6 | 70 | 71 | 48 |
| 496 | 496 | G | | | | | | 50 | 42 | 36 | 26 | 5 | | 20 | 12 | 6 | 15 | 69 | 51 | 9 | -24 | -12 | 36 | 14 | 6 |
| 497 | 497 | G | | | | 1.5 | 2 | 54 | 67 | 62 | 54 | 4 | | 32 | -4 | 20 | 31 | 90 | 83 | 64 | 18 | -5 | 60 | 49 | 32 |
| 498 | 498 | G | | | | 1.2 | 3 | 87 | 91 | 85 | 75 | 6 | | 45 | 3 | 22 | 32 | 88 | 99 | 95 | 47 | -7 | 70 | 67 | 44 |
| 499 | 499 | G | | | | 1.2 | 3 | 65 | 79 | 83 | 91 | 7 | | 44 | -9 | 22 | 27 | 53 | 78 | 69 | 42 | 18 | 55 | 53 | 42 |
| 500 | 500 | G | | | | 3.6 | 2 | 83 | 87 | 60 | 29 | -11 | | 24 | 41 | 61 | 67 | 96 | 99 | 83 | 24 | -1 | 85 | 67 | 46 |
| 501 | 501 | G | | | | 1.1 | 4 | 69 | 84 | 88 | 94 | 21 | | 50 | 11 | 54 | 61 | 100 | 100 | 93 | 62 | 19 | 83 | 77 | 59 |
| 502 | 502 | G | | | | 1.2 | 2 | 87 | 83 | 75 | 62 | -6 | | 34 | 15 | 40 | 48 | 96 | 100 | 98 | 85 | 8 | 77 | 83 | 60 |
| 503 | 503 | G | | | | 1.1 | 3 | 91 | 92 | 81 | 61 | -8 | | 27 | 1 | 15 | 18 | 37 | 99 | 95 | 88 | 49 | 88 | 90 | 77 |
| 504 | 504 | G | | | | 0.9 | 2 | 85 | 85 | 79 | 70 | -9 | | 31 | 55 | 11 | 2 | -48 | 12 | 69 | 88 | 13 | 76 | 83 | 61 |
| 505 | 505 | G | | | | 0.5 | 1 | 91 | 90 | 80 | 64 | 3 | | 34 | 20 | 11 | -2 | 35 | -6 | 99 | 13 | 8 | 35 | 20 | 16 |
| 506 | 506 | G | | | | 1.7 | 2 | 81 | 67 | 35 | -18 | -4 | | 15 | 21 | -8 | -2 | 45 | 30 | 10 | 0 | 8 | 45 | 6 | 4 |
| 507 | 507 | G | | | | 5.2 | 2 | 70 | 69 | 45 | 5 | -9 | | 17 | 1 | 15 | 18 | 37 | 12 | -3 | -5 | -1 | 15 | -6 | -4 |
| 508 | 508 | G | | | | 2.0 | 2 | 75 | 60 | 38 | 1 | -19 | | 9 | 4 | 11 | 2 | -48 | -6 | -2 | -15 | -1 | -2 | -6 | -1 |
| 509 | 509 | G | | | | 2.0 | 3 | 93 | 95 | 86 | 72 | 2 | | 33 | 5 | -8 | -2 | 35 | 13 | 7 | -13 | -2 | 6 | -1 | 1 |
| 510 | 510 | G | | | | 0.8 | 3 | 95 | 98 | 88 | 75 | 0 | | 38 | 40 | 43 | 48 | 69 | 46 | 13 | 9 | -1 | 47 | 29 | 21 |
| 511 | 511 | G | | | | 1.9 | 2 | 96 | 96 | 91 | 84 | 9 | | 44 | 51 | 65 | 67 | 77 | 93 | 76 | 28 | 1 | 81 | 63 | 44 |
| 512 | 512 | G | | | | 2.6 | 3 | 98 | 98 | 93 | 85 | 3 | | 42 | 76 | 79 | 79 | 80 | 87 | 57 | 22 | 18 | 83 | 59 | 47 |
| 513 | 513 | G | | | | 39.6 | 2 | 76 | 88 | 93 | 102 | 34 | | 55 | 29 | 72 | 65 | 80 | 60 | 16 | 5 | -5 | 66 | 39 | 25 |
| 514 | 514 | G | | | | 64.7 | 2 | 93 | 96 | 98 | 100 | 19 | | 50 | 26 | 56 | 64 | 99 | 100 | 96 | 53 | -2 | 84 | 76 | 51 |
| 515 | 515 | G | | | | 48.5 | 1 | 79 | 90 | 93 | 98 | 20 | | 46 | 62 | 57 | 70 | 96 | 97 | 70 | 53 | 1 | 83 | 71 | 48 |
| 516 | 516 | G | | | | 0.7 | 3 | 99 | 96 | 95 | 90 | 22 | | 48 | 27 | 24 | 28 | 48 | 56 | 34 | 10 | 1 | 45 | 51 | 35 |
| 517 | 517 | G | | | | 1.8 | 2 | 98 | 99 | 87 | 69 | 4 | | 38 | 38 | 48 | 53 | 69 | -7 | 16 | 11 | -1 | 21 | 33 | 25 |
| 518 | 518 | G | | | | 3.6 | 2 | 98 | 99 | 87 | 69 | -3 | | 34 | 65 | 78 | 83 | 100 | 13 | 39 | -9 | -7 | 77 | 11 | 6 |
| 519 | 519 | G | | | | 1.7 | 1 | 99 | 98 | 89 | 74 | -10 | | 31 | 47 | 62 | 71 | 100 | 72 | 38 | 4 | -4 | 78 | 48 | 33 |
| 520 | 520 | G | | | | 1.8 | 2 | 88 | 92 | 89 | 84 | -2 | | 35 | 25 | 45 | 57 | 98 | 84 | 45 | 16 | 2 | 70 | 52 | 37 |
| 521 | 521 | G | | | | 2.1 | 2 | 85 | 91 | 91 | 91 | 22 | | 50 | 8 | 28 | 32 | 54 | 82 | 17 | 3 | -8 | 29 | 45 | 29 |
| 522 | 522 | G | | | | 2.9 | 2 | 96 | 98 | 95 | 90 | 18 | | 49 | 35 | 48 | 46 | 42 | 27 | -1 | -1 | 12 | 32 | 18 | 16 |
| 523 | 523 | G | | | | 2.0 | 3 | 92 | 84 | 72 | 53 | 6 | | 32 | 8 | 58 | 56 | 94 | 13 | -10 | 2 | 3 | 28 | 15 | 12 |
| 524 | 524 | G | | | | 1.6 | 2 | 98 | 99 | 85 | 94 | 13 | | 46 | 26 | 81 | 83 | 32 | 12 | 54 | 2 | 7 | 32 | 16 | 12 |
| 525 | 525 | G | | | | 3.2 | 3 | 95 | 94 | 87 | 76 | 17 | | 45 | 40 | 53 | 49 | 42 | 79 | 55 | 11 | 5 | 81 | 55 | 40 |
| 526 | 526 | G | | | | | | 90 | 93 | 77 | 44 | -21 | | 16 | 26 | 25 | 19 | -20 | 8 | -9 | 23 | -2 | 59 | 47 | 34 |
| | | | | | | | | | | | | | | | | | | | | | | | 13 | 9 | 5 |

Fig. 2 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 527 | 527 | G | 881 | His | Ser | Gln | Gly | Thr | Phe | Thr | Ser | Asp | Tyr | Ser | His | Tyr | Leu | Glu | Glu |
| 528 | 528 | G | 882 | His | Ser | Gln | Gly | Thr | Phe | Thr | Ser | Asp | Tyr | Ser | His | Tyr | Leu | Glu | Glu |
| 529 | 529 | G | 883 | His | Ser | Gln | Gly | Thr | Phe | Thr | Ser | Asp | Tyr | Ser | His | Tyr | Leu | Glu | Glu |
| 530 | 530 | G | 885 | His | Ser | Gln | Gly | Thr | Phe | Thr | Ser | Asp | Tyr | Ser | His | Tyr | Leu | Glu | Ser |
| 531 | 531 | G | 886 | His | Ser | Gln | Gly | Thr | Phe | Thr | Ser | Asp | Tyr | Ser | His | Tyr | Leu | Glu | Glu |
| 532 | 532 | G | 887 | His | Ser | Gln | Gly | Thr | Phe | Thr | Ser | Asp | Tyr | Ser | His | Tyr | Leu | Glu | Glu |
| 533 | 533 | G | 888 | His | Ser | Glu | Gly | Thr | Phe | Thr | Ser | Asp | Tyr | Ser | His | Tyr | Leu | Glu | Glu |
| 534 | 534 | G | 889 | His | Gly | Gln | Gly | Thr | Phe | Thr | Ser | Asp | Tyr | Ser | His | Tyr | Leu | Glu | Ser |
| 535 | 535 | G | 890 | His | Gly | Gln | Gly | Thr | Phe | Thr | Ser | Asp | Tyr | Ser | His | Tyr | Leu | Glu | Ser |
| 536 | 536 | G | 892 | His | Ser | Gln | Gly | Thr | Phe | Thr | Ser | Asp | Tyr | Ser | His | Tyr | Leu | Glu | Ser |
| 537 | 537 | G | 907 | His | Ser | Gln | Gly | Thr | Phe | Thr | Ser | Asp | Tyr | Ser | His | Tyr | Leu | Glu | Ser |
| 538 | 538 | G | 908 | His | Ser | Gln | Gly | Thr | Phe | Thr | Ser | Asp | Tyr | Ser | His | Tyr | Leu | Glu | Ser |
| 539 | 539 | G | 909 | His | Ser | Gln | Gly | Thr | Phe | Thr | Ser | Asp | Tyr | Ser | His | Tyr | Leu | Glu | Ser |
| 540 | 540 | G | 910 | His | Gly | Gln | Gly | Thr | Phe | Thr | Ser | Asp | Tyr | Ser | His | Tyr | Leu | Glu | Ser |
| 541 | 541 | G | 911 | His | Ser | Glu | Gly | Thr | Phe | Thr | Ser | Asp | Tyr | Ser | His | Tyr | Leu | Glu | Ser |
| 542 | 542 | G | 912 | His | Ser | Gln | Gly | Thr | Phe | Thr | Ser | Asp | Tyr | Ser | His | Tyr | Leu | Glu | Ser |
| 543 | 543 | G | 913 | His | Ser | Gln | Gly | Thr | Phe | Thr | Ser | Asp | Tyr | Ser | His | Tyr | Leu | Glu | Ser |
| 544 | 544 | G | 914 | His | Ser | Gln | Gly | Thr | Phe | Thr | Ser | Asp | Tyr | Ser | His | Tyr | Leu | Glu | Ser |
| 545 | 545 | G | 915 | His | Ser | Glu | Gly | Thr | Phe | Thr | Ser | Asp | Tyr | Ser | His | Tyr | Leu | Glu | Ser |
| 546 | 546 | G | 916 | His | Ser | Gln | Gly | Thr | Phe | Thr | Ser | Asp | Tyr | Ser | His | Tyr | Leu | Glu | Ser |
| 547 | 547 | G | 918 | His | Gly | Glu | Gly | Thr | Phe | Thr | Ser | Asp | Tyr | Ser | His | Tyr | Leu | Glu | Ser |
| 548 | 548 | G | 919 | His | Ser | Glu | Gly | Thr | Phe | Thr | Ser | Asp | Tyr | Ser | His | Tyr | Leu | Glu | Ser |
| 549 | 549 | G | 927 | His | Ser | Gln | Gly | Thr | Phe | Thr | Ser | Asp | Tyr | Ser | His | Tyr | Leu | Glu | Ser |
| 550 | 550 | G | 928 | His | Ser | Gln | Gly | Thr | Phe | Thr | Ser | Asp | Tyr | Ser | His | Tyr | Leu | Glu | Ser |
| 551 | 551 | G | 929 | His | Ser | Gln | Gly | Thr | Phe | Thr | Ser | Asp | Tyr | Ser | Lys | Tyr | Leu | Glu | Ser |
| 552 | 552 | G | 930 | His | Ser | Glu | Gly | Thr | Phe | Thr | Ser | Asp | Tyr | Ser | Lys | Tyr | Leu | Glu | Ser |
| 553 | 553 | G | 931 | His | Ser | Glu | Gly | Thr | Phe | Thr | Ser | Asp | Tyr | Ser | Lys | Tyr | Leu | Glu | Ser |
| 554 | 554 | G | 934 | His | Ser | Glu | Gly | Thr | Phe | Thr | Ser | Asp | Tyr | Ser | Lys | Tyr | Leu | Glu | Ser |
| 555 | 555 | G | 935 | His | Ser | Glu | Gly | Thr | Phe | Thr | Ser | Asp | Tyr | Ser | Lys | Tyr | Leu | Glu | Ser |
| 556 | 556 | G | 936 | His | Ser | Glu | Gly | Thr | Phe | Thr | Ser | Asp | Tyr | Ser | Lys | Tyr | Leu | Glu | Ser |
| 557 | 557 | G | 937 | His | Ser | Glu | Gly | Thr | Phe | Thr | Ser | Asp | Tyr | Ser | His | Tyr | Leu | Glu | Ser |
| 558 | 558 | G | 938 | His | Ser | Glu | Gly | Thr | Phe | Thr | Ser | Asp | Tyr | Ser | Lys | Tyr | Leu | Glu | Ser |
| 559 | 559 | G | 939 | His | Ser | Glu | Gly | Thr | Phe | Thr | Ser | Asp | Tyr | Ser | Lys | Tyr | Leu | Glu | Ser |
| 560 | 560 | G | 940 | His | Ser | Glu | Gly | Thr | Phe | Thr | Ser | Asp | Tyr | Ser | Lys | Tyr | Leu | Glu | Ser |
| 561 | 561 | G | 941 | His | Ser | Glu | Gly | Thr | Phe | Thr | Ser | Asp | Tyr | Ser | Lys | Tyr | Leu | Glu | Ser |
| 562 | 562 | G | 942 | His | Ser | Glu | Gly | Thr | Phe | Thr | Ser | Asp | Tyr | Ser | Lys | Tyr | Leu | Glu | Ser |
| 563 | 563 | G | 943 | His | Ser | Glu | Gly | Thr | Phe | Thr | Ser | Asp | Tyr | Ser | His | Tyr | Leu | Glu | Ser |
| 564 | 564 | G | 944 | His | Ser | Glu | Gly | Thr | Phe | Thr | Ser | Asp | Tyr | Ser | Lys | Tyr | Leu | Glu | Ser |
| 565 | 565 | G | 945 | His | Ser | Glu | Gly | Thr | Phe | Thr | Ser | Asp | Tyr | Ser | Lys | Tyr | Leu | Glu | Ser |
| 566 | 566 | G | 946 | His | Ser | Glu | Gly | Thr | Phe | Thr | Ser | Asp | Tyr | Ser | Lys | Tyr | Leu | Glu | Ser |
| 567 | 567 | G | 947 | His | Ser | Glu | Gly | Thr | Phe | Thr | Ser | Asp | Tyr | Ser | Lys | Tyr | Leu | Glu | Ser |
| 568 | 568 | G | 948 | His | Ser | Glu | Gly | Thr | Phe | Thr | Ser | Asp | Tyr | Ser | Lys | Tyr | Leu | Glu | Ser |
| 569 | 569 | G | 949 | His | Ser | Glu | Gly | Thr | Phe | Thr | Ser | Asp | Tyr | Ser | His | Tyr | Leu | Glu | Ser |
| 570 | 570 | G | 950 | His | Ser | Glu | Gly | Thr | Phe | Thr | Ser | Asp | Tyr | Ser | Lys | Tyr | Leu | Glu | Glu |
| 571 | 571 | G | 951 | His | Ser | Glu | Gly | Thr | Phe | Thr | Ser | Asp | Tyr | Ser | Lys | Tyr | Leu | Glu | Glu |
| 572 | 572 | G | 959 | His | Ser | Glu | Gly | Thr | Phe | Thr | Ser | Asp | Tyr | Ser | Lys | Tyr | Leu | Glu | Glu |
| 573 | 573 | G | 960 | His | Ser | Glu | Gly | Thr | Phe | Thr | Ser | Asp | Tyr | Ser | Lys | Tyr | Leu | Glu | Glu |
| 574 | 574 | G | 961 | His | Ser | Glu | Gly | Thr | Phe | Thr | Ser | Asp | Tyr | Ser | Lys | Tyr | Leu | Glu | Glu |
| 575 | 575 | G | 962 | His | Ser | Gln | Gly | Thr | Phe | Thr | Ser | Asp | Tyr | Ser | Lys | Tyr | Leu | Glu | Ser |
| 576 | 576 | G | 963 | His | Ser | Gln | Gly | Thr | Phe | Thr | Ser | Asp | Tyr | Ser | Lys | Tyr | Leu | Glu | Glu |

Fig. 2 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|
| 527 | 527 | G | Gln | Ala | Val | His | Ile | Phe | Ile | Gln | Trp | Leu | Lys | Asn | Thr | His | NH2 | |
| 528 | 528 | G | Glu | Ala | Val | His | Leu | Phe | Ile | Glu | Trp | Leu | Lys | Asn | Gly | His | His | NH2 |
| 529 | 529 | G | Gln | Ala | Val | His | Leu | Phe | Ile | Gln | Trp | Leu | Lys | Asn | Thr | Gly | His | |
| 530 | 530 | G | Gln | Ala | Val | His | Leu | Phe | Ile | Gln | Trp | Leu | Lys | Asn | Thr | His | NH2 | |
| 531 | 531 | G | Gln | Ala | Val | His | Leu | Phe | Ile | Gln | Trp | Leu | Lys | Asn | Thr | His | NH2 | |
| 532 | 532 | G | Gln | Ala | Val | His | Leu | Phe | Ile | Gln | Trp | Leu | Lys | Asn | Thr | His | NH2 | |
| 533 | 533 | G | Gln | Ala | Val | His | Leu | Phe | Ile | Gln | Trp | Leu | Lys | Asn | Thr | His | NH2 | |
| 534 | 534 | G | Gln | Ala | Val | His | Leu | Phe | Ile | Gln | Trp | Leu | Lys | Asn | Thr | His | NH2 | |
| 535 | 535 | G | Gln | Ala | Val | His | Leu | Phe | Ile | Gln | Trp | Leu | Lys | Asn | Thr | His | NH2 | |
| 536 | 536 | G | Gln | Ala | Val | His | Leu | Phe | Ile | Gln | Trp | Leu | Leu | Asn | Thr | His | His | |
| 537 | 537 | G | Gln | Ala | Val | His | Leu | Phe | Ile | Gln | Trp | Leu | Lys | Asn | Thr | His | His | |
| 538 | 538 | G | Gln | Ala | Val | His | Leu | Phe | Ile | Gln | Trp | Leu | Lys | Asn | Thr | His | His | |
| 539 | 539 | G | Gln | Ala | Val | His | Leu | Phe | Ile | Gln | Trp | Leu | Lys | Asn | Thr | His | His | NH2 |
| 540 | 540 | G | Gln | Ala | Val | His | Leu | Phe | Ile | Gln | Trp | Leu | Lys | Asn | Thr | His | His | |
| 541 | 541 | G | Gln | Ala | Ala | His | Leu | Phe | Ile | Gln | Trp | Leu | Lys | Asn | Thr | His | NH2 | |
| 542 | 542 | G | Gln | Ala | Val | His | Leu | Phe | Val | Gln | Trp | Leu | Lys | Asn | Thr | His | NH2 | |
| 543 | 543 | G | Gln | Ala | Val | His | Leu | Phe | Ile | Gln | Trp | Leu | Lys | Asn | Thr | His | NH2 | |
| 544 | 544 | G | Gln | Ala | Ala | His | Leu | Phe | Val | Gln | Trp | Leu | Lys | Asn | Thr | His | His | |
| 545 | 545 | G | Gln | Ala | Val | His | Leu | Phe | Ile | Gln | Trp | Leu | Lys | Asn | Thr | His | His | |
| 546 | 546 | G | Gln | Ala | Val | His | Leu | Phe | Ile | Gln | Trp | Leu | Lys | Asn | Thr | His | His | |
| 547 | 547 | G | Gln | Ala | Val | His | Leu | Phe | Ile | Gln | Trp | Leu | Lys | Asn | Thr | His | NH2 | NH2 |
| 548 | 548 | G | Gln | Ala | Val | His | Leu | Phe | Ile | Gln | Trp | Leu | Lys | Asn | Thr | His | NH2 | NH2 |
| 549 | 549 | G | Gln | Ala | Val | His | Leu | Phe | Ile | Gln | Trp | Leu | Lys | Asn | Thr | His | His | |
| 550 | 550 | G | Gln | Ala | Val | Arg | Leu | Phe | Ile | Gln | Trp | Leu | Leu | Asn | Thr | His | His | NH2 |
| 551 | 551 | G | Gln | Ala | Ala | Arg | Leu | Phe | Ile | Gln | Trp | Leu | Leu | Asn | Thr | His | His | |
| 552 | 552 | G | Gln | Ala | Ala | Arg | Leu | Phe | Ile | Gln | Trp | Leu | Leu | Asn | Thr | His | His | |
| 553 | 553 | G | Gln | Ala | Leu | Arg | Leu | Phe | Ile | Gln | Trp | Leu | Leu | Asn | Thr | His | His | NH2 |
| 554 | 554 | G | Glu | Ala | Leu | Arg | Leu | Phe | Ile | Gln | Trp | Leu | Leu | Asn | Thr | His | His | NH2 |
| 555 | 555 | G | Gln | Ala | Val | Arg | Ile | Phe | Ile | Gln | Trp | Leu | Leu | Asn | Thr | His | His | NH2 |
| 556 | 556 | G | Gln | Ala | Val | Arg | Ile | Phe | Ile | Gln | Trp | Leu | Leu | Asn | Thr | His | His | NH2 |
| 557 | 557 | G | Gln | Ala | Val | Arg | Ile | Phe | Ile | Gln | Trp | Leu | Leu | Asn | Gly | His | His | NH2 |
| 558 | 558 | G | Gln | Ala | Val | Arg | Ile | Phe | Ile | Gln | Trp | Leu | Leu | Asn | Gly | His | His | NH2 |
| 559 | 559 | G | Gln | Ala | Val | Arg | Ile | Phe | Ile | Gln | Trp | Leu | Leu | Asn | Gly | His | His | NH2 |
| 560 | 560 | G | Gln | Ala | Val | Arg | Ile | Phe | Ile | Gln | Trp | Leu | Leu | Asn | Thr | His | His | NH2 |
| 561 | 561 | G | Gln | Ala | Leu | His | Ile | Phe | Ile | Gln | Trp | Leu | Leu | Asn | Thr | His | His | NH2 |
| 562 | 562 | G | Gln | Ala | Val | Arg | Leu | Phe | Ile | Gln | Trp | Leu | Leu | Asn | Thr | His | His | NH2 |
| 563 | 563 | G | Glu | Ala | Val | Arg | Leu | Phe | Ile | Gln | Trp | Leu | Lys | Asn | Thr | His | His | NH2 |
| 564 | 564 | G | Glu | Ala | Val | Arg | Leu | Phe | Ile | Gln | Trp | Leu | Lys | Asn | Thr | His | His | NH2 |
| 565 | 565 | G | Gln | Ala | Val | Arg | Leu | Phe | Ile | Gln | Trp | Leu | Lys | Asn | Thr | His | His | NH2 |
| 566 | 566 | G | Gln | Ala | Val | Arg | Leu | Phe | Ile | Gln | Trp | Leu | Lys | Asn | Thr | His | His | |
| 567 | 567 | G | Gln | Ala | Val | Arg | Leu | Phe | Ile | Gln | Trp | Leu | Lys | Asn | Gly | His | His | NH2 |
| 568 | 568 | G | Gln | Ala | Val | Arg | Leu | Phe | Ile | Gln | Trp | Leu | Lys | Asn | Gly | His | His | NH2 |
| 569 | 569 | G | Gln | Ala | Val | Arg | Leu | Phe | Ile | Gln | Trp | Leu | Lys | Asn | Gly | His | His | NH2 |
| 570 | 570 | G | Gln | Ala | Val | Arg | Ile | Phe | Ile | Gln | Trp | Leu | Lys | Asn | Gly | His | His | NH2 |
| 571 | 571 | G | Gln | Ala | Val | His | Ile | Phe | Ile | Gln | Trp | Leu | Lys | Asn | Thr | His | His | |
| 572 | 572 | G | Gln | Ala | Leu | His | Ile | Phe | Ile | Gln | Trp | Leu | Lys | Asn | Thr | His | His | NH2 |
| 573 | 573 | G | Gln | Ala | Leu | Arg | Leu | Phe | Ile | Gln | Trp | Leu | Lys | Asn | Thr | His | His | |
| 574 | 574 | G | Gln | Ala | Leu | Arg | Leu | Phe | Ile | Gln | Trp | Leu | Lys | Asn | Gly | His | His | NH2 |
| 575 | 575 | G | Gln | Ala | Leu | Arg | Leu | Phe | Ile | Gln | Trp | Leu | Lys | Asn | Thr | His | His | NH2 |
| 576 | 576 | G | Gln | Ala | Leu | Arg | Ile | Phe | Ile | Gln | Trp | Leu | Leu | Asn | Gly | His | His | NH2 |

Fig. 2 (continued)

| SEQ ID NO. | Analogue no. | Grp. | n | hGCGr cAMP vs hGCG | hGLP-1r cAMP vs hGLP-1 | n | Mouse food intake inhibition (500nmol/kg) | | | | | | | Rat food intake inhibition (500 nmol/kg with 1:1 Zn) | | | | | | | | |
|---|---|---|---|---|---|---|---|---|---|---|---|---|---|---|---|---|---|---|---|---|---|---|
| | | | | | | | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 527 | 527 | G | 1 | | 0.4 | | 86 | 90 | 77 | 49 | -17 | | 18 | 14 | 21 | 23 | 32 | 18 | 10 | 10 | -7 | 20 | 15 | 13 |
| 528 | 528 | G | 1 | | 12.5 | | 96 | 77 | 47 | -15 | -7 | | 14 | 73 | 84 | 75 | 87 | 79 | 49 | 20 | -5 | 81 | 56 | 37 |
| 529 | 529 | G | 1 | | 1.1 | | 97 | 87 | 60 | 2 | -15 | | 16 | 57 | 73 | 78 | 90 | 78 | 41 | 20 | -2 | 77 | 53 | 36 |
| 530 | 530 | G | 1 | | 0.7 | | 92 | 90 | 62 | 15 | -11 | | 18 | 24 | 42 | 41 | 35 | 70 | 19 | 14 | -2 | 57 | 38 | 26 |
| 531 | 531 | G | 1 | | 1.7 | | 98 | 89 | 67 | 31 | -11 | | 20 | 27 | 41 | 45 | 72 | 77 | 55 | 49 | 12 | 63 | 57 | 43 |
| 532 | 532 | G | 1 | | 1.9 | | 97 | 89 | 75 | 52 | 11 | | 23 | 18 | 49 | 53 | 79 | 89 | 67 | 41 | 8 | 73 | 61 | 45 |
| 533 | 533 | G | 1 | | 0.8 | | 99 | 70 | 41 | -16 | -17 | | 5 | 32 | 50 | 48 | 32 | 72 | 62 | 34 | 7 | 61 | 52 | 38 |
| 534 | 534 | G | 1 | | 2.5 | | 100 | 98 | 70 | 10 | -17 | | 16 | 37 | 51 | 55 | 80 | 86 | 86 | 52 | -4 | 72 | 66 | 45 |
| 535 | 535 | G | 1 | | 3.0 | | 95 | 96 | 63 | -8 | -19 | | 12 | 15 | 30 | 34 | 58 | 90 | 80 | 43 | 0 | 65 | 59 | 40 |
| 536 | 536 | G | 1 | | | | 43 | 53 | 53 | 51 | -6 | | 16 | 16 | 14 | 7 | 44 | 0 | 6 | 2 | -2 | 3 | 3 | 2 |
| 537 | 537 | G | 1 | | | | 106 | 91 | 38 | -46 | -14 | | 2 | 16 | 44 | 49 | 68 | 55 | 28 | 23 | -15 | 53 | 39 | 22 |
| 538 | 538 | G | 2 | | 0.8 | | 103 | 91 | 57 | -7 | -3 | | 19 | 63 | 63 | 64 | 68 | 87 | 88 | 59 | 12 | 78 | 73 | 53 |
| 539 | 539 | G | 2 | | 1.4 | | 98 | 83 | 48 | -25 | -4 | | 17 | 21 | 29 | 39 | 89 | 73 | 51 | 39 | 6 | 59 | 52 | 38 |
| 540 | 540 | G | 2 | | 0.8 | | 93 | 95 | 73 | 30 | -7 | | 25 | 26 | 30 | 37 | 74 | 84 | 57 | 43 | 14 | 65 | 57 | 44 |
| 541 | 541 | G | 2 | | 0.8 | | 92 | 83 | 75 | 58 | 1 | | 29 | 30 | 16 | 17 | 23 | 31 | 5 | 10 | -1 | 26 | 18 | 12 |
| 542 | 542 | G | 1 | | 0.8 | | 95 | 95 | 84 | 63 | 2 | | 32 | 21 | 21 | 21 | 38 | 48 | 11 | 10 | -3 | 38 | 25 | 18 |
| 543 | 543 | G | 1 | | 1.7 | | 95 | 89 | 54 | -19 | -5 | | 18 | 32 | 27 | 29 | 37 | 63 | 31 | 29 | 13 | 49 | 40 | 32 |
| 544 | 544 | G | 1 | | 0.9 | | 89 | 26 | 12 | -18 | -1 | | 3 | 21 | 14 | 15 | 20 | 30 | -23 | 10 | 7 | 24 | 14 | 12 |
| 545 | 545 | G | 1 | | 1.1 | | 87 | 91 | 82 | 64 | 21 | | 48 | -2 | 5 | 6 | 6 | -1 | 3 | -9 | -3 | 2 | -1 | -2 |
| 546 | 546 | G | 2 | | 0.5 | | 91 | 78 | 55 | 12 | 0 | | 25 | 64 | 74 | 74 | 73 | 91 | 65 | 35 | -12 | 84 | 65 | 40 |
| 547 | 547 | G | 2 | | 0.6 | | 100 | 99 | 74 | 27 | -6 | | 31 | 7 | 46 | 48 | 53 | 89 | 90 | 59 | 13 | 73 | 70 | 52 |
| 548 | 548 | G | 2 | | 0.6 | | 96 | 90 | 69 | 36 | -16 | | 20 | 60 | 75 | 77 | 86 | 95 | 78 | 46 | -1 | 88 | 72 | 49 |
| 549 | 549 | G | 1 | | 2.3 | | 88 | 96 | 87 | 70 | -2 | | 39 | 6 | 19 | 13 | 16 | 16 | 7 | 7 | 9 | 15 | 15 | 13 |
| 550 | 550 | G | 1 | | | | 77 | 83 | 67 | 41 | -23 | | 16 | 1 | 8 | 1 | -35 | 3 | -3 | 2 | 11 | 2 | 2 | 5 |
| 551 | 551 | G | 1 | | | | 99 | 101 | 72 | 11 | -13 | | 3 | 3 | 7 | -1 | -43 | 21 | 18 | 1 | 6 | 11 | 9 | 8 |
| 552 | 552 | G | 1 | | 1.4 | | 74 | 85 | 72 | 52 | -15 | | 28 | 7 | 17 | 9 | -28 | 2 | 9 | -1 | 2 | 5 | 4 | 3 |
| 553 | 553 | G | 1 | | | | 63 | 11 | 3 | -12 | -3 | | -1 | 1 | 19 | 20 | 23 | 4 | 8 | -6 | 6 | 2 | 0 | 2 |
| 554 | 554 | G | 3 | | 0.8 | | 86 | 91 | 93 | 95 | 68 | | 79 | 11 | 57 | 64 | 94 | 99 | 78 | 44 | -12 | 85 | 70 | 44 |
| 555 | 555 | G | 3 | | 1.4 | | 60 | 87 | 95 | 108 | 37 | | 55 | 4 | 43 | 46 | 55 | 77 | 48 | 14 | 7 | 65 | 46 | 33 |
| 556 | 556 | G | 3 | | 0.3 | | 94 | 103 | 105 | 108 | 39 | | 60 | 2 | 53 | 58 | 75 | 90 | 80 | 33 | -3 | 77 | 63 | 41 |
| 557 | 557 | G | 2 | | 3.9 | | 51 | 77 | 87 | 104 | 13 | | 36 | -30 | 15 | 32 | 91 | 86 | 48 | 17 | -4 | 65 | 47 | 30 |
| 558 | 558 | G | 1 | | 2.3 | | 55 | 82 | 91 | 106 | 10 | | 35 | -22 | 14 | 19 | 37 | 52 | 33 | 10 | 5 | 39 | 28 | 21 |
| 559 | 559 | G | 2 | | 0.4 | | 16 | 60 | 76 | 100 | 5 | | 26 | 31 | 18 | 14 | -3 | 20 | 3 | 5 | 3 | 18 | 11 | 9 |
| 560 | 560 | G | 2 | | 3.1 | | 12 | 57 | 73 | 99 | 19 | | 36 | -38 | -4 | 9 | 50 | 14 | 3 | 8 | 11 | 12 | 11 | 11 |
| 561 | 561 | G | 2 | | 2.1 | | 11 | 54 | 77 | 113 | 7 | | 29 | -9 | -6 | -6 | 82 | 4 | 15 | -3 | 11 | 8 | 7 | 8 |
| 562 | 562 | G | 1 | | 2.5 | | 8 | 56 | 77 | 109 | 6 | | 28 | -33 | 9 | 14 | 12 | 23 | 28 | 4 | 8 | 18 | 14 | 12 |
| 563 | 563 | G | 1 | | 6.6 | | -8 | 45 | 68 | 103 | 15 | | 31 | -16 | 2 | 10 | 3 | 8 | 13 | 1 | 8 | 6 | 5 | 6 |
| 564 | 564 | G | 3 | | 0.8 | | 85 | 92 | 95 | 98 | 49 | | 66 | 33 | 72 | 72 | 73 | 93 | 100 | 56 | 8 | 85 | 77 | 55 |
| 565 | 565 | G | 1 | | 8.6 | | 103 | 110 | 93 | 66 | -11 | | 21 | 55 | 70 | 68 | 59 | 67 | 39 | 9 | 0 | 67 | 44 | 29 |
| 566 | 566 | G | 3 | | 0.7 | | 80 | 93 | 96 | 100 | 37 | | 57 | 14 | 41 | 52 | 94 | 100 | 99 | 83 | 20 | 78 | 82 | 63 |
| 567 | 567 | G | 2 | | 0.5 | | 62 | 79 | 84 | 93 | 31 | | 50 | 21 | 46 | 52 | 75 | 94 | 80 | 51 | 5 | 75 | 68 | 49 |
| 568 | 568 | G | 2 | | 0.3 | | 71 | 92 | 71 | 29 | -1 | | 33 | 89 | 87 | 85 | 78 | 73 | 38 | 24 | -8 | 78 | 54 | 38 |
| 569 | 569 | G | 1 | | | | 97 | 91 | 70 | 27 | -1 | | 27 | 70 | 75 | 72 | 60 | 46 | 11 | 3 | 1 | 58 | 33 | 20 |
| 570 | 570 | G | 1 | | 0.2 | | 92 | 86 | 58 | 11 | -19 | | 18 | 9 | 37 | 41 | 61 | -2 | 2 | -6 | -10 | 15 | 6 | 1 |
| 571 | 571 | G | 2 | | | | 41 | 76 | 88 | 108 | 6 | | 31 | 14 | 6 | 20 | 59 | 49 | 12 | 9 | -3 | 36 | 23 | 15 |
| 572 | 572 | G | 2 | | 3.7 | | 73 | 83 | 87 | 98 | 33 | | 53 | 4 | 19 | 20 | 78 | 88 | 55 | 11 | -4 | 64 | 44 | 30 |
| 573 | 573 | G | 2 | | 1.0 | | 86 | 92 | 92 | 93 | 24 | | 49 | 48 | 63 | 65 | 94 | 54 | 26 | 1 | -4 | 59 | 35 | 23 |
| 574 | 574 | G | 2 | | 0.6 | | 83 | 90 | 91 | 94 | 14 | | 42 | 13 | 21 | 33 | 75 | 83 | 49 | 17 | -1 | 60 | 44 | 30 |
| 575 | 575 | G | 1 | | 1.2 | | 81 | 75 | 81 | 100 | 22 | | 43 | -8 | -9 | 1 | 38 | 20 | -11 | 6 | -5 | 12 | 7 | 3 |
| 576 | 576 | G | 1 | | 2.5 | | 43 | 67 | 75 | 95 | 19 | | 41 | -20 | -7 | -8 | -16 | 16 | 17 | -2 | 2 | 6 | 4 | 4 |

Fig. 2 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 577 | 577 | G | His | Ser | Gln | Gly | Thr | Phe | Thr | Ser | Asp | Tyr | Ser | Lys | Tyr | Leu | Glu | Glu |
| 578 | 578 | G | His | Ser | Gln | Gly | Thr | Phe | Thr | Ser | Asp | Tyr | Ser | Lys | Tyr | Leu | Glu | Glu |
| 579 | 579 | G | His | Ser | Gln | Gly | Thr | Phe | Thr | Ser | Asp | Tyr | Ser | Lys | Tyr | Leu | Glu | Glu |
| 580 | 580 | G | His | Ser | Gln | Gly | Thr | Phe | Thr | Ser | Asp | Tyr | Ser | Lys | Tyr | Leu | Glu | Glu |
| 581 | 581 | G | His | Ser | Gln | Gly | Thr | Phe | Thr | Ser | Asp | Tyr | Ser | Lys | Tyr | Leu | Glu | Glu |
| 582 | 582 | G | His | Ser | Gln | Gly | Thr | Phe | Thr | Ser | Asp | Tyr | Ser | Lys | Tyr | Leu | Glu | Glu |
| 583 | 583 | G | His | Ser | Gln | Gly | Thr | Phe | Thr | Ser | Asp | Tyr | Ser | Lys | Tyr | Leu | Glu | Glu |
| 584 | 584 | G | His | Ser | Gln | Gly | Thr | Phe | Thr | Ser | Asp | Tyr | Ser | Lys | Tyr | Leu | Glu | Glu |
| 585 | 585 | G | His | Ser | Gln | Gly | Thr | Phe | Thr | Ser | Asp | Tyr | Ser | Lys | Tyr | Leu | Glu | Ser |
| 586 | 586 | G | His | Ser | Gln | Gly | Thr | Phe | Thr | Ser | Asp | Tyr | Ser | Lys | Gln | Leu | Glu | Ser |
| 587 | 587 | G | His | Ser | Gln | Gly | Thr | Phe | Thr | Ser | Asp | Leu | Ser | Lys | Tyr | Leu | Glu | Ser |
| 588 | 588 | G | His | Ser | Gln | Gly | Thr | Phe | Thr | Ser | Asp | Tyr | Ser | His | Tyr | Leu | Glu | Ser |
| 589 | 589 | G | His | Ser | Gln | Gly | Thr | Phe | Thr | Ser | Asp | Tyr | Ser | His | Tyr | Leu | Glu | Ser |
| 590 | 590 | G | His | Ser | Gln | Gly | Thr | Phe | Thr | Ser | Asp | Tyr | Ser | His | Tyr | Leu | Glu | Ser |
| 591 | 591 | G | His | Ser | Gln | Gly | Thr | Phe | Thr | Ser | Asp | Tyr | Ser | His | Tyr | Leu | Glu | Ser |
| 592 | 592 | G | His | Gly | Gln | Gly | Thr | Phe | Thr | Ser | Asp | Tyr | Ser | His | Tyr | Leu | Glu | Ser |
| 593 | 593 | G | His | Gly | Gln | Gly | Thr | Phe | Thr | Ser | Asp | Leu | Ser | Lys | Tyr | Leu | Glu | Gln |
| 594 | 594 | G | His | Gly | Gln | Gly | Thr | Phe | Thr | Ser | Asp | Leu | Ser | Lys | Tyr | Leu | Glu | Gln |
| 595 | 595 | G | His | Gly | Gln | Gly | Thr | Phe | Thr | Ser | Asp | Leu | Ser | His | Gln | Leu | Glu | Gln |
| 596 | 596 | G | His | Gly | Gln | Gly | Thr | Phe | Thr | Ser | Asp | Leu | Ser | His | Tyr | Leu | Glu | Gln |
| 597 | 597 | G | His | Gly | Gln | Gly | Thr | Phe | Thr | Ser | Asp | Leu | Ser | His | Tyr | Leu | Glu | Ser |
| 598 | 598 | G | His | Gly | Gln | Gly | Thr | Phe | Thr | Ser | Asp | Leu | Ser | Lys | Tyr | Leu | Glu | Gln |
| 599 | 599 | G | His | Gly | Gln | Gly | Thr | Phe | Thr | Ser | Asp | Leu | Ser | His | Tyr | Leu | Glu | Gln |
| 600 | 600 | G | His | Ser | Gln | Gly | Thr | Phe | Thr | Ser | Asp | Leu | Ser | Lys | Gln | Leu | Glu | Gln |
| 601 | 601 | G | His | Gly | Gln | Gly | Thr | Phe | Thr | Ser | Asp | Leu | Ser | Lys | Tyr | Leu | Glu | Gln |
| 602 | 602 | G | His | Gly | Gln | Gly | Thr | Phe | Thr | Ser | Asp | Leu | Ser | Lys | Tyr | Leu | Glu | Gln |
| 603 | 603 | G | His | Gly | Gln | Gly | Thr | Phe | Thr | Ser | Asp | Leu | Ser | Lys | Tyr | Leu | Glu | Gln |
| 604 | 604 | G | His | Gly | Gln | Gly | Thr | Phe | Thr | Ser | Asp | Leu | Ser | Lys | Tyr | Leu | Glu | Gln |
| 605 | 605 | G | His | Gly | Gln | Gly | Thr | Phe | Thr | Ser | Asp | Leu | Ser | His | Tyr | Leu | Glu | Gln |
| 606 | 606 | G | His | Gly | Gln | Gly | Thr | Phe | Thr | Ser | Asp | Leu | Ser | His | Tyr | Leu | Glu | Gln |
| 607 | 607 | G | His | Gly | Gln | Gly | Thr | Phe | Thr | Ser | Asp | Leu | Ser | Lys | Tyr | Leu | Glu | Gln |
| 608 | 608 | G | His | Gly | Gln | Gly | Thr | Phe | Thr | Ser | Asp | Leu | Ser | Lys | Tyr | Leu | Glu | Gln |
| 609 | 609 | G | His | Gly | Gln | Gly | Thr | Phe | Thr | Ser | Asp | Leu | Ser | Lys | Gln | Leu | Glu | Gln |
| 610 | 610 | G | His | Gly | Gln | Gly | Thr | Phe | Thr | Ser | Asp | Leu | Ser | His | Tyr | Leu | Glu | Gln |
| 611 | 611 | G | His | Gly | Gln | Gly | Thr | Phe | Thr | Ser | Asp | Leu | Ser | Lys | Tyr | Leu | Glu | Gln |
| 612 | 612 | G | His | Gly | Gln | Gly | Thr | Phe | Thr | Ser | Asp | Leu | Ser | His | Gln | Leu | Glu | Gln |
| 613 | 613 | G | His | Gly | Gln | Gly | Thr | Phe | Thr | Ser | Asp | Leu | Ser | Lys | Tyr | Leu | Glu | Gln |
| 614 | 614 | G | His | Gly | Gln | Gly | Thr | Phe | Thr | Ser | Asp | Leu | Ser | Lys | Tyr | Leu | Glu | Gln |
| 615 | 615 | G | His | Gly | Gln | Gly | Thr | Phe | Thr | Ser | Asp | Leu | Ser | His | Tyr | Leu | Glu | Gln |
| 616 | 616 | G | His | Gly | Gln | Gly | Thr | Phe | Thr | Ser | Asp | Leu | Ser | Lys | Tyr | Leu | Glu | Gln |
| 617 | 617 | G | His | Gly | Gln | Gly | Thr | Phe | Thr | Ser | Asp | Leu | Ser | Lys | Tyr | Leu | Glu | Gln |
| 618 | 618 | G | His | Gly | Gln | Gly | Thr | Phe | Thr | Ser | Asp | Leu | Ser | His | Gln | Leu | Glu | Ser |
| 619 | 619 | G | His | Gly | Gln | Gly | Thr | Phe | Thr | Ser | Asp | Leu | Ser | Lys | Tyr | Leu | Glu | Ser |
| 620 | 620 | G | His | Gly | Gln | Gly | Thr | Phe | Thr | Ser | Asp | Leu | Ser | Lys | Tyr | Leu | Glu | Ser |
| 621 | 621 | G | His | Gly | Gln | Gly | Thr | Phe | Thr | Ser | Asp | Leu | Ser | Lys | Tyr | Leu | Glu | Ser |
| 622 | 622 | G | His | Gly | Gln | Gly | Thr | Phe | Thr | Ser | Asp | Leu | Ser | Lys | Tyr | Leu | Glu | Ser |
| 623 | 623 | G | His | Ser | Gln | Gly | Thr | Phe | Thr | Ser | Asp | Leu | Ser | Lys | Tyr | Leu | Glu | Ser |
| 624 | 624 | G | His | Gly | Gln | Gly | Thr | Phe | Thr | Ser | Asp | Tyr | Ser | Lys | Tyr | Leu | Glu | Glu |
| 625 | 625 | G | His | Gly | Gln | Gly | Thr | Phe | Thr | Ser | Asp | Tyr | Ser | Lys | Tyr | Leu | Glu | Ser |
| 626 | 626 | G | His | Gly | Glu | Gly | Thr | Phe | Thr | Ser | Asp | Tyr | Ser | His | Tyr | Leu | Glu | Ser |

Fig. 2 (continued)

| SEQ ID NO | Analogue no. | G no. | | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|---|
| 577 | 577 | G | 964 | Glu | Ala | Leu | Arg | Ile | Phe | Ile | Gln | Trp | Leu | Leu | Asn | Thr | Gly | His | NH2 |
| 578 | 578 | G | 965 | Glu | Ala | Leu | His | Ile | Phe | Ile | Gln | Trp | Leu | Leu | Asn | Thr | His | His | NH2 |
| 579 | 579 | G | 967 | Gln | Ala | Leu | Arg | Ile | Phe | Ile | Gln | Trp | Leu | Leu | Asn | Thr | His | His | NH2 |
| 580 | 580 | G | 968 | Gln | Ala | Leu | Arg | Leu | Phe | Ile | Gln | Trp | Leu | Leu | Asn | Thr | Gly | His | NH2 |
| 581 | 581 | G | 969 | Gln | Ala | Leu | Arg | Leu | Phe | Ile | Gln | Trp | Leu | Leu | Asn | Gly | His | His | NH2 |
| 582 | 582 | G | 970 | Gln | Ala | Leu | Arg | Ile | Phe | Ile | Gln | Trp | Leu | Leu | Asn | Thr | His | His | NH2 |
| 583 | 583 | G | 971 | Gln | Ala | Leu | Arg | Ile | Phe | Ile | Gln | Trp | Leu | Leu | Asn | Thr | His | His | NH2 |
| 584 | 584 | G | 972 | Gln | Ala | Leu | Arg | Ile | Phe | Ile | Gln | Trp | Leu | Leu | Asn | Thr | His | His | NH2 |
| 585 | 585 | G | 973 | Gln | Ala | Leu | Arg | Ile | Phe | Ile | Gln | Trp | Leu | Lys | Asn | Thr | His | His | NH2 |
| 586 | 586 | G | 974 | Gln | Ala | Leu | Arg | Leu | Phe | Ile | Gln | Trp | Leu | Leu | Asn | Gly | Gly | His | NH2 |
| 587 | 587 | G | 1000 | Gln | Ala | Leu | Arg | Ile | Phe | Ile | Gln | Trp | Leu | Leu | Asn | Gly | Gly | His | |
| 588 | 588 | G | 1001 | Gln | Ala | Val | Arg | Leu | Phe | Ile | Gln | Trp | Leu | Leu | Asn | Gly | Gly | His | |
| 589 | 589 | G | 1002 | Glu | Ala | Val | Arg | Val | Phe | Ile | Glu | Trp | Leu | Leu | Asn | Thr | Gly | His | |
| 590 | 590 | G | 1003 | Glu | Ala | Val | Arg | Leu | Phe | Ile | Glu | Trp | Leu | Leu | Asn | Thr | Gly | His | |
| 591 | 591 | G | 1004 | Gln | Ala | Val | Arg | Ile | Phe | Ile | Gln | Trp | Leu | Leu | Asn | Thr | Gly | His | |
| 592 | 592 | G | 1005 | Glu | Ala | Val | Arg | Ile | Phe | Ile | Glu | Trp | Leu | Leu | Asn | Thr | Gly | His | |
| 593 | 593 | G | 1006 | Gln | Ala | Leu | Arg | Ile | Phe | Ile | Gln | Trp | Leu | Leu | Asn | Thr | Gly | His | |
| 594 | 594 | G | 1017 | Glu | Ala | Val | Arg | Leu | Phe | Ile | Glu | Trp | Leu | Leu | Asn | Thr | Gly | His | NH2 |
| 595 | 595 | G | 1055 | Gln | Ala | Val | Arg | Ile | Phe | Ile | Gln | Trp | Leu | Leu | Asn | Thr | Gly | NH2 | NH2 |
| 596 | 596 | G | 1058 | Gln | Ala | Val | Arg | Ile | Phe | Ile | Gln | Trp | Leu | Leu | Asn | Thr | Gly | His | |
| 597 | 597 | G | 1059 | Gln | Ala | Val | His | Ile | Phe | Ile | Gln | Trp | Leu | Lys | Asn | Gly | Gly | NH2 | |
| 598 | 598 | G | 1069 | Gln | Ala | Val | His | Leu | Phe | Ile | Gln | Trp | Leu | Lys | Asn | Thr | Gly | NH2 | |
| 599 | 599 | G | 1070 | Gln | Ala | Val | His | Leu | Phe | Ile | Gln | Trp | Leu | Lys | Asn | Thr | Gly | His | |
| 600 | 600 | G | 1071 | Gln | Ala | Val | Arg | Leu | Phe | Ile | Gln | Trp | Leu | Leu | Asn | Thr | Gly | His | NH2 |
| 601 | 601 | G | 1072 | Gln | Ala | Val | Arg | Ile | Phe | Ile | Gln | Trp | Leu | Leu | Asn | Thr | Gly | His | NH2 |
| 602 | 602 | G | 1073 | Gln | Ala | Leu | Arg | Ile | Phe | Ile | Gln | Trp | Leu | Leu | Asn | Thr | Gly | His | NH2 |
| 603 | 603 | G | 1095 | Glu | Ala | Val | Arg | Ile | Phe | Ile | Glu | Trp | Leu | Leu | Asn | Gly | Gly | His | NH2 |
| 604 | 604 | G | 1096 | Glu | Ala | Val | Arg | Ile | Phe | Ile | Glu | Trp | Leu | Leu | Asn | Gly | Gly | His | NH2 |
| 605 | 605 | G | 1097 | Glu | Ala | Val | Arg | Ile | Phe | Ile | Glu | Trp | Leu | Leu | Asn | Gly | Gly | His | NH2 |
| 606 | 606 | G | 1098 | Glu | Ala | Val | Arg | Ile | Phe | Ile | Glu | Trp | Leu | Leu | Asn | Thr | Gly | His | NH2 |
| 607 | 607 | G | 1100 | Glu | Ala | Val | Arg | Ile | Phe | Ile | Glu | Trp | Leu | Leu | Asn | Thr | Gly | His | NH2 |
| 608 | 608 | G | 1101 | Glu | Ala | Val | Arg | Ile | Phe | Ile | Glu | Trp | Leu | Leu | Asn | Thr | Gly | His | NH2 |
| 609 | 609 | G | 1102 | Glu | Ala | Leu | Arg | Ile | Phe | Ile | Glu | Trp | Leu | Leu | Asn | Thr | Gly | His | NH2 |
| 610 | 610 | G | 1103 | Glu | Ala | Val | Arg | Ile | Phe | Ile | Glu | Trp | Leu | Leu | Asn | Thr | Gly | His | NH2 |
| 611 | 611 | G | 1106 | Gln | Ala | Val | Arg | Ile | Phe | Ile | Gln | Trp | Leu | Leu | Asn | Thr | Gly | His | NH2 |
| 612 | 612 | G | 1107 | Gln | Ala | Val | Arg | Leu | Phe | Ile | Gln | Trp | Leu | Leu | Asn | Thr | Gly | His | NH2 |
| 613 | 613 | G | 1108 | Gln | Ala | Leu | Arg | Ile | Phe | Ile | Gln | Trp | Leu | Leu | Asn | Thr | Gly | His | NH2 |
| 614 | 614 | G | 1109 | Gln | Ala | Val | Arg | Ile | Phe | Ile | Gln | Trp | Leu | Leu | Asn | Gly | Gly | His | NH2 |
| 615 | 615 | G | 1110 | Gln | Ala | Val | Arg | Ile | Phe | Ile | Gln | Trp | Leu | Leu | Asn | Gly | Gly | His | NH2 |
| 616 | 616 | G | 1111 | Gln | Ala | Val | Arg | Ile | Phe | Ile | Gln | Trp | Leu | Leu | Asn | Gly | Gly | His | NH2 |
| 617 | 617 | G | 1112 | Gln | Ala | Val | Arg | Ile | Phe | Ile | Gln | Trp | Leu | Leu | Asn | Gly | Gly | His | NH2 |
| 618 | 618 | G | 1113 | Gln | Ala | Leu | Arg | Leu | Phe | Ile | Gln | Trp | Leu | Leu | Asn | Thr | Gly | His | NH2 |
| 619 | 619 | G | 1114 | Gln | Ala | Val | Arg | Ile | Phe | Ile | Gln | Trp | Leu | Leu | Asn | Gly | Gly | His | |
| 620 | 620 | G | 1115 | Gln | Ala | Val | Arg | Ile | Phe | Ile | Gln | Trp | Leu | Leu | Asn | Gly | Gly | His | |
| 621 | 621 | G | 1116 | Gln | Ala | Val | Arg | Ile | Phe | Ile | Gln | Trp | Leu | Leu | Asn | Thr | Gly | His | NH2 |
| 622 | 622 | G | 1117 | Gln | Ala | Val | Arg | Ile | Phe | Ile | Gln | Trp | Leu | Leu | Asn | Gly | Gly | His | NH2 |
| 623 | 623 | G | 1124 | Gln | Ala | Val | Arg | Leu | Phe | Ile | Gln | Trp | Leu | Leu | Asn | Gly | Gly | NH2 | |
| 624 | 624 | G | 1125 | Gln | Ala | Ala | Arg | Ile | Phe | Ile | Gln | Trp | Leu | Leu | Asn | Gly | Gly | His | NH2 |
| 625 | 625 | G | 1159 | Gln | Ala | Val | Arg | Ile | Phe | Ile | Gln | Trp | Leu | Leu | Asn | Gly | Gly | His | NH2 |
| 626 | 626 | G | 1160 | Gln | Ala | Val | His | Leu | Phe | Ile | Gln | Trp | Leu | Leu | Asn | Gly | Gly | NH2 | NH2 |

Fig. 2 (continued)

| SEQ ID NO. | Analogue no. | hGCGr G no. | hGCGr cAMP vs hGCG n | hGLP-1r cAMP vs hGLP-1 | hGLP-1r n | Mouse food intake inhibition (500nmol/kg) | | | | | | Rat food intake inhibition (500 nmol/kg with 1:1 Zn) | | | | | | | | |
|---|---|---|---|---|---|---|---|---|---|---|---|---|---|---|---|---|---|---|---|---|
| | | | | | | 0-1 | 0-4 | 0-8 | 4-8 | 8-24 | 0-24 | 24-32 | 0-1 | 0-4 | 0-8 | 4-8 | 8-24 | 0-24 | 24-32 | 32-48 | 48-72 | 0-48 | 0-72 |
| 577 | 577 | G | | | | 31 | 49 | 53 | 60 | 6 | 27 | | -4 | -9 | -6 | 9 | 0 | 0 | -15 | -2 | -9 | -4 | -6 |
| 578 | 578 | G | | 2.9 | 1 | 73 | 78 | 69 | 51 | 16 | 39 | | -17 | 17 | -6 | -131 | -5 | -7 | -24 | -13 | -6 | -11 | -9 |
| 579 | 579 | G | | 9.1 | 1 | 24 | 52 | 62 | 81 | 39 | 49 | | -3 | 16 | -5 | -101 | -2 | -3 | 12 | -9 | -6 | -3 | -4 |
| 580 | 580 | G | | 17.5 | 1 | 48 | 73 | 77 | 86 | -3 | 34 | | 14 | 23 | 24 | 31 | 45 | 36 | 1 | 9 | 1 | 22 | 18 |
| 581 | 581 | G | | 9.0 | 1 | 36 | 65 | 73 | 90 | 12 | 40 | | 20 | -2 | -5 | -19 | 25 | 13 | 12 | 3 | 7 | 9 | 9 |
| 582 | 582 | G | | 14.3 | 1 | 16 | 48 | 50 | 53 | 22 | 34 | | -3 | -1 | 2 | 9 | 7 | 5 | 19 | 0 | 6 | 5 | 6 |
| 583 | 583 | G | | | | 13 | 36 | 40 | 47 | 20 | 29 | | -17 | 10 | 7 | -6 | 9 | 8 | 17 | 1 | 16 | 6 | 9 |
| 584 | 584 | G | | | | -36 | 37 | 37 | 38 | -9 | 8 | | 7 | 9 | 4 | -16 | 19 | 12 | -3 | 7 | 2 | 8 | 6 |
| 585 | 585 | G | | | | 72 | 61 | 35 | -45 | 5 | 16 | | -5 | -9 | 4 | 55 | -1 | 1 | 3 | -13 | 6 | -3 | -1 |
| 586 | 586 | G | | 16.3 | 1 | 22 | 46 | 46 | 46 | 1 | 17 | | 37 | 9 | 7 | 1 | 2 | 4 | 21 | -3 | 5 | 4 | 4 |
| 587 | 587 | G | | 1.0 | 1 | 71 | 81 | 78 | 73 | 15 | 42 | | -5 | 9 | 4 | 35 | 18 | 15 | 11 | 4 | 7 | 11 | 10 |
| 588 | 588 | G | | 3.5 | 1 | 75 | 87 | 74 | 51 | -6 | 28 | | -12 | 19 | 12 | 51 | 69 | 40 | 18 | -3 | 9 | 38 | 29 |
| 589 | 589 | G | | 1.1 | 1 | 68 | 84 | 80 | 72 | -3 | 32 | | 22 | 9 | 13 | 31 | 77 | -4 | 3 | 0 | 1 | 28 | 19 |
| 590 | 590 | G | | 1.1 | 1 | 86 | 87 | 54 | -3 | -14 | 15 | | 6 | 7 | 25 | 88 | 49 | -11 | 3 | 7 | 6 | 19 | 15 |
| 591 | 591 | G | | 1.5 | 1 | 77 | 86 | 80 | 69 | 4 | 36 | | -10 | 10 | 13 | 31 | 30 | 15 | 0 | 2 | 2 | 18 | 13 |
| 592 | 592 | G | | 0.8 | 1 | 56 | 69 | 76 | 87 | 17 | 42 | | -9 | -6 | 23 | 88 | 49 | 21 | 7 | 7 | 3 | 10 | 8 |
| 593 | 593 | G | | 4.3 | 1 | -4 | 11 | 13 | 18 | -1 | 5 | | -13 | -26 | 18 | 26 | 8 | 12 | 23 | 3 | -1 | -3 | -3 |
| 594 | 594 | G | | 1.5 | 2 | 82 | 91 | 89 | 86 | 5 | 41 | | 32 | 48 | 60 | 93 | 87 | 75 | 34 | -14 | -5 | 43 | 28 |
| 595 | 595 | G | | | | 25 | 38 | 28 | 7 | -8 | 5 | | -17 | -8 | -13 | 1 | -2 | -1 | -1 | -11 | 1 | -4 | -3 |
| 596 | 596 | G | | 1.2 | 2 | 88 | 94 | 95 | 95 | 46 | 63 | | -22 | 2 | 19 | 35 | 99 | 66 | 60 | -7 | -7 | 69 | 46 |
| 597 | 597 | G | | 1.3 | 2 | 57 | 80 | 86 | 99 | 52 | 64 | | -8 | 2 | 17 | 63 | 74 | 49 | 74 | 60 | 5 | 49 | 35 |
| 598 | 598 | G | | 2.2 | 1 | 91 | 95 | 84 | 60 | -5 | 47 | | 4 | 13 | 26 | 67 | 5 | 15 | 8 | 38 | 3 | 9 | 7 |
| 599 | 599 | G | | 2.1 | 1 | 96 | 95 | 78 | 41 | -5 | 23 | | 22 | 35 | 49 | 95 | 55 | 52 | 32 | -4 | -5 | 32 | 22 |
| 600 | 600 | G | | 0.3 | 1 | 90 | 83 | 55 | -6 | -5 | 15 | | 35 | 48 | 21 | 73 | 82 | 69 | 66 | -15 | -1 | 43 | 29 |
| 601 | 601 | G | | 1.5 | 2 | 83 | 92 | 93 | 96 | 35 | 53 | | 1 | 1 | 14 | 60 | 74 | 46 | 85 | 27 | 3 | 46 | 31 |
| 602 | 602 | G | | | | -3 | 14 | 9 | -2 | -5 | 12 | | 11 | 3 | 3 | -44 | 2 | 4 | 4 | 3 | 8 | 1 | -1 |
| 603 | 603 | G | | 0.9 | 2 | 54 | 77 | 86 | 102 | 49 | 60 | | -8 | 28 | 43 | 97 | 99 | 74 | 66 | 69 | -2 | 76 | 54 |
| 604 | 604 | G | | | | 36 | 68 | 79 | 100 | 32 | 45 | | -6 | 7 | 25 | 93 | 100 | 98 | 85 | 54 | -5 | 67 | 44 |
| 605 | 605 | G | | 1.1 | 1 | 58 | 78 | 84 | 96 | 43 | 54 | | -5 | 3 | 21 | 80 | 94 | 61 | 91 | 44 | 4 | 60 | 42 |
| 606 | 606 | G | | 0.7 | 2 | 61 | 81 | 87 | 100 | 50 | 61 | | -13 | 3 | 22 | 92 | 91 | 59 | 87 | 54 | -5 | 62 | 44 |
| 607 | 607 | G | | | | 81 | 85 | 83 | 79 | 17 | 42 | | 2 | 9 | 4 | -29 | 5 | 4 | 4 | -11 | 2 | -1 | -2 |
| 608 | 608 | G | | | | 95 | 98 | 92 | 85 | 1 | 36 | | 37 | 43 | 35 | 2 | -6 | 10 | 16 | -7 | 2 | 5 | 4 |
| 609 | 609 | G | | | | 61 | 78 | 83 | 91 | 5 | 35 | | 8 | 7 | 9 | 16 | 4 | 6 | 16 | -5 | 5 | 3 | 4 |
| 610 | 610 | G | | | | 62 | 77 | 81 | 87 | 63 | 70 | | 6 | 20 | 25 | 55 | 18 | 21 | 13 | -5 | -2 | 11 | 7 |
| 611 | 611 | G | | | | -56 | -26 | -10 | 15 | 1 | -4 | | 3 | 13 | 8 | -17 | -7 | -1 | 39 | -7 | 8 | 3 | 4 |
| 612 | 612 | G | | | | 11 | 24 | 21 | 12 | 7 | 12 | | -27 | -22 | -17 | -62 | 12 | 1 | -18 | -3 | -2 | -2 | -1 |
| 613 | 613 | G | | | | 3 | 10 | 11 | 14 | -1 | 4 | | -14 | -5 | -13 | 10 | 3 | -3 | -23 | 9 | 18 | -5 | -11 |
| 614 | 614 | G | | | | 6 | 10 | 15 | 26 | 8 | 11 | | 1 | -2 | 1 | -10 | 15 | 9 | -4 | 15 | 9 | 8 | 6 |
| 615 | 615 | G | | | | 3 | 18 | 11 | -2 | 7 | 9 | | -23 | -11 | -17 | -52 | 19 | 5 | 93 | 10 | 9 | -1 | 6 |
| 616 | 616 | G | | | | 1 | 6 | 4 | 1 | 11 | 8 | | -22 | 1 | -6 | -42 | 15 | 7 | -14 | 7 | 5 | 4 | 5 |
| 617 | 617 | G | | | | -8 | 8 | 1 | -16 | 10 | 6 | | -20 | -10 | -10 | -71 | 15 | -1 | -13 | -5 | 3 | -2 | 1 |
| 618 | 618 | G | | | | -4 | 7 | 2 | -8 | 7 | 5 | | -35 | 1 | -5 | 20 | 11 | 5 | -2 | 12 | 8 | 7 | 7 |
| 619 | 619 | G | | 2.6 | 1 | 90 | 93 | 93 | 93 | 47 | 64 | | 21 | 28 | 38 | 85 | 80 | 62 | 52 | 15 | 4 | 46 | 33 |
| 620 | 620 | G | | 1.2 | 1 | 82 | 81 | 79 | 75 | 31 | 49 | | 31 | 63 | 69 | 97 | 98 | 85 | 93 | 58 | -3 | 78 | 54 |
| 621 | 621 | G | | 2.0 | 1 | 90 | 95 | 94 | 93 | 17 | 47 | | 14 | 57 | 62 | 93 | 93 | 81 | 54 | 32 | 2 | 62 | 43 |
| 622 | 622 | G | | 2.1 | 1 | 70 | 85 | 91 | 100 | 39 | 59 | | -34 | 22 | 36 | 95 | 81 | 62 | 65 | 40 | 2 | 55 | 39 |
| 623 | 623 | G | | | | 52 | 76 | 75 | 73 | 15 | 39 | | 10 | 30 | 36 | 66 | 48 | 42 | 20 | -17 | -4 | 21 | 13 |
| 624 | 624 | G | | 1.0 | 1 | 64 | 82 | 87 | 100 | 39 | 58 | | 41 | 71 | 71 | 93 | 93 | 83 | 74 | 51 | 18 | 72 | 50 |
| 625 | 625 | G | | 1.9 | 1 | 76 | 88 | 90 | 94 | 55 | 68 | | 9 | 38 | 49 | 70 | 98 | 77 | 96 | 59 | 9 | 74 | 53 |
| 626 | 626 | G | | 1.3 | 1 | 81 | 90 | 89 | 87 | 23 | 47 | | 26 | 47 | 54 | 81 | 44 | 48 | 21 | 1 | -3 | 30 | 19 |

Fig. 2 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 627 | 627 | G | 1161 | His | Gly | Gln | Gly | Thr | Phe | Thr | Ser | Asp | Tyr | Ser | His | Tyr | Leu | Glu | Ser |
| 628 | 628 | G | 1172 | His | Ser | Gln | Gly | Thr | Phe | Thr | Ser | Asp | Tyr | Ser | His | Tyr | Leu | Glu | Glu |
| 629 | 629 | G | 1173 | His | Ser | Gln | Gly | Thr | Phe | Thr | Ser | Asp | Tyr | Ser | His | Tyr | Leu | Glu | Ser |
| 630 | 630 | G | 1174 | His | Gly | Gln | Gly | Thr | Phe | Thr | Ser | Asp | Tyr | Ser | Lys | Tyr | Leu | Glu | Glu |
| 631 | 631 | G | 1176 | His | Ser | Gln | Gly | Thr | Phe | Thr | Ser | Asp | Leu | Ser | Lys | Tyr | Leu | Glu | Glu |
| 632 | 632 | G | 1178 | His | Gly | Gln | Gly | Thr | Phe | Thr | Ser | Asp | Tyr | Ser | His | Tyr | Leu | Glu | Ser |
| 633 | 633 | G | 1179 | His | Gly | Gln | Gly | Thr | Phe | Thr | Ser | Asp | Tyr | Ser | His | Gln | Leu | Glu | Ser |
| 634 | 634 | G | 1180 | His | Gly | Gln | Gly | Thr | Phe | Thr | Ser | Asp | Tyr | Ser | His | Tyr | Leu | Glu | Ser |
| 635 | 635 | G | 1181 | His | Gly | Gln | Gly | Thr | Phe | Thr | Ser | Asp | Tyr | Ser | His | Tyr | Leu | Glu | Ser |
| 636 | 636 | G | 1182 | His | Gly | Gln | Gly | Thr | Phe | Thr | Ser | Asp | Leu | Ser | His | Tyr | Leu | Glu | Glu |
| 637 | 637 | G | 1183 | His | Gly | Gln | Gly | Thr | Phe | Thr | Ser | Asp | Leu | Ser | His | Tyr | Leu | Glu | Glu |
| 638 | 638 | G | 1184 | His | Gly | Gln | Gly | Thr | Phe | Thr | Ser | Asp | Leu | Ser | His | Tyr | Leu | Glu | Glu |
| 639 | 639 | G | 1185 | His | Gly | Gln | Gly | Thr | Phe | Thr | Ser | Asp | Leu | Ser | His | Tyr | Leu | Glu | Glu |
| 640 | 640 | G | 1189 | His | Ser | Gln | Gly | Thr | Phe | Thr | Ser | Asp | Tyr | Ser | His | Tyr | Leu | Glu | Glu |
| 641 | 641 | G | 1190 | His | Gly | Gln | Gly | Thr | Phe | Thr | Ser | Asp | Tyr | Ser | His | Tyr | Leu | Glu | Glu |
| 642 | 642 | G | 1191 | His | Ser | Gln | Gly | Thr | Phe | Thr | Ser | Asp | Tyr | Ser | Lys | Tyr | Leu | Glu | Glu |
| 643 | 643 | G | 1217 | His | Ser | Gln | Gly | Thr | Phe | Thr | Ser | Asp | Leu | Ser | His | Gln | Leu | Glu | Glu |
| 644 | 644 | G | 1218 | His | Gly | Gln | Gly | Thr | Phe | Thr | Ser | Asp | Leu | Ser | Lys | Tyr | Leu | Glu | Glu |
| 645 | 645 | G | 1219 | His | Gly | Gln | Gly | Thr | Phe | Thr | Ser | Asp | Leu | Ser | Lys | Tyr | Leu | Glu | Glu |
| 646 | 646 | G | 1220 | His | Ser | Gln | Gly | Thr | Phe | Thr | Ser | Asp | Leu | Ser | Lys | Tyr | Leu | Glu | Glu |
| 647 | 647 | G | 1221 | His | Gly | Gln | Gly | Thr | Phe | Thr | Ser | Asp | Leu | Ser | Lys | Gln | Leu | Glu | Glu |
| 648 | 648 | G | 1222 | His | Gly | Gln | Gly | Thr | Phe | Thr | Ser | Asp | Leu | Ser | Lys | Gln | Leu | Glu | Glu |
| 649 | 649 | G | 1248 | His | Gly | Gln | Gly | Thr | Phe | Thr | Ser | Asp | Tyr | Ser | Lys | Tyr | Leu | Glu | Glu |
| 650 | 650 | G | 1249 | His | Ser | Gln | Gly | Thr | Phe | Thr | Ser | Asp | Leu | Ser | Lys | Tyr | Leu | Glu | Glu |
| 651 | 651 | G | 1250 | His | Ser | Gln | Gly | Thr | Phe | Thr | Ser | Asp | Tyr | Ser | Lys | Tyr | Leu | Glu | Ala |
| 652 | 652 | G | 1251 | His | Ser | Gln | Gly | Thr | Phe | Thr | Ser | Asp | Tyr | Ser | Lys | Tyr | Leu | Glu | Glu |
| 653 | 653 | G | 1252 | His | Ser | Gln | Gly | Thr | Phe | Thr | Ser | Asp | Tyr | Ser | Lys | Tyr | Leu | Glu | Ala |
| 654 | 654 | G | 1253 | His | Ser | Gln | Gly | Thr | Phe | Thr | Ser | Asp | Leu | Ser | Lys | Tyr | Leu | Glu | Glu |
| 655 | 655 | G | 1254 | His | Gly | Gln | Gly | Thr | Phe | Thr | Ser | Asp | Leu | Ser | Lys | Tyr | Leu | Glu | Glu |
| 656 | 656 | G | 1255 | His | Ser | Gln | Gly | Thr | Phe | Thr | Ser | Asp | Leu | Ser | Lys | Tyr | Leu | Glu | Glu |
| 657 | 657 | G | 1256 | His | Gly | Gln | Gly | Thr | Phe | Thr | Ser | Asp | Leu | Ser | Lys | Tyr | Leu | Glu | Glu |
| 658 | 658 | G | 1260 | His | Gly | Gln | Gly | Thr | Phe | Thr | Ser | Asp | Leu | Ser | Lys | Gln | Leu | Glu | Ala |
| 659 | 659 | G | 1264 | His | Gly | Gln | Gly | Thr | Phe | Thr | Ser | Asp | Tyr | Ser | Lys | Tyr | Leu | Glu | Glu |
| 660 | 660 | G | 1265 | His | Ser | Gln | Gly | Thr | Phe | Thr | Ser | Asp | Tyr | Ser | Lys | Tyr | Leu | Glu | Glu |
| 661 | 661 | G | 1277 | His | Gly | Gln | Gly | Thr | Phe | Thr | Ser | Asp | Tyr | Ser | Lys | Tyr | Leu | Glu | Glu |
| 662 | 662 | G | 1278 | His | Ser | Gln | Gly | Thr | Phe | Thr | Ser | Asp | Leu | Ser | Lys | Tyr | Leu | Glu | Glu |
| 663 | 663 | G | 1279 | His | Ser | Gln | Gly | Thr | Phe | Thr | Ser | Asp | Tyr | Ser | Lys | Tyr | Leu | Glu | Glu |
| 664 | 664 | G | 1280 | His | Gly | Gln | Gly | Thr | Phe | Thr | Ser | Asp | Tyr | Ser | Lys | Tyr | Leu | Glu | Glu |
| 665 | 665 | G | 1281 | His | Ser | Gln | Gly | Thr | Phe | Thr | Ser | Asp | Tyr | Ser | Lys | Tyr | Leu | Glu | Glu |
| 666 | 666 | G | 1282 | His | Ser | Gln | Gly | Thr | Phe | Thr | Ser | Asp | Tyr | Ser | Lys | Tyr | Leu | Glu | Glu |
| 667 | 667 | G | 1284 | His | Gly | Gln | Gly | Thr | Phe | Thr | Ser | Asp | Tyr | Ser | Lys | Gln | Leu | Glu | Glu |
| 668 | 668 | G | 1307 | His | Gly | Gln | Gly | Thr | Phe | Thr | Ser | Asp | Tyr | Ser | Lys | Tyr | Leu | Glu | Glu |
| 669 | 669 | G | 1308 | His | Gly | Gln | Gly | Thr | Phe | Thr | Ser | Asp | Tyr | Ser | Lys | Tyr | Leu | Glu | Ala |
| 670 | 670 | G | 1309 | His | Gly | Gln | Gly | Thr | Phe | Thr | Ser | Asp | Tyr | Ser | Lys | Tyr | Leu | Glu | Glu |
| 671 | 671 | G | 1310 | His | Ser | Gln | Gly | Thr | Phe | Thr | Ser | Asp | Tyr | Ser | Lys | Tyr | Leu | Glu | Glu |
| 672 | 672 | G | 1311 | His | Gly | Gln | Gly | Thr | Phe | Thr | Ser | Asp | Tyr | Ser | Lys | Tyr | Leu | Glu | Glu |
| 673 | 673 | G | 1312 | His | Ser | Gln | Gly | Thr | Phe | Thr | Ser | Asp | Tyr | Ser | Lys | Tyr | Leu | Glu | Glu |
| 674 | 674 | G | 1313 | His | Gly | Gln | Gly | Thr | Phe | Thr | Ser | Asp | Leu | Ser | Lys | Gln | Leu | Glu | Glu |
| 675 | 675 | G | 1314 | His | Ser | Gln | Gly | Thr | Phe | Thr | Ser | Asp | Leu | Ser | Lys | Gln | Leu | Glu | Glu |
| 676 | 676 | G | 1315 | His | Gly | Gln | Gly | Thr | Phe | Thr | Ser | Asp | Tyr | Ser | Lys | Tyr | Leu | Glu | Glu |

Fig. 2 (continued)

| SEQ ID NO. | Analogue no. | C no. | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|
| 627 | 627 | G | Gln | Ala | Leu | Arg | Ile | Phe | Ile | Glu | Trp | Leu | Lys | Asn | Thr | Gly | NH2 | |
| 628 | 628 | G | Glu | Ala | Val | Arg | Leu | Phe | Ile | Glu | Trp | Leu | Leu | Asn | Gly | Gly | His | |
| 629 | 629 | G | Glu | Ala | Val | Arg | Leu | Phe | Ile | Glu | Trp | Leu | Leu | Asn | Thr | Gly | His | NH2 |
| 630 | 630 | G | Glu | Ala | Val | Arg | Leu | Phe | Ile | Glu | Trp | Leu | Leu | Asn | Gly | Gly | His | NH2 |
| 631 | 631 | G | Glu | Ala | Leu | Arg | Leu | Phe | Ile | Glu | Trp | Leu | Leu | Asn | Thr | Gly | His | NH2 |
| 632 | 632 | G | Gln | Ala | Val | Arg | Leu | Phe | Ile | Glu | Trp | Leu | Lys | Asn | Gly | Gly | His | |
| 633 | 633 | G | Gln | Ala | Val | Arg | Leu | Phe | Ile | Glu | Trp | Leu | Lys | Asn | Thr | Gly | His | NH2 |
| 634 | 634 | G | Gln | Ala | Val | Arg | Leu | Phe | Ile | Glu | Trp | Leu | Lys | Asn | Gly | Gly | His | |
| 635 | 635 | G | Gln | Ala | Val | Arg | Leu | Phe | Ile | Glu | Trp | Leu | Tyr | Asn | Gly | Gly | NH2 | |
| 636 | 636 | G | Glu | Ala | Val | Arg | Leu | Phe | Ile | Glu | Trp | Leu | Leu | Asn | Thr | Gly | His | NH2 |
| 637 | 637 | G | Glu | Ala | Val | Arg | Leu | Phe | Ile | Glu | Trp | Leu | Leu | Asn | Gly | Gly | His | NH2 |
| 638 | 638 | G | Glu | Ala | Val | Arg | Leu | Phe | Ile | Glu | Trp | Leu | Leu | Asn | Thr | Gly | His | NH2 |
| 639 | 639 | G | Glu | Ala | Val | Arg | Leu | Phe | Ile | Glu | Trp | Leu | Leu | Asn | Gly | Gly | His | NH2 |
| 640 | 640 | G | Gln | Ala | Val | Arg | Ile | Phe | Ile | Gln | Trp | Leu | Leu | Asn | Gly | Gly | His | NH2 |
| 641 | 641 | G | Gln | Ala | Val | Arg | Ile | Phe | Ile | Gln | Trp | Leu | Leu | Asn | Gly | Gly | His | NH2 |
| 642 | 642 | G | Gln | Ala | Val | Arg | Ile | Phe | Ile | Gln | Trp | Leu | Leu | Asn | Gly | Gly | His | NH2 |
| 643 | 643 | G | Gln | Ala | Val | Arg | Ile | Phe | Ile | Gln | Trp | Leu | Leu | Asn | Gly | Gly | His | NH2 |
| 644 | 644 | G | Glu | Ala | Val | Arg | Leu | Phe | Ile | Glu | Trp | Leu | Leu | Asn | Gly | Gly | His | NH2 |
| 645 | 645 | G | Glu | Ala | Val | Arg | Ile | Phe | Ile | Glu | Trp | Leu | Leu | Asn | Gly | Gly | His | NH2 |
| 646 | 646 | G | Gln | Ala | Val | Arg | Leu | Phe | Ile | Gln | Trp | Leu | Leu | Asn | Gly | Gly | His | NH2 |
| 647 | 647 | G | Gln | Ala | Val | Arg | Leu | Phe | Ile | Gln | Trp | Leu | Leu | Asn | Gly | Gly | His | NH2 |
| 648 | 648 | G | Gln | Ala | Val | Arg | Ile | Phe | Ile | Gln | Trp | Leu | Leu | Asn | Gly | Gly | His | NH2 |
| 649 | 649 | G | Gln | Ala | Val | Arg | Ile | Phe | Ile | Gln | Trp | Leu | Leu | Asn | Gly | Gly | His | NH2 |
| 650 | 650 | G | Gln | Ala | Val | Arg | Leu | Phe | Ile | Gln | Trp | Leu | Leu | Asn | Gly | Gly | His | NH2 |
| 651 | 651 | G | Gln | Ala | Leu | Arg | Ile | Phe | Ile | Gln | Trp | Leu | Leu | Asn | Gly | Gly | His | NH2 |
| 652 | 652 | G | Glu | Ala | Val | Arg | Leu | Phe | Ile | Glu | Trp | Leu | Leu | Asn | Gly | Gly | His | NH2 |
| 653 | 653 | G | Glu | Ala | Leu | Arg | Ile | Phe | Ile | Glu | Trp | Leu | Leu | Asn | Gly | Gly | His | NH2 |
| 654 | 654 | G | Glu | Ala | Leu | Arg | Leu | Phe | Ile | Glu | Trp | Leu | Leu | Asn | Gly | Gly | His | NH2 |
| 655 | 655 | G | Glu | Ala | Leu | Arg | Leu | Phe | Ile | Glu | Trp | Leu | Leu | Asn | Gly | Gly | His | NH2 |
| 656 | 656 | G | Glu | Ala | Leu | Arg | Leu | Phe | Ile | Glu | Trp | Leu | Leu | Asn | Gly | Gly | His | NH2 |
| 657 | 657 | G | Gln | Ala | Val | Arg | Leu | Phe | Ile | Gln | Trp | Leu | Leu | Asn | Gly | Gly | His | NH2 |
| 658 | 658 | G | Gln | Ala | Val | Arg | Ile | Phe | Ile | Gln | Trp | Leu | Leu | Asn | Gly | Gly | His | NH2 |
| 659 | 659 | G | Glu | Ala | Val | Arg | Ile | Phe | Val | Glu | Trp | Leu | Leu | Asn | Gly | Gly | His | NH2 |
| 660 | 660 | G | Glu | Ala | Val | Arg | Leu | Phe | Ile | Glu | Trp | Leu | Leu | Asn | Gly | Gly | His | NH2 |
| 661 | 661 | G | Glu | Ala | Val | Arg | Ile | Phe | Ile | Glu | Trp | Leu | Leu | Asn | Gly | Gly | His | NH2 |
| 662 | 662 | G | Glu | Ala | Val | Arg | Ile | Phe | Ile | Glu | Trp | Leu | Leu | Asn | Gly | Gly | His | NH2 |
| 663 | 663 | G | Glu | Ala | Val | Arg | Ile | Phe | Ile | Glu | Trp | Leu | Leu | Asn | Gly | Gly | His | NH2 |
| 664 | 664 | G | Gln | Ala | Val | Arg | Leu | Phe | Ile | Gln | Trp | Leu | Leu | Asn | Gly | Gly | NH2 | |
| 665 | 665 | G | Gln | Ala | Val | Arg | Ile | Phe | Ile | Gln | Trp | Leu | Leu | Asn | Gly | Gly | His | NH2 |
| 666 | 666 | G | Gln | Ala | Ala | Arg | Ile | Phe | Ile | Gln | Trp | Leu | Leu | Asn | Gly | Gly | His | NH2 |
| 667 | 667 | G | Gln | Ala | Val | Arg | Ile | Phe | Ile | Gln | Trp | Leu | Leu | Asn | Gly | Gly | His | NH2 |
| 668 | 668 | G | Gln | Ala | Val | Arg | Ile | Phe | Ile | Gln | Trp | Leu | Leu | Asn | Gly | Gly | His | NH2 |
| 669 | 669 | G | Gln | Ala | Ile | Arg | Ile | Phe | Ile | Gln | Trp | Leu | Leu | Asn | Gly | Gly | His | NH2 |
| 670 | 670 | G | Gln | Ala | Val | Arg | Ile | Phe | Ile | Gln | Trp | Leu | Leu | Asn | Gly | Gly | His | NH2 |
| 671 | 671 | G | Gln | Ala | Val | Arg | Leu | Phe | Ile | Gln | Trp | Leu | Leu | Asn | Thr | Gly | His | NH2 |
| 672 | 672 | G | Gln | Ala | Ile | Arg | Leu | Phe | Ile | Gln | Trp | Leu | Leu | Asn | Gly | Gly | His | NH2 |
| 673 | 673 | G | Gln | Ala | Val | Arg | Ile | Phe | Ile | Gln | Trp | Leu | Leu | Asn | Gly | Gly | His | NH2 |
| 674 | 674 | G | Gln | Ala | Val | Arg | Ile | Phe | Ile | Gln | Trp | Leu | Leu | Asn | Gly | Gly | His | NH2 |
| 675 | 675 | G | Gln | Ala | Val | Arg | Ile | Phe | Ile | Gln | Trp | Leu | Leu | Asn | Gly | Gly | His | NH2 |
| 676 | 676 | G | Gln | Ala | Val | Arg | Ile | Phe | Ile | Gln | Trp | Leu | Leu | Asn | Gly | Gly | His | NH2 |

Fig. 2 (continued)

| SEQ ID NO. | Analogue no. | G no. | hGcGr cAMP vs hGCG n | hGcGr cAMP vs hGCG EC50 | hGLP-1r cAMP vs hGLP-1 n | hGLP-1r cAMP vs hGLP-1 EC50 | Mouse food intake inhibition (500nmol/kg) 0-1 | 0-4 | 0-8 | 4-8 | 8-24 | 24-32 | 0-24 | 0-1 | 0-4 | 0-8 | 4-8 | 8-24 | Rat food intake inhibition (500 nmol/kg with 1:1 Zn) 24-32 | 32-48 | 48-72 | 0-24 | 0-48 | 0-72 |
|---|---|---|---|---|---|---|---|---|---|---|---|---|---|---|---|---|---|---|---|---|---|---|---|---|
| 627 | 628 | G | 1161 | | | 1 | 4.8 | 100 | 96 | 89 | 74 | 25 | | 49 | 27 | 32 | 35 | 49 | 9 | 16 | 7 | 5 | 20 | 16 | 12 |
| 628 | 629 | G | 1172 | | | 1 | 1.1 | 78 | 89 | 93 | 100 | 8 | | 32 | 73 | 84 | 87 | 97 | 93 | 55 | 12 | -6 | 90 | 61 | 49 |
| 629 | 630 | G | 1173 | | | 1 | 8.7 | 76 | 88 | 89 | 89 | 14 | | 35 | 55 | 74 | 77 | 89 | 93 | 46 | 11 | -4 | 86 | 57 | 38 |
| 630 | 631 | G | 1174 | | | 1 | 8.1 | 56 | 78 | 85 | 89 | 51 | | 61 | 8 | 45 | 54 | 93 | 99 | 99 | 76 | -2 | 80 | 81 | 55 |
| 631 | 632 | G | 1176 | | | | | 93 | 93 | 90 | 83 | 31 | | 53 | 37 | 58 | 63 | 84 | 64 | 13 | 7 | -10 | 64 | 39 | 23 |
| 632 | 633 | G | 1178 | | | | | 99 | 96 | 72 | 22 | -3 | | 25 | 77 | 83 | 81 | 72 | 55 | 25 | 5 | -5 | 66 | 42 | 27 |
| 633 | 634 | G | 1179 | | | | | 94 | 78 | 54 | 5 | 4 | | 23 | 95 | 83 | 78 | 60 | 22 | 10 | -8 | -4 | 47 | 25 | 16 |
| 634 | 635 | G | 1180 | | | 1 | 1.1 | 94 | 89 | 59 | -4 | 4 | | 25 | 90 | 84 | 82 | 72 | 71 | 24 | 2 | -4 | 76 | 46 | 30 |
| 635 | 636 | G | 1181 | | | | | 67 | 70 | 55 | 24 | 16 | | 31 | 92 | 86 | 82 | 63 | 46 | 21 | -2 | -9 | 62 | 36 | 22 |
| 636 | 637 | G | 1182 | | | | | 97 | 97 | 78 | 43 | 1 | | 22 | 20 | 34 | 46 | 93 | 84 | 70 | 24 | 4 | 66 | 54 | 38 |
| 637 | 638 | G | 1183 | | | | | 91 | 96 | 97 | 100 | 35 | | 54 | -6 | 25 | 45 | 94 | 100 | 69 | 21 | 4 | 77 | 57 | 41 |
| 638 | 639 | G | 1184 | | | | | 87 | 89 | 81 | 69 | -5 | | 27 | 3 | 36 | 50 | 96 | 81 | 42 | 10 | -3 | 69 | 45 | 30 |
| 639 | 640 | G | 1185 | | | | | 76 | 89 | 79 | 59 | -2 | | 26 | -4 | 36 | 49 | 98 | 98 | 81 | 37 | -7 | 75 | 64 | 42 |
| 640 | 641 | G | 1189 | | | | | 71 | 83 | 89 | 95 | 12 | | 42 | 32 | 9 | 15 | 35 | 40 | 34 | 8 | 1 | 30 | 23 | 18 |
| 641 | 642 | G | 1190 | | | | | 91 | 96 | 98 | 100 | 15 | | 47 | 46 | 60 | 53 | 56 | 56 | 36 | 1 | 7 | 55 | 34 | 23 |
| 642 | 643 | G | 1191 | | | | | 80 | 91 | 92 | 94 | 9 | | 32 | 10 | 20 | 32 | 78 | 79 | 68 | 39 | 9 | 54 | 51 | 39 |
| 643 | 644 | G | 1217 | | | 2 | 1.6 | 71 | 86 | 91 | 100 | 49 | | 61 | -6 | 9 | 24 | 81 | 93 | 97 | 84 | 31 | 61 | 74 | 60 |
| 644 | 645 | G | 1218 | | | 2 | 1.1 | 74 | 82 | 85 | 90 | 36 | | 53 | 8 | 8 | 51 | 96 | 96 | 98 | 81 | 28 | 76 | 81 | 64 |
| 645 | 646 | G | 1219 | | | 1 | 1.3 | 76 | 88 | 92 | 100 | 26 | | 45 | 17 | 48 | 58 | 96 | 100 | 97 | 66 | -3 | 81 | 78 | 53 |
| 646 | 647 | G | 1220 | | | | | 51 | 69 | 76 | 90 | 40 | | 53 | 16 | 16 | 35 | 85 | 95 | 64 | 24 | -10 | 74 | 53 | 34 |
| 647 | 648 | G | 1221 | | | | | 34 | 67 | 78 | 99 | 55 | | 61 | 17 | -14 | -5 | 19 | 59 | 18 | 34 | -6 | 37 | 34 | 22 |
| 648 | 649 | G | 1222 | | | | | 81 | 91 | 93 | 97 | 11 | | 34 | 30 | 66 | 71 | 81 | 66 | 0 | 12 | -1 | 68 | 39 | 27 |
| 649 | 650 | G | 1248 | | | | | 45 | 65 | 73 | 87 | 53 | | 60 | 15 | 1 | 11 | 37 | 59 | 27 | 36 | 9 | 42 | 38 | 28 |
| 650 | 651 | G | 1249 | | | | | 27 | 57 | 67 | 86 | 30 | | 43 | -29 | -4 | 14 | 58 | 62 | 43 | 30 | 1 | 45 | 39 | 27 |
| 651 | 652 | G | 1250 | | | 1 | 1.3 | 32 | 61 | 72 | 80 | 24 | | 41 | 2 | 18 | 37 | 87 | 75 | -5 | 25 | 2 | 62 | 40 | 29 |
| 652 | 653 | G | 1251 | | | | | 59 | 74 | 80 | 84 | 49 | | 60 | -3 | 4 | 21 | 67 | 88 | 61 | 20 | -7 | 65 | 46 | 30 |
| 653 | 654 | G | 1252 | | | | | 13 | 50 | 64 | 89 | 40 | | 49 | -28 | -11 | 16 | 84 | 89 | 3 | 18 | 3 | 63 | 39 | 25 |
| 654 | 655 | G | 1253 | | | | | 35 | 61 | 69 | 84 | 68 | | 68 | -50 | -21 | -6 | 34 | 47 | -9 | 3 | -11 | 29 | 15 | 7 |
| 655 | 656 | G | 1254 | | | 1 | 1.9 | 53 | 75 | 83 | 97 | 55 | | 65 | -1 | 1 | 23 | 80 | 79 | 34 | 19 | 3 | 60 | 41 | 29 |
| 656 | 657 | G | 1255 | | | 2 | 0.7 | 36 | 64 | 72 | 88 | 69 | | 70 | -37 | 10 | 35 | 100 | 98 | 45 | 16 | -6 | 76 | 49 | 32 |
| 657 | 658 | G | 1256 | | | | | 73 | 79 | 84 | 93 | 50 | | 62 | -52 | 17 | 39 | 96 | 64 | -14 | 6 | -10 | 55 | 29 | 17 |
| 658 | 659 | G | 1260 | | | 1 | 0.8 | 57 | 77 | 85 | 99 | 26 | | 47 | -40 | 12 | 36 | 50 | 100 | 100 | 56 | -5 | 83 | 71 | 48 |
| 659 | 660 | G | 1264 | | | 1 | 1.0 | 68 | 82 | 86 | 92 | 36 | | 53 | 34 | 64 | 70 | 89 | 92 | 61 | 13 | -1 | 63 | 56 | 38 |
| 660 | 661 | G | 1265 | | | | | 46 | 73 | 73 | 74 | 18 | | 44 | 8 | 11 | 28 | 43 | 86 | 58 | 8 | 1 | 52 | 44 | 30 |
| 661 | 662 | G | 1277 | | | | | 38 | 65 | 80 | 100 | 20 | | 55 | 17 | 24 | 31 | 51 | 65 | 43 | 18 | 1 | 39 | 39 | 29 |
| 662 | 663 | G | 1278 | | | 1 | 1.3 | 56 | 75 | 84 | 95 | 37 | | 53 | 7 | 22 | 28 | 43 | 73 | 54 | 32 | 4 | 55 | 47 | 33 |
| 663 | 664 | G | 1279 | | | 3 | 1.7 | 65 | 80 | 89 | 101 | 30 | | 50 | 4 | 28 | 42 | 94 | 100 | 93 | 51 | 9 | 77 | 70 | 51 |
| 664 | 665 | G | 1280 | | | | | 76 | 87 | 93 | 102 | 54 | | 70 | 16 | 29 | 38 | 65 | 92 | 75 | 43 | 11 | 71 | 62 | 46 |
| 665 | 666 | G | 1281 | | | | | 70 | 83 | 90 | 100 | 26 | | 51 | -21 | 10 | 20 | 54 | 77 | 59 | 39 | 7 | 54 | 50 | 37 |
| 666 | 667 | G | 1282 | | | 2 | 0.9 | 81 | 90 | 91 | 93 | 22 | | 49 | 10 | 24 | 33 | 50 | 81 | 66 | 32 | 4 | 62 | 52 | 38 |
| 667 | 668 | G | 1284 | | | | | 50 | 72 | 85 | 101 | 52 | | 65 | 16 | 37 | 49 | 89 | 97 | 95 | 69 | 13 | 78 | 78 | 57 |
| 668 | 669 | G | 1307 | | | | | 11 | 48 | 65 | 92 | 38 | | 48 | -5 | 7 | 13 | 43 | 55 | 32 | 32 | 13 | 36 | 35 | 28 |
| 669 | 670 | G | 1308 | | | | | 10 | 45 | 62 | 91 | 49 | | 54 | -9 | -13 | -9 | 13 | 64 | 38 | 20 | 6 | 31 | 29 | 22 |
| 670 | 671 | G | 1309 | | | | | 40 | 67 | 74 | 85 | 44 | | 55 | -6 | 4 | -4 | -13 | 73 | 55 | 14 | -5 | 42 | 34 | 22 |
| 671 | 672 | G | 1310 | | | 1 | 0.9 | 51 | 70 | 78 | 92 | 51 | | 61 | -3 | 15 | 21 | 49 | 73 | 62 | 52 | 19 | 50 | 52 | 42 |
| 672 | 673 | G | 1311 | | | 1 | 0.4 | 56 | 74 | 81 | 94 | 73 | | 76 | -1 | 13 | 15 | 28 | 44 | 14 | 7 | 1 | 33 | 21 | 15 |
| 673 | 674 | G | 1312 | | | 3 | 3.5 | 30 | 60 | 71 | 90 | 74 | | 73 | 9 | 9 | 16 | 45 | 42 | 57 | 30 | 15 | 30 | 34 | 28 |
| 674 | 675 | G | 1313 | | | | | 96 | 99 | 76 | 46 | 10 | | 31 | 1 | 24 | 34 | 80 | 98 | 96 | 55 | -1 | 69 | 69 | 47 |
| 675 | 676 | G | 1314 | | | 3 | 0.6 | 92 | 100 | 93 | 100 | 36 | | 57 | -8 | 16 | 26 | 74 | 81 | 90 | 57 | 22 | 56 | 62 | 50 |
| 676 | 676 | G | 1315 | | | 1 | 10.0 | 37 | 72 | 84 | 100 | 59 | | 68 | 20 | 12 | 21 | 59 | 90 | 78 | 54 | 29 | 59 | 60 | 51 |

Fig. 2 (continued)

| SEQ ID NO. | Analogue no. | G no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 677 | 677 | G | 1316 | His | Ser | Glu | Gly | Thr | Phe | Thr | Ser | Asp | Tyr | Ser | Lys | Tyr | Leu | Glu | Glu |
| 678 | 678 | G | 1317 | His | Gly | Glu | Gly | Thr | Phe | Thr | Ser | Asp | Tyr | Ser | Lys | Tyr | Leu | Glu | Glu |
| 679 | 679 | G | 1318 | His | Ser | Glu | Gly | Thr | Phe | Thr | Ser | Asp | Tyr | Ser | Lys | Tyr | Leu | Glu | Glu |
| 680 | 680 | G | 1319 | His | Ser | Glu | Gly | Thr | Phe | Thr | Ser | Asp | Tyr | Ser | Lys | Tyr | Leu | Glu | Glu |
| 681 | 681 | G | 1336 | His | Gly | Gln | Gly | Thr | Phe | Thr | Ser | Asp | Leu | Ser | Lys | Tyr | Leu | Glu | Glu |
| 682 | 682 | G | 1337 | His | Gly | Glu | Gly | Thr | Phe | Thr | Ser | Asp | Tyr | Ser | Lys | Tyr | Leu | Glu | Glu |
| 683 | 683 | G | 1338 | His | Ser | Glu | Gly | Thr | Phe | Thr | Ser | Asp | Tyr | Ser | Lys | Tyr | Leu | Glu | Glu |
| 684 | 684 | G | 1339 | His | Ser | Glu | Gly | Thr | Phe | Thr | Ser | Asp | Tyr | Ser | Lys | Tyr | Leu | Glu | Glu |
| 685 | 685 | G | 1340 | His | Ser | Glu | Gly | Thr | Phe | Thr | Ser | Asp | Tyr | Ser | Lys | Tyr | Leu | Glu | Glu |
| 686 | 686 | G | 1344 | His | Ser | Glu | Gly | Thr | Phe | Thr | Ser | Asp | Tyr | Ser | Lys | Tyr | Leu | Glu | Glu |
| 687 | 687 | G | 1358 | His | Ser | Glu | Gly | Thr | Phe | Thr | Ser | Asp | Tyr | Ser | Lys | Tyr | Leu | Glu | Glu |
| 688 | 688 | G | 1359 | His | Gly | Glu | Gly | Thr | Phe | Thr | Ser | Asp | Tyr | Ser | Lys | Tyr | Leu | Glu | Glu |
| 689 | 689 | G | 1360 | His | Gly | Glu | Gly | Thr | Phe | Thr | Ser | Asp | Tyr | Ser | Lys | Tyr | Leu | Glu | Glu |
| 690 | 690 | G | 1362 | His | Gly | Gln | Gly | Thr | Phe | Thr | Ser | Asp | Leu | Ser | Lys | Gln | Leu | Glu | Glu |
| 691 | 691 | G | 1363 | His | Gly | Gln | Gly | Thr | Phe | Thr | Ser | Asp | Tyr | Ser | Lys | Gln | Leu | Glu | Glu |
| 692 | 692 | G | 1365 | His | Gly | Glu | Gly | Thr | Phe | Thr | Ser | Asp | Leu | Ser | Lys | Tyr | Leu | Glu | Glu |
| 693 | 693 | G | 1391 | His | Ser | Glu | Gly | Thr | Phe | Thr | Ser | Asp | Tyr | Ser | Lys | Tyr | Leu | Glu | Glu |
| 694 | 694 | G | 1393 | His | Ser | Glu | Gly | Thr | Phe | Thr | Ser | Asp | Tyr | Ser | Lys | Tyr | Leu | Glu | Ala |
| 695 | 695 | G | 1406 | His | Ser | Glu | Gly | Thr | Phe | Thr | Ser | Asp | Tyr | Ser | Lys | Tyr | Leu | Glu | Glu |
| 696 | 696 | G | 1407 | His | Ser | Glu | Gly | Thr | Phe | Thr | Ser | Asp | Leu | Ser | Lys | Tyr | Leu | Glu | Glu |
| 697 | 697 | G | 1408 | His | Ser | Glu | Gly | Thr | Phe | Thr | Ser | Asp | Tyr | Ser | Lys | Tyr | Leu | Glu | Glu |
| 698 | 698 | G | 1409 | His | Gly | Glu | Gly | Thr | Phe | Thr | Ser | Asp | Tyr | Ser | Lys | Tyr | Leu | Glu | Glu |
| 699 | 699 | G | 1410 | His | Gly | Gln | Gly | Thr | Phe | Thr | Ser | Asp | Leu | Ser | Lys | Gln | Leu | Glu | Glu |
| 700 | 700 | G | 1411 | His | Gly | Glu | Gly | Thr | Phe | Thr | Ser | Asp | Leu | Ser | Lys | Tyr | Leu | Glu | Glu |
| 701 | 701 | G | 1412 | His | Gly | Gln | Gly | Thr | Phe | Thr | Ser | Asp | Tyr | Ser | Lys | Gln | Leu | Glu | Glu |
| 702 | 702 | G | 1413 | His | Ser | Glu | Gly | Thr | Phe | Thr | Ser | Asp | Tyr | Ser | Lys | Tyr | Leu | Glu | Glu |
| 703 | 703 | G | 1414 | His | Ser | Glu | Gly | Thr | Phe | Thr | Ser | Asp | Tyr | Ser | Lys | Tyr | Leu | Glu | Glu |
| 704 | 704 | G | 1415 | His | Ser | Glu | Gly | Thr | Phe | Thr | Ser | Asp | Tyr | Ser | Lys | Tyr | Leu | Glu | Glu |
| 705 | 705 | G | 1416 | His | Ser | Glu | Gly | Thr | Phe | Thr | Ser | Asp | Tyr | Ser | Lys | Tyr | Leu | Glu | Glu |
| 706 | 706 | G | 1417 | His | Ser | Glu | Gly | Thr | Phe | Thr | Ser | Asp | Tyr | Ser | Lys | Tyr | Leu | Glu | Glu |
| 707 | 707 | G | 1418 | His | Ser | Glu | Gly | Thr | Phe | Thr | Ser | Asp | Tyr | Ser | Lys | Tyr | Leu | Glu | Glu |
| 708 | 708 | G | 1419 | His | Ser | Glu | Gly | Thr | Phe | Thr | Ser | Asp | Tyr | Ser | Lys | Tyr | Leu | Glu | Glu |
| 709 | 709 | G | 1440 | His | Ser | Glu | Gly | Thr | Phe | Thr | Ser | Asp | Tyr | Ser | Lys | Tyr | Leu | Glu | Glu |
| 710 | 710 | G | 1441 | His | Ser | Glu | Gly | Thr | Phe | Thr | Ser | Asp | Tyr | Ser | Lys | Tyr | Leu | Glu | Glu |
| 711 | 711 | G | 1442 | His | Ser | Glu | Gly | Thr | Phe | Thr | Ser | Asp | Tyr | Ser | Lys | Tyr | Leu | Glu | Glu |
| 712 | 712 | G | 1443 | His | Ser | Glu | Gly | Thr | Phe | Thr | Ser | Asp | Tyr | Ser | Lys | Tyr | Leu | Glu | Glu |
| 713 | 713 | G | 1444 | His | Ser | Glu | Gly | Thr | Phe | Thr | Ser | Asp | Tyr | Ser | Lys | Tyr | Leu | Glu | Glu |
| 714 | 714 | G | 1485 | His | Ser | Glu | Gly | Thr | Phe | Thr | Ser | Asp | Tyr | Ser | Lys | Tyr | Leu | Glu | Glu |
| 715 | 715 | G | 1487 | His | Gly | Glu | Gly | Thr | Phe | Thr | Ser | Asp | Tyr | Ser | Lys | Tyr | Leu | Glu | Glu |

Fig. 2 (continued)

| SEQ ID NO. | Analogue no. | G no. | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|
| 677 | 677 | G | Glu | Ala | Val | Arg | Ile | Phe | Ile | Glu | Trp | Leu | Leu | Asn | Gly | His | His | NH2 |
| 678 | 678 | G | Glu | Ala | Val | Arg | Ile | Phe | Ile | Glu | Trp | Leu | Leu | Asn | Gly | His | His | NH2 |
| 679 | 679 | G | Glu | Ala | Leu | Arg | Leu | Phe | Ile | Glu | Trp | Leu | Leu | Asn | Gly | His | His | NH2 |
| 680 | 680 | G | Gln | Ala | Leu | Arg | Leu | Phe | Ile | Gln | Trp | Leu | Leu | Asn | Gly | His | His | NH2 |
| 681 | 681 | G | Glu | Ala | Val | Arg | Leu | Phe | Ile | Glu | Trp | Leu | Leu | Asn | Gly | His | His | |
| 682 | 682 | G | Glu | Ala | Val | Arg | Leu | Phe | Ile | Glu | Trp | Leu | Leu | Asn | Gly | His | His | |
| 683 | 683 | G | Gln | Ala | Val | Arg | Ile | Phe | Ile | Gln | Trp | Leu | Leu | Asn | Thr | Gly | His | NH2 |
| 684 | 684 | G | Gln | Ala | Val | Arg | Ile | Phe | Ile | Gln | Trp | Leu | Leu | Asn | Thr | Gly | His | NH2 |
| 685 | 685 | G | Gln | Ala | Val | Arg | Ile | Phe | Ile | Gln | Trp | Leu | Leu | Gln | Thr | Gly | His | |
| 686 | 686 | G | Gln | Ala | Val | Arg | Ile | Phe | Ile | Gln | Trp | Leu | Leu | Asn | Gly | His | His | NH2 |
| 687 | 687 | G | Glu | Ala | Val | Arg | Ile | Phe | Ile | Glu | Trp | Leu | Leu | Asn | Thr | Gly | His | |
| 688 | 688 | G | Gln | Ala | Val | Arg | Ile | Phe | Ile | Gln | Trp | Leu | Leu | Asn | Thr | Gly | His | |
| 689 | 689 | G | Glu | Ala | Val | Arg | Ile | Phe | Ile | Glu | Trp | Leu | Leu | Asn | Thr | Gly | His | NH2 |
| 690 | 690 | G | Gln | Ala | Val | Arg | Ile | Phe | Ile | Gln | Trp | Leu | Leu | Asn | Gly | His | His | NH2 |
| 691 | 691 | G | Gln | Ala | Val | Arg | Ile | Phe | Ile | Gln | Trp | Leu | Leu | Asn | Thr | Gly | His | NH2 |
| 692 | 692 | G | Gln | Ala | Val | Arg | Ile | Phe | Ile | Gln | Trp | Leu | Lys | Asn | Thr | Gly | His | NH2 |
| 693 | 693 | G | Gln | Ala | Val | Arg | Ile | Phe | Ile | Gln | Trp | Leu | Leu | Asn | Gly | His | His | NH2 |
| 694 | 694 | G | Gln | Ala | Val | Arg | Ile | Phe | Ile | Gln | Trp | Leu | Leu | Asn | Gly | His | His | NH2 |
| 695 | 695 | G | Gln | Ala | Val | Arg | Ile | Phe | Ile | Gln | Trp | Leu | Leu | Asn | Gly | Gly | His | NH2 |
| 696 | 696 | G | Gln | Ala | Val | His | Ile | Phe | Ile | Gln | Trp | Leu | Leu | Asn | Thr | Gly | His | NH2 |
| 697 | 697 | G | Gln | Ala | Val | Arg | Ile | Phe | Ile | Gln | Trp | Leu | Leu | Asn | Gly | Gly | His | NH2 |
| 698 | 698 | G | Gln | Ala | Val | Arg | Ile | Phe | Ile | Gln | Trp | Leu | Leu | Asn | Thr | Gly | His | NH2 |
| 699 | 699 | G | Gln | Ala | Val | Arg | Ile | Phe | Ile | Gln | Trp | Leu | Leu | Asn | Gly | Gly | His | NH2 |
| 700 | 700 | G | Gln | Ala | Val | Arg | Ile | Phe | Ile | Gln | Trp | Leu | Leu | Asn | Thr | Gly | His | NH2 |
| 701 | 701 | G | Gln | Ala | Val | Arg | Ile | Phe | Ile | Gln | Trp | Leu | Leu | Asn | Gly | Gly | His | NH2 |
| 702 | 702 | G | Gln | Ala | Val | Arg | Ile | Phe | Ile | Gln | Trp | Leu | Leu | Asn | Thr | Gly | His | NH2 |
| 703 | 703 | G | Gln | Ala | Val | Arg | Ile | Phe | Ile | Gln | Trp | Leu | Leu | Asn | Gly | Gly | His | NH2 |
| 704 | 704 | G | Gln | Ala | Val | Arg | Ile | Phe | Ile | Gln | Trp | Leu | Leu | Asn | Thr | Gly | His | NH2 |
| 705 | 705 | G | Gln | Ala | Val | Arg | Ile | Phe | Ile | Gln | Trp | Leu | Leu | Asn | Gly | Gly | His | NH2 |
| 706 | 706 | G | Gln | Ala | Val | Arg | Ile | Phe | Ile | Gln | Trp | Leu | Leu | Asn | Gly | Lys | His | |
| 707 | 707 | G | Gln | Ala | Val | Arg | Ile | Phe | Ile | Gln | Trp | Leu | Leu | Asn | Gly | Lys | His | |
| 708 | 708 | G | Glu | Ala | Val | Arg | Ile | Phe | Ile | Glu | Trp | Leu | Leu | Asn | Thr | Gly | His | NH2 |
| 709 | 709 | G | Glu | Ala | Val | Arg | Ile | Phe | Ile | Glu | Trp | Leu | Leu | Gln | Gly | Gly | His | NH2 |
| 710 | 710 | G | Gln | Ala | Val | Arg | Ile | Phe | Ile | Gln | Trp | Leu | Leu | Gln | Thr | Gly | His | |
| 711 | 711 | G | Glu | Ala | Val | Arg | Ile | Phe | Ile | Glu | Trp | Leu | Leu | Asn | Thr | Gly | His | |
| 712 | 712 | G | Glu | Ala | Val | Arg | Ile | Phe | Ile | Glu | Trp | Leu | Leu | Gln | Gly | Gly | His | |
| 713 | 713 | G | Glu | Ala | Val | Arg | Ile | Phe | Ile | Glu | Trp | Leu | Leu | Gln | Gly | Gly | His | |
| 714 | 714 | G | Glu | Ala | Val | Arg | Ile | Phe | Ile | Glu | Trp | Leu | Leu | Asn | Gly | Lys | His | NH2 |
| 715 | 715 | G | Gln | Ala | Val | Arg | Ile | Phe | Ile | Gln | Trp | Leu | Leu | Asn | Gly | Lys | His | NH2 |

Fig. 2 (continued)

| SEQ ID NO. | Analogue no. | G no. | hGCGr cAMP vs hGCG | n | hGLP-1r cAMP vs hGLP-1 | n | Mouse food intake inhibition (500nmol/kg) | | | | | | | Rat food intake inhibition (500 nmol/kg with 1:1 Zn) | | | | | |
|---|---|---|---|---|---|---|---|---|---|---|---|---|---|---|---|---|---|---|---|
| | | | | | | | 0-1 | 0-4 | 0-8 | 4-8 | 8-24 | 24-32 | 0-24 | 0-1 | 0-4 | 0-8 | 4-8 | 8-24 | 24-32 | 32-48 | 48-72 | 0-24 | 0-48 | 0-72 |
| 677 | 677 | G | | | 1.6 | 1 | 86 | 96 | 98 | 100 | 47 | | 63 | 31 | 45 | 55 | 100 | 100 | 99 | 66 | 7 | 80 | 79 | 56 |
| 678 | 678 | G | | | 1.1 | 1 | 76 | 91 | 95 | 100 | 41 | | 58 | 34 | 54 | 63 | 100 | 99 | 100 | 67 | -6 | 80 | 79 | 53 |
| 679 | 679 | G | | | | | 62 | 84 | 75 | 63 | 43 | | 53 | 5 | 15 | 20 | 44 | 90 | 91 | 48 | 11 | 58 | 60 | 45 |
| 680 | 680 | G | | | | | 25 | 66 | 81 | 100 | 56 | | 64 | -1 | 7 | 4 | -18 | 25 | 9 | 11 | 6 | 16 | 13 | 11 |
| 681 | 681 | G | | | 1.5 | 1 | 62 | 77 | 82 | 90 | 46 | | 59 | 13 | 46 | 55 | 100 | 97 | 99 | 48 | 1 | 78 | 73 | 50 |
| 682 | 682 | G | | | 0.5 | 2 | 69 | 79 | 84 | 92 | 57 | | 67 | 45 | 66 | 72 | 97 | 100 | 93 | 61 | 16 | 87 | 80 | 60 |
| 683 | 683 | G | | | | | 35 | 64 | 72 | 86 | 52 | | 59 | 15 | 9 | 10 | 13 | 47 | 34 | 12 | 12 | 30 | 26 | 21 |
| 684 | 684 | G | | | 1.1 | 3 | 55 | 74 | 79 | 87 | 41 | | 55 | 21 | 9 | 11 | 19 | 80 | 93 | 73 | 31 | 49 | 63 | 53 |
| 685 | 685 | G | | | 1.2 | 3 | 78 | 84 | 87 | 92 | 62 | | 72 | 4 | 22 | 35 | 96 | 100 | 100 | 83 | 1 | 71 | 79 | 54 |
| 686 | 686 | G | | | 0.6 | 1 | 20 | 56 | 70 | 94 | 47 | | 56 | 14 | 2 | 14 | 69 | 79 | 74 | 47 | 12 | 45 | 59 | 38 |
| 687 | 687 | G | | | 2.5 | 1 | 92 | 95 | 97 | 100 | 57 | -44 | 68 | 34 | 48 | 58 | 100 | 100 | 99 | 51 | 1 | 78 | 73 | 51 |
| 688 | 688 | G | | | | | 89 | 92 | 95 | 100 | 81 | -37 | 85 | 34 | 59 | 66 | 95 | 98 | 93 | 42 | 2 | 81 | 71 | 50 |
| 689 | 689 | G | | | 1.0 | 1 | 85 | 84 | 90 | 100 | 63 | -42 | 71 | 13 | 36 | 47 | 96 | 99 | 97 | 57 | 3 | 72 | 71 | 51 |
| 690 | 690 | G | | | | | 20 | 46 | 65 | 97 | 16 | | 30 | 16 | 21 | 21 | 39 | 47 | 61 | 10 | 13 | 33 | 30 | 25 |
| 691 | 691 | G | | | 0.7 | 1 | 92 | 96 | 97 | 98 | 35 | | 52 | 26 | 31 | 44 | 98 | 97 | 96 | 78 | 23 | 69 | 76 | 60 |
| 692 | 692 | G | | | 4.9 | 1 | 90 | 94 | 97 | 100 | 52 | | 64 | 8 | 19 | 29 | 71 | 77 | 74 | 31 | -2 | 52 | 49 | 34 |
| 693 | 693 | G | | | 0.9 | 1 | 96 | 98 | 98 | 98 | 8 | -47 | 35 | 35 | 59 | 68 | 95 | 98 | 99 | 65 | 3 | 83 | 79 | 56 |
| 694 | 694 | G | | | | | 69 | 72 | 64 | 52 | 4 | | 17 | -16 | 1 | 8 | 29 | 2 | 20 | -7 | -5 | 5 | 3 | 1 |
| 695 | 695 | G | | | 0.9 | 1 | 85 | 94 | 88 | 78 | 42 | | 59 | 18 | 40 | 46 | 67 | 95 | 99 | 81 | 21 | 72 | 78 | 61 |
| 696 | 696 | G | | | 1.0 | 1 | 63 | 80 | 87 | 97 | 42 | -54 | 58 | -2 | 31 | 50 | 100 | 98 | 99 | 69 | 28 | 78 | 78 | 63 |
| 697 | 697 | G | | | | | 85 | 94 | 95 | 96 | 36 | | 58 | 6 | 39 | 51 | 98 | 82 | 43 | 13 | 4 | 68 | 48 | 34 |
| 698 | 698 | G | | | 0.7 | 1 | 62 | 79 | 88 | 101 | 41 | | 58 | 24 | 40 | 52 | 82 | 90 | 83 | 57 | 5 | 74 | 70 | 50 |
| 699 | 699 | G | | | | | 54 | 76 | 86 | 101 | 24 | | 46 | -28 | -1 | 7 | 25 | 73 | 75 | 43 | 3 | 45 | 48 | 34 |
| 700 | 700 | G | | | 1.7 | 1 | 91 | 95 | 98 | 100 | 29 | | 53 | 8 | 44 | 59 | 99 | 97 | 94 | 53 | 6 | 81 | 74 | 53 |
| 701 | 701 | G | | | | | 50 | 71 | 82 | 88 | 46 | | 56 | 8 | 15 | 29 | 67 | 59 | 70 | 22 | 1 | 44 | 40 | 28 |
| 702 | 702 | G | | | | | 43 | 79 | 82 | 88 | 18 | | 42 | 4 | 13 | 17 | 33 | 36 | 36 | 24 | -2 | 27 | 28 | 18 |
| 703 | 703 | G | | | 1.0 | 1 | 86 | 89 | 93 | 98 | 58 | -34 | 68 | 23 | 54 | 67 | 100 | 100 | 100 | 80 | 15 | 84 | 85 | 63 |
| 704 | 704 | G | | | 2.4 | 3 | 78 | 79 | 87 | 100 | 55 | -85 | 64 | 12 | 46 | 60 | 99 | 97 | 96 | 53 | 22 | 79 | 72 | 57 |
| 705 | 705 | G | | | 0.6 | 2 | 98 | 100 | 100 | 100 | 64 | -50 | 74 | 30 | 57 | 69 | 100 | 100 | 97 | 75 | 13 | 85 | 83 | 62 |
| 706 | 706 | G | | | 1.6 | 1 | 95 | 97 | 98 | 100 | 36 | | 53 | 56 | 76 | 83 | 100 | 100 | 97 | 68 | 25 | 93 | 85 | 67 |
| 707 | 707 | G | | | | | 56 | 83 | 88 | 97 | 45 | | 61 | 19 | 47 | 57 | 100 | 99 | 84 | 76 | 49 | 80 | 79 | 70 |
| 708 | 708 | G | | | 1.1 | 1 | 76 | 86 | 92 | 99 | 24 | | 48 | 11 | 44 | 59 | 96 | 99 | 95 | 69 | 26 | 82 | 80 | 63 |
| 709 | 709 | G | | | | | 74 | 91 | 88 | 82 | 26 | | 49 | 1 | 32 | 49 | 75 | 76 | 77 | 43 | -56 | 59 | 57 | 22 |
| 710 | 710 | G | | | 0.6 | 1 | 75 | 84 | 89 | 95 | 40 | | 57 | 5 | 48 | 62 | 100 | 100 | 99 | 64 | 1 | 84 | 80 | 55 |
| 711 | 711 | G | | | | | 65 | 88 | 91 | 98 | 43 | | 61 | 50 | 63 | 70 | 100 | 100 | 78 | 32 | -8 | 79 | 69 | 45 |
| 712 | 712 | G | | | | | 87 | 95 | 95 | 100 | 55 | | 70 | 64 | 81 | 85 | 100 | 100 | 69 | 27 | -6 | 86 | 70 | 46 |
| 713 | 713 | G | | | | | 62 | 86 | 89 | 95 | 37 | | 56 | 59 | 77 | 81 | 98 | 100 | 92 | 47 | -4 | 91 | 78 | 53 |
| 714 | 714 | G | | | | | | | | | | | | | | | | | | | | | | |
| 715 | 715 | G | | | | | | | | | | | | | | | | | | | | | | |

G778 / Analogue no. 14

B.

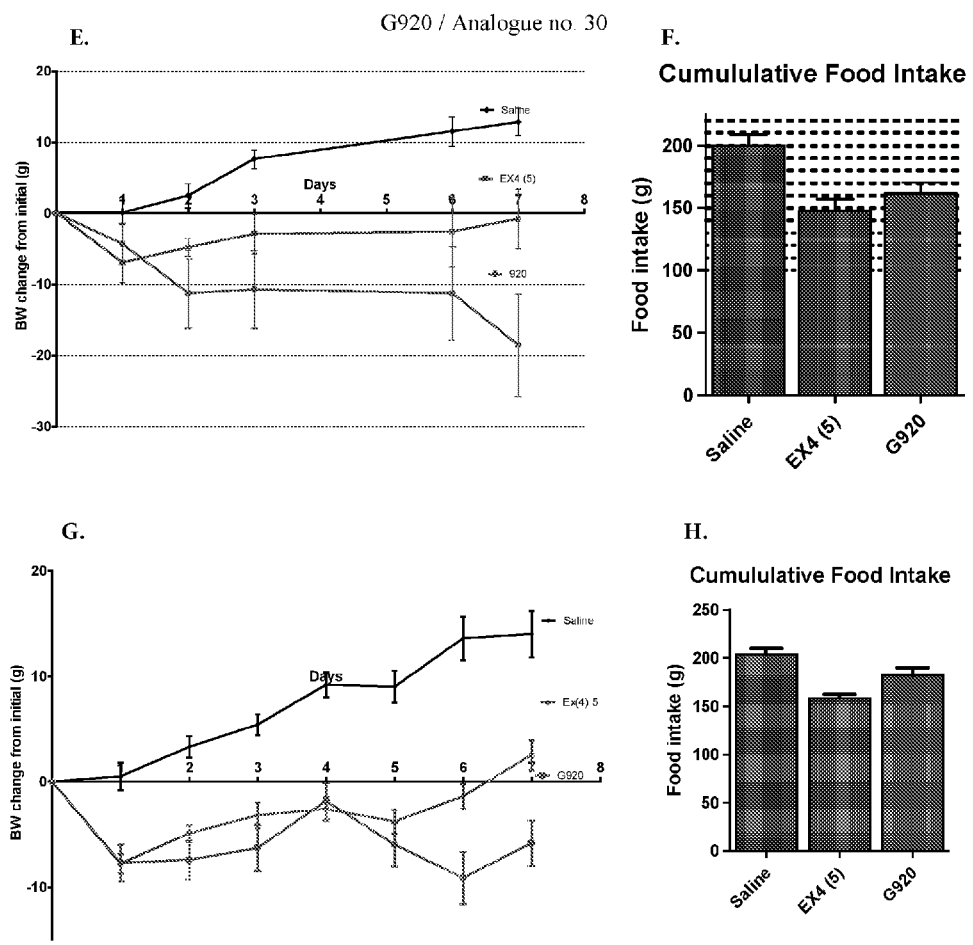
Fig.4 contd.

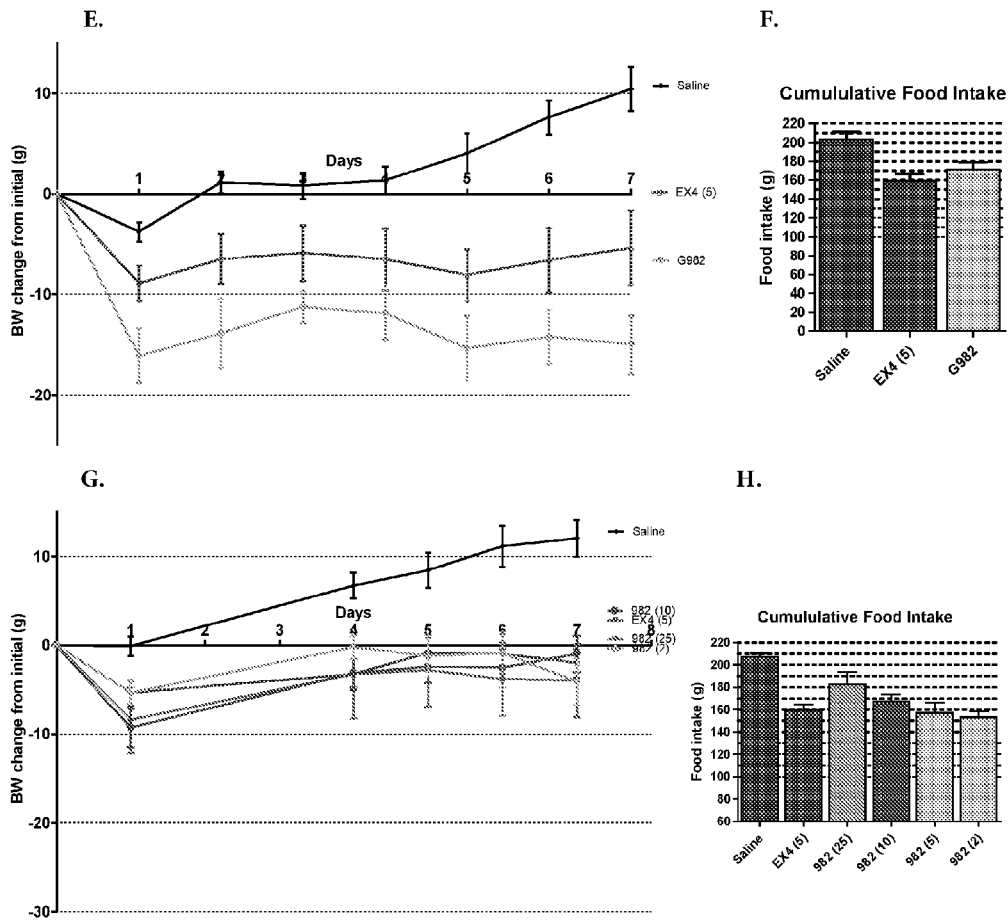
Fig. 6 contd.

G1233 / Analogue no. 92
E.
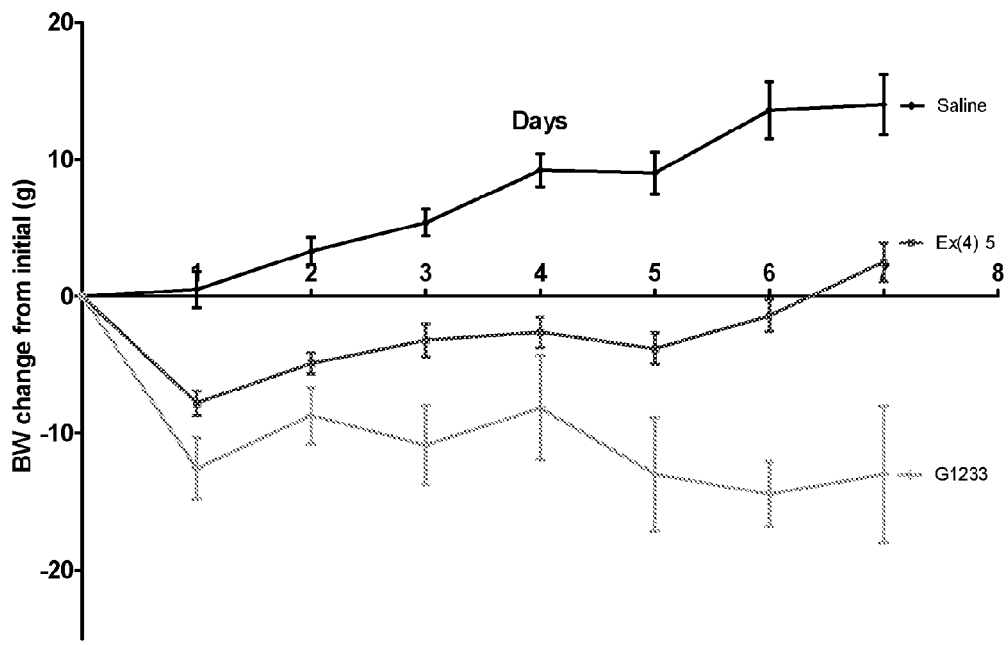
F.
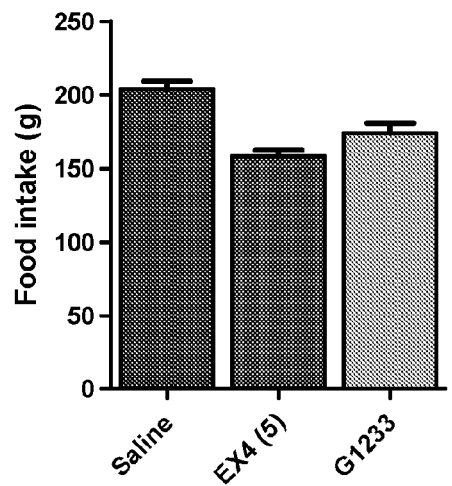
Fig.7 contd.

G1168 / Analogue no. 62

A. 4 day

B. 7 day

A. 4 day

B. 7 day

A. 4 day

B. 7 day

A. 4 day

B. 7 day

A. 4 day

B. 7 day

G946 / Analogue no. 566

A.

B.

G1314 / Analogue no. 675

A.

B.

G1337 / Analogue no. 682

G791 / Analogue no. 484

A.

B.

G822 / Analogue no. 494

A.

B.

G832 / Analogue no. 503

A.

B.

G1095 / Analogue no. 603

A.

B.

G1260 / Analogue no. 658

G1284 / Analogue no. 667

G1415 / Analogue no. 704

A.

B.

US 9,546,205 B2

PEPTIDE ANALOGUES OF GLUCAGON AND GLP1

CROSS-REFERENCE TO RELATED APPLICATIONS

This application is a United States national stage filing under 35 U.S.C. §371 of international (PCT) application no. PCT/GB2013/052422, filed Sep. 17, 2013, and designating the US, which claims priority to United Kingdom (GB) application nos. 1216551.0, filed Sep. 17, 2012, and 1216548.6, filed Sep. 17, 2012.

FIELD OF THE INVENTION

This invention relates to analogues of glucagon which are useful in treating diabetes and obesity. It also relates to use of the glucagon analogues as neuroprotective or cardioprotective agents.

This invention also relates to analogues of GLP1 which are useful in treating diabetes and obesity. It also relates to use of the GLP1 analogues as neuroprotective or cardioprotective agents.

BACKGROUND OF THE INVENTION

According to the National Health and Nutrition Examination Survey (NHANES III, 1988 to 1994), between one third and one half of men and women in the United States are overweight. In the United States, sixty percent of men and fifty-one percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347:358, 2002). In addition, there is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia. Recently it has been shown that considerable weight loss can effectively cure type 2 diabetes (Lim et al, Diabetologia June 2011).

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have proven to have serious adverse side effects, and have had to be withdrawn. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects as well as subjects who are of normal weight.

A number of derivatives of peptides deriving from the pro-glucagon molecule have been proposed for use in treatment of obesity and/or diabetes. Pro-glucagon is a precursor peptide of glucagon, as well as other hormones including oxyntomodulin (OXM) and GLP1 (glucagon-like peptide 1). Glucagon is released in vivo when blood glucose levels fall low and has the activity of causing the liver to convert stored glycogen into glucose which is released into the bloodstream raising blood glucose levels. GLP1 is produced in vivo in the intestinal L cell in response to the presence of nutrients in the lumen of the gut. Once in the circulation, native GLP1 has a half-life of only a few minutes in humans due to rapid degradation by the enzyme dipeptidyl peptidase. GLP1 possesses a number of physiological functions including increasing insulin secretion from the pancreas in a glucose-dependent manner, decreasing glucagon secretion from the pancreas, inhibiting gastric emptying and decreasing food intake by increasing satiety. Increased insulin secretion leads to a decrease in circulating glucose concentration.

WO2008/086086 (Indiana University Research and Technology Corporation) discloses certain glucagon peptides which have been modified by the incorporation of charged amino acids at the carboxy terminus of the peptide. The peptides are disclosed as having enhanced aqueous solubility at a pH ranging from about 5.5 to about 8.

WO2011/075393 (Indiana University Research and Technology Corporation) discloses certain peptides having activity at the GLP1 and/or glucagon receptors, including peptides which are based on the sequence of glucagon but which are modified such that the glucagon residues at positions 18 to 24 are substituted for exendin-4 residues. Exendin-4 is a lizard venom peptide which is a structural homolog of GLP1 (50% amino acid identity) and which also has activity at the GLP-1 receptor. WO2011/075393 teaches that, in order to achieve prolonged half-life/extended duration of action, the peptides may contain acylated or alkylated amino acids.

Despite significant advances, the process of identifying substances useful as drugs remains a complex and, in many cases, unpredictable field. Compounds must possess a suitable balance of properties, for example in addition to having efficacy at the biological target of interest, they must have good in vivo pharmacokinetic properties as well as low toxicity.

The present invention is based on the discovery that analogues of glucagon containing His residues at specified positions can be administered to a subject in order to cause an alteration in energy metabolism, so as to promote weight loss. In many case the glucagon analogues of the present invention have an improved pharmacokinetic profile, having a longer duration of action than native glucagon. In particular, glucagon analogues may have an improved pharmacokinetic profile characterised by a slower increase of plasma levels following administration, a lower Cmax and/or a more stable plateau. Such a pharmacokinetic profile may be associated with a decrease in side effects such as nausea, which are associated with a rapid onset of high plasma levels. Glucagon analogues of the invention may display improved potency and/or fewer side effects compared with native glucagon. Increased potency at the glucagon receptor results in lower doses being required to decrease food intake, thereby decreasing the side effects associated with high doses.

The present invention is also based on the discovery that analogues of GLP1 containing His residues at specified positions can be administered to a subject in order to cause prolonged reduction in appetite and hence food intake, so as to promote weight loss. In many cases the GLP1 analogues of the present invention exhibit improved pharmacokinetic properties (e.g. longer duration of action) compared with native GLP1. In particular, GLP1 analogues may have an improved pharmacokinetic profile characterised by a slower increase of plasma levels following administration, a lower Cmax and/or a more stable plateau. Such a pharmacokinetic profile may be associated with a decrease in side effects such as nausea, which are associated with a rapid onset of high plasma levels. GLP1 analogues of the invention may display improved potency and/or fewer side effects compared with native GLP1. Increased potency at the GLP-1 receptor results in lower doses being required to decrease food intake, thereby decreasing the side effects associated with high doses.

SUMMARY OF THE INVENTION

In a first aspect, the invention provides an analogue of glucagon which is:
a compound comprising an amino acid sequence represented by formula (I)

His-Ser-Gln-Gly-Thr-Phe-Thr-Ser-Asp-Xaa$^{10}$-Ser-Xaa$^{12}$-Xaa$^{13}$-Leu-Xaa$^{15}$-Xaa$^{16}$-Xaa$^{17}$-Xaa$^{18}$-Ala-Xaa$^{20}$-Xaa$^{21}$-Phe-Xaa$^{23}$-Xaa$^{24}$-Trp-Leu-Leu-Asn-Xaa$^{29}$-V   (I)

wherein V is selected from the group consisting of His (SEQ ID NO. 716), His-NH$_2$ (SEQ ID NO. 717), His-His (SEQ ID NO. 718), His-His-NH$_2$ (SEQ ID NO. 719), Gly-His (SEQ ID NO. 720), Gly-His-NH$_2$ (SEQ ID NO. 721), Lys-His (SEQ ID NO. 722), Lys-His-NH$_2$ (SEQ ID NO. 723), Gly-His-His (SEQ ID NO. 724), Gly-His-His-NH$_2$ (SEQ ID NO. 725), His-His-His (SEQ ID NO. 726) and His-His-His-NH$_2$ (SEQ ID NO. 727);

Xaa$^{10}$ is selected from the group consisting of Tyr and Leu;

Xaa$^{12}$ is selected from the group consisting of Lys, His and Arg;

Xaa$^{13}$ is selected from the group consisting of Tyr, Gln and His;

Xaa$^{15}$ is selected from the group consisting of Asp and Glu;

Xaa$^{16}$ is selected from the group consisting of Glu, Gln and Ser;

Xaa$^{17}$ is selected from the group consisting of Arg, His and Lys;

Xaa$^{18}$ is selected from the group consisting of Arg and Lys;

Xaa$^{20}$ is selected from the group consisting of His and Gln;

Xaa$^{21}$ is selected from the group consisting of Glu, His and Asp;

Xaa$^{23}$ is selected from the group consisting of Ile and Val;

Xaa$^{24}$ is selected from the group consisting of Gln and Glu; and

Xaa$^{29}$ is selected from the group consisting of Thr and Gly;

wherein —NH$_2$ represents a C-terminal amide group;
or a derivative of the compound;
or a salt of the compound or the derivative.

According to a further aspect of the invention, there is provided a pharmaceutical composition comprising a glucagon analogue of the invention together with a pharmaceutically acceptable carrier and optionally other therapeutic ingredients.

According to a further aspect of the invention, there is provided a glucagon analogue of the invention, or a pharmaceutical composition comprising a glucagon analogue of the invention, for use as a medicament. The glucagon analogue of the invention or pharmaceutical composition comprising the glucagon analogue of the invention finds use in the treatment of obesity and/or diabetes. The glucagon analogue or pharmaceutical composition is for use in increasing the energy expenditure of a subject, enhancing insulin release in a subject and/or improving carbohydrate metabolism in a subject and/or improving the lipid profile of a subject. The glucagon analogue or pharmaceutical composition also finds use as a cytoprotective agent, e.g. in preventing or treating neurodegeneration, providing neuroprotection and/or providing cardiac protection.

According to a further aspect of the invention, there is provided use of a glucagon analogue of the invention for the manufacture of a medicament for the treatment of obesity and/or diabetes. There is also provided use of a glucagon analogue for the manufacture of a medicament for increasing the energy expenditure of a subject, enhancing insulin release in a subject, improving carbohydrate metabolism in a subject and/or improving the lipid profile of a subject. There is also provided use of a glucagon analogue for the manufacture of a medicament for providing cytoprotection.

According to a further aspect of the invention, there is provided a method of treating or preventing a disease or disorder or other non-desired physiological state in a subject comprising administration of a therapeutically effective amount of a glucagon analogue of the invention, or a pharmaceutical composition comprising the glucagon analogue of the invention. There is also provided a method of treating obesity or diabetes in a subject in need thereof comprising administration of a therapeutically effective amount of a glucagon analogue or pharmaceutical composition. There is also provided a method of increasing the energy expenditure of a subject, enhancing insulin release in a subject, improving carbohydrate metabolism in a subject and/or improving the lipid profile of a subject, comprising administration of a therapeutically effective amount of a glucagon analogue or pharmaceutical composition. There is also provided a method of providing cytoprotection in a subject, comprising administration of a therapeutically effective amount of a glucagon analogue or pharmaceutical composition.

In a further aspect, the invention provides an analogue of GLP1 which is:
a compound comprising an amino acid sequence represented by formula (II)

His-Xaa$^2$-Xaa$^3$-Gly-Thr-Phe-Thr-Ser-Asp-Xaa$^{10}$-Ser-Xaa$^{12}$-Xaa$^{13}$-Leu-Glu-Xaa$^{16}$-Xaa$^{17}$-Ala-Xaa$^{19}$-Xaa$^{20}$-Xaa$^{21}$-Phe-Xaa$^{23}$-Xaa$^{24}$-Trp-Leu-Xaa$^{27}$-Xaa$^{28}$-Xaa$^{29}$-V   (II)

wherein V is selected from the group consisting of His (SEQ ID NO. 728), His-NH$_2$ (SEQ ID NO. 729), His-His (SEQ ID NO. 730), His-His-NH$_2$ (SEQ ID NO. 731), Gly-His (SEQ ID NO. 732), Gly-His-NH$_2$ (SEQ ID NO. 733), Lys-His (SEQ ID NO. 734) and Lys-His-NH$_2$ (SEQ ID NO. 735);

Xaa$^2$ is selected from the group consisting of Ser and Gly;
Xaa$^3$ is selected from the group consisting of Glu and Gln;
Xaa$^{10}$ is selected from the group consisting of Tyr and Leu;
Xaa$^{12}$ is selected from the group consisting of Lys and His;
Xaa$^{13}$ is selected from the group consisting of Tyr and Gln;
Xaa$^{16}$ is selected from the group consisting of Glu, Ala and Ser;
Xaa$^{17}$ is selected from the group consisting of Gln and Glu;
Xaa$^{19}$ is selected from the group consisting of Val, Ala, Ile and Leu;
Xaa$^{20}$ is selected from the group consisting of Arg and His;
Xaa$^{21}$ is selected from the group consisting of Ile and Leu;
Xaa$^{23}$ is selected from the group consisting of Ile and Val;
Xaa$^{24}$ is selected from the group consisting of Glu and Gln;
Xaa$^{27}$ is selected from the group consisting of Leu and Lys;
Xaa$^{28}$ is selected from the group consisting of Asn, Lys and Gln; and
Xaa$^{29}$ is selected from the group consisting of Gly and Thr;

wherein —NH$_2$ represents a C-terminal amide group;
or a derivative of the compound;
or a salt of the compound or the derivative;

According to a further aspect of the invention, there is provided a pharmaceutical composition comprising a GLP1 analogue of the invention together with a pharmaceutically acceptable carrier and optionally other therapeutic ingredients.

According to a further aspect of the invention, there is provided a GLP1 analogue of the invention, or a pharmaceutical composition comprising a GLP1 analogue of the invention, for use as a medicament. The GLP1 analogue of the invention or pharmaceutical composition comprising the GLP1 analogue of the invention finds use in the treatment of obesity and/or diabetes. The GLP1 analogue or pharmaceutical composition is for use in the reduction of appetite in a subject, reduction of food intake in a subject, reduction of calorie intake in a subject, enhancing insulin release in a subject, improving carbohydrate tolerance in a subject and/or improving the lipid profile of a subject. The GLP1 analogue or pharmaceutical composition also finds use as a cytoprotective agent, e.g. in preventing or treating neurodegeneration, providing neuroprotection and/or providing cardiac protection.

According to a further aspect of the invention, there is provided use of a GLP1 analogue of the invention for the manufacture of a medicament for the treatment of obesity and/or diabetes. There is also provided use of a GLP1 analogue for the manufacture of a medicament for the reduction of appetite in a subject, reduction of food intake in a subject, reduction of calorie intake in a subject, enhancing insulin release in a subject, improving carbohydrate tolerance in a subject and/or improving the lipid profile of a subject. There is also provided use of a GLP1 analogue for the manufacture of a medicament for providing cytoprotection.

According to a further aspect of the invention, there is provided a method of treating or preventing a disease or disorder or other non-desired physiological state in a subject comprising administration of a therapeutically effective amount of a GLP1 analogue of the invention, or a pharmaceutical composition comprising the GLP1 analogue of the invention. There is also provided a method of treating obesity or diabetes in a subject in need thereof comprising administration of a therapeutically effective amount of a GLP1 analogue or pharmaceutical composition. There is also provided a method of reducing appetite in a subject, reducing food intake in a subject, reducing calorie intake in a subject, enhancing insulin release in a subject, improving carbohydrate tolerance in a subject and/or improving the lipid profile of a subject, comprising administration of a therapeutically effective amount of a GLP1 analogue or pharmaceutical composition. There is also provided a method of providing cytoprotection in a subject, comprising administration of a therapeutically effective amount of a GLP1 analogue or pharmaceutical composition.

BRIEF DESCRIPTION OF THE DRAWINGS

FIG. 1 shows the amino acid sequences of glucagon analogues of the invention. The peptide analogues in the table of FIG. 1 are presented with the N-terminal residue at the left hand side of the table and the C-terminal residue at the right hand side of the table. Analogues in the table containing the group "—NH2" have a C-terminal amide group (i.e. the C-terminal residue has a —C(O)NH2 group in place of a C-terminus carboxylic acid). FIG. 1 also shows data relating to cAMP signaling in cells over-expressing the human glucagon receptor or the human GLP-1 receptor following contact with glucagon analogues of the invention. FIG. 1 also show summary food intake data for glucagon analogues of the invention.

FIG. 2 shows the amino acid sequences of GLP1 analogues of the invention. The peptide analogues in the table of FIG. 2 are presented with the N-terminal residue at the left hand side of the table and the C-terminal residue at the right hand side of the table. Analogues in the table containing the group "—NH2" have a C-terminal amide group (i.e. the C-terminal residue has a —C(O)NH2 group in place of a C-terminus carboxylic acid). FIG. 2 also shows data relating to cAMP signaling in cells over-expressing the human glucagon receptor or the human GLP-1 receptor following contact with GLP1 analogues of the invention. FIG. 2 also shows summary food intake data for GLP1 analogues of the invention.

FIG. 3B. shows the cumulative food intake over seven days in rats treated with G778 (analogue no. 14) compared with exendin-4.

FIGS. 4A., 4C., 4E., and 4G. show the change in body weight over seven days in rats treated with G920 (analogue no. 30) compared with exendin-4. FIGS. 4B., 4D., 4F., and 4H. show the cumulative food intake over seven days in rats treated with G920 (analogue no. 30) compared with exendin-4.

FIGS. 5A. and 5C. show the change in body weight over seven days in rats treated with G922 (analogue no. 32) compared with exendin-4. FIGS. 5B. and 5D. show the cumulative food intake over seven days in rats treated with G922 (analogue no. 32) compared with exendin-4.

FIGS. 6A., 6C., 6E., and 6G. show the change in body weight over seven days in rats treated with G982 (analogue no. 38) compared with exendin-4. FIGS. 6B., 6D., 6F., and 6H. show the cumulative food intake over seven days in rats treated with G982 (analogue no. 38) compared with exendin-4.

FIGS. 7A., 7C., and 7E. show the change in body weight over seven days in rats treated with G1233 (analogue no. 92) compared with exendin-4. FIGS. 7B., 7D., and 7F. show the cumulative food intake over seven days in rats treated with G1233 (analogue no. 92) compared with exendin-4.

FIGS. 8A. and 8C. show the change in body weight over seven days in rats treated with G1449 (analogue no. 174) compared with exendin-4. FIGS. 8B. and 8D. show the cumulative food intake over seven days in rats treated with G1449 (analogue no. 174) compared with exendin-4.

FIGS. 9A. and 9C. show the change in body weight over seven days in rats treated with G1167 (analogue no. 61) compared with exendin-4. FIGS. 9B. and 9D. show the cumulative food intake over seven days in rats treated with G1167 (analogue no. 61) compared with exendin-4.

FIG. 10A. shows the change in body weight over seven days in rats treated with G1168 (analogue no. 62) compared with exendin-4. FIG. 10B. shows the cumulative food intake over seven days in rats treated with G1168 (analogue no. 62) compared with exendin-4.

FIGS. 11A. and 11C. show the change in body weight over seven days in rats treated with G1335 (analogue no. 130) compared with exendin-4. FIGS. 11B. and 11D. show the cumulative food intake over seven days in rats treated with G1335 (analogue no. 130) compared with exendin-4.

FIGS. 12A. and 12C. show the change in body weight over seven days in rats treated with G1355 (analogue no. 141) compared with exendin-4. FIGS. 12B. and 12D. show the cumulative food intake over seven days in rats treated with G1355 (analogue no. 141) compared with exendin-4.

FIGS. 14A. and 14B. show the pharmacokinetic profiles of glucagon analogue G920 over a 4 day and a 7 day time period, respectively.

FIGS. 15A. and 15B. show the pharmacokinetic profiles of glucagon analogue G922 over a 4 day and a 7 day time period, respectively.

FIGS. 16A. and 16B. show the pharmacokinetic profiles of glucagon analogue G982 over a 4 day and a 7 day time period, respectively.

FIGS. 17A., 17B., and 17C. show the pharmacokinetic profiles of glucagon analogue G1233 over a 4 day and a 7 day time period, respectively.

FIG. 18 shows the pharmacokinetic profile of glucagon analogue G1449 over a 4 day time period.

FIGS. 19A. and 19B. show the pharmacokinetic profiles of glucagon analogue G1167 over a 4 day and a 7 day time period, respectively.

FIGS. 20A. and 20B. show the pharmacokinetic profiles of glucagon analogue G1168 over a 4 day and a 7 day time period, respectively.

FIG. 21 shows the pharmacokinetic profile of glucagon analogue G1335 over a 7 day time period.

FIG. 22 shows the pharmacokinetic profile of glucagon analogue G1355 over a 7 day time period.

FIG. 23B. shows the cumulative food intake over 24 hours in mice to which GLP1 analogue G946 (analogue no. 566) had been administered, compared with the cumulative food intake in mice to which saline had been administered.

FIG. 24A. shows the cumulative food intake over 72 hours in rats to which GLP1 analogue G947 (analogue no. 567) had been administered, compared with the cumulative food intake for rats to which saline had been administered. FIG. 24B. shows the cumulative food intake over 24 hours in mice to which GLP1 analogue G947 (analogue no. 567) had been administered, compared with the cumulative food intake in mice to which saline had been administered.

FIG. 25A. shows the cumulative food intake over 72 hours in rats to which GLP1 analogue G1280 (analogue no. 664) had been administered, compared with the cumulative food intake for rats to which saline had been administered. FIG. 25B. shows the cumulative food intake over 24 hours in mice to which GLP1 analogue G1280 (analogue no. 664) had been administered, compared with the cumulative food intake in mice to which saline had been administered.

FIG. 26A. shows the cumulative food intake over 72 hours in rats to which GLP1 analogue G1314 (analogue no. 675) had been administered, compared with the cumulative food intake for rats to which saline had been administered. FIG. 26B. shows the cumulative food intake over 24 hours in mice to which GLP1 analogue G1314 (analogue no. 675) had been administered, compared with the cumulative food intake in mice to which saline had been administered.

FIG. 27A. shows the cumulative food intake over 72 hours in rats to which GLP1 analogue G1337 (analogue no. 682) had been administered, compared with the cumulative food intake for rats to which saline had been administered. FIG. 27B. shows the cumulative food intake over 24 hours in mice to which GLP1 analogue G1337 (analogue no. 682) had been administered, compared with the cumulative food intake in mice to which saline had been administered.

FIG. 28A. shows the cumulative food intake over 72 hours in rats to which GLP1 analogue G791 (analogue no. 484) had been administered, compared with the cumulative food intake for rats to which saline had been administered. FIG. 28B. shows the cumulative food intake over 24 hours in mice to which GLP1 analogue G791 (analogue no. 484) had been administered, compared with the cumulative food intake in mice to which saline had been administered.

FIG. 29A. shows the cumulative food intake over 72 hours in rats to which GLP1 analogue G822 (analogue no. 494) had been administered, compared with the cumulative food intake for rats to which saline had been administered. FIG. 29B. shows the cumulative food intake over 24 hours in mice to which GLP1 analogue G822 (analogue no. 494) had been administered, compared with the cumulative food intake in mice to which saline had been administered.

FIG. 30A. shows the cumulative food intake over 72 hours in rats to which GLP1 analogue G832 (analogue no. 503) had been administered, compared with the cumulative food intake for rats to which saline had been administered. FIG. 30B. shows the cumulative food intake over 24 hours in mice to which GLP1 analogue G832 (analogue no. 503) had been administered, compared with the cumulative food intake in mice to which saline had been administered.

FIG. 31A. shows the cumulative food intake over 72 hours in rats to which GLP1 analogue G1095 (analogue no.

603) had been administered, compared with the cumulative food intake for rats to which saline had been administered. FIG. 31B. shows the cumulative food intake over 24 hours in mice to which GLP1 analogue G1095 (analogue no. 603) had been administered, compared with the cumulative food intake in mice to which saline had been administered.

FIG. 32A. shows the cumulative food intake over 72 hours in rats to which GLP1 analogue G1260 (analogue no. 658) had been administered, compared with the cumulative food intake for rats to which saline had been administered. FIG. 32B. shows the cumulative food intake over 24 hours in mice to which GLP1 analogue G1260 (analogue no. 658) had been administered, compared with the cumulative food intake in mice to which saline had been administered.

FIG. 33A. shows the cumulative food intake over 72 hours in rats to which GLP1 analogue G1284 (analogue no. 667) had been administered, compared with the cumulative food intake for rats to which saline had been administered. FIG. 33B. shows the cumulative food intake over 24 hours in mice to which GLP1 analogue G1284 (analogue no. 667) had been administered, compared with the cumulative food intake in mice to which saline had been administered.

FIG. 34A. shows the cumulative food intake over 72 hours in rats to which GLP1 analogue G1415 (analogue no. 704) had been administered, compared with the cumulative food intake for rats to which saline had been administered. FIG. 34B. shows the cumulative food intake over 24 hours in mice to which GLP1 analogue G1415 (analogue no. 704) had been administered, compared with the cumulative food intake in mice to which saline had been administered.

DEFINITIONS

Figure 3:
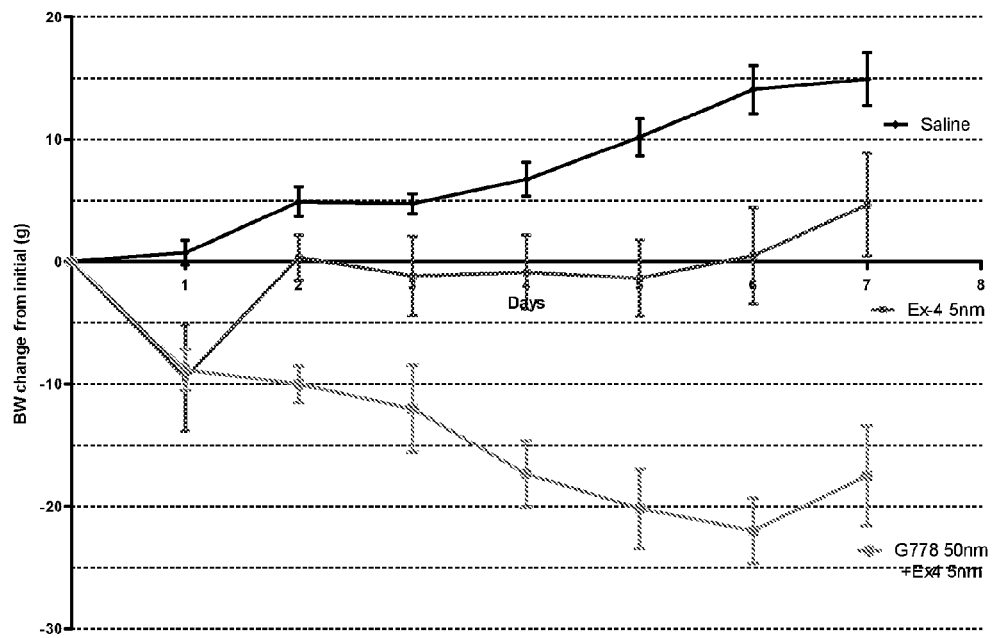
FIGS. 3 to 12 show more detailed rat food intake and body weight change data for selected glucagon analogues of the invention compared with exendin-4. Specifically, FIG. 3A. shows the change in body weight over seven days in rats treated with G778 (analogue no. 14) compared with exendin-4.
Figure 3:
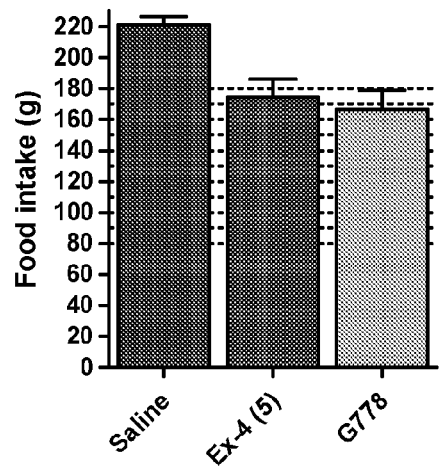

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity (which is sometimes referred to as being "overweight" rather than obesity) corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J Clin. Nutr.* 45:1035-47, 1987). Ideal body weight will vary among species and individuals based on height, body build, bone structure, and sex.

Cardioprotection refers to the protection of cardiac cells (and especially the myocardial cells) from apoptosis, necrotic cell death or degeneration (loss of function). Cardioprotection is most often required following myocardial infarction, but may also be used in subjects suffering from ischemic heart disease (for example angina)

Conservative substitutions: The replacement of an amino acid residue by another, biologically similar residue in a polypeptide. The term "conservative variation" also includes the use of a substituted amino acid, i.e. an amino acid with one or more atoms replaced with another atom or group, in place of a parent amino acid provided that the polypeptide retains its activity or provided that antibodies raised to the substituted polypeptide also immunoreact with the unsubstituted polypeptide Cytoprotection refers to the protection of cells from apoptosis, necrotic cell death or degeneration (loss of function).

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Energy Metabolism: The body has to expend a certain amount of energy to maintain normal metabolism. In civilized man this is often set at about 2,800 Calories daily. If food consumption does not provide this, weight loss results. However, energy metabolism is also regulated and, for example, administration of glucagon is thought to increase the metabolic rate so that a greater food intake is required to achieve energy balance and maintain weight. Thus, if food intake is maintained at the usual level, but energy metabolism is increased, weight loss will result.

Food intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

GLP1: Glucagon-like peptide 1 (GLP1) is derived from the transcription product of the proglucagon gene. The biologically active forms of GLP1 are truncated forms known as GLP1$_{(7-37)}$ and GLP1$_{(7-36)}$-C(O)NH$_2$/GLP$_{(7-36)}$-NH$_2$ (i.e. the C-terminus has a —C(O)NH$_2$ group in place of a carboxylic acid). The sequence of human GLP1$_{(7-36)}$-C(O)NH$_2$ is His-Ala-Glu-Gly-Thr-Phe-Thr-Ser-Asp-Val-Ser- Ser-Tyr-Leu-Glu-Gly-Gln-Ala-Ala-Lys-Glu-Phe-Ile-Ala-Trp-Leu-Val-Lys-Gly-Arg- C(O)NH$_2$.

Glucagon: Glucagon is a peptide derived from the proglucagon gene. It is a 29-amino acid polypeptide in humans and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr.

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Although the threshold voltage of the cell is uncharged, a hyperpolarized cell requires a stronger excitatory stimulus to reach threshold.

Neuroprotection refers to the protection of neurons within the nervous system (preferably within the central nervous system) from apoptosis, necrotic cell death or degeneration (loss of function). Neuroprotective treatments, including those relating to various aspects of the present invention may be required following a brain injury (for example those following physical trauma or non-traumatic injury such as stroke, brain tumours, infection, poisoning, hypoxia, ischemia, encephalopathy or substance abuse). Neuroprotective treatments, including those relating to various aspects of the present invention may also be indicated in subjects having a chronic neurodegenerative disease such as Alzheimer's disease, Parkinson's disease, Gehrig's disease or Huntington's disease.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 kg/m$^2$ to 29.9 kg/m$^2$ is overweight, while a BMI of 30 kg/m$^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Famr. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 kg/m$^2$ to 29.9 kg/m$^2$ PEGylated and PEGylation: the process of reacting a poly(alkylene glycol), preferably an activated poly(alkylene glycol) to form a covalent bond. A facilitator may be used, for example an amino acid, e.g. lysine. Although "PEGylation" is often carried out using poly(ethylene glycol) or derivatives thereof, such as methoxy poly(ethylene glycol), the term is not limited herein to the use of methoxy poly (ethylene glycol) but also includes the use of any other useful poly(alkylene glycol), for example poly(propylene glycol).

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called isoelectric focusing which is an electrophoretic method that utilises a pH gradient contained within a polyacrylamide gel.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein encompass any amino acid sequence and include modified sequences such as glycoproteins. The term "polypeptide" covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH 4 and pH 10 are usually regarded as tolerably comfortable.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake or increase energy expenditure.

DETAILED DESCRIPTION

Glucagon Analogues

According to a first aspect of the invention, there is provided an analogue of glucagon which is:
a compound comprising an amino acid sequence represented by formula (I)

His-Ser-Gln-Gly-Thr-Phe-Thr-Ser-Asp-$Xaa^{10}$-Ser-
$Xaa^{12}$-$Xaa^{13}$-Leu-$Xaa^{15}$-$Xaa^{16}$-$Xaa^{17}$-$Xaa^{18}$-
Ala-$Xaa^{20}$-$Xaa^{21}$-Phe-$Xaa^{23}$-$Xaa^{24}$-Trp-Leu-
Leu-Asn-$Xaa^{29}$-V (SEQ ID NO. 716)     (I)

wherein V is selected from the group consisting of His, His-$NH_2$, His-His, His-His-$NH_2$, Gly-His, Gly-His-$NH_2$, Lys-His, Lys-His-$NH_2$, Gly-His-His, Gly-His-His-$NH_2$, His-His-His and His-His-His-$NH_2$;

$Xaa^{10}$ is selected from the group consisting of Tyr and Leu;
$Xaa^{12}$ is selected from the group consisting of Lys, His and Arg;
$Xaa^{13}$ is selected from the group consisting of Tyr, Gln and His;
$Xaa^{15}$ is selected from the group consisting of Asp and Glu;
$Xaa^{16}$ is selected from the group consisting of Glu, Gln and Ser;
$Xaa^{17}$ is selected from the group consisting of Arg, His and Lys;
$Xaa^{18}$ is selected from the group consisting of Arg and Lys;
$Xaa^{20}$ is selected from the group consisting of His and Gln;
$Xaa^{21}$ is selected from the group consisting of Glu, His and Asp;
$Xaa^{23}$ is selected from the group consisting of Ile and Val;
$Xaa^{24}$ is selected from the group consisting of Gln and Glu; and
$Xaa^{29}$ is selected from the group consisting of Thr and Gly;
wherein —$NH_2$ represents a C-terminal amide group;
or a derivative of the compound;
or a salt of the compound or the derivative.

The amino acid sequence of formula (I) above is shown with the N-terminus to the top left and the C-terminus to the bottom right.

$Xaa^{10}$ is selected from the group consisting of Tyr and Leu. According to certain preferred embodiments, $Xaa^{10}$ is Tyr. According to other embodiments $Xaa^{10}$ is Leu.

$Xaa^{12}$ is selected from the group consisting of Lys, His and Arg. According to certain preferred embodiments $Xaa^{12}$ is Lys. According to other preferred embodiments $Xaa^{12}$ is His. According to other preferred embodiments $Xaa^{12}$ is Arg.

$Xaa^{13}$ is selected from the group consisting of Tyr, Gln and His. According to certain preferred embodiments, $Xaa^{13}$ is Tyr. According to other preferred embodiments $Xaa^{13}$ is His. According to other embodiments $Xaa^{13}$ is Gln. According to certain preferred embodiments $Xaa^{13}$ is selected from the group consisting of Tyr and His.

$Xaa^{15}$ is selected from the group consisting of Asp and Glu. According to certain preferred embodiments, $Xaa^{15}$ is Asp. According to other preferred embodiments $Xaa^{15}$ is Glu.

$Xaa^{16}$ is selected from the group consisting of Glu, Gln and Ser. According to certain preferred embodiments, $Xaa^{16}$ is Ser. According to other embodiments, $Xaa^{16}$ is Glu. According to other embodiments, $Xaa^{16}$ is Gln.

$Xaa^{17}$ is selected from the group consisting of Arg, His and Lys. According to certain preferred embodiments, $Xaa^{17}$ is Arg. According to other preferred embodiments $Xaa^{17}$ is Lys. According to other embodiments $Xaa^{17}$ is His. According to certain preferred embodiments $Xaa^{17}$ is selected from the group consisting of Arg and Lys.

$Xaa^{18}$ is selected from the group consisting of Arg and Lys. According to certain preferred embodiments, $Xaa^{18}$ is Arg. According to other preferred embodiments $Xaa^{18}$ is Lys.

$Xaa^{20}$ is selected from the group consisting of His and Gln. According to certain preferred embodiments, $Xaa^{20}$ is His. According to other embodiments, $Xaa^{20}$ is Gln.

$Xaa^{21}$ is selected from the group consisting of Glu, His and Asp. According to certain preferred embodiments $Xaa^{21}$ is Glu. According to other preferred embodiments $Xaa^{21}$ is Asp. According to other embodiments $Xaa^{21}$ is His. According to certain preferred embodiments $Xaa^{21}$ is selected from the group consisting of Glu and Asp.

$Xaa^{23}$ is selected from the group consisting of Ile and Val. According to certain preferred embodiments $Xaa^{23}$ is Val. According to other preferred embodiments $Xaa^{23}$ is Ile.

$Xaa^{24}$ is selected from the group consisting of Gln and Glu. According to certain preferred embodiments $Xaa^{24}$ is Gln. According to other preferred embodiments $Xaa^{24}$ is Glu.

$Xaa^{29}$ is selected from the group consisting of Thr and Gly. According to certain preferred embodiments $Xaa^{29}$ is Thr. According to other preferred embodiments $Xaa^{29}$ is Gly.

V is selected from the group consisting of His, His-$NH_2$, His-His, His-His-$NH_2$, Gly-His, Gly-His-$NH_2$, Lys-His, Lys-His-$NH_2$, Gly-His-His, Gly-His-His-$NH_2$, His-His-His and His-His-His-$NH_2$. According to certain preferred embodiments, V is His-His. According to other preferred embodiments, V is His-His-$NH_2$. According to other preferred embodiments, V is Gly-His. According to other preferred embodiments, V is Gly-His-$NH_2$. According to other embodiments, V is His. According to other embodiments, V is His-$NH_2$. According to other embodiments, V is Lys-His. According to other embodiments, V is Lys-His-$NH_2$. According to other embodiments, V is Gly-His-His. According to other embodiments, V is Gly-His-His-$NH_2$. According to other embodiments, V is His-His-His. According to other embodiments, V is His-His-His-$NH_2$. According to certain preferred embodiments, V is selected from the group consisting of His, His-$NH_2$, His-His, His-His-$NH_2$, Gly-His, and Gly-His-$NH_2$. More preferably, V is selected from the group consisting of His-His, His-His-NH$_2$, Gly-His and Gly-His-NH$_2$. In certain embodiments, V is not His-NH$_2$.

Where V is His-NH$_2$, His-His-NH$_2$, Lys-His-NH$_2$ or Gly-His-NH$_2$, the group —NH$_2$ denotes the presence of a —C(O)NH$_2$ group at the C-terminus (in place of a carboxylic acid group). In certain embodiments, the analogue is a compound which has a C-terminal amide group (i.e. —C(O)NH$_2$), or a derivative of such a compound, or a salt of such a compound or such a derivative.

In one preferred group of glucagon analogues of the invention, Xaa$^{10}$ is Tyr and Xaa$^{16}$ is Ser. In another preferred group of glucagon analogues of the invention, Xaa$^{10}$ is Tyr and Xaa$^{20}$ is His. In another preferred group of glucagon analogues of the invention, Xaa$^{16}$ is Ser and Xaa$^{20}$ is His.

In one preferred group of glucagon analogues of the invention, Xaa$^{10}$ is Tyr, Xaa$^{16}$ is Ser and Xaa$^{20}$ is His.

In one preferred group of glucagon analogues of the invention, Xaa$^{10}$ is Tyr, Xaa$^{16}$ is Ser, and V is selected from the group consisting of His-His, His-His-NH$_2$, Gly-His and Gly-His-NH$_2$. In another preferred group of glucagon analogues of the invention, Xaa$^{10}$ is Tyr, Xaa$^{20}$ is His, and V is selected from the group consisting of His-His, His-His-NH$_2$, Gly-His and Gly-His-NH$_2$. In another preferred group of glucagon analogues of the invention, Xaa$^{16}$ is Ser, Xaa$^{20}$ is His, and V is selected from the group consisting of His-His, His-His-NH$_2$, Gly-His and Gly-His-NH$_2$.

In one preferred group of glucagon analogues of the invention, Xaa$^{10}$ is Tyr, Xaa$^{16}$ is Ser, Xaa$^{20}$ is His, and V is selected from the group consisting of His-His, His-His-NH$_2$, Gly-His and Gly-His-NH$_2$.

In one preferred group of glucagon analogues of the invention, Xaa$^{13}$ is Tyr and/or Xaa$^{15}$ is Asp and/or Xaa$^{17}$ is Arg and/or Xaa$^{18}$ is Arg and/or Xaa$^{21}$ is Glu and/or Xaa$^{23}$ is Val. In one embodiment, Xaa$^{13}$ is Tyr and Xaa$^{15}$ is Asp. In another embodiment Xaa$^{13}$ is Tyr and Xaa$^{17}$ is Arg. In another embodiment Xaa$^{13}$ is Tyr and Xaa$^{18}$ is Arg. In another embodiment Xaa$^{13}$ is Tyr and Xaa$^{21}$ is Glu. In another embodiment Xaa$^{13}$ is Tyr and Xaa$^{23}$ is Val. In another embodiment Xaa$^{15}$ is Asp and Xaa$^{17}$ is Arg. In another embodiment Xaa$^{15}$ is Asp and Xaa$^{18}$ is Arg. In another embodiment Xaa$^{15}$ is Asp and Xaa$^{21}$ is Glu. In another embodiment Xaa$^{15}$ is Asp and Xaa$^{23}$ is Val. In another embodiment Xaa$^{17}$ is Arg and Xaa$^{18}$ is Arg. In another embodiment Xaa$^{17}$ is Arg and Xaa$^{21}$ is Glu. In another embodiment Xaa$^{17}$ is Arg and Xaa$^{23}$ is Val. In another embodiment Xaa$^{18}$ is Arg and Xaa$^{21}$ is Glu. In another embodiment Xaa$^{18}$ is Arg and Xaa$^{23}$ is Val. In another embodiment Xaa$^{21}$ is Glu and Xaa$^{23}$ is Val.

In one preferred group of glucagon analogues of the invention, Xaa$^{10}$ is Tyr, Xaa$^{12}$ is Lys, Xaa$^{16}$ is Ser and Xaa$^{20}$ is His. In another preferred group of glucagon analogues of the invention, Xaa$^{10}$ is Tyr, Xaa$^{12}$ is Arg, Xaa$^{16}$ is Ser and Xaa$^{20}$ is His. In another preferred group of glucagon analogues of the invention, Xaa$^{10}$ is Tyr, Xaa$^{12}$ is His, Xaa$^{16}$ is Ser and Xaa$^{20}$ is His.

In one preferred group of glucagon analogues of the invention, Xaa$^{10}$ is Tyr, Xaa$^{13}$ is Tyr, Xaa$^{16}$ is Ser and Xaa$^{20}$ is His. In another preferred group of glucagon analogues of the invention, Xaa$^{10}$ is Tyr, Xaa$^{13}$ is His, Xaa$^{16}$ is Ser and Xaa$^{20}$ is His.

In one preferred group of glucagon analogues of the invention, Xaa$^{10}$ is Tyr, Xaa$^{15}$ is Asp, Xaa$^{16}$ is Ser and Xaa$^{20}$ is His. In another preferred group of glucagon analogues of the invention, Xaa$^{10}$ is Tyr, Xaa$^{15}$ is Glu, Xaa$^{16}$ is Ser and Xaa$^{20}$ is His.

In one preferred group of glucagon analogues of the invention, Xaa$^{10}$ is Tyr, Xaa$^{16}$ is Ser, Xaa$^{17}$ is Arg and Xaa$^{20}$ is His. In another preferred group of glucagon analogues of the invention, Xaa$^{10}$ is Tyr, Xaa$^{16}$ is Ser, Xaa$^{17}$ is Lys and Xaa$^{20}$ is His.

In one preferred group of glucagon analogues of the invention, Xaa$^{10}$ is Tyr, Xaa$^{16}$ is Ser, Xaa$^{18}$ is Arg and Xaa$^{20}$ is His. In another preferred group of glucagon analogues of the invention, Xaa$^{10}$ is Tyr, Xaa$^{16}$ is Ser, Xaa$^{18}$ is Lys and Xaa$^{20}$ is His.

In one preferred group of glucagon analogues of the invention, Xaa$^{10}$ is Tyr, Xaa$^{16}$ is Ser, Xaa$^{20}$ is His and Xaa$^{21}$ is Glu. In another preferred group of glucagon analogues of the invention, Xaa$^{10}$ is Tyr, Xaa$^{16}$ is Ser, Xaa$^{20}$ is His and Xaa$^{21}$ is Asp.

In one preferred group of glucagon analogues of the invention, Xaa$^{10}$ is Tyr, Xaa$^{16}$ is Ser, Xaa$^{20}$ is His and Xaa$^{23}$ is Val. In another preferred group of glucagon analogues of the invention, Xaa$^{10}$ is Tyr, Xaa$^{16}$ is Ser, Xaa$^{20}$ is His and Xaa$^{23}$ is Ile.

In one preferred group of glucagon analogues of the invention, Xaa$^{10}$ is Tyr, Xaa$^{16}$ is Ser, Xaa$^{20}$ is His and Xaa$^{24}$ is Gln. In another preferred group of glucagon analogues of the invention, Xaa$^{10}$ is Tyr, Xaa$^{16}$ is Ser, Xaa$^{20}$ is His and Xaa$^{24}$ is Glu.

In one preferred group of glucagon analogues of the invention, Xaa$^{10}$ is Tyr, Xaa$^{16}$ is Ser, Xaa$^{20}$ is His and Xaa$^{29}$ is Thr. In another preferred group of glucagon analogues of the invention, Xaa$^{10}$ is Tyr, Xaa$^{16}$ is Ser, Xaa$^{20}$ is His and Xaa$^{29}$ is Gly.

In one preferred group of glucagon analogues of the invention, Xaa$^{10}$ is Tyr, Xaa$^{13}$ is Tyr, Xaa$^{15}$ is Asp, Xaa$^{16}$ is Ser and Xaa$^{20}$ is His. In another preferred group of glucagon analogues of the invention, Xaa$^{10}$ is Tyr, Xaa$^{13}$ is Tyr, Xaa$^{16}$ is Ser, Xaa$^{17}$ is Arg and Xaa$^{20}$ is His. In another preferred group of glucagon analogues of the invention, Xaa$^{10}$ is Tyr, Xaa$^{13}$ is Tyr, Xaa$^{16}$ is Ser, Xaa$^{18}$ is Arg and Xaa$^{20}$ is His. In another preferred group of glucagon analogues of the invention, Xaa$^{10}$ is Tyr, Xaa$^{13}$ is Tyr, Xaa$^{16}$ is Ser, Xaa$^{20}$ is His and Xaa$^{21}$ is Glu. In another preferred group of glucagon analogues of the invention, Xaa$^{10}$ is Tyr, Xaa$^{13}$ is Tyr, Xaa$^{16}$ is Ser, Xaa$^{20}$ is His and Xaa$^{23}$ is Val. In another preferred group of glucagon analogues of the invention, Xaa$^{10}$ is Tyr, Xaa$^{15}$ is Asp, Xaa$^{16}$ is Ser, Xaa$^{17}$ is Arg and Xaa$^{20}$ is His. In another preferred group of glucagon analogues of the invention, Xaa$^{10}$ is Tyr, Xaa$^{15}$ is Asp, Xaa$^{16}$ is Ser, Xaa$^{18}$ is Arg and Xaa$^{20}$ is His. In another preferred group of glucagon analogues of the invention, Xaa$^{10}$ is Tyr, Xaa$^{15}$ is Asp, Xaa$^{16}$ is Ser, Xaa$^{20}$ is His and Xaa$^{21}$ is Glu. In another preferred group of glucagon analogues of the invention, Xaa$^{10}$ is Tyr, Xaa$^{15}$ is Asp, Xaa$^{16}$ is Ser, Xaa$^{20}$ is His and Xaa$^{23}$ is Val. In another preferred group of glucagon analogues of the invention, Xaa$^{10}$ is Tyr, Xaa$^{16}$ is Ser, Xaa$^{17}$ is Arg, Xaa$^{18}$ is Arg and Xaa$^{20}$ is His. In another preferred group of glucagon analogues of the invention, Xaa$^{10}$ is Tyr, Xaa$^{16}$ is Ser, Xaa$^{17}$ is Arg, Xaa$^{20}$ is His and Xaa$^{21}$ is Glu. In another preferred group of glucagon analogues of the invention, Xaa$^{10}$ is Tyr, Xaa$^{16}$ is Ser, Xaa$^{17}$ is Arg, Xaa$^{20}$ is His and Xaa$^{23}$ is Val. In another preferred group of glucagon analogues of the invention, Xaa$^{10}$ is Tyr, Xaa$^{16}$ is Ser, Xaa$^{18}$ is Arg, Xaa$^{20}$ is His and Xaa$^{21}$ is Glu. In another preferred group of glucagon analogues of the invention, Xaa$^{10}$ is Tyr, Xaa$^{16}$ is Ser, Xaa$^{18}$ is Arg, Xaa$^{20}$ is His and Xaa$^{23}$ is Val. In another preferred group of glucagon analogues of the invention, Xaa$^{10}$ is Tyr, Xaa$^{16}$ is Ser, Xaa$^{20}$ is His, Xaa$^{21}$ is Glu and Xaa$^{23}$ is Val.

In one preferred group of glucagon analogues of the invention, $Xaa^{10}$ is Tyr, $Xaa^{16}$ is Ser, $Xaa^{20}$ is His, $Xaa^{29}$ is Gly and V is selected from the group consisting of Gly-His and Gly-His-NH$_2$.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V is His-His.

In one preferred group of glucagon analogues of the invention, $Xaa^{10}$ is Tyr, $Xaa^{12}$ is Arg, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V is His-His-NH$_2$.

In one preferred group of glucagon analogues of the invention, $Xaa^{10}$ is Tyr, $Xaa^{12}$ is Arg, $Xaa^{13}$ is His, $Xaa^{15}$ is Asp, $Xaa^{16}$ is Ser, $Xaa^{17}$ is Lys, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V is His-His-NH$_2$.

In one preferred group of glucagon analogues of the invention, $Xaa^{10}$ is Tyr, $Xaa^{12}$ is Arg, $Xaa^{13}$ is Tyr, $Xaa^{15}$ is Asp, $Xaa^{16}$ is Ser, $Xaa^{17}$ is Lys, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V is Gly-His.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V is Gly-His.

In one preferred group of glucagon analogues of the invention, $Xaa^{10}$ is Tyr, $Xaa^{12}$ is Lys, $Xaa^{13}$ is Tyr, $Xaa^{15}$ is Glu, $Xaa^{16}$ is Ser, $Xaa^{17}$ is Arg, $Xaa^{18}$ is Lys, $Xaa^{20}$ is His, $Xaa^{21}$ is Glu, $Xaa^{23}$ is Ile, $Xaa^{24}$ is Glu, $Xaa^{29}$ is Thr and V is Gly-His.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Thr and V is Gly-His.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Gly and V is Gly-His-NH$_2$.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Asp, $Xaa^{23}$ is Val, $Xaa^{24}$ is Glu, $Xaa^{29}$ is Thr and V is His-His-NH$_2$.

In one preferred group of glucagon analogues of the invention, $Xaa^{10}$ is Tyr, $Xaa^{12}$ is His, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V is Gly-His-NH$_2$.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu and $Xaa^{23}$ is Val.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu and $Xaa^{23}$ is Val.

In one preferred group of glucagon analogues of the invention, $Xaa^{10}$ is Tyr, $Xaa^{12}$ is Arg, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu and $Xaa^{23}$ is Val.

In one preferred group of glucagon analogues of the invention, $Xaa^{10}$ is Tyr, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu and $Xaa^{23}$ is Val.

In one preferred group of glucagon analogues of the invention, $Xaa^{10}$ is Tyr, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu and $Xaa^{23}$ is Val.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{24}$ is Gln.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{24}$ is Glu.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{29}$ is Gly.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{29}$ is Thr.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V is His-His.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V is Gly-His.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V is His.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V is His-NH$_2$.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V is His-His-NH$_2$.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V is Gly-His-NH$_2$.

In one preferred group of glucagon analogues of the invention, $Xaa^{10}$ is Tyr, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{24}$ is Gln and $Xaa^{23}$ is Val.

In one preferred group of glucagon analogues of the invention, $Xaa^{10}$ is Tyr, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu, $Xaa^{24}$ is Glu and $Xaa^{23}$ is Val.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V is His-His.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V is Gly-His.

In one preferred group of glucagon analogues of the invention, Xaa$^{10}$ is Tyr, Xaa$^{12}$ is Lys, Xaa$^{13}$ is Tyr, Xaa$^{15}$ is Asp, Xaa$^{16}$ is Glu, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Glu, Xaa$^{29}$ is Gly and V is Gly-His.

In one preferred group of glucagon analogues of the invention, Xaa$^{10}$ is Tyr, Xaa$^{12}$ is Arg, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Thr and V is His-His.

In one preferred group of glucagon analogues of the invention, Xaa$^{10}$ is Tyr, Xaa$^{12}$ is Lys, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Thr and V is His-His-NH$_2$.

In one preferred group of glucagon analogues of the invention, Xaa$^{10}$ is Tyr, Xaa$^{12}$ is Arg, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Thr and V is His-His-NH$_2$.

In one preferred group of glucagon analogues of the invention, Xaa$^{10}$ is Tyr, Xaa$^{12}$ is Lys, Xaa$^{13}$ is Tyr, Xaa$^{15}$ is Asp, Xaa$^{16}$ is Glu, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Glu, Xaa$^{29}$ is Thr and V is His-NH$_2$.

In one preferred group of glucagon analogues of the invention, Xaa$^{10}$ is Tyr, Xaa$^{12}$ is Lys, Xaa$^{13}$ is Tyr, Xaa$^{15}$ is Asp, Xaa$^{16}$ is Glu, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Glu, Xaa$^{29}$ is Gly and V is His-NH$_2$.

In one preferred group of glucagon analogues of the invention, Xaa$^{10}$ is Tyr, Xaa$^{12}$ is His, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Glu, Xaa$^{29}$ is Gly and V is Gly-His-NH$_2$.

In one preferred group of glucagon analogues of the invention, Xaa$^{10}$ is Tyr, Xaa$^{12}$ is His, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Gly and V is Gly-His-NH$_2$.

According to certain embodiments, where Xaa$^{12}$ is Lys, Xaa$^{13}$ is not His. According to certain embodiments, where Xaa$^{13}$ is His, Xaa$^{17}$ is not His.

Glucagon analogues of the invention include, but are not limited to, the compounds set out in FIG. 1 or any of the relevant Examples, or a derivative of such a compound, or a salt of such a compound or such a derivative.

The glucagon analogues of the invention have amino acid sequences that differ from the sequence of native glucagon in that they contain a His residue at position 30 and/or position 31. The glucagon analogues may comprise an amino acid sequence having additional changes compared with the native glucagon sequence. For example the glucagon analogues of the invention may contain 1, 2, 3, 4, 5, 6, 7, 8, 9, 10, 11 or 12 amino acid residues that are substitutions of amino acid residues present in the native glucagon sequence. Preferably the glucagon analogues of the invention contain up to 7 amino acid residues that are substitutions of amino acid residues present in the native glucagon sequence, more preferably from 3 to 7 amino acid residues that are substitutions of amino acid residues present in the native glucagon sequence.

According to certain preferred embodiments, the glucagon analogue is a compound consisting of an amino acid sequence represented by formula (I), or a derivative of the compound, or a salt of the compound or the derivative. The preferences for amino acid residues and combinations of amino acid residues set out above are also preferred for such glucagon analogues. In certain embodiments, the glucagon analogue is a compound consisting of an amino acid sequence represented by formula (I). In certain embodiments, the glucagon analogue is a derivative of such a compound. In certain embodiments, the glucagon analogue is a salt of such a compound or derivative.

Glucagon analogues of the invention may be produced by recombinant methods well known in the art or alternatively they may be produced by synthetic methods, again well known in the art.

GLP1 Analogues

According to a further aspect of the invention, there is provided an analogue of GLP1 which is:
a compound comprising an amino acid sequence represented by formula (II)

His-Xaa$^2$-Xaa$^3$-Gly-Thr-Phe-Thr-Ser-Asp-Xaa$^{10}$-Ser-Xaa$^{12}$-Xaa$^{13}$-Leu-Glu-Xaa$^{16}$-Xaa$^{17}$-Ala-Xaa$^{19}$-Xaa$^{20}$-Xaa$^{21}$-Phe-Xaa$^{23}$-Xaa$^{24}$-Trp-Leu-Xaa$^{27}$-Xaa$^{28}$-Xaa$^{29}$-V                    (II)

wherein V is selected from the group consisting of His, His-NH$_2$, His-His,
His-His-NH$_2$, Gly-His, Gly-His-NH$_2$, Lys-His and Lys-His-NH$_2$;
Xaa$^2$ is selected from the group consisting of Ser and Gly;
Xaa$^3$ is selected from the group consisting of Glu and Gln;
Xaa$^{10}$ is selected from the group consisting of Tyr and Leu;
Xaa$^{12}$ is selected from the group consisting of Lys and His;
Xaa$^{13}$ is selected from the group consisting of Tyr and Gln;
Xaa$^{16}$ is selected from the group consisting of Glu, Ala and Ser;
Xaa$^{17}$ is selected from the group consisting of Gln and Glu;
Xaa$^{19}$ is selected from the group consisting of Val, Ala, Ile and Leu;
Xaa$^{20}$ is selected from the group consisting of Arg and His;
Xaa$^{21}$ is selected from the group consisting of Ile and Leu;
Xaa$^{23}$ is selected from the group consisting of Ile and Val;
Xaa$^{24}$ is selected from the group consisting of Glu and Gln;
Xaa$^{27}$ is selected from the group consisting of Leu and Lys;
Xaa$^{28}$ is selected from the group consisting of Asn, Lys and Gln; and
Xaa$^{29}$ is selected from the group consisting of Gly and Thr;
wherein —NH$_2$ represents a C-terminal amide group;
wherein the compound is not analogue nos. 428, 429, or 431-439, or 441-458; and optionally wherein the compound is not analogue no. 440;
or a derivative of the compound;
or a salt of the compound or the derivative.

The amino acid sequence of formula (II) above is shown with the N-terminus to the top left and the C-terminus to the bottom right.

Xaa$^2$ is selected from the group consisting of Ser and Gly. According to certain preferred embodiments Xaa$^2$ is Ser. According to other preferred embodiments Xaa$^2$ is Gly.

Xaa$^3$ is selected from the group consisting of Glu and Gln. According to certain preferred embodiments Xaa$^3$ is Glu. According to other preferred embodiments Xaa$^3$ is Gln.

Xaa$^{10}$ is selected from the group consisting of Tyr and Leu. According to certain preferred embodiments Xaa$^{10}$ is Tyr. According to other preferred embodiments Xaa$^{10}$ is Leu.

Xaa$^{12}$ is selected from the group consisting of Lys and His. According to certain preferred embodiments Xaa$^{12}$ is Lys. According to other preferred embodiments Xaa$^{12}$ is His.

Xaa$^{13}$ is selected from the group consisting of Tyr and Gln. According to certain preferred embodiments Xaa$^{13}$ is Tyr. According to other preferred embodiments Xaa$^{13}$ is Gln.

Xaa$^{16}$ is selected from the group consisting of Glu, Ala and Ser. According to certain preferred embodiments, Xaa$^{16}$ is Glu. According to other preferred embodiments Xaa$^{16}$ is Ala. According to other embodiments Xaa$^{16}$ is Ser. According to certain preferred embodiments Xaa$^{16}$ is selected from the group consisting of Glu and Ala.

Xaa$^{17}$ is selected from the group consisting of Gln and Glu. According to certain preferred embodiments, Xaa$^{17}$ is Gln. According to other preferred embodiments Xaa$^{17}$ is Glu.

Xaa$^{19}$ is selected from the group consisting of Val, Ala, Ile and Leu. According to certain preferred embodiments Xaa$^{19}$ is Val. According to other preferred embodiments, Xaa$^{19}$ is Leu. According to other embodiments Xaa$^{19}$ is Ile. According to other embodiments Xaa$^{19}$ is Ala. According to certain preferred embodiments Xaa$^{19}$ is selected from the group consisting of Val and Leu.

Xaa$^{20}$ is selected from the group consisting of Arg and His. According to certain preferred embodiments Xaa$^{20}$ is Arg. According to other preferred embodiments Xaa$^{20}$ is His.

Xaa$^{21}$ is selected from the group consisting of Ile and Leu. According to certain preferred embodiments Xaa$^{21}$ is Ile. According to other preferred embodiments Xaa$^{21}$ is Leu.

Xaa$^{23}$ is selected from the group consisting of Ile and Val. According to certain preferred embodiments Xaa$^{23}$ is Ile. According to other embodiments Xaa$^{23}$ is Val.

Xaa$^{24}$ is selected from the group consisting of Gln and Glu. According to certain preferred embodiments Xaa$^{24}$ is Gln. According to other preferred embodiments Xaa$^{24}$ is Glu.

Xaa$^{27}$ is selected from the group consisting of Leu and Lys. According to certain preferred embodiments Xaa$^{27}$ is Leu. According to other preferred embodiments Xaa$^{27}$ is Lys.

Xaa$^{28}$ is selected from the group consisting of Asn, Lys and Gln. According to certain preferred embodiments Xaa$^{28}$ is Asn. According to other embodiments Xaa$^{28}$ is Gln. According to other embodiments Xaa$^{28}$ is Lys.

Xaa$^{29}$ is selected from the group consisting of Gly and Thr. According to certain preferred embodiments Xaa$^{29}$ is Gly. According to other embodiments Xaa$^{29}$ is Thr.

V is selected from the group consisting of His, His-NH$_2$, His-His, His-His-NH$_2$, Gly-His, Gly-His-NH$_2$, Lys-His and Lys-His-NH$_2$. According to certain preferred embodiments, V is His-His. According to other preferred embodiments, V is His-His-NH$_2$. According to other preferred embodiments, V is Gly-His-NH$_2$. According to other embodiments, V is His. According to other embodiments, V is His-NH$_2$. According to other embodiments, V is Gly-His. According to certain preferred embodiments, V is selected from the group consisting of His, His-NH$_2$, His-His, His-His-NH$_2$, Gly-His, and Gly-His-NH$_2$. More preferably, V is selected from the group consisting of His-His, His-His-NH$_2$ and Gly-His-NH$_2$. In certain embodiments, V is not His-NH$_2$.

Where V is His-NH$_2$, His-His-NH$_2$, Lys-His-NH$_2$ or Gly-His-NH$_2$, the group —NH$_2$ denotes the presence of a —C(O)NH$_2$ group at the C-terminus (in place of a carboxylic acid group). In certain embodiments, the analogue is a compound which has a C-terminal amide group (i.e. —C(O)NH$_2$), or a derivative of such a compound, or a salt of such a compound or such a derivative.

In one preferred group of GLP1 analogues of the invention, Xaa$^{12}$ is Lys, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{2}$ is Ser, Xaa$^{12}$ is Lys, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{2}$ is Gly, Xaa$^{12}$ is Lys, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{13}$ is Tyr, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{13}$ is Gln, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{16}$ is Glu, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{16}$ is Ala, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{16}$ is Ser, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{19}$ is Val, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{19}$ is Ala, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{19}$ is Ile, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{19}$ is Leu, Xaa$^{20}$ is Arg, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{20}$ is Arg, Xaa$^{21}$ is Ile, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{20}$ is Arg, Xaa$^{21}$ is Leu, Xaa$^{23}$ is Ile, Xaa$^{28}$ is Asn and Xaa$^{29}$ is Gly.

In one preferred group of GLP1 analogues of the invention, Xaa$^{12}$ is Lys, Xaa$^{20}$ is Arg, Xaa$^{23}$ is Ile, Xaa$^{27}$ is Leu, Xaa$^{28}$ is Asn and Xaa$^{29}$ is Gly.

In one preferred group of GLP1 analogues of the invention, Xaa$^{12}$ is Lys, Xaa$^{20}$ is Arg, Xaa$^{23}$ is Ile, Xaa$^{27}$ is Lys, Xaa$^{28}$ is Asn and Xaa$^{29}$ is Gly.

In one preferred group of GLP1 analogues of the invention, Xaa$^{12}$ is Lys, Xaa$^{20}$ is Arg, Xaa$^{23}$ is Ile, Xaa$^{28}$ is Asn, Xaa$^{29}$ is Gly and V is His-His.

In one preferred group of GLP1 analogues of the invention, Xaa$^{12}$ is Lys, Xaa$^{20}$ is Arg, Xaa$^{23}$ is Ile, Xaa$^{28}$ is Asn, Xaa$^{29}$ is Gly and V is His-His-NH$_2$.

In one preferred group of GLP1 analogues of the invention, Xaa$^{12}$ is Lys, Xaa$^{20}$ is Arg, Xaa$^{23}$ is Ile, Xaa$^{28}$ is Asn, Xaa$^{29}$ is Gly and V is Gly-His-NH$_2$.

In one preferred group of GLP1 analogues of the invention, Xaa$^{12}$ is Lys, Xaa$^{20}$ is Arg, Xaa$^{23}$ is Ile, Xaa$^{28}$ is Asn, Xaa$^{29}$ is Gly and V is His.

In one preferred group of GLP1 analogues of the invention, $Xaa^{12}$ is Lys, $Xaa^{20}$ is Arg, $Xaa^{23}$ is Ile, $Xaa^{28}$ is Asn, $Xaa^{29}$ is Gly and V is His-NH$_2$.

In one preferred group of GLP1 analogues of the invention, $Xaa^{12}$ is Lys, $Xaa^{20}$ is Arg, $Xaa^{23}$ is Ile, $Xaa^{28}$ is Asn, $Xaa^{29}$ is Gly and V is Gly-His.

In one preferred group of GLP1 analogues of the invention, $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is His-His-NH$_2$.

In one preferred group of GLP1 analogues of the invention, $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is His-His.

In one preferred group of GLP1 analogues of the invention, $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V is His-His-NH$_2$.

In one preferred group of GLP1 analogues of the invention, $Xaa^2$ is Ser, $Xaa^3$ is Glu, $Xaa^{10}$ is Leu, $Xaa^{12}$ is Lys, $Xaa^{13}$ is Gln, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is His-His-NH$_2$.

In one preferred group of GLP1 analogues of the invention, $Xaa^2$ is Gly, $Xaa^3$ is Glu, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Leu, $Xaa^{23}$ is Ile, $Xaa^{24}$ is Glu, $Xaa^{27}$ is Leu, $Xaa^{28}$ is Asn, $Xaa^{29}$ is Gly and V is His-His.

In one preferred group of GLP1 analogues of the invention, $Xaa^2$ is Ser, $Xaa^3$ is Gln, $Xaa^{10}$ is Tyr, $Xaa^{12}$ is Lys, $Xaa^{13}$ is Tyr, $Xaa^{16}$ is Glu, $Xaa^{17}$ is Glu, $Xaa^{19}$ is Leu, $Xaa^{20}$ is Arg, $Xaa^{21}$ is Leu, $Xaa^{23}$ is Ile, $Xaa^{24}$ is Glu, $Xaa^{27}$ is Leu, $Xaa^{28}$ is Asn, $Xaa^{29}$ is Gly and V is Gly-His-NH$_2$.

In one preferred group of GLP1 analogues of the invention, $Xaa^2$ is Gly, $Xaa^3$ is Glu, $Xaa^{10}$ is Leu, $Xaa^{12}$ is Lys, $Xaa^{13}$ is Gln, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is Gly-His-NH$_2$.

In one preferred group of GLP1 analogues of the invention, $Xaa^2$ is Ser, $Xaa^3$ is Gln, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Leu, $Xaa^{23}$ is Ile, $Xaa^{24}$ is Glu, $Xaa^{27}$ is Lys, $Xaa^{28}$ is Asn, $Xaa^{29}$ is Gly and V is Gly-His-NH$_2$.

In one preferred group of GLP1 analogues of the invention, $Xaa^2$ is Gly, $Xaa^3$ is Gln, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V is Gly-His-NH$_2$.

In one preferred group of GLP1 analogues of the invention, $Xaa^2$ is Gly, $Xaa^3$ is Glu, $Xaa^{10}$ is Tyr, $Xaa^{12}$ is Lys, $Xaa^{13}$ is Tyr, $Xaa^{16}$ is Ala, $Xaa^{17}$ is Glu, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V is Gly-His-NH$_2$.

In one preferred group of GLP1 analogues of the invention, $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is Gly-His-NH$_2$.

In one preferred group of GLP1 analogues of the invention, $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is His-His.

GLP1 analogues of the invention may include, but are not limited to, the compounds set out in FIG. 2 or any of the relevant Examples, or a derivative of such a compound, or a salt of such a compound or such a derivative, with the exception that the GLP1 analogue is not analogue nos. 428, 429, 431-439 or 441 to 458 (G nos. G417, G418, G454, G488, G489, G490, G495, G504, G509, G512, G514, G536, G537, G538, G539, G540, G541, G543, G544, G545, G546, G547, G550, G557, G559, G560, G561, G562, and G563), or a derivative of such a compound, or a salt of such a compound or such a derivative. In certain embodiments, the GLP1 analogue is also not analogue no. 440 (G535).

It will be appreciated that GLP1 analogues of the invention comprise an amino acid sequence combining multiple changes from the native GLP1 sequence, those multiple changes preferably being those presented above as preferred.

According to certain preferred embodiments, the GLP1 analogue is a compound consisting of an amino acid sequence represented by formula (II), or a derivative of the compound, or a salt of the compound or the derivative. The preferences for amino acid residues and combinations of amino acid residues set out above are also preferred for such GLP1 analogues. In certain embodiments, the GLP1 analogue is a compound consisting of an amino acid sequence represented by formula (II). In certain embodiments, the GLP1 analogue is a derivative of such a compound. In certain embodiments, the GLP1 analogue is a salt of such a compound or derivative.

GLP1 analogues of the invention may be produced by recombinant methods well known in the art or alternatively they may be produced by synthetic methods, again well known in the art.

Derivatives

An analogue of the invention may comprise the structure of formula (I) or formula (II) modified by well-known processes including amidation, glycosylation, carbamylation, acylation, for example acetylation, sulfation, phosphorylation, cyclization, lipidization and PEGylation. The structure of formula (I) or formula (II) may be modified at random positions within the molecule, or at predetermined positions within the molecule and may include one, two, three or more attached chemical moieties.

An analogue of the invention may be a fusion protein, whereby the structure of formula (I) or formula (II) is fused to another protein or polypeptide (the fusion partner) using recombinant methods known in the art. Alternatively, such a fusion protein may be synthetically synthesized by any known method. Such a fusion protein comprises the structure of formula (I) or formula (II). Any suitable peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers D-D-D-D-Y, G-P-R, A-G-G and H-P-F-H-L, which can be cleaved by enterokinase, thrombin, ubiquitin cleaving enzyme and renin, respectively. See, e.g., U.S. Pat. No. 6,410,707, the contents of which are incorporated herein by reference.

An analogue of the invention may be a physiologically functional derivative of the structure of formula (I) or formula (II). The term "physiologically functional derivative" is used herein to denote a chemical derivative of a compound of formula (I) or formula (II) having the same physiological function as the corresponding unmodified compound of formula (I) or formula (II). For example, a physiologically functionally derivative may be convertible in the body to a compound of formula (I) or formula (II). According to the present invention, examples of physiologically functional derivatives include esters, amides, and carbamates; preferably esters and amides.

Pharmaceutically acceptable esters and amides of the compounds of the invention may comprise a $C_{1-20}$ alkyl-, $C_{2-20}$ alkenyl-, $C_{5-10}$ aryl-, $C_{5-10}$ ar-$C_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H_{29}$) or stearyl ($C_{17}H_{35}$)) and bile acids (e.g. cholate or deoxycholate).

Methods for lipidization of sulfhydryl-containing compounds with fatty acid derivatives are disclosed in U.S. Pat. No. 5,936,092; U.S. Pat. No. 6,093,692; and U.S. Pat. No. 6,225,445, the contents of which are incorporated herein by reference. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in a lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H_{29}$) or stearyl ($C_{17}H_{35}$)) and bile acids (e.g. cholate or deoxycholate).

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

An analogue of the invention may be a PEGylated structure of formula (I) or formula (II). PEGylated compounds of the invention may provide additional advantages such as increased solubility, stability and circulating time of the polypeptide, or decreased immunogenicity (see U.S. Pat. No. 4,179,337, the contents of which are incorporated herein by reference).

Chemical moieties for derivitization of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any, on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In certain embodiments, the glucagon analogue of the invention is not a derivative. In certain embodiments, the GLP-1 analogue of the invention is not a derivative.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". It will be understood by the skilled person that the invention also encompasses solvates of the compounds of formula (I) and formula (II), of derivatives of the compounds, and of salts of the compounds and derivatives.

Salts of compounds of formula (I) and formula (II) which are suitable for use in medicine are those wherein a counterion is pharmaceutically acceptable. However, salts having non-pharmaceutically acceptable counterions are within the scope of the present invention, for example, for use as intermediates in the preparation of the compounds of formula (I) and formula (II) and pharmaceutically acceptable salts and/or derivatives thereof.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycolic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Biological Activity—Glucagon Analogues

The glucagon analogues of the invention are active at the human glucagon receptor, and are glucagon receptor agonists. This may be assessed by, for example, an in vitro or cellular binding assay or by a reporter assay. Preferably, the glucagon analogues show binding to the human glucagon receptor with an affinity of at least $1/200,000^{th}$, $1/20,000^{th}$, $1/10,000^{th}$, $1/5,000^{th}$, $1/1,1000^{th}$ or $1/400^{th}$ of the affinity of human glucagon. More preferably, the analogues show affinity similar to that of human glucagon. Still more preferably, glucagon analogues of the invention show binding to the human glucagon-receptor with an affinity of at least 2-fold, 5-fold, 10-fold the binding affinity of human glucagon. Methods of assessing activity of analogues at the glucagon receptor are well known. For example, Thermo Scientific (Lafayette, Colo., USA) market an in vitro glucagon receptor assay. The activity of the glucagon analogues of the invention at the glucagon receptor is preferably longer lasting in vivo than native glucagon.

Preferably, the glucagon analogues of the invention fulfil some or more preferably all, of the following criteria.
1) Sustained bioactivity at the human glucagon receptor resulting in enhancement of energy expenditure.
2) High solubility in aqueous solution at pH 5 to allow an effective dose to be administered in a low volume injection (thereby resulting in lower pain of injection). Solubility may be easily assessed by simple in vitro tests.
3) Long period of activity in vivo (as assessed in humans or an animal model) so as to permit injections no more frequently than daily and preferably no more than twice, or more preferably no more than once a week, whilst still producing acceptable therapeutic or cosmetic benefits.
4) Good weight loss (as assessed in human subjects or an animal model).
5) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm ((Jameson & Wolf (1988) Comput. Appl. Biosci. 4(1): 181-6), or the PREDITOP algorithm (Pellequer & Westhof, (1993) J. Mol. Graph. 11(3):204-10, or using the methods of Kolaskar & Tongankar (1990) FEBS Leu. 10:276(1-2):172-4, the contents of which are incorporated herein by reference).

In addition to having activity at the glucagon receptor, glucagon analogues of the invention may also have activity at the glucagon-like peptide 1 (GLP1) receptor. In other words, analogues of the invention may be GLP-1 receptor agonists as well as glucagon receptor agonists. GLP-1 is derived from the transcription product of the proglucagon gene. The biologically active forms of GLP1 are truncated forms known as GLP-1$_{(7-37)}$ and GLP-1$_{(7-36)}$-NH$_2$. GLP-1 is produced in vivo in the intestinal L cell in response to the presence of nutrients in the lumen of the gut. Once in the circulation, native GLP-1 has a half-life of only a few minutes in humans due to rapid degradation by the enzyme dipeptidyl peptidase. GLP-1 possesses a number of physiological functions including increasing insulin secretion from the pancreas in a glucose-dependent manner, decreasing glucagon secretion from the pancreas, inhibiting gastric emptying and decreasing food intake by increasing satiety. Increased insulin secretion leads to a decrease in circulating glucose concentration.

Biological Activity—GLP1 Analogues

The GLP1 analogues of the invention are active at the human GLP1 receptor, and are GLP1 receptor agonists. This may be assessed by, for example, an in vitro or cellular binding assay or by a reporter assay. Preferably, the GLP1 analogues show binding to the human GLP1 receptor with an affinity of at least $1/20,000^{th}$, $1/10,000^{th}$, $1/5,000^{th}$, $1/1,1000^{th}$ or $1/400^{th}$ of the affinity of human GLP1. More preferably, the analogues show affinity similar to that of human GLP1. Still more preferably, GLP1 analogues of the invention show binding to the human GLP1 receptor with an affinity of at least 2-fold, 5-fold, 10-fold of the binding affinity of human GLP1 (i.e. in those embodiments the analogues have a greater affinity for the human GLP1 receptor than human GLP1). Methods of assessing activity of analogues at the GLP1 receptor are well known. For example, Mukai et al (2009) Biochem. Biophys. Re. Comm. 28993:523-6 discloses a method of assaying for GLP1 receptor binding. The activity of the GLP1 analogues of the invention at the GLP1 receptor is preferably longer lasting in vivo than native GLP1.

GLP1 analogues according to the present invention preferably have a more sustained effect on food intake reduction or have a stronger effect on food intake reduction than human GLP1. Preferably they have an effect on food intake reduction which is at least as strong as native human GLP1 but which is more sustained. Increased duration of appetite suppression can be particularly important to avoid the effect known as "escape". A short duration of appetite suppressant may reduce appetite or the time covered by one meal and in that meal the subject typically eats less food. If, however, the appetite suppressant is then metabolized or otherwise removed from circulation then by the time of the next meal the subject can regain its "normal" appetite. In view of the subject having eaten a small meal at the previous mealtime, the subject may in fact have an increased appetite at the time of the second meal. If the subject satisfies that appetite it is possible for the food intake over the two meals in total to be no lower than the food intake would have been without the appetite suppressant. That is to say, the subject may have "escaped" from the effects of the appetite suppressant. "Escape" can be reduced by using additional doses of appetite suppressant or by using an appetite suppressant with a longer duration of action. If the subject has a reduced appetite for longer, then the degree to which it can make up the deficit from one meal in the next meal is reduced as there is a practical limit to total capacity in a particular single meal.

Preferably, the GLP1 analogues of the invention fulfil some or more preferably all, of the following criteria.
1) Sustained bioactivity at the human GLP1 receptor resulting in inhibition of appetite.
2) High solubility in aqueous solution at pH 5 to allow an effective dose to be administered in a low volume injection (thereby resulting in lower pain of injection). Solubility may be easily assessed by simple in vitro tests.
3) Long period of activity in vivo (as assessed in humans or an animal model) so as to permit injections no more frequently than daily and preferably no more than twice, or more preferably no more than once a week, whilst still producing acceptable therapeutic or cosmetic benefits.
4) Good weight loss or appetite suppression (as assessed in human subjects or an animal model).
5) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm ((Jameson & Wolf (1988) Comput. Appl. Biosci. 4(1): 181-6), or the PREDITOP algorithm (Pellequer &

Westhof, (1993) J. Mol. Graph. 11(3):204-10, or using the methods of Kolaskar & Tongankar (1990) FEBS Leu. 10:276(1-2): 172-4, the contents of which are incorporated herein by reference).

In addition to having activity at the GLP1 receptor, GLP1 analogues of the invention may also have activity at the glucagon receptor. In other words, analogues of the invention may be glucagon receptor agonists as well as GLP1 receptor agonists. Glucagon is released in vivo when blood glucose levels fall low and has the activity of causing the liver to convert stored glycogen into glucose which is released into the bloodstream raising blood glucose levels. Glucagon activity is associated with effects such as increasing energy expenditure of a subject.

Zinc & Solubility

The glucagon or GLP1 analogues of the invention preferably have enhanced solubility at pH 5. Enhanced solubility at pH 5 may be provided by incorporating histidine residues in the glucagon or GLP1 analogues of the invention. Histidine is unique among naturally occurring amino acids in that it is not charged at pH 7.4 (i.e. under physiological conditions in the circulation or subcutaneously following subcutaneous injection), but that it is fully charged at pH 5 since the pI of the NH side chain group of histidine is about 6.0. The inclusion of histidine residues in the glucagon and GLP1 analogues of the invention therefore increase solubility at pH 5 which is a desirable feature. Histidine residues also bring an additional advantage in that when the analogue is injected subcutaneously, the solubility falls and this leads to subcutaneous precipitation of peptide. This is unexpected because in vitro zinc precipitation of His-containing peptides (as used for example in the purification of insulin) is typically slower and not expected to be sufficiently rapid in vivo to prevent dispersion of the subcutaneous precipitate. The precipitate will resolubilise over time and this will produce an advantageous slow-release effect. The inclusion of histidine residues is especially advantageous wherein the glucagon or GLP1 analogue is to be formulated into a pharmaceutical composition containing zinc ions. This is because at pH 7.4 but not at pH 5 zinc ions co-ordinate with histidine residues and result in a further reduction in solubility which can contribute to increased precipitation at a subcutaneous injection site, or which can contribute to increased stability of the precipitate. A zinc-containing precipitate will more gradually re-dissolve because the solubilisation is dependent on the zinc washing out of the injection site into the circulation and/or surrounding tissue fluid, increasing the longevity of the release into the circulation and decreasing the frequency of injections needed to sustain a useful biological effect.

The glucagon analogues of the invention contain a His residue at position 1, as found in native glucagon. In addition, the glucagon analogues of the invention contain His at positions 30 and/or 31, in contrast with native glucagon. The glucagon analogues of the invention may also contain additional non-native histidine residues, at positions 12, 13, 17, 20 and/or 21. Preferably, the glucagon analogues contain His at position 20, in contrast with native glucagon which contains Gln at that position. In certain embodiments, the glucagon analogues of the invention comprise 2, 3, 4, 5 or 6 His residues (i.e. 1, 2, 3, 4 or 5 non-native His residues), preferably 3, 4 or 5 His residues (i.e. 2, 3 or 4 non-native His residues). Pharmaceutical compositions containing the glucagon analogues of the invention preferably contain zinc ions (preferably at a molar ratio of 1:4, 1:2, 1:1, 2:1 or 4:1 of zinc ions to glucagon analogue, or at a ratio which is a range between any two of the whole number ratios given immediately above).

The GLP1 analogues of the invention contain a His residue at position 1, as found in native GLP1. In addition, the GLP1 analogues of the invention also contain His at position 30 and/or 31, in contrast with native GLP1. The GLP1 analogues of the invention may also contain additional non-native histidine residues, at positions 12 and/or 20. In certain embodiments, the GLP1 analogues of the invention comprise 2, 3, 4 or 5 His residues (i.e. 1, 2, 3 or 4 non-native His residues), preferably 2 or 3 His residues (i.e. 1 or 2 non-native His residues). Pharmaceutical compositions containing the GLP1 analogues of the invention preferably contain zinc ions (preferably at a molar ratio of 1:4, 1:2, 1:1, 2:1 or 4:1 of zinc ions to GLP1 analogue, or at a ratio which is a range between any two of the whole number ratios given immediately above).

According to certain embodiments of various aspects of the invention, especially embodiments relating to weight loss, obesity, carbohydrate metabolism and diabetes, glucagon analogues of the invention have one, several or all of the following features:
  A) Sufficient solubility between pH 4 and pH5 to permit an effective dose to be administered in a volume of less than 1 ml, less than 0.5 ml or less than 0.3 ml.
  B) Activation of cAMP signaling in cells over-expressing the human glucagon receptor,
  C) One, several or all of the further 1 to 5 features listed above for glucagon analogues.

According to certain embodiments of various aspects of the invention, especially embodiments relating to weight loss, obesity, carbohydrate metabolism and diabetes, GLP1 analogues of the invention have one, several or all of the following features:
  D) Sufficient solubility between pH 4 and pH 5 to permit an effective dose to be administered in a volume of less than 1 ml, less than 0.5 ml or less than 0.3 ml.
  E) Activation of cAMP signaling in human embryonic kidney cells over-expressing the human GLP1 Receptor.
  F) One, several or all of the further 1 to 5 features listed above for GLP1 analogues.

Conditions

The invention also provides a glucagon or GLP1 analogue of the invention, or a pharmaceutical composition comprising the glucagon or GLP1 analogue of the invention, for use as a medicament.

The invention also provides a method of treating or preventing a disease or disorder or other non-desired physiological state in a subject comprising administration of a therapeutically effective amount of a glucagon or GLP1 analogue of the invention or of a pharmaceutical composition comprising a glucagon or GLP1 analogue of the invention. Preferably the glucagon or GLP1 analogue or pharmaceutical composition is administered subcutaneously.

According to certain embodiments the disease or disorder or other non-desired physiological state is obesity or diabetes. Accordingly, the invention also provides a method for treating obesity or diabetes in a subject comprising administering to a subject a therapeutically effective amount of a glucagon or GLP1 analogue of the invention or of a pharmaceutical composition comprising the glucagon or GLP1 analogue of the invention.

According to certain embodiments the disease or disorder or other non-desired physiological state may be being the physiological state of being overweight.

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acanthosis nigricans; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, *Nature* 404:635-43; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e.g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatil hernia.

According to certain embodiments the disease or disorder or other non-desired physiological state may be being of a non-desired weight despite not being obese or overweight. The subject may be of normal weight (this includes but is not limited to subjects who were previously overweight or obese and who wish to prevent a return to an unhealthy weight). A subject may be a subject who desires weight loss, for example female and male subjects who desire a change in their appearance. In some cases where the subject is of a normal weight, aspects of the invention may relate to cosmetic treatment rather than to therapeutic treatment.

The invention also provides a method of increasing the energy expenditure of a subject, enhancing insulin release in a subject, and/or improving carbohydrate metabolism in a subject, comprising administration of a therapeutically effective amount of a glucagon analogue of the invention, or of a pharmaceutical composition comprising the glucagon analogue of the invention. Such methods may relate to treating subjects having a pre-diabetic state such as insulin insensitivity or pre-diabetes.

The invention also provides a method of reducing appetite in a subject, reducing food intake in a subject, reducing calorie intake in a subject, enhancing insulin release in a subject and/or improving carbohydrate tolerance in a subject, comprising administration of a therapeutically effective amount of a GLP1 analogue of the invention, or of a pharmaceutical composition comprising the GLP1 analogue of the invention. Such methods may relate to treating subjects having a pre-diabetic state such as insulin insensitivity or pre-diabetes.

As discussed above, GLP1 analogues of the invention may also have activity against the glucagon receptor. Accordingly, the invention also provides a method of increasing the energy expenditure of a subject, enhancing insulin release in a subject, and/or improving carbohydrate metabolism in a subject, comprising administration of a therapeutically effective amount of a GLP1 analogue of the invention, or of a pharmaceutical composition comprising the GLP1 analogue of the invention.

Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect, the method of the invention involves manipulation of the arcuate circuitry that alter food intake coordinately and reciprocally alter energy expenditure. Energy expenditure is a result of cellular metabolism, protein synthesis, metabolic rate, and calorie utilization. Thus, in this aspect of the invention, administration of a glucagon or GLP1 analogue of the invention results in increased energy expenditure, and decreased efficiency of calorie utilization.

The increase in energy expenditure may manifest as a lessening of the normal reduction in energy expenditure seen following reduced food intake, or it may manifest as an absolute increase in energy expenditure for example by the promotion of increased physical activity levels or by an increase in the basal metabolic rate.

The invention also provides a method for improving a lipid profile in a subject comprising administration of a therapeutically effective amount of a glucagon or GLP1 analogue of the invention, or of a pharmaceutical composition comprising the glucagon or GLP1 analogue of the invention. The invention also provides a method for alleviating a condition or disorder that can be alleviated by reducing nutrient availability comprising administration of a therapeutically effective amount of a glucagon or GLP1 analogue of the invention, or of a pharmaceutical composition comprising the glucagon or GLP1 analogue of the invention.

A glucagon or GLP1 analogue of the invention may be used for weight control and treatment, for example reduction or prevention of obesity, in particular any one or more of the following: preventing and reducing weight gain; inducing and promoting weight loss; and reducing obesity as measured by the Body Mass Index. A glucagon or GLP1 analogue of the invention may be used in maintaining any one or more of a desired body weight, a desired Body Mass Index, a desired appearance and good health.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

As discussed above, glucagon analogues of the invention may also have activity against the GLP-1 receptor. Accordingly, the invention provides a method of reducing appetite in a subject, reducing food intake in a subject, reducing calorie intake in a subject, enhancing insulin release in a subject and/or improving carbohydrate tolerance in a subject, comprising administration of a therapeutically effective amount of a glucagon analogue of the invention, or of a pharmaceutical composition comprising the glucagon analogue. J. Cereb. Blood Flow Metab. 2011 Apr. 13 (Teramoto S et al) discusses the use of both GLP-1 and exendin-4 to confer cardioprotection after myocardial infarction, and demonstrates that exendin-4 may be used to provide neuroprotection against cerebral ischemia-reperfusion injury. The study showed that mice receiving a transvenous injection of exendin-4, after a 60-minute focal cerebral ischemia showed significantly reduced infarct volume and improved functional deficit as well as suppressed oxidative stress, inflammatory response, and cell death after reperfusion. The study provided evidence that the protective effect of exendin-4 is mediated through increased intracellular cAMP levels and suggested that Exendin-4 is potentially useful in the treatment of acute ischemic stroke.

Accordingly, the invention also provides a method of providing cytoprotection in a subject, such as providing cardiac protection, providing neuroprotection and/or treating or preventing neurodegeneration, comprising administration of a therapeutically effective amount of a glucagon or GLP1 analogue of the invention, or of a pharmaceutical composition comprising the glucagon or GLP1 analogue of the invention.

In certain embodiments the disease or disorder or other non-desired physiological state which the glucagon or GLP1 analogue may be used to treat or prevent is neurodegeneration. Such neurodegeneration may be caused by apoptosis, necrosis or loss of function of neuronal cells, preferably in the CNS. Neurodegeneration treated or prevented may be that following a brain injury (for example following physical trauma or following a non-traumatic injury such a stroke, tumour, hypoxia, poisoning, infection, ischemia, encephalopathy or substance abuse.). Alternatively or additionally, neurodegeneration may be prevented or treated in a subject having (or diagnosed as having a predisposition to) a neurodegenerative disease such as Alzheimer's disease, Parkinson's disease, Gehrig's disease (Amyotrophic Lateral Sclerosis), Huntington's disease, Multiple Sclerosis, other demyelination related disorders, senile dementia, subcortical dementia, arteriosclerotic dementia, AIDS-associated dementia, other dementias, cerebral vasculitis, epilepsy, Tourette's syndrome, Guillain Barre Syndrome, Wilson's disease, Pick's disease, neuroinflammatory disorders, encephalitis, encephalomyelitis, meningitis, other central nervous system infections, prion diseases, cerebellar ataxias, cerebellar degeneration, spinocerebellar degeneration syndromes, Friedrich's ataxia, ataxia teangiectasia, spinal dysmyotrophy, progressive supranuclear palsy, dystonia, muscle spasticity, tremor, retinitis pigmentosa, striatonigral degeneration, mitochondrial encephalomyopathies, neuronal ceroid lipofuscinosis. Preferably, the neurodegenerative disease is selected from the group consisting of Alzheimer's disease, Parkinson's disease, Gehrig's disease (Amyotrophic Lateral Sclerosis) and Huntington's disease. In such circumstances the treatment would be regarded as neuroprotective. According to certain preferred embodiments, the treatment is neuroprotective following cerebral ischemia or neuroprotective in a subject having a neurodegenerative disease or diagnosed as having a predisposition to a neurodegenerative disease.

According to other embodiments the disease or disorder or other non-desired physiological state is cardiac degeneration (in particular myocardial degeneration by apoptosis, necrosis or loss of function of myocardial cells), in which case the glucagon or GLP1 analogue or pharmaceutical composition comprising the glucagon or GLP1 analogue provides cardiac protection. According to certain preferred embodiments that treatment is protective of myocardial function following myocardiac infarction.

The invention also provides a glucagon or GLP1 analogue of the invention, or a pharmaceutical composition comprising the glucagon or GLP1 analogue of the invention, for use in the treatment of obesity or diabetes.

The invention also provides a glucagon or GLP1 analogue of the invention or a pharmaceutical composition comprising the glucagon or GLP1 analogue of the invention for use in increasing energy expenditure of a subject, enhancing insulin release in a subject, improving carbohydrate tolerance in a subject and/or improving carbohydrate metabolism in a subject. Such use may relate to treating subjects having a pre-diabetic state such as insulin insensitivity or pre-diabetes.

The invention also provides a glucagon or GLP1 analogue of the invention or a pharmaceutical composition comprising the glucagon or GLP1 analogue of the invention for use in the reduction of appetite in a subject, use in the reduction of food intake in a subject, use in the reduction of calorie intake in a subject, use in enhancing insulin release in a subject, and/or use in improving carbohydrate tolerance in a subject. Such use may relate to treating subjects having a pre-diabetic state such as insulin insensitivity or pre-diabetes.

The invention also provides a glucagon or GLP1 analogue of the invention, or a pharmaceutical composition comprising the glucagon or GLP1 analogue of the invention, for use as a cytoprotective agent (e.g. in treating or preventing neurodegeneration, providing neuroprotection and/or providing cardiac protection). For example, the glucagon or GLP1 analogue or pharmaceutical composition may be for use in myocardial protection in a subject following myocardial infarction, or for use in neuroprotection in a subject following cerebral ischemia or stroke, or for use in neuroprotection in a subject having a chronic neurodegenerative disease. Various features of neuroprotective or cardioprotective use of the glucagon or GLP1 analogue or pharmaceutical composition may be as outlined above in relation to methods of the invention.

In the case of neuroprotection the subject may have experienced previously a brain injury, stroke or other event causing cerebral ischemia. Alternatively, the subject may have or have been diagnosed with a predisposition to develop a chronic neurodegenerative disease. In the case of cardioprotection the subject may have experienced previously an event causing myocardial ischemia such as a myocardial infarction and angina. According to some embodiments a glucagon or GLP1 analogue or pharmaceutical composition comprising the glucagon or GLP1 analogue of the invention may be administered as soon as possible after the subject has experienced a suspected myocardial infarction. According to certain embodiments a glucagon or GLP1 analogue or pharmaceutical composition comprising the glucagon or GLP1 analogues of the invention may be administered as soon as possible after the subject has experienced as suspected stroke.

The invention also provides use of a glucagon or GLP1 analogue of the invention for the manufacture of a medicament for the treatment of obesity or diabetes, of a subject who may be as described above in reference to other aspects of the invention.

The invention also provides use of a glucagon or GLP1 analogue of the invention for the manufacture of a medicament for increasing energy expenditure in a subject, for enhancing insulin release in a subject, for improving carbohydrate tolerance in a subject and/or improving carbohydrate metabolism in a subject. Such use may relate to treating subjects with a pre-diabetic state such as insulin insensitivity or pre-diabetes.

The invention also provides use of a glucagon or GLP1 analogue of the invention for the manufacture of a medicament for the reduction of appetite in a subject, reducing food intake in a subject, reducing calorie intake in a subject, enhancing insulin release in a subject, and/or use in improving carbohydrate tolerance in a subject.

The invention also provides use of a glucagon or GLP1 analogue of the invention for the manufacture of a medicament for providing cytoprotection (e.g. preventing or treating neurodegeneration, providing neuroprotection and/or providing cardiac protection) of a subject who may be as described above in reference to other aspects of the invention.

According to certain embodiments the glucagon or GLP1 analogue or pharmaceutical composition is to be administered parentally. According to other embodiments the glucagon or GLP1 analogue or pharmaceutical composition is to be administered subcutaneously, intravenously, intramuscularly, intranasally, transdermally or sublingually. According to other embodiments the glucagon or GLP1 analogue or pharmaceutical composition is to be administered orally.

According to the present invention, a glucagon or GLP1 analogue of the invention is preferably used in the treatment of a human. However, while the glucagon or GLP1 analogues of the invention will typically be used to treat human subjects they may also be used to treat similar or identical conditions in other vertebrates for example other primates; farm animals for example swine, cattle and poultry; sport animals for example horses; or companion animals for example dogs and cats.

Compositions

While it is possible for the active ingredient to be administered alone, it is preferable for it to be present in a pharmaceutical formulation or composition. Accordingly, the invention provides a pharmaceutical formulation comprising a glucagon or GLP1 analogue of the invention together with a pharmaceutically acceptable excipient and optionally other therapeutic ingredients. According to certain preferred embodiments the pharmaceutical composition is present in a syringe or other administration device for subcutaneous administration to humans. According to certain preferred embodiments the composition has a pH of less than 5 prior to administration and the composition comprises zinc ions. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intra-articular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988, the contents of which are incorporated herein by reference.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present glucagon or GLP1 analogues can, for example, be administered in a form suitable for immediate release or extended release. Immediate release or extended release can be achieved by the use of suitable pharmaceutical compositions comprising the present glucagon or GLP1 analogues, or, particularly in the case of extended release, by the use of devices such as subcutaneous implants or osmotic pumps. The present glucagon or GLP1 analogues can also be administered liposomally.

Preferably, compositions according to the invention are suitable for subcutaneous administration, for example by injection. According to certain embodiments the composition may contain metal ions, for example copper, iron, aluminium, zinc, nickel or cobalt ions. The presence of such ions may limit solubility and thus delay absorption into the circulatory system from the site of subcutaneous administration. In a particularly preferred embodiment, the composition contains zinc ions as described in more detail above.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The glucagon or GLP1 analogues of the invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to glucagon or GLP1 analogues of the invention and related molecules. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The glucagon or GLP1 analogues of the invention may also be suitably administered as sustained-release systems. Suitable examples of sustained-release systems of the invention include suitable polymeric materials, for example semipermeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracistemally; intravaginally; intraperitoneally; topically, for example as a powder, ointment, gel, drop or transdermal patch; bucally; or as an oral or nasal spray.

Preparations for administration can be suitably formulated to give controlled release of glucagon or GLP1 analogues of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of particles of the glucagon analogues. These compositions exhibit certain biocompatibility features which allow a controlled release of the active substance, see U.S. Pat. No. 5,700,486, the contents of which are incorporated by reference.

Controlled release of glucagon or GLP1 analogues of the invention may also be achieved by the use of pharmaceutical compositions comprising the glucagon or GLP1 analogue and zinc ions. As described above, at pH 7.4 but not at pH 5 zinc ions co-ordinate with histidine residues and result in increased precipitation at a subcutaneous injection site. A zinc-containing precipitate will more gradually re-dissolve because the solubilisation is dependent on the zinc washing out of the injection site into the circulation and/or surrounding tissue fluid, increasing the longevity of the release into the circulation. The use of a controlled release composition is preferred for indications such as the treatment of obesity and/or diabetes, where maximising the time period between injections is desirable. However, for indications such as providing neuroprotection or cardiac protection (e.g. following suspected myocardial infarction or stroke), where it is desired to achieve a therapeutic plasma concentration of the glucagon or GLP1 analogue in as short a time period as possible, an immediate release formulation will be preferred. In such cases, a dosage regime comprising administration of a dose of an immediate release formulation of the glucagon or GLP1 analogue (i.e. as soon as possible after suspected myocardial infarction or stroke) and subsequent administration of a dose of a controlled release formulation of the glucagon or GLP1 analogue may be preferred.

A glucagon or GLP1 analogue of the invention may be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by a continuous subcutaneous infusion, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990) which is incorporated herein by reference. In another aspect of the disclosure, glucagon or GLP1 analogues of the invention are delivered by way of an implanted pump, described, for example, in U.S. Pat. No. 6,436,091; U.S. Pat. No. 5,939,380; U.S. Pat. No. 5,993,414, the contents of which are incorporated herein by reference.

Implantable drug infusion devices are used to provide patients with a constant and long term dosage or infusion of a drug or any other therapeutic agent. Essentially such device may be categorized as either active or passive. A glucagon or GLP1 analogue of the present invention may be formulated as a depot preparation. Such a long acting depot formulation can be administered by implantation, for example subcutaneously or intramuscularly; or by intramuscular injection. Thus, for example, the glucagon or GLP1 analogues can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a glucagon or GLP1 analogue of the invention may be administered as a single pulse dose, as a bolus dose, or as pulse doses administered over time. Thus, in pulse doses, a bolus administration of a glucagon or GLP1 analogue of the invention is provided, followed by a time period wherein no glucagon or GLP1 analogue of the invention is administered to the subject, followed by a second bolus administration. In specific, non-limiting examples, pulse doses of a glucagon or GLP1 analogue of the invention are administered during the course of a day, during the course of a week, or during the course of a month.

In certain embodiments, a therapeutically effective amount of a glucagon or GLP1 analogue of the invention is administered with a therapeutically effective amount of another agent. The glucagon or GLP1 analogue may be administered simultaneously with the further therapeutic agent, or it may be administered sequentially or separately. In certain embodiments, a glucagon or GLP1 analogue of the invention is formulated and administered with a further therapeutic agent as a single dose.

In certain embodiments, the further therapeutic agent is an additional anti-diabetic, appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, phendimetrazine, benzphetamine, sibutramine, rimonabant, topiramate, fluoxetine, bupropion, zonisamide, naltrexone, orlistat and cetilistat. Specific, non-limiting examples of an additional anti-diabetic agent include metformin, phenformin, rosiglitazone, pioglitazone, troglitazone, repaglinide, nateglinide, tolbutamide, acetohexamide, tolazamide, chlorpropamide, glipizide, glyburide, glimepiride, gliclazide, fibroblast growth factor 21, miglitol, acarbose, exenatide, pramlintide, vildagliptin and sitagliptin.

In alternative embodiments, the further therapeutic agent is an additional cardioprotective or neuroprotective agent. Specific, non-limiting, examples of additional cardioprotective agents include aspirin, N-acetylcysteine, phenethylamines, coenzyme Q10, vitamin E, vitamin C,L-carnitine, carvedilol and dexrazoxane. Specific, non-limiting examples of neuroprotective agents include statins such as simvastatin, steroids such as progesterone, minocycline, resveratrol and vitamin E. Examples of agents used for the treatment of Parkinson's disease include anticholinergics, pramipexole, bromocriptine, levodopa, carbidopa, rasagiline, amantadine and ropinirole.

A glucagon or GLP1 analogue of the invention may be administered whenever the effect, e.g., appetite suppression, decreased food intake, increased energy expenditure or decreased caloric intake, is desired, or slightly before to whenever the effect is desired, such as, but not limited to, about 10 minutes, about 15 minutes, about 30 minutes, about 60 minutes, about 90 minutes, or about 120 minutes, before the time the effect is desired.

The therapeutically effective amount of a glucagon or GLP1 analogue of the invention will be dependent on the molecule utilized, the subject being treated, the severity and type of the affliction, and the manner and route of administration. For example, a therapeutically effective amount of a glucagon or GLP1 analogue of the invention may vary from about 0.01 µg per kilogram (kg) body weight to about 1 g per kg body weight, for example about 0.1 µg to about 20 mg per kg body weight, for example about 1 µg to about 5 mg per kg body weight, or about 5 µg to about 1 mg per kg body weight.

In one embodiment of the invention, a glucagon or GLP1 analogue of the invention may be administered to a subject at from 4 to 1333 nmol per kg bodyweight, for example from 5 to 1000 nmol per kg bodyweight, for example at from 10 to 750 nmol per kg bodyweight, for example at from 20 to 500 nmol per kg bodyweight, in particular at from 30 to 240 nmol per kg bodyweight. For a 75 kg subject, such doses correspond to dosages of from 300 nmol to 100 µmol, for example from 375 nmol to 75 µmol, for example from 750 nmol to 56.25 µmol, for example from 1.5 to 37.5 µmol, in particular from 2.25 to 18 µmol. The invention also contemplates dosages ranges bounded by any of the specific dosages mentioned herein.

In an alternative embodiment, a glucagon or GLP1 analogue of the invention may be administered to a subject at 0.5 to 135 picomole (pmol) per kg body weight, for example 5 to 100 picomole (pmol) per kg body weight, for example 10 to 90 picomole (pmol) per kg body weight, for example about 72 pmol per kg body weight. In one specific, non-limiting example, a glucagon or GLP1 analogue of the invention is administered in a dose of about 1 nmol or more, 2 nmol or more, or 5 nmol or more. In this example, the dose of the glucagon or GLP1 analogue of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, examples of non-limiting dose ranges of glucagon or GLP1 analogues of the invention are within the range of from 1 to 100 nmols, from 2 to 90 mols, from 5 to 80 nmols.

In one specific, non-limiting example, from about 1 to about 50 nmol of a glucagon or GLP1 analogue of the invention is administered, for example about 2 to about 20 nmol, for example about 10 nmol is administered as a subcutaneous injection. The exact dose is readily determined by one of skill in the art based on the potency of the specific compound utilized, the route of delivery of the compound and the age, weight, sex and physiological condition of the subject.

The doses discussed above may be given, for example, once, twice, three-times or four-times a day or once or twice a week. Preferably a dose may be given no more frequently than once a week. Alternatively, they may be given once every 2, 3 or 4 days. According to certain embodiments they may be administered once shortly before each meal to be taken.

The present invention also relates to the following sections:

§1. An analogue of GLP1 which is:
a compound comprising an amino acid sequence represented by formula (II)

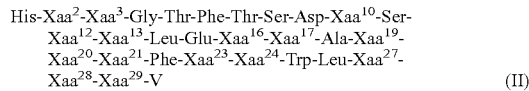

wherein V is selected from the group consisting of His (SEQ ID NO 728), His-NH$_2$ (SEQ ID NO 729), His-His (SEQ ID NO 730), His-His-NH$_2$ (SEQ ID NO 731), Gly-His (SEQ ID NO 732), Gly-His-NH$_2$ (SEQ ID NO 733), Lys-His (SEQ ID NO 734) and Lys-His-NH$_2$ (SEQ ID NO 735);

Xaa$^2$ is selected from the group consisting of Ser and Gly;
Xaa$^3$ is selected from the group consisting of Glu and Gln;
Xaa$^{10}$ is selected from the group consisting of Tyr and Leu;
Xaa$^{12}$ is selected from the group consisting of Lys and His;
Xaa$^{13}$ is selected from the group consisting of Tyr and Gln;
Xaa$^{16}$ is selected from the group consisting of Glu, Ala and Ser;
Xaa$^{17}$ is selected from the group consisting of Gln and Glu;
Xaa$^{19}$ is selected from the group consisting of Val, Ala, Ile and Leu;
Xaa$^{20}$ is selected from the group consisting of Arg and His;
Xaa$^{21}$ is selected from the group consisting of Ile and Leu;
Xaa$^{23}$ is selected from the group consisting of Ile and Val;
Xaa$^{24}$ is selected from the group consisting of Glu and Gln;
Xaa$^{27}$ is selected from the group consisting of Leu and Lys;
Xaa$^{28}$ is selected from the group consisting of Asn, Lys and Gln; and
Xaa$^{29}$ is selected from the group consisting of Gly and Thr;

wherein —NH$_2$ represents a C-terminal amide group;
wherein the compound is not analogue nos. 428, 429, or 431-439, or 441-458; and optionally wherein the compound is not analogue no. 440;
or a derivative of the compound;
or a salt of the compound or the derivative.

§2. An analogue according to §1, wherein Xaa$^{12}$ is Lys, Xaa$^{20}$ is Arg, Xaa$^{23}$ is Ile, Xaa$^{28}$ is Asn and Xaa$^{29}$ is Gly.

§3. An analogue according to §1 or §2, wherein Xaa$^2$ is Ser.

§4. An analogue according to §1 or §2, wherein Xaa$^2$ is Gly.

§5. An analogue according to any one of §1 to 4, wherein Xaa$^{13}$ is Tyr.

§6. An analogue according to any one of §1 to 5, wherein Xaa$^{16}$ is Glu.

§7. An analogue according to any one of §1 to 6, wherein Xaa$^{19}$ is Val.

§8. An analogue according to any one of §1 to 7, wherein Xaa$^{21}$ is Le.

§9. An analogue according to any one of §1 to 8, wherein Xaa$^{27}$ is Leu.

§10. An analogue according to any one of §1 to 9, wherein V is selected from the group consisting of His-His, His-His-NH$_2$ and Gly-His-NH$_2$.

§11. An analogue according to any one of §1 to 10, wherein the compound consists of an amino acid sequence represented by formula (II).

§12. An analogue according to §11, wherein
i) Xaa$^2$ is Ser, Xaa$^3$ is Glu, Xaa$^{10}$ is Tyr, Xaa$^{12}$ is Lys, Xaa$^{13}$ is Tyr, Xaa$^{16}$ is Glu, Xaa$^{17}$ is Gln, Xaa$^{19}$ is Val, Xaa$^{20}$ is Arg, Xaa$^{21}$ is Ile, Xaa$^{23}$ is Ile, Xaa$^{24}$ is Gln, Xaa$^{27}$ is Leu, Xaa$^{28}$ is Asn, Xaa$^{29}$ is Gly and V is His-His-NH$_2$ (SEQ ID NO 567);
ii) Xaa$^2$ is Ser, Xaa$^3$ is Glu, Xaa$^{10}$ is Tyr, Xaa$^{12}$ is Lys, Xaa$^{13}$ is Tyr, Xaa$^{16}$ is Glu, Xaa$^{17}$ is Gln, Xaa$^{19}$ is Val, Xaa$^{20}$ is Arg, Xaa$^{21}$ is Ile, Xaa$^{23}$ is Ile, Xaa$^{24}$ is Gln, Xaa$^{27}$ is Leu, Xaa$^{28}$ is Asn, Xaa$^{29}$ is Gly and V is His-His (SEQ ID NO 566);
iii) Xaa$^2$ is Ser, Xaa$^3$ is Glu, Xaa$^{10}$ is Tyr, Xaa$^{12}$ is Lys, Xaa$^{13}$ is Tyr, Xaa$^{16}$ is Glu, Xaa$^{17}$ is Gln, Xaa$^{19}$ is Val, Xaa$^{20}$ is Arg, Xaa$^{21}$ is Ile, Xaa$^{23}$ is Ile, Xaa$^{24}$ is Glu, Xaa$^{27}$ is Leu, Xaa$^{28}$ is Asn, Xaa$^{29}$ is Gly and V is His-His-NH$_2$ (SEQ ID NO 664);

iv) $Xaa^2$ is Ser, $Xaa^3$ is Glu, $Xaa^{10}$ is Leu, $Xaa^{12}$ is Lys, $Xaa^{13}$ is Gln, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is His-His-NH$_2$(SEQ ID NO 675);

v) $Xaa^2$ is Gly, $Xaa^3$ is Glu, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Leu, $Xaa^{23}$ is Ile, $Xaa^{24}$ is Glu, $Xaa^{27}$ is Leu, $Xaa^{28}$ is Asn, $Xaa^{29}$ is Gly and V is His-His (SEQ ID NO 682);

vi) $Xaa^2$ is Ser, $Xaa^3$ is Gln, $Xaa^{10}$ is Tyr, $Xaa^{12}$ is Lys, $Xaa^{13}$ is Tyr, $Xaa^{16}$ is Glu, $Xaa^{17}$ is Glu, $Xaa^{19}$ is Leu, $Xaa^{20}$ is Arg, $Xaa^{21}$ is Leu, $Xaa^{23}$ is Ile, $Xaa^{24}$ is Glu, $Xaa^{27}$ is Leu, $Xaa^{28}$ is Asn, $Xaa^{29}$ is Gly and V is Gly-His-NH$_2$ (SEQ ID NO 484);

vii) $Xaa^2$ is Gly, $Xaa^3$ is Glu, $Xaa^{10}$ is Leu, $Xaa^{12}$ is Lys, $Xaa^{13}$ is Gln, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is Gly-His-NH$_2$ (SEQ ID NO 494);

viii) $Xaa^2$ is Ser, $Xaa^3$ is Gln, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Leu, $Xaa^{23}$ is Ile, $Xaa^{24}$ is Glu, $Xaa^{27}$ is Lys, $Xaa^{28}$ is Asn, $Xaa^{29}$ is Gly and V is Gly-His-NH$_2$ (SEQ ID NO 503);

ix) $Xaa^2$ is Gly, $Xaa^3$ is Gln, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V is Gly-His-NH$_2$ (SEQ ID NO 659);

x) $Xaa^2$ is Gly, $Xaa^3$ is Glu, $Xaa^{10}$ is Tyr, $Xaa^{12}$ is Lys, $Xaa^{13}$ is Tyr, $Xaa^{16}$ is Ala, $Xaa^{17}$ is Glu, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V is Gly-His-NH$_2$ (SEQ ID NO 658);

xi) $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V is Gly-His-NH$_2$ (SEQ ID NO 667); or xii) $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V is His-His (SEQ ID NO 704).

§13. An analogue according to any one of §1 to 12 which is a derivative that has been modified by one or more processes selected from amidation, glycosylation, carbamylation, acylation, sulfation, phosphorylation, cyclization, lipidization, pegylation and fusion to another peptide or protein to form a fusion protein.

§14. An analogue according to any one of §1 to 12 which is not a derivative.

§15. An analogue according to §1, which is any one of the compounds listed in FIG. 2.

§16. An analogue according to any one of §1 to 15 together with a further therapeutic agent, for simultaneous, sequential or separate administration.

§17. A pharmaceutical composition comprising an analogue according to any one of §1 to 16 together with a pharmaceutically acceptable carrier and optionally other therapeutic ingredients.

§18. A pharmaceutical composition according to §17, present in a syringe or other administration device for subcutaneous administration to humans.

§19. A pharmaceutical composition according to §17 or §18 wherein the composition has a pH of less than 5 prior to administration and wherein the composition comprises zinc ions.

§20. An analogue according to any one of §1 to 16, or a pharmaceutical composition according to any one of §17 to 19, for use as a medicament.

§21. A method of treating or preventing a disease or disorder or other non-desired physiological state in a subject comprising administration of a therapeutically effective amount of an analogue according to any one of §1 to 16, or a pharmaceutical composition according to any one of §17 to 19.

§22. An analogue according to any one of §1 to 16 or a pharmaceutical composition according to any one of §17 to 19 for use in the treatment of obesity or diabetes.

§23. An analogue according to any one of §1 to 16, or a pharmaceutical composition according to any one of §17 to 19 for use in the reduction of appetite in a subject, use in the reduction of food intake in a subject, use in the reduction of calorie intake in a subject, use in enhancing insulin release in a subject, use in improving carbohydrate tolerance in a subject and/or use in improving the lipid profile of a subject.

§24. An analogue according to any one of §1 to 16 or a pharmaceutical composition according to any one of §17 to 19 for use in increasing the energy expenditure of a subject, enhancing insulin release in a subject and/or improving carbohydrate metabolism in a subject.

§25. An analogue according to any one of §1 to 16 or a pharmaceutical composition according to any one of §17 to 19 for use as a cytoprotective agent.

§26. A method of treating obesity or diabetes in a subject in need thereof comprising administration of a therapeutically effective amount of an analogue according to any one of §1 to 16, or a pharmaceutical composition according to any one of §17 to 19.

§27. A method of reducing appetite in a subject, reducing food intake in a subject, reducing calorie intake in a subject, enhancing insulin release in a subject, improving carbohydrate tolerance in a subject and/or improving the lipid profile of a subject, comprising administration of a therapeutically effective amount of an analogue according to any one of §1 to 16, or a pharmaceutical composition according to any one of §17 to 19.

§28. A method of increasing the energy expenditure of a subject, enhancing insulin release in a subject and/or improving carbohydrate metabolism in a subject, comprising administration of a therapeutically effective amount of an analogue according to any one of §1 to 16, or a pharmaceutical composition according to any one of §17 to 19.

§29. A method of providing cytoprotection in a subject, comprising administration of a therapeutically effective amount of an analogue according to any one of §1 to 16, or a pharmaceutical composition according to any one of §17 to 19.

§30. Use of an analogue according to any one of §1 to 16 for the manufacture of a medicament for the treatment of obesity or diabetes.

§31. Use of an analogue according to any one of §1 to 16 for the manufacture of a medicament for the reduction of appetite in a subject, reducing food intake in a subject, reducing calorie intake in a subject, enhancing insulin release in a subject, improving carbohydrate tolerance in a subject and/or improving the lipid profile of a subject.

§32. Use of an analogue according to any one of §1 to 16 for the manufacture of a medicament for increasing the energy expenditure of a subject, enhancing insulin release in a subject and/or improving carbohydrate metabolism in a subject.

§33. Use of an analogue according to any one of §1 to 16 for the manufacture of a medicament for providing cytoprotection in a subject.

§34. An analogue or pharmaceutical composition according to any one of §22 to 24, a method according to any one of §26 to 28, or a use according to any one of §30 to 32, wherein the subject is overweight and/or obese and/or diabetic.

§35. An analogue or pharmaceutical composition for use according to §25, a method according to §29, or a use according to §33, wherein the analogue or composition is for treating or preventing neurodegeneration, providing neuroprotection and/or providing cardiac protection.

§36. An analogue or pharmaceutical composition for use, a method or use according to §35, wherein the analogue or pharmaceutical composition is for providing cardiac protection in a subject following a myocardial infarction.

§37. An analogue or pharmaceutical composition for use, a method or use according to §35, wherein the analogue or pharmaceutical composition is for providing neuroprotection in a subject having or diagnosed as being at risk of a chronic neurodegenerative disease.

§38. An analogue or pharmaceutical composition for use, a method or use according to §37, wherein the chronic neurodegenerative disease is selected from the group consisting of Alzheimer's disease, Parkinson's disease, Gehrig's disease (Amyotrophic Lateral Sclerosis), Huntington's disease, Multiple Sclerosis, other demyelination related disorders, senile dementia, subcortical dementia, arteriosclerotic dementia, AIDS-associated dementia, other dementias, cerebral vasculitis, epilepsy, Tourette's syndrome, Guillain Barre Syndrome, Wilson's disease, Pick's disease, neuroinflammatory disorders, encephalitis, encephalomyelitis, meningitis, other central nervous system infections, prion diseases, cerebellar ataxias, cerebellar degeneration, spinocerebellar degeneration syndromes, Friedrich's ataxia, ataxia teangiectasia, spinal dysmyotrophy, progressive supranuclear palsy, dystonia, muscle spasticity, tremor, retinitis pigmentosa, striatonigral degeneration, mitochondrial encephalomyopathies and neuronal ceroid lipofuscinosis The invention is illustrated by the following non-limiting Examples.

Materials and Methods:
Animals

Male C57BL/6 mice (Harlan) or male Wistar rats (Charles River Ltd, Margate, UK) were used for all animal experiments.

Peptide Synthesis

Peptides were made by a standard automated fluorenylmethoxycarbonyl (Fmoc) solid phase peptide synthesis (SPPS) method. Peptide synthesis was carried out on a tricyclic amide linker resin. Amino acids were attached using the Fmoc strategy. Each amino acid was added sequentially from the C- to the N-termini. Peptide couplings were mediated by the reagent TBTU. Peptide cleavage from the resin was achieved with trifluoracetic acid in the presence of scavengers.

Peptides were purified by reverse phase HPLC. Full quality control was performed on all purified peptides and peptides were shown to be greater than 95% pure by HPLC in two buffer systems. Amino acid analysis following acid hydrolysis confirmed the amino acid composition. MALDI-MS showed the expected molecular ion.

EXAMPLE 1

Cellular Assays

Cells (Chinese hamster ovary—hGCGr, or Human embryonic kidney—hGLP-lr) were plated at a density of 150000 cells/ml in 24 well plates. The cells were left for 18 hours, and were then serum starved for 1 hour by replacing with serum free media. The media was then replaced with that containing the example glucagon analogue at 12 concentrations in duplicate ranging from 0 up to 30 nM (1 analogue per 24 well plate). Each plate was incubated for exactly 30 minutes. The incubation media was removed, and replaced with 120 ul of lysis buffer (0.1M HCl 0.5% TritonX). 120 ul of sample (or a dilution thereof so as to hit ELISA standard curve) was added to an eppendorf tube, and was spun for 3 minutes at >5000 g to remove cell debris. 100 ul of sample was added to an ELISA plate (Direct cyclic AMP Enzyme Immunoassay Kit—Enzolifesciences). The ELISA assay was run as described in the manual.

Acute Feeding Studies in Mice

Mice were individually housed in IVC cages. Animals were randomised into treatment groups, with stratification by body weight. Mice were fasted overnight (16 hrs) prior to peptide or vehicle administration. All peptide solutions were prepared freshly, immediately prior to administration. The vehicle used for all studies was 5% v/v water and 95% v/v sodium chloride (0.9% w/v). Peptide and vehicle were administered by subcutaneous injection, with dosage corrected for bodyweight. The injection volume was 50 µl. Vehicle or peptide was administered at 09:00 and animals were returned to their home cage with a known amount of food. Food intake was measured at 1, 4, 8 and 24 hours post injection. All statistics are calculated using a one-way ANOVA with Dunnett's post-test or one-way ANOVA with Bonferroni post-test.

Acute Feeding Studies in Rats

Rats were individually housed in IVC cages. Animals were randomised into treatment groups, with stratification by body weight. Rats were fasted overnight (24 hrs) prior to peptide or vehicle administration. All peptide solutions were prepared freshly, immediately prior to administration. The vehicle used for all studies was 5% v/v water and 95% v/v sodium chloride (0.9% w/v) with zinc chloride added at a 1:1 molar ratio to the peptide. Peptide and vehicle were administered by subcutaneous injection, with dosage corrected for bodyweight. The injection volume was 50 µl. Vehicle or peptide was administered at 09:00 and animals were returned to their home cage with a known amount of food. Food intake was measured at 1, 4, 8, 24, 32, 48 and 72 hours post injection. All statistics are calculated using a one-way ANOVA with Dunnett's post-test.

Results—Glucagon Analogues

FIG. 1 shows a table providing amino acid sequences of glucagon analogues of the invention (each compound is identified by a G no., as well as an analogue no.). The table also provides the results of cellular assay experiments, and the results of experiments in which appetite suppressant effects in mice and rats were determined.

The column headed "hGCGr cAMP" shows signaling in human embryonic kidney cells or Chinese hamster ovary cells over-expressing human glucagon receptor following administration of the example glucagon analogues. The values provided in the column are EC50 ratios relative to native glucagon (e.g. a value of 0.5 indicates that the concentration of the glucagon analogue required to stimulate 50% maximum release of cAMP is half the concentration of native glucagon that is required, and a value of 5 indicates that the concentration of the glucagon analogue required to stimulate 50% maximum release of cAMP is 5 times that of native glucagon).

The column headed "hGLP-lr cAMP" shows signaling in human embryonic kidney cells or chinese hamster ovary cells over-expressing human GLP1 receptor. The values provided in the column are EC50 ratios relative to native GLP-1 (e.g. a value of 0.5 indicates that the concentration of the glucagon analogue required to stimulate 50% maximum release of cAMP is half the concentration of native GLP-1 that is required, and a value of 5 indicates that the concentration of the glucagon analogue required to stimulate 50% maximum release of cAMP is 5 times that of native GLP-1).

In the section of the table headed "Mouse food intake inhibition", the columns headed "0-1", "0-4", "0-8", "4-8", "8-24" and "0-24" show the reduction in food intake relative to saline during the indicated time periods (in hours) since administration of the glucagon analogue. A positive value indicates that less food was consumed by mice to whom the glucagon analogue was administered compared with mice to whom saline was administered during the relevant time period (a value of 100 indicates that nothing was eaten). A negative value indicates that more food was consumed by mice to whom the glucagon analogue was administered compared with mice to whom saline was administered during the relevant time period (e.g. a value of −5 indicates that the glucagon analogue mice consumed 5% more food (in grams) than the saline mice). A value of 0 indicates that the same quantity of food was consumed by the glucagon analogue mice and the saline mice.

In the section of the table headed "Rat food intake inhibition", the columns headed "0-1", "0-4", "0-8", "4-8", "8-24", "24-32", "32-48", "48-72", "0-24", "0-48" and "0-72" show the reduction in food intake relative to saline during the indicated time periods (in hours) since administration of the glucagon analogue. A positive value indicates that less food was consumed by rats to whom the glucagon analogue was administered compared with rats to whom saline was administered during the relevant time period (a value of 100 indicates that nothing was eaten). A negative value indicates that more food was consumed by rats to whom the glucagon analogue was administered compared with rats to whom saline was administered during the relevant time period (e.g. a value of −5 indicates that the glucagon analogue rats consumed 5% more food (in grams) than the saline mice). A value of 0 indicates that the same quantity of food was consumed by the glucagon analogue rats and the saline rats.

Results—GLP1 Analogues

FIG. 2 shows a table providing amino acid sequences of GLP1 analogues of the invention (each compound is identified by a G no., as well as an analogue no.). The table also provides the results of cellular assay experiments, and the results of experiments in which appetite suppressant effects in mice and rats were determined.

The column headed "hGCGr cAMP" shows signaling in human embryonic kidney cells or Chinese hamster ovary cells over-expressing human glucagon receptor following administration of the example glucagon analogues. The values provided in the column are EC50 ratios relative to native glucagon (e.g. a value of 0.5 indicates that the concentration of the GLP1 analogue required to stimulate 50% maximum release of cAMP is half the concentration of native glucagon that is required, and a value of 5 indicates that the concentration of the GLP1 analogue required to stimulate 50% maximum release of cAMP is 5 times that of native glucagon).

The column headed "hGLP-lr cAMP" shows signaling in human embryonic kidney cells or chinese hamster ovary cells over-expressing human GLP1 receptor. The values provided in the column are EC50 ratios relative to native GLP-1 (e.g. a value of 0.5 indicates that the concentration of the GLP1 analogue required to stimulate 50% maximum release of cAMP is half the concentration of native GLP-1 that is required, and a value of 5 indicates that the concentration of the GLP1 analogue required to stimulate 50% maximum release of cAMP is 5 times that of native GLP-1).

In the section of the table headed "Mouse food intake inhibition", the columns headed "0-1", "0-4", "0-8", "4-8", "8-24" and "0-24" show the reduction in food intake relative to saline during the indicated time periods (in hours) since administration of the GLP1 analogue. A positive value indicates that less food was consumed by mice to whom the glucagon analogue was administered compared with mice to whom saline was administered during the relevant time period (a value of 100 indicates that nothing was eaten). A negative value indicates that more food was consumed by mice to whom the GLP1 analogue was administered compared with mice to whom saline was administered during the relevant time period (e.g. a value of −5 indicates that the GLP1 analogue mice consumed 5% more food (in grams) than the saline mice). A value of 0 indicates that the same quantity of food was consumed by the GLP1 analogue mice and the saline mice.

In the section of the table headed "Rat food intake inhibition", the columns headed "0-1", "0-4", "0-8", "4-8", "8-24", "24-32", "32-48", "48-72", "0-24", "0-48" and "0-72" show the reduction in food intake relative to saline during the indicated time periods (in hours) since administration of the GLP1 analogue. A positive value indicates that less food was consumed by rats to whom the GLP1 analogue was administered compared with rats to whom saline was administered during the relevant time period (a value of 100 indicates that nothing was eaten). A negative value indicates that more food was consumed by rats to whom the GLP1 analogue was administered compared with rats to whom saline was administered during the relevant time period (e.g. a value of −5 indicates that the GLP1 analogue rats consumed 5% more food (in grams) than the saline mice). A value of 0 indicates that the same quantity of food was consumed by the GLP1 analogue rats and the saline rats.

EXAMPLE 2

Rat Weight Loss Studies—Glucagon Analogues

Figure 4:
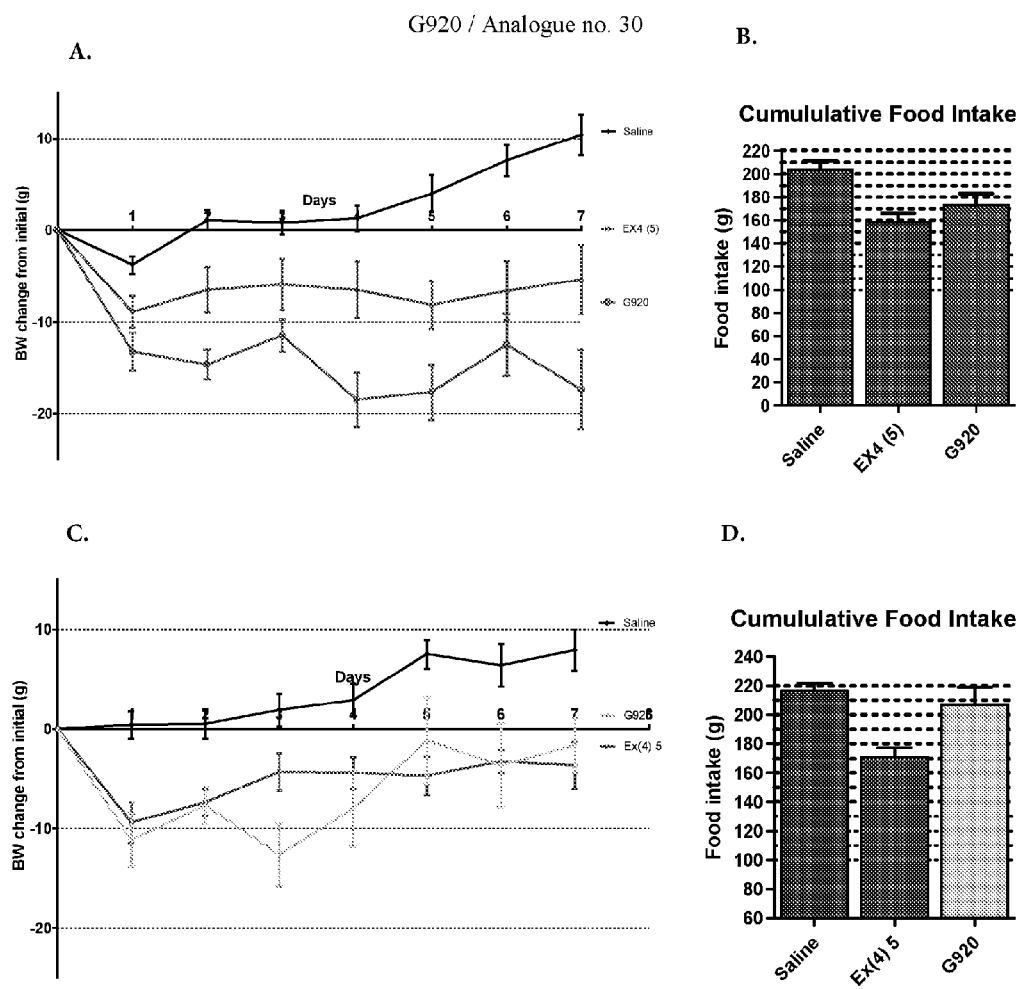
Figure 5:
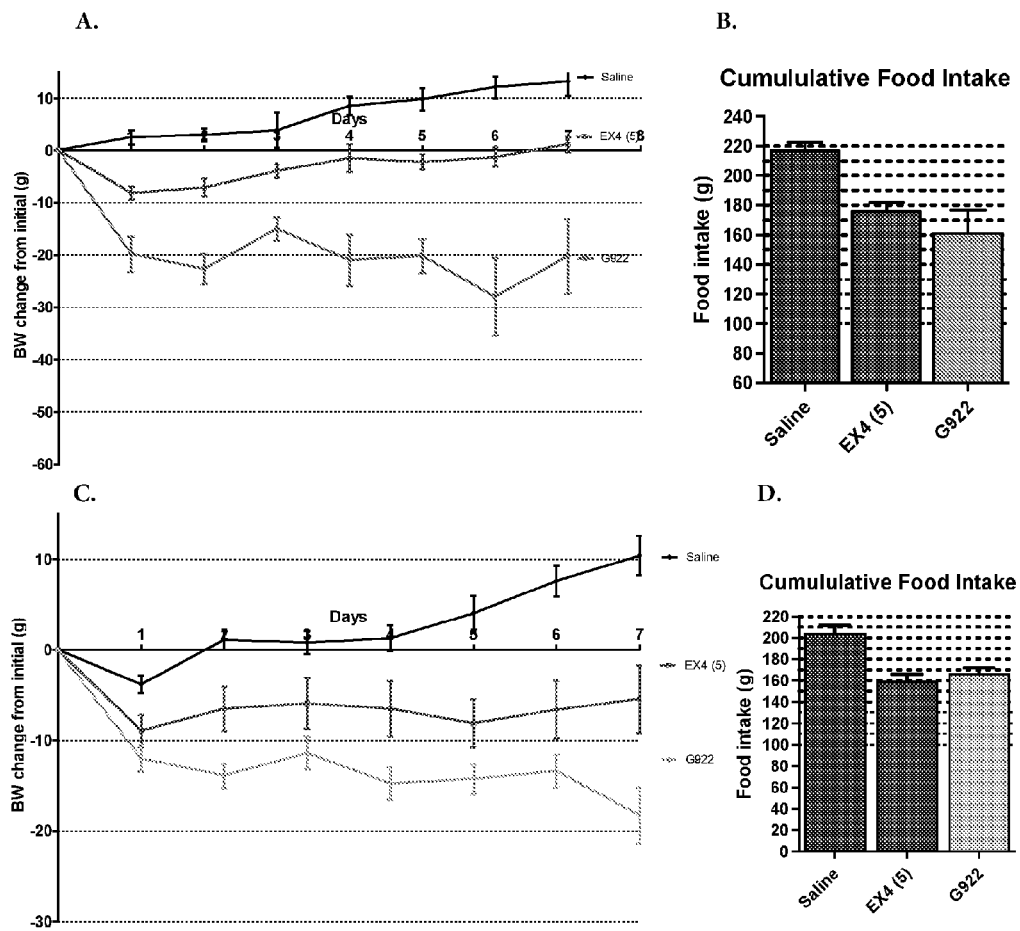
Figure 6:
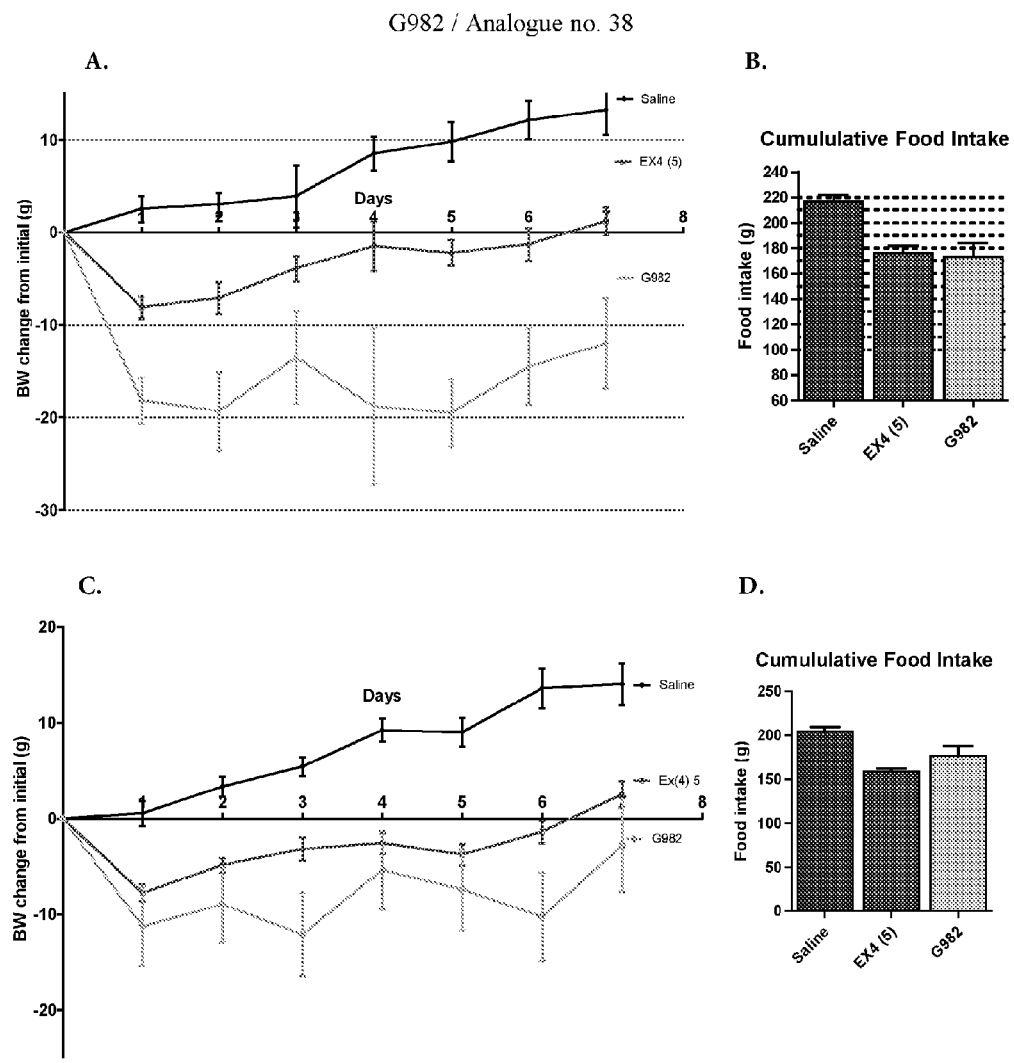
Figure 7:
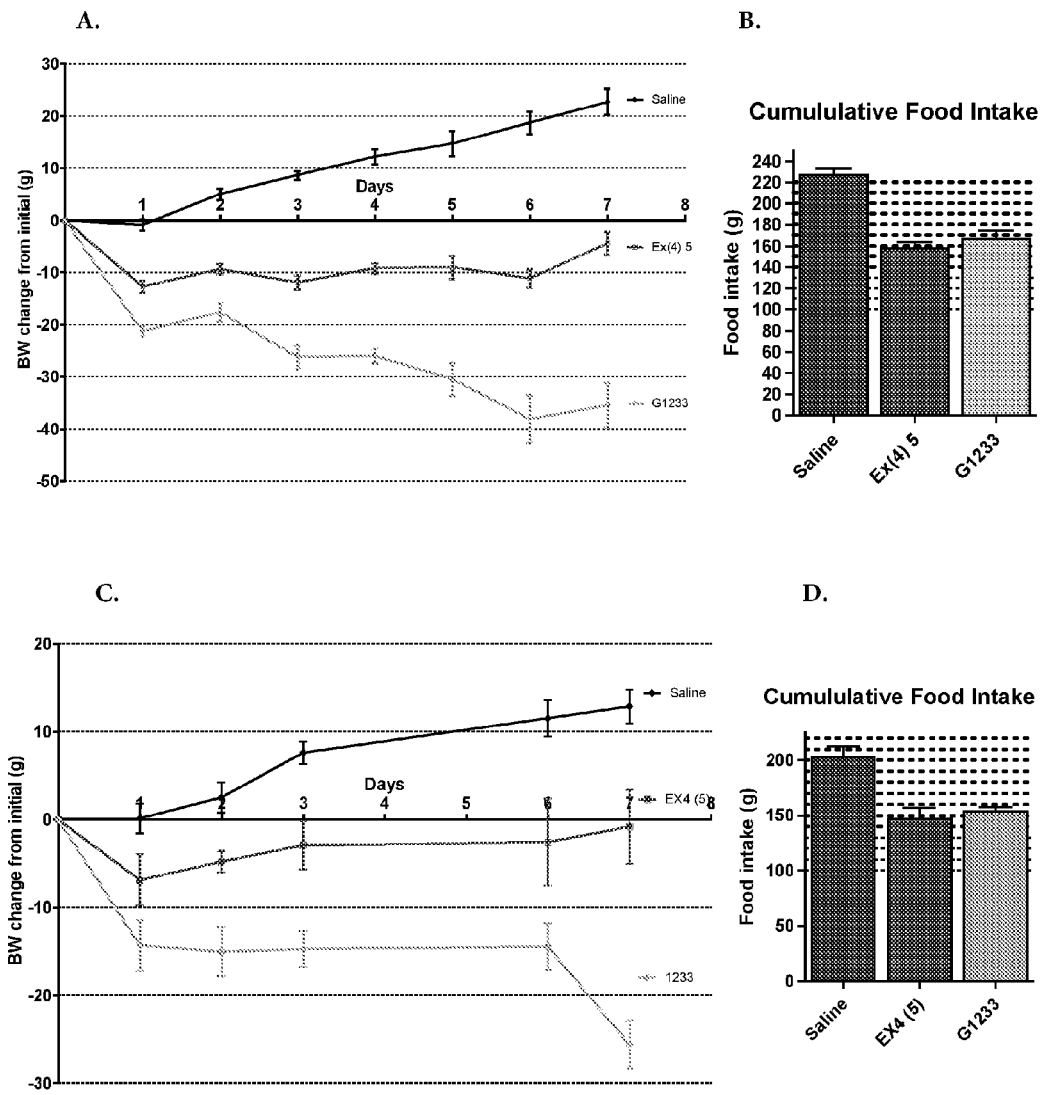
Figure 8:
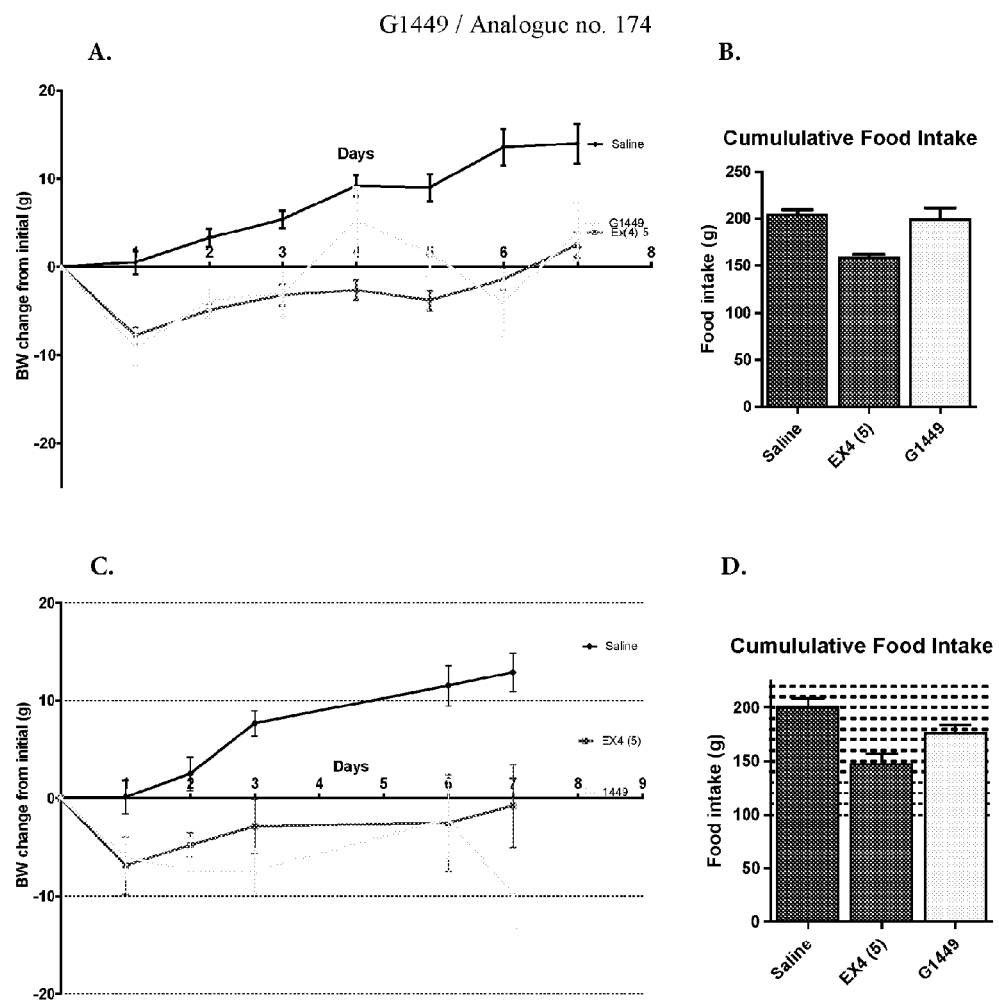
Figure 9:
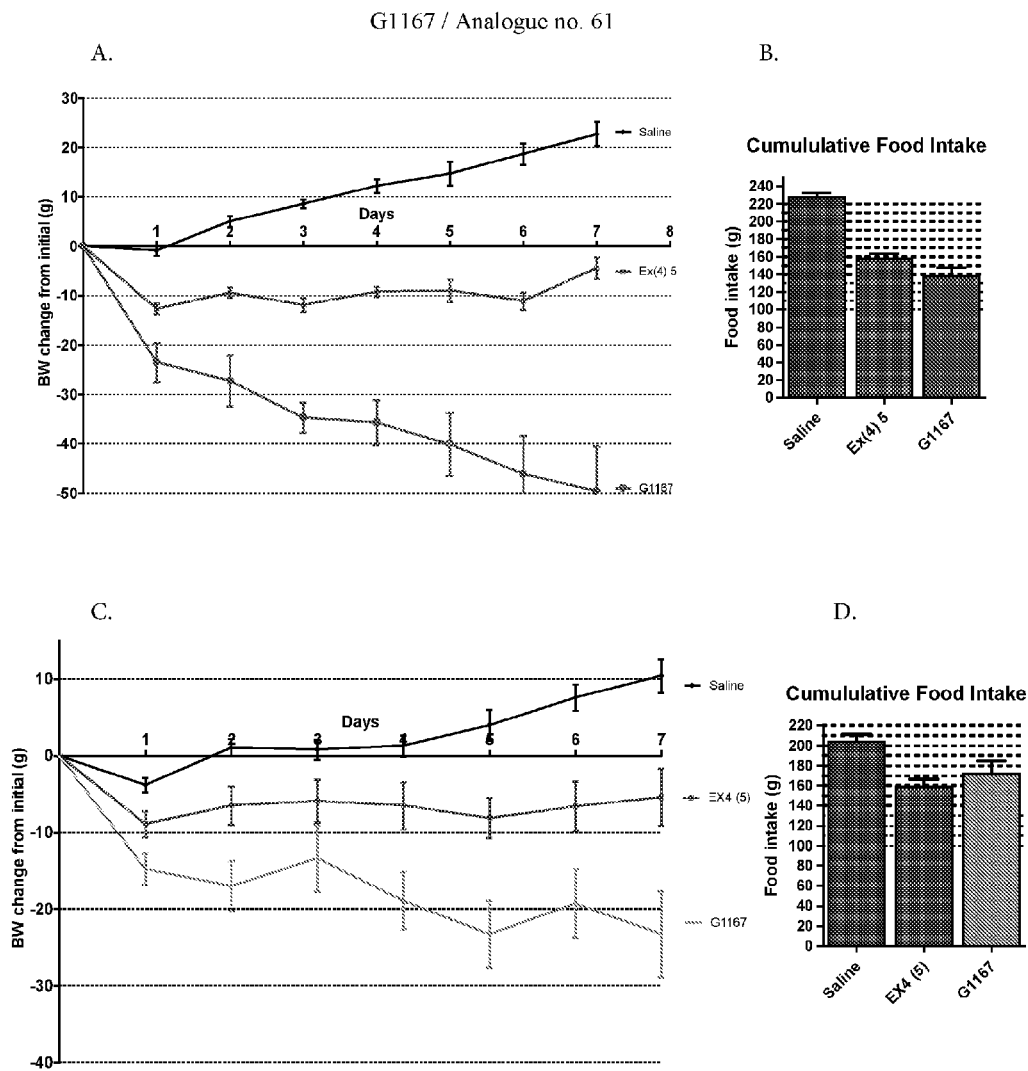
Figure 10:
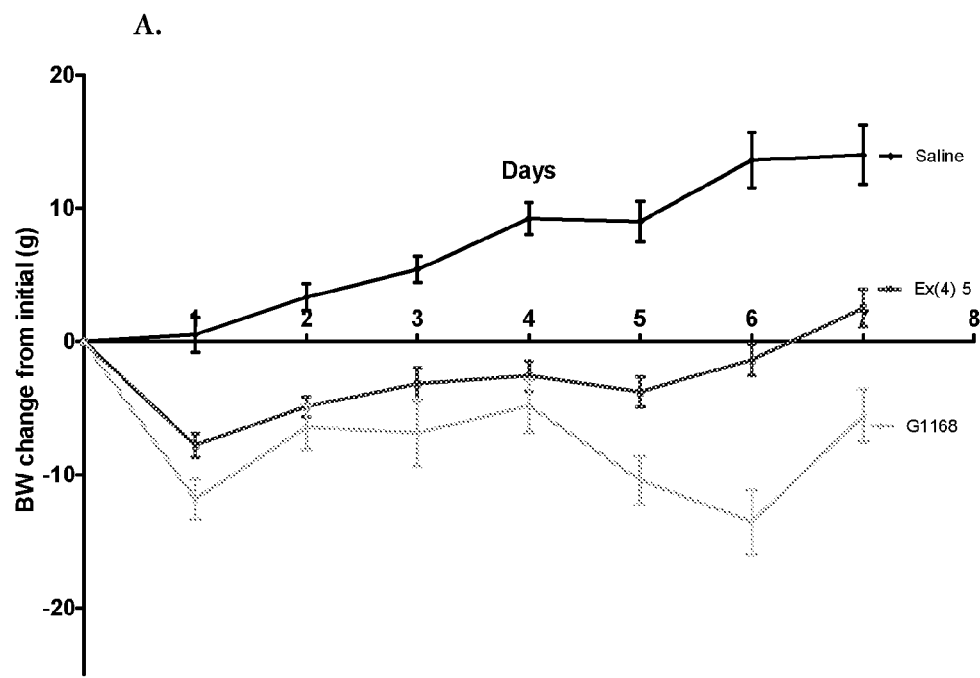
Figure 10:
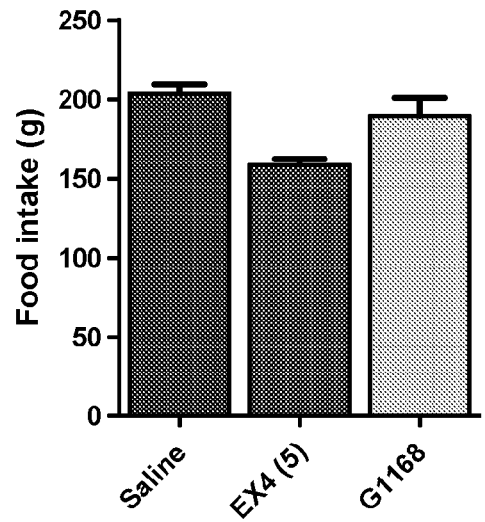
Figure 11:
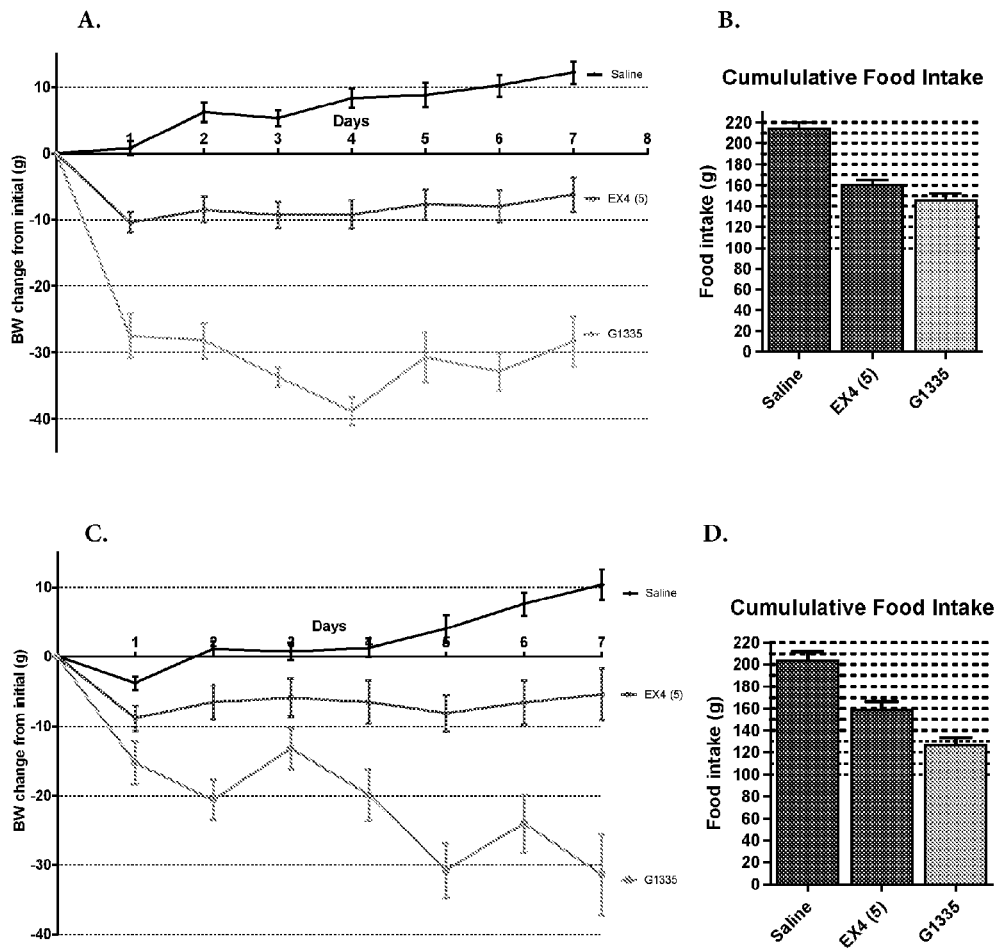
Figure 12:
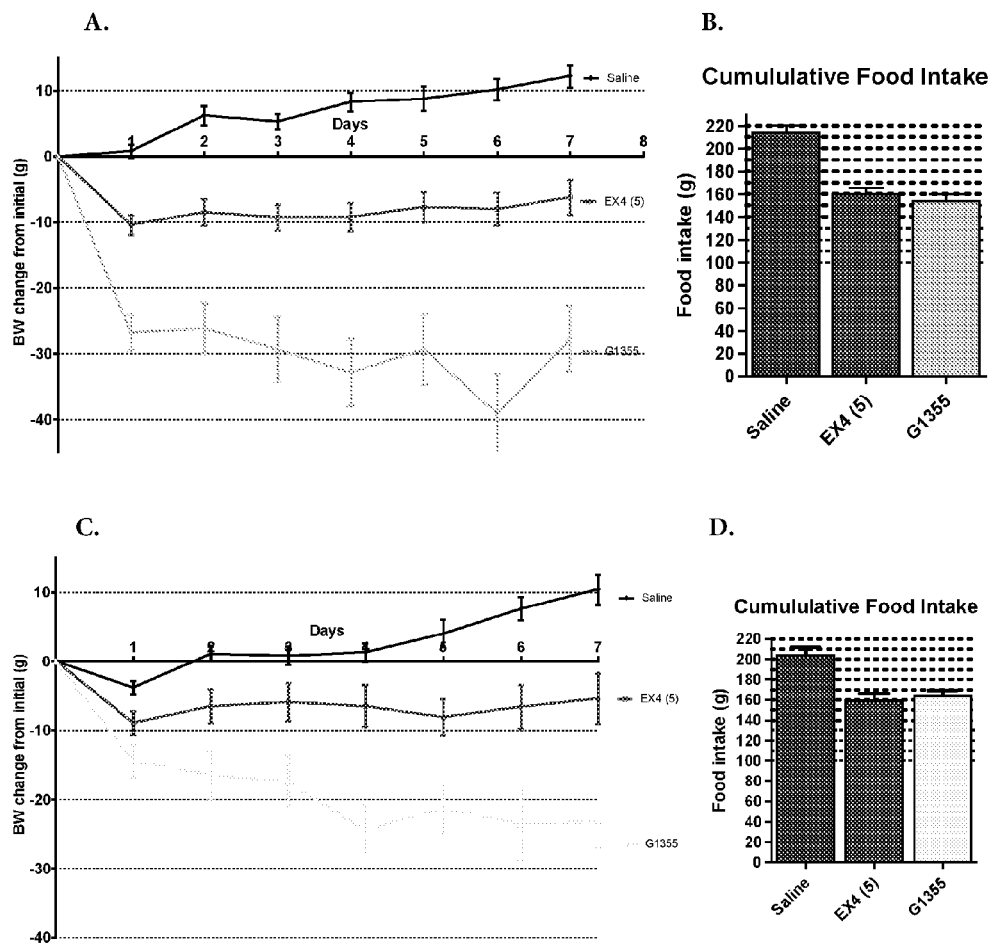

Male Wistar rats were individually housed in IVC cages. Animals were randomised into treatment groups, with stratification by body weight. Rats were injected with a) vehicle, b) exendin-4 or c) a glucagon analogue of the invention in combination with exendin-4 at 16:00 and animals were returned to their home cage. The vehicle used for all studies was 5% v/v water and 95% v/v sodium chloride (0.9% w/v) with zinc chloride added at a 1:1 molar ratio to the peptide (glucagon analogue). All peptide solutions were prepared freshly, immediately prior to administration. Peptide doses are stated in the figure legends. Food intake (in grams) and change in body weight (in grams) were measured daily over 7 days. Peptide and vehicle were administered by subcutaneous injection, with dosage corrected for bodyweight. The injection volume was 50 µl. The results of the studies are shown in FIGS. 3 to 12, which show cumulative food intake over 7 days for rats to which a glucagon analogue of the invention was administered (in conjunction with exendin-4), compared with cumulative food intake for rats to which saline or exendin-4 was administered. FIGS. 3 to 12 also show the change in body weight over 7 days for rats to which a glucagon analogue of the invention was administered (in conjunction with exendin-4), compared with results for saline or exendin-4.

Since the glucagon analogues normally have no or minimal anorectic effect, both the exendin-4-treated and the combination-treated rats can be expected to lose the same amount of body weight through food intake inhibition. Accordingly, additional weight loss observed in the combination-treated rats can be attributed to effects of the glucagon analogue through a mechanism independent of food intake.

EXAMPLE 3

Rat Pharmacokinetic Studies—Glucagon Analogues

Figure 13:
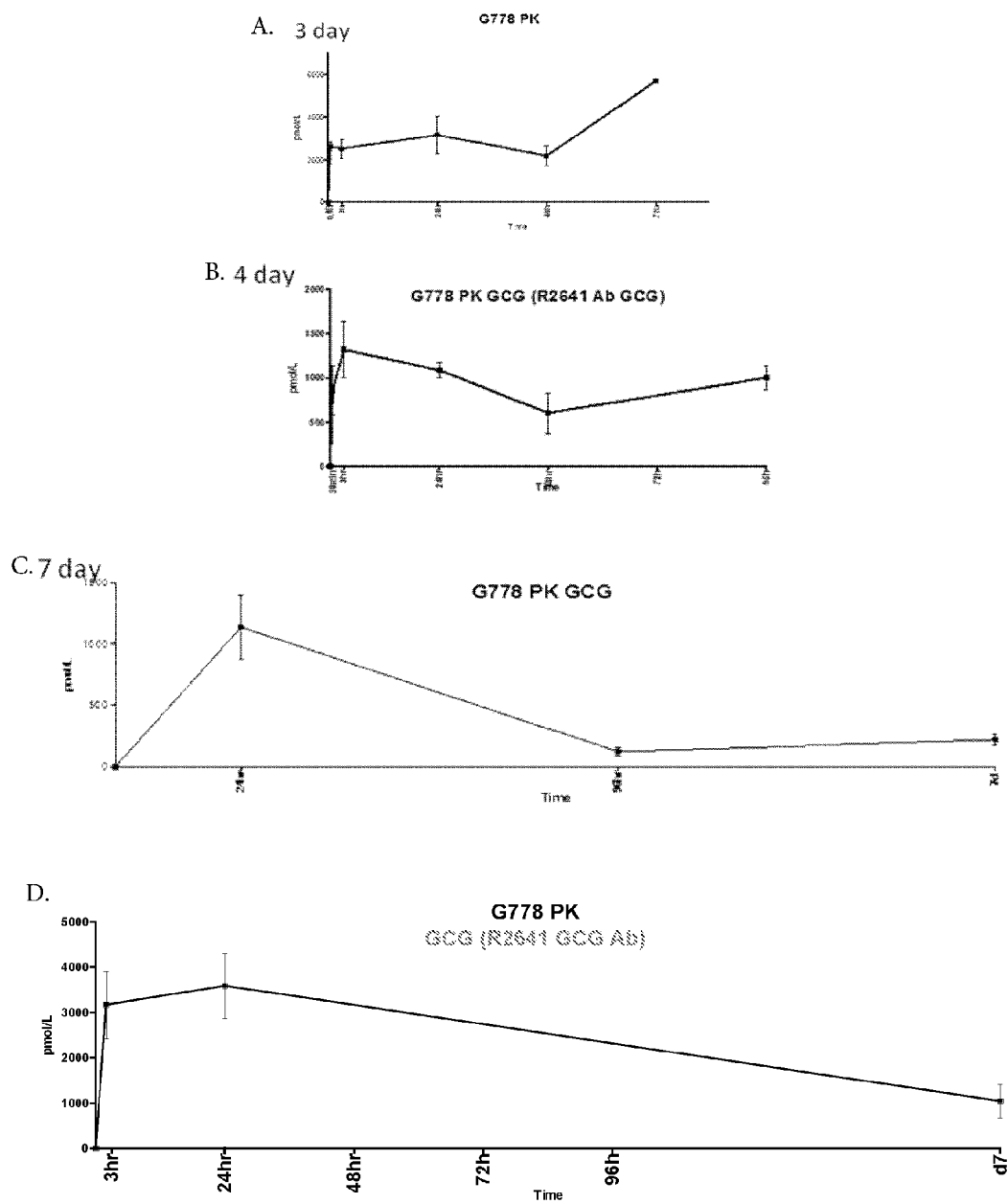
FIGS. 13 to 22 show the results of rat pharmacokinetic studies with selected glucagon analogues of the invention. Specifically, FIGS. 13A., 13B., 13C. and 13D show the pharmacokinetic profiles of glucagon analogue G778 over a 3 day, a 4 day, and a 7 day time period, respectively.
Figure 14:
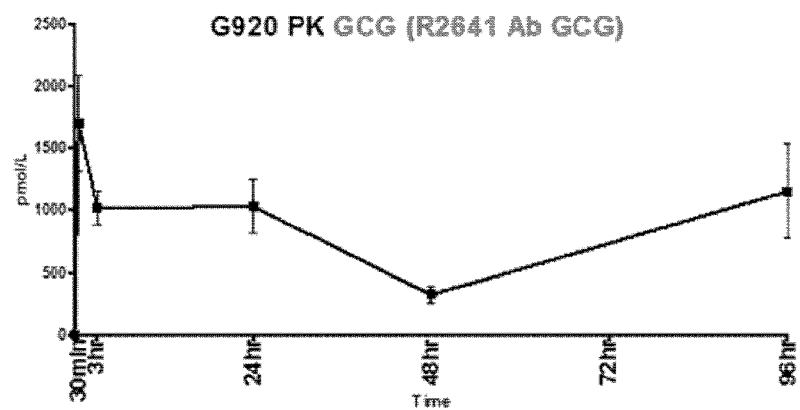
Figure 14:
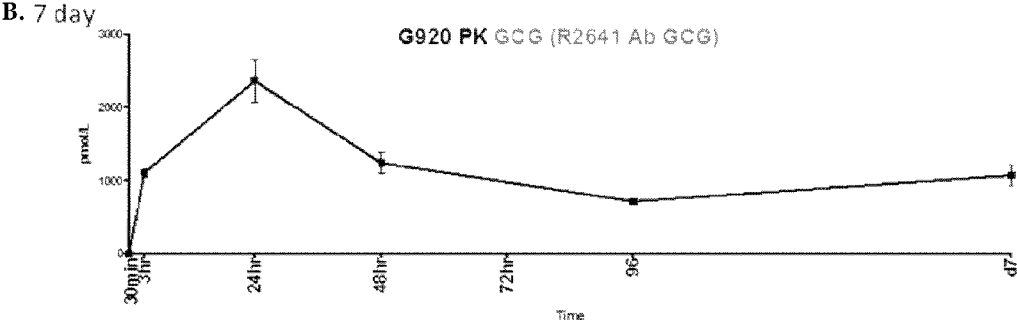
Figure 15:
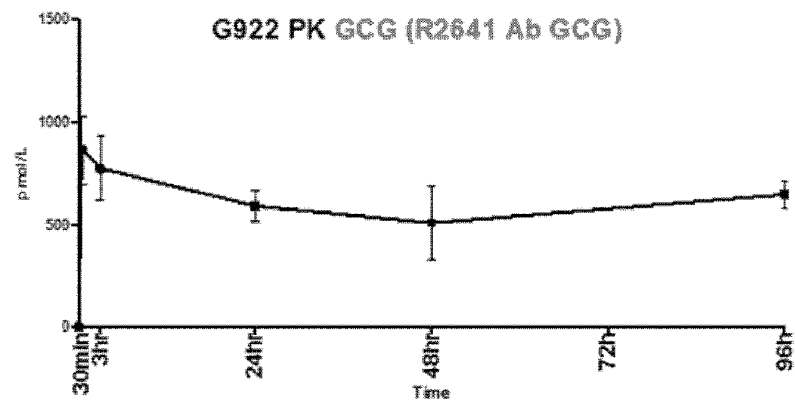
Figure 15:
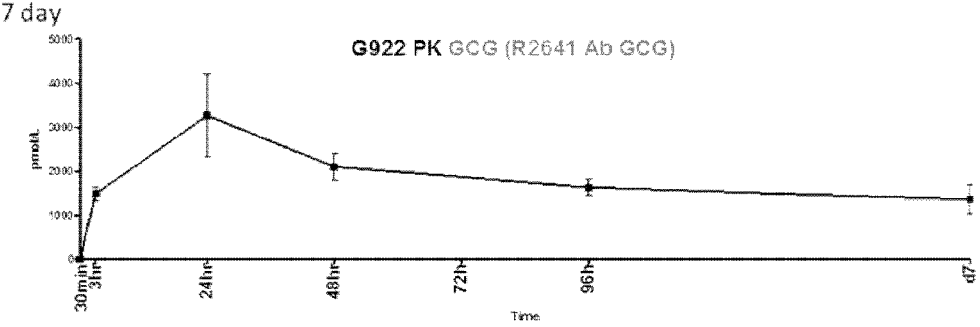
Figure 16:
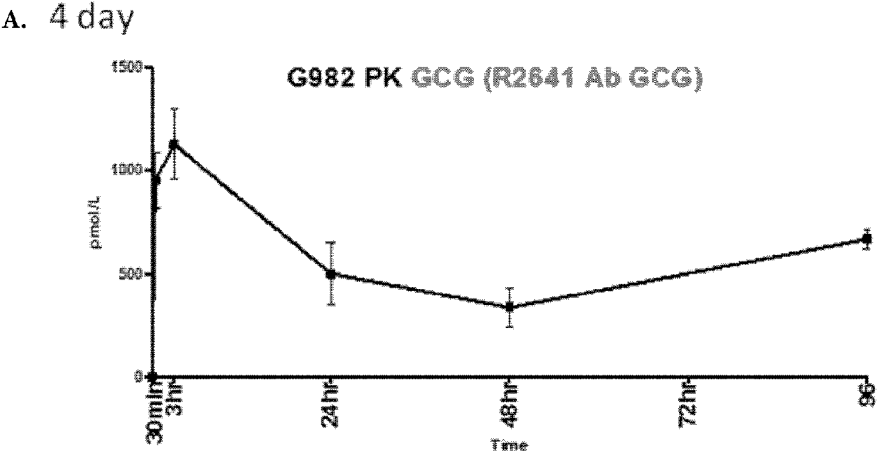
Figure 16:
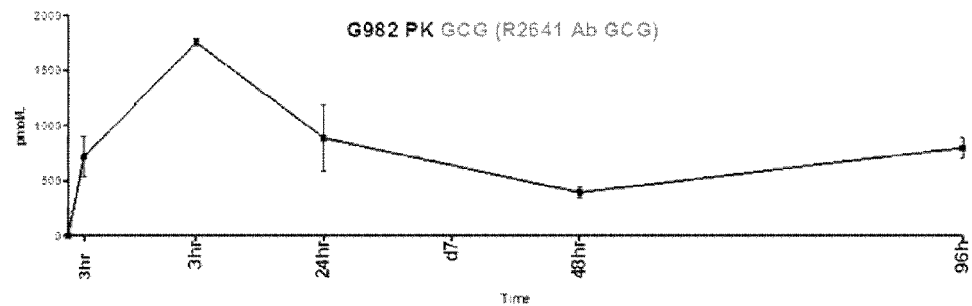
Figure 17:
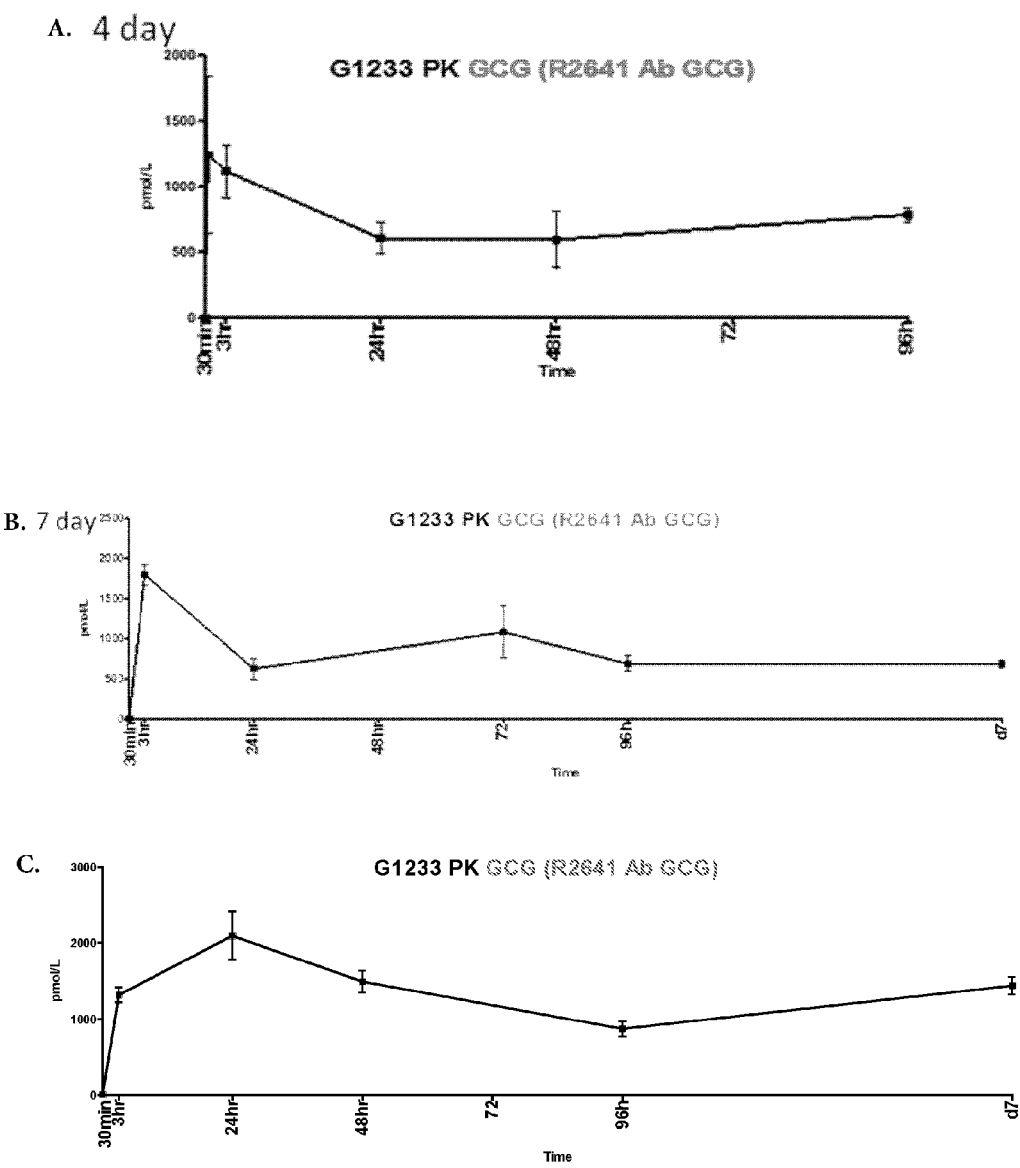
Figure 18:
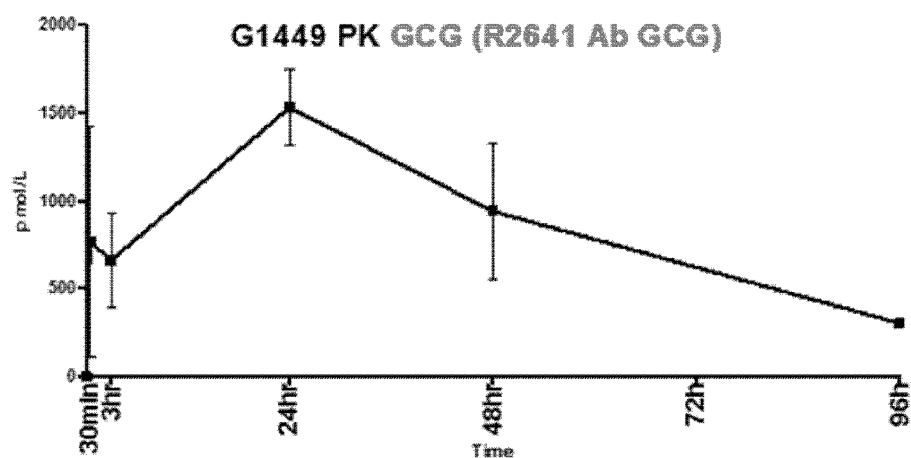
Figure 19:
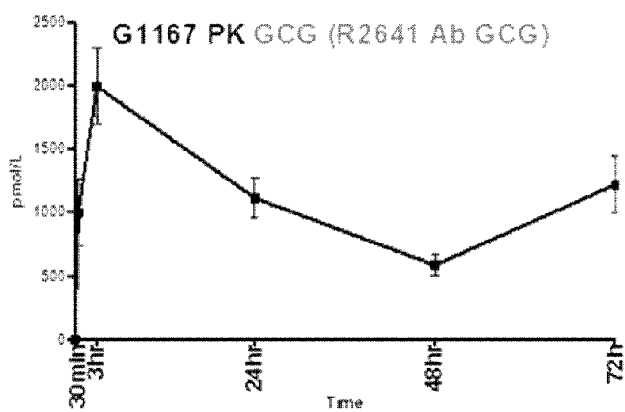
Figure 19:
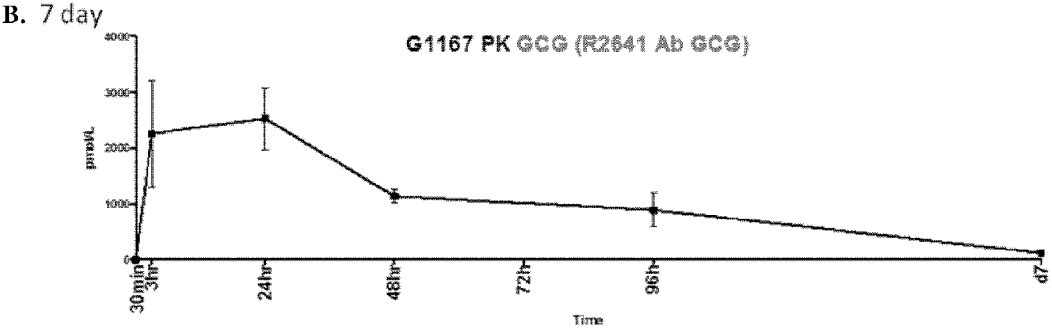
Figure 20:
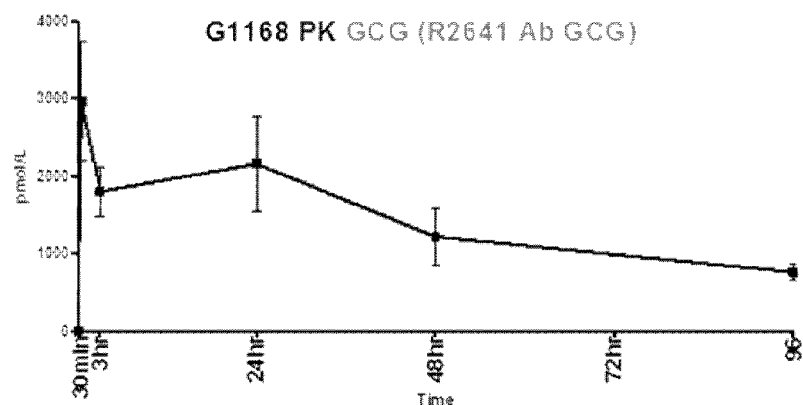
Figure 20:
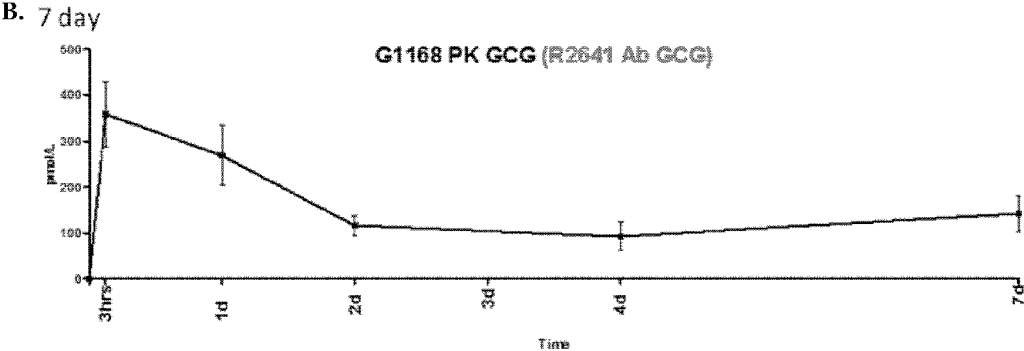
Figure 21:
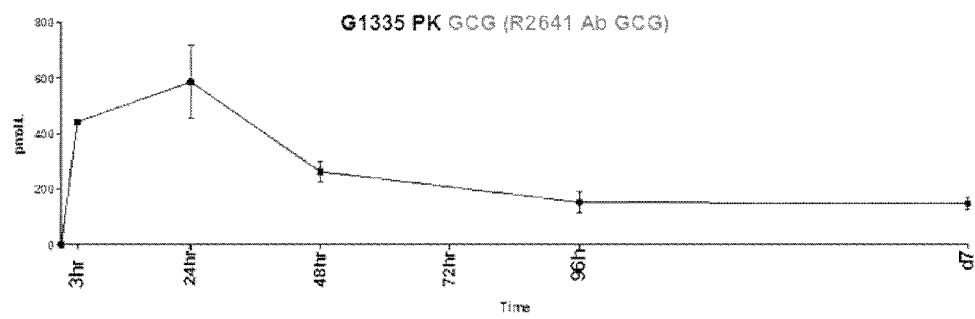
Figure 22:
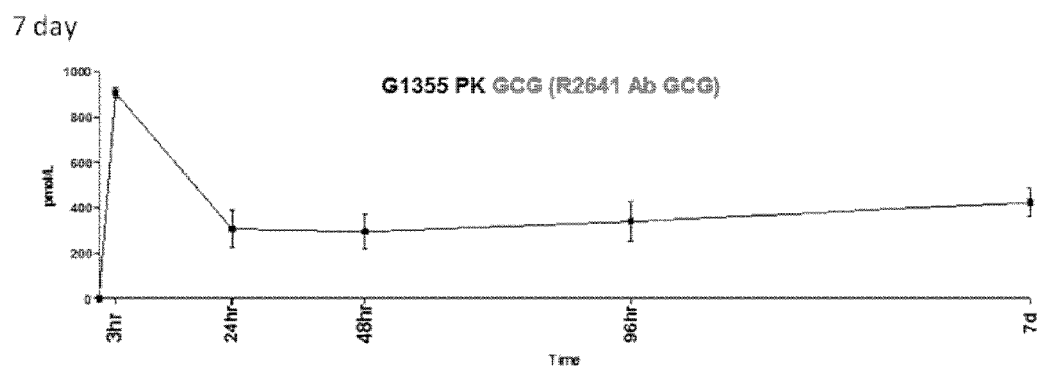

The pharmacokinetics of glucagon analogues of the invention in rats over 3 day, 4 day or 7 day time periods were evaluated. Rats were injected subcutaneously with a glucagon analogue. Each injection was of 20 µl total volume/rat containing 1 mg peptide and 1 zinc ion (as $ZnCl_2$) per peptide molecule. Blood was collected at the indicated time points, and the concentration of the glucagon analogue was determined. Peptide levels were assessed radioimmunoassay using R2641 glucagon antibody. The results are presented in FIGS. 13 to 22, and show that glucagon analogues of the invention can achieve good in vivo pharmacokinetic profiles over extended periods of time.

EXAMPLE 4

Rat Feeding Studies—GLP1 Analogues

GLP1 analogues of the invention (50 nmol/kg dosage, in aqueous zinc chloride solution, 1:1 molar ratio of zinc ions to GLP1 analogue) (peptide group) or saline (vehicle control group) were administered subcutaneously to male wistar rats (5 animals in vehicle control group, 4-5 animals in peptide group). The animals had been fasted for 24 hours prior to administration. Food intake (in grams) was measured at time intervals over 72 hours. Food intake was measured at 1, 2, 4, 8, 24, 36, 48 and 72 hours following injection.

Figure 23:
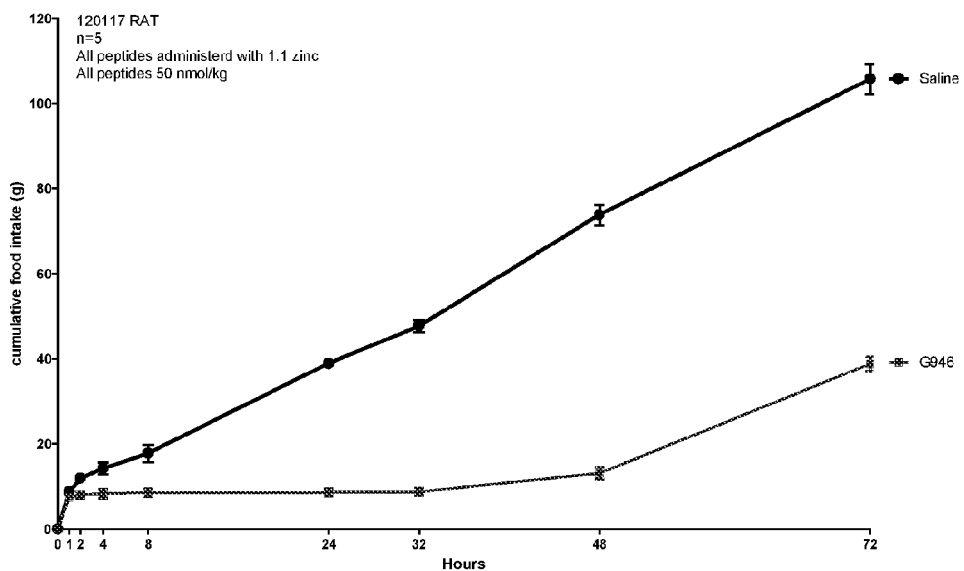
FIGS. 23 to 34 show more detailed food intake data in rats and mice for selected GLP1 analogues of the invention. Specifically, FIG. 23A. shows the cumulative food intake over 72 hours in rats to which GLP1 analogue G946 (analogue no. 566) had been administered, compared with the cumulative food intake for rats to which saline had been administered.
Figure 23:
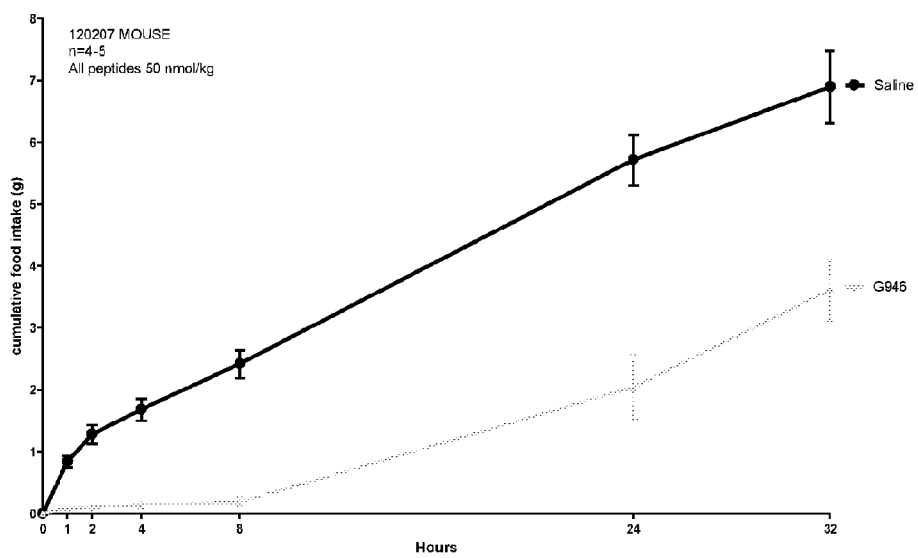
Figure 24:
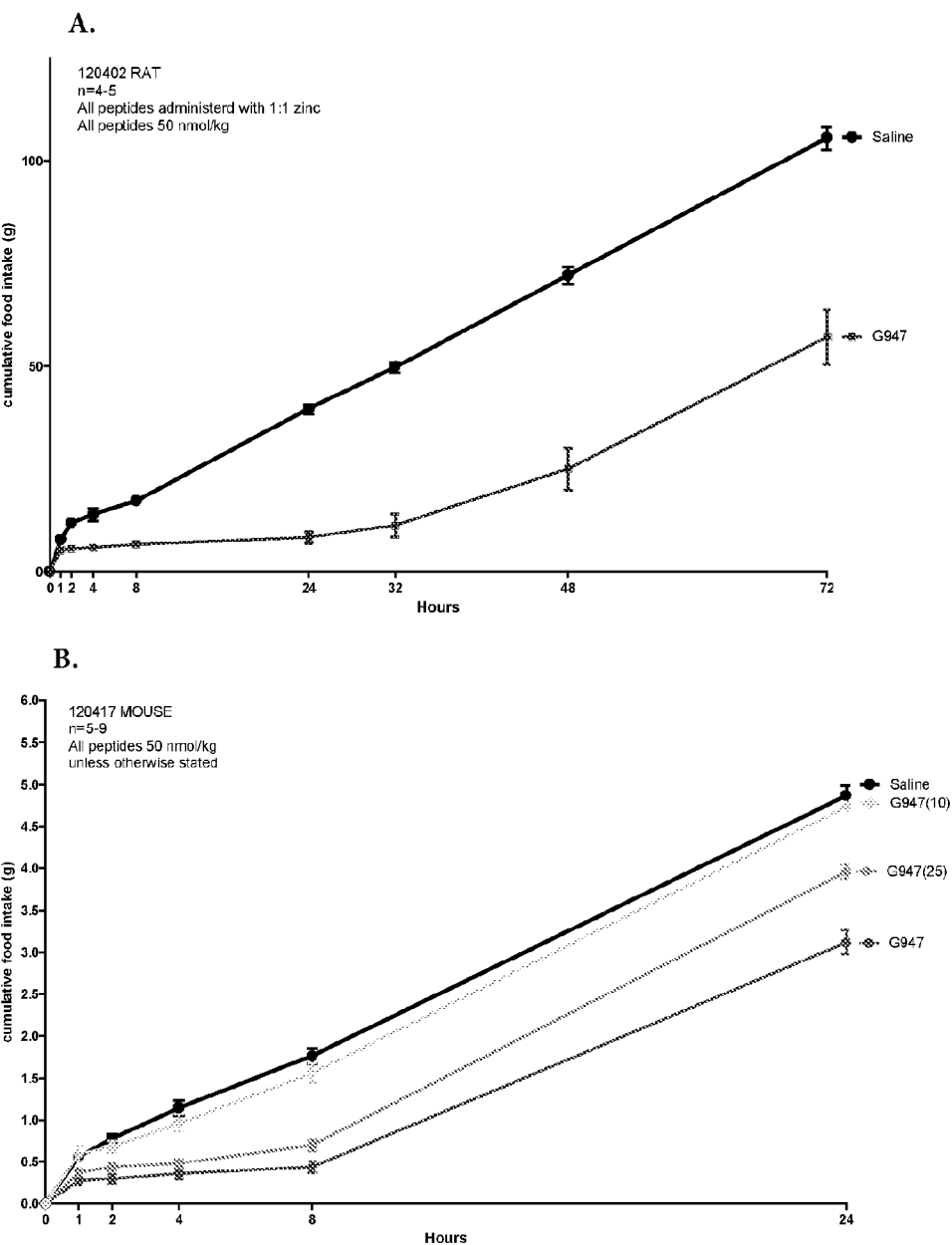
Figure 25:
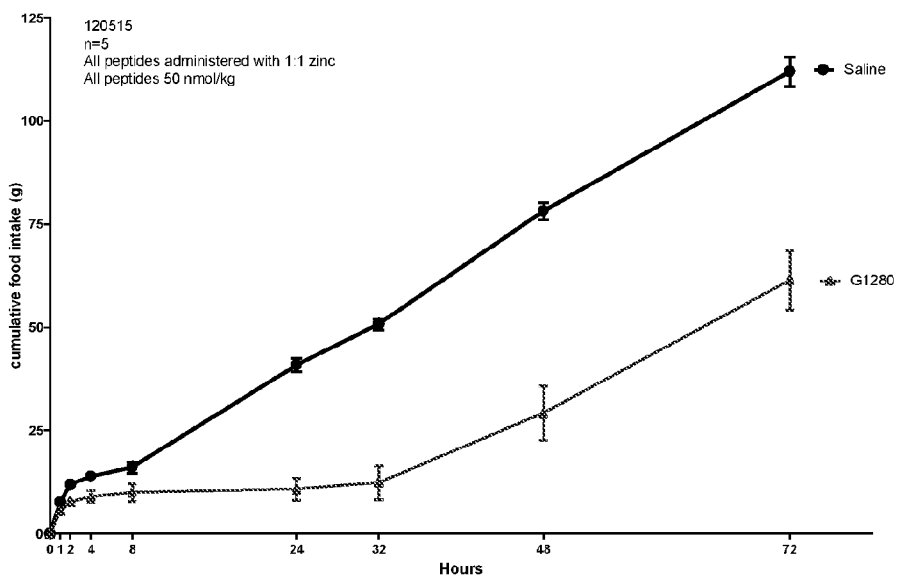
Figure 25:
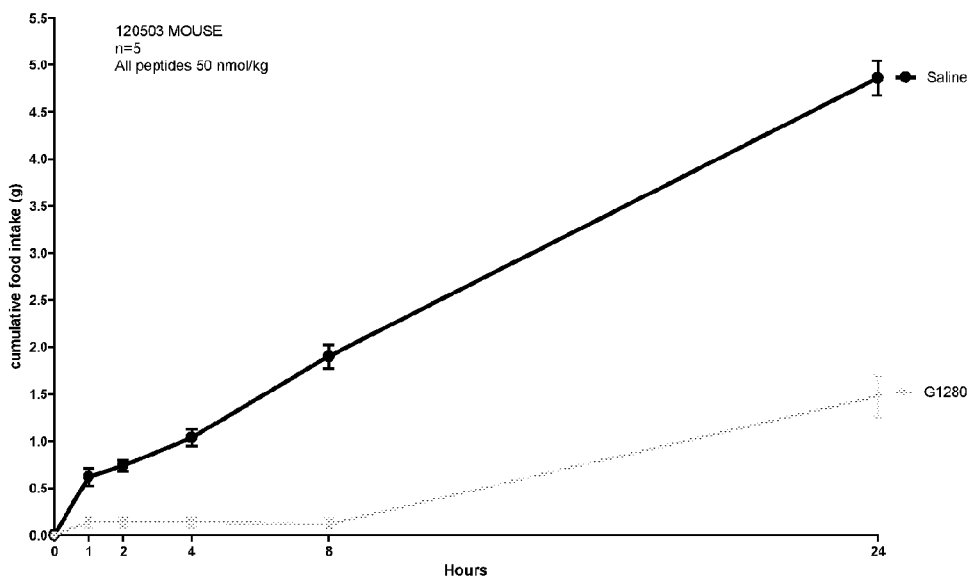
Figure 26:
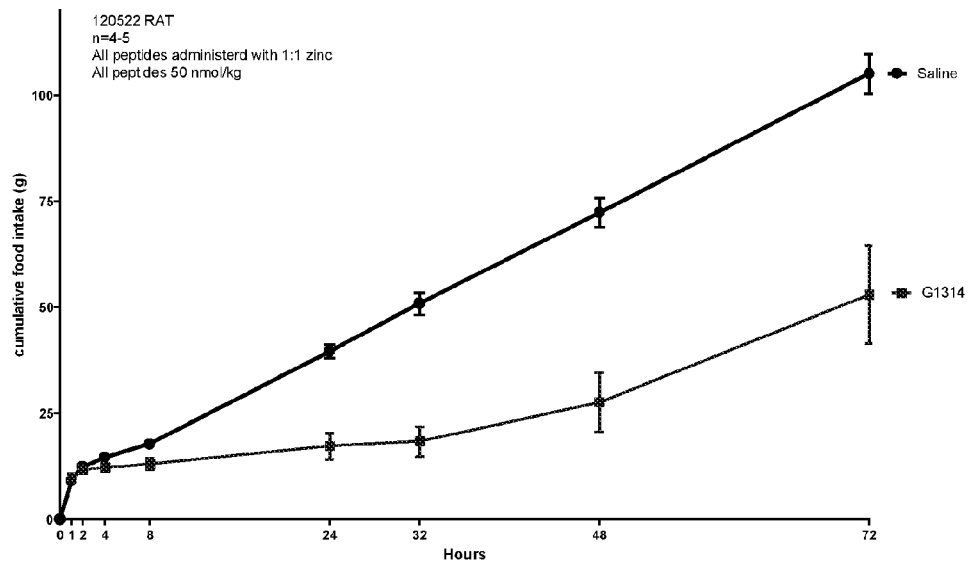
Figure 26:
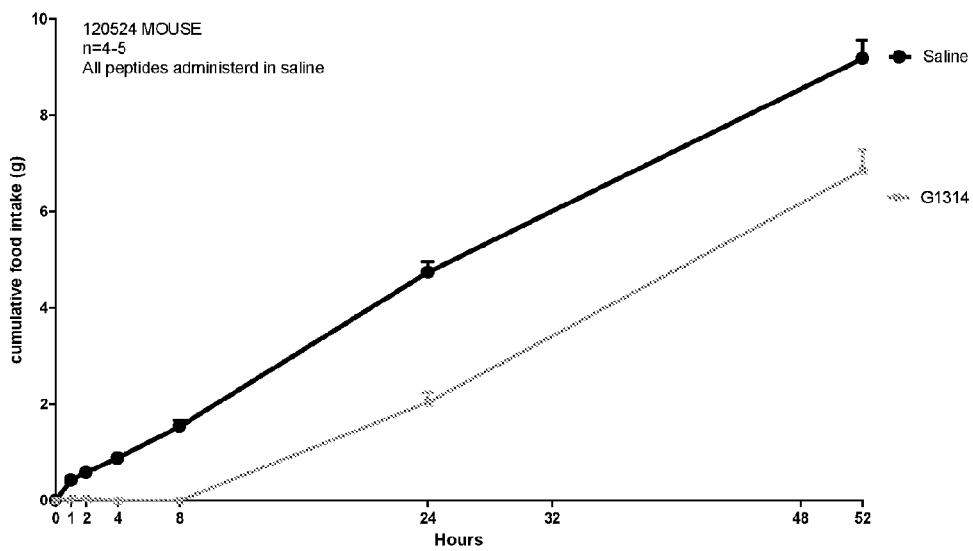
Figure 27:
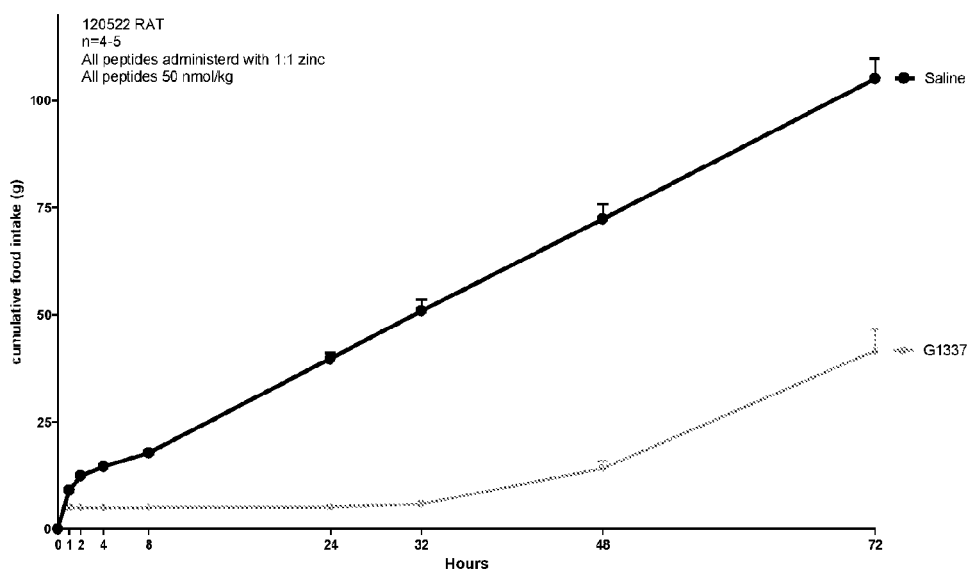
Figure 27:
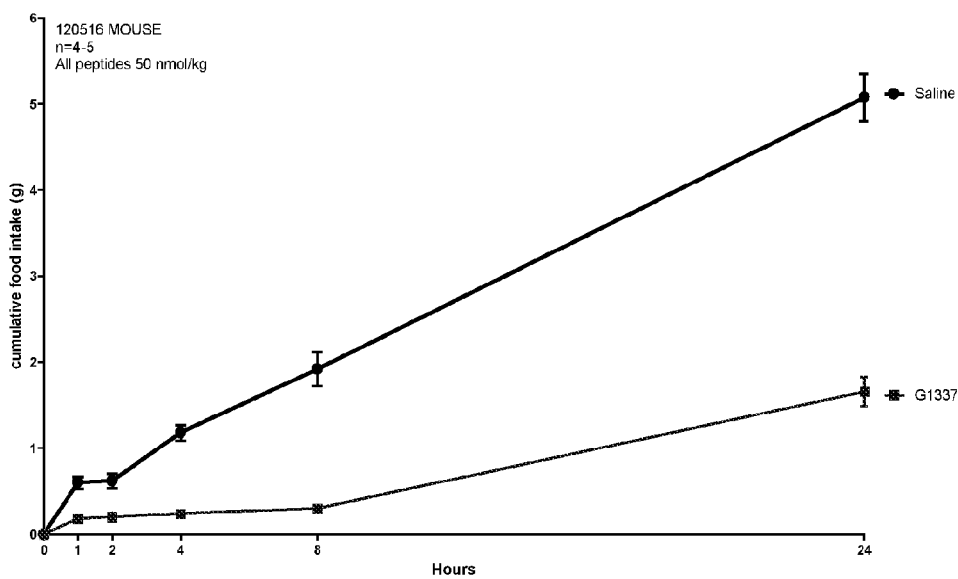
Figure 28:
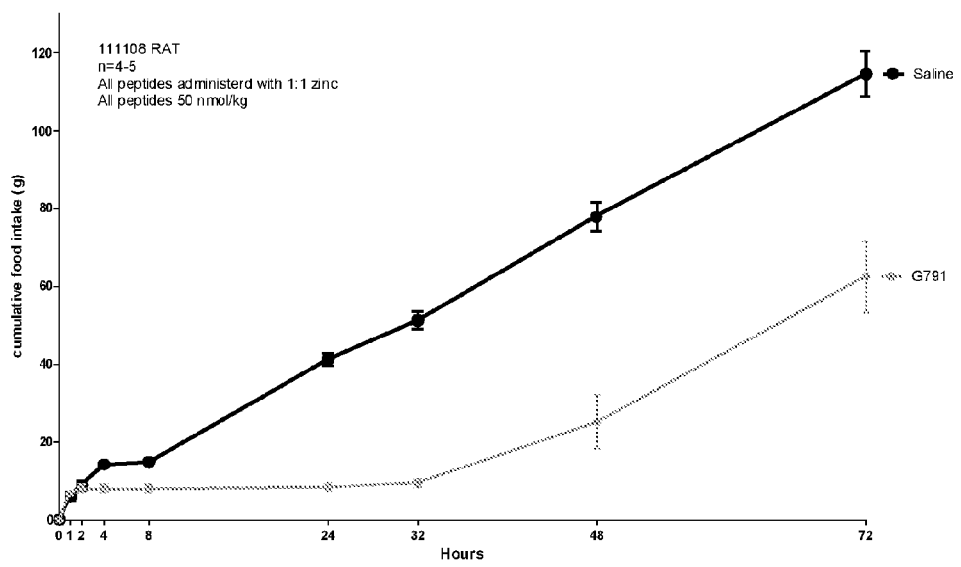
Figure 28:
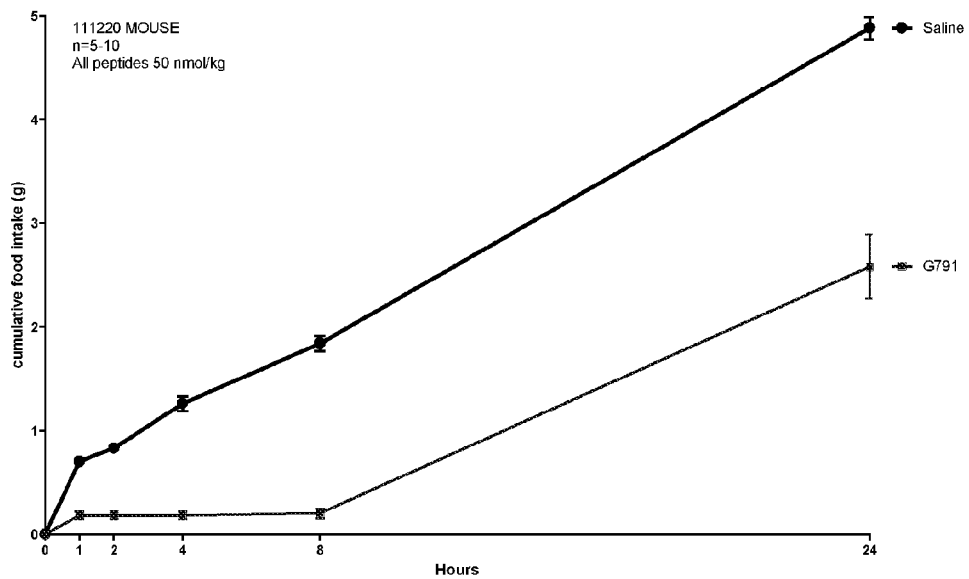
Figure 29:
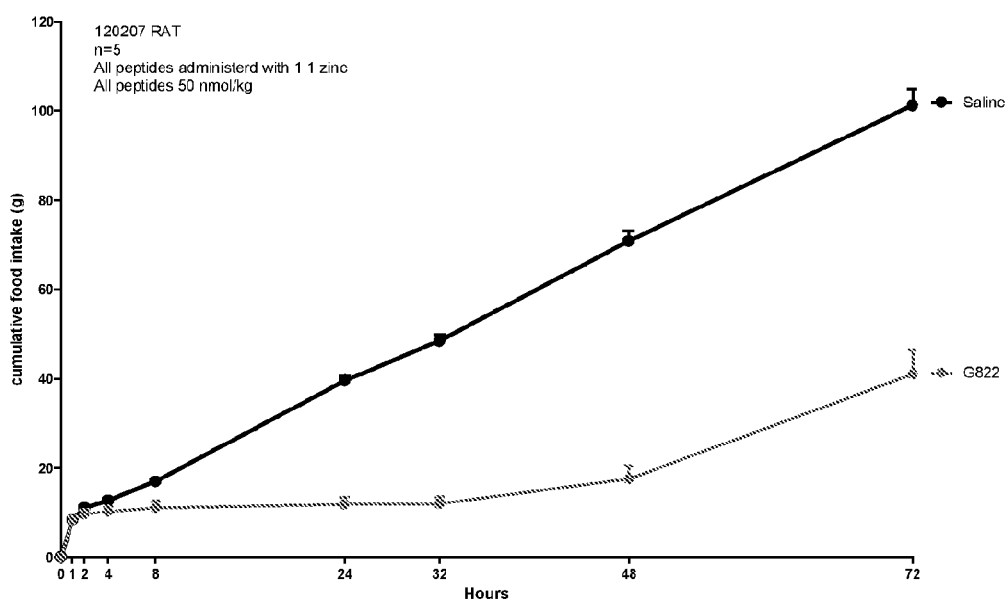
Figure 29:
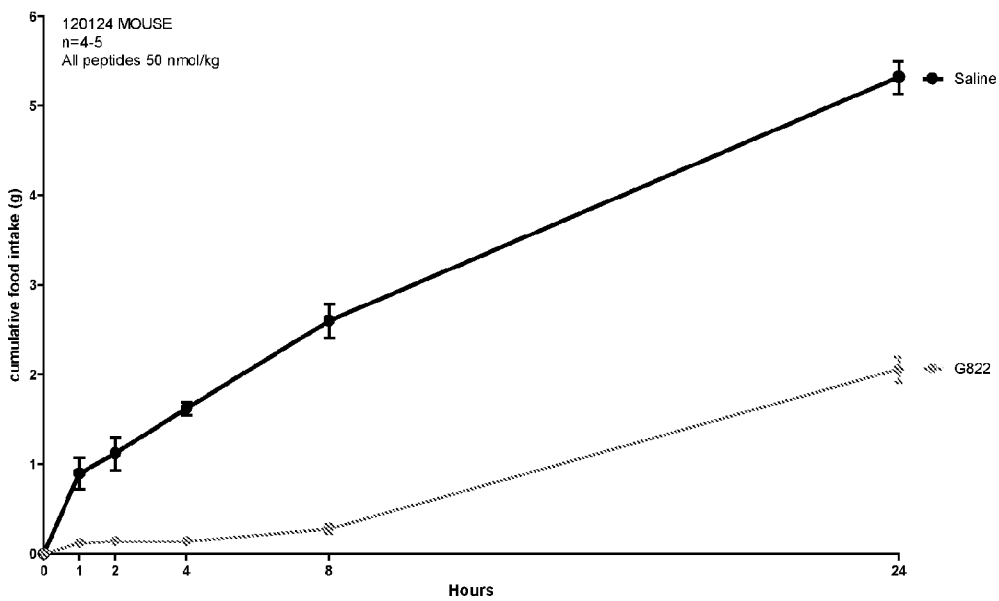
Figure 30:
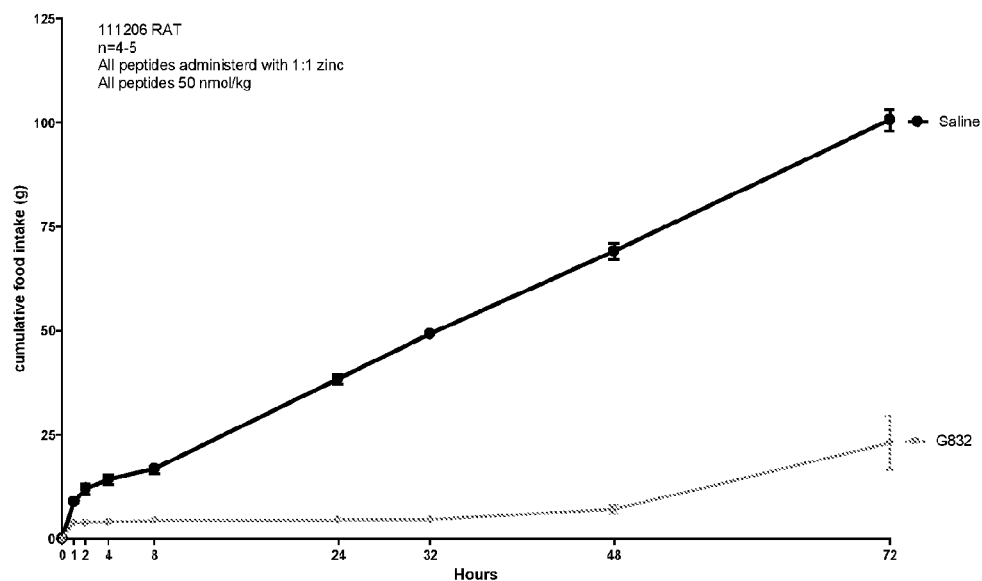
Figure 30:
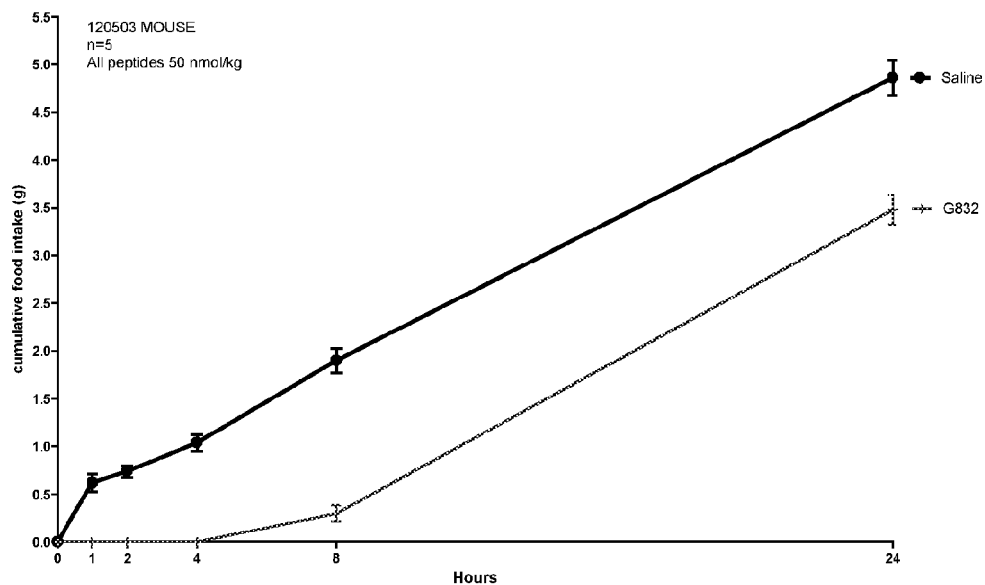
Figure 31:
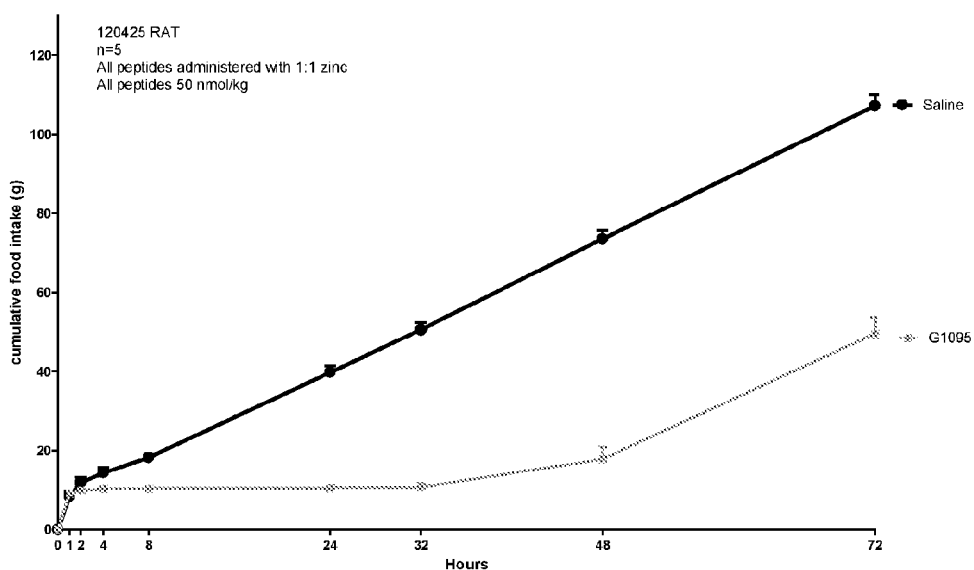
Figure 31:
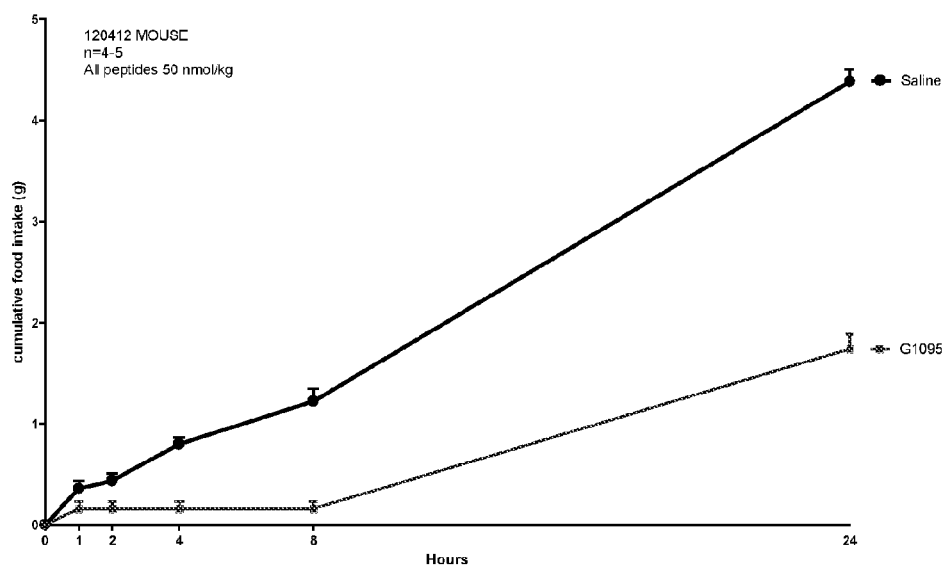
Figure 32:
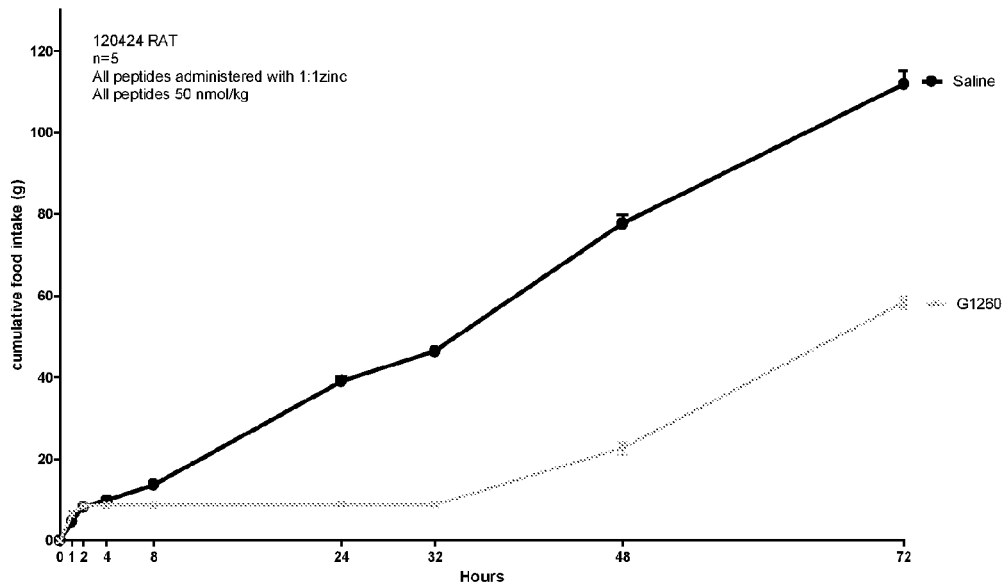
Figure 32:
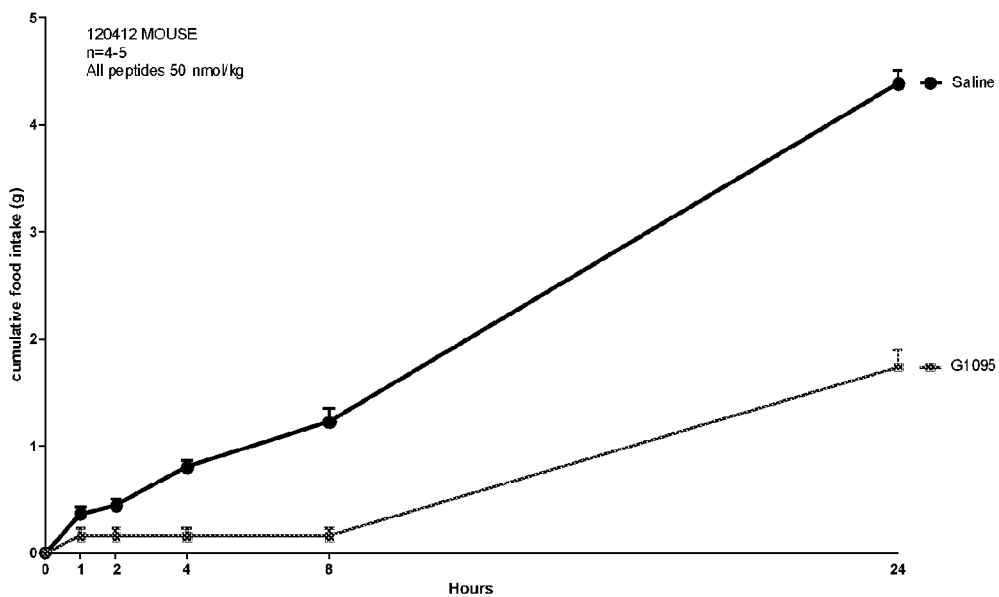
Figure 33:
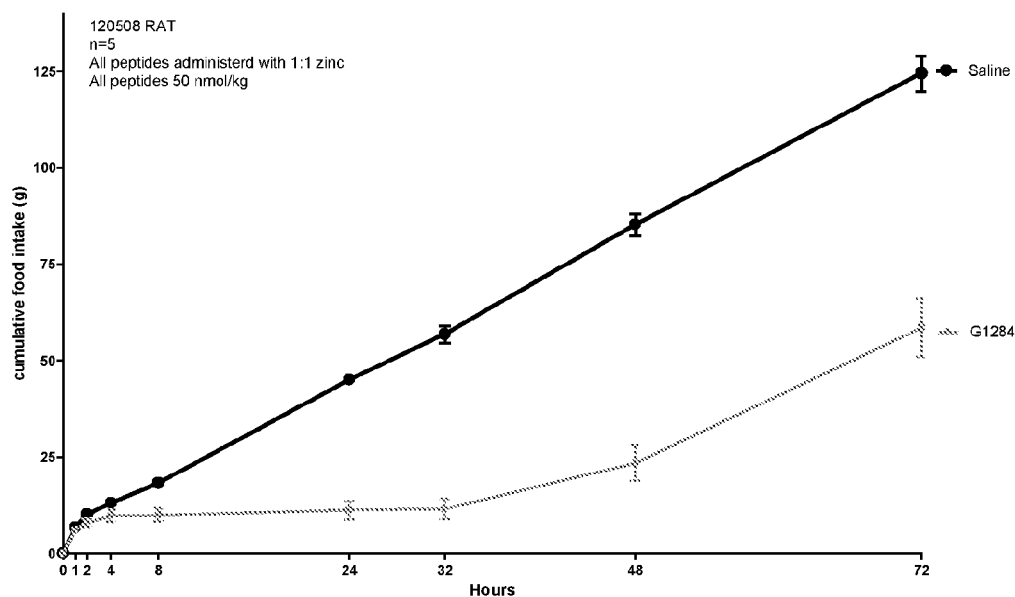
Figure 33:
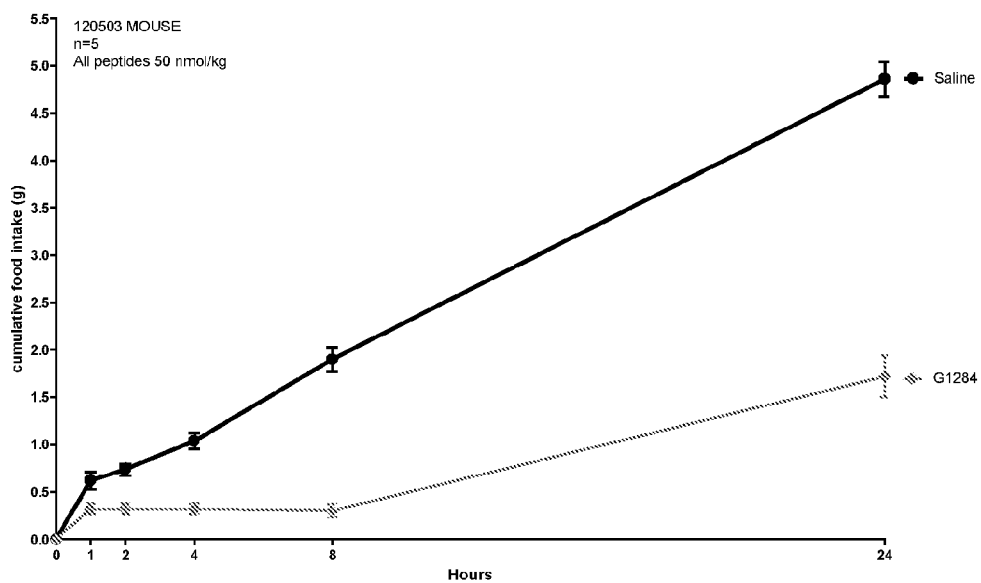
Figure 34:
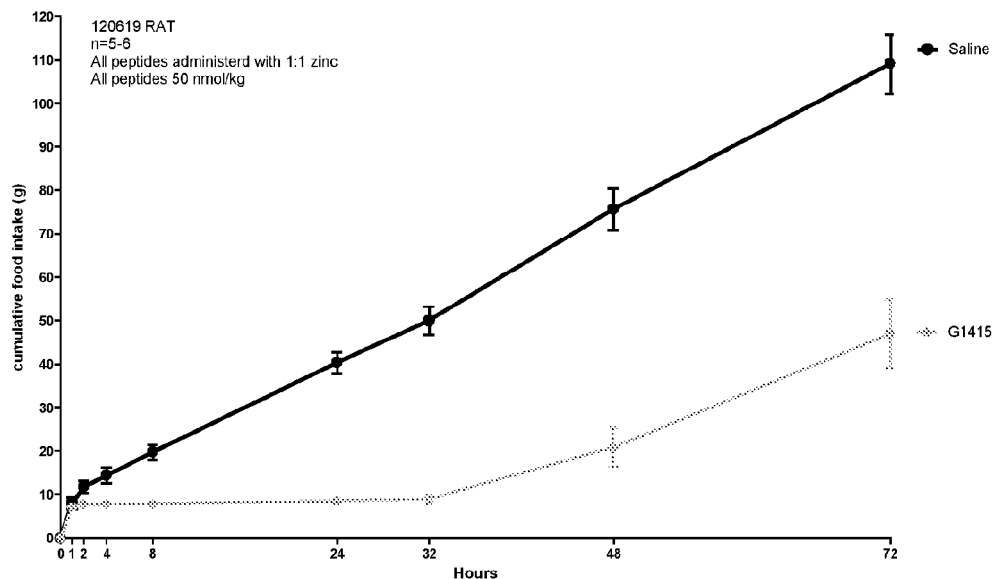
Figure 34:
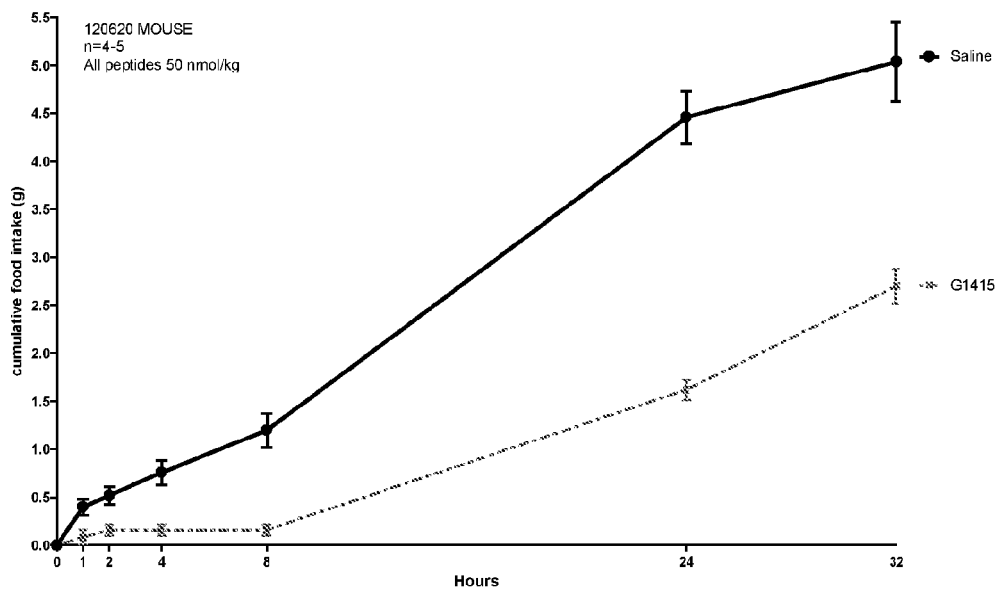

FIGS. 23 to 34 (top figures) show cumulative food intake over 72 hours for rats to which a GLP1 analogue of the invention had been administered, compared with cumulative food intake for rats to which saline had been administered. The GLP1 analogues showed a reduction in cumulative food intake compared with the saline control group.

EXAMPLE 5

Mice Feeding Studies—GLP1 Analogues

GLP1 analogues of the invention (50, 25 or 10 nmol/kg dosage, reconstituted in saline) (peptide group) or saline (vehicle control group) were administered subcutaneously to mice (5 animals in vehicle control group, 4-5 animals in peptide group). The animals had been fasted for 16 hours prior to administration. Food intake (in grams) was measured at time intervals over 24 hours.

FIGS. 23 to 34 (bottom figures) show cumulative food intake over 24 hours for mice to which a GLP1 analogue of the invention had been administered, compared with cumulative food intake for mice to which saline had been administered. The GLP1 analogues showed a reduction in cumulative food intake compared with the saline control group. In the case of G947 (analogue no. 141), a dose dependent response was observed following administration at 10 nmol/kg, 25 nmol/kg and 50 nmol/kg.

EXAMPLE 6

Rat Pharmacokinetic Studies—GLP Analogues

Figure 35:
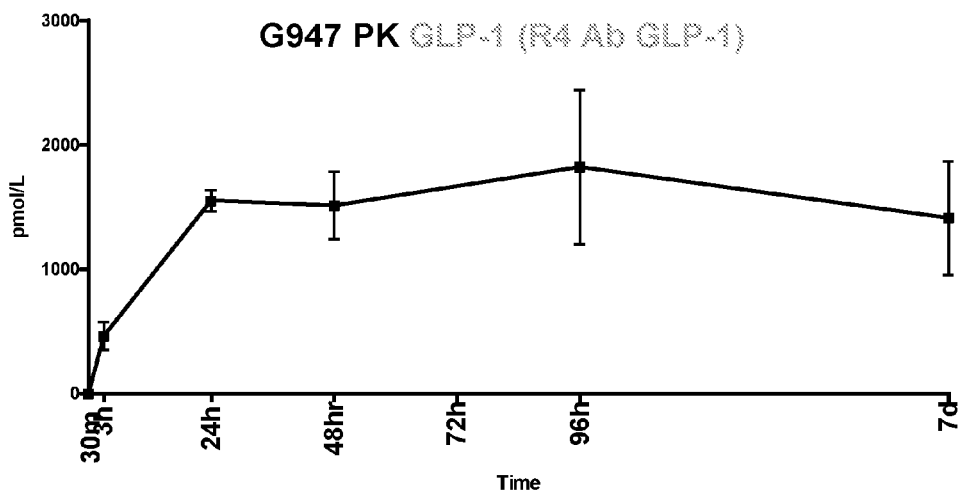
FIGS. 35 to 46 show the results of rat pharmacokinetic studies with selected GLP1 analogues of the invention.
Figure 36:
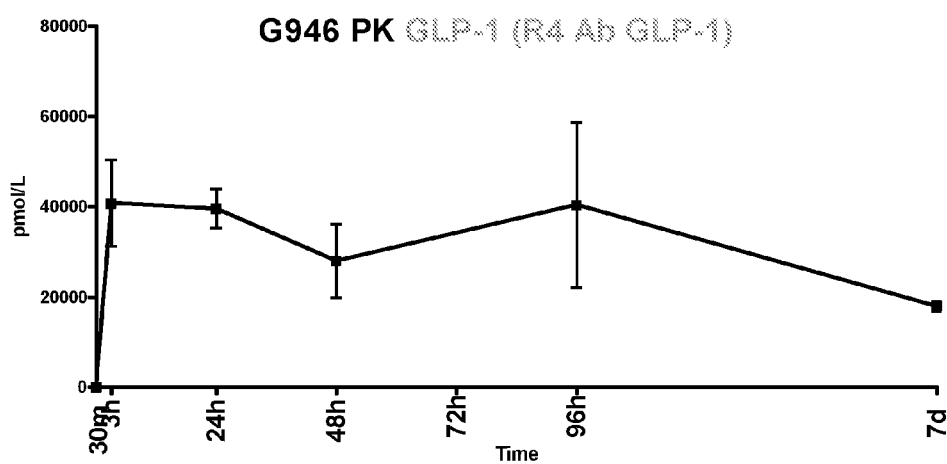
Figure 37:
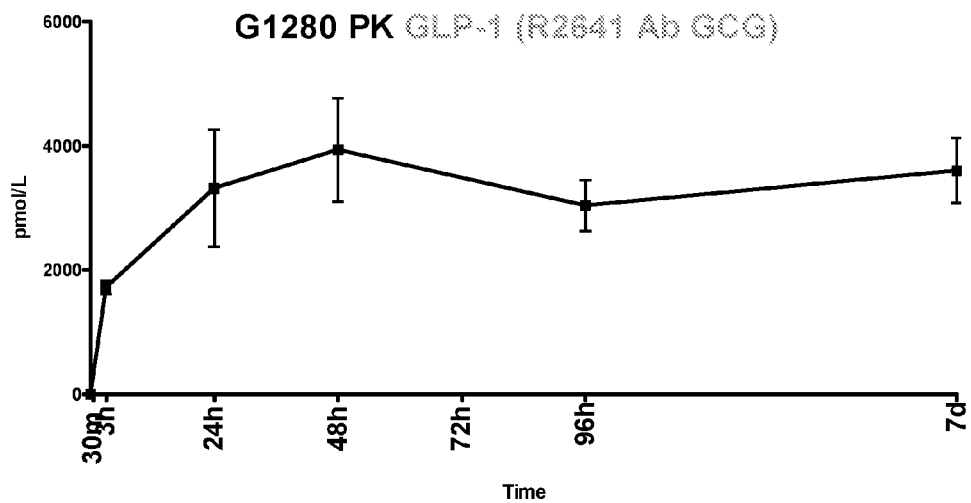
Figure 38:
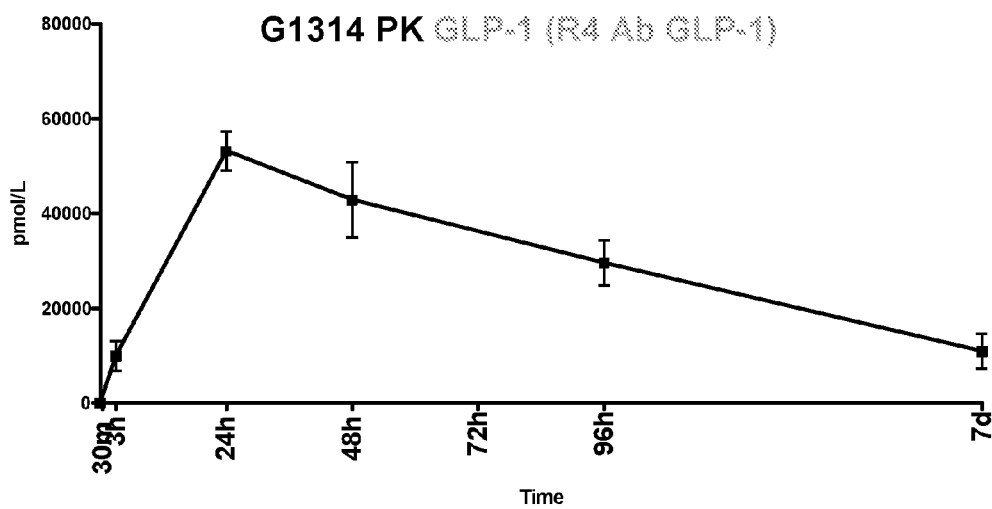
Figure 39:
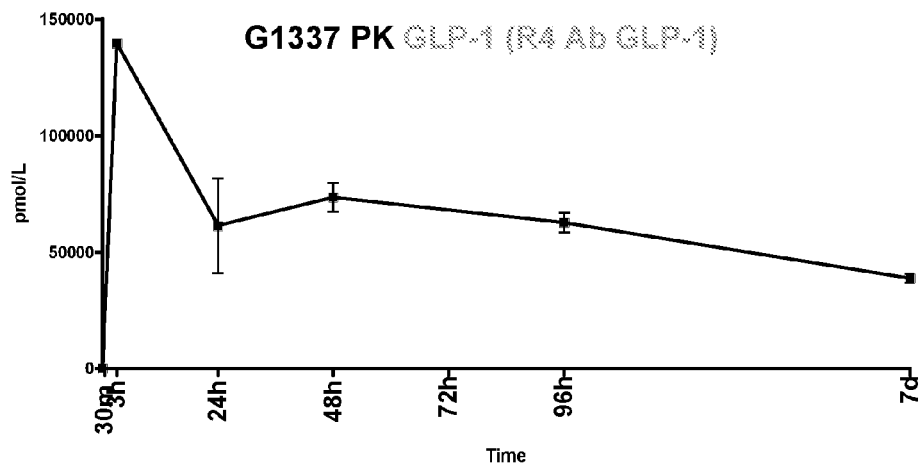
Figure 40:
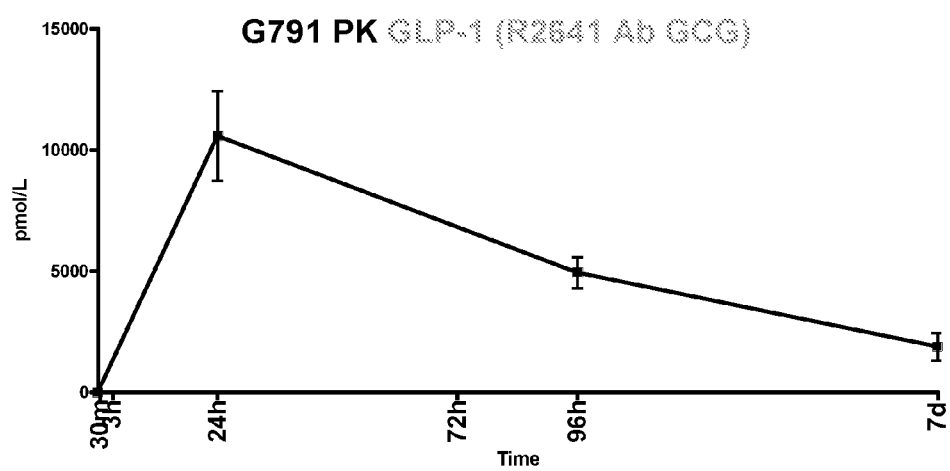
Figure 41:
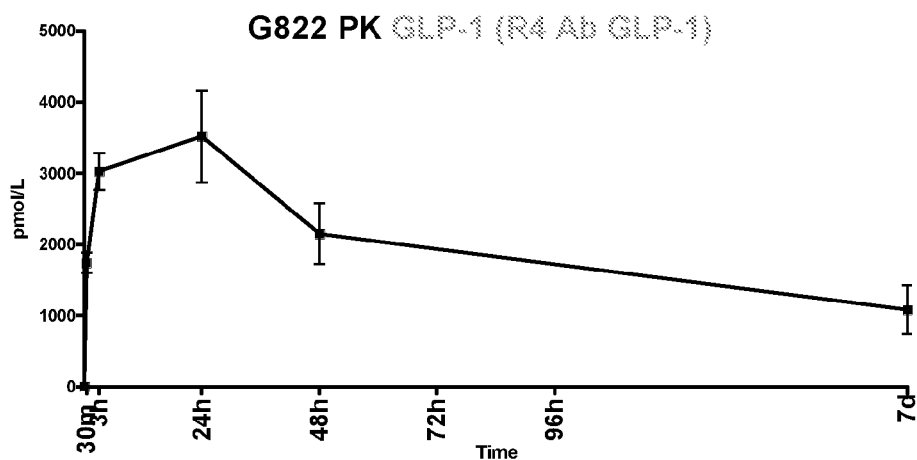
Figure 42:
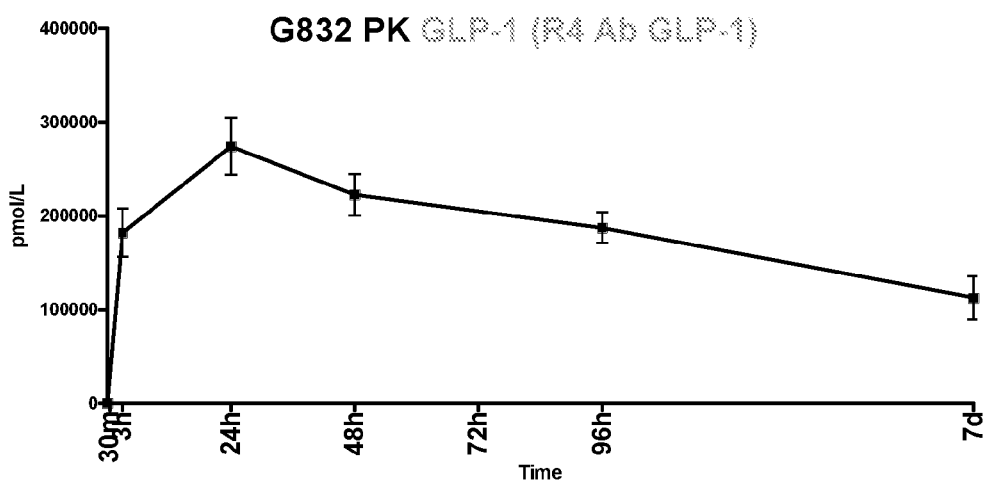
Figure 43:
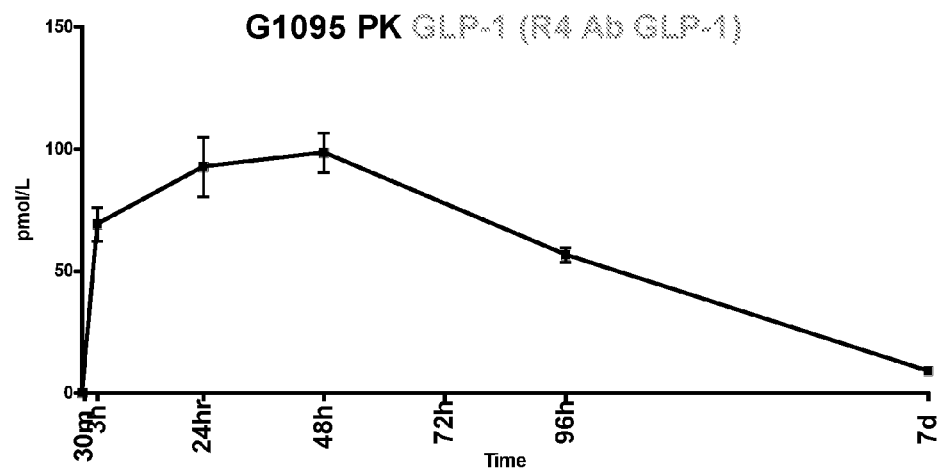
Figure 44:
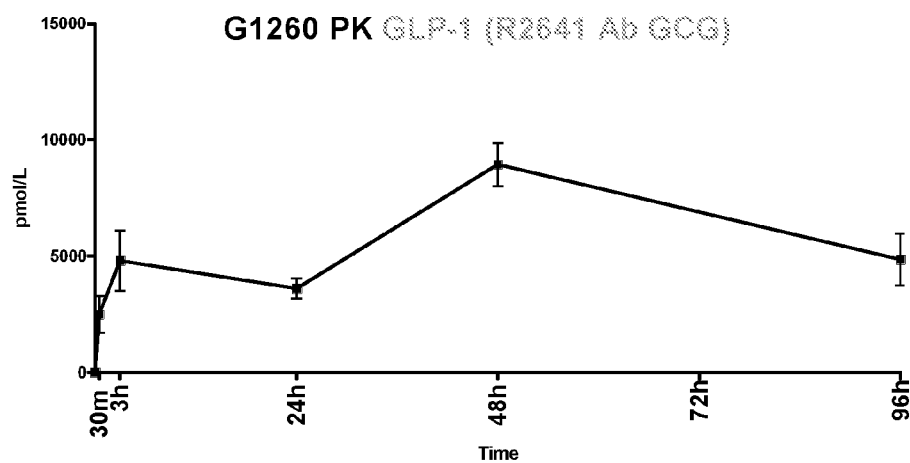
Figure 45:
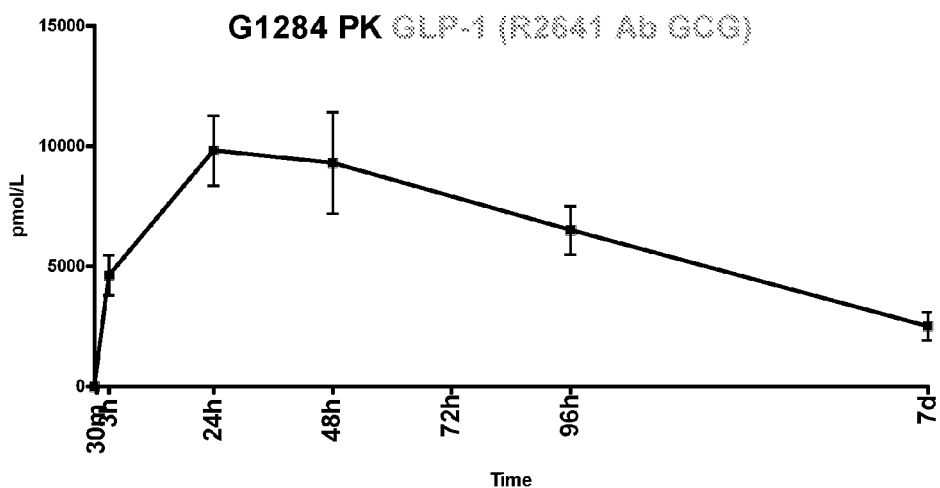
Figure 46:
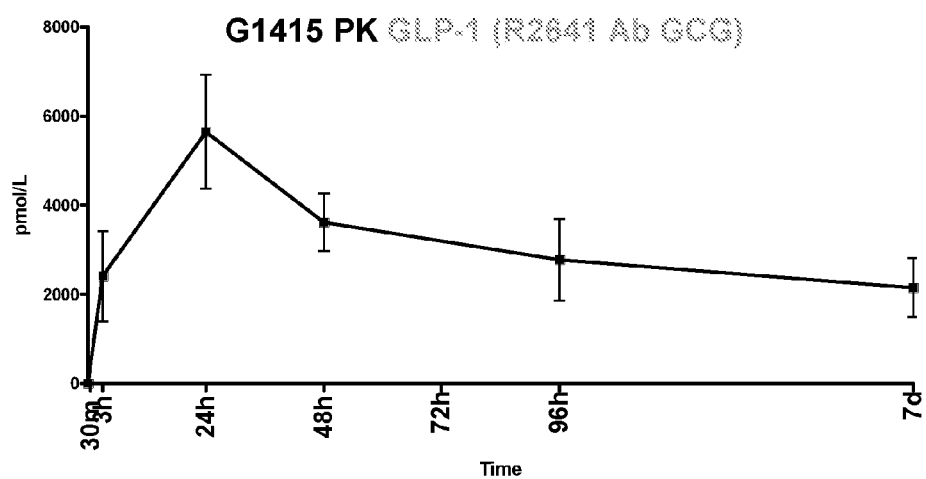

The pharmacokinetics of GLP1 analogues of the invention in rats over 7 day time periods were evaluated. Rats were injected subcutaneously with a GLP1 analogue. Each injection was of 20 µl total volume/rat containing 1 mg peptide and 1 zinc ion (as $ZnCl_2$) per peptide molecule. Blood was collected at the indicated time points, and the concentration of the GLP1 analogue was determined. Peptide levels were assessed radioimmunoassay using R4 exendin-4 antibody. The results are presented in FIGS. 35 to 46, and show that GLP1 analogues of the invention can achieve good in vivo pharmacokinetic profiles over extended periods of time.

The invention claimed is:

1. An analogue of glucagon which is:

a compound comprising the amino acid sequence represented by formula (I)

His-Ser-Gln-Gly-Thr-Phe-Thr-Ser-Asp-Xaa$^{10}$-Ser-Xaa$^{12}$-Xaa$^{13}$-Leu-Xaa$^{15}$-Xaa$^{16}$-Xaa$^{17}$-Xaa$^{18}$-Ala-Xaa$^{20}$-Xaa$^{21}$-Phe-Xaa$^{23}$-Xaa$^{24}$-Trp-Leu-Leu-Asn-Xaa$^{29}$-V     (I)

wherein V is selected from the group consisting of His (SEQ ID NO: 716), His-NH$_2$ (SEQ ID NO: 717), His-His (SEQ ID NO: 718), His-His-NH$_2$ (SEQ ID NO: 719), Gly-His (SEQ ID NO: 720), Gly-His-NH$_2$ (SEQ ID NO: 721), Lys-His (SEQ ID NO: 722), Lys-His-NH$_2$ (SEQ ID NO: 723), Gly-His-His (SEQ ID NO: 724), Gly-His-His-NH$_2$ (SEQ ID NO: 725), His-His-His (SEQ ID NO: 726) and His-His-His-NH$_2$ (SEQ ID NO: 727);

Xaa$^{10}$ is selected from the group consisting of Tyr and Leu;

Xaa$^{12}$ is selected from the group consisting of Lys, His and Arg;

Xaa$^{13}$ is selected from the group consisting of Tyr, Gln and His;

Xaa$^{15}$ is selected from the group consisting of Asp and Glu;

Xaa$^{16}$ is selected from the group consisting of Glu, Gln and Ser;

Xaa$^{17}$ is selected from the group consisting of Arg, His and Lys;

Xaa$^{18}$ is selected from the group consisting of Arg and Lys;

Xaa$^{20}$ is selected from the group consisting of His and Gln;

Xaa$^{21}$ is selected from the group consisting of Glu, His and Asp;

Xaa$^{23}$ is selected from the group consisting of Be and Val;

Xaa$^{24}$ is selected from the group consisting of Gln and Glu; and

Xaa$^{29}$ is selected from the group consisting of Thr and Gly; and wherein —NH$_2$ represents a C-terminal amide group; or a derivative of the compound;

or a salt of the compound or the derivative.

2. The analogue as claimed in claim 1, wherein Xaa$^{20}$ is His.

3. The analogue as claimed in claim 2, wherein Xaa$^{10}$ is Tyr and Xaa$^{16}$ is Ser.

4. The analogue as claimed in claim 1, wherein V is selected from the group consisting of His-His (SEQ ID NO: 718), His-His-NH$_2$ (SEQ ID NO: 719), Gly-His (SEQ ID NO: 720), and Gly-His-NH$_2$ (SEQ ID NO 721).

5. The analogue as claimed in claim 1, wherein Xaa$^{13}$ is Tyr.

6. The analogue as claimed in claim 1, wherein the compound consists of the amino acid sequence represented by formula (I).

7. The analogue as claimed in claim 1, wherein the analogue is selected from the group consisting of:

i) Xaa$^{10}$ is Tyr, Xaa$^{12}$ is Lys, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Thr and V is His-His (SEQ ID NO: 30);

ii) Xaa$^{10}$ is Tyr, Xaa$^{12}$ is Arg, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Thr and V is His-His-NH$_2$ (SEQ ID NO: 32);

iii) Xaa$^{10}$ is Tyr, Xaa$^{12}$ is Arg, Xaa$^{13}$ is His, Xaa$^{15}$ is Asp, Xaa$^{16}$ is Ser, Xaa$^{17}$ is Lys, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Thr and V is His-His-NH$_2$ (SEQ ID NO: 143);

iv) Xaa$^{10}$ is Tyr, Xaa$^{12}$ is Arg, Xaa$^{13}$ is Tyr, Xaa$^{15}$ is Asp, Xaa$^{16}$ is Ser, Xaa$^{17}$ is Lys, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Thr and V is Gly-His (SEQ ID NO: 157);

v) Xaa$^{10}$ is Tyr, Xaa$^{12}$ is Lys, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Gln, Xaa$^{29}$ is Gly and V is Gly-His (SEQ ID NO: 38);

vi) Xaa$^{10}$ is Tyr, Xaa$^{12}$ is Lys, Xaa$^{13}$ is Tyr, Xaa$^{15}$ is Glu, Xaa$^{16}$ is Ser, Xaa$^{17}$ is Arg, Xaa$^{18}$ is Lys, Xaa$^{20}$ is His, Xaa$^{21}$ is Glu, Xaa$^{23}$ is Ile, Xaa$^{24}$ is Glu, Xaa$^{29}$ is Thr and V is Gly-His (SEQ ID NO: 101);

vii) Xaa$^{10}$ is Tyr, Xaa$^{12}$ is Lys, Xaa$^{13}$ is Tyr, Xaa$^{15}$ is Asp, Xaa$^{16}$ is Ser, Xaa$^{17}$ is Arg, Xaa$^{18}$ is Arg, Xaa$^{20}$ is His, Xaa$^{21}$ is Glu, Xaa$^{23}$ is Val, Xaa$^{24}$ is Glu, Xaa$^{29}$ is Thr and V is Gly-His (SEQ ID NO: 79);

viii) $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Gly and V is Gly-His-NH$_2$ (SEQ ID NO: 117);

ix) $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Asp, $Xaa^{23}$ is Val, $Xaa^{24}$ is Glu, $Xaa^{29}$ is Thr and V is His-His-NH$_2$ (SEQ ID NO: 120); and x) $Xaa^{10}$ is Tyr, $Xaa^{12}$ is His, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V is Gly-His-NH$_2$ (SEQ ID NO: 130).

8. The analogue as claimed in claim 1, which is a derivative selected from the group consisting of amidation, glycosylation, carbamylation, acylation, sulfation, phosphorylation, cyclization, lipidization, pegylation and fusion to another peptide or protein to form a fusion protein.

9. The analogue as claimed in claim 1, which is not a derivative.

10. The analogue as claimed in claim 1, wherein said compound comprises any one of the amino acid sequences selected from the group consisting of SEQ ID NOS: 1-426.

11. A pharmaceutical composition comprising an analogue as claimed in claim 1, together with a pharmaceutically acceptable carrier and optionally other therapeutic ingredients.

12. The pharmaceutical composition as claimed in claim 11, together with said therapeutic ingredients, for simultaneous, sequential or separate administration.

13. The pharmaceutical composition as claimed in claim 11, present in a syringe or other administration device for subcutaneous administration to humans.

14. The pharmaceutical composition as claimed in claim 11, wherein the composition has a pH of less than 5 prior to administration and wherein the composition comprises zinc ions.

15. The analogue as claimed in claim 1, wherein $Xaa^{15}$ is Asp.

16. The analogue as claimed in claim 1, wherein $Xaa^{17}$ is Arg.

17. The analogue as claimed in claim 1, wherein $Xaa^{18}$ is Arg.

18. The analogue as claimed in claim 1, wherein $Xaa^{21}$ is Glu.

19. The analogue as claimed in claim 1, wherein $Xaa^{23}$ is Val.

20. A method of treating obesity or diabetes in a subject in need thereof comprising administration of a therapeutically effective amount of an analogue as claimed in claim 1.

21. The method as claimed in claim 20, wherein the subject is at least one of the following: overweight, obese, or diabetic.

22. A method of treating obesity or diabetes in a subject in need thereof comprising administration of a therapeutically effective amount of a pharmaceutical composition as claimed in claim 11.

23. The method as claimed in claim 22, wherein the subject is at least one of the following: overweight, obese, or diabetic.

* * * * *

UNITED STATES PATENT AND TRADEMARK OFFICE
CERTIFICATE OF CORRECTION

| | | |
|---|---|---|
| PATENT NO. | : 9,546,205 B2 | Page 1 of 1 |
| APPLICATION NO. | : 14/428599 | |
| DATED | : January 17, 2017 | |
| INVENTOR(S) | : Stephen Robert Bloom | |

It is certified that error appears in the above-identified patent and that said Letters Patent is hereby corrected as shown below:

In the Claims

In Claim 1, Column 427, Lines 59-60, delete:
"Xaa23 is selected from the group consisting of Be and Val;"
And insert therefor:
--Xaa23 is selected from the group consisting of Ile and Val;--

In Claim 8, Column 429, Lines 15-17, delete:
"glycosylation, carbamylation, acylation, sulfation, phosphorylation, cyclization, lipidization, pegylation and fusion to another peptide or protein to form a fusion protein."
And insert therefor:
--glycosylation, carbamylation, acylation, sulfation, phosphorylation, cyclization, lipidization, pegylation, and fusion to another peptide or protein to form a fusion protein.--

Signed and Sealed this
Twenty-sixth Day of June, 2018

Andrei Iancu
*Director of the United States Patent and Trademark Office*

SEQUENCE LISTING

```
<160> NUMBER OF SEQ ID NOS: 739

<210> SEQ ID NO 1
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 1

His Ser Gln Gly Thr Phe Thr Ser Asp Tyr Ser Lys Tyr Leu Glu Glu
1               5                   10                  15

Lys Lys Ala Gln Glu Phe Ile Glu Trp Leu Leu Asn Gly Gly His
```

20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Gly His
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 3

His Ser Gln Gly Thr Phe Thr Ser Asp Tyr Ser Lys Tyr Leu Asp Ser
1               5                   10                  15

Arg Arg Ala His Asp Phe Val Gln Trp Leu Leu Asn Thr His
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 4

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Thr His
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 5

His Ser Gln Gly Thr Phe Thr Ser Asp Tyr Ser Arg Tyr Leu Asp Ser
1               5                   10                  15

Lys Lys Ala Gln Glu Phe Val Gln Trp Leu Leu Asn Thr His
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Thr His
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 7

His Ser Gln Gly Thr Phe Thr Ser Asp Tyr Ser His Tyr Leu Asp Ser
1               5                   10                  15

Lys Lys Ala His Asp Phe Val Gln Trp Leu Leu Asn Thr His
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 8

His Ser Gln Gly Thr Phe Thr Ser Asp Tyr Ser Arg Tyr Leu Asp Ser
1               5                   10                  15

His Lys Ala Gln Glu Phe Val Gln Trp Leu Leu Asn Gly His His
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 9

His Ser Gln Gly Thr Phe Thr Ser Asp Tyr Ser Lys Tyr Leu Asp Ser
1               5                   10                  15

Arg Arg Ala His Asp Phe Val Gln Trp Leu Leu Asn Thr His His
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 10

His Ser Gln Gly Thr Phe Thr Ser Asp Tyr Ser Lys Tyr Leu Asp Ser
1               5                   10                  15

Arg Arg Ala His His Phe Val Gln Trp Leu Leu Asn Thr His
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 11

His Ser Gln Gly Thr Phe Thr Ser Asp Tyr Ser His Tyr Leu Asp Ser
1               5                   10                  15

Arg Arg Ala Gln His Phe Val Gln Trp Leu Leu Asn Thr His
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 12

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Thr His
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 13

His Ser Gln Gly Thr Phe Thr Ser Asp Tyr Ser Lys Tyr Leu Asp Ser

```
1               5                   10                  15
Arg Arg Ala His Asp Phe Val Gln Trp Leu Leu Asn Gly His
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 14

His Ser Gln Gly Thr Phe Thr Ser Asp Tyr Ser Lys Tyr Leu Asp Ser
1               5                   10                  15
Arg Arg Ala His Glu Phe Val Gln Trp Leu Leu Asn Thr His His
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Glucagon analogue

<400> SEQUENCE: 15

His Ser Gln Gly Thr Phe Thr Ser Asp Tyr Ser Lys Tyr Leu Asp Ser
1               5                   10                  15
Arg Arg Ala His Asp Phe Val Gln Trp Leu Leu Asn Thr His His
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 16

His Ser Gln Gly Thr Phe Thr Ser Asp Tyr Ser Lys Tyr Leu Asp Ser
1               5                   10                  15
Arg Arg Ala His Glu Phe Val Gln Trp Leu Leu Asn Gly His His
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Glucagon analogue

<400> SEQUENCE: 17

His Ser Gln Gly Thr Phe Thr Ser Asp Tyr Ser Lys Tyr Leu Asp Ser
1               5                   10                  15
Arg Arg Ala His Glu Phe Val Gln Trp Leu Leu Asn Gly His His
            20                  25                  30

<210> SEQ ID NO 18
```

```
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 18

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Thr Gly His
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 19

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Thr Gly His His
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 20

His Ser Gln Gly Thr Phe Thr Ser Asp Tyr Ser Arg Tyr Leu Asp Ser
1               5                   10                  15

Arg Arg Ala His Asp Phe Val Gln Trp Leu Leu Asn Thr His
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 21

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Thr His
            20                  25                  30
```

-continued

```
<210> SEQ ID NO 22
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 22

His Ser Gln Gly Thr Phe Thr Ser Asp Tyr Ser Lys Tyr Leu Glu Ser
1               5                   10                  15

Arg Arg Ala His Asp Phe Val Gln Trp Leu Leu Asn Thr His
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 23

His Ser Gln Gly Thr Phe Thr Ser Asp Tyr Ser Lys Tyr Leu Asp Ser
1               5                   10                  15

Arg Arg Ala His Asp Phe Val Glu Trp Leu Leu Asn Thr His
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 24

His Ser Gln Gly Thr Phe Thr Ser Asp Tyr Ser Lys Tyr Leu Asp Ser
1               5                   10                  15

Lys Lys Ala His Glu Phe Val Gln Trp Leu Leu Asn Thr His
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 25

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Gly His
            20                  25                  30
```

<210> SEQ ID NO 26
<211> LENGTH: 31
<212> TYPE: PRT
<213> ORGANISM: Artificial Sequence
<220> FEATURE:
<223> OTHER INFORMATION: Glucagon analogue

<400> SEQUENCE: 26

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Thr His His
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 27

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Thr His His
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Glucagon analogue

<400> SEQUENCE: 28

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Thr His
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 29

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Thr His His
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Glucagon analogue

```
<400> SEQUENCE: 30

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Thr His His
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Glucagon analogue

<400> SEQUENCE: 31

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Thr His His His
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 32

His Ser Gln Gly Thr Phe Thr Ser Asp Tyr Ser Arg Tyr Leu Asp Ser
1               5                   10                  15

Arg Arg Ala His Glu Phe Val Gln Trp Leu Leu Asn Thr His His
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 33

His Ser Gln Gly Thr Phe Thr Ser Asp Tyr Ser Lys Tyr Leu Asp Ser
1               5                   10                  15

Lys Lys Ala His Glu Phe Val Gln Trp Leu Leu Asn Thr His His
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 34
```

-continued

```
His Ser Gln Gly Thr Phe Thr Ser Asp Tyr Ser Lys Tyr Leu Asp Ser
1               5                   10                  15

Arg Arg Ala His His Phe Val Gln Trp Leu Leu Asn Thr His His
            20                  25                  30
```

<210> SEQ ID NO 35
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 35

```
His Ser Gln Gly Thr Phe Thr Ser Asp Tyr Ser Lys Tyr Leu Asp Ser
1               5                   10                  15

Arg Arg Ala His Glu Phe Val Glu Trp Leu Leu Asn Thr His His
            20                  25                  30
```

<210> SEQ ID NO 36
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 36

```
His Ser Gln Gly Thr Phe Thr Ser Asp Tyr Ser Lys Tyr Leu Glu Ser
1               5                   10                  15

Arg Arg Ala Gln Asp Phe Ile Glu Trp Leu Leu Asn Gly Gly His
            20                  25                  30
```

<210> SEQ ID NO 37
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 37

```
His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Gly Gly His
            20                  25                  30
```

<210> SEQ ID NO 38
<211> LENGTH: 31
<212> TYPE: PRT
<213> ORGANISM: Artificial Sequence
<220> FEATURE:
<223> OTHER INFORMATION: Glucagon analogue

<400> SEQUENCE: 38

```
His Ser Gln Gly Thr Phe Thr Ser Asp Tyr Ser Lys Tyr Leu Asp Ser
1               5                   10                  15
```

-continued

Arg Arg Ala His Glu Phe Val Gln Trp Leu Leu Asn Gly Gly His
          20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Glucagon analogue

<400> SEQUENCE: 39

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Thr Gly His
          20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 40

His Ser Gln Gly Thr Phe Thr Ser Asp Tyr Ser His Tyr Leu Asp Ser
1               5                   10                  15

Arg Arg Ala Gln Asp Phe Val Gln Trp Leu Leu Asn Thr His
          20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Glucagon analogue

<400> SEQUENCE: 41

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Thr Gly His
          20                  25                  30

<210> SEQ ID NO 42
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 42

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Thr Gly His
          20                  25                  30

<210> SEQ ID NO 43
<211> LENGTH: 30
<212> TYPE: PRT

```
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 43

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Thr His
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 44

His Ser Gln Gly Thr Phe Thr Ser Asp Tyr Ser His Tyr Leu Asp Ser
1               5                   10                  15

Lys Lys Ala His Glu Phe Val Glu Trp Leu Leu Asn Thr His
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 45

His Ser Gln Gly Thr Phe Thr Ser Asp Tyr Ser His Tyr Leu Asp Ser
1               5                   10                  15

Lys Lys Ala His Glu Phe Val Glu Trp Leu Leu Asn Gly His
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 46

His Ser Gln Gly Thr Phe Thr Ser Asp Tyr Ser His Tyr Leu Glu Ser
1               5                   10                  15

Lys Lys Ala His Glu Phe Val Glu Trp Leu Leu Asn Gly His
            20                  25                  30

<210> SEQ ID NO 47
<211> LENGTH: 30
```

```
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 47

His Ser Gln Gly Thr Phe Thr Ser Asp Tyr Ser His Tyr Leu Glu Ser
1               5                   10                  15

Lys Lys Ala His Glu Phe Ile Glu Trp Leu Leu Asn Gly His
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 48

His Ser Gln Gly Thr Phe Thr Ser Asp Tyr Ser His Tyr Leu Asp Ser
1               5                   10                  15

Lys Lys Ala His Glu Phe Val Gln Trp Leu Leu Asn Thr His
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Glucagon analogue

<400> SEQUENCE: 49

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Gly Gly His
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 50

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Gly Gly
            20                  25                  30

<210> SEQ ID NO 51
<211> LENGTH: 31
<212> TYPE: PRT
<213> ORGANISM: Artificial Sequence
<220> FEATURE:
```

-continued

<223> OTHER INFORMATION: Glucagon analogue

<400> SEQUENCE: 51

His Ser Gln Gly Thr Phe Thr Ser Asp Tyr Ser His Tyr Leu Asp Ser
1               5                   10                  15

Lys Lys Ala His Glu Phe Val Glu Trp Leu Leu Asn Gly Gly His
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Glucagon analogue

<400> SEQUENCE: 52

His Ser Gln Gly Thr Phe Thr Ser Asp Tyr Ser His Tyr Leu Glu Ser
1               5                   10                  15

Arg Arg Ala His Glu Phe Val Gln Trp Leu Leu Asn Gly Gly His
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Glucagon analogue

<400> SEQUENCE: 53

His Ser Gln Gly Thr Phe Thr Ser Asp Tyr Ser His Tyr Leu Glu Ser
1               5                   10                  15

Lys Lys Ala His Glu Phe Val Glu Trp Leu Leu Asn Gly Gly His
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Glucagon analogue

<400> SEQUENCE: 54

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Thr His
            20                  25              30

<210> SEQ ID NO 55
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 55

His Ser Gln Gly Thr Phe Thr Ser Asp Tyr Ser His Tyr Leu Glu Ser
1               5                   10                  15

Arg Arg Ala His Glu Phe Val Glu Trp Leu Leu Asn Thr His
            20                  25              30

```
<210> SEQ ID NO 56
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 56

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Gly His
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Glucagon analogue

<400> SEQUENCE: 57

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Gly His
            20                  25                  30

<210> SEQ ID NO 58
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 58

His Ser Gln Gly Thr Phe Thr Ser Asp Tyr Ser His Tyr Leu Asp Ser
1               5                   10                  15

Lys Arg Ala His Glu Phe Val Glu Trp Leu Leu Asn Gly His
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Glucagon analogue

<400> SEQUENCE: 59

His Ser Gln Gly Thr Phe Thr Ser Asp Tyr Ser His Tyr Leu Asp Ser
1               5                   10                  15

Lys Arg Ala His Glu Phe Val Glu Trp Leu Leu Asn Gly Gly His
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Glucagon analogue
<220> FEATURE:
```

```
<221> NAME/KEY: MOD_RES
<222> LOCATION: (30)..(30)
<223> OTHER INFORMATION: AMIDATION

<400> SEQUENCE: 60

His Ser Gln Gly Thr Phe Thr Ser Asp Tyr Ser Lys Tyr Leu Asp Glu
1               5                   10                  15

Arg Arg Ala His Asp Phe Val Gln Trp Leu Leu Asn Thr His
            20                  25                  30

<210> SEQ ID NO 61
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 61

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr His
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 62

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly His
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 63

His Ser Gln Gly Thr Phe Thr Ser Asp Tyr Ser Lys Tyr Leu Asp Glu
1               5                   10                  15

Lys Arg Ala His Glu Phe Val Glu Trp Leu Leu Asn Gly His
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Glucagon analogue
```

```
<400> SEQUENCE: 64

His Ser Gln Gly Thr Phe Thr Ser Asp Tyr Ser His Tyr Leu Asp Ser
1               5                   10                  15

Arg Arg Ala His Asp Phe Val Gln Trp Leu Leu Asn Gly Gly His
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Glucagon analogue

<400> SEQUENCE: 65

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Gly Gly His
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: Glucagon analogue

<400> SEQUENCE: 66

His Ser Gln Gly Thr Phe Thr Ser Asp Tyr Ser His Tyr Leu Asp Ser
1               5                   10                  15

Lys Lys Ala His Glu Phe Ile Glu Trp Leu Leu Asn Gly Gly His
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Glucagon analogue

<400> SEQUENCE: 67

His Ser Gln Gly Thr Phe Thr Ser Asp Tyr Ser His Tyr Leu Asp Ser
1               5                   10                  15

Arg Arg Ala His Asp Phe Val Glu Trp Leu Leu Asn Thr His
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 68

His Ser Gln Gly Thr Phe Thr Ser Asp Tyr Ser His Tyr Leu Asp Ser
1               5                   10                  15

Arg Arg Ala His Asp Phe Val Glu Trp Leu Leu Asn Thr His
            20                  25                  30

<210> SEQ ID NO 69
```

<211> LENGTH: 31
<212> TYPE: PRT
<213> ORGANISM: Artificial Sequence
<220> FEATURE:
<223> OTHER INFORMATION: Glucagon analogue

<400> SEQUENCE: 69

His Ser Gln Gly Thr Phe Thr Ser Asp Tyr Ser His Tyr Leu Asp Ser
1               5                   10                  15

Arg Arg Ala His Asp Phe Val Glu Trp Leu Leu Asn Gly Gly His
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Glucagon analogue

<400> SEQUENCE: 70

His Ser Gln Gly Thr Phe Thr Ser Asp Tyr Ser His Tyr Leu Asp Ser
1               5                   10                  15

Arg Arg Ala His Asp Phe Val Glu Trp Leu Leu Asn Thr Gly His
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 71

His Ser Gln Gly Thr Phe Thr Ser Asp Tyr Ser His Tyr Leu Asp Ser
1               5                   10                  15

Lys Arg Ala His Asp Phe Val Glu Trp Leu Leu Asn Thr His
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Glucagon analogue

<400> SEQUENCE: 72

His Ser Gln Gly Thr Phe Thr Ser Asp Tyr Ser His Tyr Leu Asp Ser
1               5                   10                  15

Lys Lys Ala His Asp Phe Val Glu Trp Leu Leu Asn Gly Gly His
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 73

His Ser Gln Gly Thr Phe Thr Ser Asp Leu Ser His Tyr Leu Asp Ser
1               5                   10                  15

Lys Arg Ala His Asp Phe Val Glu Trp Leu Leu Asn Thr His
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 74

His Ser Gln Gly Thr Phe Thr Ser Asp Leu Ser His Gln Leu Asp Ser
1               5                   10                  15

Lys Arg Ala His Asp Phe Val Glu Trp Leu Leu Asn Thr His
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 75

His Ser Gln Gly Thr Phe Thr Ser Asp Tyr Ser His Tyr Leu Asp Ser
1               5                   10                  15

Lys Arg Ala His Asp Phe Ile Glu Trp Leu Leu Asn Thr His
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 76

His Ser Gln Gly Thr Phe Thr Ser Asp Tyr Ser His Tyr Leu Asp Ser
1               5                   10                  15

Arg Arg Ala His Asp Phe Val Glu Trp Leu Leu Asn Gly His
            20                  25                  30

<210> SEQ ID NO 77
<211> LENGTH: 31
<212> TYPE: PRT
<213> ORGANISM: Artificial Sequence
<220> FEATURE:
<223> OTHER INFORMATION: Glucagon analogue

<400> SEQUENCE: 77

His Ser Gln Gly Thr Phe Thr Ser Asp Tyr Ser His Tyr Leu Asp Ser
1               5                   10                  15

```
Arg Arg Ala His Asp Phe Val Glu Trp Leu Leu Asn Thr His His
        20                  25                  30
```

<210> SEQ ID NO 78
<211> LENGTH: 30
<212> TYPE: PRT
<213> ORGANISM: Artificial Sequence
<220> FEATURE:
<223> OTHER INFORMATION: Glucagon analogue

<400> SEQUENCE: 78

```
His Ser Gln Gly Thr Phe Thr Ser Asp Tyr Ser His Tyr Leu Asp Ser
1               5                   10                  15

Arg Arg Ala His Asp Phe Val Glu Trp Leu Leu Asn Gly His
        20                  25                  30
```

<210> SEQ ID NO 79
<211> LENGTH: 31
<212> TYPE: PRT
<213> ORGANISM: Artificial Sequence
<220> FEATURE:
<223> OTHER INFORMATION: Glucagon analogue

<400> SEQUENCE: 79

```
His Ser Gln Gly Thr Phe Thr Ser Asp Tyr Ser Lys Tyr Leu Asp Ser
1               5                   10                  15

Arg Arg Ala His Glu Phe Val Glu Trp Leu Leu Asn Thr Gly His
        20                  25                  30
```

<210> SEQ ID NO 80
<211> LENGTH: 31
<212> TYPE: PRT
<213> ORGANISM: Artificial Sequence
<220> FEATURE:
<223> OTHER INFORMATION: Glucagon analogue

<400> SEQUENCE: 80

```
His Ser Gln Gly Thr Phe Thr Ser Asp Tyr Ser Lys Tyr Leu Asp Ser
1               5                   10                  15

Lys Arg Ala His Glu Phe Val Glu Trp Leu Leu Asn Thr Gly His
        20                  25                  30
```

<210> SEQ ID NO 81
<211> LENGTH: 31
<212> TYPE: PRT
<213> ORGANISM: Artificial Sequence
<220> FEATURE:
<223> OTHER INFORMATION: Glucagon analogue

<400> SEQUENCE: 81

```
His Ser Gln Gly Thr Phe Thr Ser Asp Tyr Ser Arg Tyr Leu Asp Ser
1               5                   10                  15

Lys Arg Ala His Glu Phe Ile Glu Trp Leu Leu Asn Thr Gly His
        20                  25                  30
```

<210> SEQ ID NO 82
<211> LENGTH: 31
<212> TYPE: PRT
<213> ORGANISM: Artificial Sequence
<220> FEATURE:
<223> OTHER INFORMATION: Glucagon analogue

<400> SEQUENCE: 82

```
His Ser Gln Gly Thr Phe Thr Ser Asp Tyr Ser Arg Tyr Leu Asp Ser
```

-continued

```
1               5                   10                  15
Lys Lys Ala His Glu Phe Ile Glu Trp Leu Leu Asn Thr Gly His
            20                  25                  30

<210> SEQ ID NO 83
<211> LENGTH: 31
<212> TYPE: PRT
<213> ORGANISM: Artificial Sequence
<220> FEATURE:
<223> OTHER INFORMATION: Glucagon analogue

<400> SEQUENCE: 83

His Ser Gln Gly Thr Phe Thr Ser Asp Tyr Ser Arg Tyr Leu Asp Ser
1               5                   10                  15

Lys Lys Ala His Glu Phe Ile Glu Trp Leu Leu Asn Gly Gly His
            20                  25                  30

<210> SEQ ID NO 84
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 84

His Ser Gln Gly Thr Phe Thr Ser Asp Tyr Ser Lys Tyr Leu Glu Ser
1               5                   10                  15

Arg Arg Ala His Glu Phe Val Gln Trp Leu Leu Asn Gly Gly His
            20                  25                  30

<210> SEQ ID NO 85
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 85

His Ser Gln Gly Thr Phe Thr Ser Asp Tyr Ser Lys His Leu Glu Ser
1               5                   10                  15

Arg Arg Ala His Glu Phe Val Gln Trp Leu Leu Asn Gly Gly His
            20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 86

His Ser Gln Gly Thr Phe Thr Ser Asp Tyr Ser Lys His Leu Asp Ser
1               5                   10                  15

Arg Arg Ala His Glu Phe Val Gln Trp Leu Leu Asn Gly Gly His
```

<210> SEQ ID NO 87
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 87

His Ser Gln Gly Thr Phe Thr Ser Asp Tyr Ser Lys His Leu Glu Ser
1               5                   10                  15

Arg Arg Ala His Glu Phe Val Glu Trp Leu Leu Asn Gly Gly His
            20                  25                  30

<210> SEQ ID NO 88
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 88

His Ser Gln Gly Thr Phe Thr Ser Asp Tyr Ser Lys His Leu Asp Ser
1               5                   10                  15

Lys Arg Ala His Glu Phe Val Gln Trp Leu Leu Asn Gly Gly His
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 89

His Ser Gln Gly Thr Phe Thr Ser Asp Tyr Ser Lys His Leu Glu Ser
1               5                   10                  15

Lys Arg Ala His Glu Phe Val Glu Trp Leu Leu Asn Gly Gly His
            20                  25                  30

<210> SEQ ID NO 90
<211> LENGTH: 31
<212> TYPE: PRT
<213> ORGANISM: Artificial Sequence
<220> FEATURE:
<223> OTHER INFORMATION: Glucagon analogue

<400> SEQUENCE: 90

His Ser Gln Gly Thr Phe Thr Ser Asp Tyr Ser Lys His Leu Glu Ser
1               5                   10                  15

Lys Arg Ala His Glu Phe Val Glu Trp Leu Leu Asn Gly Gly His
            20                  25                  30

```
<210> SEQ ID NO 91
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 91

His Ser Gln Gly Thr Phe Thr Ser Asp Tyr Ser His Tyr Leu Glu Ser
1               5                   10                  15
Lys Arg Ala His Glu Phe Val Glu Trp Leu Leu Asn Thr His
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 92

His Ser Gln Gly Thr Phe Thr Ser Asp Tyr Ser His Tyr Leu Asp Ser
1               5                   10                  15
Arg Arg Ala His Glu Phe Val Glu Trp Leu Leu Asn Gly Gly His
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 93

His Ser Gln Gly Thr Phe Thr Ser Asp Tyr Ser His Tyr Leu Glu Ser
1               5                   10                  15
Lys Arg Ala His Glu Phe Ile Glu Trp Leu Leu Asn Thr His
            20                  25                  30

<210> SEQ ID NO 94
<211> LENGTH: 31
<212> TYPE: PRT
<213> ORGANISM: Artificial Sequence
<220> FEATURE:
<223> OTHER INFORMATION: Glucagon analogue

<400> SEQUENCE: 94

His Ser Gln Gly Thr Phe Thr Ser Asp Leu Ser Lys Tyr Leu Glu Ser
1               5                   10                  15
Arg Arg Ala His Glu Phe Val Glu Trp Leu Leu Asn Thr Gly His
            20                  25                  30

<210> SEQ ID NO 95
<211> LENGTH: 31
<212> TYPE: PRT
```

<213> ORGANISM: Artificial Sequence
<220> FEATURE:
<223> OTHER INFORMATION: Glucagon analogue

<400> SEQUENCE: 95

His Ser Gln Gly Thr Phe Thr Ser Asp Tyr Ser Lys Tyr Leu Glu Ser
1               5                   10                  15

Arg Arg Ala His Glu Phe Ile Glu Trp Leu Leu Asn Thr Gly His
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Glucagon analogue

<400> SEQUENCE: 96

His Ser Gln Gly Thr Phe Thr Ser Asp Tyr Ser Lys His Leu Glu Ser
1               5                   10                  15

Arg Arg Ala His Glu Phe Val Glu Trp Leu Leu Asn Thr Gly His
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: Glucagon analogue

<400> SEQUENCE: 97

His Ser Gln Gly Thr Phe Thr Ser Asp Tyr Ser Lys His Leu Glu Ser
1               5                   10                  15

Arg Arg Ala His Glu Phe Ile Glu Trp Leu Leu Asn Thr Gly His
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: Glucagon analogue

<400> SEQUENCE: 98

His Ser Gln Gly Thr Phe Thr Ser Asp Tyr Ser Arg His Leu Glu Ser
1               5                   10                  15

Arg Arg Ala His Glu Phe Val Glu Trp Leu Leu Asn Thr Gly His
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Glucagon analogue

<400> SEQUENCE: 99

His Ser Gln Gly Thr Phe Thr Ser Asp Tyr Ser Lys Tyr Leu Glu Ser
1               5                   10                  15

Lys Lys Ala His Glu Phe Ile Glu Trp Leu Leu Asn Thr Gly His
            20                  25                  30

<210> SEQ ID NO 100
<211> LENGTH: 31

<212> TYPE: PRT
<213> ORGANISM: Artificial Sequence
<220> FEATURE:
<223> OTHER INFORMATION: Glucagon analogue

<400> SEQUENCE: 100

His Ser Gln Gly Thr Phe Thr Ser Asp Tyr Ser Lys Tyr Leu Glu Ser
1               5                   10                  15

Lys Arg Ala His Glu Phe Ile Glu Trp Leu Leu Asn Thr Gly His
            20                  25                  30

<210> SEQ ID NO 101
<211> LENGTH: 31
<212> TYPE: PRT
<213> ORGANISM: Artificial Sequence
<220> FEATURE:
<223> OTHER INFORMATION: Glucagon analogue

<400> SEQUENCE: 101

His Ser Gln Gly Thr Phe Thr Ser Asp Tyr Ser Lys Tyr Leu Glu Ser
1               5                   10                  15

Arg Lys Ala His Glu Phe Ile Glu Trp Leu Leu Asn Thr Gly His
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: Glucagon analogue

<400> SEQUENCE: 102

His Ser Gln Gly Thr Phe Thr Ser Asp Tyr Ser His Tyr Leu Glu Ser
1               5                   10                  15

Arg Arg Ala His Glu Phe Ile Glu Trp Leu Leu Asn Thr Gly His
            20                  25                  30

<210> SEQ ID NO 103
<211> LENGTH: 31
<212> TYPE: PRT
<213> ORGANISM: Artificial Sequence
<220> FEATURE:
<223> OTHER INFORMATION: Glucagon analogue

<400> SEQUENCE: 103

His Ser Gln Gly Thr Phe Thr Ser Asp Tyr Ser Lys His Leu Glu Ser
1               5                   10                  15

Lys Arg Ala His Glu Phe Ile Glu Trp Leu Leu Asn Gly Gly His
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 104

His Ser Gln Gly Thr Phe Thr Ser Asp Tyr Ser Lys His Leu Glu Ser
1               5                   10                  15

Lys Arg Ala His Glu Phe Ile Glu Trp Leu Leu Asn Gly Gly His

<210> SEQ ID NO 105
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 105

His Ser Gln Gly Thr Phe Thr Ser Asp Tyr Ser Lys His Leu Asp Ser
1               5                   10                  15
Lys Arg Ala His Glu Phe Val Gln Trp Leu Leu Asn Thr Gly His
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Glucagon analogue

<400> SEQUENCE: 106

His Ser Gln Gly Thr Phe Thr Ser Asp Tyr Ser Lys His Leu Glu Ser
1               5                   10                  15
Lys Arg Ala His Glu Phe Val Glu Trp Leu Leu Asn Thr Gly His
            20                  25                  30

<210> SEQ ID NO 107
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 107

His Ser Gln Gly Thr Phe Thr Ser Asp Tyr Ser Lys His Leu Asp Glu
1               5                   10                  15
Lys Arg Ala His Glu Phe Val Gln Trp Leu Leu Asn Gly Gly His
            20                  25                  30

<210> SEQ ID NO 108
<211> LENGTH: 31
<212> TYPE: PRT
<213> ORGANISM: Artificial Sequence
<220> FEATURE:
<223> OTHER INFORMATION: Glucagon analogue

<400> SEQUENCE: 108

His Ser Gln Gly Thr Phe Thr Ser Asp Tyr Ser Lys His Leu Glu Glu
1               5                   10                  15
Lys Arg Ala His Glu Phe Val Glu Trp Leu Leu Asn Gly Gly His
            20                  25                  30

<210> SEQ ID NO 109
<211> LENGTH: 31
<212> TYPE: PRT
<213> ORGANISM: Artificial Sequence

```
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 109

His Ser Gln Gly Thr Phe Thr Ser Asp Tyr Ser Lys His Leu Glu Glu
1               5                   10                  15

Lys Arg Ala His Glu Phe Val Glu Trp Leu Leu Asn Gly Gly His
            20                  25                  30

<210> SEQ ID NO 110
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 110

His Ser Gln Gly Thr Phe Thr Ser Asp Tyr Ser Lys His Leu Asp Ser
1               5                   10                  15

Lys Lys Ala His Glu Phe Val Gln Trp Leu Leu Asn Gly Gly His
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: Glucagon analogue

<400> SEQUENCE: 111

His Ser Gln Gly Thr Phe Thr Ser Asp Tyr Ser Lys His Leu Glu Ser
1               5                   10                  15

Lys Lys Ala His Glu Phe Val Glu Trp Leu Leu Asn Gly Gly His
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 112

His Ser Gln Gly Thr Phe Thr Ser Asp Tyr Ser Lys His Leu Glu Ser
1               5                   10                  15

Lys Arg Ala His Glu Phe Ile Glu Trp Leu Leu Asn Thr His
            20                  25                  30

<210> SEQ ID NO 113
<211> LENGTH: 31
<212> TYPE: PRT
<213> ORGANISM: Artificial Sequence
<220> FEATURE:
<223> OTHER INFORMATION: Glucagon analogue
<220> FEATURE:
```

<221> NAME/KEY: MOD_RES
<222> LOCATION: (31)..(31)
<223> OTHER INFORMATION: AMIDATION

<400> SEQUENCE: 113

His Ser Gln Gly Thr Phe Thr Ser Asp Tyr Ser Lys His Leu Glu Ser
1               5                   10                  15

Lys Arg Ala His Glu Phe Ile Glu Trp Leu Leu Asn Thr Gly His
            20                  25                  30

<210> SEQ ID NO 114
<211> LENGTH: 31
<212> TYPE: PRT
<213> ORGANISM: Artificial Sequence
<220> FEATURE:
<223> OTHER INFORMATION: Glucagon analogue

<400> SEQUENCE: 114

His Ser Gln Gly Thr Phe Thr Ser Asp Tyr Ser Lys His Leu Glu Ser
1               5                   10                  15

Lys Arg Ala His Glu Phe Ile Glu Trp Leu Leu Asn Thr Gly His
            20                  25                  30

<210> SEQ ID NO 115
<211> LENGTH: 31
<212> TYPE: PRT
<213> ORGANISM: Artificial Sequence
<220> FEATURE:
<223> OTHER INFORMATION: Glucagon analogue

<400> SEQUENCE: 115

His Ser Gln Gly Thr Phe Thr Ser Asp Tyr Ser Lys Tyr Leu Asp Ser
1               5                   10                  15

Arg Arg Ala His Glu Phe Val Glu Trp Leu Leu Asn Thr Gly His
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 116

His Ser Gln Gly Thr Phe Thr Ser Asp Tyr Ser Lys Tyr Leu Asp Ser
1               5                   10                  15

Arg Arg Ala His Glu Phe Val Glu Trp Leu Leu Asn Thr His
            20                  25                  30

<210> SEQ ID NO 117
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 117

His Ser Gln Gly Thr Phe Thr Ser Asp Tyr Ser Lys Tyr Leu Asp Ser

```
                1               5                   10                  15
Arg Arg Ala His Glu Phe Val Glu Trp Leu Leu Asn Gly Gly His
                20                  25                  30

<210> SEQ ID NO 118
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 118

His Ser Gln Gly Thr Phe Thr Ser Asp Tyr Ser Lys Tyr Leu Asp Ser
1               5                   10                  15

Arg Arg Ala His Glu Phe Val Glu Trp Leu Leu Asn Gly His His
                20                  25                  30

<210> SEQ ID NO 119
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 119

His Ser Gln Gly Thr Phe Thr Ser Asp Tyr Ser Lys Tyr Leu Asp Ser
1               5                   10                  15

Arg Arg Ala His Asp Phe Val Gln Trp Leu Leu Asn Gly His His
                20                  25                  30

<210> SEQ ID NO 120
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 120

His Ser Gln Gly Thr Phe Thr Ser Asp Tyr Ser Lys Tyr Leu Asp Ser
1               5                   10                  15

Arg Arg Ala His Asp Phe Val Glu Trp Leu Leu Asn Thr His His
                20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Glucagon analogue

<400> SEQUENCE: 121

His Ser Gln Gly Thr Phe Thr Ser Asp Tyr Ser Lys Tyr Leu Asp Ser
1               5                   10                  15

Arg Arg Ala His Asp Phe Val Glu Trp Leu Leu Asn Thr His
```

<210> SEQ ID NO 122
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 122

His Ser Gln Gly Thr Phe Thr Ser Asp Tyr Ser Lys Tyr Leu Asp Ser
1               5                   10                  15

Arg Arg Ala His Asp Phe Val Glu Trp Leu Leu Asn Gly His His
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 123

His Ser Gln Gly Thr Phe Thr Ser Asp Tyr Ser Lys Tyr Leu Asp Ser
1               5                   10                  15

Arg Arg Ala His Asp Phe Val Glu Trp Leu Leu Asn Gly His
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 124

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Gly His
            20                  25                  30

<210> SEQ ID NO 125
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 125

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Thr His His
            20                  25                  30

<210> SEQ ID NO 126
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 126

His Ser Gln Gly Thr Phe Thr Ser Asp Tyr Ser His Tyr Leu Asp Ser
1               5                   10                  15

Arg Arg Ala His Asp Phe Val Glu Trp Leu Leu Asn Thr His His
            20                  25                  30

<210> SEQ ID NO 127
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 127

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Thr Gly His
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 128

His Ser Gln Gly Thr Phe Thr Ser Asp Tyr Ser Arg Tyr Leu Asp Ser
1               5                   10                  15

Arg Arg Ala His Asp Phe Val Glu Trp Leu Leu Asn Thr His
            20                  25                  30

<210> SEQ ID NO 129
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 129

His Ser Gln Gly Thr Phe Thr Ser Asp Tyr Ser Arg Tyr Leu Asp Ser
1               5                   10                  15

```
Arg Arg Ala His Glu Phe Val Glu Trp Leu Leu Asn Thr His His
            20                  25                  30

<210> SEQ ID NO 130
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 130

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Gly Gly His
            20                  25                  30

<210> SEQ ID NO 131
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 131

His Ser Gln Gly Thr Phe Thr Ser Asp Tyr Ser Lys His Leu Asp Ser
1               5                   10                  15

Arg Arg Ala His Glu Phe Val Gln Trp Leu Leu Asn Thr His His
            20                  25                  30

<210> SEQ ID NO 132
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 132

His Ser Gln Gly Thr Phe Thr Ser Asp Tyr Ser Lys Tyr Leu Asp Ser
1               5                   10                  15

Lys Arg Ala His Glu Phe Val Gln Trp Leu Leu Asn Thr His His
            20                  25                  30

<210> SEQ ID NO 133
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 133

His Ser Gln Gly Thr Phe Thr Ser Asp Tyr Ser Lys Tyr Leu Glu Ser
```

```
                1               5                  10                 15
Arg Arg Ala His Glu Phe Val Gln Trp Leu Leu Asn Thr His His
                20                 25                 30
```

<210> SEQ ID NO 134
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 134

```
                1               5                  10                 15
His Ser Gln Gly Thr Phe Thr Ser Asp Tyr Ser Lys His Leu Asp Ser
                20                 25                 30
Lys Arg Ala His Glu Phe Val Gln Trp Leu Leu Asn Thr His His
```

<210> SEQ ID NO 135
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 135

```
                1               5                  10                 15
His Ser Gln Gly Thr Phe Thr Ser Asp Tyr Ser Lys His Leu Glu Ser
                20                 25                 30
Lys Arg Ala His Glu Phe Val Gln Trp Leu Leu Asn Thr His His
```

<210> SEQ ID NO 136
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 136

```
                1               5                  10                 15
His Ser Gln Gly Thr Phe Thr Ser Asp Tyr Ser Lys His Leu Asp Ser
                20                 25                 30
Lys Arg Ala His Glu Phe Val Glu Trp Leu Leu Asn Thr Gly His
```

<210> SEQ ID NO 137
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 137

```
His Ser Gln Gly Thr Phe Thr Ser Asp Tyr Ser Lys His Leu Glu Ser
 1               5                  10                  15

Lys Arg Ala His Glu Phe Val Gln Trp Leu Leu Asn Thr Gly His
            20                  25                  30
```

<210> SEQ ID NO 138
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 138

```
His Ser Gln Gly Thr Phe Thr Ser Asp Tyr Ser Arg Tyr Leu Asp Ser
 1               5                  10                  15

Lys Arg Ala His Glu Phe Val Gln Trp Leu Leu Asn Thr His His
            20                  25                  30
```

<210> SEQ ID NO 139
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 139

```
His Ser Gln Gly Thr Phe Thr Ser Asp Tyr Ser Arg Tyr Leu Glu Ser
 1               5                  10                  15

Arg Arg Ala His Glu Phe Val Gln Trp Leu Leu Asn Thr His His
            20                  25                  30
```

<210> SEQ ID NO 140
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 140

```
His Ser Gln Gly Thr Phe Thr Ser Asp Tyr Ser Arg Tyr Leu Asp Ser
 1               5                  10                  15

Arg Arg Ala His Glu Phe Val Gln Trp Leu Leu Asn Thr Gly His
            20                  25                  30
```

<210> SEQ ID NO 141
<211> LENGTH: 31
<212> TYPE: PRT
<213> ORGANISM: Artificial Sequence
<220> FEATURE:
<223> OTHER INFORMATION: Glucagon analogue

<400> SEQUENCE: 141

```
His Ser Gln Gly Thr Phe Thr Ser Asp Tyr Ser Arg Tyr Leu Asp Ser
 1               5                  10                  15
```

Arg Arg Ala His Glu Phe Val Gln Trp Leu Leu Asn Thr His His
        20                  25                  30

<210> SEQ ID NO 142
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 142

His Ser Gln Gly Thr Phe Thr Ser Asp Tyr Ser Arg His Leu Asp Ser
1               5                   10                  15

Arg Arg Ala His Glu Phe Val Gln Trp Leu Leu Asn Thr His His
        20                  25                  30

<210> SEQ ID NO 143
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 143

His Ser Gln Gly Thr Phe Thr Ser Asp Tyr Ser Arg His Leu Asp Ser
1               5                   10                  15

Lys Arg Ala His Glu Phe Val Gln Trp Leu Leu Asn Thr His His
        20                  25                  30

<210> SEQ ID NO 144
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 144

His Ser Gln Gly Thr Phe Thr Ser Asp Leu Ser Lys Tyr Leu Asp Ser
1               5                   10                  15

Arg Arg Ala His Glu Phe Val Gln Trp Leu Leu Asn Thr His His
        20                  25                  30

<210> SEQ ID NO 145
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 145

His Ser Gln Gly Thr Phe Thr Ser Asp Tyr Ser Lys Gln Leu Asp Ser
1               5                   10                  15

```
Arg Arg Ala His Glu Phe Val Gln Trp Leu Leu Asn Thr His His
            20                  25                  30
```

<210> SEQ ID NO 146
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 146

```
His Ser Gln Gly Thr Phe Thr Ser Asp Leu Ser Lys Gln Leu Asp Ser
1               5                   10                  15
Arg Arg Ala His Glu Phe Val Gln Trp Leu Leu Asn Thr His His
            20                  25                  30
```

<210> SEQ ID NO 147
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 147

```
His Ser Gln Gly Thr Phe Thr Ser Asp Tyr Ser Lys Tyr Leu Asp Ser
1               5                   10                  15
Arg Arg Ala Gln His Phe Val Gln Trp Leu Leu Asn Thr His His
            20                  25                  30
```

<210> SEQ ID NO 148
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 148

```
His Ser Gln Gly Thr Phe Thr Ser Asp Tyr Ser Lys Tyr Leu Asp Ser
1               5                   10                  15
Lys Arg Ala Gln His Phe Val Gln Trp Leu Leu Asn Thr His His
            20                  25                  30
```

<210> SEQ ID NO 149
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 149

```
His Ser Gln Gly Thr Phe Thr Ser Asp Tyr Ser Lys His Leu Asp Ser
```

```
                1               5                  10                  15
Lys Arg Ala Gln His Phe Val Gln Trp Leu Leu Asn Thr His His
            20                  25                  30

<210> SEQ ID NO 150
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 150

His Ser Gln Gly Thr Phe Thr Ser Asp Tyr Ser His Tyr Leu Asp Ser
1               5                   10                  15

Lys Arg Ala Gln His Phe Val Gln Trp Leu Leu Asn Thr His His
            20                  25                  30

<210> SEQ ID NO 151
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 151

His Ser Gln Gly Thr Phe Thr Ser Asp Tyr Ser His Tyr Leu Asp Ser
1               5                   10                  15

Lys Arg Ala His Asp Phe Val Glu Trp Leu Leu Asn Thr His His
            20                  25                  30

<210> SEQ ID NO 152
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 152

His Ser Gln Gly Thr Phe Thr Ser Asp Tyr Ser His Tyr Leu Asp Ser
1               5                   10                  15

Lys Arg Ala His Asp Phe Val Glu Trp Leu Leu Asn Thr Gly His
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 153
```

His Ser Gln Gly Thr Phe Thr Ser Asp Tyr Ser His Tyr Leu Asp Ser
1               5                   10                  15

Lys Arg Ala His Glu Phe Val Glu Trp Leu Leu Asn Thr His
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 154

His Ser Gln Gly Thr Phe Thr Ser Asp Tyr Ser His Tyr Leu Glu Ser
1               5                   10                  15

Lys Arg Ala His Asp Phe Val Glu Trp Leu Leu Asn Thr His
            20                  25                  30

<210> SEQ ID NO 155
<211> LENGTH: 31
<212> TYPE: PRT
<213> ORGANISM: Artificial Sequence
<220> FEATURE:
<223> OTHER INFORMATION: Glucagon analogue

<400> SEQUENCE: 155

His Ser Gln Gly Thr Phe Thr Ser Asp Tyr Ser His Tyr Leu Asp Ser
1               5                   10                  15

Lys Arg Ala His Asp Phe Val Glu Trp Leu Leu Asn Gly Gly His
            20                  25                  30

<210> SEQ ID NO 156
<211> LENGTH: 31
<212> TYPE: PRT
<213> ORGANISM: Artificial Sequence
<220> FEATURE:
<223> OTHER INFORMATION: Glucagon analogue

<400> SEQUENCE: 156

His Ser Gln Gly Thr Phe Thr Ser Asp Tyr Ser Arg Tyr Leu Asp Ser
1               5                   10                  15

Arg Arg Ala His Glu Phe Val Gln Trp Leu Leu Asn Thr Gly His
            20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Glucagon analogue

<400> SEQUENCE: 157

His Ser Gln Gly Thr Phe Thr Ser Asp Tyr Ser Arg Tyr Leu Asp Ser
1               5                   10                  15

Lys Arg Ala His Glu Phe Val Gln Trp Leu Leu Asn Thr Gly His
            20                  25                  30

<210> SEQ ID NO 158
<211> LENGTH: 31
<212> TYPE: PRT
<213> ORGANISM: Artificial Sequence

```
<220> FEATURE:
<223> OTHER INFORMATION: Glucagon analogue

<400> SEQUENCE: 158

His Ser Gln Gly Thr Phe Thr Ser Asp Tyr Ser Lys Tyr Leu Asp Ser
1               5                   10                  15

Lys Arg Ala His Glu Phe Val Gln Trp Leu Leu Asn Thr Gly His
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 159

His Ser Gln Gly Thr Phe Thr Ser Asp Tyr Ser His Tyr Leu Asp Ser
1               5                   10                  15

Lys Arg Ala His Asp Phe Val Gln Trp Leu Leu Asn Thr His
            20                  25                  30

<210> SEQ ID NO 160
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 160

His Ser Gln Gly Thr Phe Thr Ser Asp Tyr Ser His Tyr Leu Asp Ser
1               5                   10                  15

Lys Arg Ala His Glu Phe Val Gln Trp Leu Leu Asn Thr His
            20                  25                  30

<210> SEQ ID NO 161
<211> LENGTH: 31
<212> TYPE: PRT
<213> ORGANISM: Artificial Sequence
<220> FEATURE:
<223> OTHER INFORMATION: Glucagon analogue

<400> SEQUENCE: 161

His Ser Gln Gly Thr Phe Thr Ser Asp Tyr Ser His Tyr Leu Asp Ser
1               5                   10                  15

Lys Arg Ala His Asp Phe Val Glu Trp Leu Leu Asn Thr Gly His
            20                  25                  30

<210> SEQ ID NO 162
<211> LENGTH: 31
<212> TYPE: PRT
<213> ORGANISM: Artificial Sequence
<220> FEATURE:
<223> OTHER INFORMATION: Glucagon analogue

<400> SEQUENCE: 162

His Ser Gln Gly Thr Phe Thr Ser Asp Tyr Ser His Tyr Leu Glu Ser
1               5                   10                  15
```

```
Arg Arg Ala His Glu Phe Val Glu Trp Leu Leu Asn Thr Gly His
            20                  25                  30

<210> SEQ ID NO 163
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 163

His Ser Gln Gly Thr Phe Thr Ser Asp Tyr Ser His Tyr Leu Glu Ser
1               5                   10                  15

Arg Arg Ala His Glu Phe Val Glu Trp Leu Leu Asn Thr Gly His
            20                  25                  30

<210> SEQ ID NO 164
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 164

His Ser Gln Gly Thr Phe Thr Ser Asp Tyr Ser Lys His Leu Asp Ser
1               5                   10                  15

His Arg Ala His Glu Phe Val Gln Trp Leu Leu Asn Gly Gly His
            20                  25                  30

<210> SEQ ID NO 165
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 165

His Ser Gln Gly Thr Phe Thr Ser Asp Tyr Ser Lys Tyr Leu Glu Glu
1               5                   10                  15

Arg Arg Ala His Glu Phe Val Gln Trp Leu Leu Asn Gly Gly His
            20                  25                  30

<210> SEQ ID NO 166
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 166

His Ser Gln Gly Thr Phe Thr Ser Asp Tyr Ser Lys His Leu Glu Glu
```

```
1               5                   10                  15
Lys Arg Ala His Glu Phe Val Gln Trp Leu Leu Asn Gly Gly His
                20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 167

His Ser Gln Gly Thr Phe Thr Ser Asp Tyr Ser Lys Tyr Leu Glu Glu
1               5                   10                  15
Arg Arg Ala His Asp Phe Val Gln Trp Leu Leu Asn Thr His
                20                  25                  30

<210> SEQ ID NO 168
<211> LENGTH: 31
<212> TYPE: PRT
<213> ORGANISM: Artificial Sequence
<220> FEATURE:
<223> OTHER INFORMATION: Glucagon analogue

<400> SEQUENCE: 168

His Ser Gln Gly Thr Phe Thr Ser Asp Tyr Ser His Tyr Leu Asp Ser
1               5                   10                  15
Arg Arg Ala Gln Asp Phe Val Gln Trp Leu Leu Asn Gly Gly His
                20                  25                  30

<210> SEQ ID NO 169
<211> LENGTH: 31
<212> TYPE: PRT
<213> ORGANISM: Artificial Sequence
<220> FEATURE:
<223> OTHER INFORMATION: Glucagon analogue

<400> SEQUENCE: 169

His Ser Gln Gly Thr Phe Thr Ser Asp Tyr Ser His Tyr Leu Asp Ser
1               5                   10                  15
Arg Arg Ala Gln Asp Phe Val Gln Trp Leu Leu Asn Thr Gly His
                20                  25                  30

<210> SEQ ID NO 170
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 170

His Ser Gln Gly Thr Phe Thr Ser Asp Tyr Ser His Tyr Leu Asp Ser
1               5                   10                  15
Arg Arg Ala Gln Asp Phe Val Gln Trp Leu Leu Asn Gly Gly His
                20                  25                  30

<210> SEQ ID NO 171
```

```
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 171

His Ser Gln Gly Thr Phe Thr Ser Asp Tyr Ser His Tyr Leu Asp Ser
1               5                   10                  15

Arg Arg Ala Gln Asp Phe Val Gln Trp Leu Leu Asn Thr Gly His
            20                  25                  30

<210> SEQ ID NO 172
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 172

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr Gly His
            20                  25                  30

<210> SEQ ID NO 173
<211> LENGTH: 31
<212> TYPE: PRT
<213> ORGANISM: Artificial Sequence
<220> FEATURE:
<223> OTHER INFORMATION: Glucagon analogue

<400> SEQUENCE: 173

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr Gly His
            20                  25                  30

<210> SEQ ID NO 174
<211> LENGTH: 31
<212> TYPE: PRT
<213> ORGANISM: Artificial Sequence
<220> FEATURE:
<223> OTHER INFORMATION: Glucagon analogue

<400> SEQUENCE: 174

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly Gly His
            20                  25                  30

<210> SEQ ID NO 175
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
```

<222> LOCATION: (31)..(31)
<223> OTHER INFORMATION: AMIDATION

<400> SEQUENCE: 175

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly Gly His
            20                  25                  30

<210> SEQ ID NO 176
<211> LENGTH: 31
<212> TYPE: PRT
<213> ORGANISM: Artificial Sequence
<220> FEATURE:
<223> OTHER INFORMATION: Glucagon analogue

<400> SEQUENCE: 176

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Thr Gly His
            20                  25                  30

<210> SEQ ID NO 177
<211> LENGTH: 31
<212> TYPE: PRT
<213> ORGANISM: Artificial Sequence
<220> FEATURE:
<223> OTHER INFORMATION: Glucagon analogue

<400> SEQUENCE: 177

His Ser Gln Gly Thr Phe Thr Ser Asp Tyr Ser Lys Tyr Leu Glu Ser
1               5                   10                  15

Arg Lys Ala His Glu Phe Ile Glu Trp Leu Leu Asn Gly Gly His
            20                  25                  30

<210> SEQ ID NO 178
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 178

His Ser Gln Gly Thr Phe Thr Ser Asp Tyr Ser Lys Tyr Leu Glu Ser
1               5                   10                  15

Arg Lys Ala His Glu Phe Ile Glu Trp Leu Leu Asn Gly Gly His
            20                  25                  30

<210> SEQ ID NO 179
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 179

His Ser Gln Gly Thr Phe Thr Ser Asp Tyr Ser Lys Tyr Leu Glu Ser
1               5                   10                  15

Arg Lys Ala His Glu Phe Ile Glu Trp Leu Leu Asn Thr Gly His
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 180

His Ser Gln Gly Thr Phe Thr Ser Asp Tyr Ser Lys Tyr Leu Asp Glu
1               5                   10                  15

Arg Arg Ala His Glu Phe Val Gln Trp Leu Leu Asn Thr His
            20                  25                  30

<210> SEQ ID NO 181
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 181

His Ser Gln Gly Thr Phe Thr Ser Asp Tyr Ser Lys Tyr Leu Asp Glu
1               5                   10                  15

Arg Arg Ala His Glu Phe Val Gln Trp Leu Leu Asn Thr His His
            20                  25                  30

<210> SEQ ID NO 182
<211> LENGTH: 31
<212> TYPE: PRT
<213> ORGANISM: Artificial Sequence
<220> FEATURE:
<223> OTHER INFORMATION: Glucagon analogue

<400> SEQUENCE: 182

His Ser Gln Gly Thr Phe Thr Ser Asp Tyr Ser Lys Tyr Leu Asp Glu
1               5                   10                  15

Arg Arg Ala His Glu Phe Val Gln Trp Leu Leu Asn Thr His His
            20                  25                  30

<210> SEQ ID NO 183
<211> LENGTH: 31
<212> TYPE: PRT
<213> ORGANISM: Artificial Sequence
<220> FEATURE:
<223> OTHER INFORMATION: Glucagon analogue

<400> SEQUENCE: 183

His Ser Gln Gly Thr Phe Thr Ser Asp Tyr Ser Lys Tyr Leu Asp Glu
1               5                   10                  15

Arg Arg Ala His Glu Phe Val Gln Trp Leu Leu Asn Gly Gly His
            20                  25                  30

<210> SEQ ID NO 184
<211> LENGTH: 31

```
<212> TYPE: PRT
<213> ORGANISM: Artificial Sequence
<220> FEATURE:
<223> OTHER INFORMATION: Glucagon analogue

<400> SEQUENCE: 184

His Ser Gln Gly Thr Phe Thr Ser Asp Tyr Ser Lys Tyr Leu Asp Gln
1               5                   10                  15

Arg Arg Ala His Glu Phe Val Gln Trp Leu Leu Asn Thr His His
            20                  25                  30

<210> SEQ ID NO 185
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 185

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Gly His His
            20                  25                  30

<210> SEQ ID NO 186
<211> LENGTH: 31
<212> TYPE: PRT
<213> ORGANISM: Artificial Sequence
<220> FEATURE:
<223> OTHER INFORMATION: Glucagon analogue

<400> SEQUENCE: 186

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Gly His His
            20                  25                  30

<210> SEQ ID NO 187
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 187

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Gly His His
            20                  25                  30

<210> SEQ ID NO 188
<211> LENGTH: 31
<212> TYPE: PRT
<213> ORGANISM: Artificial Sequence
<220> FEATURE:
<223> OTHER INFORMATION: Glucagon analogue

<400> SEQUENCE: 188
```

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Gly His His
            20                  25                  30

<210> SEQ ID NO 189
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 189

His Ser Gln Gly Thr Phe Thr Ser Asp Tyr Ser His Tyr Leu Asp Ser
1               5                   10                  15

Lys Arg Ala His Glu Phe Val Gln Trp Leu Leu Asn Gly His His
            20                  25                  30

<210> SEQ ID NO 190
<211> LENGTH: 31
<212> TYPE: PRT
<213> ORGANISM: Artificial Sequence
<220> FEATURE:
<223> OTHER INFORMATION: Glucagon analogue

<400> SEQUENCE: 190

His Ser Gln Gly Thr Phe Thr Ser Asp Tyr Ser His Tyr Leu Asp Ser
1               5                   10                  15

Lys Arg Ala His Glu Phe Val Gln Trp Leu Leu Asn Gly His His
            20                  25                  30

<210> SEQ ID NO 191
<211> LENGTH: 31
<212> TYPE: PRT
<213> ORGANISM: Artificial Sequence
<220> FEATURE:
<223> OTHER INFORMATION: Glucagon analogue

<400> SEQUENCE: 191

His Ser Gln Gly Thr Phe Thr Ser Asp Tyr Ser Arg His Leu Asp Ser
1               5                   10                  15

Arg Arg Ala His Glu Phe Val Gln Trp Leu Leu Asn Thr His His
            20                  25                  30

<210> SEQ ID NO 192
<211> LENGTH: 31
<212> TYPE: PRT
<213> ORGANISM: Artificial Sequence
<220> FEATURE:
<223> OTHER INFORMATION: Glucagon analogue

<400> SEQUENCE: 192

His Ser Gln Gly Thr Phe Thr Ser Asp Tyr Ser Lys His Leu Asp Ser
1               5                   10                  15

Arg Arg Ala His Glu Phe Val Gln Trp Leu Leu Asn Thr His His
            20                  25                  30

<210> SEQ ID NO 193
<211> LENGTH: 31
<212> TYPE: PRT
<213> ORGANISM: Artificial Sequence

```
<220> FEATURE:
<223> OTHER INFORMATION: Glucagon analogue

<400> SEQUENCE: 193

His Ser Gln Gly Thr Phe Thr Ser Asp Tyr Ser Arg Tyr Leu Asp Glu
1               5                   10                  15

Arg Arg Ala His Glu Phe Val Gln Trp Leu Leu Asn Thr His His
            20                  25                  30

<210> SEQ ID NO 194
<211> LENGTH: 31
<212> TYPE: PRT
<213> ORGANISM: Artificial Sequence
<220> FEATURE:
<223> OTHER INFORMATION: Glucagon analogue

<400> SEQUENCE: 194

His Ser Gln Gly Thr Phe Thr Ser Asp Tyr Ser Arg Tyr Leu Asp Gln
1               5                   10                  15

Arg Arg Ala His Glu Phe Val Gln Trp Leu Leu Asn Thr His His
            20                  25                  30

<210> SEQ ID NO 195
<211> LENGTH: 31
<212> TYPE: PRT
<213> ORGANISM: Artificial Sequence
<220> FEATURE:
<223> OTHER INFORMATION: Glucagon analogue

<400> SEQUENCE: 195

His Ser Gln Gly Thr Phe Thr Ser Asp Tyr Ser His Tyr Leu Asp Ser
1               5                   10                  15

Arg Arg Ala His Glu Phe Val Glu Trp Leu Leu Asn Thr His His
            20                  25                  30

<210> SEQ ID NO 196
<211> LENGTH: 31
<212> TYPE: PRT
<213> ORGANISM: Artificial Sequence
<220> FEATURE:
<223> OTHER INFORMATION: Glucagon analogue

<400> SEQUENCE: 196

His Ser Gln Gly Thr Phe Thr Ser Asp Tyr Ser His Tyr Leu Asp Ser
1               5                   10                  15

Arg Arg Ala His Glu Phe Val Gln Trp Leu Leu Asn Thr His His
            20                  25                  30

<210> SEQ ID NO 197
<211> LENGTH: 31
<212> TYPE: PRT
<213> ORGANISM: Artificial Sequence
<220> FEATURE:
<223> OTHER INFORMATION: Glucagon analogue

<400> SEQUENCE: 197

His Ser Gln Gly Thr Phe Thr Ser Asp Leu Ser Arg Gln Leu Asp Ser
1               5                   10                  15

Arg Arg Ala His Glu Phe Val Gln Trp Leu Leu Asn Thr His His
            20                  25                  30

<210> SEQ ID NO 198
<211> LENGTH: 31
<212> TYPE: PRT
```

<210> SEQ ID NO 198
<211> LENGTH: 31
<212> TYPE: PRT
<213> ORGANISM: Artificial Sequence
<220> FEATURE:
<223> OTHER INFORMATION: Glucagon analogue

<400> SEQUENCE: 198

His Ser Gln Gly Thr Phe Thr Ser Asp Tyr Ser Lys Tyr Leu Asp Ser
1               5                   10                  15
Arg Arg Ala His Glu Phe Val Glu Trp Leu Leu Asn Thr His His
            20                  25                  30

<210> SEQ ID NO 199
<211> LENGTH: 31
<212> TYPE: PRT
<213> ORGANISM: Artificial Sequence
<220> FEATURE:
<223> OTHER INFORMATION: Glucagon analogue

<400> SEQUENCE: 199

His Ser Gln Gly Thr Phe Thr Ser Asp Tyr Ser Arg Tyr Leu Asp Ser
1               5                   10                  15
Arg Arg Ala His Glu Phe Val Glu Trp Leu Leu Asn Thr His His
            20                  25                  30

<210> SEQ ID NO 200
<211> LENGTH: 31
<212> TYPE: PRT
<213> ORGANISM: Artificial Sequence
<220> FEATURE:
<223> OTHER INFORMATION: Glucagon analogue

<400> SEQUENCE: 200

His Ser Gln Gly Thr Phe Thr Ser Asp Tyr Ser Lys Tyr Leu Asp Ser
1               5                   10                  15
Arg Arg Ala His Glu Phe Val Glu Trp Leu Leu Asn Gly His His
            20                  25                  30

<210> SEQ ID NO 201
<211> LENGTH: 31
<212> TYPE: PRT
<213> ORGANISM: Artificial Sequence
<220> FEATURE:
<223> OTHER INFORMATION: Glucagon analogue

<400> SEQUENCE: 201

His Ser Gln Gly Thr Phe Thr Ser Asp Tyr Ser Lys Tyr Leu Asp Ser
1               5                   10                  15
Arg Arg Ala His Glu Phe Val Glu Trp Leu Leu Asn Gly Gly His
            20                  25                  30

<210> SEQ ID NO 202
<211> LENGTH: 31
<212> TYPE: PRT
<213> ORGANISM: Artificial Sequence
<220> FEATURE:
<223> OTHER INFORMATION: Glucagon analogue

<400> SEQUENCE: 202

His Ser Gln Gly Thr Phe Thr Ser Asp Tyr Ser Lys Tyr Leu Asp Ser
1               5                   10                  15
Arg Arg Ala His Asp Phe Val Glu Trp Leu Leu Asn Gly Gly His
            20                  25                  30

<210> SEQ ID NO 203
<211> LENGTH: 31

```
<212> TYPE: PRT
<213> ORGANISM: Artificial Sequence
<220> FEATURE:
<223> OTHER INFORMATION: Glucagon analogue

<400> SEQUENCE: 203

His Ser Gln Gly Thr Phe Thr Ser Asp Tyr Ser Arg Tyr Leu Asp Ser
1               5                   10                  15

Arg Arg Ala His Glu Phe Val Glu Trp Leu Leu Asn Gly Gly His
            20                  25                  30

<210> SEQ ID NO 204
<211> LENGTH: 31
<212> TYPE: PRT
<213> ORGANISM: Artificial Sequence
<220> FEATURE:
<223> OTHER INFORMATION: Glucagon analogue

<400> SEQUENCE: 204

His Ser Gln Gly Thr Phe Thr Ser Asp Leu Ser Arg Gln Leu Asp Ser
1               5                   10                  15

Arg Arg Ala His Glu Phe Val Glu Trp Leu Leu Asn Gly Gly His
            20                  25                  30

<210> SEQ ID NO 205
<211> LENGTH: 31
<212> TYPE: PRT
<213> ORGANISM: Artificial Sequence
<220> FEATURE:
<223> OTHER INFORMATION: Glucagon analogue

<400> SEQUENCE: 205

His Ser Gln Gly Thr Phe Thr Ser Asp Leu Ser Arg Gln Leu Asp Ser
1               5                   10                  15

Arg Arg Ala His Glu Phe Ile Glu Trp Leu Leu Asn Gly Gly His
            20                  25                  30

<210> SEQ ID NO 206
<211> LENGTH: 31
<212> TYPE: PRT
<213> ORGANISM: Artificial Sequence
<220> FEATURE:
<223> OTHER INFORMATION: Glucagon analogue

<400> SEQUENCE: 206

His Ser Gln Gly Thr Phe Thr Ser Asp Tyr Ser Lys Tyr Leu Asp Ser
1               5                   10                  15

Arg Arg Ala His Glu Phe Ile Gln Trp Leu Leu Asn Gly Gly His
            20                  25                  30

<210> SEQ ID NO 207
<211> LENGTH: 32
<212> TYPE: PRT
<213> ORGANISM: Artificial Sequence
<220> FEATURE:
<223> OTHER INFORMATION: Glucagon analogue

<400> SEQUENCE: 207

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Gly Gly His His
            20                  25                  30

<210> SEQ ID NO 208
```

```
<211> LENGTH: 31
<212> TYPE: PRT
<213> ORGANISM: Artificial Sequence
<220> FEATURE:
<223> OTHER INFORMATION: Glucagon analogue

<400> SEQUENCE: 208

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Gly Lys His
            20                  25                  30

<210> SEQ ID NO 209
<211> LENGTH: 31
<212> TYPE: PRT
<213> ORGANISM: Artificial Sequence
<220> FEATURE:
<223> OTHER INFORMATION: Glucagon analogue

<400> SEQUENCE: 209

His Ser Gln Gly Thr Phe Thr Ser Asp Tyr Ser Lys Tyr Leu Glu Ser
1               5                   10                  15

Arg Arg Ala His Glu Phe Val Gln Trp Leu Leu Asn Gly Gly His
            20                  25                  30

<210> SEQ ID NO 210
<211> LENGTH: 31
<212> TYPE: PRT
<213> ORGANISM: Artificial Sequence
<220> FEATURE:
<223> OTHER INFORMATION: Glucagon analogue

<400> SEQUENCE: 210

His Ser Gln Gly Thr Phe Thr Ser Asp Leu Ser Lys Tyr Leu Asp Ser
1               5                   10                  15

Arg Arg Ala His Glu Phe Val Gln Trp Leu Leu Asn Gly Gly His
            20                  25                  30

<210> SEQ ID NO 211
<211> LENGTH: 31
<212> TYPE: PRT
<213> ORGANISM: Artificial Sequence
<220> FEATURE:
<223> OTHER INFORMATION: Glucagon analogue

<400> SEQUENCE: 211

His Ser Gln Gly Thr Phe Thr Ser Asp Leu Ser Lys Gln Leu Asp Ser
1               5                   10                  15

Arg Arg Ala His Glu Phe Val Gln Trp Leu Leu Asn Gly Gly His
            20                  25                  30

<210> SEQ ID NO 212
<211> LENGTH: 31
<212> TYPE: PRT
<213> ORGANISM: Artificial Sequence
<220> FEATURE:
<223> OTHER INFORMATION: Glucagon analogue

<400> SEQUENCE: 212

His Ser Gln Gly Thr Phe Thr Ser Asp Tyr Ser Lys Gln Leu Asp Ser
1               5                   10                  15

Arg Arg Ala His Glu Phe Val Gln Trp Leu Leu Asn Gly Gly His
            20                  25                  30
```

```
<210> SEQ ID NO 213
<211> LENGTH: 31
<212> TYPE: PRT
<213> ORGANISM: Artificial Sequence
<220> FEATURE:
<223> OTHER INFORMATION: Glucagon analogue

<400> SEQUENCE: 213

His Ser Gln Gly Thr Phe Thr Ser Asp Leu Ser Arg Tyr Leu Asp Ser
1               5                   10                  15

Arg Arg Ala His Glu Phe Val Gln Trp Leu Leu Asn Gly Gly His
            20                  25                  30

<210> SEQ ID NO 214
<211> LENGTH: 31
<212> TYPE: PRT
<213> ORGANISM: Artificial Sequence
<220> FEATURE:
<223> OTHER INFORMATION: Glucagon analogue

<400> SEQUENCE: 214

His Ser Gln Gly Thr Phe Thr Ser Asp Tyr Ser Arg Gln Leu Asp Ser
1               5                   10                  15

Arg Arg Ala His Glu Phe Val Gln Trp Leu Leu Asn Gly Gly His
            20                  25                  30

<210> SEQ ID NO 215
<211> LENGTH: 31
<212> TYPE: PRT
<213> ORGANISM: Artificial Sequence
<220> FEATURE:
<223> OTHER INFORMATION: Glucagon analogue

<400> SEQUENCE: 215

His Ser Gln Gly Thr Phe Thr Ser Asp Tyr Ser Arg Gln Leu Asp Ser
1               5                   10                  15

Arg Arg Ala His Glu Phe Ile Gln Trp Leu Leu Asn Gly Gly His
            20                  25                  30

<210> SEQ ID NO 216
<211> LENGTH: 31
<212> TYPE: PRT
<213> ORGANISM: Artificial Sequence
<220> FEATURE:
<223> OTHER INFORMATION: Glucagon analogue

<400> SEQUENCE: 216

His Ser Gln Gly Thr Phe Thr Ser Asp Tyr Ser Arg Tyr Leu Asp Ser
1               5                   10                  15

Arg Arg Ala His Glu Phe Ile Gln Trp Leu Leu Asn Gly Gly His
            20                  25                  30

<210> SEQ ID NO 217
<211> LENGTH: 31
<212> TYPE: PRT
<213> ORGANISM: Artificial Sequence
<220> FEATURE:
<223> OTHER INFORMATION: Glucagon analogue

<400> SEQUENCE: 217

His Ser Gln Gly Thr Phe Thr Ser Asp Tyr Ser Arg Tyr Leu Asp Ser
1               5                   10                  15

Arg Arg Ala His Glu Phe Ile Glu Trp Leu Leu Asn Gly Gly His
            20                  25                  30
```

<210> SEQ ID NO 218
<211> LENGTH: 31
<212> TYPE: PRT
<213> ORGANISM: Artificial Sequence
<220> FEATURE:
<223> OTHER INFORMATION: Glucagon analogue

<400> SEQUENCE: 218

His Ser Gln Gly Thr Phe Thr Ser Asp Tyr Ser Lys Tyr Leu Asp Ser
1               5                   10                  15

Lys Arg Ala His Glu Phe Val Gln Trp Leu Leu Asn Gly Gly His
            20                  25                  30

<210> SEQ ID NO 219
<211> LENGTH: 31
<212> TYPE: PRT
<213> ORGANISM: Artificial Sequence
<220> FEATURE:
<223> OTHER INFORMATION: Glucagon analogue

<400> SEQUENCE: 219

His Ser Gln Gly Thr Phe Thr Ser Asp Tyr Ser Lys Tyr Leu Asp Ser
1               5                   10                  15

Lys Arg Ala His Glu Phe Ile Gln Trp Leu Leu Asn Gly Gly His
            20                  25                  30

<210> SEQ ID NO 220
<211> LENGTH: 31
<212> TYPE: PRT
<213> ORGANISM: Artificial Sequence
<220> FEATURE:
<223> OTHER INFORMATION: Glucagon analogue

<400> SEQUENCE: 220

His Ser Gln Gly Thr Phe Thr Ser Asp Tyr Ser Arg Tyr Leu Asp Ser
1               5                   10                  15

Arg Arg Ala His Glu Phe Ile Glu Trp Leu Leu Asn Gly His His
            20                  25                  30

<210> SEQ ID NO 221
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 221

His Ser Gln Gly Thr Phe Thr Ser Asp Tyr Ser His Tyr Leu Asp Ser
1               5                   10                  15

Arg Arg Ala His Glu Phe Ile Glu Trp Leu Leu Asn Gly Gly His
            20                  25                  30

<210> SEQ ID NO 222
<211> LENGTH: 31
<212> TYPE: PRT
<213> ORGANISM: Artificial Sequence
<220> FEATURE:
<223> OTHER INFORMATION: Glucagon analogue

<400> SEQUENCE: 222

His Ser Gln Gly Thr Phe Thr Ser Asp Tyr Ser His Tyr Leu Asp Ser

```
                1               5                  10                  15
Arg Arg Ala His Glu Phe Ile Glu Trp Leu Leu Asn Gly Gly His
                20                  25                  30

<210> SEQ ID NO 223
<211> LENGTH: 31
<212> TYPE: PRT
<213> ORGANISM: Artificial Sequence
<220> FEATURE:
<223> OTHER INFORMATION: Glucagon analogue

<400> SEQUENCE: 223

His Ser Gln Gly Thr Phe Thr Ser Asp Tyr Ser His Tyr Leu Asp Ser
1               5                  10                  15

Arg Arg Ala His Glu Phe Ile Glu Trp Leu Leu Asn Gly His His
                20                  25                  30

<210> SEQ ID NO 224
<211> LENGTH: 31
<212> TYPE: PRT
<213> ORGANISM: Artificial Sequence
<220> FEATURE:
<223> OTHER INFORMATION: Glucagon analogue

<400> SEQUENCE: 224

His Ser Gln Gly Thr Phe Thr Ser Asp Tyr Ser Lys Tyr Leu Asp Glu
1               5                  10                  15

Arg Arg Ala His Glu Phe Ile Glu Trp Leu Leu Asn Gly Gly His
                20                  25                  30

<210> SEQ ID NO 225
<211> LENGTH: 31
<212> TYPE: PRT
<213> ORGANISM: Artificial Sequence
<220> FEATURE:
<223> OTHER INFORMATION: Glucagon analogue

<400> SEQUENCE: 225

His Ser Gln Gly Thr Phe Thr Ser Asp Tyr Ser Arg Tyr Leu Asp Glu
1               5                  10                  15

Arg Arg Ala His Glu Phe Ile Glu Trp Leu Leu Asn Gly Gly His
                20                  25                  30

<210> SEQ ID NO 226
<211> LENGTH: 31
<212> TYPE: PRT
<213> ORGANISM: Artificial Sequence
<220> FEATURE:
<223> OTHER INFORMATION: Glucagon analogue

<400> SEQUENCE: 226

His Ser Gln Gly Thr Phe Thr Ser Asp Tyr Ser Arg Tyr Leu Asp Glu
1               5                  10                  15

Arg Arg Ala His Glu Phe Val Glu Trp Leu Leu Asn Gly Gly His
                20                  25                  30

<210> SEQ ID NO 227
<211> LENGTH: 31
<212> TYPE: PRT
<213> ORGANISM: Artificial Sequence
<220> FEATURE:
<223> OTHER INFORMATION: Glucagon analogue

<400> SEQUENCE: 227
```

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly His His
            20                  25                  30

<210> SEQ ID NO 228
<211> LENGTH: 31
<212> TYPE: PRT
<213> ORGANISM: Artificial Sequence
<220> FEATURE:
<223> OTHER INFORMATION: Glucagon analogue

<400> SEQUENCE: 228

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr His His
            20                  25                  30

<210> SEQ ID NO 229
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 229

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr His His
            20                  25                  30

<210> SEQ ID NO 230
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 230

His Ser Gln Gly Thr Phe Thr Ser Asp Tyr Ser Arg Tyr Leu Asp Ser
1               5                   10                  15

Arg Arg Ala His Glu Phe Ile Gln Trp Leu Leu Asn Thr His His
            20                  25                  30

<210> SEQ ID NO 231
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 231

His Ser Gln Gly Thr Phe Thr Ser Asp Tyr Ser Arg Tyr Leu Asp Ser
1               5                   10                  15

Arg Arg Ala His Glu Phe Ile Glu Trp Leu Leu Asn Thr His His
            20                  25                  30

<210> SEQ ID NO 232
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 232

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly His His
            20                  25                  30

<210> SEQ ID NO 233
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 233

His Ser Gln Gly Thr Phe Thr Ser Asp Tyr Ser Arg His Leu Asp Ser
1               5                   10                  15

Lys Arg Ala His Glu Phe Ile Gln Trp Leu Leu Asn Thr His His
            20                  25                  30

<210> SEQ ID NO 234
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 234

His Ser Gln Gly Thr Phe Thr Ser Asp Tyr Ser Arg His Leu Asp Ser
1               5                   10                  15

Lys Arg Ala His Glu Phe Ile Glu Trp Leu Leu Asn Thr His His
            20                  25                  30

<210> SEQ ID NO 235
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 235

His Ser Gln Gly Thr Phe Thr Ser Asp Tyr Ser Arg His Leu Asp Ser
1               5                   10                  15

Lys Arg Ala His Glu Phe Val Glu Trp Leu Leu Asn Thr His His
            20                  25                  30

<210> SEQ ID NO 236
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 236

His Ser Gln Gly Thr Phe Thr Ser Asp Tyr Ser Arg His Leu Asp Ser
1               5                   10                  15

Lys Arg Ala His Glu Phe Val Gln Trp Leu Leu Asn Gly His His
            20                  25                  30

<210> SEQ ID NO 237
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 237

His Ser Gln Gly Thr Phe Thr Ser Asp Tyr Ser Arg His Leu Asp Ser
1               5                   10                  15

Lys Arg Ala His Glu Phe Val Gln Trp Leu Leu Asn Gly Gly His
            20                  25                  30

<210> SEQ ID NO 238
<211> LENGTH: 31
<212> TYPE: PRT
<213> ORGANISM: Artificial Sequence
<220> FEATURE:
<223> OTHER INFORMATION: Glucagon analogue

<400> SEQUENCE: 238

His Ser Gln Gly Thr Phe Thr Ser Asp Tyr Ser Arg His Leu Asp Ser
1               5                   10                  15

Lys Arg Ala His Glu Phe Val Gln Trp Leu Leu Asn Gly Gly His
            20                  25                  30

<210> SEQ ID NO 239
<211> LENGTH: 31
<212> TYPE: PRT
<213> ORGANISM: Artificial Sequence
<220> FEATURE:
<223> OTHER INFORMATION: Glucagon analogue

<400> SEQUENCE: 239

His Ser Gln Gly Thr Phe Thr Ser Asp Tyr Ser Arg Tyr Leu Asp Ser
1               5                   10                  15

Lys Arg Ala His Glu Phe Ile Gln Trp Leu Leu Asn Thr Gly His
            20                  25                  30

<210> SEQ ID NO 240
<211> LENGTH: 31

```
<212> TYPE: PRT
<213> ORGANISM: Artificial Sequence
<220> FEATURE:
<223> OTHER INFORMATION: Glucagon analogue

<400> SEQUENCE: 240

His Ser Gln Gly Thr Phe Thr Ser Asp Tyr Ser Arg Tyr Leu Asp Ser
1               5                   10                  15

Lys Arg Ala His Glu Phe Val Glu Trp Leu Leu Asn Thr Gly His
            20                  25                  30

<210> SEQ ID NO 241
<211> LENGTH: 31
<212> TYPE: PRT
<213> ORGANISM: Artificial Sequence
<220> FEATURE:
<223> OTHER INFORMATION: Glucagon analogue

<400> SEQUENCE: 241

His Ser Gln Gly Thr Phe Thr Ser Asp Tyr Ser Arg Tyr Leu Asp Ser
1               5                   10                  15

Lys Arg Ala His Glu Phe Val Gln Trp Leu Leu Asn Gly Gly His
            20                  25                  30

<210> SEQ ID NO 242
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 242

His Ser Gln Gly Thr Phe Thr Ser Asp Tyr Ser Arg Tyr Leu Asp Ser
1               5                   10                  15

Lys Arg Ala His Glu Phe Val Gln Trp Leu Leu Asn Thr Gly His
            20                  25                  30

<210> SEQ ID NO 243
<211> LENGTH: 31
<212> TYPE: PRT
<213> ORGANISM: Artificial Sequence
<220> FEATURE:
<223> OTHER INFORMATION: Glucagon analogue

<400> SEQUENCE: 243

His Ser Gln Gly Thr Phe Thr Ser Asp Tyr Ser Lys Tyr Leu Asp Ser
1               5                   10                  15

Arg Arg Ala His Glu Phe Ile Gln Trp Leu Leu Asn Thr His His
            20                  25                  30

<210> SEQ ID NO 244
<211> LENGTH: 31
<212> TYPE: PRT
<213> ORGANISM: Artificial Sequence
<220> FEATURE:
<223> OTHER INFORMATION: Glucagon analogue

<400> SEQUENCE: 244

His Ser Gln Gly Thr Phe Thr Ser Asp Leu Ser Lys Tyr Leu Asp Glu
1               5                   10                  15

Arg Arg Ala His Glu Phe Val Glu Trp Leu Leu Asn Gly Gly His
            20                  25                  30
```

20                  25                  30

<210> SEQ ID NO 245
<211> LENGTH: 31
<212> TYPE: PRT
<213> ORGANISM: Artificial Sequence
<220> FEATURE:
<223> OTHER INFORMATION: Glucagon analogue

<400> SEQUENCE: 245

His Ser Gln Gly Thr Phe Thr Ser Asp Leu Ser Lys Gln Leu Asp Glu
1               5                   10                  15

Arg Arg Ala His Glu Phe Val Glu Trp Leu Leu Asn Gly Gly His
            20                  25                  30

<210> SEQ ID NO 246
<211> LENGTH: 31
<212> TYPE: PRT
<213> ORGANISM: Artificial Sequence
<220> FEATURE:
<223> OTHER INFORMATION: Glucagon analogue

<400> SEQUENCE: 246

His Ser Gln Gly Thr Phe Thr Ser Asp Tyr Ser Lys Gln Leu Asp Glu
1               5                   10                  15

Arg Arg Ala His Glu Phe Val Glu Trp Leu Leu Asn Gly Gly His
            20                  25                  30

<210> SEQ ID NO 247
<211> LENGTH: 31
<212> TYPE: PRT
<213> ORGANISM: Artificial Sequence
<220> FEATURE:
<223> OTHER INFORMATION: Glucagon analogue

<400> SEQUENCE: 247

His Ser Gln Gly Thr Phe Thr Ser Asp Tyr Ser Lys Tyr Leu Asp Glu
1               5                   10                  15

Lys Lys Ala His Glu Phe Val Glu Trp Leu Leu Asn Gly Gly His
            20                  25                  30

<210> SEQ ID NO 248
<211> LENGTH: 31
<212> TYPE: PRT
<213> ORGANISM: Artificial Sequence
<220> FEATURE:
<223> OTHER INFORMATION: Glucagon analogue

<400> SEQUENCE: 248

His Ser Gln Gly Thr Phe Thr Ser Asp Leu Ser Arg Gln Leu Asp Ser
1               5                   10                  15

Arg Arg Ala His Glu Phe Ile Glu Trp Leu Leu Asn Thr His His
            20                  25                  30

<210> SEQ ID NO 249
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 249

His Ser Gln Gly Thr Phe Thr Ser Asp Leu Ser Arg Gln Leu Asp Ser
1               5                   10                  15

Arg Arg Ala His Glu Phe Ile Glu Trp Leu Leu Asn Gly Gly His
            20                  25                  30

<210> SEQ ID NO 250
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 250

His Ser Gln Gly Thr Phe Thr Ser Asp Leu Ser Arg Gln Leu Asp Ser
1               5                   10                  15

Arg Arg Ala His Glu Phe Ile Glu Trp Leu Leu Asn Thr His
            20                  25                  30

<210> SEQ ID NO 251
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 251

His Ser Gln Gly Thr Phe Thr Ser Asp Leu Ser His Gln Leu Asp Ser
1               5                   10                  15

Arg Arg Ala His Glu Phe Ile Glu Trp Leu Leu Asn Thr His
            20                  25                  30

<210> SEQ ID NO 252
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 252

His Ser Gln Gly Thr Phe Thr Ser Asp Leu Ser Arg Gln Leu Asp Ser
1               5                   10                  15

Arg Arg Ala His Glu Phe Ile Glu Trp Leu Leu Asn Thr His His
            20                  25                  30

<210> SEQ ID NO 253
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

```
<400> SEQUENCE: 253

His Ser Gln Gly Thr Phe Thr Ser Asp Leu Ser Arg His Leu Asp Ser
1               5                   10                  15

Lys Arg Ala His Glu Phe Val Gln Trp Leu Leu Asn Thr His His
            20                  25                  30

<210> SEQ ID NO 254
<211> LENGTH: 31
<212> TYPE: PRT
<213> ORGANISM: Artificial Sequence
<220> FEATURE:
<223> OTHER INFORMATION: Glucagon analogue

<400> SEQUENCE: 254

His Ser Gln Gly Thr Phe Thr Ser Asp Leu Ser Arg Gln Leu Asp Ser
1               5                   10                  15

Arg Arg Ala His Glu Phe Ile Gln Trp Leu Leu Asn Thr His His
            20                  25                  30

<210> SEQ ID NO 255
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 255

His Ser Gln Gly Thr Phe Thr Ser Asp Leu Ser Arg Gln Leu Asp Ser
1               5                   10                  15

Arg Arg Ala His Glu Phe Val Gln Trp Leu Leu Asn Thr His
            20                  25                  30

<210> SEQ ID NO 256
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 256

His Ser Gln Gly Thr Phe Thr Ser Asp Leu Ser Arg Gln Leu Asp Ser
1               5                   10                  15

Arg Arg Ala His Glu Phe Val Gln Trp Leu Leu Asn Thr His His
            20                  25                  30

<210> SEQ ID NO 257
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 257

His Ser Gln Gly Thr Phe Thr Ser Asp Leu Ser Arg Gln Leu Asp Glu
```

```
                1               5                  10                  15
Arg Arg Ala His Glu Phe Val Glu Trp Leu Leu Asn Thr His His
            20                  25              30
```

<210> SEQ ID NO 258
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 258

```
His Ser Gln Gly Thr Phe Thr Ser Asp Leu Ser Arg Gln Leu Asp Glu
1               5                  10                  15
Arg Arg Ala His Glu Phe Val Gln Trp Leu Leu Asn Thr His His
            20                  25              30
```

<210> SEQ ID NO 259
<211> LENGTH: 31
<212> TYPE: PRT
<213> ORGANISM: Artificial Sequence
<220> FEATURE:
<223> OTHER INFORMATION: Glucagon analogue

<400> SEQUENCE: 259

```
His Ser Gln Gly Thr Phe Thr Ser Asp Tyr Ser Lys Gln Leu Asp Ser
1               5                  10                  15
Arg Arg Ala His Glu Phe Val Gln Trp Leu Leu Asn Thr His His
            20                  25              30
```

<210> SEQ ID NO 260
<211> LENGTH: 31
<212> TYPE: PRT
<213> ORGANISM: Artificial Sequence
<220> FEATURE:
<223> OTHER INFORMATION: Glucagon analogue

<400> SEQUENCE: 260

```
His Ser Gln Gly Thr Phe Thr Ser Asp Leu Ser Lys Gln Leu Asp Ser
1               5                  10                  15
Arg Arg Ala His Glu Phe Val Gln Trp Leu Leu Asn Thr His His
            20                  25              30
```

<210> SEQ ID NO 261
<211> LENGTH: 31
<212> TYPE: PRT
<213> ORGANISM: Artificial Sequence
<220> FEATURE:
<223> OTHER INFORMATION: Glucagon analogue

<400> SEQUENCE: 261

```
His Ser Gln Gly Thr Phe Thr Ser Asp Leu Ser Arg Gln Leu Asp Ser
1               5                  10                  15
Lys Arg Ala His Glu Phe Val Gln Trp Leu Leu Asn Thr His His
            20                  25              30
```

<210> SEQ ID NO 262
<211> LENGTH: 31
<212> TYPE: PRT
<213> ORGANISM: Artificial Sequence
<220> FEATURE:

<223> OTHER INFORMATION: Glucagon analogue

<400> SEQUENCE: 262

His Ser Gln Gly Thr Phe Thr Ser Asp Tyr Ser Arg Tyr Leu Asp Glu
1               5                   10                  15

Lys Arg Ala His Glu Phe Val Gln Trp Leu Leu Asn Thr His His
            20                  25                  30

<210> SEQ ID NO 263
<211> LENGTH: 31
<212> TYPE: PRT
<213> ORGANISM: Artificial Sequence
<220> FEATURE:
<223> OTHER INFORMATION: Glucagon analogue

<400> SEQUENCE: 263

His Ser Gln Gly Thr Phe Thr Ser Asp Tyr Ser Arg His Leu Asp Ser
1               5                   10                  15

Lys Arg Ala His Glu Phe Val Gln Trp Leu Leu Asn Thr His His
            20                  25                  30

<210> SEQ ID NO 264
<211> LENGTH: 31
<212> TYPE: PRT
<213> ORGANISM: Artificial Sequence
<220> FEATURE:
<223> OTHER INFORMATION: Glucagon analogue

<400> SEQUENCE: 264

His Ser Gln Gly Thr Phe Thr Ser Asp Tyr Ser Lys Tyr Leu Asp Ser
1               5                   10                  15

Lys Arg Ala His Glu Phe Val Gln Trp Leu Leu Asn Thr His His
            20                  25                  30

<210> SEQ ID NO 265
<211> LENGTH: 31
<212> TYPE: PRT
<213> ORGANISM: Artificial Sequence
<220> FEATURE:
<223> OTHER INFORMATION: Glucagon analogue

<400> SEQUENCE: 265

His Ser Gln Gly Thr Phe Thr Ser Asp Tyr Ser Arg Tyr Leu Asp Ser
1               5                   10                  15

Lys Arg Ala His Glu Phe Val Gln Trp Leu Leu Asn Thr His His
            20                  25                  30

<210> SEQ ID NO 266
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 266

His Ser Gln Gly Thr Phe Thr Ser Asp Tyr Ser Arg Tyr Leu Glu Glu
1               5                   10                  15

Arg Arg Ala His Glu Phe Val Gln Trp Leu Leu Asn Gly Gly His
            20                  25                  30

```
<210> SEQ ID NO 267
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 267

His Ser Gln Gly Thr Phe Thr Ser Asp Leu Ser Arg Gln Leu Glu Glu
1               5                   10                  15

Arg Arg Ala His Glu Phe Val Gln Trp Leu Leu Asn Gly Gly His
            20                  25                  30

<210> SEQ ID NO 268
<211> LENGTH: 31
<212> TYPE: PRT
<213> ORGANISM: Artificial Sequence
<220> FEATURE:
<223> OTHER INFORMATION: Glucagon analogue

<400> SEQUENCE: 268

His Ser Gln Gly Thr Phe Thr Ser Asp Leu Ser Arg Gln Leu Glu Glu
1               5                   10                  15

Arg Arg Ala His Glu Phe Val Gln Trp Leu Leu Asn Gly Gly His
            20                  25                  30

<210> SEQ ID NO 269
<211> LENGTH: 31
<212> TYPE: PRT
<213> ORGANISM: Artificial Sequence
<220> FEATURE:
<223> OTHER INFORMATION: Glucagon analogue

<400> SEQUENCE: 269

His Ser Gln Gly Thr Phe Thr Ser Asp Leu Ser Arg Gln Leu Glu Glu
1               5                   10                  15

Arg Arg Ala His Glu Phe Val Glu Trp Leu Leu Asn Gly Gly His
            20                  25                  30

<210> SEQ ID NO 270
<211> LENGTH: 31
<212> TYPE: PRT
<213> ORGANISM: Artificial Sequence
<220> FEATURE:
<223> OTHER INFORMATION: Glucagon analogue

<400> SEQUENCE: 270

His Ser Gln Gly Thr Phe Thr Ser Asp Leu Ser Arg Gln Leu Glu Glu
1               5                   10                  15

Lys Arg Ala His Glu Phe Val Gln Trp Leu Leu Asn Gly Gly His
            20                  25                  30

<210> SEQ ID NO 271
<211> LENGTH: 31
<212> TYPE: PRT
<213> ORGANISM: Artificial Sequence
<220> FEATURE:
<223> OTHER INFORMATION: Glucagon analogue

<400> SEQUENCE: 271

His Ser Gln Gly Thr Phe Thr Ser Asp Leu Ser Lys Gln Leu Asp Gln
1               5                   10                  15
```

```
Arg Arg Ala His Glu Phe Val Gln Trp Leu Leu Asn Thr His His
        20                  25                  30

<210> SEQ ID NO 272
<211> LENGTH: 31
<212> TYPE: PRT
<213> ORGANISM: Artificial Sequence
<220> FEATURE:
<223> OTHER INFORMATION: Glucagon analogue

<400> SEQUENCE: 272

His Ser Gln Gly Thr Phe Thr Ser Asp Tyr Ser Lys Gln Leu Asp Gln
1               5                   10                  15

Arg Arg Ala His Glu Phe Val Gln Trp Leu Leu Asn Thr His His
        20                  25                  30

<210> SEQ ID NO 273
<211> LENGTH: 31
<212> TYPE: PRT
<213> ORGANISM: Artificial Sequence
<220> FEATURE:
<223> OTHER INFORMATION: Glucagon analogue

<400> SEQUENCE: 273

His Ser Gln Gly Thr Phe Thr Ser Asp Tyr Ser Lys Tyr Leu Asp Gln
1               5                   10                  15

Lys Arg Ala His Glu Phe Val Gln Trp Leu Leu Asn Thr His His
        20                  25                  30

<210> SEQ ID NO 274
<211> LENGTH: 31
<212> TYPE: PRT
<213> ORGANISM: Artificial Sequence
<220> FEATURE:
<223> OTHER INFORMATION: Glucagon analogue

<400> SEQUENCE: 274

His Ser Gln Gly Thr Phe Thr Ser Asp Tyr Ser Lys Tyr Leu Asp Gln
1               5                   10                  15

Arg Arg Ala His Glu Phe Val Gln Trp Leu Leu Asn Gly His His
        20                  25                  30

<210> SEQ ID NO 275
<211> LENGTH: 31
<212> TYPE: PRT
<213> ORGANISM: Artificial Sequence
<220> FEATURE:
<223> OTHER INFORMATION: Glucagon analogue

<400> SEQUENCE: 275

His Ser Gln Gly Thr Phe Thr Ser Asp Tyr Ser Lys Tyr Leu Glu Gln
1               5                   10                  15

Arg Arg Ala His Glu Phe Val Gln Trp Leu Leu Asn Thr His His
        20                  25                  30

<210> SEQ ID NO 276
<211> LENGTH: 31
<212> TYPE: PRT
<213> ORGANISM: Artificial Sequence
<220> FEATURE:
<223> OTHER INFORMATION: Glucagon analogue

<400> SEQUENCE: 276

His Ser Gln Gly Thr Phe Thr Ser Asp Tyr Ser Lys Tyr Leu Asp Gln
```

```
                1               5                  10                  15
Arg Arg Ala His Glu Phe Val Glu Trp Leu Leu Asn Thr His His
                20                  25                  30

<210> SEQ ID NO 277
<211> LENGTH: 31
<212> TYPE: PRT
<213> ORGANISM: Artificial Sequence
<220> FEATURE:
<223> OTHER INFORMATION: Glucagon analogue

<400> SEQUENCE: 277

His Ser Gln Gly Thr Phe Thr Ser Asp Leu Ser Arg Gln Leu Glu Gln
1               5                   10                  15

Arg Arg Ala His Glu Phe Val Gln Trp Leu Leu Asn Thr His His
                20                  25                  30

<210> SEQ ID NO 278
<211> LENGTH: 31
<212> TYPE: PRT
<213> ORGANISM: Artificial Sequence
<220> FEATURE:
<223> OTHER INFORMATION: Glucagon analogue

<400> SEQUENCE: 278

His Ser Gln Gly Thr Phe Thr Ser Asp Tyr Ser Arg Tyr Leu Glu Gln
1               5                   10                  15

Arg Arg Ala His Glu Phe Val Gln Trp Leu Leu Asn Thr His His
                20                  25                  30

<210> SEQ ID NO 279
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 279

His Ser Gln Gly Thr Phe Thr Ser Asp Leu Ser Arg Gln Leu Glu Glu
1               5                   10                  15

Arg Arg Ala His Glu Phe Val Glu Trp Leu Leu Asn Gly His His
                20                  25                  30

<210> SEQ ID NO 280
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 280

His Ser Gln Gly Thr Phe Thr Ser Asp Leu Ser Arg Gln Leu Glu Glu
1               5                   10                  15

Arg Arg Ala His Glu Phe Ile Glu Trp Leu Leu Asn Gly His His
                20                  25                  30

<210> SEQ ID NO 281
```

<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 281

His Ser Gln Gly Thr Phe Thr Ser Asp Leu Ser Arg Gln Leu Asp Ser
1               5                   10                  15

Arg Arg Ala His Glu Phe Ile Glu Trp Leu Leu Asn Gly His His
            20                  25                  30

<210> SEQ ID NO 282
<211> LENGTH: 31
<212> TYPE: PRT
<213> ORGANISM: Artificial Sequence
<220> FEATURE:
<223> OTHER INFORMATION: Glucagon analogue

<400> SEQUENCE: 282

His Ser Gln Gly Thr Phe Thr Ser Asp Tyr Ser Lys Tyr Leu Glu Glu
1               5                   10                  15

Arg Arg Ala His Glu Phe Val Gln Trp Leu Leu Asn Gly Gly His
            20                  25                  30

<210> SEQ ID NO 283
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 283

His Ser Gln Gly Thr Phe Thr Ser Asp Tyr Ser Lys Tyr Leu Glu Glu
1               5                   10                  15

Arg Arg Ala His Glu Phe Val Glu Trp Leu Leu Asn Gly Gly His
            20                  25                  30

<210> SEQ ID NO 284
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 284

His Ser Gln Gly Thr Phe Thr Ser Asp Tyr Ser Lys Tyr Leu Glu Glu
1               5                   10                  15

Arg Arg Ala His Glu Phe Val Glu Trp Leu Leu Asn Gly His His
            20                  25                  30

<210> SEQ ID NO 285
<211> LENGTH: 31
<212> TYPE: PRT
<213> ORGANISM: Artificial Sequence

```
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 285

His Ser Gln Gly Thr Phe Thr Ser Asp Leu Ser Arg Gln Leu Asp Gln
1               5                   10                  15

Arg Arg Ala His Glu Phe Val Gln Trp Leu Leu Asn Thr His His
            20                  25                  30

<210> SEQ ID NO 286
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 286

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Thr His His
            20                  25                  30

<210> SEQ ID NO 287
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 287

His Ser Gln Gly Thr Phe Thr Ser Asp Tyr Ser Lys Tyr Leu Asp Gln
1               5                   10                  15

Arg Arg Ala His Glu Phe Val Gln Trp Leu Leu Asn Gly Gly His
            20                  25                  30

<210> SEQ ID NO 288
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 288

His Ser Gln Gly Thr Phe Thr Ser Asp Tyr Ser Arg Tyr Leu Asp Glu
1               5                   10                  15

Arg Arg Ala His Glu Phe Val Gln Trp Leu Leu Asn Thr His His
            20                  25                  30

<210> SEQ ID NO 289
<211> LENGTH: 31
<212> TYPE: PRT
```

-continued

<213> ORGANISM: Artificial Sequence
<220> FEATURE:
<223> OTHER INFORMATION: Glucagon analogue

<400> SEQUENCE: 289

His Ser Gln Gly Thr Phe Thr Ser Asp Tyr Ser Lys Tyr Leu Asp Gln
1               5                   10                  15

Arg Arg Ala His Glu Phe Val Gln Trp Leu Leu Asn Thr Gly His
            20                  25                  30

<210> SEQ ID NO 290
<211> LENGTH: 31
<212> TYPE: PRT
<213> ORGANISM: Artificial Sequence
<220> FEATURE:
<223> OTHER INFORMATION: Glucagon analogue

<400> SEQUENCE: 290

His Ser Gln Gly Thr Phe Thr Ser Asp Tyr Ser Lys Tyr Leu Asp Gln
1               5                   10                  15

Arg Arg Ala His Glu Phe Val Gln Trp Leu Leu Asn Gly Gly His
            20                  25                  30

<210> SEQ ID NO 291
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (30)..(30)
<223> OTHER INFORMATION: AMIDATION

<400> SEQUENCE: 291

His Ser Gln Gly Thr Phe Thr Ser Asp Tyr Ser Lys Tyr Leu Asp Gln
1               5                   10                  15

Arg Arg Ala His Glu Phe Val Glu Trp Leu Leu Asn Gly His
            20                  25                  30

<210> SEQ ID NO 292
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 292

His Ser Gln Gly Thr Phe Thr Ser Asp Tyr Ser Arg His Leu Asp Glu
1               5                   10                  15

Lys Arg Ala His Glu Phe Val Gln Trp Leu Leu Asn Thr His His
            20                  25                  30

<210> SEQ ID NO 293
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

```
<400> SEQUENCE: 293

His Ser Gln Gly Thr Phe Thr Ser Asp Tyr Ser Arg His Leu Asp Ser
1               5                   10                  15

Lys Arg Ala His Glu Phe Val Gln Trp Leu Leu Asn Gly Gly His
            20                  25                  30

<210> SEQ ID NO 294
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 294

His Ser Gln Gly Thr Phe Thr Ser Asp Tyr Ser Arg His Leu Asp Ser
1               5                   10                  15

Lys Arg Ala His Asp Phe Val Gln Trp Leu Leu Asn Thr His His
            20                  25                  30

<210> SEQ ID NO 295
<211> LENGTH: 31
<212> TYPE: PRT
<213> ORGANISM: Artificial Sequence
<220> FEATURE:
<223> OTHER INFORMATION: Glucagon analogue

<400> SEQUENCE: 295

His Ser Gln Gly Thr Phe Thr Ser Asp Tyr Ser His Tyr Leu Asp Ser
1               5                   10                  15

Arg Arg Ala His Glu Phe Ile Gln Trp Leu Leu Asn Gly His His
            20                  25                  30

<210> SEQ ID NO 296
<211> LENGTH: 31
<212> TYPE: PRT
<213> ORGANISM: Artificial Sequence
<220> FEATURE:
<223> OTHER INFORMATION: Glucagon analogue

<400> SEQUENCE: 296

His Ser Gln Gly Thr Phe Thr Ser Asp Tyr Ser His Tyr Leu Asp Glu
1               5                   10                  15

Arg Arg Ala His Glu Phe Val Gln Trp Leu Leu Asn Gly His His
            20                  25                  30

<210> SEQ ID NO 297
<211> LENGTH: 31
<212> TYPE: PRT
<213> ORGANISM: Artificial Sequence
<220> FEATURE:
<223> OTHER INFORMATION: Glucagon analogue

<400> SEQUENCE: 297

His Ser Gln Gly Thr Phe Thr Ser Asp Tyr Ser His Tyr Leu Asp Glu
1               5                   10                  15

Lys Arg Ala His Glu Phe Val Gln Trp Leu Leu Asn Gly His His
            20                  25                  30

<210> SEQ ID NO 298
```

```
<211> LENGTH: 31
<212> TYPE: PRT
<213> ORGANISM: Artificial Sequence
<220> FEATURE:
<223> OTHER INFORMATION: Glucagon analogue

<400> SEQUENCE: 298

His Ser Gln Gly Thr Phe Thr Ser Asp Tyr Ser His Tyr Leu Asp Gln
 1               5                  10                  15

Arg Arg Ala His Glu Phe Val Gln Trp Leu Leu Asn Gly His His
            20                  25                  30

<210> SEQ ID NO 299
<211> LENGTH: 31
<212> TYPE: PRT
<213> ORGANISM: Artificial Sequence
<220> FEATURE:
<223> OTHER INFORMATION: Glucagon analogue

<400> SEQUENCE: 299

His Ser Gln Gly Thr Phe Thr Ser Asp Tyr Ser His Tyr Leu Asp Gln
 1               5                  10                  15

Lys Arg Ala His Glu Phe Val Gln Trp Leu Leu Asn Gly His His
            20                  25                  30

<210> SEQ ID NO 300
<211> LENGTH: 31
<212> TYPE: PRT
<213> ORGANISM: Artificial Sequence
<220> FEATURE:
<223> OTHER INFORMATION: Glucagon analogue

<400> SEQUENCE: 300

His Ser Gln Gly Thr Phe Thr Ser Asp Tyr Ser His Tyr Leu Asp Ser
 1               5                  10                  15

Lys Arg Ala His Glu Phe Val Gln Trp Leu Leu Lys Gly His His
            20                  25                  30

<210> SEQ ID NO 301
<211> LENGTH: 31
<212> TYPE: PRT
<213> ORGANISM: Artificial Sequence
<220> FEATURE:
<223> OTHER INFORMATION: Glucagon analogue

<400> SEQUENCE: 301

His Ser Gln Gly Thr Phe Thr Ser Asp Tyr Ser His Tyr Leu Asp Ser
 1               5                  10                  15

Lys Arg Ala His Glu Phe Val Gln Trp Leu Leu Asn Gly Lys His
            20                  25                  30

<210> SEQ ID NO 302
<211> LENGTH: 31
<212> TYPE: PRT
<213> ORGANISM: Artificial Sequence
<220> FEATURE:
<223> OTHER INFORMATION: Glucagon analogue

<400> SEQUENCE: 302

His Ser Gln Gly Thr Phe Thr Ser Asp Tyr Ser His Gln Leu Asp Ser
 1               5                  10                  15

Lys Arg Ala His Glu Phe Val Gln Trp Leu Leu Asn Gly His His
            20                  25                  30
```

<210> SEQ ID NO 303
<211> LENGTH: 31
<212> TYPE: PRT
<213> ORGANISM: Artificial Sequence
<220> FEATURE:
<223> OTHER INFORMATION: Glucagon analogue

<400> SEQUENCE: 303

His Ser Gln Gly Thr Phe Thr Ser Asp Leu Ser His Gln Leu Asp Ser
1               5                   10                  15

Lys Arg Ala His Glu Phe Val Gln Trp Leu Leu Asn Gly His His
            20                  25                  30

<210> SEQ ID NO 304
<211> LENGTH: 31
<212> TYPE: PRT
<213> ORGANISM: Artificial Sequence
<220> FEATURE:
<223> OTHER INFORMATION: Glucagon analogue

<400> SEQUENCE: 304

His Ser Gln Gly Thr Phe Thr Ser Asp Tyr Ser His Tyr Leu Asp Ser
1               5                   10                  15

Lys Lys Ala His Glu Phe Val Gln Trp Leu Leu Asn Gly His His
            20                  25                  30

<210> SEQ ID NO 305
<211> LENGTH: 31
<212> TYPE: PRT
<213> ORGANISM: Artificial Sequence
<220> FEATURE:
<223> OTHER INFORMATION: Glucagon analogue

<400> SEQUENCE: 305

His Ser Gln Gly Thr Phe Thr Ser Asp Tyr Ser Arg His Leu Asp Ser
1               5                   10                  15

Lys Arg Ala His Glu Phe Val Gln Trp Leu Leu Asn Gly His His
            20                  25                  30

<210> SEQ ID NO 306
<211> LENGTH: 31
<212> TYPE: PRT
<213> ORGANISM: Artificial Sequence
<220> FEATURE:
<223> OTHER INFORMATION: Glucagon analogue

<400> SEQUENCE: 306

His Ser Gln Gly Thr Phe Thr Ser Asp Tyr Ser His Tyr Leu Asp Ser
1               5                   10                  15

Lys Arg Ala His Glu Phe Val Glu Trp Leu Leu Asn Gly His His
            20                  25                  30

<210> SEQ ID NO 307
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 307

His Ser Gln Gly Thr Phe Thr Ser Asp Tyr Ser Arg Tyr Leu Asp Glu
1               5                   10                  15

```
Arg Arg Ala His Glu Phe Val Glu Trp Leu Leu Asn Gly His His
            20                  25                  30

<210> SEQ ID NO 308
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 308

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His
            20                  25                  30

<210> SEQ ID NO 309
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 309

His Ser Gln Gly Thr Phe Thr Ser Asp Tyr Ser Arg Tyr Leu Asp Glu
1               5                   10                  15

Arg Arg Ala His Glu Phe Val Glu Trp Leu Leu Asn Thr His His
            20                  25                  30

<210> SEQ ID NO 310
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 310

His Ser Gln Gly Thr Phe Thr Ser Asp Tyr Ser Lys Tyr Leu Asp Gln
1               5                   10                  15

Arg Arg Ala His Glu Phe Val Glu Trp Leu Leu Asn Gly His His
            20                  25                  30

<210> SEQ ID NO 311
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 311

His Ser Gln Gly Thr Phe Thr Ser Asp Tyr Ser Arg Tyr Leu Asp Glu
```

```
                1               5                  10                  15
Lys Arg Ala His Glu Phe Val Glu Trp Leu Leu Asn Thr His His
                20                  25                  30
```

<210> SEQ ID NO 312
<211> LENGTH: 31
<212> TYPE: PRT
<213> ORGANISM: Artificial Sequence
<220> FEATURE:
<223> OTHER INFORMATION: Glucagon analogue

<400> SEQUENCE: 312

```
His Ser Gln Gly Thr Phe Thr Ser Asp Tyr Ser Arg Tyr Leu Asp Glu
1               5                   10                  15
Arg Arg Ala His Glu Phe Val Glu Trp Leu Leu Asn Thr His His
                20                  25                  30
```

<210> SEQ ID NO 313
<211> LENGTH: 31
<212> TYPE: PRT
<213> ORGANISM: Artificial Sequence
<220> FEATURE:
<223> OTHER INFORMATION: Glucagon analogue

<400> SEQUENCE: 313

```
His Ser Gln Gly Thr Phe Thr Ser Asp Tyr Ser Lys Tyr Leu Asp Glu
1               5                   10                  15
Arg Arg Ala His Glu Phe Ile Glu Trp Leu Leu Asn Thr His His
                20                  25                  30
```

<210> SEQ ID NO 314
<211> LENGTH: 31
<212> TYPE: PRT
<213> ORGANISM: Artificial Sequence
<220> FEATURE:
<223> OTHER INFORMATION: Glucagon analogue

<400> SEQUENCE: 314

```
His Ser Gln Gly Thr Phe Thr Ser Asp Tyr Ser His Tyr Leu Asp Glu
1               5                   10                  15
Arg Arg Ala His Glu Phe Val Glu Trp Leu Leu Asn Thr His His
                20                  25                  30
```

<210> SEQ ID NO 315
<211> LENGTH: 31
<212> TYPE: PRT
<213> ORGANISM: Artificial Sequence
<220> FEATURE:
<223> OTHER INFORMATION: Glucagon analogue

<400> SEQUENCE: 315

```
His Ser Gln Gly Thr Phe Thr Ser Asp Tyr Ser Lys His Leu Asp Glu
1               5                   10                  15
Arg Arg Ala His Glu Phe Val Glu Trp Leu Leu Asn Thr His His
                20                  25                  30
```

<210> SEQ ID NO 316
<211> LENGTH: 32
<212> TYPE: PRT
<213> ORGANISM: Artificial Sequence
<220> FEATURE:
<223> OTHER INFORMATION: Glucagon analogue

<400> SEQUENCE: 316

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly Gly His His
                20                  25                  30

<210> SEQ ID NO 317
<211> LENGTH: 31
<212> TYPE: PRT
<213> ORGANISM: Artificial Sequence
<220> FEATURE:
<223> OTHER INFORMATION: Glucagon analogue

<400> SEQUENCE: 317

His Ser Gln Gly Thr Phe Thr Ser Asp Tyr Ser Arg Tyr Leu Asp Glu
1               5                   10                  15

Lys Arg Ala His Glu Phe Val Glu Trp Leu Leu Asn Thr His His
                20                  25                  30

<210> SEQ ID NO 318
<211> LENGTH: 31
<212> TYPE: PRT
<213> ORGANISM: Artificial Sequence
<220> FEATURE:
<223> OTHER INFORMATION: Glucagon analogue

<400> SEQUENCE: 318

His Ser Gln Gly Thr Phe Thr Ser Asp Tyr Ser Arg Tyr Leu Asp Glu
1               5                   10                  15

Lys Arg Ala His Glu Phe Ile Glu Trp Leu Leu Asn Thr His His
                20                  25                  30

<210> SEQ ID NO 319
<211> LENGTH: 31
<212> TYPE: PRT
<213> ORGANISM: Artificial Sequence
<220> FEATURE:
<223> OTHER INFORMATION: Glucagon analogue

<400> SEQUENCE: 319

His Ser Gln Gly Thr Phe Thr Ser Asp Tyr Ser Lys Gln Leu Asp Gln
1               5                   10                  15

Arg Arg Ala His Glu Phe Val Glu Trp Leu Leu Asn Thr His His
                20                  25                  30

<210> SEQ ID NO 320
<211> LENGTH: 31
<212> TYPE: PRT
<213> ORGANISM: Artificial Sequence
<220> FEATURE:
<223> OTHER INFORMATION: Glucagon analogue

<400> SEQUENCE: 320

His Ser Gln Gly Thr Phe Thr Ser Asp Tyr Ser Lys Gln Leu Asp Glu
1               5                   10                  15

Arg Arg Ala His Glu Phe Val Glu Trp Leu Leu Asn Thr His His
                20                  25                  30

<210> SEQ ID NO 321
<211> LENGTH: 31
<212> TYPE: PRT
<213> ORGANISM: Artificial Sequence
<220> FEATURE:
<223> OTHER INFORMATION: Glucagon analogue

<400> SEQUENCE: 321

His Ser Gln Gly Thr Phe Thr Ser Asp Tyr Ser Lys Gln Leu Asp Glu
1               5                   10                  15

Lys Arg Ala His Glu Phe Val Glu Trp Leu Leu Asn Thr His His
            20                  25                  30

<210> SEQ ID NO 322
<211> LENGTH: 31
<212> TYPE: PRT
<213> ORGANISM: Artificial Sequence
<220> FEATURE:
<223> OTHER INFORMATION: Glucagon analogue

<400> SEQUENCE: 322

His Ser Gln Gly Thr Phe Thr Ser Asp Tyr Ser Lys Tyr Leu Asp Glu
1               5                   10                  15

Lys Arg Ala His Glu Phe Val Glu Trp Leu Leu Asn Thr His His
            20                  25                  30

<210> SEQ ID NO 323
<211> LENGTH: 31
<212> TYPE: PRT
<213> ORGANISM: Artificial Sequence
<220> FEATURE:
<223> OTHER INFORMATION: Glucagon analogue

<400> SEQUENCE: 323

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr His His
            20                  25                  30

<210> SEQ ID NO 324
<211> LENGTH: 31
<212> TYPE: PRT
<213> ORGANISM: Artificial Sequence
<220> FEATURE:
<223> OTHER INFORMATION: Glucagon analogue

<400> SEQUENCE: 324

His Ser Gln Gly Thr Phe Thr Ser Asp Tyr Ser His Tyr Leu Asp Ser
1               5                   10                  15

Arg Arg Ala His Glu Phe Ile Glu Trp Leu Leu Asn Thr His His
            20                  25                  30

<210> SEQ ID NO 325
<211> LENGTH: 31
<212> TYPE: PRT
<213> ORGANISM: Artificial Sequence
<220> FEATURE:
<223> OTHER INFORMATION: Glucagon analogue

<400> SEQUENCE: 325

His Ser Gln Gly Thr Phe Thr Ser Asp Tyr Ser His Tyr Leu Asp Ser
1               5                   10                  15

Lys Arg Ala His Glu Phe Val Glu Trp Leu Leu Asn Thr His His
            20                  25                  30

<210> SEQ ID NO 326
<211> LENGTH: 31
<212> TYPE: PRT
<213> ORGANISM: Artificial Sequence
<220> FEATURE:
<223> OTHER INFORMATION: Glucagon analogue

```
<400> SEQUENCE: 326

His Ser Gln Gly Thr Phe Thr Ser Asp Tyr Ser His Tyr Leu Asp Ser
1               5                   10                  15

Lys Arg Ala His Glu Phe Ile Glu Trp Leu Leu Asn Thr His His
            20                  25                  30

<210> SEQ ID NO 327
<211> LENGTH: 31
<212> TYPE: PRT
<213> ORGANISM: Artificial Sequence
<220> FEATURE:
<223> OTHER INFORMATION: Glucagon analogue

<400> SEQUENCE: 327

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His
            20                  25                  30

<210> SEQ ID NO 328
<211> LENGTH: 31
<212> TYPE: PRT
<213> ORGANISM: Artificial Sequence
<220> FEATURE:
<223> OTHER INFORMATION: Glucagon analogue

<400> SEQUENCE: 328

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Thr His His
            20                  25                  30

<210> SEQ ID NO 329
<211> LENGTH: 31
<212> TYPE: PRT
<213> ORGANISM: Artificial Sequence
<220> FEATURE:
<223> OTHER INFORMATION: Glucagon analogue

<400> SEQUENCE: 329

His Ser Gln Gly Thr Phe Thr Ser Asp Tyr Ser His Tyr Leu Asp Gln
1               5                   10                  15

Arg Arg Ala His Glu Phe Val Gln Trp Leu Leu Asn Thr His His
            20                  25                  30

<210> SEQ ID NO 330
<211> LENGTH: 31
<212> TYPE: PRT
<213> ORGANISM: Artificial Sequence
<220> FEATURE:
<223> OTHER INFORMATION: Glucagon analogue

<400> SEQUENCE: 330

His Ser Gln Gly Thr Phe Thr Ser Asp Tyr Ser His Tyr Leu Asp Gln
1               5                   10                  15

Arg Arg Ala His Glu Phe Ile Gln Trp Leu Leu Asn Thr His His
            20                  25                  30

<210> SEQ ID NO 331
<211> LENGTH: 31
<212> TYPE: PRT
<213> ORGANISM: Artificial Sequence
<220> FEATURE:
<223> OTHER INFORMATION: Glucagon analogue
```

```
<220> FEATURE:
<221> NAME/KEY: MOD_RES
<222> LOCATION: (31)..(31)
<223> OTHER INFORMATION: AMIDATION

<400> SEQUENCE: 331

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His His
            20                  25                  30

<210> SEQ ID NO 332
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 332

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr His His
            20                  25                  30

<210> SEQ ID NO 333
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 333

His Ser Gln Gly Thr Phe Thr Ser Asp Tyr Ser Lys Tyr Leu Asp Glu
1               5                   10                  15

Lys Arg Ala His Glu Phe Val Gln Trp Leu Leu Asn Thr His His
            20                  25                  30

<210> SEQ ID NO 334
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 334

His Ser Gln Gly Thr Phe Thr Ser Asp Tyr Ser Lys Tyr Leu Asp Glu
1               5                   10                  15

Lys Arg Ala His Glu Phe Val Glu Trp Leu Leu Asn Thr His His
            20                  25                  30

<210> SEQ ID NO 335
<211> LENGTH: 31
<212> TYPE: PRT
<213> ORGANISM: Artificial Sequence
<220> FEATURE:
```

<223> OTHER INFORMATION: Glucagon analogue

<400> SEQUENCE: 335

His Ser Gln Gly Thr Phe Thr Ser Asp Tyr Ser Arg Tyr Leu Asp Gln
1               5                   10                  15
Arg Arg Ala His Glu Phe Val Glu Trp Leu Leu Asn Thr His His
            20                  25                  30

<210> SEQ ID NO 336
<211> LENGTH: 31
<212> TYPE: PRT
<213> ORGANISM: Artificial Sequence
<220> FEATURE:
<223> OTHER INFORMATION: Glucagon analogue

<400> SEQUENCE: 336

His Ser Gln Gly Thr Phe Thr Ser Asp Tyr Ser Arg Tyr Leu Asp Gln
1               5                   10                  15
Lys Arg Ala His Glu Phe Val Glu Trp Leu Leu Asn Thr His His
            20                  25                  30

<210> SEQ ID NO 337
<211> LENGTH: 31
<212> TYPE: PRT
<213> ORGANISM: Artificial Sequence
<220> FEATURE:
<223> OTHER INFORMATION: Glucagon analogue

<400> SEQUENCE: 337

His Ser Gln Gly Thr Phe Thr Ser Asp Tyr Ser Lys Tyr Leu Asp Gln
1               5                   10                  15
Lys Arg Ala His Glu Phe Val Glu Trp Leu Leu Asn Thr His His
            20                  25                  30

<210> SEQ ID NO 338
<211> LENGTH: 31
<212> TYPE: PRT
<213> ORGANISM: Artificial Sequence
<220> FEATURE:
<223> OTHER INFORMATION: Glucagon analogue

<400> SEQUENCE: 338

His Ser Gln Gly Thr Phe Thr Ser Asp Tyr Ser Arg Gln Leu Asp Gln
1               5                   10                  15
Lys Arg Ala His Glu Phe Val Glu Trp Leu Leu Asn Thr His His
            20                  25                  30

<210> SEQ ID NO 339
<211> LENGTH: 31
<212> TYPE: PRT
<213> ORGANISM: Artificial Sequence
<220> FEATURE:
<223> OTHER INFORMATION: Glucagon analogue

<400> SEQUENCE: 339

His Ser Gln Gly Thr Phe Thr Ser Asp Tyr Ser Arg Gln Leu Asp Glu
1               5                   10                  15
Lys Arg Ala His Glu Phe Val Glu Trp Leu Leu Asn Thr His His
            20                  25                  30

<210> SEQ ID NO 340
<211> LENGTH: 31
<212> TYPE: PRT
<213> ORGANISM: Artificial Sequence

```
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 340

His Ser Gln Gly Thr Phe Thr Ser Asp Tyr Ser His Tyr Leu Asp Gln
1               5                   10                  15

Arg Arg Ala His Glu Phe Val Gln Trp Leu Leu Asn Gly His His
            20                  25                  30

<210> SEQ ID NO 341
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 341

His Ser Gln Gly Thr Phe Thr Ser Asp Tyr Ser His Tyr Leu Asp Gln
1               5                   10                  15

Arg Arg Ala His Glu Phe Val Glu Trp Leu Leu Asn Gly His His
            20                  25                  30

<210> SEQ ID NO 342
<211> LENGTH: 31
<212> TYPE: PRT
<213> ORGANISM: Artificial Sequence
<220> FEATURE:
<223> OTHER INFORMATION: Glucagon analogue

<400> SEQUENCE: 342

His Ser Gln Gly Thr Phe Thr Ser Asp Tyr Ser His Tyr Leu Asp Gln
1               5                   10                  15

Arg Arg Ala His Glu Phe Val Glu Trp Leu Leu Asn Gly His His
            20                  25                  30

<210> SEQ ID NO 343
<211> LENGTH: 31
<212> TYPE: PRT
<213> ORGANISM: Artificial Sequence
<220> FEATURE:
<223> OTHER INFORMATION: Glucagon analogue

<400> SEQUENCE: 343

His Ser Gln Gly Thr Phe Thr Ser Asp Tyr Ser His Tyr Leu Asp Gln
1               5                   10                  15

Arg Arg Ala His Glu Phe Val Glu Trp Leu Leu Asn Thr His His
            20                  25                  30

<210> SEQ ID NO 344
<211> LENGTH: 32
<212> TYPE: PRT
<213> ORGANISM: Artificial Sequence
<220> FEATURE:
<223> OTHER INFORMATION: Glucagon analogue

<400> SEQUENCE: 344

His Ser Gln Gly Thr Phe Thr Ser Asp Tyr Ser Lys Tyr Leu Asp Glu
1               5                   10                  15
```

Arg Arg Ala His Glu Phe Val Glu Trp Leu Leu Asn Gly His His His
            20                  25                  30

<210> SEQ ID NO 345
<211> LENGTH: 31
<212> TYPE: PRT
<213> ORGANISM: Artificial Sequence
<220> FEATURE:
<223> OTHER INFORMATION: Glucagon analogue

<400> SEQUENCE: 345

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Gly His His
            20                  25                  30

<210> SEQ ID NO 346
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 346

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Gly His His
            20                  25                  30

<210> SEQ ID NO 347
<211> LENGTH: 31
<212> TYPE: PRT
<213> ORGANISM: Artificial Sequence
<220> FEATURE:
<223> OTHER INFORMATION: Glucagon analogue

<400> SEQUENCE: 347

His Ser Gln Gly Thr Phe Thr Ser Asp Tyr Ser His Tyr Leu Asp Ser
1               5                   10                  15

Lys Arg Ala His Glu Phe Ile Glu Trp Leu Leu Asn Gly His His
            20                  25                  30

<210> SEQ ID NO 348
<211> LENGTH: 31
<212> TYPE: PRT
<213> ORGANISM: Artificial Sequence
<220> FEATURE:
<223> OTHER INFORMATION: Glucagon analogue

<400> SEQUENCE: 348

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Gly Gly His
            20                  25                  30

<210> SEQ ID NO 349
<211> LENGTH: 31
<212> TYPE: PRT
<213> ORGANISM: Artificial Sequence
<220> FEATURE:
<223> OTHER INFORMATION: Glucagon analogue -continued

<400> SEQUENCE: 349

His Ser Gln Gly Thr Phe Thr Ser Asp Tyr Ser Arg His Leu Asp Glu
1               5                   10                  15

Arg Arg Ala His Glu Phe Val Glu Trp Leu Leu Asn Thr His His
            20                  25                  30

<210> SEQ ID NO 350
<211> LENGTH: 31
<212> TYPE: PRT
<213> ORGANISM: Artificial Sequence
<220> FEATURE:
<223> OTHER INFORMATION: Glucagon analogue

<400> SEQUENCE: 350

His Ser Gln Gly Thr Phe Thr Ser Asp Tyr Ser Arg Tyr Leu Asp Glu
1               5                   10                  15

Arg Arg Ala His Glu Phe Ile Glu Trp Leu Leu Asn Thr His His
            20                  25                  30

<210> SEQ ID NO 351
<211> LENGTH: 31
<212> TYPE: PRT
<213> ORGANISM: Artificial Sequence
<220> FEATURE:
<223> OTHER INFORMATION: Glucagon analogue

<400> SEQUENCE: 351

His Ser Gln Gly Thr Phe Thr Ser Asp Tyr Ser Arg His Leu Asp Glu
1               5                   10                  15

Arg Arg Ala His Glu Phe Ile Glu Trp Leu Leu Asn Thr His His
            20                  25                  30

<210> SEQ ID NO 352
<211> LENGTH: 31
<212> TYPE: PRT
<213> ORGANISM: Artificial Sequence
<220> FEATURE:
<223> OTHER INFORMATION: Glucagon analogue

<400> SEQUENCE: 352

His Ser Gln Gly Thr Phe Thr Ser Asp Tyr Ser Lys His Leu Asp Glu
1               5                   10                  15

Arg Arg Ala His Glu Phe Ile Glu Trp Leu Leu Asn Thr His His
            20                  25                  30

<210> SEQ ID NO 353
<211> LENGTH: 31
<212> TYPE: PRT
<213> ORGANISM: Artificial Sequence
<220> FEATURE:
<223> OTHER INFORMATION: Glucagon analogue

<400> SEQUENCE: 353

His Ser Gln Gly Thr Phe Thr Ser Asp Tyr Ser Lys His Leu Asp Glu
1               5                   10                  15

Lys Arg Ala His Glu Phe Val Glu Trp Leu Leu Asn Thr His His
            20                  25                  30

<210> SEQ ID NO 354
<211> LENGTH: 31
<212> TYPE: PRT
<213> ORGANISM: Artificial Sequence
<220> FEATURE:

<223> OTHER INFORMATION: Glucagon analogue

<400> SEQUENCE: 354

His Ser Gln Gly Thr Phe Thr Ser Asp Tyr Ser Lys His Leu Asp Glu
1               5                   10                  15

Lys Arg Ala His Glu Phe Ile Glu Trp Leu Leu Asn Thr His His
            20                  25                  30

<210> SEQ ID NO 355
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 355

His Ser Gln Gly Thr Phe Thr Ser Asp Tyr Ser Lys His Leu Asp Glu
1               5                   10                  15

Arg Arg Ala His Glu Phe Ile Glu Trp Leu Leu Asn Thr His His
            20                  25                  30

<210> SEQ ID NO 356
<211> LENGTH: 31
<212> TYPE: PRT
<213> ORGANISM: Artificial Sequence
<220> FEATURE:
<223> OTHER INFORMATION: Glucagon analogue

<400> SEQUENCE: 356

His Ser Gln Gly Thr Phe Thr Ser Asp Tyr Ser Lys His Leu Asp Glu
1               5                   10                  15

Arg Arg Ala His Glu Phe Ile Glu Trp Leu Leu Asn Gly His His
            20                  25                  30

<210> SEQ ID NO 357
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 357

His Ser Gln Gly Thr Phe Thr Ser Asp Tyr Ser Lys His Leu Asp Glu
1               5                   10                  15

Arg Arg Ala His Glu Phe Ile Glu Trp Leu Leu Asn Gly His His
            20                  25                  30

<210> SEQ ID NO 358
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 358

His Ser Gln Gly Thr Phe Thr Ser Asp Tyr Ser Lys His Leu Asp Glu
1               5                   10                  15

Arg Arg Ala His Glu Phe Ile Glu Trp Leu Leu Asn Gly Gly His
            20                  25                  30

<210> SEQ ID NO 359
<211> LENGTH: 31
<212> TYPE: PRT
<213> ORGANISM: Artificial Sequence
<220> FEATURE:
<223> OTHER INFORMATION: Glucagon analogue

<400> SEQUENCE: 359

His Ser Gln Gly Thr Phe Thr Ser Asp Tyr Ser Lys His Leu Asp Glu
1               5                   10                  15

Arg Arg Ala His Glu Phe Ile Glu Trp Leu Leu Asn Gly Gly His
            20                  25                  30

<210> SEQ ID NO 360
<211> LENGTH: 31
<212> TYPE: PRT
<213> ORGANISM: Artificial Sequence
<220> FEATURE:
<223> OTHER INFORMATION: Glucagon analogue

<400> SEQUENCE: 360

His Ser Gln Gly Thr Phe Thr Ser Asp Tyr Ser His Tyr Leu Asp Ser
1               5                   10                  15

Arg Arg Ala His Glu Phe Ile Gln Trp Leu Leu Asn Gly Gly His
            20                  25                  30

<210> SEQ ID NO 361
<211> LENGTH: 31
<212> TYPE: PRT
<213> ORGANISM: Artificial Sequence
<220> FEATURE:
<223> OTHER INFORMATION: Glucagon analogue

<400> SEQUENCE: 361

His Ser Gln Gly Thr Phe Thr Ser Asp Tyr Ser His Tyr Leu Asp Ser
1               5                   10                  15

Arg Arg Ala His Glu Phe Ile Gln Trp Leu Leu Asn Thr His His
            20                  25                  30

<210> SEQ ID NO 362
<211> LENGTH: 31
<212> TYPE: PRT
<213> ORGANISM: Artificial Sequence
<220> FEATURE:
<223> OTHER INFORMATION: Glucagon analogue

<400> SEQUENCE: 362

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Thr His His
            20                  25                  30

<210> SEQ ID NO 363
<211> LENGTH: 32
<212> TYPE: PRT
<213> ORGANISM: Artificial Sequence
<220> FEATURE:
<223> OTHER INFORMATION: Glucagon analogue

```
<400> SEQUENCE: 363

His Ser Gln Gly Thr Phe Thr Ser Asp Tyr Ser Arg Tyr Leu Asp Ser
1               5                   10                  15

Arg Arg Ala His Glu Phe Ile Glu Trp Leu Leu Asn Gly Gly His His
            20                  25                  30

<210> SEQ ID NO 364
<211> LENGTH: 31
<212> TYPE: PRT
<213> ORGANISM: Artificial Sequence
<220> FEATURE:
<223> OTHER INFORMATION: Glucagon analogue

<400> SEQUENCE: 364

His Ser Gln Gly Thr Phe Thr Ser Asp Tyr Ser Arg Tyr Leu Asp Ser
1               5                   10                  15

Lys Arg Ala His Glu Phe Ile Glu Trp Leu Leu Asn Gly Gly His
            20                  25                  30

<210> SEQ ID NO 365
<211> LENGTH: 31
<212> TYPE: PRT
<213> ORGANISM: Artificial Sequence
<220> FEATURE:
<223> OTHER INFORMATION: Glucagon analogue

<400> SEQUENCE: 365

His Ser Gln Gly Thr Phe Thr Ser Asp Tyr Ser Arg His Leu Asp Ser
1               5                   10                  15

Arg Arg Ala His Glu Phe Ile Glu Trp Leu Leu Asn Gly Gly His
            20                  25                  30

<210> SEQ ID NO 366
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 366

His Ser Gln Gly Thr Phe Thr Ser Asp Tyr Ser Lys Tyr Leu Asp Glu
1               5                   10                  15

Lys Arg Ala His Glu Phe Val Glu Trp Leu Leu Asn Gly His His
            20                  25                  30

<210> SEQ ID NO 367
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 367

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His
            20                  25                  30
```

```
<210> SEQ ID NO 368
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 368

His Ser Gln Gly Thr Phe Thr Ser Asp Tyr Ser Lys His Leu Asp Glu
1               5                   10                  15

Arg Arg Ala His Glu Phe Val Glu Trp Leu Leu Asn Gly His His
            20                  25                  30

<210> SEQ ID NO 369
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 369

His Ser Gln Gly Thr Phe Thr Ser Asp Tyr Ser His Tyr Leu Asp Glu
1               5                   10                  15

Arg Arg Ala His Glu Phe Val Glu Trp Leu Leu Asn Gly His His
            20                  25                  30

<210> SEQ ID NO 370
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 370

His Ser Gln Gly Thr Phe Thr Ser Asp Tyr Ser Arg Tyr Leu Asp Ser
1               5                   10                  15

Arg Arg Ala His Glu Phe Ile Glu Trp Leu Leu Asn Gly Gly His
            20                  25                  30

<210> SEQ ID NO 371
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 371

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
```

-continued

```
                 20                  25                  30

<210> SEQ ID NO 372
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 372

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His
                20                  25                  30

<210> SEQ ID NO 373
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 373

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly Gly His
                20                  25                  30

<210> SEQ ID NO 374
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 374

His Ser Gln Gly Thr Phe Thr Ser Asp Tyr Ser His Tyr Leu Asp Glu
1               5                   10                  15

Arg Arg Ala His Glu Phe Ile Glu Trp Leu Leu Asn Gly His His
                20                  25                  30

<210> SEQ ID NO 375
<211> LENGTH: 31
<212> TYPE: PRT
<213> ORGANISM: Artificial Sequence
<220> FEATURE:
<223> OTHER INFORMATION: Glucagon analogue

<400> SEQUENCE: 375

His Ser Gln Gly Thr Phe Thr Ser Asp Tyr Ser Lys Tyr Leu Asp Ser
1               5                   10                  15

Lys Arg Ala His Glu Phe Ile Gln Trp Leu Leu Asn Thr His His
                20                  25                  30
```

```
<210> SEQ ID NO 376
<211> LENGTH: 31
<212> TYPE: PRT
<213> ORGANISM: Artificial Sequence
<220> FEATURE:
<223> OTHER INFORMATION: Glucagon analogue

<400> SEQUENCE: 376

His Ser Gln Gly Thr Phe Thr Ser Asp Tyr Ser His Tyr Leu Asp Ser
1               5                   10                  15

Arg Arg Ala His Glu Phe Ile Gln Trp Leu Leu Asn Gly His His
            20                  25                  30

<210> SEQ ID NO 377
<211> LENGTH: 31
<212> TYPE: PRT
<213> ORGANISM: Artificial Sequence
<220> FEATURE:
<223> OTHER INFORMATION: Glucagon analogue

<400> SEQUENCE: 377

His Ser Gln Gly Thr Phe Thr Ser Asp Tyr Ser Arg Tyr Leu Asp Glu
1               5                   10                  15

Arg Arg Ala His Glu Phe Ile Gln Trp Leu Leu Asn Thr His His
            20                  25                  30

<210> SEQ ID NO 378
<211> LENGTH: 31
<212> TYPE: PRT
<213> ORGANISM: Artificial Sequence
<220> FEATURE:
<223> OTHER INFORMATION: Glucagon analogue

<400> SEQUENCE: 378

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His
            20                  25                  30

<210> SEQ ID NO 379
<211> LENGTH: 31
<212> TYPE: PRT
<213> ORGANISM: Artificial Sequence
<220> FEATURE:
<223> OTHER INFORMATION: Glucagon analogue

<400> SEQUENCE: 379

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Thr His His
            20                  25                  30

<210> SEQ ID NO 380
<211> LENGTH: 31
<212> TYPE: PRT
<213> ORGANISM: Artificial Sequence
<220> FEATURE:
<223> OTHER INFORMATION: Glucagon analogue

<400> SEQUENCE: 380

His Ser Gln Gly Thr Phe Thr Ser Asp Tyr Ser Lys Tyr Leu Asp Ser
1               5                   10                  15

Arg Arg Ala His Glu Phe Ile Glu Trp Leu Leu Asn Gly His His
            20                  25                  30
```

<210> SEQ ID NO 381
<211> LENGTH: 31
<212> TYPE: PRT
<213> ORGANISM: Artificial Sequence
<220> FEATURE:
<223> OTHER INFORMATION: Glucagon analogue

<400> SEQUENCE: 381

His Ser Gln Gly Thr Phe Thr Ser Asp Tyr Ser His Tyr Leu Asp Gln
1               5                   10                  15

Arg Arg Ala His Glu Phe Ile Gln Trp Leu Leu Asn Gly His His
            20                  25                  30

<210> SEQ ID NO 382
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 382

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

<210> SEQ ID NO 383
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 383

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly Gly His His
            20                  25                  30

<210> SEQ ID NO 384
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 384

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Gly His His
            20                  25                  30

<210> SEQ ID NO 385
<211> LENGTH: 31

```
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 385

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His
            20                  25                  30

<210> SEQ ID NO 386
<211> LENGTH: 31
<212> TYPE: PRT
<213> ORGANISM: Artificial Sequence
<220> FEATURE:
<223> OTHER INFORMATION: Glucagon analogue

<400> SEQUENCE: 386

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His
            20                  25                  30

<210> SEQ ID NO 387
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 387

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

<210> SEQ ID NO 388
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 388

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His
            20                  25                  30

<210> SEQ ID NO 389
<211> LENGTH: 31
<212> TYPE: PRT
<213> ORGANISM: Artificial Sequence
<220> FEATURE:
```

```
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 389

His Ser Gln Gly Thr Phe Thr Ser Asp Tyr Ser His Tyr Leu Asp Ser
1               5                   10                  15

Lys Arg Ala His Glu Phe Ile Glu Trp Leu Leu Asn Gly His His
            20                  25                  30

<210> SEQ ID NO 390
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 390

His Ser Gln Gly Thr Phe Thr Ser Asp Tyr Lys Tyr Leu Asp Glu
1               5                   10                  15

Lys Arg Ala His Glu Phe Ile Gln Trp Leu Leu Asn Gly His His
            20                  25                  30

<210> SEQ ID NO 391
<211> LENGTH: 31
<212> TYPE: PRT
<213> ORGANISM: Artificial Sequence
<220> FEATURE:
<223> OTHER INFORMATION: Glucagon analogue

<400> SEQUENCE: 391

His Ser Gln Gly Thr Phe Thr Ser Asp Tyr Lys Tyr Leu Asp Glu
1               5                   10                  15

Lys Arg Ala His Glu Phe Ile Gln Trp Leu Leu Asn Gly His His
            20                  25                  30

<210> SEQ ID NO 392
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 392

His Ser Gln Gly Thr Phe Thr Ser Asp Tyr Lys Tyr Leu Asp Glu
1               5                   10                  15

Arg Arg Ala His Glu Phe Ile Gln Trp Leu Leu Asn Gly His His
            20                  25                  30

<210> SEQ ID NO 393
<211> LENGTH: 31
<212> TYPE: PRT
<213> ORGANISM: Artificial Sequence
<220> FEATURE:
<223> OTHER INFORMATION: Glucagon analogue

<400> SEQUENCE: 393
```

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His
            20                  25                  30

<210> SEQ ID NO 394
<211> LENGTH: 32
<212> TYPE: PRT
<213> ORGANISM: Artificial Sequence
<220> FEATURE:
<223> OTHER INFORMATION: Glucagon analogue

<400> SEQUENCE: 394

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His
            20                  25                  30

<210> SEQ ID NO 395
<211> LENGTH: 32
<212> TYPE: PRT
<213> ORGANISM: Artificial Sequence
<220> FEATURE:
<223> OTHER INFORMATION: Glucagon analogue

<400> SEQUENCE: 395

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Gly Lys His His
            20                  25                  30

<210> SEQ ID NO 396
<211> LENGTH: 32
<212> TYPE: PRT
<213> ORGANISM: Artificial Sequence
<220> FEATURE:
<223> OTHER INFORMATION: Glucagon analogue

<400> SEQUENCE: 396

His Ser Gln Gly Thr Phe Thr Ser Asp Tyr Ser Lys Tyr Leu Asp Ser
1               5                   10                  15

Arg Arg Ala His Glu Phe Val Glu Trp Leu Leu Asn Gly Gly His His
            20                  25                  30

<210> SEQ ID NO 397
<211> LENGTH: 31
<212> TYPE: PRT
<213> ORGANISM: Artificial Sequence
<220> FEATURE:
<223> OTHER INFORMATION: Glucagon analogue

<400> SEQUENCE: 397

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His
            20                  25                  30

<210> SEQ ID NO 398
<211> LENGTH: 31
<212> TYPE: PRT
<213> ORGANISM: Artificial Sequence
<220> FEATURE:
<223> OTHER INFORMATION: Glucagon analogue -continued

```
<400> SEQUENCE: 398

His Ser Gln Gly Thr Phe Thr Ser Asp Tyr Ser His Tyr Leu Asp Glu
1               5                   10                  15

Lys Arg Ala His Glu Phe Ile Glu Trp Leu Leu Asn Gly His His
            20                  25                  30

<210> SEQ ID NO 399
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 399

His Ser Gln Gly Thr Phe Thr Ser Asp Tyr Ser His Tyr Leu Asp Gln
1               5                   10                  15

Arg Arg Ala His Glu Phe Ile Glu Trp Leu Leu Asn Gly His His
            20                  25                  30

<210> SEQ ID NO 400
<211> LENGTH: 32
<212> TYPE: PRT
<213> ORGANISM: Artificial Sequence
<220> FEATURE:
<223> OTHER INFORMATION: Glucagon analogue

<400> SEQUENCE: 400

His Ser Gln Gly Thr Phe Thr Ser Asp Tyr Ser His Tyr Leu Asp Gln
1               5                   10                  15

Arg Arg Ala His Glu Phe Val Glu Trp Leu Leu Asn Gly His His His
            20                  25                  30

<210> SEQ ID NO 401
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 401

His Ser Gln Gly Thr Phe Thr Ser Asp Tyr Ser His Tyr Leu Asp Gln
1               5                   10                  15

Arg Arg Ala His Glu Phe Ile Gln Trp Leu Leu Asn Gly His His
            20                  25                  30

<210> SEQ ID NO 402
<211> LENGTH: 31
<212> TYPE: PRT
<213> ORGANISM: Artificial Sequence
<220> FEATURE:
<223> OTHER INFORMATION: Glucagon analogue

<400> SEQUENCE: 402

His Ser Gln Gly Thr Phe Thr Ser Asp Tyr Ser His Tyr Leu Asp Gln
1               5                   10                  15

Arg Arg Ala His Glu Phe Ile Glu Trp Leu Leu Asn Gly His His
            20                  25                  30
```

```
<210> SEQ ID NO 403
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 403

His Ser Gln Gly Thr Phe Thr Ser Asp Tyr Ser His Tyr Leu Asp Gln
1               5                   10                  15

Lys Arg Ala His Glu Phe Val Glu Trp Leu Leu Asn Gly His His
            20                  25                  30

<210> SEQ ID NO 404
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 404

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly His His
            20                  25                  30

<210> SEQ ID NO 405
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 405

His Ser Gln Gly Thr Phe Thr Ser Asp Tyr Ser His Tyr Leu Asp Gln
1               5                   10                  15

Arg Arg Ala His Glu Phe Val Glu Trp Leu Leu Asn Gly His His His
            20                  25                  30

<210> SEQ ID NO 406
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 406

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly His His His
```

-continued

```
                 20                  25                  30

<210> SEQ ID NO 407
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 407

His Ser Gln Gly Thr Phe Thr Ser Asp Tyr Ser His Tyr Leu Asp Gln
1               5                   10                  15

Arg Arg Ala His Glu Phe Ile Glu Trp Leu Leu Asn Gly His His His
                20                  25                  30

<210> SEQ ID NO 408
<211> LENGTH: 32
<212> TYPE: PRT
<213> ORGANISM: Artificial Sequence
<220> FEATURE:
<223> OTHER INFORMATION: Glucagon analogue

<400> SEQUENCE: 408

His Ser Gln Gly Thr Phe Thr Ser Asp Tyr Ser His Tyr Leu Asp Gln
1               5                   10                  15

Arg Arg Ala His Glu Phe Ile Glu Trp Leu Leu Asn Gly His His His
                20                  25                  30

<210> SEQ ID NO 409
<211> LENGTH: 32
<212> TYPE: PRT
<213> ORGANISM: Artificial Sequence
<220> FEATURE:
<223> OTHER INFORMATION: Glucagon analogue

<400> SEQUENCE: 409

His Ser Gln Gly Thr Phe Thr Ser Asp Tyr Ser His Tyr Leu Asp Gln
1               5                   10                  15

Arg Arg Ala His Glu Phe Ile Gln Trp Leu Leu Asn Gly His His His
                20                  25                  30

<210> SEQ ID NO 410
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 410

His Ser Gln Gly Thr Phe Thr Ser Asp Tyr Ser His Tyr Leu Asp Gln
1               5                   10                  15

Arg Arg Ala His Glu Phe Ile Gln Trp Leu Leu Asn Gly His His His
                20                  25                  30

<210> SEQ ID NO 411
<211> LENGTH: 32
<212> TYPE: PRT
<213> ORGANISM: Artificial Sequence
```

```
<220> FEATURE:
<223> OTHER INFORMATION: Glucagon analogue

<400> SEQUENCE: 411

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Gly His His His
            20                  25                  30

<210> SEQ ID NO 412
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 412

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Gly His His His
            20                  25                  30

<210> SEQ ID NO 413
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 413

His Ser Gln Gly Thr Phe Thr Ser Asp Tyr Ser Lys Tyr Leu Asp Glu
1               5                   10                  15

Lys Arg Ala His Glu Phe Val Glu Trp Leu Leu Asn Gly His His His
            20                  25                  30

<210> SEQ ID NO 414
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 414

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly His His His
            20                  25                  30

<210> SEQ ID NO 415
<211> LENGTH: 32
<212> TYPE: PRT
<213> ORGANISM: Artificial Sequence
<220> FEATURE:
<223> OTHER INFORMATION: Glucagon analogue
<220> FEATURE:
```

```
<221> NAME/KEY: MOD_RES
<222> LOCATION: (32)..(32)
<223> OTHER INFORMATION: AMIDATION

<400> SEQUENCE: 415

His Ser Gln Gly Thr Phe Thr Ser Asp Tyr Ser His Tyr Leu Asp Gln
1               5                   10                  15

Lys Arg Ala His Glu Phe Ile Gln Trp Leu Leu Asn Gly His His His
            20                  25                  30

<210> SEQ ID NO 416
<211> LENGTH: 31
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (31)..(31)
<223> OTHER INFORMATION: AMIDATION

<400> SEQUENCE: 416

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His
            20                  25                  30

<210> SEQ ID NO 417
<211> LENGTH: 32
<212> TYPE: PRT
<213> ORGANISM: Artificial Sequence
<220> FEATURE:
<223> OTHER INFORMATION: Glucagon analogue

<400> SEQUENCE: 417

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

<210> SEQ ID NO 418
<211> LENGTH: 31
<212> TYPE: PRT
<213> ORGANISM: Artificial Sequence
<220> FEATURE:
<223> OTHER INFORMATION: Glucagon analogue

<400> SEQUENCE: 418

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His
            20                  25                  30

<210> SEQ ID NO 419
<211> LENGTH: 32
<212> TYPE: PRT
<213> ORGANISM: Artificial Sequence
<220> FEATURE:
<223> OTHER INFORMATION: Glucagon analogue

<400> SEQUENCE: 419

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30
```

<210> SEQ ID NO 420
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 420

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

<210> SEQ ID NO 421
<211> LENGTH: 31
<212> TYPE: PRT
<213> ORGANISM: Artificial Sequence
<220> FEATURE:
<223> OTHER INFORMATION: Glucagon analogue

<400> SEQUENCE: 421

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Thr Gly His
            20                  25                  30

<210> SEQ ID NO 422
<211> LENGTH: 32
<212> TYPE: PRT
<213> ORGANISM: Artificial Sequence
<220> FEATURE:
<223> OTHER INFORMATION: Glucagon analogue

<400> SEQUENCE: 422

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Thr Gly His His
            20                  25                  30

<210> SEQ ID NO 423
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 423

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Thr Gly His His
            20                  25                  30

<210> SEQ ID NO 424
<211> LENGTH: 32
<212> TYPE: PRT
<213> ORGANISM: Artificial Sequence
<220> FEATURE:

<223> OTHER INFORMATION: Glucagon analogue

<400> SEQUENCE: 424

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr His His His
            20                  25                  30

<210> SEQ ID NO 425
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 425

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr His His His
            20                  25                  30

<210> SEQ ID NO 426
<211> LENGTH: 32
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (32)..(32)
<223> OTHER INFORMATION: AMIDATION

<400> SEQUENCE: 426

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
            20                  25                  30

<210> SEQ ID NO 427
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 427

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Thr His
            20                  25                  30

<210> SEQ ID NO 428
<211> LENGTH: 30
<212> TYPE: PRT
<213> ORGANISM: Artificial Sequence
<220> FEATURE:
<223> OTHER INFORMATION: GLP-1 analogue

<400> SEQUENCE: 428

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Thr His
            20                  25                  30

<210> SEQ ID NO 429
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 429

His Ser Gln Gly Thr Phe Thr Ser Asp Tyr Ser Lys Tyr Leu Glu Ser
1               5                   10                  15

Glu Ala Val Arg Leu Phe Ile Gln Trp Leu Leu Asn Thr His
            20                  25                  30

<210> SEQ ID NO 430
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 430

His Ser Gln Gly Thr Phe Thr Ser Asp Tyr Ser Lys Tyr Leu Glu Ser
1               5                   10                  15

Gln Ala Val His Leu Phe Ile Gln Trp Leu Leu Asn Thr His
            20                  25                  30

<210> SEQ ID NO 431
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 431

His Ser Gln Gly Thr Phe Thr Ser Asp Tyr Ser His Tyr Leu Glu Ser
1               5                   10                  15

Gln Ala Val Arg Leu Phe Ile Gln Trp Leu Leu Asn Thr His
            20                  25                  30

<210> SEQ ID NO 432
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 432

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 433
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 433

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly His
            20                  25                  30

<210> SEQ ID NO 434
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 434

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly His His
            20                  25                  30

<210> SEQ ID NO 435
<211> LENGTH: 30
<212> TYPE: PRT
<213> ORGANISM: Artificial Sequence
<220> FEATURE:
<223> OTHER INFORMATION: GLP-1 analogue

<400> SEQUENCE: 435

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr His
            20                  25                  30

<210> SEQ ID NO 436
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 436

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr His
            20                  25                  30

<210> SEQ ID NO 437
<211> LENGTH: 30

-continued

```
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 437

His Ser Gln Gly Thr Phe Thr Ser Asp Tyr Ser His Tyr Leu Glu Ser
1               5                   10                  15

Gln Ala Val His Leu Phe Ile Glu Trp Leu Lys Asn Thr His
            20                  25                  30

<210> SEQ ID NO 438
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 438

His Ser Gln Gly Thr Phe Thr Ser Asp Tyr Ser His Tyr Leu Glu Glu
1               5                   10                  15

Glu Ala Val His Leu Phe Ile Glu Trp Leu Lys Asn Thr His
            20                  25                  30

<210> SEQ ID NO 439
<211> LENGTH: 30
<212> TYPE: PRT
<213> ORGANISM: Artificial Sequence
<220> FEATURE:
<223> OTHER INFORMATION: GLP-1 analogue

<400> SEQUENCE: 439

His Ser Gln Gly Thr Phe Thr Ser Asp Tyr Ser Lys Tyr Leu Glu Ser
1               5                   10                  15

Gln Ala Val Arg Leu Phe Ile Glu Trp Leu Leu Asn Thr His
            20                  25                  30

<210> SEQ ID NO 440
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 440

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 441
<211> LENGTH: 31
<212> TYPE: PRT
<213> ORGANISM: Artificial Sequence
<220> FEATURE:
```

```
<223> OTHER INFORMATION: GLP-1 analogue

<400> SEQUENCE: 441

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr Gly His
            20                  25                  30

<210> SEQ ID NO 442
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 442

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Lys Asn Gly Gly His
            20                  25                  30

<210> SEQ ID NO 443
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 443

His Ser Gln Gly Thr Phe Thr Ser Asp Tyr Ser Lys Tyr Leu Glu Glu
1               5                   10                  15

Glu Ala Val Arg Leu Phe Ile Gln Trp Leu Leu Asn Gly Gly His
            20                  25                  30

<210> SEQ ID NO 444
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 444

His Ser Gln Gly Thr Phe Thr Ser Asp Tyr Ser Lys Tyr Leu Glu Glu
1               5                   10                  15

Glu Ala Val His Leu Phe Ile Glu Trp Leu Leu Asn Gly Gly His
            20                  25                  30

<210> SEQ ID NO 445
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 445

His Ser Gln Gly Thr Phe Thr Ser Asp Tyr Ser His Tyr Leu Glu Glu
1               5                   10                  15

Glu Ala Val His Leu Phe Ile Glu Trp Leu Leu Asn Gly Gly His
            20                  25                  30

<210> SEQ ID NO 446
<211> LENGTH: 31
<212> TYPE: PRT
<213> ORGANISM: Artificial Sequence
```

<220> FEATURE:
<223> OTHER INFORMATION: GLP-1 analogue

<400> SEQUENCE: 446

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Lys His
            20                  25                  30

<210> SEQ ID NO 447
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 447

His Ser Gln Gly Thr Phe Thr Ser Asp Tyr Ser Lys Tyr Leu Glu Glu
1               5                   10                  15

Glu Ala Val His Leu Phe Ile Gln Trp Leu Leu Asn Gly Gly His
            20                  25                  30

<210> SEQ ID NO 448
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 448

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 449
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 449

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 450
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 450

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Gly Gly His
            20                  25                  30

<210> SEQ ID NO 451
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 451

His Ser Gln Gly Thr Phe Thr Ser Asp Tyr Ser His Tyr Leu Glu Ser
1               5                   10                  15

Glu Ala Val Arg Leu Phe Ile Glu Trp Leu Leu Asn Gly Gly His
            20                  25                  30

<210> SEQ ID NO 452
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 452

His Ser Gln Gly Thr Phe Thr Ser Asp Tyr Ser Lys Tyr Leu Glu Glu
1               5                   10                  15

Gln Ala Val Arg Leu Phe Ile Glu Trp Leu Leu Asn Gly Gly His
            20                  25                  30

<210> SEQ ID NO 453
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 453

His Ser Gln Gly Thr Phe Thr Ser Asp Tyr Ser Lys Tyr Leu Glu Glu
1               5                   10                  15

Gln Ala Val Arg Leu Phe Ile Glu Trp Leu Leu Asn Thr Gly His
            20                  25                  30

<210> SEQ ID NO 454
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 454

His Ser Gln Gly Thr Phe Thr Ser Asp Tyr Ser Lys Tyr Leu Glu Glu
1               5                   10                  15

Gln Ala Val His Leu Phe Ile Glu Trp Leu Leu Asn Gly Gly His
            20                  25                  30

<210> SEQ ID NO 455
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 455

His Ser Gln Gly Thr Phe Thr Ser Asp Tyr Ser His Tyr Leu Glu Glu

```
1               5                   10                  15
Gln Ala Val Arg Leu Phe Ile Gln Trp Leu Leu Asn Gly Gly His
            20                  25                  30

<210> SEQ ID NO 456
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 456

His Ser Gln Gly Thr Phe Thr Ser Asp Tyr Ser Lys Tyr Leu Glu Ser
1               5                   10                  15

Gln Ala Val Arg Leu Phe Ile Glu Trp Leu Leu Asn Thr Gly His
            20                  25                  30

<210> SEQ ID NO 457
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 457

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Thr Gly His
            20                  25                  30

<210> SEQ ID NO 458
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 458

His Ser Gln Gly Thr Phe Thr Ser Asp Tyr Ser Lys Tyr Leu Glu Glu
1               5                   10                  15

Glu Ala Val Arg Leu Phe Ile Gln Trp Leu Leu Asn Thr Gly His
            20                  25                  30

<210> SEQ ID NO 459
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 459

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly His His
            20                  25                  30

<210> SEQ ID NO 460
<211> LENGTH: 31
<212> TYPE: PRT
<213> ORGANISM: Artificial Sequence
<220> FEATURE:
```

<223> OTHER INFORMATION: GLP-1 analogue

<400> SEQUENCE: 460

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr His His
            20                  25                  30

<210> SEQ ID NO 461
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 461

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Lys Asn Gly His
            20                  25                  30

<210> SEQ ID NO 462
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 462

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Gly Gly His
            20                  25                  30

<210> SEQ ID NO 463
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 463

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Gly His
            20                  25                  30

<210> SEQ ID NO 464
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 464

His Ser Gln Gly Thr Phe Thr Ser Asp Tyr Ser Lys Tyr Leu Glu Ser
1               5                   10                  15

Glu Ala Val Arg Leu Phe Ile Glu Trp Leu Leu Asn Gly Gly His
            20                  25                  30

<210> SEQ ID NO 465
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 465

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Thr Gly His
            20                  25                  30

<210> SEQ ID NO 466
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 466

His Ser Gln Gly Thr Phe Thr Ser Asp Tyr Ser Lys Tyr Leu Glu Glu
1               5                   10                  15

Glu Ala Val Arg Leu Phe Val Glu Trp Leu Leu Asn Gly Gly His
            20                  25                  30

<210> SEQ ID NO 467
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 467

His Ser Gln Gly Thr Phe Thr Ser Asp Tyr Ser Lys Tyr Leu Glu Glu
1               5                   10                  15

Gln Ala Val Arg Leu Phe Ile Glu Trp Leu Leu Asn Gly Lys His
            20                  25                  30

<210> SEQ ID NO 468
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION -continued

```
<400> SEQUENCE: 468

His Ser Gln Gly Thr Phe Thr Ser Asp Tyr Ser His Tyr Leu Glu Glu
1               5                   10                  15

Gln Ala Val Arg Leu Phe Ile Gln Trp Leu Leu Asn Gly Gly His
            20                  25                  30

<210> SEQ ID NO 469
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 469

His Ser Gln Gly Thr Phe Thr Ser Asp Tyr Ser His Tyr Leu Glu Glu
1               5                   10                  15

Glu Ala Val His Leu Phe Ile Glu Trp Leu Lys Asn Gly Gly His
            20                  25                  30

<210> SEQ ID NO 470
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 470

His Ser Gln Gly Thr Phe Thr Ser Asp Tyr Ser His Tyr Leu Glu Glu
1               5                   10                  15

Glu Ala Val His Leu Phe Ile Glu Trp Leu Lys Asn Gly His
            20                  25                  30

<210> SEQ ID NO 471
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 471

His Gly Glu Gly Thr Phe Thr Ser Asp Leu Ser His Gln Leu Glu Ser
1               5                   10                  15

Gln Ala Val His Leu Phe Ile Glu Trp Leu Lys Asn Thr His
            20                  25                  30

<210> SEQ ID NO 472
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION
```

-continued

```
<400> SEQUENCE: 472

His Ser Gln Gly Thr Phe Thr Ser Asp Tyr Ser His Tyr Leu Glu Ser
1               5                   10                  15

Gln Ala Val His Leu Phe Ile Glu Trp Leu Lys Asn Gly His
            20                  25                  30

<210> SEQ ID NO 473
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 473

His Gly Glu Gly Thr Phe Thr Ser Asp Leu Ser Lys Gln Leu Glu Glu
1               5                   10                  15

Glu Ala Val Arg Leu Phe Ile Glu Trp Leu Leu Asn Gly His His
            20                  25                  30

<210> SEQ ID NO 474
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 474

His Ser Gln Gly Thr Phe Thr Ser Asp Tyr Ser His Tyr Leu Glu Ser
1               5                   10                  15

Gln Ala Val His Leu Phe Ile Glu Trp Leu Leu Asn Gly His His
            20                  25                  30

<210> SEQ ID NO 475
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 475

His Ser Gln Gly Thr Phe Thr Ser Asp Tyr Ser His Tyr Leu Glu Ser
1               5                   10                  15

Gln Ala Val His Leu Phe Ile Glu Trp Leu Leu Asn Thr Gly His
            20                  25                  30

<210> SEQ ID NO 476
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
```

<223> OTHER INFORMATION: AMIDATION

<400> SEQUENCE: 476

His Ser Gln Gly Thr Phe Thr Ser Asp Tyr Ser Lys Tyr Leu Glu Glu
1               5                   10                  15

Gln Ala Val Arg Leu Phe Ile Glu Trp Leu Leu Asn Gly Gly His
        20                  25                  30

<210> SEQ ID NO 477
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 477

His Gly Gln Gly Thr Phe Thr Ser Asp Leu Ser Lys Tyr Leu Glu Glu
1               5                   10                  15

Glu Ala Val Arg Leu Phe Ile Glu Trp Leu Lys Asn Gly Gly His
        20                  25                  30

<210> SEQ ID NO 478
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 478

His Gly Gln Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly His
        20                  25                  30

<210> SEQ ID NO 479
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 479

His Ser Glu Gly Thr Phe Thr Ser Asp Tyr Ser His Tyr Leu Glu Glu
1               5                   10                  15

Glu Ala Val His Leu Phe Ile Glu Trp Leu Lys Asn Gly His
        20                  25                  30

<210> SEQ ID NO 480
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES

```
<222> LOCATION: (30)..(30)
<223> OTHER INFORMATION: AMIDATION

<400> SEQUENCE: 480

His Gly Glu Gly Thr Phe Thr Ser Asp Leu Ser His Gln Leu Glu Glu
1               5                   10                  15

Glu Ala Val His Leu Phe Ile Glu Trp Leu Lys Asn Gly His
            20                  25                  30

<210> SEQ ID NO 481
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 481

His Ser Gln Gly Thr Phe Thr Ser Asp Tyr Ser His Tyr Leu Glu Glu
1               5                   10                  15

Glu Ala Val His Leu Phe Ile Glu Trp Leu Lys Asn Thr His His
            20                  25                  30

<210> SEQ ID NO 482
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 482

His Ser Gln Gly Thr Phe Thr Ser Asp Tyr Ser Lys Tyr Leu Glu Glu
1               5                   10                  15

Glu Ala Leu Arg Leu Phe Ile Glu Trp Leu Leu Asn Gly His His
            20                  25                  30

<210> SEQ ID NO 483
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 483

His Ser Gln Gly Thr Phe Thr Ser Asp Tyr Ser Lys Tyr Leu Glu Glu
1               5                   10                  15

Glu Ala Leu Arg Leu Phe Ile Glu Trp Leu Leu Asn Thr His
            20                  25                  30

<210> SEQ ID NO 484
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 484

His Ser Gln Gly Thr Phe Thr Ser Asp Tyr Ser Lys Tyr Leu Glu Glu
1               5                   10                  15
```

-continued

Glu Ala Leu Arg Leu Phe Ile Glu Trp Leu Leu Asn Gly Gly His
            20                  25                  30

<210> SEQ ID NO 485
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 485

His Ser Gln Gly Thr Phe Thr Ser Asp Tyr Ser His Tyr Leu Glu Glu
1               5                   10                  15

Glu Ala Leu His Leu Phe Ile Glu Trp Leu Lys Asn Thr His
            20                  25              30

<210> SEQ ID NO 486
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 486

His Ser Gln Gly Thr Phe Thr Ser Asp Tyr Ser Lys Tyr Leu Glu Glu
1               5                   10                  15

Glu Ala Leu Arg Leu Phe Ile Glu Trp Leu Leu Asn Gly His
            20                  25              30

<210> SEQ ID NO 487
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 487

His Ser Gln Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly His His
            20                  25                  30

<210> SEQ ID NO 488
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 488

His Gly Glu Gly Thr Phe Thr Ser Asp Leu Ser Lys Gln Leu Glu Glu
1               5                   10                  15

Glu Ala Leu Arg Ile Phe Ile Glu Trp Leu Leu Asn Gly His His
            20                  25                  30

<210> SEQ ID NO 489
<211> LENGTH: 30

```
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 489
```

His Gly Glu Gly Thr Phe Thr Ser Asp Leu Ser His Gln Leu Glu Glu
1               5                   10                  15

Glu Ala Val His Ile Phe Ile Glu Trp Leu Lys Asn Thr His
            20                  25                  30

```
<210> SEQ ID NO 490
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 490
```

His Gly Glu Gly Thr Phe Thr Ser Asp Leu Ser His Gln Leu Glu Glu
1               5                   10                  15

Glu Ala Leu His Leu Phe Ile Glu Trp Leu Lys Asn Thr His
            20                  25                  30

```
<210> SEQ ID NO 491
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 491
```

His Gly Glu Gly Thr Phe Thr Ser Asp Leu Ser Lys Tyr Leu Glu Glu
1               5                   10                  15

Glu Ala Val Arg Ile Phe Ile Glu Trp Leu Leu Asn Gly His His
            20                  25                  30

```
<210> SEQ ID NO 492
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 492
```

His Gly Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly His His
            20                  25                  30

```
<210> SEQ ID NO 493
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
```

<223> OTHER INFORMATION: AMIDATION

<400> SEQUENCE: 493

His Gly Glu Gly Thr Phe Thr Ser Asp Leu Ser Lys Gln Leu Glu Glu
1               5                   10                  15

Glu Ala Val Arg Ile Phe Ile Glu Trp Leu Leu Asn Gly Gly His
            20                  25                  30

<210> SEQ ID NO 494
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 494

His Gly Glu Gly Thr Phe Thr Ser Asp Leu Ser Lys Gln Leu Glu Glu
1               5                   10                  15

Gln Ala Val Arg Ile Phe Ile Gln Trp Leu Leu Asn Gly Gly His
            20                  25                  30

<210> SEQ ID NO 495
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 495

His Ser Gln Gly Thr Phe Thr Ser Asp Leu Ser Lys Gln Leu Glu Glu
1               5                   10                  15

Gln Ala Val Arg Ile Phe Ile Gln Trp Leu Leu Asn Gly Gly His
            20                  25                  30

<210> SEQ ID NO 496
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 496

His Ser Gln Gly Thr Phe Thr Ser Asp Leu Ser Lys Gln Leu Glu Glu
1               5                   10                  15

Glu Ala Val Arg Ile Phe Ile Glu Trp Leu Leu Asn Thr His
            20                  25                  30

<210> SEQ ID NO 497
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES

<222> LOCATION: (30)..(30)
<223> OTHER INFORMATION: AMIDATION

<400> SEQUENCE: 497

His Ser Gln Gly Thr Phe Thr Ser Asp Leu Ser Lys Gln Leu Glu Glu
1               5                   10                  15

Glu Ala Val Arg Ile Phe Ile Glu Trp Leu Leu Asn Gly His
            20                  25                  30

<210> SEQ ID NO 498
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 498

His Ser Gln Gly Thr Phe Thr Ser Asp Leu Ser Lys Gln Leu Glu Glu
1               5                   10                  15

Glu Ala Val Arg Ile Phe Ile Glu Trp Leu Leu Asn Gly His His
            20                  25                  30

<210> SEQ ID NO 499
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 499

His Ser Gln Gly Thr Phe Thr Ser Asp Leu Ser Lys Gln Leu Glu Glu
1               5                   10                  15

Gln Ala Val Arg Ile Phe Ile Gln Trp Leu Leu Asn Gly His His
            20                  25                  30

<210> SEQ ID NO 500
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 500

His Ser Gln Gly Thr Phe Thr Ser Asp Tyr Ser Lys Tyr Leu Glu Glu
1               5                   10                  15

Glu Ala Val Arg Leu Phe Ile Glu Trp Leu Lys Asn Gly Gly His
            20                  25                  30

<210> SEQ ID NO 501
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 501

His Gly Gln Gly Thr Phe Thr Ser Asp Leu Ser Lys Tyr Leu Glu Glu
1               5                   10                  15

```
Glu Ala Val Arg Leu Phe Ile Glu Trp Leu Leu Asn Gly Gly His
            20                  25                  30

<210> SEQ ID NO 502
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 502

His Gly Gln Gly Thr Phe Thr Ser Asp Tyr Ser Lys Tyr Leu Glu Glu
1               5                   10                  15

Glu Ala Val Arg Leu Phe Ile Glu Trp Leu Lys Asn Gly Gly His
            20                  25                  30

<210> SEQ ID NO 503
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 503

His Ser Gln Gly Thr Phe Thr Ser Asp Leu Ser Lys Tyr Leu Glu Glu
1               5                   10                  15

Glu Ala Val Arg Leu Phe Ile Glu Trp Leu Lys Asn Gly Gly His
            20                  25                  30

<210> SEQ ID NO 504
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 504

His Gly Gln Gly Thr Phe Thr Ser Asp Leu Ser Lys Tyr Leu Glu Glu
1               5                   10                  15

Glu Ala Leu Arg Leu Phe Ile Glu Trp Leu Lys Asn Gly Gly His
            20                  25                  30

<210> SEQ ID NO 505
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 505

His Gly Gln Gly Thr Phe Thr Ser Asp Leu Ser His Gln Leu Glu Ser
```

```
1               5                   10                  15
Gln Ala Val His Leu Phe Ile Glu Trp Leu Lys Asn Thr His
            20                  25                  30
```

<210> SEQ ID NO 506
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 506

```
His Gly Gln Gly Thr Phe Thr Ser Asp Leu Ser His Gln Leu Glu Ser
1               5                   10                  15
Gln Ala Val His Leu Phe Ile Gln Trp Leu Lys Asn Thr His
            20                  25                  30
```

<210> SEQ ID NO 507
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 507

```
His Gly Gln Gly Thr Phe Thr Ser Asp Leu Ser His Gln Leu Glu Ser
1               5                   10                  15
Gln Ala Val His Ile Phe Ile Gln Trp Leu Lys Asn Thr His
            20                  25                  30
```

<210> SEQ ID NO 508
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 508

```
His Gly Gln Gly Thr Phe Thr Ser Asp Leu Ser His Gln Leu Glu Ser
1               5                   10                  15
Gln Ala Leu His Leu Phe Ile Gln Trp Leu Lys Asn Thr His
            20                  25                  30
```

<210> SEQ ID NO 509
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 509

His Gly Gln Gly Thr Phe Thr Ser Asp Tyr Ser His Tyr Leu Glu Ser
1               5                   10                  15

Gln Ala Val His Leu Phe Ile Glu Trp Leu Lys Asn Thr His
            20                  25                  30

<210> SEQ ID NO 510
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 510

His Ser Glu Gly Thr Phe Thr Ser Asp Tyr Ser His Tyr Leu Glu Ser
1               5                   10                  15

Gln Ala Val His Leu Phe Ile Glu Trp Leu Lys Asn Thr His
            20                  25                  30

<210> SEQ ID NO 511
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 511

His Gly Glu Gly Thr Phe Thr Ser Asp Tyr Ser His Tyr Leu Glu Ser
1               5                   10                  15

Gln Ala Val His Leu Phe Ile Glu Trp Leu Lys Asn Thr His
            20                  25                  30

<210> SEQ ID NO 512
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 512

His Gly Gln Gly Thr Phe Thr Ser Asp Tyr Ser His Tyr Leu Glu Glu
1               5                   10                  15

Glu Ala Val His Leu Phe Ile Glu Trp Leu Lys Asn Thr His
            20                  25                  30

<210> SEQ ID NO 513
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 513

His Gly Glu Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 514
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 514

His Gly Gln Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 515
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 515

His Ser Glu Gly Thr Phe Thr Ser Asp Tyr Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 516
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 516

His Gly Gln Gly Thr Phe Thr Ser Asp Leu Ser His Gln Leu Glu Glu
1               5                   10                  15

Gln Ala Val His Leu Phe Ile Glu Trp Leu Lys Asn Thr His
            20                  25                  30

<210> SEQ ID NO 517
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

```
<400> SEQUENCE: 517

His Gly Gln Gly Thr Phe Thr Ser Asp Leu Ser His Gln Leu Glu Glu
1               5                   10                  15

Glu Ala Val His Leu Phe Ile Glu Trp Leu Lys Asn Thr His
            20                  25                  30

<210> SEQ ID NO 518
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 518

His Gly Glu Gly Thr Phe Thr Ser Asp Leu Ser Lys Gln Leu Glu Glu
1               5                   10                  15

Glu Ala Val Arg Leu Phe Ile Glu Trp Leu Leu Asn Gly His His
            20                  25                  30

<210> SEQ ID NO 519
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 519

His Gly Gln Gly Thr Phe Thr Ser Asp Leu Ser Lys Gln Leu Glu Glu
1               5                   10                  15

Glu Ala Val Arg Leu Phe Ile Glu Trp Leu Leu Asn Gly His His
            20                  25                  30

<210> SEQ ID NO 520
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 520

His Gly Glu Gly Thr Phe Thr Ser Asp Leu Ser Lys Gln Leu Glu Glu
1               5                   10                  15

Glu Ala Val Arg Leu Phe Ile Glu Trp Leu Leu Asn Thr His His
            20                  25                  30

<210> SEQ ID NO 521
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 521

His Ser Gln Gly Thr Phe Thr Ser Asp Tyr Ser His Tyr Leu Glu Glu
1               5                   10                  15

Glu Ala Val His Leu Phe Ile Glu Trp Leu Leu Asn Thr His
            20                  25                  30

<210> SEQ ID NO 522
<211> LENGTH: 30
```

```
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 522

His Ser Glu Gly Thr Phe Thr Ser Asp Tyr Ser His Tyr Leu Glu Glu
 1               5                  10                  15

Glu Ala Val His Leu Phe Ile Glu Trp Leu Leu Asn Thr His
            20                  25                  30

<210> SEQ ID NO 523
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 523

His Ser Gln Gly Thr Phe Thr Ser Asp Tyr Ser His Tyr Leu Glu Glu
 1               5                  10                  15

Glu Ala Val His Ile Phe Ile Glu Trp Leu Lys Asn Thr His
            20                  25                  30

<210> SEQ ID NO 524
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 524

His Ser Glu Gly Thr Phe Thr Ser Asp Tyr Ser His Tyr Leu Glu Glu
 1               5                  10                  15

Glu Ala Val His Leu Phe Ile Glu Trp Leu Lys Asn Thr His
            20                  25                  30

<210> SEQ ID NO 525
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 525

His Ser Gln Gly Thr Phe Thr Ser Asp Tyr Ser His Tyr Leu Glu Glu
 1               5                  10                  15

Gln Ala Val His Leu Phe Ile Glu Trp Leu Lys Asn Thr His
            20                  25                  30

<210> SEQ ID NO 526
```

```
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 526

His Ser Gln Gly Thr Phe Thr Ser Asp Leu Ser His Gln Leu Glu Glu
1               5                   10                  15

Gln Ala Val His Ile Phe Ile Gln Trp Leu Lys Asn Thr His
            20                  25                  30

<210> SEQ ID NO 527
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 527

His Ser Gln Gly Thr Phe Thr Ser Asp Tyr Ser His Tyr Leu Glu Glu
1               5                   10                  15

Gln Ala Val His Ile Phe Ile Gln Trp Leu Lys Asn Thr His
            20                  25                  30

<210> SEQ ID NO 528
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 528

His Ser Gln Gly Thr Phe Thr Ser Asp Tyr Ser His Tyr Leu Glu Glu
1               5                   10                  15

Glu Ala Val His Leu Phe Ile Glu Trp Leu Lys Asn Gly His His
            20                  25                  30

<210> SEQ ID NO 529
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 529

His Ser Gln Gly Thr Phe Thr Ser Asp Tyr Ser His Tyr Leu Glu Glu
1               5                   10                  15

Glu Ala Val His Leu Phe Ile Glu Trp Leu Lys Asn Thr Gly His
            20                  25                  30

<210> SEQ ID NO 530
<211> LENGTH: 30
<212> TYPE: PRT
<213> ORGANISM: Artificial Sequence
```

```
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 530

His Ser Gln Gly Thr Phe Thr Ser Asp Tyr Ser His Tyr Leu Glu Ser
1               5                   10                  15

Gln Ala Val His Leu Phe Ile Gln Trp Leu Lys Asn Thr His
            20                  25                  30

<210> SEQ ID NO 531
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 531

His Ser Gln Gly Thr Phe Thr Ser Asp Tyr Ser His Tyr Leu Glu Glu
1               5                   10                  15

Gln Ala Val His Leu Phe Ile Gln Trp Leu Lys Asn Thr His
            20                  25                  30

<210> SEQ ID NO 532
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 532

His Ser Glu Gly Thr Phe Thr Ser Asp Tyr Ser His Tyr Leu Glu Glu
1               5                   10                  15

Gln Ala Val His Leu Phe Ile Gln Trp Leu Lys Asn Thr His
            20                  25                  30

<210> SEQ ID NO 533
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 533

His Ser Gln Gly Thr Phe Thr Ser Asp Tyr Ser His Tyr Leu Glu Glu
1               5                   10                  15

Gln Ala Val His Leu Phe Ile Gln Trp Leu Lys Asn Thr His His
            20                  25                  30

<210> SEQ ID NO 534
<211> LENGTH: 30
<212> TYPE: PRT
<213> ORGANISM: Artificial Sequence
<220> FEATURE:
<223> OTHER INFORMATION: GLP-1 analogue
<220> FEATURE:
```

<221> NAME/KEY: MOD_RES
<222> LOCATION: (30)..(30)
<223> OTHER INFORMATION: AMIDATION

<400> SEQUENCE: 534

His Gly Glu Gly Thr Phe Thr Ser Asp Tyr Ser His Tyr Leu Glu Ser
1               5                   10                  15

Gln Ala Val His Leu Phe Ile Gln Trp Leu Lys Asn Thr His
            20                  25                  30

<210> SEQ ID NO 535
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 535

His Gly Gln Gly Thr Phe Thr Ser Asp Tyr Ser His Tyr Leu Glu Ser
1               5                   10                  15

Gln Ala Val His Leu Phe Ile Gln Trp Leu Lys Asn Thr His
            20                  25                  30

<210> SEQ ID NO 536
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 536

His Gly Gln Gly Thr Phe Thr Ser Asp Tyr Ser His Tyr Leu Glu Ser
1               5                   10                  15

Gln Ala Val His Leu Phe Ile Gln Trp Leu Leu Asn Thr His
            20                  25                  30

<210> SEQ ID NO 537
<211> LENGTH: 30
<212> TYPE: PRT
<213> ORGANISM: Artificial Sequence
<220> FEATURE:
<223> OTHER INFORMATION: GLP-1 analogue

<400> SEQUENCE: 537

His Ser Gln Gly Thr Phe Thr Ser Asp Tyr Ser His Tyr Leu Glu Ser
1               5                   10                  15

Gln Ala Val His Leu Phe Ile Glu Trp Leu Lys Asn Thr His
            20                  25                  30

<210> SEQ ID NO 538
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 538

His Gly Glu Gly Thr Phe Thr Ser Asp Tyr Ser His Tyr Leu Glu Ser

```
            1               5                  10                  15
Gln Ala Val His Leu Phe Ile Glu Trp Leu Lys Asn Thr His His
                    20                  25                  30
```

<210> SEQ ID NO 539
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 539

```
His Gly Gln Gly Thr Phe Thr Ser Asp Tyr Ser His Tyr Leu Glu Ser
 1               5                  10                  15
Gln Ala Val His Leu Phe Ile Glu Trp Leu Lys Asn Thr His His
                    20                  25                  30
```

<210> SEQ ID NO 540
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 540

```
His Gly Gln Gly Thr Phe Thr Ser Asp Tyr Ser His Tyr Leu Glu Ser
 1               5                  10                  15
Gln Ala Val His Leu Phe Ile Glu Trp Leu Lys Asn Thr His His
                    20                  25                  30
```

<210> SEQ ID NO 541
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 541

```
His Ser Gln Gly Thr Phe Thr Ser Asp Tyr Ser His Tyr Leu Glu Ser
 1               5                  10                  15
Gln Ala Ala His Leu Phe Ile Glu Trp Leu Lys Asn Thr His
                    20                  25                  30
```

<210> SEQ ID NO 542
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 542

```
His Ser Gln Gly Thr Phe Thr Ser Asp Tyr Ser His Tyr Leu Glu Ser
 1               5                  10                  15
Gln Ala Val His Leu Phe Val Glu Trp Leu Lys Asn Thr His
```

-continued

```
<210> SEQ ID NO 543
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 543

His Ser Gln Gly Thr Phe Thr Ser Asp Tyr Ser His Tyr Leu Glu Ser
1               5                   10                  15

Gln Ala Val His Leu Phe Ile Gln Trp Leu Lys Asn Thr His
            20                  25                  30

<210> SEQ ID NO 544
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 544

His Ser Gln Gly Thr Phe Thr Ser Asp Tyr Ser His Tyr Leu Glu Ser
1               5                   10                  15

Gln Ala Ala His Leu Phe Val Gln Trp Leu Lys Asn Thr His
            20                  25                  30

<210> SEQ ID NO 545
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 545

His Gly Glu Gly Thr Phe Thr Ser Asp Tyr Ser His Tyr Leu Glu Ser
1               5                   10                  15

Gln Ala Val His Leu Phe Ile Glu Trp Leu Leu Asn Thr His
            20                  25                  30

<210> SEQ ID NO 546
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 546

His Ser Glu Gly Thr Phe Thr Ser Asp Tyr Ser His Tyr Leu Glu Ser
1               5                   10                  15

Gln Ala Val His Leu Phe Ile Glu Trp Leu Lys Asn Thr His His
            20                  25                  30
```

<210> SEQ ID NO 547
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 547

His Ser Glu Gly Thr Phe Thr Ser Asp Tyr Ser His Tyr Leu Glu Ser
1               5                   10                  15
Gln Ala Val His Leu Phe Ile Glu Trp Leu Lys Asn Thr His His
            20                  25                  30

<210> SEQ ID NO 548
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 548

His Gly Glu Gly Thr Phe Thr Ser Asp Tyr Ser His Tyr Leu Glu Ser
1               5                   10                  15
Gln Ala Val His Leu Phe Ile Glu Trp Leu Lys Asn Thr His His
            20                  25                  30

<210> SEQ ID NO 549
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 549

His Ser Gln Gly Thr Phe Thr Ser Asp Tyr Ser Lys Tyr Leu Glu Ser
1               5                   10                  15
Gln Ala Val His Leu Phe Ile Gln Trp Leu Leu Asn Thr His His
            20                  25                  30

<210> SEQ ID NO 550
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 550

His Ser Gln Gly Thr Phe Thr Ser Asp Tyr Ser Lys Tyr Leu Glu Ser
1               5                   10                  15
Gln Ala Val His Leu Phe Val Gln Trp Leu Leu Asn Thr His His
            20                  25                  30

<210> SEQ ID NO 551
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 551

His Ser Gln Gly Thr Phe Thr Ser Asp Tyr Ser Lys Tyr Leu Glu Ser
1               5                   10                  15

Gln Ala Ala His Leu Phe Val Gln Trp Leu Leu Asn Thr His His
            20                  25                  30

<210> SEQ ID NO 552
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 552

His Ser Gln Gly Thr Phe Thr Ser Asp Tyr Ser Lys Tyr Leu Glu Ser
1               5                   10                  15

Gln Ala Ala His Leu Phe Val Gln Trp Leu Leu Asn Thr His His
            20                  25                  30

<210> SEQ ID NO 553
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 553

His Ser Gln Gly Thr Phe Thr Ser Asp Tyr Ser Lys Tyr Leu Glu Ser
1               5                   10                  15

Gln Ala Ala His Leu Phe Val Gln Trp Leu Lys Asn Thr His His
            20                  25                  30

<210> SEQ ID NO 554
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 554

His Ser Glu Gly Thr Phe Thr Ser Asp Tyr Ser Lys Tyr Leu Glu Glu
1               5                   10                  15

Glu Ala Leu Arg Leu Phe Ile Glu Trp Leu Leu Asn Gly Gly His
            20                  25                  30

<210> SEQ ID NO 555
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 555

His Ser Glu Gly Thr Phe Thr Ser Asp Tyr Ser Lys Tyr Leu Glu Glu

```
1               5                   10                  15
Glu Ala Leu Arg Leu Phe Ile Glu Trp Leu Leu Asn Gly His His
            20                  25                  30

<210> SEQ ID NO 556
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 556

His Ser Glu Gly Thr Phe Thr Ser Asp Tyr Ser Lys Tyr Leu Glu Glu
1               5                   10                  15

Glu Ala Leu Arg Leu Phe Ile Glu Trp Leu Leu Asn Gly His His
            20                  25                  30

<210> SEQ ID NO 557
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 557

His Ser Glu Gly Thr Phe Thr Ser Asp Tyr Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 558
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 558

His Ser Glu Gly Thr Phe Thr Ser Asp Tyr Ser His Tyr Leu Glu Ser
1               5                   10                  15

Glu Ala Val Arg Leu Phe Ile Glu Trp Leu Leu Asn Thr His His
            20                  25                  30

<210> SEQ ID NO 559
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 559

His Ser Glu Gly Thr Phe Thr Ser Asp Tyr Ser His Tyr Leu Glu Ser
1               5                   10                  15

Gln Ala Val Arg Leu Phe Ile Glu Trp Leu Leu Asn Thr His His
```

```
                    20                  25                  30

<210> SEQ ID NO 560
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 560

His Ser Glu Gly Thr Phe Thr Ser Asp Tyr Ser His Tyr Leu Glu Ser
1               5                   10                  15

Gln Ala Val Arg Ile Phe Ile Glu Trp Leu Leu Asn Thr His His
            20                  25                  30

<210> SEQ ID NO 561
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 561

His Ser Glu Gly Thr Phe Thr Ser Asp Tyr Ser His Tyr Leu Glu Ser
1               5                   10                  15

Gln Ala Leu Arg Leu Phe Ile Glu Trp Leu Leu Asn Thr His His
            20                  25                  30

<210> SEQ ID NO 562
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 562

His Ser Glu Gly Thr Phe Thr Ser Asp Tyr Ser His Tyr Leu Glu Ser
1               5                   10                  15

Gln Ala Val Arg Ile Phe Ile Glu Trp Leu Leu Asn Gly His His
            20                  25                  30

<210> SEQ ID NO 563
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 563

His Ser Gln Gly Thr Phe Thr Ser Asp Tyr Ser His Tyr Leu Glu Ser
1               5                   10                  15
```

-continued

Gln Ala Val Arg Ile Phe Ile Glu Trp Leu Leu Asn Thr His His
        20                  25                  30

<210> SEQ ID NO 564
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 564

His Ser Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly His His
        20                  25                  30

<210> SEQ ID NO 565
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 565

His Ser Glu Gly Thr Phe Thr Ser Asp Tyr Ser Lys Tyr Leu Glu Glu
1               5                   10                  15

Glu Ala Val His Ile Phe Ile Glu Trp Leu Leu Asn Gly His His
        20                  25                  30

<210> SEQ ID NO 566
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 566

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly His His
        20                  25                  30

<210> SEQ ID NO 567
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 567

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly His His
        20                  25                  30

<210> SEQ ID NO 568
<211> LENGTH: 31
<212> TYPE: PRT
<213> ORGANISM: Artificial Sequence
<220> FEATURE:
<223> OTHER INFORMATION: GLP-1 analogue
<220> FEATURE:

<221> NAME/KEY: MOD_RES
<222> LOCATION: (31)..(31)
<223> OTHER INFORMATION: AMIDATION

<400> SEQUENCE: 568

His Ser Glu Gly Thr Phe Thr Ser Asp Tyr Ser Lys Tyr Leu Glu Glu
1               5                   10                  15

Gln Ala Val His Ile Phe Ile Gln Trp Leu Lys Asn Gly His His
            20                  25                  30

<210> SEQ ID NO 569
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 569

His Ser Gln Gly Thr Phe Thr Ser Asp Tyr Ser Lys Tyr Leu Glu Glu
1               5                   10                  15

Gln Ala Val His Ile Phe Ile Gln Trp Leu Lys Asn Gly His His
            20                  25                  30

<210> SEQ ID NO 570
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 570

His Ser Gln Gly Thr Phe Thr Ser Asp Tyr Ser Lys Tyr Leu Glu Glu
1               5                   10                  15

Gln Ala Val His Ile Phe Ile Gln Trp Leu Lys Asn Thr His His
            20                  25                  30

<210> SEQ ID NO 571
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 571

His Ser Gln Gly Thr Phe Thr Ser Asp Tyr Ser His Tyr Leu Glu Ser
1               5                   10                  15

Gln Ala Val Arg Ile Phe Ile Glu Trp Leu Leu Asn Thr His His
            20                  25                  30

<210> SEQ ID NO 572
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 572

His Ser Gln Gly Thr Phe Thr Ser Asp Tyr Ser Lys Tyr Leu Glu Glu

```
                1               5                   10                  15
Glu Ala Leu Arg Leu Phe Ile Glu Trp Leu Leu Asn Thr His His
                20                  25                  30

<210> SEQ ID NO 573
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 573

His Ser Gln Gly Thr Phe Thr Ser Asp Tyr Ser Lys Tyr Leu Glu Glu
1               5                   10                  15

Glu Ala Leu Arg Leu Phe Ile Glu Trp Leu Leu Asn Gly His His
                20                  25                  30

<210> SEQ ID NO 574
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 574

His Ser Gln Gly Thr Phe Thr Ser Asp Tyr Ser Lys Tyr Leu Glu Glu
1               5                   10                  15

Glu Ala Leu Arg Leu Phe Ile Gln Trp Leu Leu Asn Gly His His
                20                  25                  30

<210> SEQ ID NO 575
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 575

His Ser Gln Gly Thr Phe Thr Ser Asp Tyr Ser Lys Tyr Leu Glu Glu
1               5                   10                  15

Glu Ala Leu Arg Leu Phe Ile Gln Trp Leu Leu Asn Thr His His
                20                  25                  30

<210> SEQ ID NO 576
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 576

His Ser Gln Gly Thr Phe Thr Ser Asp Tyr Ser Lys Tyr Leu Glu Glu
1               5                   10                  15

Glu Ala Leu Arg Ile Phe Ile Gln Trp Leu Leu Asn Gly His His
```

```
<210> SEQ ID NO 577
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 577

His Ser Gln Gly Thr Phe Thr Ser Asp Tyr Ser Lys Tyr Leu Glu Glu
1               5                   10                  15

Glu Ala Leu Arg Ile Phe Ile Gln Trp Leu Leu Asn Thr His His
            20                  25                  30

<210> SEQ ID NO 578
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 578

His Ser Gln Gly Thr Phe Thr Ser Asp Tyr Ser Lys Tyr Leu Glu Glu
1               5                   10                  15

Glu Ala Leu His Ile Phe Ile Gln Trp Leu Leu Asn Thr His His
            20                  25                  30

<210> SEQ ID NO 579
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 579

His Ser Gln Gly Thr Phe Thr Ser Asp Tyr Ser Lys Tyr Leu Glu Glu
1               5                   10                  15

Gln Ala Leu Arg Ile Phe Ile Glu Trp Leu Leu Asn Thr His His
            20                  25                  30

<210> SEQ ID NO 580
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 580

His Ser Gln Gly Thr Phe Thr Ser Asp Tyr Ser Lys Tyr Leu Glu Glu
1               5                   10                  15
```

Gln Ala Leu Arg Leu Phe Ile Gln Trp Leu Leu Asn Gly Gly His
            20                  25                  30

<210> SEQ ID NO 581
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 581

His Ser Gln Gly Thr Phe Thr Ser Asp Tyr Ser Lys Tyr Leu Glu Glu
1               5                   10                  15

Gln Ala Leu Arg Leu Phe Ile Gln Trp Leu Leu Asn Gly His His
            20                  25                  30

<210> SEQ ID NO 582
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 582

His Ser Gln Gly Thr Phe Thr Ser Asp Tyr Ser Lys Tyr Leu Glu Glu
1               5                   10                  15

Gln Ala Leu Arg Leu Phe Ile Gln Trp Leu Leu Asn Thr His His
            20                  25                  30

<210> SEQ ID NO 583
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 583

His Ser Gln Gly Thr Phe Thr Ser Asp Tyr Ser Lys Tyr Leu Glu Glu
1               5                   10                  15

Gln Ala Leu Arg Ile Phe Ile Gln Trp Leu Leu Asn Thr His His
            20                  25                  30

<210> SEQ ID NO 584
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 584

His Ser Glu Gly Thr Phe Thr Ser Asp Tyr Ser Lys Tyr Leu Glu Glu
1               5                   10                  15

Gln Ala Leu Arg Ile Phe Ile Gln Trp Leu Leu Asn Thr His His
        20                  25                  30

<210> SEQ ID NO 585
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 585

His Ser Gln Gly Thr Phe Thr Ser Asp Tyr Ser Lys Tyr Leu Glu Glu
1               5                   10                  15

Gln Ala Leu Arg Ile Phe Ile Gln Trp Leu Lys Asn Thr His His
        20                  25                  30

<210> SEQ ID NO 586
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 586

His Ser Gln Gly Thr Phe Thr Ser Asp Tyr Ser Lys Tyr Leu Glu Ser
1               5                   10                  15

Gln Ala Leu Arg Leu Phe Ile Glu Trp Leu Leu Asn Gly His His
        20                  25                  30

<210> SEQ ID NO 587
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 587

His Ser Gln Gly Thr Phe Thr Ser Asp Leu Ser Lys Gln Leu Glu Glu
1               5                   10                  15

Gln Ala Leu Arg Ile Phe Ile Gln Trp Leu Leu Asn Gly His His
        20                  25                  30

<210> SEQ ID NO 588
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 588

His Ser Gln Gly Thr Phe Thr Ser Asp Tyr Ser His Tyr Leu Glu Ser
1               5                   10                  15

Gln Ala Val Arg Leu Phe Ile Glu Trp Leu Leu Asn Thr Gly His
        20                  25                  30

<210> SEQ ID NO 589
<211> LENGTH: 31

<212> TYPE: PRT
<213> ORGANISM: Artificial Sequence
<220> FEATURE:
<223> OTHER INFORMATION: GLP-1 analogue

<400> SEQUENCE: 589

His Ser Gln Gly Thr Phe Thr Ser Asp Tyr Ser His Tyr Leu Glu Ser
1               5                   10                  15

Glu Ala Val Arg Leu Phe Ile Gln Trp Leu Leu Asn Thr Gly His
            20                  25                  30

<210> SEQ ID NO 590
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 590

His Ser Gln Gly Thr Phe Thr Ser Asp Tyr Ser His Tyr Leu Glu Ser
1               5                   10                  15

Glu Ala Val His Leu Phe Ile Glu Trp Leu Leu Asn Thr Gly His
            20                  25                  30

<210> SEQ ID NO 591
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 591

His Ser Gln Gly Thr Phe Thr Ser Asp Tyr Ser His Tyr Leu Glu Ser
1               5                   10                  15

Gln Ala Val His Leu Phe Ile Gln Trp Leu Leu Asn Thr Gly His
            20                  25                  30

<210> SEQ ID NO 592
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 592

His Ser Gln Gly Thr Phe Thr Ser Asp Tyr Ser His Tyr Leu Glu Ser
1               5                   10                  15

Glu Ala Leu Arg Ile Phe Ile Glu Trp Leu Leu Asn Thr Gly His
            20                  25                  30

<210> SEQ ID NO 593
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 593

His Ser Gln Gly Thr Phe Thr Ser Asp Tyr Ser His Tyr Leu Glu Ser
1               5                   10                  15

Gln Ala Leu Arg Ile Phe Ile Glu Trp Leu Leu Asn Thr Gly His
            20                  25                  30

<210> SEQ ID NO 594

<211> LENGTH: 31
<212> TYPE: PRT
<213> ORGANISM: Artificial Sequence
<220> FEATURE:
<223> OTHER INFORMATION: GLP-1 analogue

<400> SEQUENCE: 594

His Gly Glu Gly Thr Phe Thr Ser Asp Tyr Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 595
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 595

His Gly Glu Gly Thr Phe Thr Ser Asp Tyr Ser His Tyr Leu Glu Ser
1               5                   10                  15

Gln Ala Val His Ile Phe Ile Glu Trp Leu Leu Asn Thr His
            20                  25                  30

<210> SEQ ID NO 596
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 596

His Gly Glu Gly Thr Phe Thr Ser Asp Leu Ser Lys Gln Leu Glu Glu
1               5                   10                  15

Gln Ala Val Arg Ile Phe Ile Gln Trp Leu Leu Asn Thr Gly His
            20                  25                  30

<210> SEQ ID NO 597
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 597

His Gly Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Thr Gly His
            20                  25                  30

<210> SEQ ID NO 598
<211> LENGTH: 30
<212> TYPE: PRT
<213> ORGANISM: Artificial Sequence

```
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 598

His Gly Glu Gly Thr Phe Thr Ser Asp Tyr Ser His Tyr Leu Glu Ser
1               5                   10                  15

Gln Ala Val His Ile Phe Ile Glu Trp Leu Lys Asn Thr His
            20                  25                  30

<210> SEQ ID NO 599
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 599

His Gly Glu Gly Thr Phe Thr Ser Asp Tyr Ser His Tyr Leu Glu Ser
1               5                   10                  15

Gln Ala Val His Ile Phe Ile Glu Trp Leu Lys Asn Gly His
            20                  25                  30

<210> SEQ ID NO 600
<211> LENGTH: 30
<212> TYPE: PRT
<213> ORGANISM: Artificial Sequence
<220> FEATURE:
<223> OTHER INFORMATION: GLP-1 analogue

<400> SEQUENCE: 600

His Gly Glu Gly Thr Phe Thr Ser Asp Tyr Ser His Tyr Leu Glu Ser
1               5                   10                  15

Gln Ala Val His Leu Phe Ile Glu Trp Leu Lys Asn Thr His
            20                  25                  30

<210> SEQ ID NO 601
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 601

His Ser Glu Gly Thr Phe Thr Ser Asp Leu Ser Lys Gln Leu Glu Glu
1               5                   10                  15

Gln Ala Val Arg Ile Phe Ile Gln Trp Leu Leu Asn Thr Gly His
            20                  25                  30

<210> SEQ ID NO 602
<211> LENGTH: 31
<212> TYPE: PRT
<213> ORGANISM: Artificial Sequence
<220> FEATURE:
<223> OTHER INFORMATION: GLP-1 analogue
<220> FEATURE:
```

<221> NAME/KEY: MOD_RES
<222> LOCATION: (31)..(31)
<223> OTHER INFORMATION: AMIDATION

<400> SEQUENCE: 602

His Gly Glu Gly Thr Phe Thr Ser Asp Leu Ser Lys Gln Leu Glu Glu
1               5                   10                  15

Gln Ala Leu Arg Ile Phe Ile Gln Trp Leu Leu Asn Thr Gly His
            20                  25                  30

<210> SEQ ID NO 603
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 603

His Gly Gln Gly Thr Phe Thr Ser Asp Leu Ser Lys Tyr Leu Glu Glu
1               5                   10                  15

Glu Ala Val Arg Ile Phe Ile Glu Trp Leu Leu Asn Gly Gly His
            20                  25                  30

<210> SEQ ID NO 604
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 604

His Gly Gln Gly Thr Phe Thr Ser Asp Leu Ser Lys Tyr Leu Glu Glu
1               5                   10                  15

Glu Ala Val Arg Leu Phe Ile Glu Trp Leu Leu Asn Thr Gly His
            20                  25                  30

<210> SEQ ID NO 605
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 605

His Gly Gln Gly Thr Phe Thr Ser Asp Leu Ser Lys Tyr Leu Glu Glu
1               5                   10                  15

Glu Ala Val Arg Ile Phe Ile Glu Trp Leu Leu Asn Thr Gly His
            20                  25                  30

<210> SEQ ID NO 606
<211> LENGTH: 31
<212> TYPE: PRT
<213> ORGANISM: Artificial Sequence
<220> FEATURE:
<223> OTHER INFORMATION: GLP-1 analogue

```
<220> FEATURE:
<221> NAME/KEY: MOD_RES
<222> LOCATION: (31)..(31)
<223> OTHER INFORMATION: AMIDATION

<400> SEQUENCE: 606

His Gly Gln Gly Thr Phe Thr Ser Asp Leu Ser His Tyr Leu Glu Glu
1               5                   10                  15

Glu Ala Val Arg Ile Phe Ile Glu Trp Leu Leu Asn Thr Gly His
            20                  25                  30

<210> SEQ ID NO 607
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 607

His Gly Gln Gly Thr Phe Thr Ser Asp Leu Ser Lys Tyr Leu Glu Glu
1               5                   10                  15

Glu Ala Val His Ile Phe Ile Glu Trp Leu Leu Asn Thr Gly His
            20                  25                  30

<210> SEQ ID NO 608
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 608

His Gly Gln Gly Thr Phe Thr Ser Asp Leu Ser His Tyr Leu Glu Glu
1               5                   10                  15

Glu Ala Val His Ile Phe Ile Glu Trp Leu Leu Asn Thr Gly His
            20                  25                  30

<210> SEQ ID NO 609
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 609

His Gly Gln Gly Thr Phe Thr Ser Asp Leu Ser Lys Tyr Leu Glu Glu
1               5                   10                  15

Glu Ala Leu Arg Ile Phe Ile Glu Trp Leu Leu Asn Thr Gly His
            20                  25                  30

<210> SEQ ID NO 610
<211> LENGTH: 31
<212> TYPE: PRT
<213> ORGANISM: Artificial Sequence
<220> FEATURE:
```

<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 610

His Gly Gln Gly Thr Phe Thr Ser Asp Leu Ser Lys Tyr Leu Glu Glu
1               5                   10                  15

Glu Ala Leu Arg Leu Phe Ile Glu Trp Leu Leu Asn Thr Gly His
            20                  25                  30

<210> SEQ ID NO 611
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 611

His Gly Glu Gly Thr Phe Thr Ser Asp Leu Ser Lys Tyr Leu Glu Glu
1               5                   10                  15

Gln Ala Val Arg Ile Phe Ile Gln Trp Leu Leu Asn Gly Gly His
            20                  25                  30

<210> SEQ ID NO 612
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 612

His Gly Glu Gly Thr Phe Thr Ser Asp Leu Ser His Gln Leu Glu Glu
1               5                   10                  15

Gln Ala Val Arg Ile Phe Ile Gln Trp Leu Leu Asn Gly Gly His
            20                  25                  30

<210> SEQ ID NO 613
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 613

His Gly Glu Gly Thr Phe Thr Ser Asp Leu Ser His Gln Leu Glu Glu
1               5                   10                  15

Gln Ala Val His Ile Phe Ile Gln Trp Leu Leu Asn Gly Gly His
            20                  25                  30

<210> SEQ ID NO 614
<211> LENGTH: 31
<212> TYPE: PRT
<213> ORGANISM: Artificial Sequence -continued
<220> FEATURE:
<223> OTHER INFORMATION: GLP-1 analogue

<400> SEQUENCE: 614

His Gly Glu Gly Thr Phe Thr Ser Asp Leu Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 615
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 615

His Gly Glu Gly Thr Phe Thr Ser Asp Leu Ser His Tyr Leu Glu Ser
1               5                   10                  15

Gln Ala Val Arg Leu Phe Ile Glu Trp Leu Leu Asn Thr Gly His
            20                  25                  30

<210> SEQ ID NO 616
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 616

His Gly Glu Gly Thr Phe Thr Ser Asp Leu Ser His Tyr Leu Glu Ser
1               5                   10                  15

Glu Ala Val Arg Ile Phe Ile Glu Trp Leu Leu Asn Thr Gly His
            20                  25                  30

<210> SEQ ID NO 617
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 617

His Gly Glu Gly Thr Phe Thr Ser Asp Leu Ser His Tyr Leu Glu Ser
1               5                   10                  15

Glu Ala Leu Arg Ile Phe Ile Glu Trp Leu Leu Asn Thr Gly His
            20                  25                  30

<210> SEQ ID NO 618
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 618

His Gly Glu Gly Thr Phe Thr Ser Asp Leu Ser His Tyr Leu Glu Ser
1               5                   10                  15

Glu Ala Leu Arg Leu Phe Ile Glu Trp Leu Leu Asn Thr Gly His
            20                  25                  30

<210> SEQ ID NO 619
<211> LENGTH: 31
<212> TYPE: PRT

<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 619

His Gly Glu Gly Thr Phe Thr Ser Asp Leu Ser Lys Gln Leu Glu Glu
1               5                   10                  15

Gln Ala Leu Arg Ile Phe Ile Gln Trp Leu Leu Asn Gly Gly His
            20                  25                  30

<210> SEQ ID NO 620
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 620

His Gly Glu Gly Thr Phe Thr Ser Asp Leu Ser Lys Gln Leu Glu Glu
1               5                   10                  15

Gln Ala Val Arg Ile Phe Ile Gln Trp Leu Leu Asn Gly His His
            20                  25                  30

<210> SEQ ID NO 621
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 621

His Gly Glu Gly Thr Phe Thr Ser Asp Leu Ser Lys Gln Leu Glu Glu
1               5                   10                  15

Gln Ala Val Arg Ile Phe Ile Gln Trp Leu Leu Asn Gly His His
            20                  25                  30

<210> SEQ ID NO 622
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 622

His Gly Glu Gly Thr Phe Thr Ser Asp Leu Ser Lys Gln Leu Glu Glu
1               5                   10                  15

Gln Ala Val Arg Ile Phe Ile Gln Trp Leu Leu Asn Gly His
            20                  25                  30

<210> SEQ ID NO 623
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 623

His Ser Gln Gly Thr Phe Thr Ser Asp Tyr Ser His Tyr Leu Glu Ser
1               5                   10                  15

Glu Ala Val Arg Ile Phe Ile Gln Trp Leu Leu Asn Thr Gly His
            20                  25                  30

<210> SEQ ID NO 624
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 624

His Gly Gln Gly Thr Phe Thr Ser Asp Leu Ser Lys Tyr Leu Glu Glu
1               5                   10                  15

Glu Ala Val Arg Leu Phe Ile Gln Trp Leu Leu Asn Gly Gly His
            20                  25                  30

<210> SEQ ID NO 625
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 625

His Gly Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly His His
            20                  25                  30

<210> SEQ ID NO 626
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 626

His Gly Glu Gly Thr Phe Thr Ser Asp Tyr Ser His Tyr Leu Glu Ser
1               5                   10                  15

Gln Ala Val His Leu Phe Ile Glu Trp Leu Leu Asn Gly His
            20                  25                  30

<210> SEQ ID NO 627
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)

<223> OTHER INFORMATION: AMIDATION

<400> SEQUENCE: 627

His Gly Glu Gly Thr Phe Thr Ser Asp Tyr Ser His Tyr Leu Glu Ser
1               5                   10                  15

Gln Ala Leu His Ile Phe Ile Glu Trp Leu Lys Asn Thr His
            20                  25                  30

<210> SEQ ID NO 628
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 628

His Ser Gln Gly Thr Phe Thr Ser Asp Tyr Ser His Tyr Leu Glu Glu
1               5                   10                  15

Glu Ala Val Arg Leu Phe Ile Glu Trp Leu Leu Asn Gly Gly His
            20                  25                  30

<210> SEQ ID NO 629
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 629

His Ser Glu Gly Thr Phe Thr Ser Asp Tyr Ser His Tyr Leu Glu Ser
1               5                   10                  15

Glu Ala Val Arg Leu Phe Ile Glu Trp Leu Leu Asn Thr Gly His
            20                  25                  30

<210> SEQ ID NO 630
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 630

His Gly Glu Gly Thr Phe Thr Ser Asp Leu Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 631
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 631

His Ser Gln Gly Thr Phe Thr Ser Asp Leu Ser Lys Gln Leu Glu Glu
1               5                   10                  15

Glu Ala Leu Arg Leu Phe Ile Glu Trp Leu Leu Asn Gly Gly His
            20                  25                  30

<210> SEQ ID NO 632
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 632

His Gly Gln Gly Thr Phe Thr Ser Asp Tyr Ser His Tyr Leu Glu Ser
1               5                   10                  15

Gln Ala Val His Leu Phe Ile Glu Trp Leu Lys Asn Thr Gly His
            20                  25                  30

<210> SEQ ID NO 633
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 633

His Gly Gln Gly Thr Phe Thr Ser Asp Tyr Ser His Tyr Leu Glu Ser
1               5                   10                  15

Gln Ala Val His Leu Phe Ile Glu Trp Leu Lys Asn Thr Gly His
            20                  25                  30

<210> SEQ ID NO 634
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 634

His Gly Gln Gly Thr Phe Thr Ser Asp Tyr Ser His Tyr Leu Glu Ser
1               5                   10                  15

Gln Ala Val His Leu Phe Ile Glu Trp Leu Lys Asn Gly Gly His
            20                  25                  30

<210> SEQ ID NO 635
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 635

His Gly Gln Gly Thr Phe Thr Ser Asp Tyr Ser His Tyr Leu Glu Ser
1               5                   10                  15

Gln Ala Val His Leu Phe Ile Glu Trp Leu Lys Asn Gly Gly His
            20                  25                  30

<210> SEQ ID NO 636
<211> LENGTH: 30
<212> TYPE: PRT

<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 636

His Gly Gln Gly Thr Phe Thr Ser Asp Tyr Ser His Tyr Leu Glu Ser
1               5                   10                  15

Glu Ala Val His Leu Phe Ile Glu Trp Leu Lys Asn Thr His
            20                  25                  30

<210> SEQ ID NO 637
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 637

His Gly Gln Gly Thr Phe Thr Ser Asp Leu Ser His Tyr Leu Glu Glu
1               5                   10                  15

Glu Ala Val Arg Leu Phe Ile Glu Trp Leu Leu Asn Gly Gly His
            20                  25                  30

<210> SEQ ID NO 638
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 638

His Gly Gln Gly Thr Phe Thr Ser Asp Leu Ser His Tyr Leu Glu Glu
1               5                   10                  15

Glu Ala Val His Leu Phe Ile Glu Trp Leu Leu Asn Gly Gly His
            20                  25                  30

<210> SEQ ID NO 639
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 639

His Gly Gln Gly Thr Phe Thr Ser Asp Leu Ser Lys Tyr Leu Glu Glu
1               5                   10                  15

Glu Ala Val His Leu Phe Ile Glu Trp Leu Leu Asn Gly Gly His
            20                  25                  30

<210> SEQ ID NO 640
<211> LENGTH: 31

```
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 640

His Ser Glu Gly Thr Phe Thr Ser Asp Tyr Ser His Tyr Leu Glu Glu
1               5                   10                  15

Gln Ala Val Arg Ile Phe Ile Gln Trp Leu Leu Asn Gly His His
            20                  25                  30

<210> SEQ ID NO 641
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 641

His Ser Glu Gly Thr Phe Thr Ser Asp Tyr Ser His Tyr Leu Glu Glu
1               5                   10                  15

Gln Ala Val His Ile Phe Ile Gln Trp Leu Leu Asn Gly His His
            20                  25                  30

<210> SEQ ID NO 642
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 642

His Ser Glu Gly Thr Phe Thr Ser Asp Tyr Ser Lys Tyr Leu Glu Glu
1               5                   10                  15

Gln Ala Val His Ile Phe Ile Gln Trp Leu Leu Asn Gly His His
            20                  25                  30

<210> SEQ ID NO 643
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 643

His Gly Gln Gly Thr Phe Thr Ser Asp Leu Ser Lys Gln Leu Glu Glu
1               5                   10                  15

Gln Ala Val Arg Ile Phe Ile Gln Trp Leu Leu Asn Gly Gly His
            20                  25                  30

<210> SEQ ID NO 644
```

```
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 644

His Ser Glu Gly Thr Phe Thr Ser Asp Leu Ser Lys Gln Leu Glu Glu
1               5                   10                  15

Gln Ala Val Arg Ile Phe Ile Gln Trp Leu Leu Asn Gly Gly His
            20                  25                  30

<210> SEQ ID NO 645
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 645

His Ser Gln Gly Thr Phe Thr Ser Asp Leu Ser Lys Tyr Leu Glu Glu
1               5                   10                  15

Glu Ala Val Arg Leu Phe Ile Glu Trp Leu Leu Asn Gly Gly His
            20                  25                  30

<210> SEQ ID NO 646
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 646

His Gly Gln Gly Thr Phe Thr Ser Asp Leu Ser Lys Tyr Leu Glu Glu
1               5                   10                  15

Glu Ala Val Arg Leu Phe Ile Glu Trp Leu Leu Asn Gly His His
            20                  25                  30

<210> SEQ ID NO 647
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 647

His Gly Gln Gly Thr Phe Thr Ser Asp Leu Ser Lys Tyr Leu Glu Glu
1               5                   10                  15

Gln Ala Val Arg Leu Phe Ile Glu Trp Leu Leu Asn Gly Gly His
            20                  25                  30
```

```
<210> SEQ ID NO 648
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 648

His Gly Gln Gly Thr Phe Thr Ser Asp Leu Ser Lys Gln Leu Glu Glu
1               5                   10                  15

Glu Ala Val Arg Leu Phe Ile Glu Trp Leu Leu Asn Gly Gly His
            20                  25                  30

<210> SEQ ID NO 649
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 649

His Gly Gln Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly Gly His
            20                  25                  30

<210> SEQ ID NO 650
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 650

His Ser Gln Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly Gly His
            20                  25                  30

<210> SEQ ID NO 651
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 651

His Ser Gln Gly Thr Phe Thr Ser Asp Tyr Ser Lys Tyr Leu Glu Ala
1               5                   10                  15

Glu Ala Leu Arg Leu Phe Ile Glu Trp Leu Leu Asn Gly Gly His
            20                  25                  30
```

<210> SEQ ID NO 652
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 652

His Ser Gln Gly Thr Phe Thr Ser Asp Tyr Ser Lys Tyr Leu Glu Glu
1               5                   10                  15

Glu Ala Leu Arg Ile Phe Ile Glu Trp Leu Leu Asn Gly Gly His
            20                  25                  30

<210> SEQ ID NO 653
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 653

His Gly Gln Gly Thr Phe Thr Ser Asp Leu Ser Lys Tyr Leu Glu Ala
1               5                   10                  15

Glu Ala Val Arg Leu Phe Ile Glu Trp Leu Leu Asn Gly Gly His
            20                  25                  30

<210> SEQ ID NO 654
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 654

His Gly Gln Gly Thr Phe Thr Ser Asp Leu Ser Lys Tyr Leu Glu Glu
1               5                   10                  15

Glu Ala Leu Arg Ile Phe Ile Glu Trp Leu Leu Asn Gly Gly His
            20                  25                  30

<210> SEQ ID NO 655
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 655

His Gly Gln Gly Thr Phe Thr Ser Asp Tyr Ser Lys Tyr Leu Glu Glu
1               5                   10                  15

Glu Ala Leu Arg Ile Phe Ile Glu Trp Leu Leu Asn Gly Gly His
            20                  25                  30

<210> SEQ ID NO 656
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 656

His Gly Gln Gly Thr Phe Thr Ser Asp Leu Ser Lys Tyr Leu Glu Glu
1               5                   10                  15

Glu Ala Leu Arg Leu Phe Ile Glu Trp Leu Leu Asn Gly Gly His
            20                  25                  30

<210> SEQ ID NO 657
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 657

His Gly Gln Gly Thr Phe Thr Ser Asp Leu Ser Lys Gln Leu Glu Glu
1               5                   10                  15

Glu Ala Leu Arg Leu Phe Ile Glu Trp Leu Leu Asn Gly Gly His
            20                  25                  30

<210> SEQ ID NO 658
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 658

His Gly Glu Gly Thr Phe Thr Ser Asp Tyr Ser Lys Tyr Leu Glu Ala
1               5                   10                  15

Glu Ala Val Arg Ile Phe Ile Glu Trp Leu Leu Asn Gly Gly His
            20                  25                  30

<210> SEQ ID NO 659
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 659

His Gly Gln Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly Gly His

-continued

```
                    20                  25                  30

<210> SEQ ID NO 660
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 660

His Gly Gln Gly Thr Phe Thr Ser Asp Tyr Ser Lys Tyr Leu Glu Glu
1               5                   10                  15

Glu Ala Leu Arg Ile Phe Ile Gln Trp Leu Leu Asn Gly Gly His
            20                  25                  30

<210> SEQ ID NO 661
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 661

His Ser Gln Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly His His
            20                  25                  30

<210> SEQ ID NO 662
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (30)..(30)
<223> OTHER INFORMATION: AMIDATION

<400> SEQUENCE: 662

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly His
            20                  25                  30

<210> SEQ ID NO 663
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 663

His Ser Glu Gly Thr Phe Thr Ser Asp Tyr Ser Lys Tyr Leu Glu Glu
1               5                   10                  15
```

Glu Ala Val Arg Ile Phe Ile Gln Trp Leu Leu Asn Gly His His
            20                  25                  30

<210> SEQ ID NO 664
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 664

His Ser Glu Gly Thr Phe Thr Ser Asp Tyr Ser Lys Tyr Leu Glu Glu
1               5                   10                  15

Gln Ala Val Arg Ile Phe Ile Glu Trp Leu Leu Asn Gly His His
            20                  25                  30

<210> SEQ ID NO 665
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 665

His Ser Glu Gly Thr Phe Thr Ser Asp Tyr Ser Lys Tyr Leu Glu Glu
1               5                   10                  15

Gln Ala Val Arg Ile Phe Val Gln Trp Leu Leu Asn Gly His His
            20                  25                  30

<210> SEQ ID NO 666
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 666

His Ser Glu Gly Thr Phe Thr Ser Asp Tyr Ser Lys Tyr Leu Glu Glu
1               5                   10                  15

Gln Ala Ala Arg Ile Phe Ile Gln Trp Leu Leu Asn Thr His His
            20                  25                  30

<210> SEQ ID NO 667
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 667

His Ser Glu Gly Thr Phe Thr Ser Asp Tyr Ser Lys Tyr Leu Glu Glu
1               5                   10                  15

```
Gln Ala Val Arg Ile Phe Ile Gln Trp Leu Leu Asn Gly Gly His
            20                  25                  30

<210> SEQ ID NO 668
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 668

His Gly Gln Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly His His
            20                  25                  30

<210> SEQ ID NO 669
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 669

His Ser Glu Gly Thr Phe Thr Ser Asp Tyr Ser Lys Tyr Leu Glu Glu
1               5                   10                  15

Gln Ala Ile Arg Ile Phe Ile Gln Trp Leu Leu Asn Gly His His
            20                  25                  30

<210> SEQ ID NO 670
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 670

His Gly Gln Gly Thr Phe Thr Ser Asp Tyr Ser Lys Tyr Leu Glu Glu
1               5                   10                  15

Glu Ala Val Arg Ile Phe Ile Gln Trp Leu Leu Asn Gly His His
            20                  25                  30

<210> SEQ ID NO 671
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 671

His Ser Glu Gly Thr Phe Thr Ser Asp Tyr Ser Lys Tyr Leu Glu Glu
```

-continued

```
                1               5                  10                 15
Gln Ala Val Arg Leu Phe Ile Gln Trp Leu Leu Asn Gly His His
            20                  25                 30
```

<210> SEQ ID NO 672
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 672

```
His Ser Glu Gly Thr Phe Thr Ser Asp Tyr Ser Lys Tyr Leu Glu Glu
1               5                   10                  15

Gln Ala Ile Arg Leu Phe Ile Gln Trp Leu Leu Asn Gly His His
            20                  25                  30
```

<210> SEQ ID NO 673
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 673

```
His Ser Glu Gly Thr Phe Thr Ser Asp Leu Ser Lys Tyr Leu Glu Glu
1               5                   10                  15

Gln Ala Val Arg Ile Phe Ile Gln Trp Leu Leu Asn Gly His His
            20                  25                  30
```

<210> SEQ ID NO 674
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 674

```
His Ser Glu Gly Thr Phe Thr Ser Asp Tyr Ser Lys Gln Leu Glu Glu
1               5                   10                  15

Gln Ala Val Arg Ile Phe Ile Gln Trp Leu Leu Asn Gly His His
            20                  25                  30
```

<210> SEQ ID NO 675
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 675

His Ser Glu Gly Thr Phe Thr Ser Asp Leu Ser Lys Gln Leu Glu Glu
1               5                   10                  15

Gln Ala Val Arg Ile Phe Ile Gln Trp Leu Leu Asn Gly His His
            20                  25                  30

<210> SEQ ID NO 676
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 676

His Gly Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly His His
            20                  25                  30

<210> SEQ ID NO 677
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 677

His Ser Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly His His
            20                  25                  30

<210> SEQ ID NO 678
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 678

His Gly Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly His His
            20                  25                  30

<210> SEQ ID NO 679
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 679

His Ser Glu Gly Thr Phe Thr Ser Asp Tyr Ser Lys Tyr Leu Glu Glu
1               5                   10                  15

Glu Ala Leu Arg Leu Phe Ile Gln Trp Leu Leu Asn Gly His His
            20                  25                  30

<210> SEQ ID NO 680
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 680

His Ser Glu Gly Thr Phe Thr Ser Asp Tyr Ser Lys Tyr Leu Glu Glu
1               5                   10                  15

Gln Ala Leu Arg Leu Phe Ile Gln Trp Leu Leu Asn Gly His His
            20                  25                  30

<210> SEQ ID NO 681
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 681

His Gly Gln Gly Thr Phe Thr Ser Asp Leu Ser Lys Tyr Leu Glu Glu
1               5                   10                  15

Glu Ala Val Arg Leu Phe Ile Glu Trp Leu Leu Asn Gly His His
            20                  25                  30

<210> SEQ ID NO 682
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 682

His Gly Glu Gly Thr Phe Thr Ser Asp Leu Ser Lys Tyr Leu Glu Glu
1               5                   10                  15

Glu Ala Val Arg Leu Phe Ile Glu Trp Leu Leu Asn Gly His His
            20                  25                  30

<210> SEQ ID NO 683
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 683

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Thr His His
            20                  25                  30

<210> SEQ ID NO 684
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 684

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Thr Gly His
            20                  25                  30

<210> SEQ ID NO 685
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 685

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Thr Gly His
            20                  25                  30

<210> SEQ ID NO 686
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 686

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Gln Gly His His
            20                  25                  30

<210> SEQ ID NO 687
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 687

His Gly Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Thr His His
            20                  25                  30

<210> SEQ ID NO 688
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 688

His Gly Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Thr Gly His
            20                  25                  30

<210> SEQ ID NO 689
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 689

His Gly Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Thr His His
            20                  25                  30

<210> SEQ ID NO 690
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 690

His Gly Gln Gly Thr Phe Thr Ser Asp Leu Ser Lys Tyr Leu Glu Glu
1               5                   10                  15

Gln Ala Val Arg Ile Phe Ile Gln Trp Leu Leu Asn Gly Gly His
            20                  25                  30

<210> SEQ ID NO 691
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 691

His Gly Gln Gly Thr Phe Thr Ser Asp Tyr Ser Lys Gln Leu Glu Glu
1               5                   10                  15

Gln Ala Val Arg Ile Phe Ile Gln Trp Leu Leu Asn Gly Gly His
            20                  25                  30

<210> SEQ ID NO 692
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)

<223> OTHER INFORMATION: AMIDATION

<400> SEQUENCE: 692

His Gly Gln Gly Thr Phe Thr Ser Asp Leu Ser Lys Gln Leu Glu Glu
1               5                   10                  15

Gln Ala Val Arg Ile Phe Ile Gln Trp Leu Leu Asn Thr Gly His
            20                  25                  30

<210> SEQ ID NO 693
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 693

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Lys Asn Gly His His
            20                  25                  30

<210> SEQ ID NO 694
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 694

His Ser Glu Gly Thr Phe Thr Ser Asp Tyr Ser Lys Tyr Leu Glu Ala
1               5                   10                  15

Gln Ala Val Arg Ile Phe Ile Gln Trp Leu Leu Asn Gly His His
            20                  25                  30

<210> SEQ ID NO 695
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 695

His Ser Glu Gly Thr Phe Thr Ser Asp Tyr Ser Lys Tyr Leu Glu Glu
1               5                   10                  15

Gln Ala Val Arg Ile Phe Ile Glu Trp Leu Leu Asn Gly Gly His
            20                  25                  30

<210> SEQ ID NO 696
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES

```
<222> LOCATION: (31)..(31)
<223> OTHER INFORMATION: AMIDATION

<400> SEQUENCE: 696

His Ser Glu Gly Thr Phe Thr Ser Asp Tyr Ser Lys Tyr Leu Glu Glu
1               5                   10                  15

Gln Ala Val Arg Ile Phe Ile Glu Trp Leu Leu Asn Thr Gly His
            20                  25                  30

<210> SEQ ID NO 697
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 697

His Ser Glu Gly Thr Phe Thr Ser Asp Tyr Ser Lys Tyr Leu Glu Glu
1               5                   10                  15

Gln Ala Val His Ile Phe Ile Glu Trp Leu Leu Asn Thr Gly His
            20                  25                  30

<210> SEQ ID NO 698
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 698

His Gly Glu Gly Thr Phe Thr Ser Asp Tyr Ser Lys Tyr Leu Glu Glu
1               5                   10                  15

Gln Ala Val Arg Ile Phe Ile Glu Trp Leu Leu Asn Gly Gly His
            20                  25                  30

<210> SEQ ID NO 699
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 699

His Gly Glu Gly Thr Phe Thr Ser Asp Tyr Ser Lys Tyr Leu Glu Glu
1               5                   10                  15

Gln Ala Val Arg Ile Phe Ile Glu Trp Leu Leu Asn Thr Gly His
            20                  25                  30

<210> SEQ ID NO 700
<211> LENGTH: 31
<212> TYPE: PRT
<213> ORGANISM: Artificial Sequence
<220> FEATURE:
<223> OTHER INFORMATION: GLP-1 analogue
<220> FEATURE:
```

<221> NAME/KEY: MOD_RES
<222> LOCATION: (31)..(31)
<223> OTHER INFORMATION: AMIDATION

<400> SEQUENCE: 700

His Gly Gln Gly Thr Phe Thr Ser Asp Leu Ser Lys Gln Leu Glu Glu
1               5                   10                  15

Gln Ala Val Arg Ile Phe Ile Glu Trp Leu Leu Asn Gly Gly His
            20                  25                  30

<210> SEQ ID NO 701
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 701

His Gly Gln Gly Thr Phe Thr Ser Asp Tyr Ser Lys Tyr Leu Glu Glu
1               5                   10                  15

Gln Ala Val Arg Ile Phe Ile Glu Trp Leu Leu Asn Gly Gly His
            20                  25                  30

<210> SEQ ID NO 702
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 702

His Gly Gln Gly Thr Phe Thr Ser Asp Tyr Ser Lys Tyr Leu Glu Glu
1               5                   10                  15

Gln Ala Val Arg Ile Phe Ile Glu Trp Leu Leu Asn Thr Gly His
            20                  25                  30

<210> SEQ ID NO 703
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 703

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Asn Gly Gly His
            20                  25                  30

<210> SEQ ID NO 704
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 704

His Ser Glu Gly Thr Phe Thr Ser Asp Tyr Ser Lys Tyr Leu Glu Glu

```
                1               5                  10                  15
Gln Ala Val Arg Ile Phe Ile Glu Trp Leu Leu Asn Gly His His
            20                  25                  30

<210> SEQ ID NO 705
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 705

His Ser Glu Gly Thr Phe Thr Ser Asp Tyr Ser Lys Tyr Leu Glu Glu
1               5                  10                  15

Gln Ala Val Arg Ile Phe Ile Glu Trp Leu Leu Asn Gly Gly His
            20                  25                  30

<210> SEQ ID NO 706
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 706

His Ser Glu Gly Thr Phe Thr Ser Asp Tyr Ser Lys Tyr Leu Glu Glu
1               5                  10                  15

Gln Ala Val Arg Ile Phe Ile Glu Trp Leu Leu Asn Gly Lys His
            20                  25                  30

<210> SEQ ID NO 707
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 707

His Ser Glu Gly Thr Phe Thr Ser Asp Tyr Ser Lys Tyr Leu Glu Glu
1               5                  10                  15

Gln Ala Val Arg Ile Phe Ile Glu Trp Leu Leu Asn Gly Lys His
            20                  25                  30

<210> SEQ ID NO 708
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 708

His Ser Glu Gly Thr Phe Thr Ser Asp Tyr Ser Lys Tyr Leu Glu Glu
1               5                  10                  15

Gln Ala Val Arg Ile Phe Ile Gln Trp Leu Leu Asn Gly Lys His
            20                  25                  30

<210> SEQ ID NO 709
```

```
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 709

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Gln Thr Gly His
            20                  25                  30

<210> SEQ ID NO 710
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 710

His Ser Glu Gly Thr Phe Thr Ser Asp Tyr Ser Lys Tyr Leu Glu Glu
1               5                   10                  15

Gln Ala Val Arg Ile Phe Ile Gln Trp Leu Leu Gln Gly Gly His
            20                  25                  30

<210> SEQ ID NO 711
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 711

His Gly Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly Gly His
            20                  25                  30

<210> SEQ ID NO 712
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 712

His Gly Glu Gly Thr Phe Thr Ser Asp Tyr Ser Lys Tyr Leu Glu Glu
1               5                   10                  15

Glu Ala Val Arg Ile Phe Ile Glu Trp Leu Leu Gln Gly Gly His
            20                  25                  30

<210> SEQ ID NO 713
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 713

His Gly Glu Gly Thr Phe Thr Ser Asp Tyr Ser Lys Tyr Leu Glu Glu
1               5                   10                  15
```

```
Glu Ala Val Arg Ile Phe Ile Glu Trp Leu Leu Gln Gly Gly His
            20                  25                  30

<210> SEQ ID NO 714
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 714

His Ser Glu Gly Thr Phe Thr Ser Asp Tyr Ser Lys Tyr Leu Glu Glu
1               5                   10                  15

Glu Ala Val Arg Ile Phe Ile Glu Trp Leu Leu Asn Gly Lys His
            20                  25                  30

<210> SEQ ID NO 715
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (31)..(31)
<223> OTHER INFORMATION: AMIDATION

<400> SEQUENCE: 715

His Gly Glu Gly Thr Phe Thr Ser Asp Tyr Ser Lys Tyr Leu Glu Glu
1               5                   10                  15

Gln Ala Val Arg Ile Phe Ile Glu Trp Leu Leu Asn Gly Lys His
            20                  25                  30

<210> SEQ ID NO 716
<211> LENGTH: 30
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
```

```
           Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly

<400> SEQUENCE: 716

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa His
            20                  25                  30

<210> SEQ ID NO 717
<211> LENGTH: 30
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
```

```
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MOD_RES
<222> LOCATION: (30)..(30)
<223> OTHER INFORMATION: AMIDATION

<400> SEQUENCE: 717

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa His
            20                  25                  30

<210> SEQ ID NO 718
<211> LENGTH: 31
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
```

```
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly

<400> SEQUENCE: 718

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa His His
            20                  25                  30

<210> SEQ ID NO 719
<211> LENGTH: 31
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
```

```
                Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MOD_RES
<222> LOCATION: (31)..(31)
<223> OTHER INFORMATION: AMIDATION

<400> SEQUENCE: 719

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa His His
            20                  25                  30

<210> SEQ ID NO 720
<211> LENGTH: 31
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
```

```
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly

<400> SEQUENCE: 720

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa Gly His
            20                  25                  30

<210> SEQ ID NO 721
<211> LENGTH: 31
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
```

```
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MOD_RES
<222> LOCATION: (31)..(31)
<223> OTHER INFORMATION: AMIDATION

<400> SEQUENCE: 721

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa Gly His
            20                  25                  30

<210> SEQ ID NO 722
<211> LENGTH: 31
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
```

```
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly

<400> SEQUENCE: 722

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa Lys His
            20                  25                  30

<210> SEQ ID NO 723
<211> LENGTH: 31
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
```

```
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MOD_RES
<222> LOCATION: (31)..(31)
<223> OTHER INFORMATION: AMIDATION

<400> SEQUENCE: 723

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa Lys His
                20                  25                  30

<210> SEQ ID NO 724
<211> LENGTH: 32
<212> TYPE: PRT
```

```
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly

<400> SEQUENCE: 724

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa Gly His His
            20                  25                  30

<210> SEQ ID NO 725
```

```
<211> LENGTH: 32
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MOD_RES
<222> LOCATION: (32)..(32)
<223> OTHER INFORMATION: AMIDATION

<400> SEQUENCE: 725

His Ser Gln Gly Thr Phe Thr Ser Asp Xaa Ser Xaa Xaa Leu Xaa Xaa
1               5                   10                  15
```

Xaa Xaa Ala Xaa Xaa Phe Xaa Xaa Trp Leu Leu Asn Xaa Gly His His
            20                  25                  30

<210> SEQ ID NO 726
<211> LENGTH: 32
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly

<400> SEQUENCE: 726

```
His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa His His His
            20              25                  30

<210> SEQ ID NO 727
<211> LENGTH: 32
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (10)..(10)
<223> OTHER INFORMATION: Xaa is selected from the group consisting of
      Tyr and Leu;
<220> FEATURE:
<221> NAME/KEY: MISC_FEATURE
<222> LOCATION: (12)..(12)
<223> OTHER INFORMATION: Xaa is selected from the group consisting of
      Lys, His and Arg
<220> FEATURE:
<221> NAME/KEY: MISC_FEATURE
<222> LOCATION: (13)..(13)
<223> OTHER INFORMATION: Xaa is selected from the group consisting of
      Tyr, Gln and His
<220> FEATURE:
<221> NAME/KEY: MISC_FEATURE
<222> LOCATION: (15)..(15)
<223> OTHER INFORMATION: Xaa is selected from the group consisting of
      Asp and Glu
<220> FEATURE:
<221> NAME/KEY: MISC_FEATURE
<222> LOCATION: (16)..(16)
<223> OTHER INFORMATION: Xaa is selected from the group consisting of
      Glu, Gln and Ser
<220> FEATURE:
<221> NAME/KEY: MISC_FEATURE
<222> LOCATION: (17)..(17)
<223> OTHER INFORMATION: Xaa is selected from the group consisting of
      Arg, His and Lys
<220> FEATURE:
<221> NAME/KEY: MISC_FEATURE
<222> LOCATION: (18)..(18)
<223> OTHER INFORMATION: Xaa is selected from the group consisting of
      Arg and Lys
<220> FEATURE:
<221> NAME/KEY: MISC_FEATURE
<222> LOCATION: (20)..(20)
<223> OTHER INFORMATION: Xaa is selected from the group consisting of
      His and Gln
<220> FEATURE:
<221> NAME/KEY: MISC_FEATURE
<222> LOCATION: (21)..(21)
<223> OTHER INFORMATION: Xaa is selected from the group consisting of
      Glu, His and Asp
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Gln and Glu
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
<221> NAME/KEY: MISC_FEATURE
<222> LOCATION: (29)..(29)
<223> OTHER INFORMATION: Xaa is selected from the group consisting of
      Thr and Gly
<220> FEATURE:
```

```
<221> NAME/KEY: MOD_RES
<222> LOCATION: (32)..(32)
<223> OTHER INFORMATION: AMIDATION

<400> SEQUENCE: 727

His Ser Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Leu Asn Xaa His His His
            20                  25                  30

<210> SEQ ID NO 728
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
<223> OTHER INFORMATION: Xaa is selected from the group consisting of
      Arg and His
<220> FEATURE:
<221> NAME/KEY: MISC_FEATURE
<222> LOCATION: (21)..(21)
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
<220> FEATURE:
<221> NAME/KEY: MISC_FEATURE
<222> LOCATION: (24)..(24)
<223> OTHER INFORMATION: Xaa is selected from the group consisting of
      Glu and Gln
```

```
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
<221> NAME/KEY: MISC_FEATURE
<222> LOCATION: (29)..(29)
<223> OTHER INFORMATION: Xaa is selected from the group consisting of
      Gly and Thr;

<400> SEQUENCE: 728

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa His
            20                  25                  30

<210> SEQ ID NO 729
<211> LENGTH: 30
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
<223> OTHER INFORMATION: Xaa is selected from the group consisting of
      Arg and His
<220> FEATURE:
<221> NAME/KEY: MISC_FEATURE
<222> LOCATION: (21)..(21)
```

```
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
<220> FEATURE:
<221> NAME/KEY: MISC_FEATURE
<222> LOCATION: (24)..(24)
<223> OTHER INFORMATION: Xaa is selected from the group consisting of
      Glu and Gln
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
<221> NAME/KEY: MISC_FEATURE
<222> LOCATION: (29)..(29)
<223> OTHER INFORMATION: Xaa is selected from the group consisting of
      Gly and Thr;
<220> FEATURE:
<221> NAME/KEY: MOD_RES
<222> LOCATION: (30)..(30)
<223> OTHER INFORMATION: AMIDATION

<400> SEQUENCE: 729

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa His
            20                  25                  30

<210> SEQ ID NO 730
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
```

<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
<223> OTHER INFORMATION: Xaa is selected from the group consisting of
      Arg and His
<220> FEATURE:
<221> NAME/KEY: MISC_FEATURE
<222> LOCATION: (21)..(21)
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
<220> FEATURE:
<221> NAME/KEY: MISC_FEATURE
<222> LOCATION: (24)..(24)
<223> OTHER INFORMATION: Xaa is selected from the group consisting of
      Glu and Gln
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
<221> NAME/KEY: MISC_FEATURE
<222> LOCATION: (29)..(29)
<223> OTHER INFORMATION: Xaa is selected from the group consisting of
      Gly and Thr;

<400> SEQUENCE: 730

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa His His
            20                  25                  30

<210> SEQ ID NO 731
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His

```
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
<223> OTHER INFORMATION: Xaa is selected from the group consisting of
      Arg and His
<220> FEATURE:
<221> NAME/KEY: MISC_FEATURE
<222> LOCATION: (21)..(21)
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
<220> FEATURE:
<221> NAME/KEY: MISC_FEATURE
<222> LOCATION: (24)..(24)
<223> OTHER INFORMATION: Xaa is selected from the group consisting of
      Glu and Gln
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
<221> NAME/KEY: MISC_FEATURE
<222> LOCATION: (29)..(29)
<223> OTHER INFORMATION: Xaa is selected from the group consisting of
      Gly and Thr;
<220> FEATURE:
<221> NAME/KEY: MOD_RES
<222> LOCATION: (31)..(31)
<223> OTHER INFORMATION: AMIDATION

<400> SEQUENCE: 731

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa His His
            20                  25                  30

<210> SEQ ID NO 732
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
```

-continued

```
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
<223> OTHER INFORMATION: Xaa is selected from the group consisting of
      Arg and His
<220> FEATURE:
<221> NAME/KEY: MISC_FEATURE
<222> LOCATION: (21)..(21)
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
<220> FEATURE:
<221> NAME/KEY: MISC_FEATURE
<222> LOCATION: (24)..(24)
<223> OTHER INFORMATION: Xaa is selected from the group consisting of
      Glu and Gln
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
<221> NAME/KEY: MISC_FEATURE
<222> LOCATION: (29)..(29)
<223> OTHER INFORMATION: Xaa is selected from the group consisting of
      Gly and Thr;

<400> SEQUENCE: 732

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa Gly His
            20                  25                  30
```

```
<210> SEQ ID NO 733
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
<223> OTHER INFORMATION: Xaa is selected from the group consisting of
      Arg and His
<220> FEATURE:
<221> NAME/KEY: MISC_FEATURE
<222> LOCATION: (21)..(21)
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
<220> FEATURE:
<221> NAME/KEY: MISC_FEATURE
<222> LOCATION: (24)..(24)
<223> OTHER INFORMATION: Xaa is selected from the group consisting of
      Glu and Gln
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
```

```
<221> NAME/KEY: MISC_FEATURE
<222> LOCATION: (29)..(29)
<223> OTHER INFORMATION: Xaa is selected from the group consisting of
      Gly and Thr;
<220> FEATURE:
<221> NAME/KEY: MOD_RES
<222> LOCATION: (31)..(31)
<223> OTHER INFORMATION: AMIDATION

<400> SEQUENCE: 733

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa Gly His
            20                  25                  30

<210> SEQ ID NO 734
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
<223> OTHER INFORMATION: Xaa is selected from the group consisting of
      Arg and His
<220> FEATURE:
<221> NAME/KEY: MISC_FEATURE
<222> LOCATION: (21)..(21)
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
```

```
<220> FEATURE:
<221> NAME/KEY: MISC_FEATURE
<222> LOCATION: (24)..(24)
<223> OTHER INFORMATION: Xaa is selected from the group consisting of
      Glu and Gln
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
<221> NAME/KEY: MISC_FEATURE
<222> LOCATION: (29)..(29)
<223> OTHER INFORMATION: Xaa is selected from the group consisting of
      Gly and Thr;

<400> SEQUENCE: 734

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa Lys His
            20                  25                  30

<210> SEQ ID NO 735
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (2)..(2)
<223> OTHER INFORMATION: Xaa is selected from the group consisting of
      Ser and Gly
<220> FEATURE:
<221> NAME/KEY: MISC_FEATURE
<222> LOCATION: (3)..(3)
<223> OTHER INFORMATION: Xaa is selected from the group consisting of
      Glu and Gln;
<220> FEATURE:
<221> NAME/KEY: MISC_FEATURE
<222> LOCATION: (10)..(10)
<223> OTHER INFORMATION: Xaa is selected from the group consisting of
      Tyr and Leu
<220> FEATURE:
<221> NAME/KEY: MISC_FEATURE
<222> LOCATION: (12)..(12)
<223> OTHER INFORMATION: Xaa is selected from the group consisting of
      Lys and His
<220> FEATURE:
<221> NAME/KEY: MISC_FEATURE
<222> LOCATION: (13)..(13)
<223> OTHER INFORMATION: Xaa is selected from the group consisting of
      Tyr and Gln;
<220> FEATURE:
<221> NAME/KEY: MISC_FEATURE
<222> LOCATION: (16)..(16)
<223> OTHER INFORMATION: Xaa is selected from the group consisting of
      Glu, Ala and Ser
<220> FEATURE:
<221> NAME/KEY: MISC_FEATURE
<222> LOCATION: (17)..(17)
<223> OTHER INFORMATION: Xaa is selected from the group consisting of
      Gln and Glu
<220> FEATURE:
<221> NAME/KEY: MISC_FEATURE
<222> LOCATION: (19)..(19)
<223> OTHER INFORMATION: Xaa is selected from the group consisting of
      Val, Ala, Ile and Leu
<220> FEATURE:
<221> NAME/KEY: MISC_FEATURE
<222> LOCATION: (20)..(20)
```

```
<223> OTHER INFORMATION: Xaa is selected from the group consisting of
      Arg and His
<220> FEATURE:
<221> NAME/KEY: MISC_FEATURE
<222> LOCATION: (21)..(21)
<223> OTHER INFORMATION: Xaa is selected from the group consisting of
      Ile and Leu
<220> FEATURE:
<221> NAME/KEY: MISC_FEATURE
<222> LOCATION: (23)..(23)
<223> OTHER INFORMATION: Xaa is selected from the group consisting of
      Ile and Val;
<220> FEATURE:
<221> NAME/KEY: MISC_FEATURE
<222> LOCATION: (24)..(24)
<223> OTHER INFORMATION: Xaa is selected from the group consisting of
      Glu and Gln
<220> FEATURE:
<221> NAME/KEY: MISC_FEATURE
<222> LOCATION: (27)..(27)
<223> OTHER INFORMATION: Xaa is selected from the group consisting of
      Leu and Lys;
<220> FEATURE:
<221> NAME/KEY: MISC_FEATURE
<222> LOCATION: (28)..(28)
<223> OTHER INFORMATION: Xaa is selected from the group consisting of
      Asn, Lys and Gln
<220> FEATURE:
<221> NAME/KEY: MISC_FEATURE
<222> LOCATION: (29)..(29)
<223> OTHER INFORMATION: Xaa is selected from the group consisting of
      Gly and Thr;
<220> FEATURE:
<221> NAME/KEY: MOD_RES
<222> LOCATION: (31)..(31)
<223> OTHER INFORMATION: AMIDATION

<400> SEQUENCE: 735

His Xaa Xaa Gly Thr Phe Thr Ser Asp Xaa Ser Xaa Xaa Leu Glu Xaa
1               5                   10                  15

Xaa Ala Xaa Xaa Xaa Phe Xaa Xaa Trp Leu Xaa Xaa Xaa Lys His
            20                  25                  30

<210> SEQ ID NO 736
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 736

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 737
<211> LENGTH: 29
<212> TYPE: PRT
<213> ORGANISM: Homo sapiens

<400> SEQUENCE: 737

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 738
```

```
<211> LENGTH: 5
<212> TYPE: PRT
<213> ORGANISM: Artificial Sequence
<220> FEATURE:
<223> OTHER INFORMATION: Cleavable linker

<400> SEQUENCE: 738

Asp Asp Asp Asp Tyr
1               5

<210> SEQ ID NO 739
<211> LENGTH: 5
<212> TYPE: PRT
<213> ORGANISM: Artificial Sequence
<220> FEATURE:
<223> OTHER INFORMATION: Cleavable linker

<400> SEQUENCE: 739

His Pro Phe His Leu
1               5
```